United States Patent
Kaneko et al.

(10) Patent No.: US 9,441,276 B2
(45) Date of Patent: Sep. 13, 2016

(54) DETECTION OF DIGESTIVE ORGAN CANCER, GASTRIC CANCER, COLORECTAL CANCER, PANCREATIC CANCER, AND BILIARY TRACT CANCER BY GENE EXPRESSION PROFILING

(71) Applicant: NATIONAL UNIVERSITY CORPORATION KANAZAWA UNIVERSITY, Ishikawa (JP)

(72) Inventors: Shuichi Kaneko, Ishikawa (JP); Masao Honda, Ishikawa (JP); Yoshio Sakai, Ishikawa (JP); Taro Yamashita, Ishikawa (JP)

(73) Assignee: NATIONAL UNIVERSITY CORPORATION KANAZAWA UNIVERSITY, Ishikawa (JP)

( * ) Notice: Subject to any disclaimer, the term of this patent is extended or adjusted under 35 U.S.C. 154(b) by 0 days.

(21) Appl. No.: 14/551,651

(22) Filed: Nov. 24, 2014

(65) Prior Publication Data
US 2015/0133334 A1    May 14, 2015

Related U.S. Application Data

(62) Division of application No. 13/391,858, filed as application No. PCT/JP2010/063122 on Aug. 3, 2010, now Pat. No. 8,932,990.

(30) Foreign Application Priority Data

Aug. 24, 2009 (JP) ................................. 2009-193702

(51) Int. Cl.
*C07H 21/04* (2006.01)
*C12Q 1/68* (2006.01)

(52) U.S. Cl.
CPC ....... *C12Q 1/6886* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 5,474,796 A * | 12/1995 | Brennan | ............... | B01J 19/0046 422/547 |
| 2003/0211531 A1 | 11/2003 | Hampton et al. | | |
| 2005/0014165 A1 | 1/2005 | Lee et al. | | |
| 2005/0181516 A1 * | 8/2005 | Dressman | ............ | C12Q 1/6883 436/161 |
| 2005/0260572 A1 | 11/2005 | Kato et al. | | |
| 2006/0269921 A1 | 11/2006 | Segara et al. | | |
| 2007/0065844 A1 | 3/2007 | Golub et al. | | |
| 2010/0086537 A1 | 4/2010 | Sooknanan et al. | | |
| 2012/0036101 A1 | 2/2012 | Rosenberg et al. | | |
| 2012/0040849 A1 | 2/2012 | Valles et al. | | |

FOREIGN PATENT DOCUMENTS

| | | |
|---|---|---|
| JP | 2005-523727 A | 8/2005 |
| JP | 2005-304497 A | 11/2005 |
| JP | 2007-074916 A | 3/2007 |
| JP | 2007-236253 A | 9/2007 |
| WO | 2004/091548 A2 | 10/2004 |
| WO | 2007/081740 A2 | 7/2007 |
| WO | 2007/147265 A1 | 12/2007 |
| WO | 2008/036765 A2 | 3/2008 |
| WO | 2008/147205 A1 | 12/2008 |
| WO | 2009/002175 A1 | 12/2008 |
| WO | 2009/032915 A2 | 3/2009 |
| WO | 2009/126271 A1 | 10/2009 |

OTHER PUBLICATIONS

Raslova et al. (Blood, vol. 109, No. 8, pp. 3225-3234, Apr. 2007).*
Toyota et al. (Cancer Research, vol. 68, No. 11, pp. 4123-4132, Jun. 1, 2008).*
Jun, Lu, et al: "Micro RNA expression profiles classify human cancers", Nature: International Weekly Journal of Science, Nature Publishing Group, United Kingdom, vol. 435. No. 7043, Jun. 9, 2005. pages 834-838.
Marshall, et al., "A blood-based biomarker panel for stratifying current risk for colorectal cancer", International Journal of Cancer, 126, Mar. 1, 2010, pp. 1177-1186.
Malati T., "Tumour markers: An overview", Indian Journal of Clinical Biochemistry, 2007, 22(2), pp. 17-31.
Honda, Masao, et al., "Shokaki Gan to Idenshi Ijo", Biotherapy, 2007, vol. 21, pp. 153 to 159.
Shimoji, Takashi, et al., "Shokaki Gan no Idenshi Shindan", separate volume, Igaku no Ayumi, 2006, 1st edition, 1st print, pp. 252 to 255.
Hansel, D.E., et al., "Identification of novel cellular targets in biliary tract cancers using global gene expression technology", Am. J. Pathol., 2003, vol. 163, pp. 217-229.

(Continued)

*Primary Examiner* — Jeanine A Goldberg
(74) *Attorney, Agent, or Firm* — Lucas & Mercanti, LLP

(57) ABSTRACT

The present invention provides a method and a reagent for detecting a digestive organ cancer, gastric cancer, colorectal cancer, pancreatic cancer, or biliary tract cancer patient based on expression profiles. The method comprises obtaining the expression profile of at least one gene selected from the group consisting of probes corresponding to genes with expression levels (in peripheral blood) that vary in digestive organ cancer, gastric cancer, colorectal cancer, pancreatic cancer, and biliary tract cancer cases, compared with normal healthy subjects. The reagent for detecting digestive organ cancer, gastric cancer, colorectal cancer, pancreatic cancer, or biliary tract cancer contains nucleotides or partial sequences thereof consisting of the nucleotide sequence of at least one gene selected from the group consisting of probes with expression levels that vary in digestive organ cancer, gastric cancer, colorectal cancer, pancreatic cancer, or biliary tract cancer, or nucleotides containing sequences complementary thereto.

5 Claims, 220 Drawing Sheets

(56) References Cited

OTHER PUBLICATIONS

Karamitopoulou, E., et al., "Clinical significance of cell cycle- and apoptosisrelated markers in biliary tract cancer: a tissue microarray-based approach revealing a distinctive immunophenotype for intrahepatic and extrahepatic cholangiocarcinomas", Am. J. Clin. Pathol., 2008, vol. 130, pp. 780-786.

Sasaki, Yasushi, et al., "Shokaki Shokakan no Idenshi Shindanho Idenshi Bunshi no Kosei ni Motozuita Tailor Made Iryo Shuyo Marker no Shinpo", Mebio, 2002, vol. 19, pp. 77 to 82.

Yokozaki, Hiroshi, "Shokudo Gan, I Gan no Akuseido o Kitei suru Bunshi Joho no Haaku to sore o Oyo shita Seiken Shindanho no Kakuritsu", Ministry of Health, Labour and Welfare Gan Kenkyu Joseikin ni yoru Kenkyu Hokokushu, Heisei 17 Nendo (2005), pp. 607 to 610.

Yasui, Wataru, "I Gan no Bunshi Byorigakuteki Shindan", Japanese Journal of Cancer and Chemotherapy, 2005, vol. 32, pp. 427 to 431.

Kawaguchi, K., et al., "Differential gene alteration among hepatoma cell lines demonstrated by cDNA microarray-based comparative genomic hybridization", Biochem. Biophys. Res. Commun., 2005, vol. 329, pp. 370 to 380.

Extended European Search Report dated Jul. 1, 2015, which is issued by European Patent Office for a related European Application No. EP15157502.4 (5 pgs.).

Extended European Search Report dated Jul. 3, 2015, which is issued by European Patent Office for a related European Application No. EP15157500.8 (5 pgs.).

Extended European Search Report dated Jul. 1, 2015, which is issued by European Patent Office for a related European Application No. EP15157499.3 (5 pgs.).

Antonio Jimeno, et al., "Dual mitogen-activated protein kinase and epidermal growth factor receptor inhibition in biliary and pancreatic cancer," Molecular Cancer Therapeutics, vol. 6, No. 3, Mar. 1, 2007, pp. 1079-1088.

George Miller, et al., "Genome wide analysis and clinical correlation of chromosomal and transcriptional mutations in cancers of the biliary tract," Journal of Experimental & Clinical Cancer Research, vol. 28, No. 62, Jan. 1, 2009, (13 pgs.).

Shimoji, Takashi, et al., "Genetic diagnosis of digestive tract cancer", separate volume, Igaku no Ayumi, 2006, partial English translation of the key points on p. 1.

Sasaki, Yasushi, et al., "Gene Diagnosis for Gastrointestinal Tract: Tailor-made Medicine Based on Individual Gene/Molecule, Progress of Tumor Marker", Mebio, 2002, partial English translation of the point section on p. 82.

"Whole Human Genome Microarray Kit 4x44k", Agilent Technologies, 2007, Version 2.0, pp. 1-13.

"Safety Data Sheet Whole Human Genome Kit-4x44k", Agilent Technologies, 2013, pp. 1-8.

"Specification for Whole Human Genome Microarray Kit 4x44k", Agilent Technologies, 1 page.

* cited by examiner

Fig. 1-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P100292 | ZNF598 | TGAATGTTTTTATGAGACAAGCTGAATGTGGGATCTCAAATTGCCTCTGACCTTTTATAA | SEQ ID NO: 1 | Homo sapiens mRNA for FLJ00086 protein, partial cds. [AK024487] |
| 2 | A_23_P100654 | ZBTB4 | GTATTTGAGGTGGGGAATTTGAATATGTGAGTTTCAGATGTTGGAAATTTGGGATTTG | SEQ ID NO: 2 | Homo sapiens zinc finger and BTB domain containing 4 (ZBTB4), mRNA [NM_020899] |
| 3 | A_23_P100779 | UBTF | CAGGACCGTGCAGCATATAAAGAGTACATCTCCAATAAACGTAAGAGGATGACCAAGGTG | SEQ ID NO: 3 | Homo sapiens upstream binding transcription factor, RNA polymerase I (UBTF), transcript variant 1, mRNA [NM_014233] |
| 4 | A_23_P101308 | ENST00000221462 | TAGTTCCGTTTTTCCGGTCGGTCTGCGATGAGGTGAGGCCAGAGCCATGAGAATGTGTC | SEQ ID NO: 4 | Homo sapiens hypothetical protein LOC284352, mRNA (cDNA clone IMAGE:4779950), with apparent retained intron. [BC039061] |
| 5 | A_23_P101332 | FLJ12949 | ACAGGTCTCGGACCCACACAGTAGTATCTGCTGGAGAGAATCCTCTCATCTGTGGCCAGGCA | SEQ ID NO: 5 | Homo sapiens hypothetical protein FLJ12949 (FLJ12949), transcript variant 1, mRNA [NM_023008] |
| 6 | A_23_P101551 | BCAT2 | TCCCTAGGAATGACTCAGGTGAAGTGGAATACGAAATAAAAGGCAGCGGGGGGGTCTG | SEQ ID NO: 6 | Homo sapiens branched chain aminotransferase 2, mitochondrial (BCAT2), mRNA [NM_001190] |
| 7 | A_23_P102404 | CCT7 | GGGGTACAGTGGTATGGAGTAGAACATGAACAACGAGGACATTGCTGACAACTTTGAAGTT | SEQ ID NO: 7 | Homo sapiens chaperonin containing TCP1, subunit 7 (eta) (CCT7), transcript variant 1, mRNA [NM_006429] |
| 8 | A_23_P102508 | SLC5A6 | TTTTTCTGGTCGCTTGCCAATCTGTTTTTTAAAGGATCAGGATCGTAGGGAGCAGGATCA | SEQ ID NO: 8 | Homo sapiens solute carrier family 5 (sodium-dependent vitamin transporter), member 6 (SLC5A6), mRNA [NM_021095] |
| 9 | A_23_P102973 | DGCR14 | TGGGTCATAGAGCAGTTCACAGAGCGCCTGGAGGGCAGCTGTAGACCCAGCAGAGGAGTCCA | SEQ ID NO: 9 | Homo sapiens DiGeorge syndrome critical region gene 14 (DGCR14), mRNA [NM_022719] |
| 10 | A_23_P102994 | PIK4CA | AAGAGTGAGGCCACAGCCCTTCAAGCTGGTTCATGGATGTGTGTCCGAGGGCTACGTGGCT | SEQ ID NO: 10 | Homo sapiens phosphatidylinositol 4-kinase, catalytic, alpha polypeptide (PIK4CA), transcript variant 1, mRNA [NM_002650] |
| 11 | A_23_P103104 | MFNG | CCAATTGTGATGATCCTTTTGGTCATTTCCCAGGCCTTCTTGCTGTTAGGGGGCTACCAT | SEQ ID NO: 11 | Homo sapiens MFNG O-fucosylpeptide 3-beta-N-acetylglucosaminyltransferase (MFNG), mRNA [NM_002405] |
| 12 | A_23_P103942 | DNAJC11 | CTGTAAGCATTCATCTGCATTTTTTAAAAAAGGTTTCTGTGACGGGCGCCAGGGCCGAGCC | SEQ ID NO: 12 | Homo sapiens DnaJ (Hsp40) homolog, subfamily C, member 11 (DNAJC11), mRNA [NM_018198] |
| 13 | A_23_P103968 | AKR7A3 | ACAGCCTGTGGGCCCGCTCTTTGGGAATAGCTGGGAGAGATGTACAGGAATCGGCTACTG | SEQ ID NO: 13 | Homo sapiens aldo-keto reductase family 7, member A3 (aflatoxin aldehyde reductase) (AKR7A3), mRNA [NM_012067] |
| 14 | A_23_P104641 | C1orf2 | ACTGCCACTTTCTGCAGCTCTACCTGTGGGCGTTTTGTGGCCGACGAAGAACTGGTGCACT | SEQ ID NO: 14 | Homo sapiens chromosome 11 open reading frame2 (C1orf2), mRNA [NM_013265] |
| 15 | A_23_P106632 | CHST14 | AAGGCGTTTGAGGTTGTGACTGTGTGGGCTGGTATATCTGGCTGGCCATTTGTGTGATGCATTT | SEQ ID NO: 15 | Homo sapiens dermatan 4 sulfotransferase 1 (D4ST1), mRNA [NM_130468] |
| 16 | A_23_P106675 | GOT2 | CTATTGGAGAGATTTCATCGACCATTCCTAGCTGCTTGATTGACCATCAACCTGGATCCTATCGAG | SEQ ID NO: 16 | Homo sapiens glutamic-oxaloacetic transaminase 2, mitochondrial (aspartate aminotransferase 2) (GOT2), nuclear gene encoding mitochondrial protein, mRNA [NM_002080] |

Fig. 1-2

| No. | Probe ID No. | Symbols of genes | Sequence | SEQ ID NO: | Descriptions of genes (letters and numbers within [ ] indicates GenBank accession No.) |
|---|---|---|---|---|---|
| 17 | A_23_P106887 | FUS | TATTGACTGGTTTGATGGTAAAGAATTCTCCGGAAATCGTATCAAGGTCTCATTTGCTAG | SEQ ID NO: 17 | Homo sapiens fusion (involved in t(12;16) in malignant liposarcoma) (FUS), mRNA [NM_004960] |
| 18 | A_23_P106973 | SEPT9 | AGGCTCTGTTCCTCAATGGCCTTTTGCTACGTGCCTCCCGAGAAATTTGTCTTTTTGTAT | SEQ ID NO: 18 | Homo sapiens septin 9 (SEPT9), mRNA [NM_006640] |
| 19 | A_23_P1072 | ATP1A1 | TGCCTCGAATGGGTGCTGTTGCTCTTAGGATGTATCCCTGAAACCTACCTGGTGTTGTGT | SEQ ID NO: 19 | Homo sapiens ATPase, Na+/K+ transporting, alpha 1 polypeptide (ATP1A1), transcript variant 1, mRNA [NM_000701] |
| 20 | A_23_P108376 | THADA | CTGTGTGGAGAGGCATGCATCAGGTGGAAGAAAGACTACCTGTTTGAAAAGCAAGAAGTCAA | SEQ ID NO: 20 | Homo sapiens thyroid adenoma associated (THADA), transcript variant 1, mRNA [NM_022065] |
| 21 | A_23_P109001 | KIAA0406 | TGATGGAACGGTGCATCCACTTGTTGTCAGATAAAAATCTGCAAATCCGGCCTGAAGGTC | SEQ ID NO: 21 | Homo sapiens KIAA0406 (KIAA0406), mRNA [NM_014657] |
| 22 | A_23_P110062 | EIF2B5 | CATTGAGGAGTCTTCGTCGAGAGCATGAAGGCTCTTGGTATTTGGATGGCAAGGTACTGAT | SEQ ID NO: 22 | Homo sapiens eukaryotic translation initiation factor 2B, subunit 5 epsilon, 82kDa (EIF2B5), mRNA [NM_003907] |
| 23 | A_23_P111745 | ZMIZ2 | TCGGTGGGCTCTCAGATTCAGCTCTGTGTAAAGATTCTCTAGCGGGGTGGCGGTGGCCAAGT | SEQ ID NO: 23 | Homo sapiens zinc finger, MIZ-type containing 2 (ZMIZ2), transcript variant 1, mRNA [NM_031449] |
| 24 | A_23_P112406 | GTF3C5 | AGCTGACCCTAGCACGGTGCTGGCTGTGACATGGTCGTCTTGGTGCTGCCTCTGGTCCTGAGGGGT | SEQ ID NO: 24 | Homo sapiens general transcription factor IIIC, polypeptide 5, 63kDa (GTF3C5), mRNA [NM_012087] |
| 25 | A_23_P113026 | PARN | GAGTGTCGGCTGCTGTGAAATCTGCAAAAAGAGGTGACATTCCAAGGTGCTGTGATCAGAATT | SEQ ID NO: 25 | Homo sapiens poly(A)-specific ribonuclease (deadenylation nuclease) (PARN), mRNA [NM_002582] |
| 26 | A_23_P113184 | FTO | TTTGGGCATGACCCAGCCTATGCTGGCCATACTCCCTCTTTTCTCGGTTTTTTTCATTA | SEQ ID NO: 26 | Homo sapiens fatso (FTO), mRNA [NM_001080432] |
| 27 | A_23_P116840 | C12orf44 | CTGGGGAGAGATTCCTTGGAGTTCTACCAGAAGAGAAGAGTCTCGTGGCATTCTCAGAC | SEQ ID NO: 27 | Homo sapiens chromosome 12 open reading frame 44 (C12orf44), mRNA [NM_021934] |
| 28 | A_23_P119095 | PPP1R13L | AGTCAGTGCTGACAACATCTCCCAGCAGTCTTGGGGTGGGTTGGCAAACATTGGTCT | SEQ ID NO: 28 | Homo sapiens protein phosphatase 1, regulatory (inhibitor) subunit 13 like (PPP1R13L), mRNA [NM_006663] |
| 29 | A_23_P119907 | ANKZF1 | GACAAATCAACACGTAATGAGTTCCGAAGGTTCATGGAGAGAATCCAGATGGCTACGAT | SEQ ID NO: 29 | Homo sapiens ankyrin repeat and zinc finger domain containing 1 (ANKZF1), transcript variant 1, mRNA [NM_018089] |
| 30 | A_23_P120146 | TGFBRAP1 | AAATGGTTTTGTGAGCCTGTGTTTGTTAGATACCCAAATGGTGGTCTGTGTGCACACCCA | SEQ ID NO: 30 | Homo sapiens transforming growth factor, beta receptor associated protein 1 (TGFBRAP1), mRNA [NM_004257] |
| 31 | A_23_P120915 | ANKRD54 | ACCTTGTATGGGGACAAAGGGGGCTTTGGAGATGTAATGAAGTTAAGGATCTTTGGCCAGGAA | SEQ ID NO: 31 | Homo sapiens ankyrin repeat domain 54 (ANKRD54), mRNA [NM_138797] |
| 32 | A_23_P120921 | ANKRD54 | TTTTCCTGCGAGTCATTGAAAAGACCAAAACTATTATACCGGAGAGGTGTAATAGTTTTGCT | SEQ ID NO: 32 | Homo sapiens ankyrin repeat domain 54 (ANKRD54), mRNA [NM_138797] |
| 33 | A_23_P120942 | XRCC6 | TTTATGTTTTGAGGGTTCTGTGTTGCCATGGTGATGGTGTAGCCCTGCCACTTGCTGTT | SEQ ID NO: 33 | Homo sapiens X-ray repair complementing defective repair in Chinese hamster cells 6 (Ku autoantigen 70kDa) (XRCC6), mRNA [NM_001469] |

Fig. 1-3

| No. | Probe ID No. | Symbols of genes | Sequence | SEQ ID NO: | Descriptions of genes (letters and numbers within [ ] indicates GenBank accession No.) |
|---|---|---|---|---|---|
| 34 | A_23_P120947 | XRCC6 | GCAAGATGAAGGGTATGGTTGAGAAGGTTCGGTCACATAGAGAAGTGACAGGTTTGAGA | SEQ ID NO: 34 | Homo sapiens X-ray repair complementing defective repair in Chinese hamster cells 6 (Ku autoantigen, 70kDa) (XRCC6), mRNA [NM_001469] |
| 35 | A_23_P121499 | WFS1 | CTGACGTTTCTGAGTGACGATGGCGTGCAGGCTAGAGTAGGAGGTTCCGGTGTCTGGAA | SEQ ID NO: 35 | Homo sapiens Wolfram syndrome 1 (wolframin) (WFS1), mRNA [NM_006005] |
| 36 | A_23_P122116 | DDX41 | GGCGGCTCGGGAAACACAGGCATGGCCACTACCTTCATCAACAAAGCGTGTGATGAGTCA | SEQ ID NO: 36 | Homo sapiens DEAD (Asp-Glu-Ala-Asp) box polypeptide 41 (DDX41), mRNA [NM_016222] |
| 37 | A_23_P122579 | DAXX | CAGAGGAGCCCTTCACCACTGTCTTAGAGAATGGAGCAGGCATGGTGTCTTCTACTTCCT | SEQ ID NO: 37 | Homo sapiens death-associated protein 6 (DAXX), mRNA [NM_001350] |
| 38 | A_23_P122650 | LOC649233 | CCACCGCCTGCTGGAAGATGGTGAGGACTTCAATCTTGGTGATGCCGTGGACAGCAGTAA | SEQ ID NO: 38 | PREDICTED: Homo sapiens similar to Keratin, type I cytoskeletal 18 (Cytokeratin-18) (CK-18) (Keratin-18) (K18) (LOC649233), mRNA [XR_018843] |
| 39 | A_23_P122875 | TAF6 | TTGGTTCCTTCATGTCACGTTTCTTTTAGATATTGTACAGGCAGTTTCTCAGAATAAAAG | SEQ ID NO: 39 | Homo sapiens TAF6 RNA polymerase II, TATA box binding protein (TBP)-associated factor, 80kDa (TAF6), transcript variant 1, mRNA [NM_005641] |
| 40 | A_23_P124044 | DEAF1 | GGAAGGTAAAGAAACTTGCTGGTGGTTTTTCCTGGACAGAGTCATTAACACACTTTAAGCGAATGGTGCCCTGG | SEQ ID NO: 40 | Homo sapiens deformed epidermal autoregulatory factor 1 (Drosophila) (DEAF1), mRNA [NM_021008] |
| 41 | A_23_P124522 | DCAKD | TAGCCGAAACTTGCCTGGTTTTTCCTACTAGACTGTAAGCCCTCTAGGGACAGGGACAGT | SEQ ID NO: 41 | Homo sapiens dephospho-CoA kinase domain containing (DCAKD), mRNA [NM_024819] |
| 42 | A_23_P126689 | USP21 | ACAAAGCCGGAAGTCCTGTATACCAGGTGTATGGGCTTTGGAACCAGTCAGGCAGGCGTCC | SEQ ID NO: 42 | Homo sapiens ubiquitin specific peptidase 21 (USP21), transcript variant 1, mRNA [NM_012475] |
| 43 | A_23_P128790 | SARS | CAGGACTGCAAGAACTGATCCCCTTGTGAAGCCTGCACCCATTGAGGAGGAGCCATGAA | SEQ ID NO: 43 | Homo sapiens seryl-tRNA synthetase (SARS), mRNA [NM_006513] |
| 44 | A_23_P127079 | PPRC1 | ACGGGGAAGACTTTGACCCAGCACGTGAAAGAGCAAATTTGATTCTCTTGACTTTCACA | SEQ ID NO: 44 | Homo sapiens peroxisome proliferator-activated receptor gamma, coactivator-related 1 (PPRC1), mRNA [NM_015062] |
| 45 | A_23_P127394 | CRY2 | AGATGGTTGCAGGCAAAATGCACTTTATAGAGATTTTCTATTGCTGGGAAGGTGTGTTTC | SEQ ID NO: 45 | Homo sapiens cryptochrome 2 (photolyase-like) (CRY2), mRNA [NM_021117] |
| 46 | A_23_P127525 | ETS1 | CCTGTGAGACGTTCCAAGGACAGCCGTGTTGGTTGGACTCTGAATTTTGAATTGTTATT | SEQ ID NO: 46 | Homo sapiens v-ets erythroblastosis virus E26 oncogene homolog 1 (avian) (ETS1), mRNA [NM_005238] |
| 47 | A_23_P127793 | EML3 | TGGAAGCAGGCTGAAGAAGCTGGTATGAGAGCCGAGAACCGGGAATGGGCTACCTACAGCTGT | SEQ ID NO: 47 | Homo sapiens echinoderm microtubule associated protein like 3 (EML3), mRNA [NM_153265] |
| 48 | A_23_P129678 | SETD1A | GCTGACGAGATGGTCATCGAATACGGTGGGTGAGAACATCGGTCAGATGTGGCCGACATG | SEQ ID NO: 48 | Homo sapiens SET domain containing 1A (SETD1A), mRNA [NM_014712] |
| 49 | A_23_P130149 | ENO3 | CTCGGAGCGTGTGGCCAAATACAACCAACTCATGAGGATCGAGGAGGCTTTGGGGACAA | SEQ ID NO: 49 | Homo sapiens enolase 3 (beta, muscle) (ENO3), transcript variant 1, mRNA [NM_001976] |
| 50 | A_23_P13033 | RBM4 | TTACGGGGATGAGAGTGAGTTGTCCAAGGTTGTCCAAGGCGCCAGCAGCGCGGGAATTCTCTGTACGA | SEQ ID NO: 50 | Homo sapiens RNA binding motif protein 4 (RBM4), mRNA [NM_002896] |
| 51 | A_23_P130455 | MZF1 | GTGTGGCAAGGCCTTCCGGCGAGCGCTGAGCGCTCACCGGACCAGGATCTGGGCAGCCACCGACG | SEQ ID NO: 51 | Homo sapiens myeloid zinc finger 1 (MZF1), transcript variant 2, mRNA [NM_198055] |

Fig. 1-4

| No. | Probe ID No. | Symbols of genes | Sequence | SEQ ID NO. | Descriptions of genes (letters and numbers within [ ] indicates GenBank accession No.) |
|---|---|---|---|---|---|
| 52 | A_23_P130753 | DBP | CACGAGAGCTTTGACCCTCGAAGACATGGCTTGTCAGAAGAGGAA GTTAAGCGGCAGCCA | SEQ ID NO: 52 | Homo sapiens D site of albumin promoter (albumin D-box) binding protein (DBP), mRNA [NM_001352] |
| 53 | A_23_P131626 | ASCC3L1 | CTTTTGGGTAAAGGAGTTGAGCCTGAATTAGGAATGTGTACAT TGTAGGAATCCTGGT | SEQ ID NO: 53 | Homo sapiens activating signal cointegrator 1 complex subunit 3-like 1 (ASCC3L1), mRNA [NM_014014] |
| 54 | A_23_P13338 | INTS5 | TAAAGCACCCAAGTTTGTCCAGTCACGAAATCAGCAGGAAGTGA TCTATAACACCAGA | SEQ ID NO: 54 | Homo sapiens integrator complex subunit 5 (INTS5), mRNA [NM_030628] |
| 55 | A_23_P135104 | MRPS2 | TTCTCAATCTAAATGCTTTCAGGTGGGCGCGTTGGTTGGGCTACC TGGTCCAGGGGGT | SEQ ID NO: 55 | Homo sapiens mitochondrial ribosomal protein S2 (MRPS2), nuclear gene encoding mitochondrial protein, mRNA [NM_016034] |
| 56 | A_23_P135634 | MAGED1 | TTGAGTGAGATGTTGGATATTGGTCAATGGCAGTAGTCTTTCC CCTGTGTGAGCTGAA | SEQ ID NO: 56 | Homo sapiens NRAGE mRNA, complete cds. [AF217963] |
| 57 | A_23_P135914 | SF3B3 | TTAATTGGTTTCTTGTAAATACAGTTTTGTACAATGTTATCTGT GTGGAGGAAGGAGG | SEQ ID NO: 57 | Homo sapiens splicing factor 3b, subunit 3, 130kDa (SF3B3), mRNA [NM_012426] |
| 58 | A_23_P135977 | CKAP5 | AAGTCCTCATAGTTTAAAATGGGCTCAGGAGGCCTAGTGTATAGA AAGTGGTTATGTA | SEQ ID NO: 58 | Homo sapiens cytoskeleton associated protein 5 (CKAP5), transcript variant 1, mRNA [NM_001008938] |
| 59 | A_23_P137073 | ZMYM3 | GGGTTCCTGACCCATCCGGCATAGGGTAGAGCCTCTTGTTCCTAGG CATGACTAGGAAA | SEQ ID NO: 59 | Homo sapiens zinc finger, MYM-type 3 (ZMYM3), transcript variant 1, mRNA [NM_005096] |
| 60 | A_23_P137423 | IGSF8 | TACCATCACTTGCTGCTTCATGAAGAGGCTTCGAAAACGGTGATC CCTTACTGCCAGGT | SEQ ID NO: 60 | Homo sapiens immunoglobulin superfamily, member 8 (IGSF8), mRNA [NM_052868] |
| 61 | A_23_P137715 | POGK | GGGAGCTAAAGATTTTACAAGGACCTAATTTGTTGGGTTCCTTGCT TGGAGCCATAGTTAC | SEQ ID NO: 61 | Homo sapiens pogo transposable element with KRAB domain (POGK), mRNA [NM_017542] |
| 62 | A_23_P138058 | NOC2L | TTCAGTCGCCCAGTCTTCTTTGAAATTTGTTCGTTCGTTCCTTGAAGT CACATTTCTTTAA | SEQ ID NO: 62 | Homo sapiens nucleolar complex associated 2 homolog (S. cerevisiae) (NOC2L), mRNA [NM_015658] |
| 63 | A_23_P13385 | ATN1 | CTGCCCCGTTGGTGTGATTATTCATCTGTTAGATGTGGCTGTTT TGCGTAGCATCGTGT | SEQ ID NO: 63 | Homo sapiens atrophin 1 (ATN1), transcript variant 1, mRNA [NM_001007026] |
| 64 | A_23_P141180 | TOM1L2 | GCTACTGAAAAGAGGAATGTGTTGAATGTGACTGAAGACGCAGTTTAAG TCGTCCTAGAAGTTT | SEQ ID NO: 64 | Homo sapiens target of myb1-like 2 (chicken) (TOM1L2), transcript variant 3, mRNA [NM_001082968] |
| 65 | A_23_P141484 | C17orf63 | ATTCTCTAGTGATCTGAAGCAATGTGACTGAAGACAGCAGTTTAAG TTATGTGTGGCAAG | SEQ ID NO: 65 | Homo sapiens chromosome 17 open reading frame 63 (C17orf63), transcript variant 2, mRNA [NM_018182] |
| 66 | A_23_P141779 | CXXC1 | TGCTAGGCCAAGTATGAGAGTGGCCTTATGTCCACCTGAATGCATGTA CCCAGACCATTGA | SEQ ID NO: 66 | Homo sapiens CXXC finger 1 (PHD domain) (CXXC1), mRNA [NM_014593] |
| 67 | A_23_P142018 | PRPF31 | TCAGGGGGGAGAAGAGTGGCCTTATGTCCACCTGAATGACTGGCT GTGTCCAAGGTGGCT | SEQ ID NO: 67 | Homo sapiens PRP31 pre-mRNA processing factor 31 homolog (S. cerevisiae) (PRPF31), mRNA [NM_015629] |
| 68 | A_23_P142272 | PAF1 | AAAATTGCTCGGGGAGTAGAACTGAAACGTGAAGAACAAAGCTAGGA AGGGTATGAGGAAA | SEQ ID NO: 68 | Homo sapiens Paf1, RNA polymerase II associated factor, homolog (S. cerevisiae) (PAF1), mRNA [NM_019088] |
| 69 | A_23_P143580 | KLHL22 | AGAACAATGTCCAAGGATTCGAGCAGAGAGTCCGATGCTGGAGGT ATGACCCACGGCACA | SEQ ID NO: 69 | Homo sapiens kelch-like 22 (Drosophila) (KLHL22), mRNA [NM_032775] |

Fig. 1-5

| No. | Probe ID No. | Symbols of genes | Sequence | SEQ ID NO: | Descriptions of genes (letters and numbers within [ ] indicates GenBank accession No.) |
|---|---|---|---|---|---|
| 70 | A_23_P144202 | EEFSEC | GTGATGTCTTCAGTGCTGCTCGAGATAACTTTGACCAGGAGCCTATACTGGACTGTTT | SEQ ID NO: 70 | Homo sapiens eukaryotic elongation factor, selenocysteine-tRNA-specific (EEFSEC), mRNA [NM_021937] |
| 71 | A_23_P145289 | GNL1 | AACACCCCTGGTGTGCCTGGGACATCTGTGAAGCCTGGGCAGAGAAAGCTGGTTACAAGA | SEQ ID NO: 71 | Homo sapiens guanine nucleotide binding protein-like 1 (GNL1), mRNA [NM_005275] |
| 72 | A_23_P145935 | EPHB6 | CAGGACAACTTCTCCAAGTTCTGGCTCTGTACCTCAGTGATGTGGCTCAGCTCAGCCTA | SEQ ID NO: 72 | Homo sapiens EPH receptor B6 (EPHB6), mRNA [NM_004445] |
| 73 | A_23_P146637 | OPRS1 | ATTTGAAGAATGCTTGAAGTCAGGGTCAGTCGTTCCATTCCAAAAGACCCCATTCTTCTTTG | SEQ ID NO: 73 | Homo sapiens opioid receptor, sigma 1 (OPRS1), transcript variant 1, mRNA [NM_005866] |
| 74 | A_23_P147641 | TCEA2 | ATGCAGGAATGCATGTTCGGGGACGTTGGAAAACAGACAGAAGTATAAGAACGTGTA | SEQ ID NO: 74 | Homo sapiens transcription elongation factor A (SII), 2 (TCEA2), transcript variant 1, mRNA [NM_003195] |
| 75 | A_23_P148473 | IL2RG | CTTCCTGTGTTGCATTGGAAGCCGTGGTTATGTCTGTTGGCTGGATGGGATGATTATCA | SEQ ID NO: 75 | Homo sapiens interleukin 2 receptor, gamma (severe combined immunodeficiency) (IL2RG), mRNA [NM_000206] |
| 76 | A_23_P150255 | RBM14 | GATGGTGAGGGGACAGCAGTCCCACTTCCCATCTCCGGCCAAGTAGGTGGTGTTAGAAAACGT | SEQ ID NO: 76 | Homo sapiens RNA binding motif protein 14 (RBM14), mRNA [NM_006328] |
| 77 | A_23_P150403 | VPS11 | ACGAGATCTCCATGATCAATCAATTCCAGCATCAGCTCAAGTCTCAATGACCTTTCTGT | SEQ ID NO: 77 | Homo sapiens vacuolar protein sorting 11 homolog (S. cerevisiae) (VPS11), mRNA [NM_021729] |
| 78 | A_23_P150852 | FAM62A | GCCTTTGCCTGACCAAAGAGAAGAACCTATGTTCCTTTACTGCACGGCCTTTATCCTT | SEQ ID NO: 78 | Homo sapiens family with sequence similarity 62 (C2 domain containing), member A (FAM62A), mRNA [NM_015292] |
| 79 | A_23_P150931 | LMBR1L | AGAGTTTGGACCAGGACGTCCTGGTTTTCCATACTAACTGTGGCCTCAGCATGGGTA | SEQ ID NO: 79 | Homo sapiens limb region 1 homolog (mouse)-like (LMBR1L), mRNA [NM_018113] |
| 80 | A_23_P151426 | FOXO1 | GAGGGTTAGTGAGCAGGTTACAGTTAAAGTAGTTCAGATTGTGTGACAGGAGGAACTGA | SEQ ID NO: 80 | Homo sapiens forkhead box O1A (FOXO1A), mRNA [NM_002015] |
| 81 | A_23_P15247 | C16orf5 | GTGAATGATGAGGAACCCTGGTAGCTAGGAAGGAAGTTGTCCTTTGAGTCAGTGCGAGAC | SEQ ID NO: 81 | Homo sapiens chromosome 16 open reading frame 5 (C16orf5), mRNA [NM_013399] |
| 82 | A_23_P152818 | MYST2 | CAAAGTAATGTCCACTTTCCCTTTCATGGTGCATATTAAGTGGTTAATTATACTGCGAGA | SEQ ID NO: 82 | Homo sapiens MYST histone acetyltransferase 2 (MYST2), mRNA [NM_007067] |
| 83 | A_23_P152992 | AK125672 | GGCAAGAAGCAAGAGCGCTGGTCTCCAGCAAAAATAAGTAATTAATTTTTTAAAAGGAGA | SEQ ID NO: 83 | Homo sapiens cDNA FLJ43684 fis, clone TBAES2001492. [AK125672] |
| 84 | A_23_P153692 | XRCC1 | CGATACGTGACAGCCTTCAATGGGAGCTCGAGGACTATATGAGTGACCGGGTTCAGTTT | SEQ ID NO: 84 | Homo sapiens X-ray repair complementing defective repair in Chinese hamster cells 1 (XRCC1), mRNA [NM_006297] |
| 85 | A_23_P154962 | KIAA1666 | TTGCTGATAACTATGGCAGGTATACGGAGGAAGAAGGCCTTTTCTGTGGGCCAATGTGTGTT | SEQ ID NO: 85 | Homo sapiens KIAA1666 protein, mRNA (cDNA clone IMAGE:4827837), complete cds. [BC035246] |
| 86 | A_23_P155027 | MORC2 | GCACGTTGGTTTGACTTACACGGGACATTTGTGTTTTTGGAGGAAAAGATACCCTGATTC | SEQ ID NO: 86 | Homo sapiens MORC family CW-type zinc finger 2 (MORC2), mRNA [NM_014941] |
| 87 | A_23_P155257 | FOXP1 | CAACCACAGTCCAGATTTGACCATGACAGAGATTAGAAGAATGAACCAGGGA | SEQ ID NO: 87 | Homo sapiens forkhead box P1 (FOXP1), transcript variant 1, mRNA [NM_032682] |

Fig. 1-6

| No. | Probe ID No. | Symbols of genes | Sequence | SEQ ID NO: | Descriptions of genes (letters and numbers within [ ] indicates GenBank accession No.) |
|---|---|---|---|---|---|
| 88 | A_23_P15603 | MRM1 | CCAGGCGAGGGGACCCGTTCGCTGTTGAACCAGTCATTGCCTGTGG CAAATGTGTGATGA | SEQ ID NO: 88 | Homo sapiens mitochondrial rRNA methyltransferase 1 homolog (S. cerevisiae) (MRM1), mRNA [NM_024864] |
| 89 | A_23_P158897 | BE531123 | TAGGAACATGAATACCTTAGAAAGGTGAAAGCTGAAGTTTCCCG AAAGGGTTTGGGTAT | SEQ ID NO: 89 | BE531123 601278493F1 NIH_MGC_39 Homo sapiens cDNA clone IMAGE:3610487 5', mRNA sequence [BE531123] |
| 90 | A_23_P1594 | VEGFB | TGTCTCAGTTTCGTAAGCAGTCCTGTGTGCAAGGTAAGCATCTTACAAGT GGCTCGTTGCTCCCCT | SEQ ID NO: 90 | Homo sapiens vascular endothelial growth factor B (VEGFB), mRNA [NM_003377] |
| 91 | A_23_P161257 | PDCD11 | CAGGACAGAGACCCAGCTAGTTGTTGAAGGCAGTCTTTTTTGTCTT GGTCATGAGGGAATT | SEQ ID NO: 91 | RRP5 protein homolog (Programmed cell death protein 11). [Source:Uniprot/SWISSPROT;Acc:Q14690] [ENST00000369797] |
| 92 | A_23_P18143 | GTF2F1 | ACCTGACACGGAAGCCATGACCACTAAGGACCTGCTGAAAAAGT TCCAGACCAAGAAGA | SEQ ID NO: 92 | Homo sapiens general transcription factor IIF, polypeptide 1, 74kDa (GTF2F1), mRNA [NM_002096] |
| 93 | A_23_P161552 | ZNF289 | TGTGATGAATTCTTGGAGGATCGGCTACGGTTGGTACTGATCCGA GGCTGTGAGTCAGG | SEQ ID NO: 93 | Homo sapiens zinc finger protein 289, ID1 regulated (ZNF289), mRNA [NM_032389] |
| 94 | A_23_P161918 | CCDC86 | AAATACAGACAAATAGACCAAAGTCCTGGCCTCGAGGAGCTTGA TTCTGATGGAGAGAA | SEQ ID NO: 94 | Homo sapiens coiled-coil domain containing 86 (CCDC86), mRNA [NM_024098] |
| 95 | A_23_P162120 | NUMA1 | AGAAGAAAGAGTCCAGGTTGTTCAAACAGGCTGACGGGGGGCG AGTCGATGGCCTTCA | SEQ ID NO: 95 | Homo sapiens nuclear mitotic apparatus protein 1 (NUMA1), mRNA [NM_006185] |
| 96 | A_23_P162374 | DDX54 | CTATCAGAAGTGGAAACAAGAACAGAAAATTGATGATCGTGAGTC GGAGAAGAAGGGGC | SEQ ID NO: 96 | Homo sapiens DEAD (Asp-Glu-Ala-Asp) box polypeptide 54 (DDX54), mRNA [NM_024072] |
| 97 | A_23_P162525 | UTP20 | GTAGCAATGGATCTTGGGATAGACAAGGTAAAGCGGTATCTCCCA ATGATCATAGGTCCT | SEQ ID NO: 97 | Homo sapiens UTP20, small subunit (SSU) processome component, homolog (yeast) (UTP20), mRNA [NM_014503] |
| 98 | A_23_P163258 | PARP6 | GACCCCAAAGATACAGAGAAGGAAATCGCTGTCTGTGATCGGAAGTCAG GTTTACACAAACTGA | SEQ ID NO: 98 | Homo sapiens poly (ADP-ribose) polymerase family, member 6 (PARP6), mRNA [NM_020214] |
| 99 | A_23_P164718 | SNRPA | TCAGGAAGTGCCAGAGGAGGACGAGCTGTGTGATGCCATGCTGATGC TTTCAATCAGTTCC | SEQ ID NO: 99 | Homo sapiens small nuclear ribonucleoprotein polypeptide A (SNRPA), mRNA [NM_004596] |
| 100 | A_23_P166280 | THC2614146 | GTCAGGGGAGTTCTGAGTTGCAGGTTCTGTAAGAGAGTTCAGGTTGGATGAAGATG GAACRTGCTCT | SEQ ID NO: 100 | Q59G66_HUMAN (Q59G66) Androgen-regulated short-chain dehydrogenase/reductase 1 variant (Fragment), partial (7%) [THC2614146] |
| 101 | A_23_P166491 | RUTBC3 | ATTCCGCTGTCTGGTCCTGTGTAAGAGAGTTCAGGTTGGATGAAGATG GCAAAGTCCTGACCC | SEQ ID NO: 101 | Homo sapiens RUN and TBC1 domain containing 3 (RUTBC3), mRNA [NM_015705] |
| 102 | A_23_P166899 | DHX30 | CGTGACATATAGGACGCAAATCAGGCAACATCGTCGTGGACAAGTC GACCATTAACAGGGA | SEQ ID NO: 102 | Homo sapiens DEAH (Asp-Glu-Ala-His) box polypeptide 30 (DHX30), transcript variant 2, mRNA [NM_014966] |
| 103 | A_23_P166826 | DCP1A | CATTCTCAGTGATAATGGAGGTTTCAGTGTGAAGCATCACGAGGA GATCCTTGTTTGAC | SEQ ID NO: 103 | Homo sapiens DCP1 decapping enzyme homolog A (S. cerevisiae) (DCP1A), mRNA [NM_018403] |
| 104 | A_23_P167093 | IDUA | ACATACGAGATGCAGTTCTCTCAGGAGCGGTAAGGACGTAGACGCGG GTCAGCAGGAAGCCA | SEQ ID NO: 104 | Homo sapiens iduronidase, alpha-L- (IDUA), mRNA [NM_000203] |
| 105 | A_23_P168541 | C7orf26 | TGAGGGAGGAGTCCAGGGTCTGCCGAGAGGCTGCTGGTGGAATT TTAAAGATGCCGA | SEQ ID NO: 105 | Homo sapiens chromosome 7 open reading frame 26 (C7orf26), mRNA [NM_024067] |
| 106 | A_23_P171366 | USP11 | ACTTTCATGACAACGAGGGTGTCCCGTGTCAATGAGAATCAGATCG AGTCGAAGGCAGGCCT | SEQ ID NO: 106 | Homo sapiens ubiquitin specific peptidase 11 (USP11), mRNA [NM_004651] |

Fig. 1-7

| No. | Probe ID No. | Symbols of genes | Sequence | SEQ ID NO. | Descriptions of genes (letters and numbers within [ ] indicates GenBank accession No.) |
|---|---|---|---|---|---|
| 107 | A_23_P19205 | RAD54L2 | GAGGTTGGGTTCAGCTCGAATGATGATGAGGATAAAGACGATGAT GTGATAGAGGTCAGT | SEQ ID NO: 107 | Homo sapiens RAD54-like 2 (S. cerevisiae) (RAD54L2), mRNA [NM_015106] |
| 108 | A_23_P200489 | TMEM63A | CTCCTGGGGATTCTGGGGAATGGGATGGCAACTTAAGACTTCTGCC TGAGAAGGCTCCTCC | SEQ ID NO: 108 | Homo sapiens transmembrane protein 63A (TMEM63A), mRNA [NM_014698] |
| 109 | A_23_P202156 | NFKB2 | GGCCACACGCCTCTTGACCTCACTGCACCACCAAGGTGAAGACC TTGCTGCTCAAATGCT | SEQ ID NO: 109 | Homo sapiens nuclear factor of kappa light polypeptide gene enhancer in B-cells 2 (p49/p100) (NFKB2), transcript variant 1, mRNA [NM_002502] |
| 110 | A_23_P202708 | MADD | GTGTCCTTGAGACATTGTGTGTGAGTTCCTTGCTTGTCCTTGTCCGTG GCGTTATAACTGTCC | SEQ ID NO: 110 | Homo sapiens MAP-kinase activating death domain (MADD), transcript variant 4, mRNA [NM_003682] |
| 111 | A_23_P203406 | GANAB | CCTTTGAGGGGCAGTTAAGATGGAGAAATCAGTTGTGGTTCAGT GAATCATGGTCACCT | SEQ ID NO: 111 | Homo sapiens glucosidase, alpha; neutral AB (GANAB), transcript variant 2, mRNA [NM_198334] |
| 112 | A_23_P203488 | SMPD1 | GTGTACCGAAATAGATGGAAACTAGTCCGGGAGCTCTCACGTGGTC CTGGACCATGAGACC | SEQ ID NO: 112 | Homo sapiens sphingomyelin phosphodiesterase 1, acid lysosomal (acid sphingomyelinase) (SMPD1), transcript variant 1, mRNA [NM_000543] |
| 113 | A_23_P203737 | INTS4 | ACCATTCGCTTCAGCAAGCCTGTAAAAGTTTATATAATGCCAAA CCTGCACGGCGCTAA | SEQ ID NO: 113 | Homo sapiens integrator complex subunit 4 (INTS4), mRNA [NM_033547] |
| 114 | A_23_P203819 | GOLGA3 | TCTCACAGGATCCGGAGGGAAAATGTGTTAGAGGGTCTGGAAAATT CAGTGCTTTTGAGTT | SEQ ID NO: 114 | Homo sapiens golgi autoantigen, golgin subfamily a, 3 (GOLGA3), mRNA [NM_005895] |
| 115 | A_23_P20427 | RHOBTB2 | AGGAGGTATGAATGCCAGTGCCAGGAACCTAGCTCTTTAAAGTC TGGGAGTCGGATTC | SEQ ID NO: 115 | Homo sapiens Rho-related BTB domain containing 2 (RHOBTB2), mRNA [NM_015178] |
| 116 | A_23_P204364 | NOL1 | GGGAGACTCAGAATTGTCCAGTGTACCTTCTGTCACAAAGAGCCA AGCTCCTCCACCTT | SEQ ID NO: 116 | Homo sapiens nucleolar protein 1, 120kDa (NOL1), transcript variant 1, mRNA [NM_006170] |
| 117 | A_23_P205841 | MYO9A | TGAAAGCAAAAGCCTTGGGGTTTATTTTGGGATAGTAGTAGGAGGTA GGGTAGAATATAATT | SEQ ID NO: 117 | Homo sapiens myosin IXA (MYO9A), mRNA [NM_006901] |
| 118 | A_23_P20722 | SNAPC4 | ATGGCTGTTCCCCAAGTGCACACGTGAAACGTTGGAGGAATAAAG TTCTGTTTTTAATTG | SEQ ID NO: 118 | Homo sapiens small nuclear RNA activating complex, polypeptide 4, 190kDa (SNAPC4), mRNA [NM_003086] |
| 119 | A_23_P207319 | MAP3K14 | CAGGACTCACGTAGCATTAAATCAGCTGTGAATCGTCAGGGGGTG TCTGCTAGCCTCAAC | SEQ ID NO: 119 | Homo sapiens mitogen-activated protein kinase kinase kinase 14 (MAP3K14), mRNA [NM_003954] |
| 120 | A_23_P207736 | AK023077 | TTCGTTAATTCTTGGGCAGTCGGGTTGGGGTCTGGTGGACCAGAGATGACTTTCTGCA GGGTTTATCACTGTT | SEQ ID NO: 120 | Homo sapiens cDNA FLJ13015 fis, clone NT2RP3000622. [AK023077] |
| 121 | A_23_P20793 |  | TGGGCTCCATAAGGTGGGGTTTGTAGGGGTCTTGTGGTTGCTTCT GGTCTCGTCGAAGGTT | SEQ ID NO: 121 |  |
| 122 | A_23_P208358 | RPL28 | CACCATCAACAAGAATGATGCTGCGGCACGCTCAGGAGCATCAGACA CATGACCGGCAAGAA | SEQ ID NO: 122 | Homo sapiens ribosomal protein L28 (RPL28), mRNA [NM_000991] |
| 123 | A_23_P208551 | LPHN1 | CAGGTATCTGGGGGACCAGAATTTTGGGTGTGTGGGATCTCTCTGGGGA GTGTGCTGGGCTT | SEQ ID NO: 123 | Homo sapiens latrophilin 1 (LPHN1), transcript variant 1, mRNA [NM_001008701] |
| 124 | A_23_P208582 |  | CTATTCATCATCCTGGGACTTCCTGCTGCTCATCAATAGTACCCAGTGA GCCCAGAGATCGTAC | SEQ ID NO: 124 |  |
| 125 | A_23_P208861 | MJM1 | CATTGTGGGTTCCTGAGAGTAGGACACATTGCCATGGTTTTGTGG GAATCACGGCGCCCT | SEQ ID NO: 125 | Homo sapiens melanoma associated antigen (mutated) 1 (MUM1), mRNA [NM_032853] |
| 126 | A_23_P210319 | DTNB | CAGAGGCACATTCCTCTGATCTTTCGACCGCACGGTCGGACCAG GCTTGCACGGCTGGCA | SEQ ID NO: 126 | Homo sapiens dystrobrevin, beta (DTNB), transcript variant 4, mRNA [NM_183360] |

Fig. 1-8

| No. | Probe ID No. | Symbols of genes | Sequence | SEQ ID NO: | Descriptions of genes (letters and numbers within [ ] indicates GenBank accession No.) |
|---|---|---|---|---|---|
| 127 | A_23_P210643 | TH1L | ATGGTTCACCTGCTGAGTCGAGTTATGTACTTCCTGTTGTCAGTTACATCCGAAAGTGT | SEQ ID NO: 127 | Homo sapiens TH1-like (Drosophila) (TH1L), transcript variant 1, mRNA [NM_198976] |
| 128 | A_23_P211878 | FLNB | GCCCAGCGAAGTTGATGGGTCAGTTTTCTGAAAATAATGATCTGTACAGAGGAGA | SEQ ID NO: 128 | Homo sapiens filamin B, beta (actin binding protein 278) (FLNB), mRNA [NM_001457] |
| 129 | A_23_P214587 | TRIM26 | ATTATCTGTAGATTGGTCCTTGTTGAGGGGAGTTTTAAGAATCGAGAACATGTTGCTCTTG | SEQ ID NO: 129 | Homo sapiens tripartite motif-containing 26 (TRIM26), mRNA [NM_003449] |
| 130 | A_23_P214638 | EHMT2 | GGTCTTCATGCTGCTGACCAAGACCTGCGATTTCCACGCATCGGCTTCTTCAGTTCCCGAGA | SEQ ID NO: 130 | Homo sapiens euchromatic histone-lysine N-methyltransferase 2 (EHMT2), transcript variant NG36/G9a, mRNA [NM_006709] |
| 131 | A_23_P21495 | FCGBP | TCAGTCATCCAGCAGGAAGGAAGATTCGTGAAGAAGACCTGGTCCGTGTGGAGGTTGCG | SEQ ID NO: 131 | Homo sapiens Fc fragment of IgG binding protein (FCGBP), mRNA [NM_003890] |
| 132 | A_23_P215175 | ABCF2 | GAGGGTGGTATGATGCTGGTCAGGCATGGACTTGAGACTCATTCAGCAGGTTGCACAGGGAA | SEQ ID NO: 132 | Homo sapiens ATP-binding cassette, sub-family F (GCN20), member 2 (ABCF2), nuclear gene encoding mitochondrial protein, transcript variant 2, mRNA [NM_005692] |
| 133 | A_23_P215449 | BAZ1B | CAGGCTCCTAGAACATGAGAATCAAGCCTCTTAATTTTAAACATGCGGAATGGGCTCTGC | SEQ ID NO: 133 | Homo sapiens bromodomain adjacent to zinc finger domain, 1B (BAZ1B), mRNA [NM_032408] |
| 134 | A_23_P21640 | CHD3 | GTCCAATGCTGGGGACGGAGAGAGGAGAAAGAGAGAGAACCCGGTTCATGTTCAATATCGCGA | SEQ ID NO: 134 | Homo sapiens chromodomain helicase DNA binding protein 3 (CHD3), transcript variant 1, mRNA [NM_001005273] |
| 135 | A_23_P217028 | USP20 | GGGAAGGGGTCTGGGACCAGAGCCCCGACACTACTGGGTCTTTGTTTCTATCAGTCTTT | SEQ ID NO: 135 | Homo sapiens ubiquitin specific peptidase 20 (USP20), transcript variant 1, mRNA [NM_001008563] |
| 136 | A_23_P218086 | TPCN1 | TCCATAGAAAACCATTGTGTCTCGGATGCTCTAGCACATTACTAAAAGAGCCTGCTTT | SEQ ID NO: 136 | Homo sapiens mRNA for KIAA1169 protein, partial cds [AB032995] |
| 137 | A_23_P218215 | AA601902 | AACCCTTACTATCCAGAGATCTGTGTTGCAAATGTATCTACTGGCTAAAATATATCTG | SEQ ID NO: 137 | AA601902 np02h01.s1 NCI_CGAP_Pr2 Homo sapiens cDNA clone IMAGE:1115113 similar to contains Alu repetitive element, mRNA sequence [AA601902] |
| 138 | A_23_P218654 | ZGPAT | GTGCATCTGGACAGTTAGTTGCCGACCTGCCAGTGTCTTGGGCATTTCCTTGGGAAGGA | SEQ ID NO: 138 | Homo sapiens zinc finger, CCCH-type with G patch domain (ZGPAT), transcript variant 1, mRNA [NM_032527] |
| 139 | A_23_P218751 | GNB1L | GGAGTGCCGGGTGTCTTCATGAGGTTGGTATTCCTTTTTGTGGAGTGCCGATCACAGGA | SEQ ID NO: 139 | Homo sapiens guanine nucleotide binding protein (G protein), beta polypeptide 1-like (GNB1L), mRNA [NM_053004] |
| 140 | A_23_P23411 | PRCC | GCAAGAGGAACCGAGGGAGGAGAGAGAAATCAACTTTGTGGAGATCAAAGGTGATGACCAGC | SEQ ID NO: 140 | Homo sapiens papillary renal cell carcinoma (translocation-associated) (PRCC), transcript variant 1, mRNA [NM_005973] |
| 141 | A_23_P23894 | RIPK5 | AGCGCCAAGCTATCCCTTTAGCAGAAAGGTGTCTCAGATGTGTAAAAGGTGAGGAATGTG | SEQ ID NO: 141 | Homo sapiens receptor interacting protein kinase 5 (RIPK5), transcript variant 1, mRNA [NM_015375] |
| 142 | A_23_P24368 | BMS1 | TCATGAAAGAAAGATCCTTGCACTTGGATGCTCGAGTACGGTGCATAGTCAGAAGAT | SEQ ID NO: 142 | Homo sapiens BMS1 homolog, ribosome assembly protein (yeast) (BMS1), mRNA [NM_014753] |
| 143 | A_23_P251259 | GTF2H4 | TCTGGGCAAGGATTACTCTGTGGAAGGTATGAGTGATTCTCTGTTGAACTTCCTGCAACA | SEQ ID NO: 143 | Homo sapiens general transcription factor IIH, polypeptide 4, 52kDa (GTF2H4), mRNA [NM_001517] |

Fig. 1-9

| No. | Probe ID No. | Symbols of genes | Sequence | SEQ ID NO: | Descriptions of genes (letters and numbers within [ ] indicates GenBank accession No.) |
|---|---|---|---|---|---|
| 144 | A_23_P251660 | ABCF1 | CCCACTCTGATTGCATCGATTCTCTGAAAGAGTGTTTGTTCTGCTTCTCTTCATATAA | SEQ ID NO: 144 | Homo sapiens ATP-binding cassette, sub-family F (GCN20), member 1 (ABCF1), transcript variant 2, mRNA [NM_001090] |
| 145 | A_23_P252642 | BBS5 | GAAAAGATTGAGAAATCGGATGGTTGCCGTGTGTGTGTGTGAGAAAGAAGTAGACATGGGAGA | SEQ ID NO: 145 | Homo sapiens Bardet-Biedl syndrome 5 (BBS5), mRNA [NM_152384] |
| 146 | A_23_P25348 | ACAD10 | CAGAGAGGAGGACAGCTTCTATGTCATAAACGGTCACAAATGGTGGATCACAGGGATCCT | SEQ ID NO: 146 | Homo sapiens acyl-Coenzyme A dehydrogenase family, member 10 (ACAD10), mRNA [NM_025247] |
| 147 | A_23_P255569 | DUS1L | AAAGTGTGACCAGTGTGGAAACCCAAAGGGCAACAGATGTGTTCAGCCTGTGCCGGGG | SEQ ID NO: 147 | Homo sapiens dihydrouridine synthase 1-like (S. cerevisiae) (DUS1L), mRNA [NM_022156] |
| 148 | A_23_P256021 | LAS1L | AGACACGTGGAGGACAGCCTGGATCAGCCACATCAACTCAGTGTGCAGGACAGGGAA | SEQ ID NO: 148 | Homo sapiens LAS1-like (S. cerevisiae) (LAS1L), mRNA [NM_031206] |
| 149 | A_23_P257155 | ATXN7 | TGGTGAACAGCAGTGATTCTACTCTTTCTCTGGGCCATTCATTCACCAGTCGAATGAAC | SEQ ID NO: 149 | Homo sapiens ataxin 7 (ATXN7), mRNA [NM_000333] |
| 150 | A_23_P258124 | ZNF346 | AAGCTGGGGATCTGCTTTATGTGTGAGAAGAACGTTCTCGGCGTGTTATGTAAAGGAGTGCA | SEQ ID NO: 150 | Homo sapiens zinc finger protein 346 (ZNF346), mRNA [NM_012279] |
| 151 | A_23_P258190 | AKR1B1 | GTGATCCCCAAGTCTGTGACACCAGAACGCATTGCTGAGAACTTTAAGGTGTTTGACTTT | SEQ ID NO: 151 | Homo sapiens aldo-keto reductase family 1, member B1 (aldose reductase) (AKR1B1), mRNA [NM_001628] |
| 152 | A_23_P26375 | ACD | CCAAAGAGGCATCGTGATGGTTCTGCCTTCGAGTATGAGTATGAGGGCACCGTGCAGTCC | SEQ ID NO: 152 | Homo sapiens adrenocortical dysplasia homolog (mouse) (ACD), transcript variant 2, mRNA [NM_022914] |
| 153 | A_23_P26810 | TP53 | CTGTGAGGGATGTTTGGGAGATGTAAGAAATGTTCTTGCAGTTAAGGGTTAGTTTACAAT | SEQ ID NO: 153 | Homo sapiens tumor protein p53 (Li-Fraumeni syndrome) (TP53), mRNA [NM_000546] |
| 154 | A_23_P27894 | SAFB2 | CAGGTTCCTCGAACTTGGGGGATGTCTTTTAAAAGGAACTAAATCCGCCACCATGTT | SEQ ID NO: 154 | Homo sapiens scaffold attachment factor B2 (SAFB2), mRNA [NM_014649] |
| 155 | A_23_P28857 | SIRPG | TCCATCCATGGCCTTGAGACTGACCGTAAACACACAGACGGCTCTCCAGGTCTCAAGAGT | SEQ ID NO: 155 | Homo sapiens signal-regulatory protein gamma (SIRPG), transcript variant 2, mRNA [NM_080816] |
| 156 | A_23_P300150 | NFATC1 | AGCCTTCTCAGGGGACTGTCATTGAAAAGGAAACGTTTGATGTCTGTGTCAGGTGTGTT | SEQ ID NO: 156 | Homo sapiens nuclear factor of activated T-cells, cytoplasmic, calcineurin-dependent 1 (NFATC1), transcript variant 3, mRNA [NM_172387] |
| 157 | A_23_P300714 | SORBS3 | ACGCAGCACCTTCTTAGCGATCTAGGCCTGGCAAGAGCTGTGGCCGCAAGGGCTCCTCTT | SEQ ID NO: 157 | Homo sapiens sorbin and SH3 domain containing 3 (SORBS3), transcript variant 1, mRNA [NM_005775] |
| 158 | A_23_P303826 | C6orf136 | TACAAGCGTGACAAAGAGGAGGATTACCGGACCATGATGGTACTCCAGTTTGTACCTG | SEQ ID NO: 158 | Homo sapiens chromosome 6 open reading frame 136 (C6orf136), mRNA [NM_145029] |
| 159 | A_23_P309803 | ZNF777 | TGTAGGGCCCATCCATGTCAGTTGGGGATAAGAACTTTATAATTACCTTTGGATACTGTGGTCT | SEQ ID NO: 159 | Homo sapiens zinc finger protein 777 (ZNF777), mRNA [NM_015694] |
| 160 | A_23_P309850 | RPUSD2 | GCTTCTAAAGAGACCTGCTCATACTTGGTACCTGCTCCAGTGGGAATTTGGAGAGTTTT | SEQ ID NO: 160 | Homo sapiens RNA pseudouridylate synthase domain containing 2 (RPUSD2), mRNA [NM_152260] |
| 161 | A_23_P310331 | RANBP3 | CGGCCATGTGTTTTGGAACATTTATGTAAGATTGTCATATGAAATGTATTGGGAAGTAC | SEQ ID NO: 161 | Homo sapiens RAN binding protein 3 (RANBP3), transcript variant RANBP3-a, mRNA [NM_003624] |
| 162 | A_23_P311740 | PARC | CTGCCCGTGTCATAGGGAGGGGGATTCCCAGGTCGTAGTGCTTCCTGTTTGGTGAATA | SEQ ID NO: 162 | Homo sapiens p53-associated parkin-like cytoplasmic protein (PARC), mRNA [NM_015089] |

Fig. 1-10

| No. | Probe ID No. | Symbols of genes | Sequence | SEQ ID NO: | Descriptions of genes (letters and numbers within [ ] indicates GenBank accession No.) |
|---|---|---|---|---|---|
| 163 | A_23_P312179 | ALMS1 | GAGATTGTGAAGCGGTGCCAAAAAACACAGTCGAGATGTTGGGATAACTTCCCAAGTCCA | SEQ ID NO: 163 | Homo sapiens Alstrom syndrome 1 (ALMS1), mRNA [NM_015120] |
| 164 | A_23_P3128 | YLPM1 | AAGAAGAAGAAGGATGCAGATAGGAAAAAGGGGCATAGGTTTTGTGGTCCGACAGAGTGATT | SEQ ID NO: 164 | Homo sapiens YLP motif containing 1, mRNA (cDNA clone IMAGE:3835908), complete cds. [BC023570] |
| 165 | A_23_P31477 | NUDCD3 | AAGTGATGCATGGTGTGAGAGTGCCCGTAGAGCAGGTTGTTATTTGGAGACTTTGAGAGTCAT | SEQ ID NO: 165 | Homo sapiens NudC domain containing 3 (NUDCD3), mRNA [NM_015332] |
| 166 | A_23_P31489 | URG4 | GAGGAAGTGACCTCACAGACCAGCTCAGAGATGTTACCAAGAATATCACAGCCCCAGGG | SEQ ID NO: 166 | Homo sapiens up-regulated gene 4 (URG4), transcript variant 1, mRNA [NM_017920] |
| 167 | A_23_P315252 | AK097322 | CATGCTGGGTCAATAGTACTTGGCGCAGTAGTGTTAAAACTAGGCGGCTATGGTATAAT | SEQ ID NO: 167 | Homo sapiens cDNA FLJ40003 fis, clone STOMA2003716. [AK097322] |
| 168 | A_23_P315378 | ATG16L1 | CTGTGTTCCAGTTTATACTCTTTGTCGAAAACTCAGTTTCAAAATATTTGCAATGGGAC | SEQ ID NO: 168 | Homo sapiens cDNA FLJ10035 fis, clone HEMBA1000919. [AK000897] |
| 169 | A_23_P315843 | NCOA5 | GCCCCATGGGATCTTACCAGGAGGGATTACTGAAGGTAAATCTTCAACTGTCCCAGTC | SEQ ID NO: 169 | Homo sapiens nuclear receptor coactivator 5 (NCOA5), mRNA [NM_020967] |
| 170 | A_23_P316472 | DNHD1 | TAAGCTGCAGAGGCAGGAACATGGTGATGCATCTGCGTTTAGGCACCAAGCTCAGCCCAA | SEQ ID NO: 170 | Homo sapiens Dynein heavy chain domain 1 (DNHD1), mRNA [NM_144666] |
| 171 | A_23_P319270 | AZI1 | GATGCCCACGGCTAAGACTGTGGGCTGCATTTTAACAGTAAAGGAGGGCGTGTTTTCA | SEQ ID NO: 171 | Homo sapiens 5-azacytidine induced 1 (AZI1), transcript variant 1, mRNA [NM_014984] |
| 172 | A_23_P320304 | AFAR3 | AGGCTGCCCAAGGGTTTTGTGTCAACTCTTTGGCTCTCTCGGGTTTGTAATTTAGAA | SEQ ID NO: 172 | Homo sapiens aflatoxin B1 aldehyde reductase 3 (AFAR3), mRNA [NM_201252] |
| 173 | A_23_P320837 | DKFZP434A0131 | GCCTTGACTCGGATCGATGTTGGGAAAGTCGTTGAAGGTGAAGCTGAGACGGGTGAAACGGGGCAAGT | SEQ ID NO: 173 | Homo sapiens mRNA cDNA DKFZp434A0131 (from clone DKFZp434A0131). [AL137492] |
| 174 | A_23_P32125 | PMPCA | CCGGTTCCGTGCCGTGCCGTTGTAGTTTGGACACGAATTTAGTCTAAAAAGCTGTCTGGTTGTAT | SEQ ID NO: 174 | Homo sapiens peptidase (mitochondrial processing) alpha (PMPCA), nuclear gene encoding mitochondrial protein, mRNA [NM_015160] |
| 175 | A_23_P321361 | DHX30 | ACCGGTTACACACGGTTAGGGAGCCGATGGCTGGCTGACGTATTTCATGGCAGTCAAGTCCAAT | SEQ ID NO: 175 | Homo sapiens DEAH (Asp-Glu-Ala-His) box polypeptide 30 (DHX30), transcript variant 3, mRNA [NM_138614] |
| 176 | A_23_P325093 | GGTL3 | TGGCCCGAGCTTAGGGATGTGCTTGGCAAACCGTTCTCAAGGGTCTCACAACCCAACAT | SEQ ID NO: 176 | Homo sapiens gamma-glutamyltransferase-like 3 (GGTL3), mRNA [NM_178026] |
| 177 | A_23_P326142 | NAG8 | CTGTTGGGATTAGGAGTTGGAATGAGGAATAGTTTAGGACCACAAGAGATTTGGCCTCCTT | SEQ ID NO: 177 | Homo sapiens nasopharyngeal carcinoma associated gene protein-8 (NAG8), mRNA [NM_014411] |
| 178 | A_23_P329133 | GOT2 | TCAAGTCGATCGTATCCAGATTATTTAAGAATGAAGAACATAATTTTTCTGCTGATGCGG | SEQ ID NO: 178 | Human mitochondrial aspartate aminotransferase mRNA, complete cds. [M22632] |
| 179 | A_23_P329212 | ETS1 | GTCAACCCAGGCTATCGAGAATGCGGCTATACGCTCGGATTACTTCATTAGTATGGTATT | SEQ ID NO: 179 | Homo sapiens v-ets erythroblastosis virus E26 oncogene homolog 1 (avian) (ETS1), mRNA [NM_005238] |
| 180 | A_23_P332042 | RECQL5 | CTTTGCTTGAAAGCCTATAGACCCTCTCCAGAGGCGGTCCTCATGGCTGGGTTTTTCTG | SEQ ID NO: 180 | Homo sapiens RecQ protein-like 5 (RECQL5), transcript variant 1, mRNA [NM_004259] |
| 181 | A_23_P336015 | NOC2L | GCAATTTAAAGACCTCTTTGACCTGAACAGAGTCTGAAGAGGACGACACTGAGGGATTCTC | SEQ ID NO: 181 | Homo sapiens nucleolar complex associated 2 homolog (S. cerevisiae) (NOC2L), mRNA [NM_015658] |

Fig. 1-11

| No. | Probe ID No. | Symbols of genes | Sequence | SEQ ID NO: | Descriptions of genes (letters and numbers within [ ] indicates GenBank accession No.) |
|---|---|---|---|---|---|
| 182 | A_23_P336218 | MGC27345 | TGAGTGACTGCTTTGTTGAATCAGATAGTAACAAACATTTATTTGTAGTCTGGTTGTGTC | SEQ ID NO:182 | Homo sapiens hypothetical protein MGC27345, mRNA (cDNA clone MGC:27345 IMAGE:4670552), complete cds. [BC024231] |
| 183 | A_23_P336513 | GEMIN5 | AGACCTTGGCAGAAATGATCCGACAACACCAAAAGAGTCAACTCTGTAAATCGACACGAA | SEQ ID NO:183 | Homo sapiens gem (nuclear organelle) associated protein 5 (GEMIN5), mRNA [NM_015465] |
| 184 | A_23_P338095 | SPTBN1 | AGTGGGATACTTCAAAAGGAGAACAAGTTTCCAAAACGGTTTGCCAGCTGAACAGGGAT | SEQ ID NO:184 | Homo sapiens spectrin, beta, non-erythrocytic 1 (SPTBN1), transcript variant 2, mRNA [NM_178313] |
| 185 | A_23_P342131 | CYBASC3 | GCTGACCGCTGTGAGCTGTTGTGTTTCGTTATTGCTGTCTGTGTCTGCATGTATTGTGAG | SEQ ID NO:185 | Homo sapiens cytochrome b ascorbate dependent 3 (CYBASC3), mRNA [NM_153611] |
| 186 | A_23_P34496 | TMEM29B | CCTCATCCTCTTCAGCAACTACTATGCCTTCTTCAAGCTGCTCCGGGGACCGGCTTGGTATT | SEQ ID NO:186 | Homo sapiens transmembrane protein 39B (TMEM39B), mRNA [NM_018056] |
| 187 | A_23_P349310 | TNRC6A | CGTGCGTCTCTACTATGCCTAGTGTTGGCTACCTATTGTGGTATCGTGGAGTTTTAA | SEQ ID NO:187 | Homo sapiens trinucleotide repeat containing 6A (TNRC6A), mRNA [NM_014494] |
| 188 | A_23_P3502 | NHN1 | AGTTGACAGTGTTGAATAAGGCGGCTGATAAAGACAAGGAAGCGGTATGAACCATCAG | SEQ ID NO:188 | Homo sapiens conserved nuclear protein NHN1 (NHN1), mRNA [NM_144604] |
| 189 | A_23_P355565 | KIAA0409 | TGAGGACAAAGTGTGATAAAACGTCTGGCTGAGACTTGCTCTAGTGAAGGCTTCTTGGTT | SEQ ID NO:189 | Homo sapiens KIAA0409 (KIAA0409), mRNA [NM_015324] |
| 190 | A_23_P359174 | BC069659 | CCAGGGGTGCATAGTAGGGTAAAGAAAAATTTTGTAATAGGAACAGTGGTTTGGGATTTT | SEQ ID NO:190 | Homo sapiens cDNA clone IMAGE:7262526, with apparent retained intron. [BC069659] |
| 191 | A_23_P36076 | SSRP1 | AATGCAGGATCCAAATCGTCATCTTACTTTGCCGACCTAAGGATGTAGCTGCTGTCT | SEQ ID NO:191 | Homo sapiens structure specific recognition protein 1 (SSRP1), mRNA [NM_003146] |
| 192 | A_23_P36140 | B3GAT3 | AGAGCAGTCTTGTGAGGCACCTTGTGGATCGGACAAGGAGCTGGAGGCACGGGCTGCCAACT | SEQ ID NO:192 | Homo sapiens beta-1,3-glucuronyltransferase 3 (glucuronosyltransferase I) (B3GAT3), mRNA [NM_012200] |
| 193 | A_23_P36157 | WDR74 | TAGAGACCAGGTATGGAGAGTACCGACTAAGACCATGACCCTCACTCCGGGAGGCAACT | SEQ ID NO:193 | Homo sapiens WD repeat domain 74 (WDR74), mRNA [NM_018093] |
| 194 | A_23_P364537 | DDX51 | CCTCCTTCCAGAGAGTGCTGATCAGTGACTCCTGTATGTGAGGAAAGGAATCCCCCAGT | SEQ ID NO:194 | Homo sapiens DEAD (Asp-Glu-Ala-Asp) box polypeptide 51 (DDX51), mRNA [NM_175066] |
| 195 | A_23_P367676 | SIN3A | CGTTGGAACTGTTTTGTATCTGCCTGTCTTTAGTAGTCTAGTCTTAGTGCCATCCACCAGTTT | SEQ ID NO:195 | Homo sapiens SIN3 homolog A, transcription regulator (yeast) (SIN3A), mRNA [NM_015477] |
| 196 | A_23_P369996 | LRRC56 | CAAACCAACATTCGAGCTCTGAGGTGTAGAGAAATGCGGTTTACTTTGTAGGCCAGTT | SEQ ID NO:196 | Homo sapiens leucine rich repeat containing 56 (LRRC56), mRNA [NM_198075] |
| 197 | A_23_P371765 | C21orf56 | CAACATCCCGGAGAGAAGATCGAGGAGACCTCGACCAAGTCTCTGGACGGCTTCCGTGGACCGA | SEQ ID NO:197 | Homo sapiens chromosome 21 open reading frame 56 (C21orf56), mRNA [NM_032261] |
| 198 | A_23_P37205 | NDRG2 | CGTTTGGCTGCACTAAGCTTTGGTAGCTGCATCAGTGTGGCATCTAGAGTGGGACTGGGAGGGAG | SEQ ID NO:198 | Homo sapiens NDRG family member 2 (NDRG2), transcript variant 1, mRNA [NM_201535] |
| 199 | A_23_P372255 | ITPKB | TCAGTGTATTTAGCTTTGAGTTTCTGCTGATCGTGCACCCATGTGTATATAAGCCAG | SEQ ID NO:199 | Homo sapiens inositol 1,4,5-trisphosphate 3-kinase B (ITPKB), mRNA [NM_002221] |
| 200 | A_23_P38219 | PRPF8 | CCGAGAACAGACAGCAAGGCAACAACCCCAAGGGCTACCTGCCTTCACACTATGAGAGGGT | SEQ ID NO:200 | Homo sapiens PRP8 pre-mRNA processing factor 8 homolog (S. cerevisiae) (PRPF8), mRNA [NM_006445] |

Fig. 1-12

| No. | Probe ID No. | Symbols of genes | Sequence | SEQ ID NO: | Descriptions of genes (letters and numbers within [ ] indicate GenBank accession No.) |
|---|---|---|---|---|---|
| 201 | A_23_P383060 | SLC5A6 | GAAATAGGGATGGAAGTGCATCCTCTGGGAAAAAGATAATGGCTTCTGATTCAACATAGC | SEQ ID NO: 201 | Homo sapiens solute carrier family 5 (sodium-dependent vitamin transporter), member 6 (SLC5A6), mRNA [NM_021095] |
| 202 | A_23_P384698 | LOC442075 | CACCTCACTTGACAAGGAGGAATACAAAAACTATCAGTTCATAGAGACGATCTGATAGGGAAC | SEQ ID NO: 202 | Homo sapiens cDNA FLJ35033 fis, clone OCBBF2016590, weakly similar to CELL SURFACE ANTIGEN 114/A10 PRECURSOR. [AK092352] |
| 203 | A_23_P3849 | TRAP1 | AGTCATCAGGAAACTCCGGGACGTTTTAGAGCAGAAGGGTGATCAAATTCTTCATTGACCA | SEQ ID NO: 203 | Homo sapiens TNF receptor-associated protein 1 (TRAP1), mRNA [NM_016292] |
| 204 | A_23_P38876 | LIPE | GGGGAGCGGCGGCAGACACACACCGGGTCACCGAGCGGGTGGACCGTTGCACGGCACCCGCTGCCTT | SEQ ID NO: 204 | Homo sapiens lipase, hormone-sensitive (LIPE), mRNA [NM_005357] |
| 205 | A_23_P388780 | DMAP1 | GATACCAGTATTTGATGCTGGGGCAGGAAGGACGACGGGGAAGGAAGAAGCTTGAAGGTGTGTA | SEQ ID NO: 205 | Homo sapiens DNA methyltransferase 1 associated protein 1 (DMAP1), transcript variant 1, mRNA [NM_019100] |
| 206 | A_23_P388914 | CCDC101 | CAACAAGTAGAAGGTAGATGACATCGATGAAGAAGGCAAAGAGAGACACACCCTGAGCCG | SEQ ID NO: 206 | Homo sapiens coiled-coil domain containing 101 (CCDC101), mRNA [NM_138414] |
| 207 | A_23_P389907 | ATXN2 | TTTCAGAGTCCGGCAGGTACCCCAGCTCGCTTGCCGAAACTGGAAGTTATTTATTTTTTT | SEQ ID NO: 207 | Homo sapiens ataxin 2 (ATXN2), mRNA [NM_002973] |
| 208 | A_23_P39034 | SMARCA4 | CTGGCATCCAGTAGCATCTGTAACAGGACATTAACTGTCTTAAAGAGAGAGAGGACGTCATG | SEQ ID NO: 208 | Homo sapiens SWI/SNF related, matrix associated, actin dependent regulator of chromatin, subfamily a, member 4 (SMARCA4), mRNA [NM_003072] |
| 209 | A_23_P39040 | SMARCA4 | AAGGAGCCGATTCGGACACCACAAGTACCGCAGGCCTCAACGACGTAGAGAAGGACGTCATCG | SEQ ID NO: 209 | Homo sapiens SWI/SNF related, matrix associated, actin dependent regulator of chromatin, subfamily a, member 4 (SMARCA4), mRNA [NM_003072] |
| 210 | A_23_P391275 | DSCR1L2 | TAAATTATGATTTACTCTGTGCTGTTTCGAAATTGGGACCAGGAGAGAAATATGAACTTC | SEQ ID NO: 210 | Homo sapiens Down syndrome critical region gene 1 like 2 (DSCR1L2), mRNA [NM_013441] |
| 211 | A_23_P3921 | FLJ11710 | CCTGATTCATGATTGAAGTACCATTACGATAAATGCTATACATCCATGGATTGGACTTC | SEQ ID NO: 211 | Homo sapiens cDNA FLJ11710 fis, clone HEMBA1005149 [AK021772] |
| 212 | A_23_P392501 | TNRC6C | GGTTGTGTCTGCTTTGGGGGAGCGTGGGGTTTGGGCTCCCACCTGTTTACAGACGTTT | SEQ ID NO: 212 | Homo sapiens cDNA FLJ31859 fis, clone NT2RP7001231 [AK056421] |
| 213 | A_23_P393401 | LOC339047 | CAATGACTTCTTTTACCGCCTAGGTGTCGGCAGTACTCAGTGAAGGGTGATATTATGA | SEQ ID NO: 213 | Homo sapiens hypothetical protein LOC339047, mRNA (cDNA clone IMAGE:4184431), complete cds. [BC008178] |
| 214 | A_23_P394917 | SRCAP | TGGTGGCTGTAATTCAGGATGAGACCTGGACTTAGGAGATAGCGGGCCAGGGGGTTGGAAT | SEQ ID NO: 214 | Homo sapiens Snf2-related CBP activator protein (SRCAP), mRNA [NM_006662] |
| 215 | A_23_P39844 | IMMT | GGCTTGTGAGCCAATCAAAATAATGTTTGTGATGTCTACTAGTTTGATTTTGCCCTCG | SEQ ID NO: 215 | Homo sapiens inner membrane protein, mitochondrial (mitofilin) (IMMT), mRNA [NM_006839] |
| 216 | A_23_P40049 | CAD | CCTGACACTGATGTGCTGTACATGACTCGGAATCCAGAAGGAAGGAACGATTTGGCTGTAGGGAG | SEQ ID NO: 216 | Homo sapiens carbamoyl-phosphate synthetase 2, aspartate transcarbamylase, and dihydroorotase (CAD), mRNA [NM_004341] |
| 217 | A_23_P401084 | ZNF575 | CTTGGGGAGAGATCTCAAACCATGGACGGTGGAGCTGTGGTTTGACAGCGGCTGGCTCTGCTT | SEQ ID NO: 217 | Homo sapiens zinc finger protein 575 (ZNF575), mRNA [NM_174945] |

Fig. 1-13

| No. | Probe ID No. | Symbols of genes | Sequence | SEQ ID NO: | Descriptions of genes (letters and numbers within [ ] indicates GenBank accession No.) |
|---|---|---|---|---|---|
| 218 | A_23_P40194 | DDX27 | CATGTCTGTCAATGTCCCTTGCTTGCTGATTAGGTTTCATATGACTATATTAAATGGAAGT | SEQ ID NO: 218 | Homo sapiens DEAD (Asp-Glu-Ala-Asp) box polypeptide 27 (DDX27), mRNA [NM_017895] |
| 219 | A_23_P406105 | GCN1L1 | TCTGGGGAGGGGTATAGGTTTGAAAGGGTGTGTTTGAAAGAGGAATGTTTAATAAAGGCTTT | SEQ ID NO: 219 | Homo sapiens GCN1 general control of amino-acid synthesis 1-like 1 (yeast) (GCN1L1), mRNA [NM_006836] |
| 220 | A_23_P407601 | C8orf6 | GTCTCCTAGGTTAGGTGTAGCAGAGATTGTATTCTCAGATAAGACTTCGGTGTCGGGTGAA | SEQ ID NO: 220 | Homo sapiens mRNA for hypothetical protein (C8orf6 gene). [AJ307469] |
| 221 | A_23_P407684 | ZNF598 | TGTGTGCACACAGGGACTTGTGCAACCGCGAGAAGGGTCTGAGGACCAAGTCCAAGAAGA | SEQ ID NO: 221 | Homo sapiens zinc finger protein 598 (ZNF598), mRNA [NM_178167] |
| 222 | A_23_P40989 | USP13 | TGAGATGCAAAGAAATAATGCCAATGCAGAGAAACATTATTTCTAGGCAAGCGGAAGGACCTAG | SEQ ID NO: 222 | Homo sapiens ubiquitin specific peptidase 13 (isopeptidase T-3) (USP13), mRNA [NM_003940] |
| 223 | A_23_P41021 | NISCH | TAATTTGACTGTCCTCGGAGAGAATGTGAACATGTGTGTGTTGTGTTAATTCTTCTC | SEQ ID NO: 223 | Homo sapiens nischarin (NISCH), mRNA [NM_007184] |
| 224 | A_23_P410653 | MLLT6 | AACACGAGACTGTTGTCTACGACGATCAGCAGAGATCCAAGAGAAACGGGAGCTGCAGC | SEQ ID NO: 224 | Homo sapiens myeloid/lymphoid or mixed-lineage leukemia (trithorax homolog, Drosophila); translocated to, 6 (MLLT6), mRNA [NM_005937] |
| 225 | A_23_P411246 | TMC6 | GTCCTGACGGTGTGGGTCTCGGCAGACCCAGGCAAGTTGGGGCAAGTTGCCAGGAGCCATCCACAGGGCTCGGG | SEQ ID NO: 225 | Homo sapiens transmembrane channel-like 6 (TMC6), mRNA [NM_152469] |
| 226 | A_23_P41755 | PURA | CAAGTCCATCAGCGTGCGTGGGCTACAAGGTGTGGGCAAGTTCGAAGTA | SEQ ID NO: 226 | Homo sapiens purine-rich element binding protein A (PURA), mRNA [NM_005859] |
| 227 | A_23_P422305 | SFXN4 | GATTTTAACCCTCAAGGGCGAATTTGATACTGAGAGGTTAAGGACAGAGACTCTGAATCA | SEQ ID NO: 227 | Homo sapiens cDNA FLJ37976 fis, clone CTONG2010148. [AK095295] |
| 228 | A_23_P423457 | SERINC5 | TTTTGGTTCTTTAAACTTCTGCTGTTGGGGGGGATGTGGTCAGGAGCTTTCTTCATTCCA | SEQ ID NO: 228 | Homo sapiens serine incorporator 5 (SERINC5), mRNA [NM_178276] |
| 229 | A_23_P425932 | VTI1A | TACCTCAAAAATAGAACAAGAGCACTCCATCCATGCGGATGACTGTCAAGGTCACTGA | SEQ ID NO: 229 | Vesicle transport through interaction with t-SNAREs homolog 1A (Vesicle transport v-SNARE protein Vti1-like 2) (Vti1-rp2). [Source:Uniprot/SWISSPROT;Acc:Q96AJ9] [ENST00000369399] |
| 230 | A_23_P431418 | U2AF2 | TGAAGAGATGGGCAGAGGAGTGACAGCGCGACACACGAGAGCCGGCAGCAACGTGGAA | SEQ ID NO: 230 | Homo sapiens U2 small nuclear RNA auxiliary factor 2 (U2AF2), transcript variant i, mRNA [NM_007279] |
| 231 | A_23_P45108 | QRICH1 | GAAAGGGCTTGGACTGTGAAAAGAAATGTGGCCCCTTTCCATCTTCAAGAGAGATGGAAT | SEQ ID NO: 231 | Homo sapiens glutamine-rich 1 (QRICH1), transcript variant i, mRNA [NM_017730] |
| 232 | A_23_P48964 | VPS33B | CCTCACGACCGTGGAGCAGTGGAGAGTAAAGTGAGGAAGGCTGGTGACCGGAGAGGGCTGCAGGAAAGAT | SEQ ID NO: 232 | Homo sapiens vacuolar protein sorting 33 homolog B (yeast) (VPS33B), mRNA [NM_018668] |
| 233 | A_23_P4922 | LOC374920 | GAGAGTCTCCAGCAGGGAGGGGGAATTGTTTGGACTATTGTTCTTCAGGATTGGAATAAA | SEQ ID NO: 233 | Homo sapiens hypothetical protein LOC374920 (LOC374920), mRNA [NM_199341] |
| 234 | A_23_P49327 | ZNF174 | AATCACAAAAACTGTGTGACTTACAAGAAGAAAAGCACGAAGGCCCTTGAGGAATGATGATGCA | SEQ ID NO: 234 | Homo sapiens zinc finger protein 174 (ZNF174), mRNA [NM_003450] |
| 235 | A_23_P4944 | CALM3 | CTCACTGCCAGGTCGATCAAGTGCCTTTTCCTGGGACCTGCCAGCTTTGAGAATCTCT | SEQ ID NO: 235 | Homo sapiens calmodulin 3 (phosphorylase kinase, delta) (CALM3), mRNA [NM_005184] |

Fig. 1-14

| No. | Probe ID No. | Symbols of genes | Sequence | SEQ ID NO: | Descriptions of genes (letters and numbers within [ ] indicates GenBank accession No.) |
|---|---|---|---|---|---|
| 236 | A_23_P49900 | PELP1 | TGAGTGTCCCGAAAGGTGCAGCCGAGAACCCGAACCCGG GCTGCTTTGGAAGT | SEQ ID NO: 236 | Homo sapiens proline, glutamic acid and leucine rich protein 1 (PELP1), mRNA [NM_014389] |
| 237 | A_23_P50020 | COG1 | GCATGAGAAGCACTCGAAAGGCTAAATCAACCAGAAACATCGAAA CAAAAGGTCAGGTTG | SEQ ID NO: 237 | Homo sapiens component of oligomeric golgi complex 1 (COG1), mRNA [NM_018714] |
| 238 | A_23_P501795 | SURF5 | CCATCATTCGAGTCATCTCTGTTTGCCTTCCTGGCCAG CCAGGTGAAGAAAG | SEQ ID NO: 238 | Homo sapiens surfeit 5 (SURF5), transcript variant b, mRNA [NM_133640] |
| 239 | A_23_P501887 | DHPS | GCTGATGCCCATTCTGGACGAGATGGTGATGGAGCAGAACACAGA GGGTGTAAAGTGGAG | SEQ ID NO: 239 | Homo sapiens deoxyhypusine synthase (DHPS) transcript variant 3, mRNA [NM_013407] |
| 240 | A_23_P502196 | IDH3B | CATGTGAAGTCACTTCCTGGGTATATGACTCGGACAACAATCTA GAGCTGGTGATCATT | SEQ ID NO: 240 | Homo sapiens isocitrate dehydrogenase 3 (NAD+) beta (IDH3B), nuclear gene encoding mitochondrial protein, transcript variant 2, mRNA [NM_174855] |
| 241 | A_23_P50472 | ALDH16A1 | CTGTGGGCTGCCTATGGGGGACTGATGCCTGAGCGCCACTACTGC ATTTTGGAGACCTCA | SEQ ID NO: 241 | Homo sapiens aldehyde dehydrogenase 16 family, member A1 (ALDH16A1), mRNA [NM_153329] |
| 242 | A_23_P51639 | KIAA0467 | GGTTCCAATCCCAGCTGCTGCCTTTGAAGCACTTGTGGCCAGGTC AAGTGCCTTTGGTCT | SEQ ID NO: 242 | Homo sapiens KIAA0467 (KIAA0467), mRNA [NM_015284] |
| 243 | A_23_P53015 | TUT1 | CATATAGAACAGGCAACCAAGAGAGCTGATGTGAGTCAGACTGCCCAGGTACCA ACTGGGAGTCCTCT | SEQ ID NO: 243 | Homo sapiens terminal uridylyl transferase 1, U6 snRNA-specific (TUT1), mRNA [NM_022830] |
| 244 | A_23_P53541 | CHD4 | TGGTGAGTGACATGAAAGCTCATTCAAGGTGGTGGACTCAAGGATGAAGAAGG TTGCCGAATTCCCC | SEQ ID NO: 244 | Homo sapiens chromodomain helicase DNA binding protein 4 (CHD4), mRNA [NM_001273] |
| 245 | A_23_P55091 | FTSJ3 | GAGTCAGAGGTCATTTCAAGGAAATTTCTGAGCTTTGTACATAGATGA ACCAAAGAGACAGC | SEQ ID NO: 245 | Homo sapiens FtsJ homolog 3 (E. coli) (FTSJ3), mRNA [NM_017647] |
| 246 | A_23_P553 | TARS2 | GTCCCAAATGCCGAAGAAATTTCTGAGCCTTTGTACATAGATGA GGGAAAAACGTCGA | SEQ ID NO: 246 | Homo sapiens threonyl-tRNA synthetase 2, mitochondrial (putative) (TARS2), mRNA [NM_025150] |
| 247 | A_23_P55948 | PRR12 | TGTCTTGGCCTTTGTTTGGGGTTCGTAACTTCAACTTGTATA CACTGTGTACACACA | SEQ ID NO: 247 | Homo sapiens mRNA for KIAA1205 protein, partial cds. [AB033031] |
| 248 | A_23_P56127 | C19orf61 | GTCAAGTTATTTCGTGGTAGCCTTCATGGACAGTGAAGGAGAGAGT GAAAACCGACCAAGA | SEQ ID NO: 248 | Homo sapiens hypothetical protein FLJ12886 (FLJ12886), mRNA [NM_019109] |
| 249 | A_23_P57236 | GGTL3 | CGAAGGACCAACAAGTTCATCATCGCGTTAAGGACCCTCGGAGC CCAGATGCAGGTGGA | SEQ ID NO: 249 | Homo sapiens gamma-glutamyltransferase-like 3 (GGTL3), mRNA [NM_178026] |
| 250 | A_23_P57819 | TATDN2 | TACTTTCTCTAGGATTTAGATTTATCATTTATGTGGTGGA CAGTGAAAACCTGACC | SEQ ID NO: 250 | Homo sapiens TatD DNase domain containing 2 (TATDN2), mRNA [NM_014760] |
| 251 | A_23_P586 | DMAP1 | GTCTGGTGAGCCGGCCAGTGACTGAAGCGGGACTTGGTGCTGACCG CAAGGACCACCATCAT | SEQ ID NO: 251 | Homo sapiens DNA methyltransferase 1 associated protein 1 (DMAP1), transcript variant 1, mRNA [NM_019100] |
| 252 | A_23_P60180 | ABL1 | AGGGCCCTAGGCTTTACGGCTCATCACCTAAACTTGTACTTTATTTTT CTGATAGAAATGGTT | SEQ ID NO: 252 | Homo sapiens v-abl Abelson murine leukemia viral oncogene homolog 1 (ABL1), transcript variant a, mRNA [NM_005157] |
| 253 | A_23_P60657 | KIAA0460 | TTATAAGAAAGGGGTCTCTTCCAAAGTAAGAAATCACATAGGCT TACGTTTTAGTATTC | SEQ ID NO: 253 | Homo sapiens KIAA0460 (KIAA0460), mRNA [NM_015203] |
| 254 | A_23_P61268 | C8orf30A | TGAAGGAGCTTAGCTTGTGTCTTGGCAATTGACAATGGCTCAGT CCAACACCCTAAAACT | SEQ ID NO: 254 | Homo sapiens chromosome 8 open reading frame 30A (C8orf30A), mRNA [NM_016458] |

Fig. 1-15

| No. | Probe ID No. | Symbols of genes | Sequence | SEQ ID NO: | Descriptions of genes (letters and numbers within [ ] indicates GenBank accession No.) |
|---|---|---|---|---|---|
| 255 | A_23_P6223 | SFRS15 | AAATGACCGGGAACGGGTATGGGAACGCGTAATGATGATAGAGATAATAGTAACCGTGACAG | SEQ ID NO: 255 | Homo sapiens splicing factor, arginine/serine-rich 15 (SFRS15), mRNA [NM_020706] |
| 256 | A_23_P62868 | EXOSC10 | TGGGAAACAAAAGCATGTCGTTGAACTGGAAAGTCAGACAGAGGCTTCAGGTACAACT | SEQ ID NO: 256 | Homo sapiens exosome component 10 (EXOSC10), transcript variant 1, mRNA [NM_001001998] |
| 257 | A_23_P63128 | OBSCN | GCTCGGTTCAGCGCGGGGAGGATTCTTCCCCTCATTGTTGTCATTGTTTGCATTAATATGAAT | SEQ ID NO: 257 | Homo sapiens cDNA FLJ14124 fis, clone MAMMA1002498 [AK024186] |
| 258 | A_23_P63281 | MGC10334 | GAACCAGGGTGAAGTCAGAGGTCCAGGGGTGGGAGGCTCGATCCTTTCCTTTCTGCC | SEQ ID NO: 258 | Homo sapiens hypothetical protein MGC10334 (MGC10334), mRNA [NM_001029985] |
| 259 | A_23_P64770 | DDX23 | AGTGGAATCTTACTGTCATGTGGACAGTCGGAGAGGCTGTTTCGTGTTTGGATGGTAAAGGAAGTTGA | SEQ ID NO: 259 | Homo sapiens DEAD (Asp-Glu-Ala-Asp) box polypeptide 23 (DDX23), mRNA [NM_004818] |
| 260 | A_23_P65797 | KLHL25 | GACGTGCCATGGTGCTTTGCCCAAAAGTGTGTTGCTTTATCAGTTTTGTAAGTTAATA | SEQ ID NO: 260 | Homo sapiens kelch-like 25 (Drosophila) (KLHL25), mRNA [NM_022480] |
| 261 | A_23_P65890 | CIB2 | TGTGCCTCCAAGCTCCCAGAAACAGTGGCAGCCTCGTGGGGTTTAGACCAGAAATAT | SEQ ID NO: 261 | Homo sapiens calcium and integrin binding family member 2 (CIB2), mRNA [NM_006383] |
| 262 | A_23_P66867 | GEMIN4 | AAAGAAAATAGTTCTTGTTGTATTTGTAACGTACAAAACTATCATAAAATTCTCGTCTT | SEQ ID NO: 262 | Homo sapiens gem (nuclear organelle) associated protein 4 (GEMIN4), mRNA [NM_015721] |
| 263 | A_23_P6802 | RRP9 | GCGATGGTGGAGAATCAAAAGGGCTGGAATTCTGTCTGGATCATCCCACATTCCGCAGGGT | SEQ ID NO: 263 | Homo sapiens RRP9, small subunit (SSU) processome component, homolog (yeast) (RRP9), mRNA [NM_004704] |
| 264 | A_23_P68087 | ATIC | GCAGAGAAGAAGGAATGGGTTGAGAAACTGACTGAAGTTGTATCAGCTGATGGCTTC | SEQ ID NO: 264 | Homo sapiens 5-aminoimidazole-4-carboxamide ribonucleotide formyltransferase/IMP cyclohydrolase (ATIC), mRNA [NM_004044] |
| 265 | A_23_P71146 | POLD2 | CTCCGTGAGAGACGACGGAAGTTTCTGGTGGAGGACATTGCTTTGCTCAGCTTGCTCG | SEQ ID NO: 265 | Homo sapiens polymerase (DNA directed), delta 2, regulatory subunit 50kDa (POLD2), mRNA [NM_006230] |
| 266 | A_23_P71889 | ODF2 | AAGATCCTTAAAGATCAGAATGAACAAAAGAGATTGAGGCGGCACGAAGGCAGTTCAGTCT | SEQ ID NO: 266 | Homo sapiens outer dense fiber of sperm tails 2 (ODF2), transcript variant 2, mRNA [NM_153437] |
| 267 | A_23_P73160 | ENST00000354261 | TGGTTGTTCATTAGACTCTCGGAGTATTGTTAAAATAGAGATTCACATTCAGTAGAG | SEQ ID NO: 267 | Leucine-rich repeat and calponin homology domain-containing protein 3 precursor. [Source:Uniprot/SWISSPROT;Acc:Q96II6] [ENST00000354261] |
| 268 | A_23_P73604 | CXorf34 | ACTGCATTACGAGGGTGATTCAAGCCATTCGAAAACTTCAGGGGCCATCCACACGCTAGTTT | SEQ ID NO: 268 | Homo sapiens chromosome X open reading frame 34 (CXorf34), mRNA [NM_024917] |
| 269 | A_23_P74269 | SRM | TCCTATTACGAGCTCATGAAGACAGCGCCTCAAGGAAGATGGTGTCCTCTGCTGCCAGGGC | SEQ ID NO: 269 | Homo sapiens spermidine synthase (SRM), mRNA [NM_003132] |
| 270 | A_23_P74653 | NUDC | GGCAGGCCAGGAATCATTGATGGGAGGCTGTACAATGAAGTGAAGGTGGAGGAGCTCGT | SEQ ID NO: 270 | Homo sapiens nuclear distribution gene C homolog (A. nidulans) (NUDC), mRNA [NM_006600] |
| 271 | A_23_P76609 | CEP164 | CTGGAGCACTTTGGGTATATTCATGGCATTGTTCCATCTGTCTTTCTACGTCTGCCA | SEQ ID NO: 271 | Homo sapiens centrosomal protein 164kDa (CEP164), mRNA [NM_014956] |
| 272 | A_23_P77437 | PRMT7 | AGAAAATCTTCAAGGTACCAACCACTTGGAAGATAAAATTAACATCATATGAGAAAACGGCCG | SEQ ID NO: 272 | Homo sapiens protein arginine methyltransferase 7 (PRMT7), mRNA [NM_019023] |

Fig. 1-16

| No. | Probe ID No. | Symbols of genes | Sequence | SEQ ID NO: | Descriptions of genes (letters and numbers within [ ] indicates GenBank accession No.) |
|---|---|---|---|---|---|
| 273 | A_23_P77440 | NFATC3 | GTCTCAGTTACAACCTATTACATATGGTCTTCACATTCAGGGTC TGCTACAACAGCTTC | SEQ ID NO: 273 | Homo sapiens nuclear factor of activated T-cells, cytoplasmic, calcineurin-dependent 3 (NFATC3), transcript variant 4, mRNA [NM_173164] |
| 274 | A_23_P77502 | PKD1 | CCTGCACCGTCTCACTGTGCTCGTGCTCCGTGTCAGTAATTTATATGGT GTTAAATGTGTATA | SEQ ID NO: 274 | Homo sapiens polycystic kidney disease 1 (autosomal dominant) (PKD1), transcript variant 1, mRNA [NM_001009944] |
| 275 | A_23_P78170 | MYBBP1A | CTGGCACGGAAAAAGGCAAGGCTGTCTTTGGTCATCAGGAGTCCC AGCCTGCTTCAGAGT | SEQ ID NO: 275 | Homo sapiens MYB binding protein (P160) 1a (MYBBP1A), mRNA [NM_014520] |
| 276 | A_23_P78191 | C17orf68 | TCCTTACTTGTTCTGTGATTGAAACCAAGGAGTCCAGATTGACAAA CTGGTAGTCCAGTAT | SEQ ID NO: 276 | Homo sapiens chromosome 17 open reading frame 68 (C17orf68), mRNA [NM_025099] |
| 277 | A_23_P78685 | FARSA | CGTGCAGGGGGCCAAGCAGTGATCAAATATGGCATGAACATATCCG GGAGCTGGTGGGCCA | SEQ ID NO: 277 | Homo sapiens phenylalanyl-tRNA synthetase, alpha subunit (FARSA), mRNA [NM_004461] |
| 278 | A_23_P79927 | NOL5A | GCCAGATACTGCGGTCTTGGCTGAGTTTATTGGAAACGGAAGGGAA CTGAATGAGGACAAG | SEQ ID NO: 278 | Homo sapiens nucleolar protein 5A (56kDa with KKE/D repeat) (NOL5A), mRNA [NM_006392] |
| 279 | A_23_P80129 | RRP1 | CTCGGCTGTGGCTGTGATGACCTTGGGCCAGAAGGGTCAAACTCC GAAGACTGAAACTCT | SEQ ID NO: 279 | Homo sapiens DNA segment on chromosome 21 (unique) 2056 expressed sequence (D21S2056E), mRNA [NM_003683] |
| 280 | A_23_P80136 | RRP1 | TGAATGAACTGGACACACAGGAATGAGGAGGTGGCGTGCGACAGTG ATGAGTCTCTGAGG | SEQ ID NO: 280 | Homo sapiens DNA segment on chromosome 21 (unique) 2056 expressed sequence (D21S2056E), mRNA [NM_003683] |
| 281 | A_23_P84782 | THAP4 | CACAGGCGAATGACTGAGCATGTTCACGTCAGTCACCTACAAGAAGGTGA CCCGTAAACTTAGA | SEQ ID NO: 281 | Homo sapiens THAP domain containing 4 (THAP4), mRNA [NM_015963] |
| 282 | A_23_P8848 | RC74 | CCAGCTTTGGTTTCGTTAGTTGCCTACAGTGCGTACGCAATA AGATGATGATCCCAA | SEQ ID NO: 282 | Homo sapiens integrator complex subunit 9 (RC74), mRNA [NM_018250] |
| 283 | A_23_P89835 | THC2619205 | AGTATACATTCTCTCTTTCTGGTCGGCATCTTAAACGTCTTCTGTT GTGTGCACGCGAGA | SEQ ID NO: 283 | MARE2_HUMAN (Q15555) Microtubule-associated protein RP/EB family member 2 (APC-binding protein EB2) (End-binding protein 2) (EB2), partial (87%) [THC2619205] |
| 284 | A_23_P89884 | TRIM26 | AGTTTGCCGAAGGATGTGGGCCGACATGTTCAAGCAAGAATTCAAGCAAGT TAACTGAGGACAAGG | SEQ ID NO: 284 | Homo sapiens tripartite motif-containing 26 (TRIM26), mRNA [NM_003762] |
| 285 | A_23_P90089 | GCDH | GAATGGGATTTCTGACGAGTATCACGTGATCCGGCACGGCCATGAA CCTGGAGGCCGGTGAA | SEQ ID NO: 285 | Homo sapiens glutaryl-Coenzyme A dehydrogenase (GCDH), nuclear gene encoding mitochondrial protein, transcript variant 2, mRNA [NM_013976] |
| 286 | A_23_P91328 | NOL5A | GAGGTTCCTCAGGAGAATGAATTGGAAGACCCATCTATGTCTTTC TCCAAACCCAAGAAA | SEQ ID NO: 286 | Homo sapiens nucleolar protein 5A (56kDa with KKE/D repeat) (NOL5A), mRNA [NM_006392] |
| 287 | A_23_P93818 | DKFZP434A0131 | TTTGAATAGAGTCTCATCTTGGCTAGGCACCATGGCCGAACAAC TGGGGAGGTGGAAGT | SEQ ID NO: 287 | Homo sapiens mRNA; cDNA DKFZp434A0131 (from clone DKFZp434A0131). [AL137492] |
| 288 | A_23_P9415 | ACO1 | AATTATACCAGTTGTTAAGTGAGATAGATAGAAGAACTTTGACACTT CAAATCAGAGACAGTG | SEQ ID NO: 288 | Homo sapiens aconitase 1, soluble (ACO1), mRNA [NM_002197] |
| 289 | A_23_P9416 | ACO1 | TACCCTCTTATTGTTCGTCTTACGGTCTGCTCAATGAAACGTTCC TCTTGAGGGTCATTT | SEQ ID NO: 289 | Homo sapiens aconitase 1, soluble (ACO1), mRNA [NM_002197] |

Fig. 1-17

| No. | Probe ID No. | Symbols of genes | Sequence | SEQ ID NO: | Descriptions of genes (letters and numbers within [ ] indicates GenBank accession No.) |
|---|---|---|---|---|---|
| 290 | A_23_P9426 | GOLGA2 | CGTTCTGAGTCAACCCGTTACCCTTAGAGTAGGAAGGATAGACGG CTGTCTAACGGGGGT | SEQ ID NO: 290 | Homo sapiens golgi autoantigen, golgin subfamily a, 2 (GOLGA2), mRNA [NM_004486] |
| 291 | A_23_P96653 | FAF1 | GCGTTTCCTGGGCAGCAACAAGCTCCAGATTGTCTTTGATTTGT AGGTTCCAAAGGATT | SEQ ID NO: 291 | Homo sapiens Fas (TNFRSF6) associated factor 1 (FAF1), mRNA [NM_007051] |
| 292 | A_23_P97274 | SCAMP3 | TGCCAGGCTTCAGAAGGCCCAGAAGGGCCAGCAAGAAATTGCTGCTGGTGTGTT CTCCAACCTGCGGT | SEQ ID NO: 292 | Homo sapiens secretory carrier membrane protein 3 (SCAMP3), transcript variant 2, mRNA [NM_052837] |
| 293 | A_23_P97736 | NCDN | GCTTGGTTGAAGGAGGACCCAGAGTGTCTTGGGGCCAGATGTTTAAAC CTTTGTGTGTGTTG | SEQ ID NO: 293 | Homo sapiens neurochondrin (NCDN), transcript variant 3, mRNA [NM_014284] |
| 294 | A_23_P9823 | MLXIP | TCTTGTTCTAGAGGTTTTGTTTCGAATCTTGCCTGATGAAT CCAGCCAGAACCAAGG | SEQ ID NO: 294 | Homo sapiens MLX interacting protein (MLXIP), mRNA [NM_014938] |
| 295 | A_23_P98252 | ARL2 | TGCCGGGCAGTCGACTGGCTCCTGGACCAGGTCCAATGTGGGGAGAAATTT TCACAGGTGAGTGAA | SEQ ID NO: 295 | Homo sapiens ADP-ribosylation factor-like 2 (ARL2), mRNA [NM_001667] |
| 296 | A_23_P98645 | DCHS1 | GTTGCTTACTGACGTGTGACCAGGTCCAATGTGGGGAGAAATATG AAGGAGGTAGCAGCC | SEQ ID NO: 296 | Homo sapiens dachsous 1 (Drosophila) (DCHS1), mRNA [NM_003737] |
| 297 | A_23_P100234 | MORC2 | TGAATTCAGATGAGCTAATATCTTTCGTCTCGAAGGAGTACTTCA AGCAATATGAAGTAG | SEQ ID NO: 297 | Homo sapiens MORC family CW-type zinc finger 2 (MORC2), mRNA [NM_014941] |
| 298 | A_24_P101402 | NOL5A | GGCTGGCAAGAGCAGCTCCAACAAAGAGCCACCTCTGTCTCCCTTTGCCAGAT ATCCCAGGAAGATTA | SEQ ID NO: 298 | Homo sapiens nucleolar protein 5A (56kDa with KKE/D repeat) (NOL5A), mRNA [NM_006392] |
| 299 | A_24_P101426 | A_24_P101426 | GTTTATGAGTGGCACCAAGACACTGGGGAGAATAAATCGAAGAAAGGGG GATCGGGATGATGAGA | SEQ ID NO: 299 | |
| 300 | A_24_P102512 | CABIN1 | CTCCTGTGGGTGATATTTGTGGGGAGATAAATCGAAGAAAGGGG TAAAACGGAAGAAGA | SEQ ID NO: 300 | Homo sapiens calcineurin binding protein 1 (CABIN1), mRNA [NM_012295] |
| 301 | A_24_P105933 | VIPR1 | TCTGATAGGAATGTGAAAGCACGGGACTCTTAGTGTGCTAAGTCTTTGT GTATCGTAACCAGCG | SEQ ID NO: 301 | Homo sapiens vasoactive intestinal peptide receptor 1 (VIPR1), mRNA [NM_004624] |
| 302 | A_24_P110719 | ZNF236 | AGTTCTACAGAGACTGCTCGATGTTTTTAAGGGCCAGAGTTTCAG ACGTTAGGTCTTGAA | SEQ ID NO: 302 | Homo sapiens zinc finger protein 236 (ZNF236), mRNA [NM_007345] |
| 303 | A_24_P119337 | AK054562 | GCAGTTGCAGTTAGGACCACACTAAAAGGTTAATGTCCAGCAGAATGG TGTTGACCAAGCCT | SEQ ID NO: 303 | Homo sapiens mRNA for FLJ00054 protein, partial cds. [AK054562] |
| 304 | A_24_P127701 | LOC441616 | CCAAGCTGATGGATAGTGAGAGCGACATGGTGCAGCAGAATCCGGGG TCTAGACAGCAGACAT | SEQ ID NO: 304 | PREDICTED: Homo sapiens similar to Protein C1orf2 (Another new gene 2 protein) (LOC441616), mRNA [XM_001129707] |
| 305 | A_24_P128001 | ZNF395 | GAATTCTTGCTTTCTAAAGTCTTCCAGAAAGGAGTGTGAGCAAG ATGAATTTACTTTTC | SEQ ID NO: 305 | Homo sapiens zinc finger protein 395 (ZNF395), mRNA [NM_018660] |
| 306 | A_24_P128057 | MBNL1 | AGAATATTGCTGCAAGCACTATGTGATTGGTTATCTGTATCA TGCATTGCTTCACAA | SEQ ID NO: 306 | Homo sapiens muscleblind-like (Drosophila), mRNA (cDNA clone IMAGE:3935812), partial cds. [BC005296] |
| 307 | A_24_P142269 | HIRIP3 | GAGAGGAAGAACCGGCTCTTCCAAGAAGAGCTCCAGAAGAAAGGGAGG ACACGAAGCTGTCT | SEQ ID NO: 307 | Homo sapiens HIRA interacting protein 3 (HIRIP3), mRNA [NM_003609] |
| 308 | A_24_P142983 | PIK4CA | TCACTCTGATGTTGGACACGGGCCTGCCCTGTTTTCGCGGGCCAGA CAATCAAGGTCTTGA | SEQ ID NO: 308 | Homo sapiens phosphatidylinositol 4-kinase, catalytic, alpha polypeptide (PIK4CA), transcript variant 1, mRNA [NM_002650] |

Fig. 1-18

| No. | Probe ID No. | Symbols of genes | Sequence | SEQ ID NO: | Descriptions of genes (letters and numbers within [ ] indicates GenBank accession No.) |
|---|---|---|---|---|---|
| 309 | A_24_P144601 | POU5F1 | AACAATGAAAATCTTCAGGAGATATGCAAAGCAGAAACCCTCGTGCAGGCCCGAAAGAGA | SEQ ID NO: 309 | Homo sapiens POU domain, class 5, transcription factor 1 (POU5F1), transcript variant 1, mRNA [NM_002701] |
| 310 | A_24_P145047 | ZNF609 | ACTATTAAACCTGCCTGGGAGTTAGGGACGGATGGTTTTAGGAATGACGGAAAAGTACC | SEQ ID NO: 310 | Homo sapiens zinc finger protein 609 (ZNF609), mRNA [NM_015042] |
| 311 | A_24_P147910 | SEPT9 | GTCGATCAGGGACAGATATTGAGGAGAAAAGGGTCCGGATGAAGCTGACAGTGATTGACAC | SEQ ID NO: 311 | Homo sapiens septin 9 (SEPT9), mRNA [NM_006640] |
| 312 | A_24_P158587 | CRY2 | GACCAGATGGTGCCAGTGACAGCAGCTGACGAGGACCAGCAGGGAAACCATTCTAGTCTTT | SEQ ID NO: 312 | Homo sapiens cryptochrome 2 (photolyase-like) (CRY2), mRNA [NM_021117] |
| 313 | A_24_P166042 | IMPDH2 | TTGGAGTCTTCGGAGGGAAATTCCATCTCCAGATCAATATGATCAAGTACATCAAAGAC | SEQ ID NO: 313 | Homo sapiens IMP (inosine monophosphate) dehydrogenase 2 (IMPDH2), mRNA [NM_000884] |
| 314 | A_24_P166645 | REPIN1 | CCCGTGCGTAGGCACCCAGAGTTGGAGAGACCCGTCTGCTGTTAATACTTCCATGCTCTT | SEQ ID NO: 314 | Homo sapiens replication initiator 1 (REPIN1), transcript variant 2, mRNA [NM_014374] |
| 315 | A_24_P169645 | A_24_P169645 | AAGTTGTGGTGAAGAGGTTATTTATGAGTTGCACCAAATGGGCAAGTCGTGTCTTTCCT | SEQ ID NO: 315 | |
| 316 | A_24_P171345 | PUM1 | GAGCACGGTCGTCGTGAGGATAAAAGCAAATGTAGCAGAAATGCGAGGGAATGTACTT | SEQ ID NO: 316 | Homo sapiens pumilio homolog 1 (Drosophila) (PUM1), transcript variant 2, mRNA [NM_014676] |
| 317 | A_24_P181108 | WDR74 | TGGGTTGCAGTGCCACCCTTCAAGGCTCTACTAGGCGTCCTGTGGCTTGGACAGAGTCTT | SEQ ID NO: 317 | Homo sapiens WD repeat domain 74 (WDR74), mRNA [NM_018093] |
| 318 | A_24_P185156 | FAM134C | GCCCCTAGTGAAATGATGTGATGTGAGACAGAAACCTAAACATGGTACTTGATTCTAAAC | SEQ ID NO: 318 | Homo sapiens hypothetical protein LOC162427 (LOC162427), mRNA [NM_178126] |
| 319 | A_24_P191067 | CLSTN1 | ACCCAGATAGGACACTTTGCTCTTAGTTACATTAGATGTAAAATTTTAGATTTCTAAAACAGGTGGG | SEQ ID NO: 319 | Homo sapiens calsyntenin 1 (CLSTN1), transcript variant 1, mRNA [NM_001009566] |
| 320 | A_24_P193570 | CNOT1 | AGAGTTCCTTTCTGTGATTATGGGTTCGTGTGATGTGATCCCACCTAATTGTATCGA | SEQ ID NO: 320 | Homo sapiens CCR4-NOT transcription complex, subunit 1 (CNOT1), mRNA [NM_016284] |
| 321 | A_24_P196298 | MLL | GCACTTGAACATGGTCAGCACTGTCGGGCACTGGGAGCTGTGTCTATGCTCCAGGCAAAAATTCCAG | SEQ ID NO: 321 | Homo sapiens myeloid/lymphoid or mixed-lineage leukemia (trithorax homolog, Drosophila) (MLL), mRNA [NM_005933] |
| 322 | A_24_P200694 | RING1 | GAAATTCTGGAAGGGTGTGCCGGCACTGAGGAGCGTGTGTCTATGCTCCCACCCAAGGATCCAAA | SEQ ID NO: 322 | Homo sapiens ring finger protein 1 (RING1), mRNA [NM_002931] |
| 323 | A_24_P2093 | XAB2 | ACGTGCAGAGGACTTTGAGGTCCGGCATGGAGAATGGCAATGAGGACACCATCAAGGAAATGCTGCGT | SEQ ID NO: 323 | Homo sapiens XPA binding protein 2 (XAB2), mRNA [NM_020196] |
| 324 | A_24_P212764 | A_24_P212764 | CTCCCACTTTGTGGGCGAGAGAGGAGTTCTAGACCAGGTTGTCTCTGGGACATTGACAC | SEQ ID NO: 324 | |
| 325 | A_24_P213175 | A_24_P213175 | TTTCCCTGAGAGCTCAGATAGAATGTTGTTGAGAAGCCCATTTGCACAGGTTTTCA | SEQ ID NO: 325 | |
| 326 | A_24_P214841 | POU5F1 | AATGTTCAGGAGATATGCAAAGCAGAAACCCTCGTGCAGGCCGAAGAGAAAGCGAAGC | SEQ ID NO: 326 | Homo sapiens POU domain, class 5, transcription factor 1 (POU5F1), transcript variant 1, mRNA [NM_002701] |

Fig. 1-19

| No. | Probe ID No. | Symbols of genes | Sequence | SEQ ID NO: | Descriptions of genes (letters and numbers within [ ] indicates GenBank accession No.) |
|---|---|---|---|---|---|
| 327 | A_24_P216087 | PAF1 | GACGATGCCGACTCTGATGATGAGGAGGACAGGAGCAGGCCCAAGGTGGGCAGTGACAATGAT | SEQ ID NO:327 | Homo sapiens Paf1, RNA polymerase II associated factor, homolog (S. cerevisiae) (PAF1), mRNA [NM_019088] |
| 328 | A_24_P221668 | AW172589 | GGAGGTCTGGGATGCTGCATTATATCTGAATTGTGAGCTCTGGGCATGGAGGTCTGTCTG | SEQ ID NO:328 | xl79h10.xl Soares_NFL_T_GBC_S1 Homo sapiens cDNA clone IMAGE:2863491 3' similar to TR:Q13116 Q13116 MEMBRANE PROTEIN-LIKE PROTEIN.; mRNA sequence [AW172589] |
| 329 | A_24_P224926 | MFNG | AGACAATCATCCACAGTCATTCCCTCCAGCATCTGGTTCTGTAGAAAAATTAAATGTTA | SEQ ID NO:329 | Homo sapiens MFNG O-fucosylpeptide 3-beta-N-acetylglucosaminyltransferase (MFNG), mRNA [NM_002405] |
| 330 | A_24_P231132 | ACVR2B | GTGTCACCAATGTGGACCTGCCGGTAAAGAGTCAAGGATCAAGCCCAAGACGATCAGTG | SEQ ID NO:330 | Homo sapiens activin A receptor, type IIB (ACVR2B), mRNA [NM_001106] |
| 331 | A_24_P231173 | PERQ1 | CCCTACTTGGGTTCGTCTCCGGCCCATTTTGGGTTTTTGTAACAGTTTTGTCTTTTGGGTTT | SEQ ID NO:331 | Homo sapiens PERQ amino acid rich, with GYF domain 1 (PERQ1) mRNA [NM_022574] |
| 332 | A_24_P235131 | TRIAD3 | TCCAGTATGCCCCATGTGAAAGGTCACTTCGGTTCTCATGAGTCAGGTGAGCATCAGCTC | SEQ ID NO:332 | Homo sapiens TRIAD3 protein (TRIAD3), transcript variant 1, mRNA [NM_207111] |
| 333 | A_24_P238215 | DKFZP586P0123 | TTGAAAACAGAATTCCCCATGTGGAATTTTCAACAGCAGTCAAGGCTATCAAAGAGC | SEQ ID NO:333 | Homo sapiens hypothetical protein (DKFZP586P0123), mRNA [NM_015531] |
| 334 | A_24_P241862 | RANBP3 | TGGCTCAGAGTCAATGACATGGGGTCCACCGATGACGGCCACACTACAGTCCGACTAGTGA | SEQ ID NO:334 | Homo sapiens RAN binding protein 3 (RANBP3), transcript variant RANBP3-b, mRNA [NM_007320] |
| 335 | A_24_P244575 | TPCN1 | CCCTTGGGAAAGCAACAACATTATGAGAGTCACTGTGATTCCCCGGGAGTCAGACTGG | SEQ ID NO:335 | Homo sapiens mRNA for KIAA1169 protein, partial cds. [AB032995] |
| 336 | A_24_P245246 | PIP5K2B | TTTGAGACCCGTGTTACTGTTGGAAATGCATGCATGTTACGATGAATCTCCAAGCTGAGG | SEQ ID NO:336 | Homo sapiens phosphatidylinositol-4-phosphate 5-kinase, type II, beta (PIP5K2B), mRNA [NM_003559] |
| 337 | A_24_P248053 | TOP1MT | GCAGAGAACAGACTTTGAATTCTAACGACGAGCGTGTTGAAAGTTCTTTGTATGTGTGT | SEQ ID NO:337 | Homo sapiens topoisomerase (DNA) I, mitochondrial (TOP1MT), nuclear gene encoding mitochondrial protein, mRNA [NM_052963] |
| 338 | A_24_P250333 | SNRPA | CAGGCTCGCGGATGCGCTGCAGGGGTTTAAGATCAGCAGGAGAACAAGGCCATAAGAGATCTCCT | SEQ ID NO:338 | Homo sapiens small nuclear ribonucleoprotein polypeptide A (SNRPA), mRNA [NM_004596] |
| 339 | A_24_P251688 | ABCF3 | TTGGGACAGAGCCTTATTCCCAAATGTCTGTATCCTTTTTGACTGGAGCATCTCTGAGAG | SEQ ID NO:339 | Homo sapiens ATP-binding cassette, sub-family F (GCN20), member 3 (ABCF3), mRNA [NM_018358] |
| 340 | A_24_P252130 | PPARD | GCTGAGGATACAGACTCTTCTCAGTGTCAGAACGAATCTGGAAAATTGAAATGTATATTT | SEQ ID NO:340 | Homo sapiens peroxisome proliferator-activated receptor delta (PPARD), mRNA [NM_006238] |
| 341 | A_24_P254437 | THC2563227 | GGGAGGGGCACTGTCTGCTTTTTTAAAATGAAGTGTTGCCTTTGTAT | SEQ ID NO:341 | CA312433 UI-CF-FN0-afk-i-18-0-UI.s1 UI-CF-FN0 Homo sapiens cDNA clone UI-CF-FN0-afk-i-18-0-UI 3', mRNA sequence [CA312433] |
| 342 | A_24_P256063 | LOC442249 | CTCAAGGACCATTGAAGATGGCAGACATGGACAGACATCCAGGCGCAATATAACGAGGTGTCTCGGA | SEQ ID NO:342 | PREDICTED: Homo sapiens hypothetical LOC442249 (LOC442249), mRNA [XR_019231] |
| 343 | A_24_P258846 | NFATC1 | CTCTGGTGGTTGAGATGGGGCCATTTCGGAATCAGAGGATAACGAGCGGCGGTTCACGTCA | SEQ ID NO:343 | Homo sapiens nuclear factor of activated T-cells, cytoplasmic, calcineurin-dependent 1 (NFATC1), transcript variant 1, mRNA [NM_172390] |

Fig. 1-20

| No. | Probe ID No. | Symbols of genes | Sequence | SEQ ID NO: | Descriptions of genes (letters and numbers within [ ] indicates GenBank accession No.) |
|---|---|---|---|---|---|
| 344 | A_24_P26170 | VPRBP | GGACACTGACAGCTCTGACAAGTCTGATTGGAAGATGACATCATCTTATCTCGAATGA | SEQ ID NO: 344 | Homo sapiens Vpr (HIV-1) binding protein (VPRBP), mRNA [NM_014703] |
| 345 | A_24_P265728 | SF1 | GCTTCCTTTATGTTTGTTTTAATCCAAATGTCTGAATGTTTGCAGTGTAGGGGT | SEQ ID NO: 345 | Homo sapiens splicing factor 1 (SF1), transcript variant 1, mRNA [NM_004630] |
| 346 | A_24_P267452 | CD3EAP | ACAGTGAAGCACGAACAGAGATTAACACTGAGCGTCTAGAAGACACAGTCCGTGCCGGACC | SEQ ID NO: 346 | Homo sapiens CD3e molecule, epsilon associated protein (CD3EAP), mRNA [NM_012099] |
| 347 | A_24_P272594 | MAPK8P1 | GCGCTGTTTTTAACGTGCCGTTTGTACTGATGATGTAGAAGTTGTCAATAAACACAATTGT | SEQ ID NO: 347 | Homo sapiens mitogen activated protein kinase binding protein 1 (MAPK8P1), mRNA [NM_014994] |
| 348 | A_24_P273823 | NPAT | TGCCATTAGCGGGCATAACCACCATAAGAGAAAGTCAATCAGAAAAGAAAGTTCTCCAAC | SEQ ID NO: 348 | Homo sapiens nuclear protein, ataxia-telangiectasia locus (NPAT), mRNA [NM_002519] |
| 349 | A_24_P294931 | PPP2R5D | TGAGAGAGCATGGAAGGGACCACCACCCTGGGCTGGTGCTCTGAACTAAACCAAGGGAGAGCTTTGGTTGGAA | SEQ ID NO: 349 | Homo sapiens protein phosphatase 2, regulatory subunit B', delta isoform (PPP2R5D), transcript variant 2, mRNA [NM_180976] |
| 350 | A_24_P29641 | NSUN5C | CAATAAAGACCAGTCACTTGGGTCGTGTTCTGAAGAACCAAGGGAAGATCTTTGCTTTG | SEQ ID NO: 350 | Homo sapiens NOL1/NOP2/Sun domain family, member 5C (NSUN5C), transcript variant 2, mRNA [NM_148936] |
| 351 | A_24_P298360 | LTBP3 | CTGGTGTTGGGGAAGCCCCAAGGATGGTCGTCTGAACAGAGACAGTTCAAGAGGAGGATTCAGACGAGTGT | SEQ ID NO: 351 | Homo sapiens latent transforming growth factor beta binding protein 3 (LTBP3), mRNA [NM_021070] |
| 352 | A_24_P307103 | lcag7.1017 | ATGTTTGATGAATCTGATGATGAGGCAGAGAAGGAGCTCGGCCCTGAGCGTCAGGAGAC | SEQ ID NO: 352 | Homo sapiens similar to Williams Beuren syndrome chromosome region 19 (MGC57359), mRNA [NM_001004351] |
| 353 | A_24_P312325 | C6orf15 | CTTGTTCAATGTGACTACTTTAGTTGGCTGCTGTCCAATATGAAGTAGAAAAGCAGATTTCTG | SEQ ID NO: 353 | Homo sapiens chromosome 6 open reading frame 15 (C6orf15), mRNA [NM_001033662] |
| 354 | A_24_P315564 | LOC646253 | AGGAGATCAGGGCTCTAGACAGCAACATGAACAAACCGTGGTCTATGAGAACTACAATAAGT | SEQ ID NO: 354 | PREDICTED: Homo sapiens similar to Protein C11orf2 (Another new gene 2 protein) (LOC646253), mRNA [XM_001130995] |
| 355 | A_24_P316414 | BC014346 | TAACCTTGGGGTCTTGGGAGTAGAACTTTAGCTTTGAATAATTTAAGGGCTTGGCGTGTA | SEQ ID NO: 355 | Homo sapiens, clone IMAGE:4042988, mRNA, partial cds. [BC014346] |
| 356 | A_24_P317827 | C9orf127 | AGCCTTCCAAGACAGACATGGATTCGTTCCCAGGGAGACAAAGCCCTGTCAGGAGCAGACAGCAT | SEQ ID NO: 356 | Homo sapiens chromosome 9 open reading frame 127 (C9orf127), transcript variant 1, mRNA [NM_001042590] |
| 357 | A_24_P321093 | SPOCK2 | CTGGAAGAAGGTTAAGCATGTGTTCAAAGAACGGTTTGTTGGTTGCTTGGTCCTGGAAGT | SEQ ID NO: 357 | Homo sapiens sparc/osteonectin, cwcv and kazal-like domains proteoglycan (testican) 2 (SPOCK2), mRNA [NM_014767] |
| 358 | A_24_P322647 | POLR3H | ACATGCCTGGGTCCTGGGTGATGAGTGATGATTAGTCTCTTCTGTGACAGGGGTGCCTGGAGA | SEQ ID NO: 358 | Homo sapiens polymerase (RNA) III (DNA directed) polypeptide H (22.9kD) (POLR3H), transcript variant 4, mRNA [NM_001018051] |
| 359 | A_24_P32295 | C19orf36 | TTAAGGTGTCTTGGAGCCCCACCACTTGGCCAACCTGACCTTGGAAGATGCTGCTGAGTGT | SEQ ID NO: 359 | Homo sapiens chromosome 19 open reading frame 36 (C19orf36), transcript variant 3, mRNA [NM_001039846] |
| 360 | A_24_P323628 | FLJ45055 | ATTGAGGAAGGACGGGCACCGAAAAGGGAAGGAAGCTCCTGCTCCTCCTAAAAGCGAAGCCAA | SEQ ID NO: 360 | Homo sapiens hypothetical protein LOC644128, mRNA (cDNA clone IMAGE:6158500). [BC064939] |

Fig. 1-21

| No. | Probe ID No. | Symbols of genes | Sequence | SEQ ID NO: | Descriptions of genes (letters and numbers within [ ] indicates GenBank accession No.) |
|---|---|---|---|---|---|
| 361 | A_24_P32646 | LOC648644 | AGAATCTGTACCCTCTGCGAAGAGCAAAAGGGTGCTGGATCCTGCCCACTGGTACCATGGCA | SEQ ID NO: 361 | PREDICTED: Homo sapiens similar to Aflatoxin B1 aldehyde reductase member 2 (AFB1-AR 1) (Aldoketoreductase 7) (LOC648644), mRNA [XR_018390] |
| 362 | A_24_P327815 | STIP1 | CACCAAACTCCTCGAGTTCCAGGTCGACTGGGAGTCAAGGACTGTGAGGAATGTATCCAGGTGGA | SEQ ID NO: 362 | Homo sapiens stress-induced-phosphoprotein 1 (Hsp70/Hsp90-organizing protein) (STIP1), mRNA [NM_006819] |
| 363 | A_24_P329939 | VPS11 | CGTCATCAGGGACTACGTGGTCAAAAACTACAGAGAACAGAGCCAGCAGATTGCAGAGGA | SEQ ID NO: 363 | Homo sapiens vacuolar protein sorting 11 homolog (S. cerevisiae) (VPS11), mRNA [NM_021729] |
| 364 | A_24_P335358 | PUS1 | CCTGGAGTTTGCGGTGATCAGGGTGAAGGGCGAGAGGTTCATGATGGATCAGAATCGGAA | SEQ ID NO: 364 | Homo sapiens pseudouridylate synthase 1 (PUS1), transcript variant 1, mRNA [NM_025215] |
| 365 | A_24_P339992 | EDC3 | TTGGCCAAAATCGAGGAGCAGTCTAGGTTACAGGCTTTTTGGTAGGTAGGTTCTGGCTG | SEQ ID NO: 365 | Homo sapiens enhancer of mRNA decapping 3 homolog (S. cerevisiae) (EDC3), mRNA [NM_025083] |
| 366 | A_24_P340891 | LOC402149 | CTACGTGCGGACGACATCATCAACAAGACGGTGGAGGCAAAGTCAGCAGCATCAGATACAT | SEQ ID NO: 366 | PREDICTED: Homo sapiens similar to ribosomal protein L28 (LOC402149), mRNA [XR_019242] |
| 367 | A_24_P349002 | POM121 | ACCTAAATTAATGAACCACTATATTTTAAAATCGTATTTTCCCAAACAGGGCCCTGTGTGGA | SEQ ID NO: 367 | Homo sapiens POM121 membrane glycoprotein (rat) (POM121), mRNA [NM_172020] |
| 368 | A_24_P350644 | ENST00000320547 | CATGTAGACCAGATATATTTGAAAGGGCAGAGATGGGTAGAGTGTAATGTGCAGGTTGTT | SEQ ID NO: 368 | Uncharacterized protein KIAA0515 [Source:Uniprot/SWISSPROT;Acc:Q5JSZ5] [ENST00000320547] |
| 369 | A_24_P356 | AAK1 | GCGGCTTATGTTCTGAATTGTTTATGAGAACTGATCATTAGTGAGACTGGCCACAGTAT | SEQ ID NO: 369 | AP2-associated protein kinase 1 (EC 2.7.11.1) (Adaptor-associated kinase 1) [Source:Uniprot/SWISSPROT;Acc:Q2M2I8] [ENST00000360555] |
| 370 | A_24_P364970 | DHX33 | ATTTAATTACAGAAGCAAGATAATGTTTCCCGAGATAATATTTTGCCCTAGAAGAAGCCG | SEQ ID NO: 370 | Homo sapiens DEAH (Asp-Glu-Ala-His) box polypeptide 33 (DHX33), mRNA [NM_020162] |
| 371 | A_24_P366263 | MMS19L | TTGTACTTGGAAGCACGCCCAAGTCATGAGGTTCAGTGTTCAGTGTGGACACCTCGTCACCAAGTTTC | SEQ ID NO: 371 | Homo sapiens MMS19-like (MET18 homolog, S. cerevisiae) (MMS19L), mRNA [NM_022362] |
| 372 | A_24_P371670 | HNRPA0 | ACTTCTCGCAGTTGGGTGGACGGTGGAAAAGGCGGAGATTATTGCGGACAAGAGTCCAGGCA | SEQ ID NO: 372 | Homo sapiens heterogeneous nuclear ribonucleoprotein A0 (HNRPA0), mRNA [NM_006805] |
| 373 | A_24_P372613 | APBB1 | AAACCTGTTGGGGTAGATGTGATTAATGGGGCCCTGAGTCAGTCCTGTCGTCCAGGAGC | SEQ ID NO: 373 | Homo sapiens amyloid beta (A4) precursor protein-binding, family B, member 1 (Fe65) (APBB1), transcript variant 1, mRNA [NM_001164] |
| 374 | A_24_P373312 | NFATC3 | GAACCAAGAATCGAGAGCCTAACTTTGCAACCATTGGTGTGCAGGAGATCACTTTAGAT | SEQ ID NO: 374 | Homo sapiens nuclear factor of activated T-cells, cytoplasmic, calcineurin-dependent 3 (NFATC3), transcript variant 4, mRNA [NM_173164] |
| 375 | A_24_P375592 | PHF20 | GCACCCAGCATTGAAAACAAAATGTTAAAATGCCAACATTTGTGTTAATTCTAGCTAG | SEQ ID NO: 375 | Homo sapiens cDNA FLJ33479 fis, clone BRAMY2002739. [AK090798] |
| 376 | A_24_P376422 | BC035371 | GAGGCAAGTTTGCATTTTCACACGCGATCTCACACTGTCTGGACTCTCAAGTTGGAGAGC | SEQ ID NO: 376 | Homo sapiens HSPC047 protein, mRNA (cDNA clone MGC:34358 IMAGE:5178752), complete cds. [BC035371] |

Fig. 1-22

| No. | Probe ID No. | Symbols of genes | Sequence | SEQ ID NO: | Descriptions of genes (letters and numbers within [ ] indicate GenBank accession No.) |
|---|---|---|---|---|---|
| 377 | A_24_P362765 | NHP2L1 | TACGTGTTCAAGTGATGAAGGGGTTTGATTTGCTCTTGGGGATTAGGTATCATTTGGGG | SEQ ID NO: 377 | Homo sapiens NHP2 non-histone chromosome protein 2-like 1 (S. cerevisiae) (NHP2L1), transcript variant 1, mRNA [NM_005008] |
| 378 | A_24_P384779 | PRKAG2 | CCATAAATACAGAGCTGAGGGAGAGAAATGGTGAGGGCACAATAGGAAATGAAAATACACAA | SEQ ID NO: 378 | Homo sapiens cDNA FLJ90194 fis, clone MAMMA1001284. [AK074675] |
| 379 | A_24_P389038 | WDR46 | TAGAGCCACCAGGTGAAGATCTTTGACTTGCCAGGGAGGATACCAGCCTCTGAGCACTCGGA | SEQ ID NO: 379 | Homo sapiens WD repeat domain 46 (WDR46), mRNA [NM_005452] |
| 380 | A_24_P38944 | CCDC86 | TTCTCCCAGATGCTTCAGGACGAAGCCCTGCGACATCGTGGCAGCGGAAGATGAAGGAA | SEQ ID NO: 380 | Homo sapiens coiled-coil domain containing 86 (CCDC86), mRNA [NM_024098] |
| 381 | A_24_P391526 | MAGED1 | GGTGAGATTCATTGGAGAGGTTCAGAAAAGAGACCGTCGTGACTGGACTGCAGAGTTCAT | SEQ ID NO: 381 | Homo sapiens melanoma antigen family D, 1 (MAGED1), transcript variant 1, mRNA [NM_001005333] |
| 382 | A_24_P396197 | PRKCSH | AGCGGTGCGTGAAGGACGATGGAGGGAGTCCATCAGGAACCTGGAGCAAGAGATTCTTTTG | SEQ ID NO: 382 | Homo sapiens protein kinase C substrate 80K-H (PRKCSH), transcript variant 1, mRNA [NM_002743] |
| 383 | A_24_P399065 | NUDT16L1 | GCCAGGTCCTCTTTGCCCTCAAGGTGCTCAACATGATGCCCAGGAGAAGCTGGTTGAGG | SEQ ID NO: 383 | Homo sapiens nudix (nucleoside diphosphate linked moiety X)-type motif 16-like 1 (NUDT16L1), mRNA [NM_032349] |
| 384 | A_24_P40010 | RPS28 | GCGCCAGGCCATCATGGAGACCAGCCGTGTGCAGCCTATCAAGCTGGCCAGGGTCAGGAAGG | SEQ ID NO: 384 | Homo sapiens ribosomal protein S28 (RPS28), mRNA [NM_001031] |
| 385 | A_24_P401521 | A_24_P401521 | GAAGCTAAGTATCTCGTGGCTATGGTCAGCGTATTTAGCCGGGCCAGAGCGTTCTCCTG | SEQ ID NO: 385 | |
| 386 | A_24_P401637 | AK095727 | AGCGGGGCTTCCTCCCTTAGAACGCTGGTCATGCATATATTTGATGTGGGTTGCCAG | SEQ ID NO: 386 | Homo sapiens cDNA FLJ38408 fis, clone FEBRA2009029. [AK095727] |
| 387 | A_24_P405621 | NISCH | TGAAGTCAGTGCCAGGTGTTGTCCCAGTGCTGAAGAGGAGAGAGAAGCTCATCTGCT | SEQ ID NO: 387 | Homo sapiens nischarin (NISCH), mRNA [NM_007184] |
| 388 | A_24_P409881 | LOC338756 | CAGGAGGGTTCCTCAGGAGAAAACAGAAGACCCATCTATCTTTCTCCAAACCCAAGAAA | SEQ ID NO: 388 | PREDICTED: Homo sapiens similar to nucleolar protein 5A (LOC338756), mRNA [XM_2919891] |
| 389 | A_24_P412976 | TMEM143 | TTATTGGTCTATCAATTTCTCCGGTCCTGTCCCAAAGTAATAAATCATGTTTAATAAG | SEQ ID NO: 389 | Homo sapiens transmembrane protein 143 (TMEM143), mRNA [NM_018273] |
| 390 | A_24_P416289 | KIAA0195 | GGGCTAAAGCCAGAACCCATTTCTGAACAGGGAGAGTTGTATCATGAATGTTTCCAGGTTT | SEQ ID NO: 390 | Homo sapiens KIAA0195 (KIAA0195), mRNA [NM_014738] |
| 391 | A_24_P42136 | KRT18 | GGTGACGAGCTGAGACTGAGAAAGGAACTCCTTGAGAAA | SEQ ID NO: 391 | Homo sapiens keratin 18 (KRT18), transcript variant 1, mRNA [NM_000224] |
| 392 | A_24_P42569 | BC030138 | AGCTTGCTTGGCTGATGAACACTTCCACACAGTCTTTTGAGCTAAGTAGTTTTGTAATTAGT | SEQ ID NO: 392 | Homo sapiens cDNA clone IMAGE:4335164, partial cds. [BC030138] |
| 393 | A_24_P44514 | CIB1 | CCATTATGCCTTCCAGCATCTTCGACTTTGACTTTGATGATGACCGAGCGTTGAACAGAAGAGCCT | SEQ ID NO: 393 | Homo sapiens calcium and integrin binding 1 (calmyrin) (CIB1), mRNA [NM_006384] |
| 394 | A_24_P44891 | TNPO2 | GATGGTCCTCACAACAGCTGGTGGAAATCATTAACCGACCGAACACACCCAAGAGAGCT | SEQ ID NO: 394 | Homo sapiens transportin 2 (importin 3, karyopherin beta 2b) (TNPO2), mRNA [NM_013433] |
| 395 | A_24_P460763 | AK022443 | GTGAGTAGCAGGCTAGTTAAGATGCCTAGTGGGTCTAAATGTCAAATGCTATTGGCAGAT | SEQ ID NO: 395 | Homo sapiens cDNA FLJ12381 fis, clone MAMMA1002566. [AK022443] |

Fig. 1-23

| No. | Probe ID No. | Symbols of genes | Sequence | SEQ ID NO. | Descriptions of genes (letters and numbers within [ ] indicates GenBank accession No.) |
|---|---|---|---|---|---|
| 396 | A_24_P477127 | PKD1 | CCAGATACGCAAGAAGAACATCACGGAGACTCTGGTGTCCGTGAGGGTCCCACAGTGTGGATGA | SEQ ID NO: 396 | Homo sapiens polycystic kidney disease 1 (autosomal dominant) (PKD1), transcript variant 2, mRNA [NM_002296] |
| 397 | A_24_P481763 | LOC390595 | GCATGTCTAGGCCCAATGCCAGAGACGTGGCAACGGATCCTAAGTGTATTATTAAAACCAAGTA | SEQ ID NO: 397 | Homo sapiens cDNA FLJ13740 fis, clone PLACE3000199 [AK023802] |
| 398 | A_24_P51360 | LARS | GAAAAGAGAAATAGAGGTGTAGGTTGCGCGCCCTGATTTTCAGATGAAGAAGGAAGA | SEQ ID NO: 398 | Homo sapiens leucyl-tRNA synthetase (LARS), mRNA [NM_020117] |
| 399 | A_24_P529786 | AK091744 | GATACATAACAGGCAATACAAATATTATCACATAGCGTCAATTTATTTTGTGAATATTGAA | SEQ ID NO: 399 | Homo sapiens cDNA FLJ34425 fis, clone HHDPC2008297 [AK091744] |
| 400 | A_24_P548264 | AL512741 | AAGAATTTGAGTTAGAACTGCCGTAATGATGTAATGCAGAATATTTCCCAATAATGCCTAGG | SEQ ID NO: 400 | Homo sapiens mRNA; cDNA DKFZp667N064 (from clone DKFZp667N064) [AL512741] |
| 401 | A_24_P55719 | SURF5 | CTCAAGCGTTTGCGGAAGCTAATGACGTGCCTCTGTGCGAAGGTTACGGGAGGCTGAGCT | SEQ ID NO: 401 | Homo sapiens surfeit 5 (SURF5), transcript variant b, mRNA [NM_133640] |
| 402 | A_24_P55971 | VEGFB | CACTGGGCAGGACGAGCCAAGTGCAGATGCAGATGCCAGAATGCCATGATCGGGTACCCGAGCAGTCAGCT | SEQ ID NO: 402 | Homo sapiens vascular endothelial growth factor B (VEGFB), mRNA [NM_003377] |
| 403 | A_24_P5743 | ALDH16A1 | CTTGCACCAAGAGGTCCAGGGCTATTTGGGATCAGCCCAGGGTTCCCAGTTTGT | SEQ ID NO: 403 | Homo sapiens aldehyde dehydrogenase 16 family, member A1 (ALDH16A1), mRNA [NM_153329] |
| 404 | A_24_P583330 | THC2657163 | GTAAGCAGTCATTATAATTTGTTGATGATAGTTTAAGTATATAGGGTATGCCCATTAGCC | SEQ ID NO: 404 | |
| 405 | A_24_P592421 | AL050185 | TTTTTTCATAGCGCCCTTTCATAGGACACGCTAATAATGAAGATGCATATCATTAAAAGCCTGA | SEQ ID NO: 405 | Homo sapiens mRNA; cDNA DKFZp586A0423 (from clone DKFZp586A0423) [AL050185] |
| 406 | A_24_P598516 | AK021595 | TGAGTTGCGTGATGATGTTCCGTGCAGTTATGTTATGCTTTTTCCTTATGATTTAAAGTCTTTAGC | SEQ ID NO: 406 | Homo sapiens cDNA FLJ11533 fis, clone HEMBA1002678 [AK021595] |
| 407 | A_24_P611114 | hCG_1730474 | CTTTTTATCAGGTAGACTGGACATGTTCATGGGCTAAGCATAGACATTACTACCCAAAT | SEQ ID NO: 407 | Homo sapiens cDNA FLJ10133 fis, clone HEMBA1003067 [AK000995] |
| 408 | A_24_P63608 | NOLA2 | ATTGAAGGTATACCTGGGATCTCCCAGTCATCATGTGTCAGGACCGAAATTTGCCTATGTGTAT | SEQ ID NO: 408 | Homo sapiens nucleolar protein family A, member 2 (H/ACA small nucleolar RNPs) (NOLA2), transcript variant 1, mRNA [NM_017838] |
| 409 | A_24_P636318 | LOC130074 | GGAAACTGGCATGTTTCAGAGAAAGTTTGTCTGTCTTTTTGCTACTCATTATTTGAAGAAGAGAG | SEQ ID NO: 409 | Homo sapiens mRNA (LOC130074), mRNA [NM_001009993] |
| 410 | A_24_P636390 | AF009267 | TTGGAGTATCACGTGTGTACGTGTGAAGTCGTGGAGTGTGTTGGGTCCTCATCAGGAG | SEQ ID NO: 410 | Homo sapiens clone FBA1 Cri-du-chat region mRNA [AF009267] |
| 411 | A_24_P6381 | SERINC5 | GGTCATTTATGACAGAGAAGGCACCGTCTACATCGTACTCCTACTTCCACTTCGTGTT | SEQ ID NO: 411 | Homo sapiens serine incorporator 5 (SERINC5), mRNA [NM_178276] |
| 412 | A_24_P65941 | C21orf96 | ATTGGGACTTCCCGGAGGATGTACTGGATGTAACTTCAAGGAGGTTTGTCTAGGTGTAGGAGAA | SEQ ID NO: 412 | Homo sapiens cDNA FLJ20856 fis, clone ADKA01509 [AK024509] |
| 413 | A_24_P662427 | AK022109 | GAAGGCCCTACCCTAAGGCATGTTTCCACAATTTCTCTAAACTTTCTTTTGTGATAGTC | SEQ ID NO: 413 | Homo sapiens cDNA FLJ12047 fis, clone HEMBB1001983 [AK022109] |
| 414 | A_24_P6649895 | AK055641 | TAAGCATTTATGTTGTTCCATAACTGACATCTGACACTGTAGCAGACGTCATTGTCTCCCGGTCTT | SEQ ID NO: 414 | Homo sapiens cDNA FLJ31079 fis, clone HSYRA2001595 [AK055641] |
| 415 | A_24_P67784 | KIAA1666 | GGAACTGCAAGAGACTCCCACTGTGGACTCGGAAAGATCATGATAGCAGCGTGGACTATG | SEQ ID NO: 415 | Homo sapiens KIAA1666 protein, mRNA (cDNA clone IMAGE:4827837), complete cds. [BC035246] |

Fig. 1-24

| No. | Probe ID No. | Symbols of genes | Sequence | SEQ ID NO: | Descriptions of genes, letters and numbers within [ ] indicates GenBank accession No.) |
|---|---|---|---|---|---|
| 416 | A_24_P677890 | BC016384 | CCTTTTGTAGCAGTTTCCCAGGTTTTTCAGAGAGTGGTGAATCCATGGCTTGGCATTCCT | SEQ ID NO: 416 | Homo sapiens, clone IMAGE:4703872, mRNA [BC016384] |
| 417 | A_24_P690273 | AK024900 | TACCTGTGTGAGATACTAGTATTGATGGTGAGACGTCAATAGTAAAATATCTTGGAGGTA | SEQ ID NO: 417 | Homo sapiens cDNA: FLJ21247 fis, clone COL01205. [AK024900] |
| 418 | A_24_P699784 | PACS1 | AAGTTCCGTGATGAAGAGTCCTATCAGAGAAGTTTATTCCCTTCATTGGCGTGGTGAAGGTG | SEQ ID NO: 418 | Homo sapiens phosphofurin acidic cluster sorting protein 1 (PACS1), mRNA [NM_018026] |
| 419 | A_24_P700170 | A_24_P700170 | ACGGCTGAACATCATCTCAACCTGGACTGTGTGAACGAGGTGATTGGGATCCGGGTCAGC | SEQ ID NO: 419 | |
| 420 | A_24_P706901 | BF895757 | TCTGGGGGTCTGGGAGAGTGGACGAAGAAGCAGCAGCCCTTTGGCTTCTAAGAAGTTGATCTAG | SEQ ID NO: 420 | BF895757 RC3-MT0162-221100-012-h03 MT0162 Homo sapiens cDNA, mRNA sequence [BF895757] |
| 421 | A_24_P713185 | THC2595309 | AATATGACTAGCTTACAGAATAGCTCAGACATAGTACAGATACTCTTTACGGACTCCAGTTA | SEQ ID NO: 421 | HL_MITCSEQ Hylobates lar complete mitochondrial DNA sequence, partial (3%) [THC2595309] |
| 422 | A_24_P713312 | THC2639056 | TTTATATGTCGAGATGCTCCATGTTAGGATTAAGGGGTAATTAATAGTAATGTATGTGGA | SEQ ID NO: 422 | ALU8_HUMAN (P39195) Alu subfamily SX sequence contamination warning entry, partial (10%) [THC2639056] |
| 423 | A_24_P726115 | AK024937 | AGTGCATAGTCAGTCACTACTTTTAGTGGAGTTTGAAATCTGTTTGGAGAGCTATGTAAGTAGCCA | SEQ ID NO: 423 | Homo sapiens cDNA: FLJ21284 fis, clone COL01911. [AK024937] |
| 424 | A_24_P782337 | AK026477 | AGTCAAAAGACCTTGCATGCTGGTGACAATAGCCAGATAGTAAGATTGTTAGGATTGTCTGAATGGGAAGTTATA | SEQ ID NO: 424 | Homo sapiens cDNA: FLJ22824 fis, clone KAIA3991. [AK026477] |
| 425 | A_24_P804451 | EHMT2 | AAATGGGGGCAATCGGCACCAGAGGAAAGATCATTCTGCGGGGACGTGGCTCGGGGCTATGA | SEQ ID NO: 425 | Homo sapiens euchromatic histone-lysine N-methyltransferase 2 (EHMT2), transcript variant NG36/G9a, mRNA [NM_006709] |
| 426 | A_24_P83183 | WHSC2 | GACACTTTTGGACTCAAGGTTACATTTTTGAATGTAGTAAGTAAGTAAATTAACCAAAAAGT | SEQ ID NO: 426 | Homo sapiens Wolf-Hirschhorn syndrome candidate 2 (WHSC2), mRNA [NM_005663] |
| 427 | A_24_P84984 | TTC3 | TGCGGTTCAAGCAGTCTCCAAAAAAGGCGTTCAATAGTATTATTGAAGAGCGTCAGT | SEQ ID NO: 427 | Homo sapiens tetratricopeptide repeat domain 3 (TTC3), transcript variant 1, mRNA [NM_003316] |
| 428 | A_24_P85283 | POLR3A | AAGATGAAGTTTGGAGTTTAAAGGGGTTCTGGAGAACAGATCAAAGCAGTCTCCCGTGTC | SEQ ID NO: 428 | Homo sapiens polymerase (RNA) III (DNA directed) polypeptide A, 155kDa (POLR3A), mRNA [NM_007055] |
| 429 | A_24_P87763 | EEF2 | CATGTTTGTGGTCAAGGGCTATCTGCCGTCAACGAGTCCTTTGGCTTCACCGGCTGAGCT | SEQ ID NO: 429 | Homo sapiens eukaryotic translation elongation factor 2 (EEF2), mRNA [NM_001961] |
| 430 | A_24_P87824 | ZMYND8 | GGGTCAGCTGAGAAAAGCAAGGAGAGTGGCTCGGACCCTTGAGCTTTCTGGCTCCAGAGA | SEQ ID NO: 430 | Homo sapiens zinc finger, MYND-type containing 8 (ZMYND8), transcript variant 2, mRNA [NM_012408] |
| 431 | A_24_P883109 | AL833452 | GGGCAACCATTGTCTCAGAGGGTGCCACTTGTGTGTGTGCATTAAATCTAAGAAATAGACA | SEQ ID NO: 431 | Homo sapiens mRNA; cDNA DKFZp686E08116 (from clone DKFZp686E08116), [AL833452] |
| 432 | A_24_P895583 | TRIM26 | TTGACCACGATTGTCTCAGAGAGGGTGCCCACTTGTGTGTGTGCACAGCTGCCTGAGTCACA | SEQ ID NO: 432 | Homo sapiens tripartite motif-containing 26 (TRIM26), mRNA [NM_003449] |
| 433 | A_24_P910490 | BX099367 | AGGGCCAGAGTTGCAGACCACCTTGGGCTACACAGTGACAGGCGTGTCTGTACAAAACTA | SEQ ID NO: 433 | BX099367 Soares_fetal_liver_spleen_1NFLS_S1 Homo sapiens cDNA clone IMAGp998G055977, mRNA sequence [BX099367] |
| 434 | A_24_P914102 | A_24_P914102 | TTAGTAGACCCTAGATTTTCTACAAATGTAAAATGTTATTTTACTGTTGAAATGAG | SEQ ID NO: 434 | |

Fig. 1-25

| No. | Probe ID No. | Symbols of genes | Sequence | SEQ ID NO: | Descriptions of genes (letters and numbers within [ ] indicates GenBank accession No.) |
|---|---|---|---|---|---|
| 435 | A_24_P916006 | AA435826 | GGAAATGGTCTTCCGGTGGAGGATCAACGAGAAGCAGTGCCTGAC CTTCCAGAAAGTGGT | SEQ ID NO: 435 | AA435826 zt80a02.s1 Soares_testis_NHT Homo sapiens cDNA clone IMAGE:728618 3' similar to TR:G790819 G790819 POLYCYSTIC KIDNEY DISEASE-ASSOCIATED PROTEIN. ; mRNA sequence [AA435826] |
| 436 | A_24_P921402 | THC2484646 | AGTCTTGGGCATCCAGTTCAGTAGAATTTCAGGTGACAATATGAT GAATCATTCAGAGAA | SEQ ID NO: 436 | |
| 437 | A_24_P923684 | SIRT3 | GGAATTGGTGACGTAGGAAAACTGTTGAATTCTAAAAAGAATGAA GTTAGTTTCTAACCG | SEQ ID NO: 437 | Homo sapiens sirtuin (silent mating type information regulation 2 homolog) 3 (S. cerevisiae) (SIRT3), transcript variant 1, mRNA [NM_012239] |
| 438 | A_24_P924462 | PRKCZ | GCATGAGATGAAAGATGAACATCTATCATTGAGGCATAG TCTTTCCAACACACC | SEQ ID NO: 438 | Homo sapiens mRNA, chromosome 1 specific transcript KIAA0505. [AB007974] |
| 439 | A_24_P92952 | ARID1A | ATCACGGTTGATGAAGTCATTGGTTTGACAAGTCATTTGTGATGT ACTGTTTTTGATTGG | SEQ ID NO: 439 | Homo sapiens AT rich interactive domain 1A (SWI-like) (ARID1A), transcript variant 1, mRNA [NM_006015] |
| 440 | A_24_P930362 | CXXC5 | GCGCTTTCCCATCAACCCAAGCTGTTCATTATGACCCGGGAG GTGTGTTCCTGGCCG | SEQ ID NO: 440 | Homo sapiens CXXC finger 5 (CXXC5), mRNA [NM_016463] |
| 441 | A_24_P930337 | THC2503773 | AGCAAGTGGAACCGACGACCACCCAAAATATGACTGAAGATGTAATT TAAAATGTAGGCATAG | SEQ ID NO: 441 | |
| 442 | A_24_P930391 | AK022351 | AAGTGGGTTTAATTTCCTTTTCATGAAGGAAAGATTAGCTTTCA TGGAAACACTTGGTC | SEQ ID NO: 442 | Homo sapiens cDNA FLJ12289 fis, clone MAMMA1001788. [AK022351] |
| 443 | A_24_P930707 | THC2653001 | ATGTTAGTTACTGGCTTGCCATGTGTACCGACAGAGTGCTTTCC ACAGATTAAAAAGAA | SEQ ID NO: 443 | BX098637 BX098637 Soares fetal liver spleen 1NFLS BX098637 Homo sapiens cDNA clone IMAGp998F16386 ; IMAGE:200847. mRNA sequence [BX098637] |
| 444 | A_24_P932418 | AP2A2 | GGGGGTCAGAGGGGCTCAGTGTGGCACTGCTCGTCAAAGAA AAATAAAGGGTAGAA | SEQ ID NO: 444 | Homo sapiens adaptor-related protein complex 2, alpha 2 subunit (AP2A2), mRNA [NM_012305] |
| 445 | A_24_P933514 | AK094334 | CGTAGTGCCCAGTGTAGAATTCGTTAGGTGGGCATATTATATAC TACGGTGAAGTCTGGC | SEQ ID NO: 445 | Homo sapiens cDNA FLJ37015 fis, clone BRACE2010208. [AK094334] |
| 446 | A_24_P934861 | A_24_P934861 | GGAAGTATCAAGGAGCAAATTCCAGTTTCTGGGAAATAGTGGACC AGATCGTCTCCATGG | SEQ ID NO: 446 | |
| 447 | A_24_P935682 | AY358248 | AGTCAGATCAGCATTCAATCAATATGAGCTCTAACATGATGCT TGACAGTTATGGAAC | SEQ ID NO: 447 | Homo sapiens clone DNA166629 MRSS6228 (UNQ6228) mRNA, complete cds. [AY358248] |
| 448 | A_24_P93703 | LOC440104 | GGGTGGCACTAATTTCCTCCTTAACCAGAACTTGTTGGAGGCAAC TGACCGATTCTAACT | SEQ ID NO: 448 | Homo sapiens cDNA FLJ36942 fis, clone BRACE2005518. [AK094261] |
| 449 | A_24_P940310 | ENST00000270201 | AGGTTGACCTGCCATGCAGGGGTCTGTATGCTGATGTAGTTCATTTT ATATCGATAGGGAGA | SEQ ID NO: 449 | Nucleolar preribosomal-associated protein ; (Fragment). [Source:Uniprot/SWISSPROT;Acc:Q602B7] [ENST00000270201] |
| 450 | A_24_P940551 | FLJ38723 | TTCCCAGTTGACCCTTACGCCTTACGGTTACAGTAGCAAAATAAGACCCT ATCAGTGAGGGAGA | SEQ ID NO: 450 | Homo sapiens hypothetical protein FLJ38723 (FLJ38723), mRNA [NM_173805] |
| 451 | A_24_P942604 | SMC1A | GGGGTGACAAGATAAGCCAGGGTCTAGAGCTCGTGGTTTGGATCATGA ACCATTTCAAGTTT | SEQ ID NO: 451 | Homo sapiens structural maintenance of chromosomes 1A (SMC1A), mRNA [NM_006306] |

Fig. 1-26

| No. | Probe ID No. | Symbols of genes | Sequence | SEQ ID NO: | Descriptions of genes (letters and numbers within [ ] indicates GenBank accession No.) |
|---|---|---|---|---|---|
| 452 | A_24_P942893 | TEX261 | GATGCAGTGGCTCGCATTGCCACTCTGATTCCTCGTTTCTTTTG GTCACAGAGAAAGGG | SEQ ID NO: 452 | Homo sapiens testis expressed 261 (TEX261), mRNA [NM_144582] |
| 453 | A_24_P945262 | AK097139 | ACAGTCTGTATACCGTGGTCAGAGTGTGGCTGAGAGACAGATG AGATGGTAAAGAATT | SEQ ID NO: 453 | Homo sapiens cDNA FLJ39820 fis, clone SPLEN2010625 [AK097139] |
| 454 | A_24_P96234 | QTRT1 | TGCCGAAGGAGAAGCCCGATATCGATGGGGGTGGCTATGCCA CTGATCTGGTAGTCT | SEQ ID NO: 454 | Homo sapiens queuine tRNA-ribosyltransferase 1 (tRNA-guanine transglycosylase) (QTRT1), mRNA [NM_031209] |
| 455 | A_24_P96325 | ZGPAT | CCAGCTCGTCGGAATGTGTTTGACTTCCTCAATGAAAAGTGCAA GGTCAGGCTCGTGGG | SEQ ID NO: 455 | Homo sapiens zinc finger, CCCH-type with G patch domain (ZGPAT), transcript variant 1, mRNA [NM_032527] |
| 456 | A_32_P10633 | BC022417 | GTTGATGTTTTAAACAGGAAGGTCACGAGGAGTTCAGCCGGTGTGTG CATTTCCTCATGTAT | SEQ ID NO: 456 | Homo sapiens cDNA clone IMAGE:4243762, partial cds [BC022417] |
| 457 | A_32_P111394 | THC2643957 | GAATACAGTGTTCCTTTTCATCCCATATTTGACTGAAGGTAAGAC AGATCAATTATAAGG | SEQ ID NO: 457 | |
| 458 | A_32_P112546 | LOC649344 | AGGGAGGTCACTATGCAGGGTAGCACTGGAACAGGAGAACCCACC TGAGGCTCAGCCCTA | SEQ ID NO: 458 | PREDICTED: Homo sapiens similar to Keratin, type II cytoskeletal 8 (Cytokeratin-8) (CK-8) (Keratin-8) (K8) (LOC649344), mRNA [XR_018597] |
| 459 | A_32_P116997 | THC2719256 | AAACATTAGGTAGCAGGTTGTAGAGGATATATTAGGGTCATGAT GTCCTCTTGTTGGC | SEQ ID NO: 459 | BE147120 PM2-HT0224-221099-001-b10 HT0224 Homo sapiens cDNA, mRNA sequence [BE147120] |
| 460 | A_32_P118220 | AK091308 | GAATGTAACACACTCTGGGGTTGCTTTCCTTGGATGAGAATGAACTGAA TATGGGCTTCTCAC | SEQ ID NO: 460 | Homo sapiens cDNA FLJ33989 fis, clone DFNES2006944. [AK091308] |
| 461 | A_32_P11899 | C12orf65 | AAGGACTAGCCTGCAGTGCTTCGTTCGTTGGAATGAAGTCGAA GAGCAGTTGTGAAA | SEQ ID NO: 461 | Homo sapiens chromosome 12 open reading frame 65 (C12orf65), mRNA [NM_152269] |
| 462 | A_32_P120454 | THC2642550 | ACACAATCAGATGACTGGACTGGTTCATCTGTTTATTGCAAGCT CAGGACAGGGTATGA | SEQ ID NO: 462 | |
| 463 | A_32_P121755 | THC2672892 | AAACCCTCGTGCTTCCAGGTGGTTGCCCGGTGGCATTTGTAGCTGG GATTCCGAGGCCAGA | SEQ ID NO: 463 | Q2TXF9_ASPOR (Q2TXF9) Predicted protein, partial (5%) [THC2672892] |
| 464 | A_32_P124493 | LOC642826 | AAAGAAAAGAGCGGTTCTTGATTCCCXGAAGAGAGGTCTCATGTAACCAG AGGAGTAACCACTTC | SEQ ID NO: 464 | Homo sapiens cDNA FLJ39589 fis, clone SKMUS2008607. [AK096908] |
| 465 | A_32_P124538 | THC2758091 | AGTAGGGTTGGTCTTGATTTTGAATGAAGTGAGATGTC GTCTTTAAACCAGAC | SEQ ID NO: 465 | |
| 466 | A_32_P125589 | THC2649341 | CGGTGTCTATCCGTTGCTTTAGCCTTTGAATGAAGTGAGATGTC CATCAGGTCAGATAG | SEQ ID NO: 466 | |
| 467 | A_32_P12703 | THC2697162 | TTGAAAGAAAGAAGTATAGGGGAGGAAGTGCCAGACTAAACGAATC CTAAGTAAATAGGGT | SEQ ID NO: 467 | |
| 468 | A_32_P127583 | THC2650423 | AGAGAGCCCTCTATGTGAGATGATGACTGTTCTGTCGGTTAGGTAGAT TAGTTCATCCAACTG | SEQ ID NO: 468 | |
| 469 | A_32_P131294 | BM854107 | AGTAGGGAGAAAAGGTTTGTTCCTTAATTAGAGGTAGTGTGGGAAA TGCTAGGCACTTGTGC | SEQ ID NO: 469 | K_ESTO135406 S22SNU16n1 Homo sapiens cDNA clone S22SNU16n1-145-F11 5', mRNA sequence [BM854107] |
| 470 | A_32_P136588 | BF928446 | GTGCCCAAATGGTGAGAAATAAAAGGAAGCATTGTGGCCTTTCAG GTTTTTCAAACTCAC | SEQ ID NO: 470 | BF928446 IL2-NT0200-061200-269-F07 NT0200 Homo sapiens cDNA, mRNA sequence [BF928446] |

Fig. 1-27

| No. | Probe ID No. | Symbols of genes | Sequence | SEQ ID NO: | Descriptions of genes (letters and numbers within [ ] indicates GenBank accession No.) |
|---|---|---|---|---|---|
| 471 | A_32_P138178 | BE835321 | AGATTTGGCTTAATCCAGAGACAAGTATGAGATACAATTCTGGGAG TTTGTCTTCGTAACG | SEQ ID NO: 471 | BE835321 RC5-FN0022-300600-022-G12 FN0022 Homo sapiens cDNA, mRNA sequence [BE835321] |
| 472 | A_32_P145385 | AK001118 | CCGCAATTAACACTCGAGGAAAGCTTAAATTTCCAGGTTTTTGATT CTCAGGAAATGAGAT | SEQ ID NO: 472 | Homo sapiens cDNA FLJ10256 fis, clone HEMBB1000870. [AK001118] |
| 473 | A_32_P146844 | THC2639689 | CCTGTGGGCTGATTCCAACGTGAGAGTTGAAGTTTGTGTGGCATC ATCATGTGGGATTAA | SEQ ID NO: 473 | |
| 474 | A_32_P151244 | AK022268 | GTAGTCAGATGTCAGAGAGACTTATTTCATGTGTAACGTTTTGA ACTGTTGATGTTCTT | SEQ ID NO: 474 | Homo sapiens cDNA FLJ12206 fis, clone MAMMA1000941. [AK022268] |
| 475 | A_32_P151544 | KRT18 | GAGGACGTTCATTCTTGGTGATGCCTTGGACAGCAGCAACTCCATG CAAACCATCCAAAAG | SEQ ID NO: 475 | Homo sapiens keratin 18 (KRT18), transcript variant 1, mRNA [NM_000224] |
| 476 | A_32_P155091 | ATXN2L | GAGGTGACCTGTGTGTGAGAGACAGAGCCCATGAGGATGGCT GGACAAGAACTTTTA | SEQ ID NO: 476 | Homo sapiens ataxin 2-like (ATXN2L), transcript variant B, mRNA. [NM_145714] |
| 477 | A_32_P155416 | PRNPIP | TAGATCCAAAACGTCAAGTCAATTTTGTCACCTGTGGGAGTGGG ACTTAAAAGTCATGC | SEQ ID NO: 477 | Homo sapiens prion protein interacting protein (PRNPIP), mRNA [NM_024066] |
| 478 | A_32_P155841 | AL079294 | GCTTCCTGTTATATACCTGCAGTTACCATGTTCTTGTTAAGGAAG AATGGCAAATGCAAA | SEQ ID NO: 478 | Homo sapiens mRNA full length insert cDNA clone EUROIMAGE 362780. [AL079294] |
| 479 | A_32_P156171 | THC2634329 | TCCTATGTGGAGTCTGATTTAAGGGCTATAAGGGGTGTGTCTTCC TACCCAATACAGGTT | SEQ ID NO: 479 | |
| 480 | A_32_P159176 | THC2744561 | CAGAAGAAGATAGAAGAGCACATCTCACCAAAGACAAGTTGACCC TAACTCTTAAATCAT | SEQ ID NO: 480 | |
| 481 | A_32_P162095 | THC2673084 | AAGGTCGTTTTATTTGTGGGCCAAATAGTAGCAGGTATTAGATACG TTGGTGGGCAAGAA | SEQ ID NO: 481 | |
| 482 | A_32_P163458 | tcag7.1017 | AGATGTGGATTTCAGGAGGAAGCTTTATTCGAATGCTAATGGCAG ACATCAGGAAGGAGG | SEQ ID NO: 482 | Homo sapiens similar to Williams Beuren syndrome chromosome region 19 (MGC57359), mRNA [NM_001004351] |
| 483 | A_32_P164573 | THC2611661 | AGCTGTTTTCTATTAACACTGAAGTACTCTGAGAGCTTGGAAATT TTCAAGTGCAAAATC | SEQ ID NO: 483 | RRI2_SPIMX (P42244) Chloroplast 30S ribosomal protein S12, partial (11%) [THC2611661] |
| 484 | A_32_P16462 | THC2567672 | GGGCCAGAAGAATTGGGAGGACAGTGATGAGGAATAATTTTCAGTC TTTATCATTTTATAT | SEQ ID NO: 484 | W18193 IMAGE:20064 Soares infant brain 1NIB Homo sapiens cDNA clone IMAGE:20064, mRNA sequence [W18193] |
| 485 | A_32_P165990 | AK094623 | TGTGGGACACAGAGACAGGACTGACATTCTTGCCATGGGTGATTAAT TTGGGCCTCAGTT | SEQ ID NO: 485 | Homo sapiens cDNA FLJ37304 fis, clone BRAMY2016070. [AK094623] |
| 486 | A_32_P166356 | THC2685727 | GTGTCTTGGATTTTTAGCCACAGTGAAAAACAAGGTGAATTGCTTA ATGGCTGCAATGCTG | SEQ ID NO: 486 | |
| 487 | A_32_P167883 | THC2697442 | AGGTAATTGGGGGTATGAGTCACTTCAGTTTTGAAATATTGGGAA CTAAATTCTCTCATT | SEQ ID NO: 487 | |
| 488 | A_32_P169316 | A_32_P169316 | AGGAAGTGGAAGCATAGTCTTAGCGCAGAGCTAGATGCAAAGCAG CTGTTTGAATATAAC | SEQ ID NO: 488 | |
| 489 | A_32_P170811 | KIAA1509 | GAGTGTGAGAGGAAAGAGAGGAGTTCATTGAAGAATCAAACAGGTG GACATTGAGACCCAG | SEQ ID NO: 489 | Homo sapiens KIAA1509 (KIAA1509), mRNA [NM_001080414] |
| 490 | A_32_P176609 | ZNF609 | CAGTGGCTCTGATGATGGACCCTCAGTGATGGATGAAACAACGCA ATGATGGCTTTGATT | SEQ ID NO: 490 | Homo sapiens zinc finger protein 609 (ZNF609), mRNA [NM_015042] |

Fig. 1-28

| No. | Probe ID No. | Symbols of genes | Sequence | SEQ ID NO: | Descriptions of genes (letters and numbers within [ ] indicates GenBank accession No.) |
|---|---|---|---|---|---|
| 491 | A_32_P179526 | ZBTB20 | TTGAAGTTGGAAATCAAGGGGAATCTAAAACCGACCAGATGTTCTGCTGCTGGAAAGG | SEQ ID NO: 491 | Homo sapiens zinc finger and BTB domain containing 20, mRNA (cDNA clone IMAGE:4291354), partial cds. [BC010934] |
| 492 | A_32_P181564 | THC2608490 | TTATAAGTGCGCTTAATATCTCCAGTATCTCACAGAGAGAATTTGTCTTCAAGCCTTGGC | SEQ ID NO: 492 | |
| 493 | A_32_P184039 | A_32_P184039 | ATCATTGTTAGTGTTGGGCCCAAAAAATAGTTGTTATGTATCATGCGTAATAACTGAGCAGG | SEQ ID NO: 493 | |
| 494 | A_32_P185361 | AL109784 | GGAAGGCTGTTTGCTGAATAAGACACAAAGATAAGACATGAAAGTAAAGGATGTGGGCGT | SEQ ID NO: 494 | Homo sapiens mRNA full length insert cDNA clone EUROIMAGE 122871. [AL109784] |
| 495 | A_32_P187304 | A_32_P187304 | ATAAATGAGGAAGACATTCACATAGAAGAAAAGGTGTGGTGGAGGCTCTGACCAGCTTAACC | SEQ ID NO: 495 | |
| 496 | A_32_P192545 | TCEAL6 | ATTTGCCAGGCCCAATGCTTAAGCTTAAGCTGATATTTTGCTTTAGATGTCAATCTCG | SEQ ID NO: 496 | Homo sapiens transcription elongation factor A (SII)-like 6 (TCEAL6), mRNA [NM_001006928] |
| 497 | A_32_P194072 | DKFZP434B0335 | ATGGGGCTCAGGGCCTCGTTTAGGATGTGCAGTGACCATTCTCAGAGCAGGAGTTGCAAA | SEQ ID NO: 497 | Homo sapiens DKFZp434B0335 protein (DKFZp434B0335), mRNA [NM_015395] |
| 498 | A_32_P196287 | THC2652466 | GCTTTCACAAAGACTGTAAGCCTTAGCCAAGCATGTTTAATTTGCTGCATAGCCGGCTGTT | SEQ ID NO: 498 | Q9BHM3_PARTE (Q9BHM3) Cyclophilin-RNA interacting protein, partial (4%) [THC2652466] |
| 499 | A_32_P198845 | THC2651047 | GCCAACCAATCAACAAGCTGTGTTCACTTGAGTGACGTGGTTGTATAGCTAAGCATTAACC | SEQ ID NO: 499 | |
| 500 | A_32_P19917 | BM684461 | ATATGATCTTAAGAGTCTAAACATTCAAGAGACGAGGGCAAGAAAGCCAGTCACATGTAG | SEQ ID NO: 500 | UI-E-EJ0-aip-c-14-0-UI.s1 UI-E-EJ0 Homo sapiens cDNA clone UI-E-EJ0-aip-c-14-0-UI 3', mRNA sequence [BM684461] |
| 501 | A_32_P200429 | A_32_P200429 | GGAGGAGCAGTTCAGATCTGCGACCATTCTTAGGACAGGAAGCGACTCATTAAAGATGTTA | SEQ ID NO: 501 | |
| 502 | A_32_P203515 | SPECC1L | CATTGCTTTTGCCTCGTCTAATAGGATGCTTAGGACACTGTGGGCTTTAGGAATGACTA | SEQ ID NO: 502 | Homo sapiens SPECC1-like (SPECC1L), mRNA [NM_015330] |
| 503 | A_32_P204565 | A_32_P204565 | CAGGATCAGATGATGACACGGGGATGTGTTTCAGTGTGATGGAAAGATTGTTTCAGTGA | SEQ ID NO: 503 | |
| 504 | A_32_P205323 | tcag7.1017 | TCATGTAGAAGAACGTGGAGCGATTCTTGACAGAGCTGAATACAGTGATCACGTTGTCGTC | SEQ ID NO: 504 | Homo sapiens similar to Williams Beuren syndrome chromosome region 19 (MGC57359), mRNA [NM_001004351] |
| 505 | A_32_P208039 | AL049390 | TTTCATGTTGAAGCATTCAGATTCAGGGCTTTATTTGTCAAGGCATGTGGCAAACCTCACAA | SEQ ID NO: 505 | Homo sapiens mRNA; cDNA DKFZp58601318 (from clone DKFZp58601318). [AL049390] |
| 506 | A_32_P209582 | THC2663167 | CAATGTAAAGCCAGAATATCAACGTGCTCCTTTTGTCAAGATTTTCAAACGTATTTGGCTGAT | SEQ ID NO: 506 | ALU1_HUMAN (P39188) Alu subfamily J sequence contamination warning entry, partial (5%) [THC2663167] |
| 507 | A_32_P211048 | A_32_P211048 | GTTCACAAAAACACCTAGTAGGTATTCAGTTCATATATTGGAATGAATGAGAAAATGAGGAG | SEQ ID NO: 507 | |
| 508 | A_32_P213509 | THC2663555 | GATTTGTTCCAGTGTTGGAGGCCTTTTTAATGAAAAATTGTCAACAGCCTACACTGGAAAAA | SEQ ID NO: 508 | |
| 509 | A_32_P214054 | THC2755661 | GGGCTTATCTCTTTGTTTAACAGTTGGGGCTTTGGGTTCCATAGCAATGATTTGCAAAT | SEQ ID NO: 509 | |

Fig. 1-29

| No. | Probe ID No. | Symbols of genes | Sequence | SEQ ID NO: | Descriptions of genes (letters and numbers within [ ] indicates GenBank accession No.) |
|---|---|---|---|---|---|
| 510 | A_32_P216122 | AK130891 | TTCTTGGTCTCTATATGTTTGGGAGGCATTCATGAAGAATTGAGTACACATATATGGGTC | SEQ ID NO: 510 | Homo sapiens cDNA FLJ27381 fis, clone UBA07680. [AK130891] |
| 511 | A_32_P220567 | A_32_P220567 | GGAAAGTGAAAAATAGTTCCTATGGTGGAAGGTGGGGGTGAGACATACCTCCTCGAAA | SEQ ID NO: 511 | |
| 512 | A_32_P220560 | AK124352 | ACCAGGAGAATGCAGACTATCTTTTGGGAAATATAAGCTGGGTCCTTATGATGGAGTCGGG | SEQ ID NO: 512 | Homo sapiens cDNA FLJ42361 fis, clone UTERU2025366. [AK124352] |
| 513 | A_32_P224522 | SLC25A23 | GTTACATTCTGCACTTCATAGTTGGATTCTGAGGTTAGGATCATCTGGAGAGGGCATGGA | SEQ ID NO: 513 | Homo sapiens solute carrier family 25 (mitochondrial carrier; phosphate carrier), member 23 (SLC25A23), mRNA [NM_024103] |
| 514 | A_32_P225625 | AA971667 | GGCAAATGTGTCGTCTTTTCCCAGAGATAGAAAGCATCTTTTAAATCATCCTCCATTTT | SEQ ID NO: 514 | AA971667 np85c06.s1 Soares_NFL_T_GBC_S1 Homo sapiens cDNA clone IMAGE:1583626 3', mRNA sequence [AA971667] |
| 515 | A_32_P227110 | THC2512148 | TAAAAGAAATCGTTTTGATTGAGCGACTGTGTATTGATAATGGCTTATTATTACAATCA | SEQ ID NO: 515 | |
| 516 | A_32_P227657 | BX114900 | GTCCAGAGCGTGAAGAGAAGGTTCCTGACAGTTAGTCAGCGCGGCGTCTTTGACGGCTGAAGGAC | SEQ ID NO: 516 | BX114900 Soares_fetal_liver_spleen_1NFLS_S1 Homo sapiens cDNA clone IMAGp998L191010 , mRNA sequence [BX114900] |
| 517 | A_32_P232851 | THC2645586 | CTTTGAAAAGGATATCCTTCACATTCGTTTTCCAGAAAATTGAGGTCACTGACTTATTTC | SEQ ID NO: 517 | Q9P3E1_NEUCR (Q9P3E1) Related to rna-binding protein fus/tls, partial (5%) [THC2645586] |
| 518 | A_32_P234661 | THC2650029 | AACCAAGATAGGTAGTAAGTCAGGRTTTGATTTGTTCCTTGCCAGCAAAAAGACTTAGG | SEQ ID NO: 518 | Q88PH0_PSEPK (Q88PH0) Dipeptide ABC transporter, permease protein, partial [THC2650029] |
| 519 | A_32_P29442 | AI911989 | ATAGTTTACATGTGRAACATGAGCTAGTGTTGTACAGTGACAGACCTTGTTTCTGAT | SEQ ID NO: 519 | AI911989 wg78e07.x1 NCI_CGAP_Lu24 Homo sapiens cDNA clone IMAGE:2337732 3', mRNA sequence [AI911989] |
| 520 | A_32_P3342 | THC2676548 | TATAGCATTTTCTGAAGATCATGTTGTAGTCTTGTTCGTGTAGATGATTTGGTCAACAG | SEQ ID NO: 520 | ALU7_HUMAN (P39194) Alu subfamily SQ sequence contamination warning entry, partial (19%) [THC2676548] |
| 521 | A_32_P38782 | BX113029 | CATCCTGAGTGGTAGAAGTCCAGTGCCCTTTCTCTACCCACAGCCAGTCAGAGCAGCGAG | SEQ ID NO: 521 | BX113029 Soares_fetal_liver_spleen_1NFLS_S1 Homo sapiens cDNA clone IMAGp998E061010, mRNA sequence [BX113029] |
| 522 | A_32_P46252 | PRPF8 | GTCGTCGTGGAACTAGAACTTCATGGGTGTTCGGCATGACCCGAACATGAAATATGAGCT | SEQ ID NO: 522 | Homo sapiens PRPF8 pre-mRNA processing factor 8 homolog (S. cerevisiae) (PRPF8), mRNA [NM_006445] |
| 523 | A_32_P40673 | A_32_P40673 | GATGACACTTGATATTAGGACAGCGTACGTACTTGTTGAGTGTCAGAGGTGATATGTA | SEQ ID NO: 523 | |
| 524 | A_32_P430359 | DDX54 | CCTTTATTGAGGACTTGGCCTCAGGGTTTGGCAATGGAATTTTTAATGTAATAAA | SEQ ID NO: 524 | Homo sapiens DEAD (Asp-Glu-Ala-Asp) box polypeptide 54 (DDX54), mRNA [NM_024072] |
| 525 | A_32_P43878 | DB111455 | ATGTGAGAAGCTTCTTTAAGGTTTAATGACGAAGTTCCATGTGAGCTCTTAGTTCGGA | SEQ ID NO: 525 | DB111455 THYMU2 Homo sapiens cDNA clone THYMU2015028 5', mRNA sequence [DB111455] |
| 526 | A_32_P46404 | AK092468 | CTCTATGCCAACCTCTTTTGGATAAATACTTATGGATTCAGCCAAGAGGAAAAGCACT | SEQ ID NO: 526 | Homo sapiens cDNA FLJ35149 fis, clone PLACE6010455. [AK092468] |
| 527 | A_32_P514790 | UNK | AAGACRAAAGGGGTTTGAATGAATTAAGTGAAAACTTTTTCCTTTTTTACAAAAATGCAA | SEQ ID NO: 527 | Homo sapiens unkempt homolog (Drosophila) (UNK), mRNA [NM_001080419] |

Fig. 1-30

| No. | Probe ID No. | Symbols of genes | Sequence | SEQ ID NO: | Descriptions of genes (letters and numbers within [ ] indicates GenBank accession No.) |
|---|---|---|---|---|---|
| 528 | A_32_P52206 | TYW1 | GAGGAAGGATCCATTGATTTCGATTTGGCAAAACTTACCTGAAG GGTATGAGAGATGCG | SEQ ID NO: 528 | Homo sapiens tRNA-yW synthesizing protein 1 homolog (S. cerevisiae) (TYW1), mRNA [NM_018264] |
| 529 | A_32_P55161 | CENTG2 | AAAGAGGGTTACAGATCATTGGACATGAAGTGAAAATATTGGGAGCAGT AAACACTTCCATTAA | SEQ ID NO: 529 | Homo sapiens centaurin, gamma 2 (CENTG2), transcript variant 1, mRNA [NM_001037131] |
| 530 | A_32_P5542 | AF131782 | GAGCCTCTTACGATCTAACTTCCACTAACTGGGAGGAGGAAATGTCTT ATAAATAAAGACACAG | SEQ ID NO: 530 | Homo sapiens clone 24941 mRNA sequence. [AF131782] |
| 531 | A_32_P55427 | THC2701763 | CAGTTTTATCCCTATCTGTAAAACAAACTAGAAATTGAGAGAGTA CATTCGATAGCTTGG | SEQ ID NO: 531 | Q9F8M7_CARHY (Q9F8M7) DTDP-glucose 4,6-dehydratase (Fragment), partial (11%) [THC2701763] |
| 532 | A_32_P55987 | THC2639487 | GAAAAGAACCCAGTGCGTGTAACGGAAGTCTAATAGCTGCTGAGTA CATAGTAAATGCTAT | SEQ ID NO: 532 | Q7QGE4_ANOGA (Q7QGE4) ENSANGP00000015281 (Fragment), partial (6%) [THC2639487] |
| 533 | A_32_P57149 | JMJD1C | GAGTGGGTTAAAGTTTATGAAGATTTTTCAACTTTCTTGGTGGAA TACGAACTTAATCTGG | SEQ ID NO: 533 | Homo sapiens jumonji domain containing 1C (JMJD1C), transcript variant 1, mRNA [NM_032776] |
| 534 | A_32_P6415 | TNRC6B | GCATAGAGGTTTAATCAAAGTCCCATATGTTGAAATTGCTCCTCA TATTACTGGTTTTAC | SEQ ID NO: 534 | Homo sapiens trinucleotide repeat containing 6B (TNRC6B), transcript variant 1, mRNA [NM_015088] |
| 535 | A_32_P65067 | THC2618074 | CCCGAAAGTGAATTTAAACTTGACTTATTTATGCCGTCTGTCAT AGGAAGGGGAGAAT | SEQ ID NO: 535 | |
| 536 | A_32_P6972 | THC2621771 | AGGGCTGATTGTGGAAAATGATGCTTAGAGTTGGTTTCAGCAGGAG TGATGAAGGGAGAAT | SEQ ID NO: 536 | |
| 537 | A_32_P70875 | CD239706 | CTTTGTTTGAGAAGTTGCTAATGCAGTAGGAGAACAAGTGACAG TTTTCTTATTTACTG | SEQ ID NO: 537 | FNPBXF03 FNP Homo sapiens cDNA, mRNA sequence [CD239706] |
| 538 | A_32_P71171 | A_32_P71171 | TCTAGATAGTAATAGGAAAACCAAGAATCCAGCCTGGTGATGGCTG GAGGGAGTGATTGAA | SEQ ID NO: 538 | |
| 539 | A_32_P718498 | MLLT6 | CCACCAGCTATTTCGCAGTGTACAGATGGGCAATTCTCACGTTCA AAGAGTCGCGACCTG | SEQ ID NO: 539 | Homo sapiens myeloid/lymphoid or mixed-lineage leukemia (trithorax homolog, Drosophila); translocated to, 6 (MLLT6), mRNA [NM_005937] |
| 540 | A_32_P749354 | MGC11102 | GTTTTGTGTTTTTGGCTGCTGTGTCTGTATTGGATGTGATATGTTAT GGATGTGATGTGTTA | SEQ ID NO: 540 | Homo sapiens hypothetical protein MGC11102 (MGC11102), mRNA [NM_032325] |
| 541 | A_32_P79103 | BM932034 | GTGGTACAGAATGAAAATAGGATTTTAGGAAGGTTGAGTCAGAGG TCGAGTGGGGGATA | SEQ ID NO: 541 | UI-E-EJi-aji-k-24-0-UI.r1 UI-E-EJi-aji-k-24-0-UI 5'. cDNA clone UI-E-EJi-aji-k-24-0-UI 5'. mRNA sequence [BM932034] |
| 542 | A_32_P81357 | FAHD2A | CAAGACCAAGCAAGAGATGCTATTCAAGACAGACCTGATAGCCTG GGTGTGCCAGTTTGT | SEQ ID NO: 542 | Homo sapiens fumarylacetoacetate hydrolase domain containing 2A (FAHD2A), mRNA [NM_016044] |
| 543 | A_32_P8251 | KIAA1542 | TCGGATTCGTGCGCTCACACGTGGTCTGTGCACCTGTGTTGCTCA CAGTTGAAAACTGGA | SEQ ID NO: 543 | Homo sapiens GTD-binding SR-like protein rA9 (KIAA1542), mRNA [NM_020901] |
| 544 | A_32_P83453 | LOC647768 | TTTTCTCTTGGGATGCTCCCGGTTTGTGATTGAGAACTGTAT TGCATTGAAGAAAGT | SEQ ID NO: 544 | PREDICTED: Homo sapiens similar to Tetratricopeptide repeat protein 3 (TPR repeat protein 3) (LOC647768), mRNA [XR_018202] |
| 545 | A_32_P84289 | C1orf93 | ACAGTGGAACGTGTCTGCGGTCTGGGATGTCTGGTTATATCTGATTCTGACC CAGTACCCGTGTGGGT | SEQ ID NO: 545 | Homo sapiens chromosome 1 open reading frame 93 (C1orf93), mRNA [NM_152371] |
| 546 | A_32_P96 | LOC728411 | TGTCCAGGAGGTCTGTGTCTGGGATGTCTGGTTATATCTGATTCTGACC CAGTACCCGTGTGGGT | SEQ ID NO: 546 | Homo sapiens, clone IMAGE:4590099, mRNA. [BC048193] |

Fig. 1-31

| No. | Probe ID No. | Symbols of genes | Sequence | SEQ ID NO: | Descriptions of genes (letters and numbers within [ ] indicates GenBank accession No.) |
|---|---|---|---|---|---|
| 547 | A_32_P86626 | PHACTR4 | TCAAGCCTGAGAGGAAGCTCAGGATGTGACATGTTGTTCCTTTG CTCACAAGTCATCAT | SEQ ID NO: 547 | Homo sapiens phosphatase and actin regulator 4 (PHACTR4), transcript variant 2, mRNA [NM_023923] |
| 548 | A_32_P88987 | AK022346 | ATGGGAAGTTACTACCCAGGCTTACCAAAAGGTCAGGTTTATATA AAGTGCGTTCCTTT | SEQ ID NO: 548 | Homo sapiens cDNA FLJ12284 fis, clone MAMMA1001757 [AK022346] |
| 549 | A_32_P90468 | A_32_P90468 | AAGCCAGGAATAATTTCTATCTCATGGTACGTAAGTCCTCGAAGC TTATCATGAGAGCCT | SEQ ID NO: 549 | |
| 550 | A_32_P91328 | THC2641595 | GTTAGGGCAATAATGTCATTGAAGTCTTTAAGCTACGTCGAGTC TAAGGCCAGGGTTCA | SEQ ID NO: 550 | |
| 551 | A_32_P92783 | STIP1 | CCAGGCACTCAGGCGAACAGTTAAAGAATCCTGTAATCGCAAAGAA GATCCAGAAGCTGAT | SEQ ID NO: 551 | Homo sapiens stress-induced-phosphoprotein 1 (Hsp70/Hsp90-organizing protein) (STIP1), mRNA [NM_006819] |
| 552 | A_32_P97365 | THC2681839 | AATATGCACACACAAAACTAAAGAAAAGATGTCACTTGAGCACAC AGCTTCGTGCCCGCT | SEQ ID NO: 552 | |
| 553 | A_32_P98847 | POLRMT | AGCAGAAGAACGGCTTCCGGCCCAACTTCATCCACTCGGCTGGACT CCTCACAGATGATGC | SEQ ID NO: 553 | Homo sapiens polymerase (RNA) mitochondrial (DNA directed) (POLRMT), nuclear gene encoding mitochondrial protein, mRNA [NM_005035] |
| 554 | A_32_P96940 | THC2745859 | AAGAGTATTCCAAGATAGGAAAGGTGTGTTGTTTTAGCAGGTG TATTCAGGTAGTTA | SEQ ID NO: 554 | |
| 555 | A_32_P99097 | TNPO1 | AAATTTGGAGGCATTTCTCTGAGGAGTTCCGTTCCCTTAAAAAAG AGCGTTGCAGCTG | SEQ ID NO: 555 | Homo sapiens transportin 1 (TNPO1), transcript variant 1, mRNA [NM_002270] |
| 556 | A_23_P102235 | SNRPG | AGAACAGAACAATATTGGAATGGTGGTAATACGAGGAAAATGTAT CATCATGTTAGAAGC | SEQ ID NO: 556 | Homo sapiens small nuclear ribonucleoprotein polypeptide G (SNRPG), mRNA [NM_003096] |
| 557 | A_23_P108835 | YPEL5 | AAAGTGACTTCTGCAGTAAGTTCCTCCTATTTGCCACTGG GCTGTTGGTTAGAAG | SEQ ID NO: 557 | Homo sapiens yippee-like 5 (Drosophila) (YPEL5), mRNA [NM_016061] |
| 558 | A_23_P110704 | SLU7 | CCTCTTTCCTTGGAGAGTAGCAAGTAGTCAAGAGAGGCATCCAAGA TAGAIGCAGGTGATA | SEQ ID NO: 558 | Homo sapiens SLU7 splicing factor homolog (S. cerevisiae) (SLU7), mRNA [NM_006425] |
| 559 | A_23_P111583 | CD36 | CTTGGGTTAATGAGACTGGGACCATTGGTGATGAGAAGGCAAAC ATGTCAGAAGTCAA | SEQ ID NO: 559 | Homo sapiens CD36 molecule (thrombospondin receptor) (CD36), transcript variant 2, mRNA [NM_001001547] |
| 560 | A_23_P115872 | CEP55 | GTAAACCAAAACTTTTAAATTTCTTCCAGGTTTCTAACATGCTT ACCACTGGGGCTACTG | SEQ ID NO: 560 | Homo sapiens centrosomal protein 55kDa (CEP55), mRNA [NM_018131] |
| 561 | A_23_P117852 | KIAA0101 | TACTGGTGCCATTTTTATTGGTGTTTGATTATTGGAATGGTGCCA TATTGTCAGTCCTTC | SEQ ID NO: 561 | Homo sapiens KIAA0101 (KIAA0101), transcript variant 1, mRNA [NM_014736] |
| 562 | A_23_P118061 | CKLF | GGACAAGCCCCTGAACCATATATTGTTCACTGGATTTGCAAGTC ACCGTTATGTTATTT | SEQ ID NO: 562 | Homo sapiens chemokine-like factor (CKLF), transcript variant 4, mRNA [NM_181641] |
| 563 | A_23_P118750 | ARL6IP1 | TTCAGATTTTCAGGTGACATTAGGCTATAGTAGATACAGAGGTTAAG AGTACGTCTATGAC | SEQ ID NO: 563 | Homo sapiens ADP-ribosylation factor-like 6 interacting protein 1 (ARL6IP1), mRNA [NM_015161] |
| 564 | A_23_P119992 | VRK2 | TTTAAGTTCCAGGTGTTCACCGAAATGTGTATTGTATTTCAG TGTTTCCTTCCAGAC | SEQ ID NO: 564 | Homo sapiens vaccinia related kinase 2 (VRK2), mRNA [NM_006296] |

Fig. 1-32

| No. | Probe ID No. | Symbols of genes | Sequence | SEQ ID NO: | Descriptions of genes (letters and numbers within [ ] indicates GenBank accession No.) |
|---|---|---|---|---|---|
| 565 | A_23_P120316 | MTHFD2 | AGGATTATTGCTTGGTATTAGTAGTCATTTATGTATGTACCGT TCAGTAAGTTCTCCG | SEQ ID NO: 565 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 566 | A_23_P120644 | A_23_P120644 | GGCTTTGTTGTTGTAGGAGGAATGACTGTTGTTATATCATGTATCGAG AATTCTGGGCAAAAC | SEQ ID NO: 566 | |
| 567 | A_23_P121253 | TNFSF10 | GCAAGAATCCATCTCTGAAGTAGTGTATCACAGAGTAGTAGGCTCCA GGTTTCCTTAAGGGA | SEQ ID NO: 567 | Homo sapiens tumor necrosis factor (ligand) superfamily, member 10 (TNFSF10), mRNA [NM_003810] |
| 568 | A_23_P121622 | SULT1B1 | GAAATAGAGATTGTGTGTAGTTGAATTGAAACGAGGGCAGTTATGA ATTGATTTGGGCAAT | SEQ ID NO: 568 | Homo sapiens mRNA for SULT1B2, complete cds. [D89479] |
| 569 | A_23_P122007 | C5orf30 | ATCAGATTTCTGGTTCGGTTGGGCTGGAAATGTTTCGCTGTGTATATT TAAAGTAAATTGCAC | SEQ ID NO: 569 | Homo sapiens chromosome 5 open reading frame 30 (C5orf30), mRNA [NM_032111] |
| 570 | A_23_P123608 | JAK2 | GGATAACATGGGTGGATGAATGAAAGAAATGACGTTCATTCTGAGAGTA AAGTAGATTTACAGA | SEQ ID NO: 570 | Homo sapiens Janus kinase 2 (a protein tyrosine kinase) (JAK2), mRNA [NM_004972] |
| 571 | A_23_P124623 | THC2510119 | GGAAGAGAGATTGCTATAGTTCACCGAGTCTGAAGATTCATGAA AAATTTGTTCCTTAT | SEQ ID NO: 571 | BC000359 SPC18 protein [Homo sapiens] {exp=-1; wgp=0; cg=0}, partial (77%) [THC2510119] |
| 572 | A_23_P126057 | SCP2 | ACATTGGCAAATAGGGTGGGATAGATTTGTTCTTAATGGGTGTG ACCAATCGTGTTTTT | SEQ ID NO: 572 | Homo sapiens sterol carrier protein 2 (SCP2), transcript variant 1, mRNA [NM_002979] |
| 573 | A_23_P127195 | PRPF18 | TGAGTTCTGTACCTGATGGTAACTCTTGATTGGTTTTAAGAACTTGT TGGCCTTCATTTCAT | SEQ ID NO: 573 | Homo sapiens PRP18 pre-mRNA processing factor 18 homolog (S. cerevisiae) (PRPF18), mRNA [NM_003675] |
| 574 | A_23_P128192 | PFDN5 | CACGTTCCATTGCTCAGCTCAAAGTAGTGGTAGAGCCAAGTATGTGGA AGCCAAGGACTGTCT | SEQ ID NO: 574 | Homo sapiens prefoldin subunit 5 (PFDN5), transcript variant 1, mRNA [NM_002624] |
| 575 | A_23_P128384 | VPS29 | CAGGTAATTGGAGAGATGAATGTGAAAGTAGAACGAATCGAATACAAA AAAGGTTAAAGGCAG | SEQ ID NO: 575 | Homo sapiens vacuolar protein sorting 29 homolog (S. cerevisiae) (VPS29), transcript variant 2, mRNA [NM_057180] |
| 576 | A_23_P128447 | LRRK2 | GCAGAAGAGATACAAATCTTGCTTGACCGTTTGGGACATCAATCT TCCACGTAAGTGCA | SEQ ID NO: 576 | Homo sapiens leucine-rich repeat kinase 2 (LRRK2), mRNA [NM_198579] |
| 577 | A_23_P130089 | IFT20 | TGGCGAATTTCAGAAAATAGTTGGTTAATTGAGCTTGTTGA TCAACTTGCAAAAGA | SEQ ID NO: 577 | Homo sapiens intraflagellar transport 20 homolog (Chlamydomonas) (IFT20), mRNA [NM_174887] |
| 578 | A_23_P130293 | ANKRD12 | TCAGATTACGAAATCCAAGAGTTAGTTCATTTGTTGTTGATG TTAACGACGACTTG | SEQ ID NO: 578 | Homo sapiens ankyrin repeat domain 12 (ANKRD12), mRNA [NM_015208] |
| 579 | A_23_P130444 | ZNF701 | CTCCTTGCAGAATATCATAACGTTCATTTTGAGGTAATAGTTAC AAATAGGGTGAGGAC | SEQ ID NO: 579 | Homo sapiens zinc finger protein 701 (ZNF701), mRNA [NM_018260] |
| 580 | A_23_P13065 | ZDHHC13 | CATACAATCTTGGATTCATGCAGAACCTGGCAGAGTTGTTTCAGT GTGGCTGCTTTGGCT | SEQ ID NO: 580 | Homo sapiens zinc finger, DHHC-type containing 13 (ZDHHC13), transcript variant 1, mRNA [NM_019028] |
| 581 | A_23_P132863 | ENST00000306024 | AGGTAAATGGTATTTTCATTTTTCTGAAGGCTCTCCAATAAATATG AGGACCAAGATGCAG | SEQ ID NO: 581 | U6 snRNA-associated Sm-like protein LSm3 [Source:Uniprot/SWISSPROT:Acc:P62310] [ENST00000306024] |
| 582 | A_23_P132936 | SPCS3 | GAATGTCACTTGACCGTCGTCTTGGAACGTCTACCAAATGCTGG AATTCTACCTCTTGT | SEQ ID NO: 582 | Homo sapiens signal peptidase complex subunit 3 homolog (S. cerevisiae) (SPCS3), mRNA [NM_021928] |

Fig. 1-33

| No. | Probe ID No. | Symbols of genes | Sequence | SEQ ID NO: | Descriptions of genes (letters and numbers within [ ] indicates GenBank accession No.) |
|---|---|---|---|---|---|
| 583 | A_23_P133438 | FAM105A | TGAGCATGGAAGGAATTAGGAGGTTTTCTTGAGGATTACAGGTAC ACTGGATGCAGCCAT | SEQ ID NO: 583 | Homo sapiens family with sequence similarity 105, member A (FAM105A), mRNA [NM_019018] |
| 584 | A_23_P133648 | FAM8A1 | ACTTCGCCGAATTACAAAATGAGTGTTTTAGATTCAAGTGACG GTAAAAGGATTGTT | SEQ ID NO: 584 | Homo sapiens family with sequence similarity 8, member A1 (FAM8A1), mRNA [NM_016255] |
| 585 | A_23_P134247 | RHEB | GTGGATGTTTTTCGAAAGATAATTTGGAGGGAGAAAAAATGGAC GGGGCAGCTTCACAA | SEQ ID NO: 585 | Homo sapiens Ras homolog enriched in brain (RHEB), mRNA [NM_005614] |
| 586 | A_23_P13701 | TMBIM4 | TGCACATCCGAATGCCTTCGTGAGAAAAGTACAAGCATTCTTT CTCTGCAGGTTCTCT | SEQ ID NO: 586 | Homo sapiens transmembrane BAX inhibitor motif containing 4 (TMBIM4), mRNA [NM_016056] |
| 587 | A_23_P137016 | SAT1 | GAAATAATAGAATGAGCACCCATTCCAAAGCTTTATTACCAGTGG CGTTGTTGCATGTTT | SEQ ID NO: 587 | Homo sapiens spermidine/spermine N1-acetyltransferase 1 (SAT1), mRNA [NM_002970] |
| 588 | A_23_P138308 | CD58 | AACCTGTATCCAAGGAGGGTGATTCAAGACACAGATATGCAGT TATACCCATACCATT | SEQ ID NO: 588 | Homo sapiens CD58 molecule (CD58), mRNA [NM_001779] |
| 589 | A_23_P138507 | CDC2 | CGGATGTCAAAAGTTGGATGAAAAATGGCTTGATTTTGCTCTCGAA AAATGTTAATCTATG | SEQ ID NO: 589 | Homo sapiens cell division cycle 2, G1 to S and G2 to M (CDC2), transcript variant 1, mRNA [NM_001786] |
| 590 | A_23_P140301 | PSMA3 | TGAACTAGAACTGAGCTCGGGTTGGTGAATTAACTAATGAAGACA TGAAATTGTTCCAAA | SEQ ID NO: 590 | Homo sapiens proteasome (prosome, macropain) subunit, alpha type, 3 (PSMA3), transcript variant 1, mRNA [NM_002788] |
| 591 | A_23_P140423 | NDUFB1 | GGATTGTTATTTAGAGAGAAAGATGTGAAGGGACTAAGTCCCTTG CCGAACAAGAGTATG | SEQ ID NO: 591 | Homo sapiens NADH dehydrogenase (ubiquinone) 1 beta subcomplex, 1, 7kDa (NDUFB1), mRNA [NM_004545] |
| 592 | A_23_P142560 | ZEB2 | CTTTAATCTGTGTTTGTGCAAGTGCGATCTGATATCTGTAAGTCAATGTGTTACAGATGTTAA GAGGGTAACATGGGT | SEQ ID NO: 592 | Homo sapiens zinc finger E-box binding homeobox 2 (ZEB2), mRNA [NM_014795] |
| 593 | A_23_P144145 | DCUN1D1 | TGTTTAGTGAATATCATCTGGAATCTGTAAGTCAATTGTGT TTCTTACAGTCCTG | SEQ ID NO: 593 | Homo sapiens RP42 protein mRNA, complete cds. [AF292100] |
| 594 | A_23_P144224 | TLOC1 | ATGGGGATTGTGAAGAGGATGAGGAAGAGGAAAATGATGAGAGAA CAGCTAAATCTTCAC | SEQ ID NO: 594 | Homo sapiens translocation protein 1 (TLOC1), mRNA [NM_003262] |
| 595 | A_23_P14564 | GPR65 | AACAAGTTTAAATTGTGTTGGTCATCCAATCTGTAGTTTTTGT AAGCGAAACAGGAAG | SEQ ID NO: 595 | Homo sapiens G protein-coupled receptor 65 (GPR65), mRNA [NM_003608] |
| 596 | A_23_P145777 | NDUFA4 | ACGGCTCTTTAGAATGAAGTTCCAGAAGGACATCGGACAA TTTCCAACTTAAGCA | SEQ ID NO: 596 | Homo sapiens NADH dehydrogenase (ubiquinone) 1 alpha subcomplex, 4, 9kDa (NDUFA4), nuclear gene encoding mitochondrial protein, mRNA [NM_002489] |
| 597 | A_23_P14734 | RPS27L | TACAAGATCACCACAGGTTTTCAGCAGTGCTCAGACAGTGGTTCTT TGTGTAGGTGTTCA | SEQ ID NO: 597 | Homo sapiens ribosomal protein S27-like (RPS27L), mRNA [NM_015920] |
| 598 | A_23_P147404 | A_23_P147404 | TGGGGTTGAAGATGAAATTAGATTAGACTGGATACTGGAAATGAAAAC CGTCGTCTCATGTG | SEQ ID NO: 598 | |
| 599 | A_23_P148273 | RP11-217H1.1 | CGTTCCCAGAGATATATAGACACTGGAATGAAATGAAAACC GAAAATCGTGTGTGT | SEQ ID NO: 599 | Homo sapiens implantation-associated protein (DKFZp564K142), mRNA [NM_032121] |
| 600 | A_23_P148297 | SH3BGRL | ATAAAACAGGTTGGGATCATTTCCAAGAATTGGTTTCCCTTGAG TTTTTTGCTAAAACAA | SEQ ID NO: 600 | Homo sapiens SH3 domain binding glutamic acid-rich protein like (SH3BGRL), mRNA [NM_003022] |
| 601 | A_23_P149692 | GALNACT-2 | CATGGTTGGTTCAGAATAGATGAGGATAAGGACATGGCTTTTGTTT TTGCTTCCATTTTC | SEQ ID NO: 601 | Homo sapiens chondroitin sulfate GalNAcT-2 (GALNACT-2), mRNA [NM_018590] |

Fig. 1-34

| No. | Probe ID No | Symbols of genes | Sequence | SEQ ID NO: | Descriptions of genes (letters and numbers within [ ] indicates GenBank accession No.) |
|---|---|---|---|---|---|
| 602 | A_23_P152202 | BCL2A1 | TGTAACCATATTTGCATTTGAAGGTATTCTGATCAAGAAAGTTCTAGGACAGCAAATTGC | SEQ ID NO: 602 | Homo sapiens BCL2-related protein A1 (BCL2A1), mRNA [NM_004049] |
| 603 | A_23_P154235 | NMI | CCATGTTTGTGAATCTTGCTTGTTTGTTTGTTTGAAATGGTGCTGCATGTTTTCAACTAGAATAAGTG | SEQ ID NO: 603 | Homo sapiens N-myc (and STAT) interactor (NMI), mRNA [NM_004688] |
| 604 | A_23_P154632 | ATP5J | TAGAAATCTAAGGACGACAGAGATCTGGAGGACCTGTTGATGCTAGTTCAGAGTATCAGCAA | SEQ ID NO: 604 | Homo sapiens ATP synthase, H+ transporting, mitochondrial F0 complex, subunit F6 (ATP5J), nuclear gene encoding mitochondrial protein, transcript variant 1, mRNA [NM_001003703] |
| 605 | A_23_P15564 | AMZ2 | AAACCCGTGAAGCCTTTAAGGAATGGAAAGAGTGGAATAATAAAATGCCTGGCTGTTCTC | SEQ ID NO: 605 | Homo sapiens archaemetzincins-2 (AMZ2), transcript variant 1, mRNA [NM_016627] |
| 606 | A_23_P155677 | HIP2 | GATTTGGGGCTCATAGAAGAATTGCTTTATTGGATACTTCAAGTCATTCTTGCTTGCACTT | SEQ ID NO: 606 | Homo sapiens huntingtin interacting protein 2 (HIP2), mRNA [NM_005339] |
| 607 | A_23_P155765 | HMGB2 | TAAAAATGCAGGTTGTAGGTTTTTGATGGGCTACTGATACAGTTAGATTTTACAGCTTC | SEQ ID NO: 607 | Homo sapiens high-mobility group box 2 (HMGB2), mRNA [NM_002129] |
| 608 | A_23_P155815 | NCAPG | AAGTTAGGAAAGAGGAATGGAAGGTGGAATCGTTAAGATTATGTCCAGTATTTGCTTAA | SEQ ID NO: 608 | Homo sapiens non-SMC condensin I complex, subunit G (NCAPG), mRNA [NM_022346] |
| 609 | A_23_P157452 | POLR2K | GGAATGCTTCACTTATAGTTGGAATTGCTCTCTTGCCATTCTGTATTGTATAGCTT | SEQ ID NO: 609 | Homo sapiens polymerase (RNA) II (DNA directed) polypeptide K, 7.0kDa (POLR2K), mRNA [NM_005034] |
| 610 | A_23_P159839 | C1GALT1C1 | TCCAAATCAGATGCATGTGATGATGAATTCGGGCATATTTGTGTGAAAGGCATTTGGGCATAT | SEQ ID NO: 610 | Homo sapiens C1GALT1-specific chaperone 1 (C1GALT1C1), transcript variant 1, mRNA [NM_152692] |
| 611 | A_23_P163216 | ATP8B4 | ATCAGTGTATTTCGATAAAGTGATTCGGAGAATGATTCGGGACATATTTGTGTGAAAACCTCAGTTCTGTCA | SEQ ID NO: 611 | Homo sapiens ATPase, Class I, type 8B, member 4 (ATP8B4), mRNA [NM_024837] |
| 612 | A_23_P165402 | SF3B14 | CATGTGATCAGGTTCAGGGATTCAATGTTTGTAAGAGATACGTTGTGGTTTTGTAGTATA | SEQ ID NO: 612 | Homo sapiens splicing factor 3B, 14 kDa subunit (SF3B14), mRNA [NM_016047] |
| 613 | A_23_P165819 | A_23_P165819 | AGCAGTGTTGTTGTTGAAGTGTGGAGTTGTAAGCTGCTGGGACTATGGACAGCACACAAT | SEQ ID NO: 613 | |
| 614 | A_23_P168592 | CCDC126 | GGGCAGTATAGAATAGGCAGTTGAAAATACACCTTGTGCTGCTGCCATCCACTGTGGATTATA | SEQ ID NO: 614 | Homo sapiens coiled-coil domain containing 126 (CCDC126), mRNA [NM_138771] |
| 615 | A_23_P169576 | EXOC6 | ATGTGAATCTTCCTTTGCCTTTCAGGATTTAGGGCTGTAAGAAGTAGCCTGATTC | SEQ ID NO: 615 | Homo sapiens exocyst complex component 6 (EXOC6), transcript variant 2, mRNA [NM_010138348] |
| 616 | A_23_P170233 | CSTA | AACTGGCTACTGAGTCATGATCCTTGCTGATAATATAACCATCAATAAAGAAGCATTGT | SEQ ID NO: 616 | Homo sapiens cystatin A (stefin A) (CSTA), mRNA [NM_005213] |
| 617 | A_23_P17287 | IAH1 | TGGGAGATGGAGAGCATTAGCCAATCACAGGAGACCCAAATGCTTGTTATCTACAGAA | SEQ ID NO: 617 | Homo sapiens isoamyl acetate-hydrolyzing esterase 1 homolog (S. cerevisiae) (IAH1), mRNA [NM_001039613] |
| 618 | A_23_P18325 | PDCD10 | CCAACGCAGTAATTCATCAAAGCAACTTAATAGTTCAGACGTTCAAAACTGTGGCTGAA | SEQ ID NO: 618 | Homo sapiens programmed cell death 10 (PDCD10), transcript variant 1, mRNA [NM_007217] |
| 619 | A_23_P200507 | CNIH4 | TGGTTGAAGTCAGGCTACACAGTTGAGGAGCCAGAGACTTGTTAAATCAT | SEQ ID NO: 619 | Homo sapiens cornichon homolog 4 (Drosophila) (CNIH4), mRNA [NM_014184] |

Fig. 1-35

| No. | Probe ID No | Symbols of genes | Sequence | SEQ ID NO. | Descriptions of genes (letters and numbers within [ ] indicates GenBank accession No.) |
|---|---|---|---|---|---|
| 620 | A_23_P201756 | CD46 | CTCATGAGTGCAACTGTGTGGGTTAGGTAATATTGGAATGTGGCTTGAATGTAGGTAGGCATC | SEQ ID NO: 620 | Homo sapiens CD46 molecule, complement regulatory protein (CD46), transcript variant a, mRNA [NM_002389] |
| 621 | A_23_P201918 | ABCB10 | CATGATGAGGGCTAGACCCTAAGAAGTAATTAAGTCAATGTAAATCAAATGGAAGTTTTC | SEQ ID NO: 621 | Homo sapiens ATP-binding cassette, sub-family B (MDR/TAP), member 10 (ABCB10), nuclear gene encoding mitochondrial protein, mRNA [NM_012089] |
| 622 | A_23_P202750 | C11orf54 | TGCAAGAGTTTCTCTATGGCATTGGTCAAGCAAAAGAGAAGAGCATTCATTGGGCCGAGATTA | SEQ ID NO: 622 | Homo sapiens chromosome 11 open reading frame 54 (C11orf54), mRNA [NM_014039] |
| 623 | A_23_P202978 | CASP1 | CTGTTCCTGTGATGTGGAGGAAATTTTCGGCAAGGTTCGATTTTCATTTGAGCAGCAGA | SEQ ID NO: 623 | Homo sapiens caspase 1, apoptosis-related cysteine peptidase (interleukin 1, beta, convertase) (CASP1), transcript variant alpha, mRNA [NM_033292] |
| 624 | A_23_P20384 | LSM1 | TGAGTGAAAGTGACATCGTGGCCAGGTCAGGCATTTGATCACAGACTGTAGAGTTTTGAA | SEQ ID NO: 624 | Homo sapiens LSM1 homolog, U6 small nuclear RNA associated (S. cerevisiae) (LSM1), mRNA [NM_014462] |
| 625 | A_23_P204550 | SCYL2 | TGTGACTTCCTGACTACGTACCTTCATATTTCATTTCAAATTCAAAGTCTGAAGGTTGCA | SEQ ID NO: 625 | Homo sapiens SCY1-like 2 (S. cerevisiae) (SCYL2), mRNA [NM_017988] |
| 626 | A_23_P205281 | C14orf2 | TGATAAAAGAAGTAAGGCTTTGAAAGGTCAGGCGCTGGCTCCTGGTCATGACTAACCAGA | SEQ ID NO: 626 | Homo sapiens chromosome 14 open reading frame 2 (C14orf2), mRNA [NM_004894] |
| 627 | A_23_P205768 | ARPP-19 | GGGCAATATTTGCCCATTCTGGTGTAACTATATGTGACTCTAGTGCTTAACAGGTGCGTT | SEQ ID NO: 627 | Homo sapiens cyclic AMP phosphoprotein, 19 kD (ARPP-19), mRNA [NM_006628] |
| 628 | A_23_P206396 | CKLF | ATTATCAACTTACTGGTAACAACAGTATTCATGCTCATCGTATCTGTGTTGGCACTGATA | SEQ ID NO: 628 | Homo sapiens chemokine-like factor (CKLF), transcript variant 1, mRNA [NM_016951] |
| 629 | A_23_P207445 | MAP2K6 | ACAGGATCAATAGAAAGTCATCTTTGAGATAATTTAACCCTGGCTCTCAGAGGGTTTTCT | SEQ ID NO: 629 | Homo sapiens mitogen-activated protein kinase kinase 6 (MAP2K6), mRNA [NM_002758] |
| 630 | A_23_P20882 | ATP6V1G1 | AGGTCCTTCGACTTTTTGGAGAGTAGCCAATCTAGCTTTTTTGTACAGAGTTAGAAATTA | SEQ ID NO: 630 | Homo sapiens ATPase, H+ transporting, lysosomal 13kDa, V1 subunit G1 (ATP6V1G1), mRNA [NM_004888] |
| 631 | A_23_P208666 | GMFG | CTCCAAGAAAAGTTGTCTTTGTTCATTGATCTCTGGGGTGGGACTGAATTCCTGATGT | SEQ ID NO: 631 | Homo sapiens glia maturation factor, gamma (GMFG), mRNA [NM_004877] |
| 632 | A_23_P210274 | PREI3 | GGATGAGTAGTGCCGTAGGATTGTACAGAAATATTTCACATGCTTATTTCATCATCGGCAG | SEQ ID NO: 632 | Homo sapiens preimplantation protein 3 (PREI3), transcript variant 1, mRNA [NM_015387] |
| 633 | A_23_P211840 | UBE1C | GCCACCCTAGAGGCGAAAAATAGAACAGTTTACTTACAGAGTCGGTAACGTGTATTGAAGAA | SEQ ID NO: 633 | Homo sapiens ubiquitin-activating enzyme E1C (UBA3 homolog, yeast) (UBE1C), transcript variant 1, mRNA [NM_003968] |
| 634 | A_23_P212706 | ATG3 | AAGAACACAGTCAGGATCATGTGAAGAAAACAGTGACCATTGAAAATCACCCTCATCTGC | SEQ ID NO: 634 | Homo sapiens ATG3 autophagy related 3 homolog (S. cerevisiae) (ATG3), mRNA [NM_022488] |
| 635 | A_23_P213247 | FBXL5 | ATGGGAGGTGATTCGTTCTGTTTACACAGTTAACACTGTAGGAAGCTTGGAGATCTTTCC | SEQ ID NO: 635 | Homo sapiens F-box and leucine-rich repeat protein 5 (FBXL5), transcript variant 2, mRNA [NM_033535] |
| 636 | A_23_P213638 | PANK3 | TGTATATAGCCACGTGATTAAATCCTAAAATGAATACAGCGTCTGATTATTGAGCTTCCTC | SEQ ID NO: 636 | Homo sapiens pantothenate kinase 3 (PANK3), mRNA [NM_024594] |
| 637 | A_23_P217236 | HMGB3 | GAGCTGTGAGTCTGCAGGGGGATCCATTAGCTTCAGGTTGTCTTGTTTCTGTATATA | SEQ ID NO: 637 | Homo sapiens high-mobility group box 3 (HMGB3), mRNA [NM_005342] |

Fig. 1-36

| No | Probe ID No. | Symbols of genes | Sequence | SEQ ID NO: | Descriptions of genes (letters and numbers within [ ] indicates GenBank accession No.) |
|---|---|---|---|---|---|
| 638 | A_23_P22671 | SYBL1 | GAAACCGAATACGGTGAGCAGTCAACTGCAGCGGTTGGGGTTGAT TCCTGTTGAATAATA | SEQ ID NO: 638 | Homo sapiens synaptobrevin-like 1 (SYBL1), mRNA [NM_005638] |
| 639 | A_23_P24515 | ACAT1 | GAGGATTGTTGGTCATTTGACTCATGCTTGAAGCAAGGAGAATA CGGTCTTGCCAGTAT | SEQ ID NO: 639 | Homo sapiens acetyl-Coenzyme A acetyltransferase 1 (acetoacetyl Coenzyme A thiolase) (ACAT1), nuclear gene encoding mitochondrial protein, mRNA [NM_000019] |
| 640 | A_23_P250042 | SELT | GGAAGATAGTGTTTCAGTGCTGCTGGCATATTTTGGAATTCTGCACAT TCATGGAGTGGAATA | SEQ ID NO: 640 | Homo sapiens selenoprotein T (SELT), mRNA [NM_016275] |
| 641 | A_23_P250904 | UBQLN1 | GTTTGACAAACATGTCCCAGCAAAGTGCCGGTTAGTACAGTTTG TTGAAATACAGTAG | SEQ ID NO: 641 | Homo sapiens ubiquilin 1 (UBQLN1), transcript variant 1, mRNA [NM_013438] |
| 642 | A_23_P251421 | CDCA7 | ATTACTTGCATATGTAAACCATTGCTGTGCCATTCAATGTTTGA TGCATAATTGGACCT | SEQ ID NO: 642 | Homo sapiens cell division cycle associated 7 (CDCA7), transcript variant 1, mRNA [NM_031942] |
| 643 | A_23_P251945 | DCTN4 | ACACGTTTGCATAGACTACAGACAGTCATGCGTTTATGGCAGGT AGTGGTATTTATTC | SEQ ID NO: 643 | Homo sapiens dynactin 4 (p62) (DCTN4), mRNA [NM_016221] |
| 644 | A_23_P252145 | C1GALT1 | ATATGTCTATATATATGAGGAACTTGTGTTTTTTAAATGGTGGCC AGGTAGGAAGCTAG | SEQ ID NO: 644 | Homo sapiens core 1 synthase, glycoprotein-N-acetylgalactosamine 3-beta-galactosyltransferase, 1 (C1GALT1), mRNA [NM_020156] |
| 645 | A_23_P252371 | RBBP8 | GGCCAGGAGCAGGAAGACATAGAGCGTTGAAACAGAAAACAAGGAT GAAGGACAGTTTTT | SEQ ID NO: 645 | Homo sapiens retinoblastoma binding protein 8 (RBBP8), transcript variant 1, mRNA [NM_002894] |
| 646 | A_23_P253524 | CENPE | CTGAGTGCAAAGTCAGTAGACTCAGTTGTCACTTCTCTGGAG ATCCAGGATTCGTTA | SEQ ID NO: 646 | Homo sapiens centromere protein E, 312kDa (CENPE), mRNA [NM_001813] |
| 647 | A_23_P256223 | VBP1 | TGAAGGTCAGGGATTGTTGGAAGAATTTATCGACTGCCACAAA GAATTCATTCCCT | SEQ ID NO: 647 | Homo sapiens von Hippel-Lindau binding protein 1 (VBP1), mRNA [NM_003372] |
| 648 | A_23_P256231 | FBXO30 | GCCTTTTAAGTTTTGCTGAAGAATGTGTGTGGTTAGGATAAGC AGAAGGATTAAGCTT | SEQ ID NO: 648 | Homo sapiens F-box protein 30 (FBXO30), mRNA [NM_032145] |
| 649 | A_23_P256868 | DCP2 | CCGTGGCATGTAATGGACATTGGAAGTTCCCGTTTCATCCAGAG CCTTTGTTGAGTTCA | SEQ ID NO: 649 | Homo sapiens DCP2 decapping enzyme homolog (S. cerevisiae) (DCP2), mRNA [NM_152624] |
| 650 | A_23_P25735 | PSMA6 | TAGCAGAGAGAGCAGGATTGTGGTAACATTGTGGTTAGTTACCAGGATCGGTG ATGCCACTTACGTGT | SEQ ID NO: 650 | Homo sapiens proteasome (prosome, macropain) subunit, alpha type, 6 (PSMA6), mRNA [NM_002791] |
| 651 | A_23_P258814 | ENST00000328644 | GGAAGGTGTGCAGAATGGTGCAGGCTGCTCTCTCATTATAAAAGT GATTATGACAAAGA | SEQ ID NO: 651 | DPH3 homolog B (CSL-type zinc finger-containing protein 1). [Source: Uniprot/SWISSPROT-Acc: Q9H4G8] [ENST00000328644] |
| 652 | A_23_P259272 | WSB2 | AACGTTACATGACTCGTTGAGAAAGTTGAGGAATTTCCTCTAGCA CCTTGTGCTGAA | SEQ ID NO: 652 | Homo sapiens WD repeat and SOCS box-containing 2 (WSB2), mRNA [NM_018639] |
| 653 | A_23_P259521 | WDR41 | TTGGGCAGTTTAAGATTATTTCAAAAATTAGAGGAAGAATGGTGAC TTATACCTTGCTGTC | SEQ ID NO: 653 | Homo sapiens WD repeat domain 41 (WDR41), mRNA [NM_018268] |
| 654 | A_23_P2705 | P2RY5 | TCTGTATTGTGTTTCCAAGTGTGTTTGTTGACCGGTATAGTTACT AGTTTACATCGGACA | SEQ ID NO: 654 | Homo sapiens purinergic receptor P2Y, G-protein coupled, 5 (P2RY5), mRNA [NM_005767] |
| 655 | A_23_P28664 | KIAA1212 | GGGAACTTCTATGATAGAGGACAACAATAAGCCTGAGTTTTTTGAGAC CTGGTCTCGAAAAA | SEQ ID NO: 655 | Homo sapiens KIAA1212 (KIAA1212), mRNA [NM_018084] |
| 656 | A_23_P29005 | SAMSN1 | CTCTGGTTGCTCTATATGTCATCAGGAAATTCAGATAATGGCAAAGA GGATCTGGAGTCTCA | SEQ ID NO: 656 | Homo sapiens SAM domain, SH3 domain and nuclear localization signals 1 (SAMSN1), mRNA [NM_022136] |

Fig. 1-37

| No. | Probe ID No. | Symbols of genes | Sequence | SEQ ID NO: | Descriptions of genes (letters and numbers within [ ] indicate GenBank accession No.) |
|---|---|---|---|---|---|
| 657 | A_23_P30069 | FLJ31033 | AGATTTGTTAAGTCCCGTAGACTTTCTTATTCTAAATGATCAAGAGTACACTTGCTGG | SEQ ID NO: 657 | Homo sapiens cDNA FLJ13681 fis, clone PLACE2000014, weakly similar to HYPOTHETICAL HELICASE C26H8.3 IN CHROMOSOME III [AK023743] |
| 658 | A_23_P30336 | CCNH | AGTGTCAAAGAAATCCAAACATGAGGAGGAATGGACTGATGACGAGGTGGTAGAAT | SEQ ID NO: 658 | Homo sapiens cyclin H (CCNH), mRNA [NM_001239] |
| 659 | A_23_P304287 | PSMC2 | GATCAGCACTGATGAGGCCAGGAGGAGTGGATAGAAAAATTGAATTTACTTGCGCGAT | SEQ ID NO: 659 | Homo sapiens proteasome (prosome, macropain) 26S subunit, ATPase, 2 (PSMC2), mRNA [NM_002803] |
| 660 | A_23_P305759 | ABHD3 | GATCGTAGAGTGAAGTCAGTAGGAATTGCAGTATTGTGTCTAAATTCTGTGGATGATGTT | SEQ ID NO: 660 | Homo sapiens abhydrolase domain containing 3 (ABHD3), mRNA [NM_138340] |
| 661 | A_23_P307940 | CAPZA2 | GTACAAGATTGGCAAAGAGATGCAGAATGCATAAGATGAACATTGCATGAGGGGATCATT | SEQ ID NO: 661 | Homo sapiens capping protein (actin filament) muscle Z-line, alpha 2 (CAPZA2), mRNA [NM_006136] |
| 662 | A_23_P31097 | OSTM1 | ACTGAAAATGTGGTCGGGTTTGTTCTCGTGACTGTTTATGGTGCTGGAACTTAGGACT | SEQ ID NO: 662 | Homo sapiens osteopetrosis associated transmembrane protein 1 (OSTM1), mRNA [NM_014028] |
| 663 | A_23_P31315 | CBX3 | GCGGTGGAAGAGTTGTTCGGGGTGTTTTTGCATCCATAGCCACTGGTTACTTTGAACAAATA | SEQ ID NO: 663 | Homo sapiens chromobox homolog 3 (HP1 gamma homolog, Drosophila) (CBX3), transcript variant 2, mRNA [NM_016587] |
| 664 | A_23_P314262 | PAPD4 | TCTGTGTAGAAGAACGTTTTGATGAAGAAATAACAGCCAGAGCAGTGGACGAAAAGCAGA | SEQ ID NO: 664 | Homo sapiens PAP associated domain containing 4 (PAPD4), mRNA [NM_173797] |
| 665 | A_23_P31660 | RIT1 | TGGTGCTTGCTCTTTCACTTAACTGATAAGAGGGACATGCCTACTAGGAGTTTTTAATGA | SEQ ID NO: 665 | Homo sapiens Ras-like without CAAX 1 (RIT1), mRNA [NM_006912] |
| 666 | A_23_P31671 | UQCRB | AAGCCATAAGAGAACTTCCTGAGAACCTTATAATGACAGGATGTTCGGATTAAGAAGGG | SEQ ID NO: 666 | Homo sapiens ubiquinol-cytochrome c reductase binding protein (UQCRB), mRNA [NM_006294] |
| 667 | A_23_P324633 | C9orf72 | TTTGGATTTAGTCCGTGGGATTCAGTCGTGTAGAAATGTCTAATAGTTCTCATAGGTCC | SEQ ID NO: 667 | Homo sapiens chromosome 9 open reading frame 72 (C9orf72), transcript variant 1, mRNA [NM_018325] |
| 668 | A_23_P32577 | DACH1 | AATATTAATGTCTAGTTGTTCTATATTATAACCACATTTGCGGTCTATGCAAGGCCCTTGG | SEQ ID NO: 668 | Homo sapiens dachshund homolog 1 (Drosophila) (DACH1), transcript variant 1, mRNA [NM_080759] |
| 669 | A_23_P326170 | CALM2 | TAAACTTGTTTAGCCACTTAAAATCTGCTTAGCGACATTTGGCTCAAAATGCATTCG | SEQ ID NO: 669 | Homo sapiens calmodulin 2 (phosphorylase kinase, delta) (CALM2), mRNA [NM_001743] |
| 670 | A_23_P328511 | HSBP1 | TCTTGAACATGGTATCTTGACATGTTGGGACGTTGGTCAGTTGT | SEQ ID NO: 670 | Homo sapiens heat shock factor binding protein 1 (HSBP1), mRNA [NM_001537] |
| 671 | A_23_P329198 | OBFC2A | ACATGCATAAGTGGTACCCAGTTGCCCTTTTTACTGTAGGGTGGATAACGTTAGGATT | SEQ ID NO: 671 | Homo sapiens oligonucleotide/oligosaccharide-binding fold containing 2A (OBFC2A), mRNA [NM_001031716] |
| 672 | A_23_P339480 | HAT1 | AACATGAACAGCTGGAAGAGAGTTTCAGGAACTAGTGAAGATTACCGGCGTGTTATTG | SEQ ID NO: 672 | Homo sapiens histone acetyltransferase 1 (HAT1), transcript variant 1, mRNA [NM_003642] |
| 673 | A_23_P339557 | MLSTD2 | GGCCAATGTAAATCTAAGCTCCAATCATCTTTATATCATTACGGATTGCTGTAAGCC | SEQ ID NO: 673 | Homo sapiens male sterility domain containing 2 (MLSTD2), mRNA [NM_032228] |
| 674 | A_23_P344973 | MYL6 | CCTATGAGGATTATGTCGAAGGACTTCGGGTGTTTGACAAGGAAGGAAATGGCACGGTCA | SEQ ID NO: 674 | Homo sapiens myosin, light chain 6, alkali, smooth muscle and non-muscle (MYL6), transcript variant 2, mRNA [NM_079423] |
| 675 | A_23_P345591 | PSMA2 | GCGTGGAAAGCACAGCAATGGAAAGAACTATGTGAATGGAAGAGTTTCCTTGAGAAAACTTTACTTGAGAAA | SEQ ID NO: 675 | Homo sapiens proteasome (prosome, macropain) subunit, alpha type, 2 (PSMA2), mRNA [NM_002787] |

Fig. 1-38

| No. | Probe ID No. | Symbols of genes | Sequence | SEQ ID NO: | Descriptions of genes (letters and numbers within [ ] indicates GenBank accession No.) |
|---|---|---|---|---|---|
| 676 | A_23_P346006 | CCPG1 | TATGGTCGGCAGTAATGCAAGAGACGAAATGGCAAATCTTGAAATAGAATTGGGGCAATTACCT | SEQ ID NO: 676 | Homo sapiens cell cycle progression 1 (CCPG1), transcript variant 2, mRNA [NM_020739] |
| 677 | A_23_P34628 | GTF2B | TGTTACAATCAGACAGTCCTATAGACTGATCTATCGTCGAGCCCCAGATCGTTCCTAC | SEQ ID NO: 677 | Homo sapiens general transcription factor IIB (GTF2B), mRNA [NM_001514] |
| 678 | A_23_P351903 | TMEM167 | AAACTGGATTGTTGGGTATATTTGGAAGTGTGCCAGAATTGGTGAACGGAAGAGTCGTT | SEQ ID NO: 678 | Homo sapiens transmembrane protein 167 (TMEM167), mRNA [NM_174909] |
| 679 | A_23_P355067 | TMCO1 | AAGTCAAGAACTCTTTATTTTCTATCATTCTTTGTAGACACAGACATCAGACTGGGAA | SEQ ID NO: 679 | Homo sapiens transmembrane and coiled-coil domains 1 (TMCO1), mRNA [NM_019026] |
| 680 | A_23_P355244 | SAMD9 | TCACTGGAGGAAGAATTTTCCCTTGCTTCTGCATAAAATTTTAACTCCATAACTTATAAGC | SEQ ID NO: 680 | Homo sapiens sterile alpha motif domain containing 9 (SAMD9), mRNA [NM_017654] |
| 681 | A_23_P357995 | ZBTB8OS | ATCAATTGGGTGGGGACGAAGAATTTCATTGTCCAAGCAGCCTCAGGGAACAGAAGTCAA | SEQ ID NO: 681 | Homo sapiens zinc finger and BTB domain containing 8 opposite strand (ZBTB8OS), mRNA [NM_178547] |
| 682 | A_23_P371266 | DNM3 | ACTGTCTCTTGGGACTTCAGGATTTCTTTCTATCTGTGTACTACAGTACTCTAGAATGGAA | SEQ ID NO: 682 | Homo sapiens dynamin 3 (DNM3), mRNA [NM_015569] |
| 683 | A_23_P37441 | B2M | TTGTCTTTCAGCAAGGACTGGTCTTCGTCCATCGTGTACTACACTGAATTCACCGCGACT | SEQ ID NO: 683 | Homo sapiens beta-2-microglobulin (B2M), mRNA [NM_004048] |
| 684 | A_23_P37535 | RAB8B | AGGGTTTCCTATTTCAGCACAATCTAGACCAGTGGGATTGGCAAGTATTGTTTTGTGTCGAAG | SEQ ID NO: 684 | Homo sapiens RAB8B, member RAS oncogene family (RAB8B), mRNA [NM_016530] |
| 685 | A_23_P378722 | SAT1 | CCATGTACTACTTTTACCATCATGACCGGTGAAGATTGGAGCAAGTATTGTATGTGAGCACTTCT | SEQ ID NO: 685 | Homo sapiens spermidine/spermine N1-acetyltransferase (SAT1), mRNA [NM_002970] |
| 686 | A_23_P380848 | TXNL5 | CTGGTGGAAATGTTGTCTCTGAAGATTAAGATTTTAGGATGGCAATGATGTCTTGATGT | SEQ ID NO: 686 | Homo sapiens thioredoxin-like 5 (TXNL5), mRNA [NM_032731] |
| 687 | A_23_P389118 | TMEM16F | TATGTTTGAGAGGGTAAAAATGTATGAGCAGCTTAAGTGAAGTAGAACTATTCATGATGCC | SEQ ID NO: 687 | Homo sapiens transmembrane protein 16F (TMEM16F), mRNA [NM_001025356] |
| 688 | A_23_P406355 | FAM76B | AAGTGTGGAACAACTTCAGGCCAAAATTCAGGCCCAAAATTGAGACTTAAAGCTTAGGAAGAACTACTCAAACT | SEQ ID NO: 688 | Homo sapiens family with sequence similarity 76, member B (FAM76B), mRNA [NM_144664] |
| 689 | A_23_P41114 | CSTA | AAAGAAAATGAGAGACTTATGGAAGATTGGAAGCTGCAGTATAAAACTCAAGTTGTTGCTG | SEQ ID NO: 689 | Homo sapiens cystatin A (stefin A) (CSTA), mRNA [NM_005213] |
| 690 | A_23_P412392 | SEC22B | GTTTTGATGGCCTTTTAAACAAGAGCCAGTATGTGAAGGTTAATTGCCTGTGCTCCACA | SEQ ID NO: 690 | Homo sapiens SEC22 vesicle trafficking protein homolog B (S. cerevisiae) (SEC22B), mRNA [NM_004892] |
| 691 | A_23_P412980 | SNX13 | CCGCATGTCAAGGCAAGAATGGGGTTGGTTTCTTCCATTCAAACTAATCAGCATTCTCCA | SEQ ID NO: 691 | Homo sapiens sorting nexin 13 (SNX13), mRNA [NM_015132] |
| 692 | A_23_P41645 | ELL2 | TGTCTTTCAAATGTCTGTTTTGAACAAATGTCTTTTGA | SEQ ID NO: 692 | Homo sapiens elongation factor, RNA polymerase II, 2 (ELL2), mRNA [NM_012081] |
| 693 | A_23_P419239 | ETNK1 | GGGCTTTGGGACTTGAAGTTACTGAAGAAAAGGAGGTAGAAATAGTCTTCATTCAAGTCAATCA | SEQ ID NO: 693 | Homo sapiens ethanolamine kinase 1 (ETNK1), transcript variant 1, mRNA [NM_018638] |
| 694 | A_23_P422794 | NSMCE2 | CATTGTTCGCATGATTGAGTCCAAGGCAAAGCGGAAGAAAAAGGCCTATTGCCCTCAAAT | SEQ ID NO: 694 | Homo sapiens non-SMC element 2, MMS21 homolog (S. cerevisiae) (NSMCE2), mRNA [NM_173685] |
| 695 | A_23_P424080 | YIPF4 | AAAGCAATTCGTTTTAAGATTGTGTGCGATATTCACCTAAAAAGTTGTGCCAAAAGCACC | SEQ ID NO: 695 | Homo sapiens Yip1 domain family, member 4 (YIPF4), mRNA [NM_032312] |

Fig. 1-39

| No. | Probe ID No. | Symbols of genes | Sequence | SEQ ID NO: | Descriptions of genes (letters and numbers within [ ] indicates GenBank accession No.) |
|---|---|---|---|---|---|
| 696 | A_23_P42514 | C6orf62 | TCCTTTGGAGTAAAACTAGTGCTTACGCAGTTTCCAATTGTATTTA GGTTCTCGTTGGAAT | SEQ ID NO: 696 | Uncharacterized protein C6orf62 (HBV X-transactivated gene 12 protein). [Source:Uniprot/SWISSPROT Acc:Q9GZU0] [ENST00000378119] |
| 697 | A_23_P429491 | FLJ25416 | GCTTGGTCACGTGAATTGTTTCATAAAAAGTCACCTGAAGCGAA TTCCTGAACTTTAA | SEQ ID NO: 697 | Homo sapiens hypothetical protein FLJ25416 (FLJ25416), mRNA [NM_145018] |
| 698 | A_23_P42975 | PRKAR2B | GCCACATTTTTAGAACACTGTTTAACATTTTTGCAAAACCTTCTT GTAGGAAAAGAGAGC | SEQ ID NO: 698 | Homo sapiens protein kinase, cAMP-dependent, regulatory, type II, beta (PRKAR2B), mRNA [NM_002736] |
| 699 | A_23_P43049 | DCTN6 | AAATACATTTGAAGTCATCCGTGAGAATACGGTGATCTATGGTGG AGACTGCCTTCGTCG | SEQ ID NO: 699 | Homo sapiens dynactin 6 (DCTN6), mRNA [NM_006571] |
| 700 | A_23_P434766 | NUP50 | TATAATCTGAGTTGTATTAGTTTTTTGAATGCTCCCATCGAGGAA GTGTAACAATCCATG | SEQ ID NO: 700 | Homo sapiens nucleoporin 50kDa (NUP50), transcript variant 2, mRNA [NM_007172] |
| 701 | A_23_P434809 | S100A8 | AAAGGCGATGAAGAAAGCCACAAAGAGTAGCTGAGTTACTGGGCC AGAGGGTGGGCCCGT | SEQ ID NO: 701 | Homo sapiens S100 calcium binding protein A8 (S100A8), mRNA [NM_002964] |
| 702 | A_23_P43945 | CIP29 | AAGGCAGAGACGGCTTTGGGATTGCGTGATGAAAGTTCCTGATA CTTCTGTGTTCTCCAG | SEQ ID NO: 702 | Homo sapiens cytokine induced protein 29 kDa (CIP29), mRNA [NM_033082] |
| 703 | A_23_P44768 | TBK1 | TGTAGTCGAGTGGGAGTAAATAAGTTATTTTCTGACCGCCTA CTGAAATATTTTA | SEQ ID NO: 703 | Homo sapiens TANK-binding kinase 1 (TBK1), mRNA [NM_013254] |
| 704 | A_23_P48897 | CCPG1 | AAGTCAGAAGAGCTCATATATATATTCTAATGTCCCACCTATGT CCATTCCATGTACCA | SEQ ID NO: 704 | Homo sapiens cell cycle progression restoration 8 protein (CPR8), mRNA, complete cds. [AF011794] |
| 705 | A_23_P50038 | HTR7 | TAACTCCATTGACATTGCTTCACGAGACATGGGAAAAGGTA CGTTCCTGAAAGGG | SEQ ID NO: 705 | Homo sapiens 5-hydroxytryptamine (serotonin) receptor 7 (adenylate cyclase-coupled) (HTR7), transcript variant d, mRNA [NM_019859] |
| 706 | A_23_P50108 | NDC80 | AAAGTGGGAAATAACTTGCAACGTCTTCAGAGATGGTTGGCTACA GATGTTGGGTCTGTA | SEQ ID NO: 706 | Homo sapiens NDC80 homolog, kinetochore complex component (S. cerevisiae) (NDC80), mRNA [NM_006101] |
| 707 | A_23_P51009 | NDUFB3 | CCGGCAATGAAGCTTGAGAATACATGGGTGGGTTTGGAAGAGTGT TTCCTTTTCTGATGT | SEQ ID NO: 707 | Homo sapiens NADH dehydrogenase (ubiquinone) 1 beta subcomplex, 3, 12kDa (NDUFB3), mRNA [NM_002491] |
| 708 | A_23_P51487 | GBP3 | AATCCTAAAGCATAAAGTTAGTGTTTTGGTGATTCTAAAGGTCAT ACTTGAAATCCTGCG | SEQ ID NO: 708 | Homo sapiens guanylate binding protein 3 (GBP3), mRNA [NM_018284] |
| 709 | A_23_P51572 | TSNAX | GAAATGGGGACATTGATACGCCCGTTTCAAGTGAGCCAGTTTTTACG TCAGGTTATGATGG | SEQ ID NO: 709 | Homo sapiens translin-associated factor X (TSNAX), mRNA [NM_005999] |
| 710 | A_23_P5389 | LOC84661 | TAGCTGGATCAGACAGTTGTGCCTATCTTATTAGAGGACTTGCT GTGCTGAAAGGAA | SEQ ID NO: 710 | Homo sapiens dpy-30-like protein (LOC84661), mRNA [NM_032574] |
| 711 | A_23_P56390 | C4orf32 | TAATACTAACTATTTTAGTACTGTCAGTACTGTACATGCCA CTGGTGTTAATAGGG | SEQ ID NO: 711 | Homo sapiens chromosome 4 open reading frame 32 (C4orf32), mRNA [NM_152400] |
| 712 | A_23_P58396 | PDGFC | CATGGAATATTTTATGTACAGAAGATATGTGTCTTAACCAGTTCAG TTATTGTACTCTGGC | SEQ ID NO: 712 | Homo sapiens platelet derived growth factor C (PDGFC), mRNA [NM_016205] |
| 713 | A_23_P59921 | SUB1 | CAGAATGGGAAAATGAGGTACGTAGTGTCGCGATTTTAAAGGG AAAGTGCTAATTGAT | SEQ ID NO: 713 | Homo sapiens SUB1 homolog (S. cerevisiae) (SUB1), mRNA [NM_006713] |

Fig. 1-40

| No. | Probe ID No. | Symbols of genes | Sequence | SEQ ID NO: | Descriptions of genes (letters and numbers within [ ] indicates GenBank accession No.) |
|---|---|---|---|---|---|
| 714 | A_23_P60248 | TXN | GGACAAAGAGGTGGGTGAATTTTCTGGAGCCAATAAGGAAAAGCTTGAAGCCACCATTAAT | SEQ ID NO: 714 | Homo sapiens thioredoxin (TXN), mRNA [NM_003329] |
| 715 | A_23_P63655 | ATP5C1 | AGAGAGGTGAAACCAGGTCGAATATATGGATTGGGATCTTTAGGTCTGTATGAAAAAGCT | SEQ ID NO: 715 | Homo sapiens ATP synthase, H+ transporting, mitochondrial F1 complex, gamma polypeptide 1 (ATP5G1), nuclear gene encoding mitochondrial protein, transcript variant 2, mRNA [NM_005174] |
| 716 | A_23_P63896 | FAS | ATGTCTATCCACAGGGTAAGCCAGCTGATGAATCAATAGAAGAAGGCTATGACGTTTTGC | SEQ ID NO: 716 | Homo sapiens Fas (TNF receptor superfamily, member 6) (FAS), transcript variant 1, mRNA [NM_000043] |
| 717 | A_23_P64129 | HTATIP2 | AAAGTCAGCATGTTTAACTTTGTGTTTAGTATCCTCAGGCATCCATTCCAATCAAGA | SEQ ID NO: 717 | Homo sapiens HIV-1 Tat interactive protein 2, 30kDa (HTATIP2), mRNA [NM_006410] |
| 718 | A_23_P65262 | RP11-298P3.3 | AGCCAAGACTTAACAAGCAGACTGACTACCGTTCCCTTGAGGCTACCATTATCACAAGGGTTT | SEQ ID NO: 718 | Human BRCA2 region, mRNA sequence CG016. [U50529] |
| 719 | A_23_P69188 | DPH3 | TGCTGTTCTGTAAGAGTGTGGATTGTTTCTATCAAGCTGCTGATATCATCTTCAGGAAGCA | SEQ ID NO: 719 | Homo sapiens DPH3, KTI11 homolog (S. cerevisiae) (DPH3), transcript variant 1, mRNA [NM_206831] |
| 720 | A_23_P69908 | GLRX | CTGATAAAACTTACAGCCCCGTACACCAAGAGTGTATCTGTGAAAGAGCTGCTACAGTTT | SEQ ID NO: 720 | Homo sapiens glutaredoxin (thioltransferase) (GLRX), mRNA [NM_002064] |
| 721 | A_23_P69958 | AP3S1 | GATCAGAAGTGGAGCATTCCTTAATTCGTTCTGCTATATGTACACAGTTGTTATTTGGA | SEQ ID NO: 721 | Homo sapiens adaptor-related protein complex 3, sigma 1 subunit (AP3S1), mRNA [NM_001284] |
| 722 | A_23_P70290 | TMEM30A | ATCTTCTGCCTCAACTGTAAACCACAGTGTAAGGCTTAATGGAGACGTGTTTCATTCTTG | SEQ ID NO: 722 | Homo sapiens transmembrane protein 30A (TMEM30A), mRNA [NM_018247] |
| 723 | A_23_P71117 | SLC25A40 | CTGAAAGAAGATGGAGACTGTTAGGCGAAGATGGTTTTCAGGATATCTCTCACAATG | SEQ ID NO: 723 | Homo sapiens solute carrier family 25, member 40 (SLC25A40), mRNA [NM_018843] |
| 724 | A_23_P74799 | SLC25A24 | GATTCTGTATCTTTGGAAAAAAGCCGAGAGTTGAAGATAGTAGTATATTTCTGGTAGTGTG | SEQ ID NO: 724 | Homo sapiens solute carrier family 25 (mitochondrial carrier; phosphate carrier), member 24 (SLC25A24), transcript variant 2, mRNA [NM_2136511] |
| 725 | A_23_P75028 | REEP3 | AGAAACGACCACCAAGTGTATTTTAGTCATCTACACGTCAAATATCCCAAGACAGATTAT | SEQ ID NO: 725 | Homo sapiens receptor accessory protein 3 (REEP3), mRNA [NM_001001330] |
| 726 | A_23_P76480 | BF213738 | AAATGAACAGAGGACAATGGGTAGATGGAGGCTAGATTTACCAAATCGTTGGCATGACAGG | SEQ ID NO: 726 | BF213738 601847628F1 NIH_MGC_55 Homo sapiens cDNA clone IMAGE:4078519 5', mRNA sequence [BF213738] |
| 727 | A_23_P76799 | BAZ1A | TACACATGAATGAATCAATCTTATAACCTTGAAGTGCTGTACCAGTGCGTGGCTGCAGGT | SEQ ID NO: 727 | Homo sapiens bromodomain adjacent to zinc finger domain, 1A (BAZ1A), transcript variant 1, mRNA [NM_013448] |
| 728 | A_23_P77073 | SPPL2A | ATGTCAGACTGGTTCTGTTAGATATAGTGTTCGTGTACAGTTGGCTATGGTATTG | SEQ ID NO: 728 | Homo sapiens signal peptide peptidase-like 2A (SPPL2A), mRNA [NM_032802] |
| 729 | A_23_P77145 | RAB11A | TATAGAATATAGTCCAGTTAAATCTTTGGTTCAGTATGTCTGAAGAGTACAGTGAGAGG | SEQ ID NO: 729 | Homo sapiens RAB11A, member RAS oncogene family (RAB11A), mRNA [NM_004663] |
| 730 | A_23_P78092 | EVI2A | GCTGAATCAGACACTTGGAAAAGAACAAAACAGCTCACAGAGACCCAACCTAGTGATGGAA | SEQ ID NO: 730 | Homo sapiens ecotropic viral integration site 2A (EVI2A), transcript variant 1, mRNA [NM_001003927] |

Fig. 1-41

| No. | Probe ID No. | Symbols of genes | Sequence | SEQ ID NO: | Descriptions of genes (letters and numbers within [ ] indicates GenBank accession No.) |
|---|---|---|---|---|---|
| 731 | A_23_P79199 | DBI | TGCTCACCATACGGCTCTAACACAGATTAGGGGCTAAAACGATTAGTGACTTCCTTGAGTA | SEQ ID NO: 731 | Homo sapiens diazepam binding inhibitor (GABA receptor modulator, acyl-Coenzyme A binding protein) (DBI), transcript variant 1, mRNA [NM_020548] |
| 732 | A_23_P81212 | MRPS18C | ATGGGTTTATGCCAGTTAGATACAAGGATCCTGCATATCTCAAGGACCGTAAAGTTTGT | SEQ ID NO: 732 | Homo sapiens mitochondrial ribosomal protein S18C (MRPS18C), nuclear gene encoding mitochondrial protein, mRNA [NM_016067] |
| 733 | A_23_P81612 | SRP19 | AGGAAAGAAAAAGAAGTAACCTAGTAGTACAAGGATCTATCAGCATCAAGTATGTGGTACTACTGTAAGAGAC | SEQ ID NO: 733 | Homo sapiens signal recognition particle 19kDa (SRP19), mRNA [NM_003135] |
| 734 | A_23_P81690 | COX7A2 | AGCTCTGTATGGACCCAGTAATCTGATAAATAACCGAGCTCTCTTTGGGATCAATATT | SEQ ID NO: 734 | Homo sapiens cytochrome c oxidase subunit VIIa polypeptide 2 (liver) (COX7A2), mRNA [NM_001865] |
| 735 | A_23_P82674 | GBAS | TTACAAGTGTAGCCAATAACTGAGAAATGTTTTAAGTCAGTCGATTTGTAAGCAGTCCAC | SEQ ID NO: 735 | Homo sapiens glioblastoma amplified sequence (GBAS), mRNA [NM_001483] |
| 736 | A_23_P82748 | ENY2 | CATTCCTGCTGTCATGCCAGCCTTTAAGATTGAATTAGAATTGTGTTGTGTGGTTTTA | SEQ ID NO: 736 | Homo sapiens enhancer of yellow 2 homolog (Drosophila) (ENY2), mRNA [NM_020189] |
| 737 | A_23_P83073 | HIATL1 | AAACAACTCAAGCATTCTGGTCGGAACATAGAGATAGTTGTAGGCTGCTTCTAAGAAAGTTAT | SEQ ID NO: 737 | Homo sapiens hippocampus abundant transcript-like 1 (HIATL1), mRNA [NM_032558] |
| 738 | A_23_P83175 | PTPLAD2 | CATCGTTTTGTGGTGATCACCAGTCAAGAGGAAGTCGAAGAGAAATATAGTGGTGTGT | SEQ ID NO: 738 | Homo sapiens protein tyrosine phosphatase-like A domain containing 2 (PTPLAD2), mRNA [NM_010109151] |
| 739 | A_23_P83278 | CHMP5 | CATTGCTCTTTATTTTTTCCATTAAGAGACTCATTGCTTGGGAAATGCTTCTCTGTAC | SEQ ID NO: 739 | Homo sapiens chromatin modifying protein 5 (CHMP5), mRNA [NM_016410] |
| 740 | A_23_P83414 | PPP1CB | AAATAGGACATATGTCCAATCCAGTGATTTAATCATACAGATTGACTGGGGAACTTTA | SEQ ID NO: 740 | Homo sapiens protein phosphatase 1, catalytic subunit, beta isoform (PPP1CB), transcript variant 1, mRNA [NM_002709] |
| 741 | A_23_P86403 | KIF5B | AACAACTAGAGTGCAATTTGGCATCTTAGGACGGAAAAAGGACAGTTAGAAGTGTG | SEQ ID NO: 741 | Homo sapiens kinesin family member 5B (KIF5B), mRNA [NM_004521] |
| 742 | A_23_P86653 | SRGN | AGGACTTGGGTCAACATGGAATTAGAACAGGATTTTATGTTATAAAAGAGGATACATTTTGCCAC | SEQ ID NO: 742 | Homo sapiens serglycin (SRGN), mRNA [NM_002727] |
| 743 | A_23_P92842 | SAR1B | TAATCTGACATCCACCCCAGCGGCGCATTTGTAAAGAGCAACTTCCAGCAGTACATTTGAAG | SEQ ID NO: 743 | Homo sapiens SAR1 gene homolog B (S. cerevisiae) (SAR1B), transcript variant 2, mRNA [NM_016103] |
| 744 | A_23_P94230 | LY96 | TGAAGCTATTTCTGGGAGCCAGAAGAAATGCTCTTTTGCTTGGAGTTTGATGGTACA | SEQ ID NO: 744 | Homo sapiens lymphocyte antigen 96 (LY96), mRNA [NM_015364] |
| 745 | A_23_P94533 | CTSL1 | AAGACATGGATCATGGTGGTGGTGGTGGCTACGGATTTGAAAGCACAGAATCAGATA | SEQ ID NO: 745 | Homo sapiens cathepsin L1 (CTSL1), transcript variant 1, mRNA [NM_001912] |
| 746 | A_23_P94932 | C2orf25 | TCGTTGATGACCTTGGATGTGTGTAAGTGATTGGTCATAGTCTCTGGGGTACCCATGTA | SEQ ID NO: 746 | Homo sapiens chromosome 2 open reading frame 25 (C2orf25), mRNA [NM_015702] |
| 747 | A_23_P95130 | SLC37A3 | TTGAGGGATACGTAATTCGATTCGGTTAGGGGATATTTTTCAACCTCTTGCTTTATACT | SEQ ID NO: 747 | Homo sapiens solute carrier family 37 (glycerol-3-phosphate transporter), member 3 (SLC37A3), transcript variant 1, mRNA [NM_207113] |
| 748 | A_23_P96382 | TIMM8B | TTGTTACTAAGGAGATTTAAGGGTCAGTGGGGGAAGGCTATCAACCCATTGTCAGATCAG | SEQ ID NO: 748 | Homo sapiens translocase of inner mitochondrial membrane 8 homolog B (yeast) (TIMM8B), mRNA [NM_012459] |

Fig. 1-42

| No. | Probe ID No. | Symbols of genes | Sequence | SEQ ID NO: | Descriptions of genes (letters and numbers within [ ] indicates GenBank accession No.) |
|---|---|---|---|---|---|
| 749 | A_24_P101859 | LOC392221 | GCTTCAGTTGGGAGGAAGTAATGGTGAGCCTGCAAAAACTTGACATCACTTACCAAGCAGCATC | SEQ ID NO: 749 | PREDICTED: Homo sapiens similar to Coiled-coil-helix-coiled-coil-helix domain-containing protein 2 (HCV NS2 trans-regulated protein) (NS2TP) (LOC392221), mRNA [XM_373252] |
| 750 | A_24_P103886 | ID1 | GTCTCGGCTCCTTCAAAACAGTGTCTTAATTAAGTTTCATATTAGCAGATTAAAGTAGGACAGAG | SEQ ID NO: 750 | Homo sapiens isopentenyl-diphosphate delta isomerase 1 (IDI1), mRNA [NM_004508] |
| 751 | A_24_P105164 | RP11-217H1.1 | GGAATAATGTGTGTGGCTGGTATTGGACTTGTTGTTGTATTATTCTTCAGTTGGATGCTCTGT | SEQ ID NO: 751 | Homo sapiens implantation-associated protein (DKFZp564K142), mRNA [NM_032121] |
| 752 | A_24_P105648 | BX111927 | TTATGAGATGGTTCAGTTGCAAATAACAGTGGAGTAATTCAGGTATATCTAAAAGACTGCC | SEQ ID NO: 752 | BX111927 Soares_multiple_sclerosis_2NbHMSP Homo sapiens cDNA clone IMAGp998G05619, mRNA sequence [BX111927] |
| 753 | A_24_P11045 | THC2785765 | CCAACCAGAAACGTACACCTGATTTTCATGACAAATACGGTAGGAACACAAGTCGGAATAG | SEQ ID NO: 753 | COX7B_HUMAN (P24311) Cytochrome c oxidase polypeptide VIIb, mitochondrial precursor, partial (78%) [THC2785765] |
| 754 | A_24_P110591 | A_24_P110591 | TGATGGAACTATAAGAACAGAATCAGGAACTGTAATGAGGTCTGTTGGGCAGAATCCCAC | SEQ ID NO: 754 | |
| 755 | A_24_P111737 | ATP11B | GCTCCTGTCAAGTGCTTGGTTCTGGTTGGTTTGGCATAATCCTGCATGGTTGTTACATGTGTATT | SEQ ID NO: 755 | Homo sapiens ATPase, Class VI, type 11B (ATP11B), mRNA [NM_014616] |
| 756 | A_24_P114249 | GALNT3 | ATTTCAAATGGAGAATACTTGACTCATTTAAAGGTAAATTTTGTTACTGATTCAATTATA | SEQ ID NO: 756 | Homo sapiens UDP-N-acetyl-alpha-D-galactosamine:polypeptide N-acetylgalactosaminyltransferase 3 (GalNAc-T3) (GALNT3), mRNA [NM_004482] |
| 757 | A_24_P114617 | CHMP2B | GGCTAATTGAAATATGTAGTCTTATTTAGACACGGCCTGTGTTAAAAGAGACCAGGTTT | SEQ ID NO: 757 | Homo sapiens chromatin modifying protein 2B (CHMP2B), mRNA [NM_014043] |
| 758 | A_24_P115774 | BIRC2 | GATACCATTTTGGTTAAAGGAAATGCTGCGGCCAAGATCTCAAAAACTGTCTAAAAGAA | SEQ ID NO: 758 | Homo sapiens baculoviral IAP repeat-containing 2 (BIRC2), mRNA [NM_001166] |
| 759 | A_24_P119141 | PROS1 | AGGAAGCACAGAAGAATCTTACTTCTGTTCCGTCTTATCCCTGTAGCATCATGAGACATCAGATTA | SEQ ID NO: 759 | Homo sapiens protein S (alpha) (PROS1), mRNA [NM_000313] |
| 760 | A_24_P12149 | CLINT1 | TTAACTTGGCAAGGCTTGGCTGTGTTTCCGTGTTTATCCCTGTAGCCATCATTTAAGTCAGGAACA | SEQ ID NO: 760 | Homo sapiens clathrin interactor 1 (CLINT1), mRNA [NM_014666] |
| 761 | A_24_P123052 | RAP2B | GGAATAAGTTCCTGGATTATAAGTATAAAGGAAGCGGAGATTTAATTTGGAGATCATCAC | SEQ ID NO: 761 | Homo sapiens RAP2B, member of RAS oncogene family (RAP2B), mRNA [NM_002886] |
| 762 | A_24_P124992 | PSMA4 | AAAGGTCCCCTTTGGTGTTCATTGCTGTAGATTGGCTGGGATAAGCAGTATGGCTTTCAG | SEQ ID NO: 762 | Homo sapiens proteasome (prosome, macropain) subunit, alpha type, 4 (PSMA4), mRNA [NM_002789] |
| 763 | A_24_P126741 | ENST00000309178 | AGCCCTGAACCACACAGTAAGCTAAGAATTCAAGATTACTTGAACAAGGTCAGAGGAGAAT | SEQ ID NO: 763 | |
| 764 | A_24_P131392 | FAM82A | CTATGCCCTGGTTATTCTAATCCCAATTACATGTACTTAGAAAGTGTTATAGTGATCTT | SEQ ID NO: 764 | Homo sapiens family with sequence similarity 82, member A (FAM82A), mRNA [NM_144713] |
| 765 | A_24_P137372 | ATP2C1 | TCCGCTTGAGAAGGTTTTCAGACTGAGAGCCTAAGGATACTGGATGTGTTGTTCTTTT | SEQ ID NO: 765 | Homo sapiens ATPase, Ca++ transporting, type 2C, member 1 (ATP2C1), transcript variant 2, mRNA [NM_001001487] |

Fig. 1-43

| No. | Probe ID No. | Symbols of genes | Sequence | SEQ ID NO: | Descriptions of genes (letters and numbers within [ ] indicates GenBank accession No.) |
|---|---|---|---|---|---|
| 766 | A_24_P140827 | PCMT1 | GGATGAATTGTAAAAGCAACATCAGGTTGACGAGTATAAAATTACAGTGGATTGCTGATC | SEQ ID NO: 766 | Homo sapiens protein-L-isoaspartate (D-aspartate) O-methyltransferase (PCMT1), mRNA [NM_005389] |
| 767 | A_24_P146670 | SLK | TGTGGTTGCTGGTGTGTGTAATTATTAATGAAATGTTCACTCGTAGTCGCTTATGAGGCT | SEQ ID NO: 767 | Homo sapiens STE20-like kinase (yeast) (SLK), mRNA [NM_014720] |
| 768 | A_24_P152385 | THC2736233 | CAAACAGGTCACAGTCAAGGAAGCTGTGTTGAATGTTCAGAGGTCACTGGGGTGTGGAT | SEQ ID NO: 768 | ATP5L_PONPY (Q5RFH0) ATP synthase subunit g, mitochondrial (ATPase subunit g), partial (91%) [THC2736233] |
| 769 | A_24_P157415 | ATP11B | CTGTACTGTAACACCAGCCTGTAAAGTTAGGCCATATAAATGCAAGGGTAATCATATATAC | SEQ ID NO: 769 | Homo sapiens ATPase, Class VI, type 11B (ATP11B), mRNA [NM_014616] |
| 770 | A_24_P169976 | LOC652912 | TTCTGTTCTGTTCTGAGTATCACCCAAAAACCAAAGGAGAACATCCTGTCCAGTGCACTA | SEQ ID NO: 770 | PREDICTED: Homo sapiens similar to High mobility group protein B1 (High mobility group protein 1) (HMG-1) (Amphoterin) (Heparin-binding protein p30) (LOC652912), mRNA [XR_019552] |
| 771 | A_24_P175187 | SAMD9 | CAACCAGCGATAGGTACGTAATCAAATGTAATTTTCGCCTAATAAAATTATGGATATGGGCAG | SEQ ID NO: 771 | Homo sapiens sterile alpha motif domain containing 9 (SAMD9), mRNA [NM_017654] |
| 772 | A_24_P175188 | SAMD9 | TGGAATGTACTGGCAGATTAACATACAACCTATGTTTTGAACAAAACAACCAAGGATA | SEQ ID NO: 772 | Homo sapiens sterile alpha motif domain containing 9 (SAMD9), mRNA [NM_017654] |
| 773 | A_24_P175519 | TXN | AAGTAGATGGATGAGACTGTCAGGATGTGGTTCGAGAGTGTGAAGTCAAATGCACGCAA | SEQ ID NO: 773 | Homo sapiens thioredoxin (TXN), mRNA [NM_003329] |
| 774 | A_24_P175989 | VPS29 | GAGAGGAGACTTCGATGAGAATCTGAATTATCGAAGAAGAAAGTTGTGACTGTGGACA | SEQ ID NO: 774 | Homo sapiens vacuolar protein sorting 29 homolog (S. cerevisiae) (VPS29), transcript variant 2, mRNA [NM_057180] |
| 775 | A_24_P177634 | A_24_P177634 | GATTCATTCAGGTCTGTATGGACGAGAAGTCTGATAAATGAGTTCTGTTTGGGGATCAA | SEQ ID NO: 775 | |
| 776 | A_24_P180424 | TMEM30A | CAATGTGATGGACATTCTCTTTAGTAAGGCAGGAATTGTTTTGGTTAGGTTTTCCTAAG | SEQ ID NO: 776 | Homo sapiens transmembrane protein 30A (TMEM30A), mRNA [NM_018247] |
| 777 | A_24_P186862 | CHMP5 | TGAGAATTTAGAAGAGACCAGCTAGTGGACATGATGGAAGATGGCAAATGAAATGCAAGAAGC | SEQ ID NO: 777 | Homo sapiens chromatin modifying protein 5 (CHMP5), mRNA [NM_016410] |
| 778 | A_24_P195327 | LOC391040 | ACAGCTTAAGAATCCTTAAGAAGTTAGCTGAAACAGTTCGATGGCAAGTCTTGGACAGTA | SEQ ID NO: 778 | PREDICTED: Homo sapiens similar to basic transcription factor 3-like 4 (LOC391040), mRNA [XR_019253] |
| 779 | A_24_P200162 | HIGD1A | TATTCCATGTATCGGGAATTCTGGGCAAAAGCCTAAGCCTTAGAAGAAGAGATGCTGTCTT | SEQ ID NO: 779 | Homo sapiens HIG1 domain family, member 1A (HIGD1A), mRNA [NM_014056] |
| 780 | A_24_P20120 | KIAA1212 | TTGGACAATGAAAATGCCTTAAAAGGAATGCATATGGATAAAGTTGCACTTATAACACCC | SEQ ID NO: 780 | Homo sapiens KIAA1212 (KIAA1212), mRNA [NM_018084] |
| 781 | A_24_P201702 | CLEC2B | ATTGGAATTCAAGTAAATACAACTGTTCCACTCAACAATGCCGACCTAACTATAATTGACA | SEQ ID NO: 781 | Homo sapiens C-type lectin domain family 2, member B (CLEC2B), mRNA [NM_005127] |
| 782 | A_24_P209204 | C6orf62 | GGTTGCATACTTTTATTGGAGTAAATCTGAATGATCCTACTCCTTTGGAGTAAGAGTAGT | SEQ ID NO: 782 | Homo sapiens chromosome 6 open reading frame 62 (C6orf62), mRNA [NM_030939] |
| 783 | A_24_P211351 | ENST00000370395 | GTTGTGGATTCGTTTCATCAACTGTGATTTCATCTTCAGGAAGCAAGTCCATAACATGA | SEQ ID NO: 783 | DPH3 homolog B (CSL-type zinc finger-containing protein 1). [Source:Uniprot/SWISSPROT;Acc:Q9H4G8] [ENST00000370395] |

Fig. 1-44

| No. | Probe ID No | Symbols of genes | Sequence | SEQ ID NO: | Descriptions of genes (letters and numbers within [ ] indicates GenBank Accession No.) |
|---|---|---|---|---|---|
| 784 | A_24_P216654 | SOAT1 | GGCAGTAATGTTCTGCACAACAGTATTGTAATTGTAATGAATCATAACCTGCTAACTAG | SEQ ID NO: 784 | Homo sapiens sterol O-acyltransferase (acyl-Coenzyme A: cholesterol acyltransferase) 1 (SOAT1), transcript variant 68113, mRNA [NM_003101] |
| 785 | A_24_P223124 | FNDC3B | GTGACTGTTGGACATAGATTCCAAGGTTTTCAACTCTAGGAGAAAAGAAAATCATGTTT | SEQ ID NO: 785 | Homo sapiens fibronectin type III domain containing 3B (FNDC3B), mRNA [NM_022763] |
| 786 | A_24_P23245 | NDUFA6 | TTCTGGTCATTAAGGGAAAGATCGAACTGGAAGAGAAACAATTAAAGTATGAAGGAGGCGGA | SEQ ID NO: 786 | Homo sapiens NADH dehydrogenase (ubiquinone) 1 alpha subcomplex, 6, 14kDa (NDUFA6), nuclear gene encoding mitochondrial protein, mRNA [NM_002490] |
| 787 | A_24_P234214 | HNRPLL | AGAGCTGTCACACACCTTAATAATGTCAAATTATTTGGGAAAAGACTTAATGTTTGGGTG | SEQ ID NO: 787 | Homo sapiens heterogeneous nuclear ribonucleoprotein L-like (HNRPLL), mRNA [NM_133394] |
| 788 | A_24_P240065 | VPS24 | CACCATGAGGAGTTGTCCAAAGAAAATGATGAAGGCTGGGATCATAGAGGAGATGTTAGA | SEQ ID NO: 788 | Homo sapiens vacuolar protein sorting 24 homolog (S. cerevisiae) (VPS24), transcript variant 1, mRNA [NM_016079] |
| 789 | A_24_P247608 | PCMT1 | GTATGGTTGGATGTAGTGGAAAAGTCATAGGAATTGATCACATTAAGAGCTAGTAGATG | SEQ ID NO: 789 | Homo sapiens protein-L-isoaspartate (D-aspartate) O-methyltransferase (PCMT1), mRNA [NM_005389] |
| 790 | A_24_P255314 | SRP14P1 | TATCGAATGGAAAAAGAAGATGAGCACTGTGGTGAACTCCAAGGAAGTGAGTAAGTTTCA | SEQ ID NO: 790 | Homo sapiens signal recognition particle 14kDa (homologous Alu RNA binding protein) pseudogene 1 (SRP14P1) on chromosome 12 (NR_003273] |
| 791 | A_24_P263524 | TXNDC9 | TGACTTCACGACACAGAAAGTTTAGAATAAGGATTACAGGAAGCAGTAGTGTTCTGACATTGTTAATTACAG | SEQ ID NO: 791 | Homo sapiens thioredoxin domain containing 9 (TXNDC9), mRNA [NM_005783] |
| 792 | A_24_P278460 | MLSTD2 | ACCCAATGGAACAATATGCTTAGGATTCAGGAAGCAGTCCTTAGTTACACTCTTGTCTG | SEQ ID NO: 792 | Homo sapiens male sterility domain containing 2 (MLSTD2), mRNA [NM_032228] |
| 793 | A_24_P283320 | PCMT1 | CAAAATGTAACCGATACAATGGATTCTGGACAATCAATAGGTTGCAAGGAAGAATCAGTG | SEQ ID NO: 793 | Homo sapiens protein-L-isoaspartate (D-aspartate) O-methyltransferase (PCMT1), mRNA [NM_005389] |
| 794 | A_24_P320284 | DHFR | CTCTCTGATGTCCAGGAGAGGAGAAAGCAATTAAGTACAAATTGAAGTATATGAAGAAT | SEQ ID NO: 794 | Homo sapiens dihydrofolate reductase (DHFR), mRNA [NM_000791] |
| 795 | A_24_P320326 | SUB1 | CCCTTGTCATCTCTAAGAAAACCTGTAAAGAAACAAAAGAACAGGTGAGACTTCAGAGAG | SEQ ID NO: 795 | Homo sapiens SUB1 homolog (S. cerevisiae) (SUB1), mRNA [NM_006713] |
| 796 | A_24_P322353 | PSTPIP2 | AGAATCTTTGGTTGCTAGAGCCCCAGAATTCAAATACAAGTATGGCTATTTCGTTTAGACTTTCACAAA | SEQ ID NO: 796 | Homo sapiens proline-serine-threonine phosphatase interacting protein 2 (PSTPIP2), mRNA [NM_024430] |
| 797 | A_24_P324506 | A_24_P324506 | GCAATATAAGGCAGCTAATTGCAAATACAAGTATGGCTATTTCGTGTGGACATGTGTGT | SEQ ID NO: 797 |  |
| 798 | A_24_P324886 | DOCK4 | ATTTTCCCTCTTTTGTTGGGAGCTCATTTTAGTTAACCATGTTTGTTTTGTTGGTAGC | SEQ ID NO: 798 | Homo sapiens dedicator of cytokinesis 4 (DOCK4), mRNA [NM_014705] |
| 799 | A_24_P325176 | KIAA1109 | TTGATCCAGTAGGTGTTCATTATATTCTTCAAAAATTGGGGTTTCATGCGTAGGACTA | SEQ ID NO: 799 | Homo sapiens KIAA1109, mRNA (cDNA clone IMAGE:3924668), complete cds, [BC106274] |
| 800 | A_24_P32766 | LOC730556 | AGAGCAGGAGCAGCCTTGCTTCTATGAGCAGTTCTGTGGAGTGTGCCGAGAACCAGGGGTGA | SEQ ID NO: 800 | PREDICTED: Homo sapiens similar to Coiled-coil-helix-coiled-coil-helix domain-containing protein 2 (HCV NS2 trans-regulated protein) (NS2TP) (LOC730556), mRNA [XR_015322] |

Fig. 1-45

| No. | Probe ID No. | Symbols of genes | Sequence | SEQ ID NO: | Descriptions of genes (letters and numbers within [ ] indicates GenBank accession No.) |
|---|---|---|---|---|---|
| 801 | A_24_P351451 | OPA1 | TTTTGGGTATAGACGGCATGCTTGCTATCACCGGCAAATAGTTTAAGGCAACAAACTTACA | SEQ ID NO: 801 | Homo sapiens optic atrophy 1 (autosomal dominant) (OPA1), nuclear gene encoding mitochondrial protein, transcript variant 8, mRNA [NM_130837] |
| 802 | A_24_P356601 | HEXIM1 | CATGAACCCCATGAAATTTATTTGTAGAGTTGTATGTACATTTTCTGGGGAGAAGGTTCA | SEQ ID NO: 802 | Homo sapiens hexamethylene bis-acetamide inducible 1 (HEXIM1), mRNA [NM_006460] |
| 803 | A_24_P362540 | DDEF2 | TGGTGCTATTGTGCAGTAACTAATAGTCTTACCAGGAGGAGAAATTATATTTAACGACC | SEQ ID NO: 803 | Homo sapiens development and differentiation enhancing factor 2 (DDEF2), mRNA [NM_003887] |
| 804 | A_24_P362846 | TXNDC9 | CTCCACATTGAGGTGTAAAAAGTAGACAGAGATCTGGCAATATTGTGCCAAGAAAACAGCT | SEQ ID NO: 804 | Homo sapiens thioredoxin domain containing 9 (TXNDC9), mRNA [NM_005783] |
| 805 | A_24_P379379 | CAPZA1 | ACCAGTTTCAGCGTAAAAACTTCGGAATGGTGGTTGGAGATCAGAGTGCAAGTTGACCA | SEQ ID NO: 805 | Homo sapiens capping protein (actin filament) muscle Z-line, alpha 1 (CAPZA1), mRNA [NM_006135] |
| 806 | A_24_P388810 | SRP19 | GTTGTATGCAGCAGAGAAATGATACCTAAAGTAAAACAACGACACAAAAAACAGGAGGTGG | SEQ ID NO: 806 | Homo sapiens signal recognition particle 19kDa (SRP19), mRNA [NM_003135] |
| 807 | A_24_P39376 | CCPG1 | TACTTTTGTGCTGGAACGAAGTTGATCAGTGATCAATAAGTTTTTCGTAAACGGTGT | SEQ ID NO: 807 | Homo sapiens cell cycle progression 1 (CCPG1), transcript variant 1, mRNA [NM_004748] |
| 808 | A_24_P400760 | LOC643454 | TCGATGTAGACAAGGTTCACAGTATTCTTGCAGAAATAATGGGGGGAATGGTATTGGAGA | SEQ ID NO: 808 | PREDICTED: Homo sapiens similar to AP-3 complex subunit sigma-1 (Adapter-related protein complex 3 sigma-1 subunit) (Sigma-adaptin 3a) (AP-3 complex sigma-3A subunit) (Sigma-3A-adaptin) (LOC643454), mRNA [XR_016772] |
| 809 | A_24_P405298 | PPP1CB | GTATTAGGTTAGGTCACAAAGGTTTTATCTGAGGTGATTAAATAACTTCGTGATTGGAG | SEQ ID NO: 809 | Homo sapiens protein phosphatase 1, catalytic subunit, beta isoform (PPP1CB), transcript variant 1, mRNA [NM_002709] |
| 810 | A_24_P409410 | A_24_P409410 | ACCAAGTAATATAATGGGATTGGGCTCTGGAGAAAAAGCTGGTATCAAGGTGCC | SEQ ID NO: 810 | |
| 811 | A_24_P414256 | CCDC72 | TCTTTGGTCCTTGTTCTTACCCTAAACTTGTATCACCTGAAATTAAACGAAGTCATTTGA | SEQ ID NO: 811 | Homo sapiens HSPC330 mRNA, partial cds. [AF161448] |
| 812 | A_24_P417261 | TXNDC10 | ATGATGAGTGATTCTTGGGAAGATAAATGTTAATGTTCCCAATAGTCAAGGTTGTTTTGC | SEQ ID NO: 812 | Homo sapiens thioredoxin domain containing 10 (TXNDC10), mRNA [NM_019022] |
| 813 | A_24_P50753 | NUDT4 | AACAGAAAATAAGTAGTTTTTGTGAATGACTTGGAGAGAAGAATAGAAACTGTGCGCAATG | SEQ ID NO: 813 | Homo sapiens nudix (nucleoside diphosphate linked moiety X)-type motif 4 (NUDT4), transcript variant 2, mRNA [NM_199040] |
| 814 | A_24_P53060 | ETFA | TGCTGTTGATGGTGGCTTTGTTGGCAATGACGAAGTTGGAGAGAGCGGAAAAATAGT | SEQ ID NO: 814 | Homo sapiens electron-transfer-flavoprotein, alpha polypeptide (glutaric aciduria II) (ETFA), nuclear gene encoding mitochondrial protein, mRNA [NM_000126] |
| 815 | A_24_P548415 | BC092452 | TATTTCTATGGTAAATCCTTGCAAACATGGAAACAATGCATTTGGCCCAGTGCTTTGTGG | SEQ ID NO: 815 | Homo sapiens cDNA clone IMAGE:30325817. [BC092452] |
| 816 | A_24_P561223 | THC2697551 | TTATGGCCAGTTACATAGAAGGATGGTGCCATATTTGAGGGACCCTAAAGTTTATAACAT | SEQ ID NO: 816 | ALU1_HUMAN (P39188) Alu subfamily J sequence contamination warning entry, partial (8%) [THC2697551] |

Fig. 1-46

| No. | Probe ID No. | Symbols of genes | Sequence | SEQ ID NO: | Descriptions of genes (letters and numbers within [ ] indicates GenBank accession No.) |
|---|---|---|---|---|---|
| 817 | A_24_P56130 | MYL6 | CCAAGAGTGATGAGATGAATGTGAAGGTGGTGGACTTTGAGGACTTTCTGCCCATGCTGC | SEQ ID NO: 817 | Homo sapiens myosin, light chain 6, alkali, smooth muscle and non-muscle (MYL6), transcript variant 2, mRNA [NM_079423] |
| 818 | A_24_P587882 | A_24_P587882 | CTGCAAATGGTGTGTATTAGGACTGAGAAGACACAGAAATCCATTCTGTATGATGAGCA | SEQ ID NO: 818 | |
| 819 | A_24_P675386 | BX109843 | ACCTGAAATGCACTTTAAATGTTTGCCTTATATCCAAGTGTTTACTTGTATCCATGACC | SEQ ID NO: 819 | BX109843 Soares placenta Nb2HP Homo sapiens cDNA clone IMAGp998B14206, mRNA sequence [BX109843] |
| 820 | A_24_P684186 | U52054 | GGTTGACTAACCCCAGATTATCTTCAAGACTTTAATCTGATCTTGTGTCTTAGAAGC | SEQ ID NO: 820 | Human S6 H-8 mRNA expressed in chromosome 6-suppressed melanoma cells. [U52054] |
| 821 | A_24_P703614 | A_24_P703614 | AAGAACATTACCCGAATGGAGTCTGACTGTAAGTCATCAGTAGCAGTTTGTGTGTGT | SEQ ID NO: 821 | |
| 822 | A_24_P724040 | SNRPB2 | ATGCTGAGGTCCTCGATTACCCTCCAAACTCCAAACTATATTTTATTCTTAATAAGTTACCAGAAAG | SEQ ID NO: 822 | Homo sapiens small nuclear ribonucleoprotein polypeptide B'' (SNRPB2), transcript variant 1, mRNA [NM_003092] |
| 823 | A_24_P745670 | A_24_P745670 | GGTAAAACAGACATGAATACATTCCCAACTTCAAATTTGAAGATCCGAAATCTGAAGTC | SEQ ID NO: 823 | |
| 824 | A_24_P787947 | YPEL2 | AAGGTAAAGGTAGAAGGAAAGTATGAAGAAAGTATTCTCATGTAGCAAATTCTATCTGCGC | SEQ ID NO: 824 | Homo sapiens yippee-like 2 (Drosophila) (YPEL2), mRNA [NM_001005404] |
| 825 | A_24_P79413 | SEC11A | GTTTTCGTTACTGGATGTTTGGAGTAGAGATACTGGTCTGTGATTGGTGGAATGGGAAACAC | SEQ ID NO: 825 | Homo sapiens SEC11 homolog A (S. cerevisiae) (SEC11A), mRNA [NM_014300] |
| 826 | A_24_P81965 | RAP2A | TTCTTTGATGTTGCAAGTTTGGGTTCTTTAAACTGTGATAGTGATGGTAACTGATGC | SEQ ID NO: 826 | Homo sapiens RAP2A, member of RAS oncogene family (RAP2A), mRNA [NM_021033] |
| 827 | A_24_P859859 | THC2553238 | TTTAACCAGAGAGTCTGCACCCGTTTTTCCTGATATACTGAGGACAGTCGGTCTCTAGCAAT | SEQ ID NO: 827 | 1305349A cystic fibrosis antigen {Homo sapiens} (exp=-1; wgp=0; cg=0), partial (65%) [THC2553238] |
| 828 | A_24_P879663 | LOC220906 | TCTAGTTGGAAGGAAAAAATTGGCAGCGTTTTGTACATTCGGTGCTGCGTCATCTGAAAT | SEQ ID NO: 828 | Homo sapiens hypothetical protein LOC220906, mRNA (cDNA clone IMAGE:4837455), [BC045818] |
| 829 | A_24_P92018 | YIPF6 | AAGTGTTAAAAGTCAACCGTTAATCATTAAGGATAGGACTACTTTCATGAGTGTTTGCCTCTG | SEQ ID NO: 829 | Protein YIPF6 (YIP1 family member 6) [Source:Uniprot/SWISSPROT;Acc:Q96EC8] [ENST00000374643] |
| 830 | A_24_P941699 | PCGF5 | TGGTATATTCAACTACAAGCTTTCTAAGGATAGGACTACTTTCATGTCTAGTAATAGAGTG | SEQ ID NO: 830 | Homo sapiens polycomb group ring finger 5 (PCGF5), mRNA [NM_032373] |
| 831 | A_24_P95029 | TAX1BP1 | TGCTTTGATTCCAGCTTGATGTTCACAAGAAGTGTCCCCTCGTGAGTTAATGTTTCGT | SEQ ID NO: 831 | Homo sapiens Tax1 (human T-cell leukemia virus type I) binding protein 1 (TAX1BP1), transcript variant 1, mRNA [NM_006024] |
| 832 | A_32_P100338 | THC2586959 | AATTAGAGAAACATTCTGTGTTTGATAAGGAATGGCAATGGCTATATTAGTGGTGTAGA | SEQ ID NO: 832 | 1PKO_D Chain D, Crystal Structure Of The Ef3-Cam 1PKO Complexed With Pmeapp {Homo sapiens} (exp=-1; wgp=0; cg=0), partial (70%) [THC2586959] |
| 833 | A_32_P10100 | A_32_P10100 | TATGAGGAAATAGTATCATCATGTTAGAAGCCTTGGAATGAGTATAAATAATGGCTGGTC | SEQ ID NO: 833 | |
| 834 | A_32_P10424 | AX721252 | AAATTTGTCAGGAAGGAGATGGGAAGCTCTAGATGTGCACAACTGATAGCAGGCTCAACAA | SEQ ID NO: 834 | Sequence 212 from Patent WO0220754 [AX721252] |

Fig. 1-47

| No. | Probe ID No. | Symbols of genes | Sequence | SEQ ID NO: | Descriptions of genes (letters and numbers within [ ] indicates GenBank accession No.) |
|---|---|---|---|---|---|
| 835 | A_32_P131377 | REEP5 | GATCACTAAAGAAGAAGGAAGAAAAGCTACCGTGAATTTACTGGGTGA AGAAAAGAGAGCAC | SEQ ID NO: 835 | Homo sapiens receptor accessory protein 5 (REEP5), mRNA [NM_005669] |
| 836 | A_32_P136402 | THOC7 | AGCTGGAATTGAGACGGGAAACAGTTTCATGTCTTCTTAGTACCA TGCATGAAGTTGAGG | SEQ ID NO: 836 | Homo sapiens THO complex 7 homolog (Drosophila) (THOC7), mRNA [NM_025075] |
| 837 | A_32_P143323 | CR613267 | AGAGAGCTCAAAGACTGGGGTTTATGCCAGTTAGATACAAGGATC CTGCATATTTCAGGG | SEQ ID NO: 837 | full-length cDNA clone CS0DL011YP14 of B cells (Ramos cell line) Cot 25-normalized of Homo sapiens (human) [CR613267] |
| 838 | A_32_P147603 | THC2499508 | GCGTTGAGTCGGGAGGAAAATATCTAAAAATTCCCGGCTGGCGTA GGGTCCTGTGTT | SEQ ID NO: 838 | |
| 839 | A_32_P147747 | THC2575761 | TTGATACCCTGATTCTGATGAGAACGCCCAATTGGGTTCTGGA GGTAGATAGAAGTTG | SEQ ID NO: 839 | HUMRPL7Y ribosomal protein L7 [Homo sapiens] (exp=-1; wgp=0; cg=0), partial (40%). [THC2575761] |
| 840 | A_32_P154930 | OSTM1 | GTTGGTAAATGTTACTTATATATTGGGACTAGTATTTTCTAATGTTT GTGGGATATGCGC | SEQ ID NO: 840 | Homo sapiens osteopetrosis associated transmembrane protein 1 (OSTM1), mRNA [NM_014028] |
| 841 | A_32_P159651 | PCAF | GAGTGGTGTCTAGATTTCTAATGAAGAATCATGATACAGTTTGGA TTAAGTATGTTGGAG | SEQ ID NO: 841 | Homo sapiens p300/CBP-associated factor (PCAF), mRNA [NM_003884] |
| 842 | A_32_P161432 | CBWD2 | GAAGAGGAAACCTGATGGCCTTATCACTGAAGAGCTACTAGACAAGTT CCTTGGACGATGCC | SEQ ID NO: 842 | Homo sapiens COBW domain containing 2 (CBWD2), mRNA [THC1720003] |
| 843 | A_32_P162250 | ARHGAP18 | AAGTCCTGAATAAGTCTACTGGAAGAATTATTCTTCTGGGTGAAA AAGCTTTTGTTGTG | SEQ ID NO: 843 | Homo sapiens Rho GTPase activating protein 18 (ARHGAP18), mRNA [NM_033515] |
| 844 | A_32_P162416 | BE218351 | GTCTATTCAAATTCAGGTTGTCCACTAGGTCAGTTTTCTAGAGAG ATGGTCTTTAACAT | SEQ ID NO: 844 | hv37e08.x1 NCI_CGAP_Lu24 Homo sapiens cDNA clone IMAGE:3175622 3' mRNA sequence [BE218351] |
| 845 | A_32_P165713 | CIP29 | AAAGCAAGAGTCTTATCCACAGACTCAGGCATATCTGAAGAAGCA TGCGAAGAGGAGG | SEQ ID NO: 845 | Homo sapiens cytokine induced protein 29 kDa (CIP29), mRNA [NM_033082] |
| 846 | A_32_P17163 | ENST00000368149 | TCCTTAGTGTAGTTTTAAATCTCAGGTAGATTTTATTTGTTTT CTGTGTGTGTATGAG | SEQ ID NO: 846 | Rho GTPase-activating protein 18 (MacGAP) [Source:Uniprot/SWISSPROT:Acc:Q8N392] [ENST00000368149] |
| 847 | A_32_P17504 | THC2698682 | ATGTCTATGGTTGACTTGCATGTGAAATATATTCCAGCTTTC CCGTTGATGCCCAAA | SEQ ID NO: 847 | |
| 848 | A_32_P195387 | DKFZP779L1068 | ATATAACGTTGGAATTCATTCATTCTATATTATGTGTTGTCTGCTGCTT GTAGTATCAGTTGGC | SEQ ID NO: 848 | Homo sapiens cDNA clone IMAGE:5555490. [BC110326] |
| 849 | A_32_P200724 | FAM19A2 | AGAGAAAAGTTAATTTTCTGAAGGGAAGCTGGAGAATATGGAAAAC ATATATTGGAGCTAC | SEQ ID NO: 849 | Homo sapiens mRNA; cDNA DKFZp781P0552 (from clone DKFZp781P0552). [CR749367] |
| 850 | A_32_P205550 | RPL26L1 | AGGTAGTTGGAGGACACTACAAAGGTCAGCAAAATTGGGAAGGTAA TCCAGGTGTACAGAA | SEQ ID NO: 850 | Homo sapiens ribosomal protein L26-like 1 (RPL26L1), mRNA [NM_016093] |
| 851 | A_32_P205553 | RPL26L1 | TTCGGAATGTCTGGAACATTTGATTTCCTGTTTTGTTACCGTGTGG CGTGTAAATCTAGT | SEQ ID NO: 851 | Homo sapiens ribosomal protein L26-like 1 (RPL26L1), mRNA [NM_016093] |
| 852 | A_32_P206641 | LOC642123 | TTAAGAAGCCCCGATACCTGGTAGAGCATGTACCATCTTACATG CTTAAATAAGTCCAC | SEQ ID NO: 852 | Homo sapiens cDNA FLJ46831 fis, clone UTERU3015647, moderately similar to Embigin precursor. [AK128714] |
| 853 | A_32_P207231 | AI630435 | TTGCTTGGCTTTTCTTAAGGGTTCTGGAACAGGAGGAACCTCC TTCTTCTTCTCTCTCT | SEQ ID NO: 853 | AI630435 ad10b05.y1 Hembase: Erythroid Progenitor Cells (LCB:ad library) Homo sapiens cDNA clone ad10b05 random. mRNA sequence [AI630435] |

Fig. 1-48

| No. | Probe ID No. | Symbols of genes | Sequence | SEQ ID NO: | Descriptions of genes (letters and numbers within [ ] indicates GenBank accession No.) |
|---|---|---|---|---|---|
| 854 | A_32_P223189 | SUMO1P3 | GAATGGAGGAAGAAGATGTGATTGAGGTTTATCAGGAAGAAATCG GAGGTCATTCAACAG | SEQ ID NO: 854 | Homo sapiens SUMO1 pseudogene 3 (SUMO1P3) on chromosome 1 [NR_002190] |
| 855 | A_32_P224666 | CAPZA2 | AATGCTGTTTGAGATCTGAAATTAAATGAAAATACTTATTCA GAAATGCATTTAATG | SEQ ID NO: 855 | Homo sapiens capping protein (actin filament) muscle Z-line, alpha 2 (CAPZA2), mRNA [NM_006136] |
| 856 | A_32_P2333 | SUB1 | AGGAAGAAAAGGTATTTCTTTAAATCCAGAACAATGGAGCCAGCT GAGAGAACAGATTC | SEQ ID NO: 856 | Homo sapiens SUB1 homolog (S. cerevisiae) (SUB1), mRNA [NM_006713] |
| 857 | A_32_P26895 | KIAA1600 | AATTCTTGGTCCTCCGTCCGTGGAGAAAGTCTTCAGATGGTCATTGTG TACCTACTCTGTCTT | SEQ ID NO: 857 | KIAA1600 (KIAA1600), mRNA [Source:RefSeq_dna;Acc:NM_020940] [ENST00000369248] |
| 858 | A_32_P30004 | AF086044 | ATTTCTTTGAAAGGGAGTAAGTTTTTAAAGCCTTCCTGATT TTAGCCTGCAATGT | SEQ ID NO: 858 | Homo sapiens full length insert cDNA clone YX74D05. [AF086044] |
| 859 | A_32_P32250 | C10orf84 | CAAAAAGGAGGTTGAAAATTCACAGCGGTCGCCGAAAAAGAAGAA ACTTGCATGGGGGTT | SEQ ID NO: 859 | Homo sapiens chromosome 10 open reading frame 84 (C10orf84), mRNA [NM_020203] |
| 860 | A_32_P32315 | A_32_P32315 | AAAGTGGGAAGATACGATTCAAGTCGTGGATTCGTCTTGGAA AAAGGTCAGTCCTCA | SEQ ID NO: 860 | |
| 861 | A_32_P43217 | PSMA6 | TTGTTGTTAGTTTACCAGAATGGGTCATGGGACTTACGTCGTGTT TGGTAACAACAAACA | SEQ ID NO: 861 | Homo sapiens proteasome (prosome, macropain) subunit, alpha type, 6 (PSMA6), mRNA [NM_002791] |
| 862 | A_32_P44394 | AIM2 | GAAGGAGATAAGGTTCGAGTTCTTCACGTGTCAAAAAT GGAGAAAAACTACAG | SEQ ID NO: 862 | Homo sapiens absent in melanoma 2 (AIM2), mRNA [NM_004833] |
| 863 | A_32_P62342 | GLT8D3 | TGTGATGTAACTGATGTAACCATTGACAATCTATGTGTGCCTTTA TACATTTGATCTCTG | SEQ ID NO: 863 | Homo sapiens glycosyltransferase 8 domain containing 3, mRNA (cDNA clone MGC:21651 IMAGE:4508300), complete cds. [BC039145] |
| 864 | A_32_P73222 | AA631847 | TTTGTTTGTTTGGACAATCTCATAAGAACTTTAGGTCTTACAGC ACGAACCCGTCGAAG | SEQ ID NO: 864 | np61b02.s1 NCI_CGAP_Br2 Homo sapiens cDNA clone IMAGE:1130763 3' similar to TR:Q971833 Q971833 60S RIBOSOMAL PROTEIN L34 .; mRNA sequence [AA631847] |
| 865 | A_32_P81768 | TMEM167 | CCTCAGTAGTGTCACTAGAATATTTAGATTCTGAAAATGTATTCT GTTGTATCAGATACG | SEQ ID NO: 865 | Homo sapiens transmembrane protein 167 (TMEM167), mRNA [NM_174909] |
| 866 | A_32_P82424 | LOC647252 | ATTGGATGCTGAGGTAGTGAAGTATAAGGACCAGATGAAGATGAAGATGAG AGGGGGTCCTACAAA | SEQ ID NO: 866 | PREDICTED: Homo sapiens similar to Charged multivesicular body protein 5 (Chromatin-modifying protein 5) (Vacuolar protein sorting 60) (Vps60) (hVps60) (SNF7 domain-containing protein 2) (LOC647252), mRNA [XR_019210] |
| 867 | A_32_P89730 | THC2544977 | GGAGAATAACTCATTCTGGTTCTTGTTCCGGTTTTCCACATAAA AGTATATTTGTGTTG | SEQ ID NO: 867 | |
| 868 | A_32_P95397 | ITGB1 | GTCTTACTTTGAGTTAGTGGCATAACAGACCACTGTATGTTTACT TCTCACCATTTGAGT | SEQ ID NO: 868 | Homo sapiens integrin, beta 1 (fibronectin receptor, beta polypeptide, antigen CD29 includes MDF2, MSK12) (ITGB1), transcript variant 1A, mRNA [NM_002211] |

Fig. 2

| No | Probe ID No. | Symbols of genes | Sequence | SEQ ID NO: | Descriptions of genes (orders and numbers within [ ] indicates GenBank accession No.) |
|---|---|---|---|---|---|
| 1 | A_23_P407601 | C8orf6 | GTCTCGTAGGTTAGTGTAGCAGAGAATCGTATTCTCAGATAAGACTTCCGTGTGGGTGAA | SEQ ID NO: 220 | Homo sapiens mRNA for hypothetical protein (C8orf6 gene). [AJ307469] |
| 2 | A_32_P209582 | THC2663167 | CAATGTAAAGGCAGAGAATATCAAGGTCCTTTTGTCAAGATTTTCAAAGGTATTTGGCTGAT | SEQ ID NO: 506 | ALU1_HUMAN (P39188) Alu subfamily J sequence contamination warning entry, partial (5%) [THC2663167] |
| 3 | A_32_P213509 | THC2663555 | GATTGTTCGAGTGTTGGAGCGGTTTTTAATGAAAATCGTCAACACCTACACTGGAAAAA | SEQ ID NO: 508 | |
| 4 | A_32_P40673 | A_32_P40673 | CATCACACTTGATATTAGGACAGGCTACCTACTCGTTCGAGTGTCACAGGCTGATATGTA | SEQ ID NO: 523 | |
| 5 | A_32_P71171 | A_32_P71171 | TCTAGATAGTAATAGGAGAAAGCCAAGAATCCAGCCTCGTGATGGGTGGAGGGAGTGATTGAA | SEQ ID NO: 538 | |
| 6 | A_32_P98940 | THC2745859 | AAGAGTATTCCAAGATAGGCAAAGGTGTGTTGTTTTAGCAGGTGTATTTCAGGTAGTTA | SEQ ID NO: 554 | |
| 7 | A_23_P123608 | JAK2 | GGATAAGCATGGCTGGATGAAAGATGACCTTCATTCTGAGACCAAAGTAGATTTACAGA | SEQ ID NO: 570 | Homo sapiens Janus kinase 2 (a protein tyrosine kinase) (JAK2), mRNA [NM_004972] |
| 8 | A_23_P138507 | CDC2 | CGGATGTCAAAAACTTGGATGAAAATGGCTTGGATTTGTCTGGAAAATGTAATGTATG | SEQ ID NO: 589 | Homo sapiens cell division cycle 2, G1 to S and G2 to M (CDC2), transcript variant 1, mRNA [NM_001786] |
| 9 | A_23_P14734 | RPS27L | TACAAGATCAGCACGGGTTTTCAGCCATGCTGCTCAGACAGTGGTTGTTTGTGTAGGTTGTTCA | SEQ ID NO: 597 | Homo sapiens ribosomal protein S27-like (RPS27L), mRNA [NM_015920] |
| 10 | A_23_P152002 | BCL2A1 | TGTAACCATATATTTGAATTTGAAGGTATTCTCATCAAGAAACTTCTACGACGAGCAAATTGC | SEQ ID NO: 602 | Homo sapiens BCL2-related protein A1 (BCL2A1), mRNA [NM_004049] |
| 11 | A_23_P18525 | PDCD10 | CCAACCGACTAATTCATCAAACCAAGCTAATACTTCAGACCTTCAAACTGTGGGCTGAA | SEQ ID NO: 618 | Homo sapiens programmed cell death 10 (PDCD10), transcript variant 1, mRNA [NM_007217] |
| 12 | A_23_P2705 | P2RY5 | TCTGTATTGCTGTTTGCAACTGTTGTTTGACCCTATAGTTTACTAGTTACATCGGACA | SEQ ID NO: 654 | Homo sapiens purinergic receptor P2Y, G-protein coupled, 5 (P2RY5), mRNA [NM_005767] |
| 13 | A_23_P41114 | CSTA | AAACAAATGAGACTATTGGAGAAAGCCACAAAGAGTAGCTGAGTTACTGGGGCCCCTCAAGTTGTTGCTG | SEQ ID NO: 689 | Homo sapiens cystatin A (stefin A) (CSTA), mRNA [NM_005213] |
| 14 | A_23_P434809 | S100A8 | AAAGGCAGGAAGCACATGGGTAGATGGAGGCTACATTTAGCCAAATCGTTGGCATGACAGG | SEQ ID NO: 701 | Homo sapiens S100 calcium binding protein A8 (S100A8), mRNA [NM_002964] |
| 15 | A_23_P76480 | BF213758 | AAATCGAACAGGACAGCATGGGTAGATGGAAGCTACATTTAGCCAAATCGTTGGCATGACAGG | SEQ ID NO: 726 | BF213758 601847628F1 NIH_MGC_55 Homo sapiens cDNA clone IMAGE 4078519 5'. mRNA sequence [BF213758] |
| 16 | A_23_P94230 | LY96 | TGAAGCTATTTCTGGGAGCGAGAAGAAAATGGCTCTCTTTTGCTTGGAGTTTGTCATCCTACA | SEQ ID NO: 744 | Homo sapiens lymphocyte antigen 96 (LY96), mRNA [NM_015364] |
| 17 | A_24_P124992 | PSMA4 | AAAGGTGCCTTTGCTTGGTCGTGTATGTATACATTGGCTGGGATAAGCAGTATGGGTTTCAG | SEQ ID NO: 762 | Homo sapiens proteasome (prosome, macropain) subunit, alpha type, 4 (PSMA4), mRNA [NM_002789] |
| 18 | A_24_P126741 | ENST00000309178 | AGCCTCCAACGACACTAACAAGATCAAGATTCAAGATTACTTGCAACAGCTCAGAGGCGGAGAAT | SEQ ID NO: 763 | |
| 19 | A_24_P201702 | CLEC2B | ATTGGAACTCAAGTAAATAAATACAACTGTTCCACTCAACATGCCGACCTAAGTATAATTGACA | SEQ ID NO: 781 | Homo sapiens C-type lectin domain family 2, member B (CLEC2B), mRNA [NM_005127] |
| 20 | A_24_P320328 | SUB1 | CAGAAAAACCTGTAAAGAAAGAAAGAGAGGTGAGACTTGGAGAGGGGTGTCATCTCTA | SEQ ID NO: 795 | Homo sapiens SUB1 homolog (S. cerevisiae) (SUB1), mRNA [NM_006713] |
| 21 | A_32_P200724 | FAM19A2 | AGAACAAAGTAATTTCTGAAGGAAAGGCTGAGAATATGGAAACATATATTGGAGCTAC | SEQ ID NO: 849 | Homo sapiens mRNA; cDNA DKFZp781P0552 (from clone DKFZp781P0552). [CR749367] |

Fig. 3-1

| No. | Probe ID No. | Symbols of genes | Sequence | SEQ ID NO: | Descriptions of genes (letters and numbers within [ ] indicates GenBank accession-No.) |
|---|---|---|---|---|---|
| 1 | A_23_P12343 | GSTM3 | AGGTTGTTTGTTCATCCTGTCGGTAAGGGGTCAGGCGTCTTG CTTTGCTCTTTCAAT | SEQ ID NO: 869 | Homo sapiens glutathione S-transferase M3 (brain) (GSTM3), mRNA [NM_000849] |
| 2 | A_23_P143247 | TSH22 | CCCACAAGAGCGTATGGAAATGTCTAAGTTTACGGCACTGTGAA TGACCACTATGAGTCA | SEQ ID NO: 870 | Homo sapiens teashirt family zinc finger 2 (TSH22), mRNA [NM_173485] |
| 3 | A_23_P146325 | DDEF1IT1 | TGGAAAGTGAAGTGAAGGATTTTTTGTCATACAGGCAAGTAAGTGC CAGAAGTGACTTGAAG | SEQ ID NO: 871 | Homo sapiens DDEF1 intronic transcript 1 (DDEF1IT1) on chromosome 8 [NR_002765] |
| 4 | A_23_P14853 | LTK | AGGTTTTGATCTTGGGGCCAGAGGGGGCGGTTACAGACACCCAG GTGTGCATGGGAGCA | SEQ ID NO: 872 | Homo sapiens leukocyte tyrosine kinase (LTK), transcript variant 1, mRNA [NM_002344] |
| 5 | A_23_P20566 | TPM2 | GGAGTATTCCACCAAGAAGAAGAATAAAATATGAAGAGGAGATGAAAC TGTTGGAAGGAGAAGCT | SEQ ID NO: 873 | Homo sapiens tropomyosin 2 (beta) (TPM2), transcript variant 2, mRNA [NM_213674] |
| 6 | A_23_P315378 | ATG16L1 | GTGTGTTTCCAGTTTATACTCTTTGTCGAAAACTGAGTTCAAA ATATTTCCAATGGGAC | SEQ ID NO: 874 | Homo sapiens ATG16 autophagy related 16-like 1 (S. cerevisiae), mRNA FLJ10035 fis, clone HEMBA1000919. [AK000897] |
| 7 | A_23_P339095 | SPTBN1 | AGTGGGATAGTTCAAAAGGAGAACAAGTTTCCAAAACGGGTTTG CCAAGCTGAACAGGGAT | SEQ ID NO: 875 | Homo sapiens spectrin, beta, non-erythrocytic 1 (SPTBN1), transcript variant 2, mRNA [NM_178313] |
| 8 | A_23_P344631 | SYNPO | TCCTGCTGCTGTGAAGATGAGAAGGTGCTCTAGTCAGTTAATG ATGAGTGACTATATTT | SEQ ID NO: 876 | Synaptopodin [Source:Uniprot/SWISSPROT;Acc:Q8N3V7] [ENST00000307662] |
| 9 | A_23_P359174 | BC069659 | AGAGGGGTGGATAGTAGGGTAAAGAAAAATTTGTAATAGAAAC AGTGGTTTGGGATTTT | SEQ ID NO: 877 | Homo sapiens cDNA clone IMAGE:7262526, with apparent retained intron. [BC069659] |
| 10 | A_23_P358870 | C8orf16 | CTGAGGTTATATTTTCACTTAACATTGTGAGTTGGCATTTTG GTTTTAGTCCAATGGT | SEQ ID NO: 878 | Homo sapiens mRNA for hypothetical protein (C8ORF16). [AJ312026] |
| 11 | A_23_P379147 | KRT74 | ATGCTCGTGGTGAGAATCCATCGTCGTGTGAGGCATCTCTGTCATCAG CAGTAGCACTACAGC | SEQ ID NO: 879 | Homo sapiens keratin 74 (KRT74), mRNA [NM_175053] |
| 12 | A_23_P8921 | FLJ11710 | CCTGATTCATGATTGAAGTAAGTACCATTAGCATAAATGCTATAGATC CATGCATTGGATGTTA | SEQ ID NO: 880 | Homo sapiens cDNA FLJ11710 fis, clone HEMBA1005149. [AK021772] |
| 13 | A_23_P407601 | C8orf6 | GTCTCCTAGGTTAGTGTAGCCAGAGAGATTGTATTCTGAGATAAGAC TCCGGTGTCGGCTGAA | SEQ ID NO: 881 | Homo sapiens mRNA for hypothetical protein (C8orf6 gene). [AJ307469] |
| 14 | A_23_P88222 | PLD4 | TGAAAGTGTTTCATCGTGCGAGGGTGGGGAAGCCAAGCATTGGCA TTCAGCAGGGTGAACC | SEQ ID NO: 882 | Homo sapiens phospholipase D family, member 4 (PLD4), mRNA [NM_138790] |
| 15 | A_24_P128057 | MBNL1 | AGAAATATTGGTGCAACAACTATGTGTGATTGGTTATCTCTCTATC ATGCATTGCTTCACAA | SEQ ID NO: 883 | Homo sapiens muscleblind-like (Drosophila), mRNA cDNA clone IMAGE:3335812), partial cds. [BC005296] |
| 16 | A_24_P312325 | C8orf15 | CTTGTTCAATGTGAGTGACTACTTTAGTTGCCTGTCCAATATGAAGTA GAAAAGCAGATTTCTG | SEQ ID NO: 884 | Homo sapiens chromosome 8 open reading frame 15 (C8orf15), mRNA [NM_010336662] |
| 17 | A_24_P350136 | LOC653370 | CCAGTAGCACCACCTGGTGGAAGATGAGGACTTCAATGTTAGC GATGGCCCTGGAGAGCA | SEQ ID NO: 885 | PREDICTED: Homo sapiens similar to Keratin, type I cytoskeletal 18 (Cytokeratin-18) (CK-18) (Keratin-18) (K18) (LOC653370), mRNA [XR_019330] |
| 18 | A_24_P360499 | DDEF1IT1 | TGTTCCTTTTAATGTAGGCCAGGTCCTATACTTGAGATTTAAGT TTGAAATGTAGGCATAG | SEQ ID NO: 886 | Homo sapiens DDEF1 intronic transcript 1 (DDEF1IT1) on chromosome 8 [NR_002765] |
| 19 | A_24_P460763 | AK022443 | GTGAGTAGGCAGGCTGATTTAAGATGGCTAGTGGGTGTCTAAATGTCA AATGCTATTGGGAGAT | SEQ ID NO: 887 | Homo sapiens cDNA FLJ12231 fis, clone MAMMA1002566. [AK022443] |
| 20 | A_24_P491923 | THC2491622 | CTTCTTGTTTCTCAATAAAGTAGACAAGTCGATCGATGCATCTGATCGGGT GTTTAGTAGGGTATGA | SEQ ID NO: 888 | |

Fig. 3-2

| No. | Probe ID No. | Symbols of genes | Sequence | SEQ ID NO: | Descriptions of genes (letters and numbers without [ ] indicates GenBank accession No.) |
|---|---|---|---|---|---|
| 21 | A_24_P548264 | AL512741 | AAGAATTGAGTTAGAAGTGGCCTATAATGTAATGGAGAATATTTCCCAATAATGGCTAGG | SEQ ID NO: 889 | Homo sapiens mRNA; cDNA DKFZp667N064 (from clone DKFZp667N064) [AL512741] |
| 22 | A_24_P558141 | A_24_P558141 | AACCCTGTGCTGTGGGATAACCTGTCTACATTTTGGATGAGCTGTGCTGATCAAAACTAA | SEQ ID NO: 890 | |
| 23 | A_24_P642771 | AK024956 | ATTCTCCATATATTTTAGTGTGTTTGTTATTGGCTAGAAAGACAAAACAAGGGGAATCTGG | SEQ ID NO: 891 | Homo sapiens cDNA: FLJ21303 fis, clone COL02107. [AK024956] |
| 24 | A_24_P693321 | AK123481 | ATCACAAGTATGCCAAATAATCAATGGTACAAATGTCCAAAATTTAGTTTAAAAGTGGAA | SEQ ID NO: 892 | Homo sapiens cDNA FLJ41487 fis, clone BRTHA2004350. [AK123481] |
| 25 | A_24_P69784 | PACS1 | AAGTTCCCTGATGAAGAACTGTATCAGAAGTTTATTGGCTTCATTGGGGTGGTGAAGGTG | SEQ ID NO: 893 | Homo sapiens phosphofurin acidic cluster sorting protein 1 (PACS1), mRNA [NM_018026] |
| 26 | A_24_P713312 | THC2639056 | TTTATATGGTCGGATGGTGCATGGTTAGGATTAAGGGGTAATTAATAGTAATGTATGTGGA | SEQ ID NO: 894 | ALUB_HUMAN (P39195) Alu subfamily SX sequence contamination warning entry, partial (10%) [THC2639056] |
| 27 | A_24_P728115 | AK024937 | ACTGCATAGTCACTACTTTTAGTGAGTTTGAAATCTGTTTGGAGAGCTATGTAAGTACCA | SEQ ID NO: 895 | Homo sapiens cDNA: FLJ21284 fis, clone COL01911. [AK024937] |
| 28 | A_24_P792389 | THC2671169 | ATGCTAAGCGGTGGAGACTAAGGCATAAGGTATGACTAGAATTGCCAGCTACACATTAGA | SEQ ID NO: 896 | |
| 29 | A_24_P79355 | ENST00000039649 | AAAACATTGGTCCCTTTTACCCAGGGAAAGGAGACTCAAGAAGCCGAACGTGATAGGAGATGG | SEQ ID NO: 897 | Homo sapiens hypothetical protein DKFZp566H0824, mRNA (cDNA clone MGC:129790 IMAGE:40021976), complete cds. [BC104430] |
| 30 | A_24_P863109 | AL833452 | GGGCAACTAGTGCATGTACTAGTTAGCTTAGCTTAAAGCCTAAGCATTAAATCTAAGAAATAGCA | SEQ ID NO: 898 | Homo sapiens mRNA, cDNA DKFZp686E0116 (from clone DKFZp686E0116). [AL833452] |
| 31 | A_24_P896819 | THC2635386 | AATGTAGCATGAGTGTTGCCGGTTTCTCTAGAAATGTAAAATGTTATTTTCTAAAGTACTTTTGT | SEQ ID NO: 899 | |
| 32 | A_24_P914102 | A_24_P914102 | TTAGTAGACCCTAGATTTTCTCTAGAAAGTTAAGATGTCCATTTAAATACAACCTAGTGTTGAAAATCAG | SEQ ID NO: 900 | |
| 33 | A_24_P926025 | DKFZp547ED67 | TGTTATTGAACATAGTTCATGTTAAGTCCATTAAATACAACCTGAAATAGCAAAGTTA | SEQ ID NO: 901 | Homo sapiens cDNA FLJ30147 fis, clone BRACE2000266. [AK054709] |
| 34 | A_24_P930337 | THC2503773 | AGGAAGTGGAACCGAGAGGGGCAAAATATGACTTGAAGAATGTAATTAAAATGTAGCATAG | SEQ ID NO: 902 | |
| 35 | A_24_P930391 | AK022351 | AAGTGGGTTTAATTTCCTTTTCATGAAAGGAAAGATTAGCTTTGATGCAAACACTTGGTG | SEQ ID NO: 903 | Homo sapiens cDNA FLJ12289 fis, clone MAMMA1001788. [AK022351] |
| 36 | A_24_P931364 | AK022062 | TCCGAACTGGAGTATGGGTTTGGTTTGGAAGTCATTGGTTTGTAGTAAGGCATTATTTCTTGGT | SEQ ID NO: 904 | Homo sapiens cDNA FLJ12000 fis, clone HEMBB1001531. [AK022062] |
| 37 | A_24_P933514 | AK094334 | CGTAGTCCCACTCTAGAATTCCTTAGGTGGGCATATTATATACTACGTGAACTCTGGGC | SEQ ID NO: 905 | Homo sapiens cDNA FLJ37015 fis, clone BRACE2010208. [AK094334] |
| 38 | A_24_P933548 | A_24_P933548 | CACCTGGCCAGGTTTATACTTATATGCTTTATACGTGAGAACTATAACTCAAGGGAAGGAAATG | SEQ ID NO: 906 | |
| 39 | A_24_P934861 | A_24_P934861 | GGAGGTATCAAGCAGCAAATTCCAGTTTGTGGGAAATAGTGGAACAGATGTCTCCATGG | SEQ ID NO: 907 | |
| 40 | A_24_P935682 | AY358248 | AGTCAGTAATCAGGATTCAATCAATATGAGCCTGTAAGATGATGCTTGACAGTTATGCAAC | SEQ ID NO: 908 | Homo sapiens clone DNA166629 MRSS6228 (UNQ6228) mRNA, complete cds. [AY358248] |

Fig. 3-3

| No. | Probe ID No. | Symbols of genes | Sequence | SEQ ID NO: | Descriptions of genes (letters and numbers within [ ] indicates GenBank accession No.) |
|---|---|---|---|---|---|
| 41 | A_32_P105940 | A_32_P105940 | GTGCCAAGGTAAGCTAGGACAGTTTTGGTTTATTTCAAGGACAA CATGAAATAAGCATTC | SEQ ID NO: 909 | |
| 42 | A_32_P118997 | THC2719256 | AAACATTAGGTAGGCAGGTTGTAGAAGGATATATTTAGGGTCATGA TGTCCTTCTTGTTGCT | SEQ ID NO: 910 | BE147120 PM2-HT0224-221098-001-b10 HT0224 Homo sapiens cDNA mRNA sequence [BE147120] |
| 43 | A_32_P120454 | THC2642550 | ACACAATGAGATGACTGGACTGGGTCGTCGTTATTGGAAGC TCAGGACAGGGTATGA | SEQ ID NO: 911 | |
| 44 | A_32_P121978 | A_32_P121978 | CAGATTAGACCAGGTCATAATGAGTTCTTGATTGGACTTCAGAT TGTCTTGATGGGGCAC | SEQ ID NO: 912 | |
| 45 | A_32_P12703 | THC2697162 | TTGAAGGAAAGAGTATAGGGGGAAGTGCCAGAACTAAACGAAT CCTAAGTAAATAGGT | SEQ ID NO: 913 | |
| 46 | A_32_P131234 | BM854107 | AGTAGGAAAAAGGTTTGTTCCTTAATTAGAGGTAGTGTGGGAA ATGGTAGCACTTGTGC | SEQ ID NO: 914 | K-ES10136406 S22SNU16n1 Homo sapiens cDNA clone S22SNU16n1-145-F11 5', mRNA sequence [BM854107] |
| 47 | A_32_P132935 | THC2673886 | AAATGGAAGTATTGACCAGATTAAAGAGTGGTAAGTCATGGCC ATGAATGAATTTACCA | SEQ ID NO: 915 | Q65549_9ALPH (Q65549) Glycoprotein C, partial (4%) [THC2673388] |
| 48 | A_32_P145385 | AK001118 | CCCGAATTAACACTGGAGGAAGGTTAAATTCCAAGCTTTTGAT TCTCAGGAAATGAGAT | SEQ ID NO: 916 | Homo sapiens cDNA FLJ10256 fis, clone HEMBB1000870, [AK001118] |
| 49 | A_32_P146844 | THC2639689 | GCTGTGGGCTGATTCCAGAGTCGAGAGTTGAAGGTTTGTGTGCAT CATCATGTGCCATTAA | SEQ ID NO: 917 | |
| 50 | A_32_P147969 | AL080232 | TAATGAGGTCTTTTCGGGATGAAGGCAAGAACTGTCCAGAAGA CCTGTGGAGAATTGTT | SEQ ID NO: 918 | Homo sapiens mRNA; cDNA DKFZp586AG61 (from clone DKFZp586AG61). [AL080232] |
| 51 | A_32_P151244 | AK022268 | GTAGTCAGATGTCAGAGAGAGTTATTTCATGTGTAACCTTTTG AACTGTTGATGTCTT | SEQ ID NO: 919 | Homo sapiens cDNA FLJ12206 fis, clone MAMMA1000941, [AK022268] |
| 52 | A_32_P164573 | THC2611661 | AGGTGTTTTCTATTAACAGTGAAGTAGTCAGCTCAGCAGAGCTTGGAAAT TTTCAAGTGCAAATC | SEQ ID NO: 920 | RPL12_SPIMX (P42344) Chloroplast 30S ribosomal protein S12, partial (11%) [THC2611661] |
| 53 | A_32_P167883 | THC2697442 | AGGTAATTGGGGTATGACTTCAGTCACTTCAGTGTGAAATATTGGGA AGTAAACTGCAAAGC | SEQ ID NO: 921 | |
| 54 | A_32_P184039 | A_32_P184039 | ATCATTGTTAGTCTTGGGCGGCAAAATAGTTGTTATGTATGCATGC GTAATAACTGAGCAGC | SEQ ID NO: 922 | |
| 55 | A_32_P184330 | AK130741 | TGTGACCGTTTGTGACGTGGGTCATACATGAGTGCGGTGTATCAGTCGCTGCAGTTGT ACATGAGTGGGTGTA | SEQ ID NO: 923 | Homo sapiens cDNA FLJ27231 fis, clone SYN06240 [AK130741] |
| 56 | A_32_P194372 | AK129547 | AGAACCAGAGAAACATAGAGCCATGATATATTGGACCAAGGATAGG TTAAAACTAGGGAGG | SEQ ID NO: 924 | Homo sapiens cDNA FLJ26036 fis, clone PRS00145 [AK129547] |
| 57 | A_32_P204565 | A_32_P204565 | CAGGATCAGTACACACCGGATGTGTTTCAGTGTGATGGAA AGATTGTTCCAGTCA | SEQ ID NO: 925 | |
| 58 | A_32_P208039 | AL049390 | TTTCATGTTCAGCATTCAGATTGGCGGTTTATTTCTCAAGGCAT GGCAAGGTCACAA | SEQ ID NO: 926 | Homo sapiens mRNA; cDNA DKFZp586G01318 (from clone DKFZp586G01318). [AL049390] |
| 59 | A_32_P209592 | THC2663167 | CAATGTAAAGCCAGAAATCAAGGTCCTTTGTGAAGATTTTCA AAGCTATTTGGCTGAT | SEQ ID NO: 927 | ALU1_HUMAN (P39188) Alu subfamily J sequence contamination warning entry, partial (5%) [THC2663167] |
| 60 | A_32_P211048 | A_32_P211048 | GTTCACAAAACACCTAGTAGGTATTCAGTTCATATTGGAATGA ATGAAAATGAGGCAG | SEQ ID NO: 928 | |
| 61 | A_32_P213509 | THC2663555 | GATTGTTCCAGTGTTGGAGCCGTTTTAATGAAAATTCTCAAG ACCTACACGTGGAAAAA | SEQ ID NO: 929 | |

Fig. 3-4

| No. | Probe ID No. | Symbols of genes | Sequence | SEQ ID NO. | Descriptions of genes (letters and numbers within [ ] indicates GenBank accession No.) |
|---|---|---|---|---|---|
| 62 | A_32_P216122 | AK130891 | TTCTTCCTGTATATGTTTGGGAGGGATTCATGAAGAATTGAGTA CACATATATGGGTC | SEQ ID NO: 930 | Homo sapiens cDNA FLJ27381 fis, clone UBA07680. [AK130891] |
| 63 | A_32_P224638 | THC2731042 | ACACCAGTCTAACTCTAGCTTAATGAGGCATGAAAACAAAATAG CTCAATCTCCTCAAC | SEQ ID NO: 931 | Q4SSA7_TETNG (Q4SSA7) Chromosome 11 SCAF14479, whole genome shotgun sequence. (Fragment), partial (5%) [THC2731042] |
| 64 | A_32_P227110 | THC2512146 | TAAACAAATCCTTTTGATTCAGGCAGCTGTGTATTGATAATGGC TTATTTATTACAATGA | SEQ ID NO: 932 | |
| 65 | A_32_P232851 | THC2645586 | GTTTGAAAGGATATCCTTCAGATTGGTTTTGCAGAAAATTGAG GTCACTGACTTATTC | SEQ ID NO: 933 | Q9P3E1_NEUCR (Q9P3E1) Related to rna-binding protein fus/tls, partial (5%) [THC2645586] |
| 66 | A_32_P25243 | THC2656826 | GGCTCTGGGCACGCATTGGAAGACTGGAGATAAAATGAGAAGTG ATTTATTTGTTTCA | SEQ ID NO: 934 | |
| 67 | A_32_P33304 | ANK3 | TGTTGGAATACCGGGGGTGATCTGTCTTTATAAACTCAGGTGA TTTAAAGAAAAGATGA | SEQ ID NO: 935 | Homo sapiens cDNA FLJ44903 fis, clone BRAMY3035184, highly similar to Mus musculus ankyrin 3, epithelial (Ank3). [AK126851] |
| 68 | A_32_P3342 | THC2676548 | TATAGCATTTTCTGAAGATCATTGTGTCTTCTTCTTCTGTCTAG ATGATTTGGTCAACAG | SEQ ID NO: 936 | ALU7_HUMAN (P39194) Alu subfamily SQ sequence contamination warning entry, partial (19%) [THC2676548] |
| 69 | A_32_P40673 | A_32_P40673 | CATCACAGTTGATATTAGGACAGGCTACCTACTGTTGTTGAGTGT CAGAGCCTGATATGTA | SEQ ID NO: 937 | |
| 70 | A_32_P41099 | THC2658419 | AGGGGCAGAAATATTTGGTTCCTCGGTTTATTAGTAAAGTGTC TTTGGACATATTGTCTC | SEQ ID NO: 938 | |
| 71 | A_32_P42976 | THC2713076 | GTTATTCTTTCCTTTGTGGTGAACGTGCGAACACATTGTGGGC TCATTCTTTCGGGTA | SEQ ID NO: 939 | |
| 72 | A_32_P43878 | DB111455 | ATGTGAGAAGGTTCTTTAAGGTTAATGACCAAGTTCCATGT GAGCTCTTACTTGGGA | SEQ ID NO: 940 | DB111455_THYMU2 Homo sapiens cDNA clone THYMU2015028 5', mRNA sequence [DB111455] |
| 73 | A_32_P5542 | AF131782 | GAGCCTTCTTACGATCTAACTTCCACTAACTGGGAGGAAATGTCT TATAAATAAACAACAG | SEQ ID NO: 941 | Homo sapiens clone 24941 mRNA sequence. [AF131782] |
| 74 | A_32_P60551 | BU567566 | GCAGAAGTAGAAGGCTTAGGGTGATATGTGATTCATCTATTGGAA TACAATAAAATTTAGCC | SEQ ID NO: 942 | AGENCOURT_10399418 NIH_MGC_82 Homo sapiens cDNA clone IMAGE:6614194 5', mRNA sequence [BU567566] |
| 75 | A_32_P65067 | THC2618074 | CGCCCAAAGTGAATTTGAATTTAAACTTGAGTTATTTATGCGGTCTCA TAGCAACACAGGAAAAGT | SEQ ID NO: 943 | |
| 76 | A_32_P67209 | BU726029 | GTGGAGTTATATTATTCTCCAGCTAGCTGGAGGTGAGGTGACACTCTG CTATTCTTCAGAGAAG | SEQ ID NO: 944 | UI-E-EJ0-aac-g-02-0-UI.s1 UI-E-EJ0 Homo sapiens cDNA clone UI-E-EJ0-aac-g-02-0-UI 3', mRNA sequence [BU726029] |
| 77 | A_32_P70875 | CD239706 | GTTTGTTTGAGAAGTTCCTAATGGAGTAGGAGGAACAAAAGTGACA GTTTCTTATTACTG | SEQ ID NO: 945 | FNPBXF03_FNP Homo sapiens cDNA, mRNA sequence. [CD239706] |
| 78 | A_32_P71171 | A_32_P71171 | TCTAGATAGTAAATGAAAATAGCATTTTAGGAAGGTTGAGTCAGCAGAA GGGAGGAGTGATTGAA | SEQ ID NO: 946 | |
| 79 | A_32_P79103 | BM932034 | GTGCTACGAAGTTACTACCAGGCTTACCAAAAGGTCAGGTTTATAT GTGGAGTGGGGCATA | SEQ ID NO: 947 | UI-E-EJI-aji-k-24-0-UI.r1 UI-E-EJI Homo sapiens cDNA clone UI-E-EJI-aji-k-24-0-UI 5', mRNA sequence [BM932034] |
| 80 | A_32_P88967 | AK022346 | ATGGGAAGTTACTACCAGGCTTACCAAAAGGTCAGGTTTATAT AAAGTGGGTTCCTTT | SEQ ID NO: 948 | Homo sapiens cDNA FLJ12284 fis, clone MAMMA1001757 [AK022346] |

Fig. 3-5

| No. | Probe ID No. | Symbols of genes | Sequence | SEQ ID NO: | Descriptions of genes (letters and numbers within [ ] indicates GenBank accession No.) |
|---|---|---|---|---|---|
| 81 | A_32_P89067 | AL134462 | TTCATGGAGGTTCTAGTCAAGGCAGAGACGGAGTAAACAGTAAAGGGACAAATAAGGATTAGT | SEQ ID NO: 949 | DKFZp547J0B5_r1 547 (synonym: hfbr1) Homo sapiens cDNA clone DKFZp547J0B5 5', mRNA sequence [AL134462] |
| 82 | A_32_P90458 | A_32_P90458 | AAGCCAGGAATAATTTGTATGTGATGCTACCTAAGTCGTGGAATCATGAGAGCCT | SEQ ID NO: 950 | |
| 83 | A_32_P91328 | THC2641595 | GTTAGCCAATAATGTCATTGAAGTCTTTAACTCTAGCGTGACTCTAAGGCCAGGGTTGA | SEQ ID NO: 951 | |
| 84 | A_32_P98940 | THC2745859 | AAGAGTATTCCGAAGAATAGCAAAGGTGTGTTGTTTTAGACAGGTGTATTTCAGGTAGTTA | SEQ ID NO: 952 | |
| 85 | A_23_P102060 | SSFA2 | GTATCATCCAAATAATGGGGGGTATGACTTGAATGAATAGAAATGAATAAGGTGGTGTTT | SEQ ID NO: 953 | Homo sapiens sperm specific antigen 2 (SSFA2), mRNA [NM_006751]. |
| 86 | A_23_P102235 | SNRPG | ACAACAGAACAATATTGGAATGGTGGTAATACGGAGGAAATAGTATCATCATGTTAGAAGC | SEQ ID NO: 954 | Homo sapiens small nuclear ribonucleoprotein polypeptide G (SNRPG), mRNA [NM_003096] |
| 87 | A_23_P104054 | C1orf9 | TAAATTTCTTCCTGTCTGCACAATTAGCTATTCAGAGCAAGAGGGCCTGATTTTTATAGA | SEQ ID NO: 955 | Homo sapiens chromosome 1 open reading frame 9 (C1orf9), transcript variant 2, mRNA [NM_016227] |
| 88 | A_23_P106131 | KTN1 | ATGTTTTCAGCGTTCTACTTTGTCAGAAAGAGTGAACAGTTTGTCTTTTTCAATCC | SEQ ID NO: 956 | Homo sapiens kinectin 1 (kinesin receptor) (KTN1), transcript variant 1, mRNA [NM_182926] |
| 89 | A_23_P106145 | ERO1L | ATTGTGTTGGTTGTTTAAATGTCGTCGTGGGGAAAGCTTCAGACTCAGGGTTGGGGA | SEQ ID NO: 957 | Homo sapiens ERO1-like (S. cerevisiae) (ERO1L), mRNA [NM_014584]. |
| 90 | A_23_P106635 | YPEL5 | AAAGTGAGTTCTGAGTACAGTTAAGTTGTGGTATTGCCACTGGGCTGTTGGTTAGAAAG | SEQ ID NO: 958 | Homo sapiens yippee-like 5 (Drosophila) (YPEL5), mRNA [NM_016061] |
| 91 | A_23_P109774 | ZBTB11 | GCCTCTCACGGTTTACTTTAAAAATGGCTTAAGGATAAAGAATAAAGTGATAGCTGTG | SEQ ID NO: 959 | Homo sapiens zinc finger and BTB domain containing 11 (ZBTB11), mRNA [NM_014415] |
| 92 | A_23_P110362 | MAP2K1IP1 | ACTGAGACAAGTTGTGAAAGTTTCTTAATCTGACAGTGGTTTGAGTGTAGGTTATCTT | SEQ ID NO: 960 | Homo sapiens mitogen-activated protein kinase kinase 1 interacting protein 1 (MAP2K1IP1), mRNA [NM_021970] |
| 93 | A_23_P110611 | ZH2C2 | CTCTTGAAAAGGAGAGTTTCAGTCTGTTGGAGCTTCAAACCAGGTTCTTGAATACTAA | SEQ ID NO: 961 | Homo sapiens zinc finger, H2C2 domain containing (ZH2C2), mRNA [NM_017676] |
| 94 | A_23_P110704 | SLU7 | CCTCTTTCCTTGGACAGTAGCAACTAGTCAGAAGACCATCAAGATAGATGCAGGTGATA | SEQ ID NO: 962 | Homo sapiens SLU7 splicing factor homolog (S. cerevisiae) (SLU7), mRNA [NM_006425] |
| 95 | A_23_P110811 | COX7C | AGCCTCTGGAAGTGGATCGAAAGTAGAACTCATATGCCATAGTAGATAGTTTGTCAATAA | SEQ ID NO: 963 | Homo sapiens cytochrome c oxidase subunit VIIc (COX7C), nuclear gene encoding mitochondrial protein, mRNA [NM_001867] |
| 96 | A_23_P114616 | ANKRD13C | GTCTCAAGAATGGATCTCAAGTTTTAGAGTGACCAGTAGCTTAAACTTTTTTCAGG | SEQ ID NO: 964 | Homo sapiens mRNA; cDNA DKFZp566D1346 (from clone DKFZp566D1346). [AL136717] |
| 97 | A_23_P11652 | USP1 | TTGGGCATGGAGTAATTTGTATGTGTTAAGTGATATTCTGCACGATCTGTATATAGTAC | SEQ ID NO: 965 | Homo sapiens ubiquitin specific peptidase 1 (USP1), transcript variant 1, mRNA [NM_003368] |
| 98 | A_23_P11685 | PLA2G4A | GAAATGGCAGGAGTTTCTGATGGTGAGGCAGTTGCAATGGGATGACAAGCTGGATTTAAA | SEQ ID NO: 966 | Homo sapiens phospholipase A2, group IVA (cytosolic, calcium-dependent) (PLA2G4A), mRNA [NM_024420] |

Fig. 3-6

| No. | Probe ID No. | Symbols of genes | Sequence | SEQ ID NO: | Descriptions of genes (letters and numbers within [ ] indicates GenBank accession No.) |
|---|---|---|---|---|---|
| 99 | A_23_P117163 | RCBTB1 | AAGTGAAGGAGGACTCTCATATTAGATATACTAAGTCATTTGTATGAATATGTGTGGCAGAGT | SEQ ID NO: 967 | Homo sapiens regulator of chromosome condensation (RCC1) and BTB (POZ) domain containing protein 1 (RCBTB1), mRNA [NM_018191] |
| 100 | A_23_P117721 | RPS17 | AATTATGTTCCTGGAGGTGTCAGCCTTGGATCAGGAGATTATTGAAGTAGATCGTGACAT | SEQ ID NO: 968 | Homo sapiens ribosomal protein S17 (RPS17), mRNA [NM_001021] |
| 101 | A_23_P117852 | KIAA0101 | TACTGCTGGCATTTTATTGGTGTTTATTATTGGAATTGGTTGCCATATTGTCACTCCTTG | SEQ ID NO: 969 | Homo sapiens KIAA0101 (KIAA0101), transcript variant 1, mRNA [NM_014736] |
| 102 | A_23_P118516 | FAM18B | TATTTCTGTAGATTGTTTCAGGAGAAAAGTTTTTGGTTGTATGGTAAGAGTGAGGACTTTG | SEQ ID NO: 970 | Homo sapiens family with sequence similarity 18, member B (FAM18B), mRNA [NM_016078] |
| 103 | A_23_P120048 | BAZ2B | TATTTCGTCTGAAGGTAATGATTAGCTATACAGTCTGTACAGTAATTACCTCTACCAAG | SEQ ID NO: 971 | Homo sapiens bromodomain adjacent to zinc finger domain, 2B (BAZ2B), mRNA [NM_013450] |
| 104 | A_23_P120316 | MTHFD2 | AGGATATTGGTTGGTATTAGTAGTCATTTTATGTATGTTAGCCTTGAGTAAGTTCTCCG | SEQ ID NO: 972 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 105 | A_23_P1206 | RPS24 | TTTGGATTCAGAAGTCATTTTGGTGGTGGCAAGACAACTGGGTTTGGATGGATTTATGAT | SEQ ID NO: 973 | Homo sapiens ribosomal protein S24 (RPS24), transcript variant 2, mRNA [NM_001026] |
| 106 | A_23_P121368 | IFT57 | TGGAACACAGACTACTCCAATCAAACGTGAACGGTGAAGGAAGGTCCAAC ATGACTAGGAACATGC | SEQ ID NO: 974 | Homo sapiens intraflagellar transport 57 homolog (Chlamydomonas) (IFT57), mRNA [NM_018010] |
| 107 | A_23_P121622 | SULT1B1 | GAAATAGAGATTGTGTGATTGAGTTGAAACGAGGGCAGTTATGAATTGATTTGGGCAAT | SEQ ID NO: 975 | Homo sapiens mRNA for ST1B2, complete cds. [D89479] |
| 108 | A_23_P121825 | FLJ13611 | CATGTGTTAGTGTTACAAAAGTTCTGTCTCCATGTAATGACACTTAGTTATGAGCAAAG | SEQ ID NO: 976 | Homo sapiens hypothetical protein FLJ13611 (FLJ13611), mRNA [NM_024941] |
| 109 | A_23_P121875 | C5orf28 | TTAAAACATGTTGGTACAGTTGGGCACTTAGTGAAGTAGTATTTTTGGTATCGTAGCC | SEQ ID NO: 977 | Homo sapiens chromosome 5 open reading frame 28 (C5orf28), mRNA [NM_022483] |
| 110 | A_23_P122007 | C5orf30 | ATCAGATTTGTCGTTGGGCTGGAAATGTTTCGTGTTGTATATTTTAAAGTAAATTGCAG | SEQ ID NO: 978 | Homo sapiens chromosome 5 open reading frame 30 (C5orf30), mRNA [NM_033211] |
| 111 | A_23_P122174 | XRCC4 | AAAACAAACTAGCTGTCTCGGGTTGGGTCAGCTGGTGGTGTAAGTAAAGATGATTGGATTAT | SEQ ID NO: 979 | Homo sapiens X-ray repair complementing defective repair in Chinese hamster cells 4 (XRCC4), transcript variant 3, mRNA [NM_022550] |
| 112 | A_23_P123315 | BC067244 | TCTGGAAATCACTGGTTTGGAGGGGGTGGATACATCCTCATTTCTGTAGATGATGCAT | SEQ ID NO: 980 | Homo sapiens cDNA clone IMAGE:4907381, partial cds. [BC067244] |
| 113 | A_23_P123343 | NUDCD1 | TTGGCCTCTTTGTACTGGAAAAGTATTCAGTGGTAGGTGGAGGTCTGGACAGTTATACTG | SEQ ID NO: 981 | Homo sapiens NudC domain containing 1 (NUDCD1), mRNA [NM_032869] |
| 114 | A_23_P123608 | JAK2 | GGATAAGCATGGCTGGATGAAAGAAAATAGACCTTCATTCTGAGACCAAGTAGATTTAGAGA | SEQ ID NO: 982 | Homo sapiens Janus kinase 2 (a protein tyrosine kinase) (JAK2), mRNA [NM_004972] |
| 115 | A_23_P127579 | PTS | GTGATTTATAAAGGAGAATAGGGTTAGGATTGGATTGCAGAAAGGCGAGTTCTTTG | SEQ ID NO: 983 | Homo sapiens 6-pyruvoyltetrahydropterin synthase (PTS), mRNA [NM_000317] |
| 116 | A_23_P128060 | ZNF26 | ATCGGTTCCAGTAGGCACAGGTGAGCATTTACCCATTGTTGGATAATGGTAATGTCTTT | SEQ ID NO: 984 | Homo sapiens zinc finger protein 26 (ZNF26), mRNA [NM_019591] |
| 117 | A_23_P128192 | PFDN5 | CACGTCCATGCTGCTGCAGGTCAAAGTCGGTACAGAGACGAAGTATGTGTGG AAGGCAAGGACTGTGT | SEQ ID NO: 985 | Homo sapiens prefoldin subunit 5 (PFDN5), transcript variant 1, mRNA [NM_002624] |

Fig. 3-7

| No | Probe ID No. | Symbols of genes | Sequence | SEQ ID NO: | Descriptions of genes (letters and numbers within [ ] indicates GenBank accession No.) |
|---|---|---|---|---|---|
| 118 | A_23_P128930 | PSMC6 | GAACAAGGAAGATTAGAACATACTGAAAATCGATGGAGGTCCATTACAAAGCATGGTGAA | SEQ ID NO: 986 | Homo sapiens proteasome (prosome, macropain) 26S subunit, ATPase, 6 (PSMC6), mRNA [NM_002806] |
| 119 | A_23_P130444 | ZNF701 | GTCGTTGCAGAATATCATAACGTTCATTTTGAGGTAATAGTTACAAATGCGGTGAGCAC | SEQ ID NO: 987 | Homo sapiens zinc finger protein 701 (ZNF701), mRNA [NM_018260] |
| 120 | A_23_P133375 | SLC25A46 | CAGTGCTAGCAACTTAATTCTCATACATTTTTAGATTGAAGTTGGTTTGCTTTGCTAGTTGTG | SEQ ID NO: 988 | Homo sapiens solute carrier family 25, member 46 (SLC25A46), mRNA [NM_138773] |
| 121 | A_23_P133648 | FAM6A1 | ACTTCGTCGGAATTACAAATGAGTGTTTTAGATTGAAGTGACGGTAAAGGATTTGTT | SEQ ID NO: 989 | Homo sapiens family with sequence similarity 6, member A1 (FAM6A1), mRNA [NM_016255] |
| 122 | A_23_P134786 | PHF20L1 | AGTTGTATGTGGCCCCAGTGCTACATACGCAGGTATGCGTAAGTGTGTATGGTTGTTTTA | SEQ ID NO: 990 | Homo sapiens PHD finger protein 20-like 1 (PHF20L1), transcript variant 1, mRNA [NM_016018] |
| 123 | A_23_P135494 | CLIC4 | CTGTCAAGCCGTAATGTTGAACAGAATGGAGAGTATTTGTTTATAATTCTTGAACAGG | SEQ ID NO: 991 | Homo sapiens chloride intracellular channel 4 (CLIC4), mRNA [NM_013943] |
| 124 | A_23_P135499 | CLIC4 | CTTCGTTTTTGATGTAGTAGATATTCTATACAGTTCTGTTGTTTTTACTACAGGAG | SEQ ID NO: 992 | Homo sapiens chloride intracellular channel 4 (CLIC4), mRNA [NM_013943] |
| 125 | A_23_P13622 | STYK1 | AGGGTTAGTAGCTCAGTCTTCTTAAGCAAGGGCTAGAAAAGACACAGATATGGAGATGCATGGAAGGA | SEQ ID NO: 993 | Homo sapiens serine/threonine/tyrosine kinase 1 (STYK1), mRNA [NM_018423] |
| 126 | A_23_P138308 | CD58 | AACCTGTATCCAAGCAGGCGGTCATTCAAGACACAGATATGGACTTATAGCCATACCATT | SEQ ID NO: 994 | Homo sapiens CD58 molecule (CD58), mRNA [NM_001779] |
| 127 | A_23_P140069 | FBXL3 | TAACCCCAGTCGAATACATAATTCTTAAAGGCGGCTGTTTCAGTAGTGACTTTAGA | SEQ ID NO: 995 | Homo sapiens F-box and leucine-rich repeat protein 3 (FBXL3), mRNA [NM_012158] |
| 128 | A_23_P140301 | PSMA3 | TGAACTAGAAGTCAGCTGGGTCAGCGGCGCTCATAAAGGTTCATTGGACAACATGAAATTGTTCAAA | SEQ ID NO: 996 | Homo sapiens proteasome (prosome, macropain) subunit, alpha type, 3 (PSMA3), transcript variant 1, mRNA [NM_002788] |
| 129 | A_23_P141549 | RPS7 | GTCAAATAGAGTGGAGCCGGCTCCATAAGGATCATCATTTGGACAAAGCAGCAGAACAAT | SEQ ID NO: 997 | Homo sapiens ribosomal protein S7 (RPS7), mRNA [NM_001011] |
| 130 | A_23_P143958 | RPL22L1 | ATTGGCTCGAGTGGTTGCATCGTGACAAGGAGAGCGTACGAACTTCGTTACTTCCAGATTA | SEQ ID NO: 998 | Homo sapiens ribosomal protein L22-like 1 mRNA (cDNA clone IMAGE:4865966), [BC049823] |
| 131 | A_23_P144224 | TLOC1 | ATGGGATTGTGAACAAGGATGAGGAAGAAGGAAAATGATGAGGAAGTTCAC | SEQ ID NO: 999 | Homo sapiens translocation protein 1 (TLOC1), mRNA [NM_003262] |
| 132 | A_23_P144497 | RPS3A | CGAAATCCGGAAGAAGATGATGAAACATGATGACCCAGAGGTGCAGACAAATGAGTTGAA | SEQ ID NO: 1000 | Homo sapiens ribosomal protein S3A (RPS3A), mRNA [NM_001006] |
| 133 | A_23_P144684 | ANKRD32 | AAACTTTACAAAACTCTAGTAACGATTAGGGCTTCTGACTTTTCCAGGGTGTAGAATTTAGTC | SEQ ID NO: 1001 | Homo sapiens ankyrin repeat domain 32 (ANKRD32), mRNA [NM_032290] |
| 134 | A_23_P145397 | CCNC | TAGTGGACAAGTAAATAAACATTGGACATGGCAATTGTGTAGTGTTTGGTCTTCAGTGGAACAC | SEQ ID NO: 1002 | Homo sapiens cyclin C (CCNC), transcript variant 1, mRNA [NM_005190] |
| 135 | A_23_P14564 | GPR65 | AACAAGTTTAAATGTGTTGCTGATCCAATGTCTAGTGTTTGTAACCGAAAGAGGAAG | SEQ ID NO: 1003 | Homo sapiens G protein-coupled receptor 65 (GPR65), mRNA [NM_003608] |
| 136 | A_23_P145777 | NDUFA4 | ACGCTGGTTTAGAATGAAGTCTTCCAGAAGGCCAGATCGGCACAATTTTCCACTTAAGCA | SEQ ID NO: 1004 | Homo sapiens NADH dehydrogenase (ubiquinone) 1 alpha subcomplex, 4, 9kDa (NDUFA4), nuclear gene encoding mitochondrial protein, mRNA [NM_002489] |
| 137 | A_23_P146347 | FAM29A | TTGGACACAAAGTGAAGCAATGGGAAGGCATTTGATTGTTGAGTAATGTTGTAAGC | SEQ ID NO: 1005 | Homo sapiens family with sequence similarity 29, member A (FAM29A), mRNA [NM_017645] |

Fig. 3-8

| No. | Probe ID No. | Symbols of genes | Sequence | SEQ ID NO: | Descriptions of genes (letters and numbers within [ ] indicates GenBank accession No.) |
|---|---|---|---|---|---|
| 138 | A_23_P14706 | SUHW4 | TCTTTGTACCTCCATACAAGTGTTAGCCTGCCAGGCTGCTAAGGTTACCTTAATTTAAACTT | SEQ ID NO: 1006 | Homo sapiens suppressor of hairy wing homolog 4 (Drosophila) (SUHW4), transcript variant 1, mRNA [NM_017611] |
| 139 | A_23_P14734 | RPS27L | ACAAGATCAGCACAGGTTTTCAGGCAGTGCTCAGACAGTGTTCTTTGTGTAGGTTGTTCA | SEQ ID NO: 1007 | Homo sapiens ribosomal protein S27-like (RPS27L), mRNA [NM_015920] |
| 140 | A_23_P147404 | A_23_P147404 | TGGGGTGAACATGAAATTGATTACATTTGTTGGATGGTGAGGAGCGTCCCTGTCATGTG | SEQ ID NO: 1008 | |
| 141 | A_23_P149775 | ARHGAP12 | TGTATAATAAAACACAGAGGTTTGGAAGAGGTTTGTTACAGGAGGATGGTCTGTTGAAGAT | SEQ ID NO: 1009 | Homo sapiens Rho GTPase activating protein 12 (ARHGAP12), mRNA [NM_018287] |
| 142 | A_23_P149892 | GALNACT-2 | CATGGTGGTTCAGAATAGATGAGCAATGGCATAGCATGGTTTTGTTGTTTTGTGCAATTTC | SEQ ID NO: 1010 | Homo sapiens chondroitin sulfate GalNAcT-2 (GALNACT-2), mRNA [NM_018590] |
| 143 | A_23_P150129 | SAPS3 | TTACCTGTTAAGAAGAGCATCACGAATGAACATTTCAGAGGAATCTGAATATTTAACAGAC | SEQ ID NO: 1011 | Homo sapiens SAPS domain family, member 3 (SAPS3), mRNA [NM_018312] |
| 144 | A_23_P151018 | LEMD3 | CCCCATCTGTGTAAGCTGTTGCAAGAGTGAATGTAAGAGTAAAAATAGTTGTGCATTTTAAAGG | SEQ ID NO: 1012 | Homo sapiens LEM domain containing 3 (LEMD3), mRNA [NM_014319] |
| 145 | A_23_P152002 | BCL2A1 | GTAAGCATATTTGACATTTGAAGGTATTCGTCAAGAAACTTCACGACAGCAAATTGC | SEQ ID NO: 1013 | Homo sapiens BCL2-related protein A1 (BCL2A1), mRNA [NM_004049] |
| 146 | A_23_P154330 | TXNDC9 | CTCAGTTCTTAATTACTGGGAAGGGTGTTTGAGATTTGCTCTGTAGGACGAGATTGACTTTAATC | SEQ ID NO: 1014 | Homo sapiens thioredoxin domain containing 9 (TXNDC9), mRNA [NM_005783] |
| 147 | A_23_P154357 | STK17B | TACCCAATGCGGATGAACTGTTTGAGATTTGCTCTGTAGGACTTTTTCTTTGACTCA | SEQ ID NO: 1015 | Homo sapiens serine/threonine kinase 17b (STK17B), mRNA [NM_004226] |
| 148 | A_23_P155765 | HMGB2 | AAAAATGGAGGTTGAGGTTGATGGGCTACTCATACAGTAGATTTTACAGGTTC | SEQ ID NO: 1016 | Homo sapiens high-mobility group box 2 (HMGB2), mRNA [NM_002129] |
| 149 | A_23_P155815 | NCAPG | AAGTTAGGAAAGACGATGAAGGTGGAATCGTTTAAGATTATGTCAGTATTTGCTTTAA | SEQ ID NO: 1017 | Homo sapiens non-SMC condensin I complex, subunit G (NCAPG), mRNA [NM_022346] |
| 150 | A_23_P156355 | TMEM161B | AGGTTGGACTTGGCATATTTGTTTATTCTGTATGCGTAACTAGTTGGTTTTAATAGG | SEQ ID NO: 1018 | Homo sapiens transmembrane protein 161B (TMEM161B), mRNA [NM_153354] |
| 151 | A_23_P156842 | EEF1E1 | AAGAAAAGAGCAATGGTTCAGCAGTAGTTAGCAATACAGGGTGACTCAAGTAGATGGGCACT | SEQ ID NO: 1019 | Homo sapiens eukaryotic translation elongation factor 1 epsilon 1 (EEF1E1), mRNA [NM_004280] |
| 152 | A_23_P157449 | POLR2K | GGTCTCTCTTGCTTCAAAATATCTTCTTGTACAGTACTCACCATTTTAGATGTGGTTTGAC | SEQ ID NO: 1020 | Homo sapiens polymerase (RNA) II (DNA directed) polypeptide K, 7.0kDa (POLR2K), mRNA [NM_005034] |
| 153 | A_23_P157452 | POLR2K | GGAATGCTTCACTTACTTGGATTTGTCTCTTCCATTTCGATTGTTGATATAAGGTT | SEQ ID NO: 1021 | Homo sapiens polymerase (RNA) II (DNA directed) polypeptide K, 7.0kDa (POLR2K), mRNA [NM_005034] |
| 154 | A_23_P159650 | COX7B | CAAATACGGTAATGCTGTGTATTAGCTAGTGAGGCACTTTCTGTATTGTTACATGGAGATA | SEQ ID NO: 1022 | Homo sapiens cytochrome c oxidase subunit VIIb (COX7B), nuclear gene encoding mitochondrial protein, mRNA [NM_001866] |
| 155 | A_23_P159839 | C1GALT1C1 | TCCAAATCAGATGCATGCATGATGATGTATGGGTATACGGCTTAGGGCATTGGGCACT | SEQ ID NO: 1023 | Homo sapiens C1GALT1-specific chaperone 1 (C1GALT1C1), transcript variant 1, mRNA [NM_152692] |
| 156 | A_23_P160466 | SLC19A2 | CTTGGTATGGTGGGCATATATTATAGAATGGTGAACTCAATGTGCAAGTTGTACTGTATGCA | SEQ ID NO: 1024 | Homo sapiens solute carrier family 19 (thiamine transporter), member 2 (SLC19A2), mRNA [NM_006996] |

Fig. 3-9

| No. | Probe ID No. | Symbols of genes | Sequence | SEQ ID NO: | Descriptions of genes (letters and numbers within [ ] indicates GenBank accession No.) |
|---|---|---|---|---|---|
| 157 | A_23_P163091 | ZMYM1 | GAAGTATTTTTCCTAAGTAGTGGTATTGTACGGTGTATACTGTTCTTCAGCTTGTCTTCTCTG | SEQ ID NO: 1025 | Homo sapiens zinc finger, MYM-type 1 (ZMYM1), mRNA [NM_024772] |
| 158 | A_23_P162279 | CCDC91 | AGTACAGGATATATGAAATGTTTGGCAGTAGTATTCAGAATGTACTTAATTCACAGGCAGG | SEQ ID NO: 1026 | Homo sapiens coiled-coil domain containing 91 (CCDC91), mRNA [NM_018318] |
| 159 | A_23_P162596 | ACTR6 | TAACGGGTCACTGGACAGTTTTCCTTAGAAGGTAGTTTTGTGTGACTGTGAGTAAAGT | SEQ ID NO: 1027 | Homo sapiens ARP6 actin-related protein 6 homolog (yeast) (ACTR6), mRNA [NM_022496] |
| 160 | A_23_P162866 | HSP90AA1 | CTGGGTATTGATGAAGATGACCGTACTGCTGATGATACCAGTGCTGGTTAACTGAAGAA | SEQ ID NO: 1028 | Homo sapiens heat shock protein 90kDa alpha (cytosolic), class A member 1 (HSP90AA1), transcript variant 2, mRNA [NM_005348] |
| 161 | A_23_P163113 | PRPF39 | TAGTAATAGGGAGAAAATGTGAATTAGTAGGTACCACAGATACTGTTCGTACGATTTA | SEQ ID NO: 1029 | Homo sapiens PRP39 pre-mRNA processing factor 39 homolog (S. cerevisiae) (PRPF39), mRNA [NM_017922] |
| 162 | A_23_P163216 | ATP8B4 | ATCAGTGTATTTTTCCATAAAGTGATTCGGGAGGCATATTGTGTGAAAACCTCAGTTCTGTCA | SEQ ID NO: 1030 | Homo sapiens ATPase, Class I, type 8B, member 4 (ATP8B4), mRNA [NM_024837] |
| 163 | A_23_P167828 | RWDD1 | GAGGATGTGTGGAAAACAACGTGGAAGGTAGATGAGTCTTTGTTCGAAGAAATGGATGACTTG | SEQ ID NO: 1031 | Homo sapiens RWD domain containing 1 (RWDD1), transcript variant 2, mRNA [NM_016104] |
| 164 | A_23_P16817 | CLK1 | ATGAAAGGATTCTTGGACCTCACGAAAAACATATGATGACCAGTAAACCAGGAAAACGTAAA | SEQ ID NO: 1032 | Homo sapiens CDC-like kinase 1 (CLK1), transcript variant 1, mRNA [NM_004071] |
| 165 | A_23_P168656 | GTPBP10 | AATTGTTGGATTTCTGATACATGTGTTCTACTGAGGCACGATCAAAGCATGGTTTACT | SEQ ID NO: 1033 | Homo sapiens GTP-binding protein 10 (putative) (GTPBP10), transcript variant 2, mRNA [NM_033107] |
| 166 | A_23_P168974 | SDCBP | GGAAAAGGAACAAGAGAATACAACGTAGCTGTAGAGGGCTAATGCAGTTCTCTTGGGAATGGAGGAGA | SEQ ID NO: 1034 | Homo sapiens cDNA FLJ46804 fis, clone TRACH3032570, highly similar to Homo sapiens syndecan binding protein (syntenin) (SDCBP). [AK128645] |
| 167 | A_23_P169050 | MRPS28 | GAGCAACAAGACAGATACAACGTAGCTAGAGGGTAATGCAGTTCTCTTGGAATGCAGTTC | SEQ ID NO: 1035 | Homo sapiens mitochondrial ribosomal protein S28 (MRPS28), nuclear gene encoding mitochondrial protein, mRNA [NM_014018] |
| 168 | A_23_P169576 | EXOC6 | ATGTGAATCTGCCTTTGCCTTTAGCAGGATTTGCAGCTAATATTAGTAACTATGGCTCATTC | SEQ ID NO: 1036 | Homo sapiens exocyst complex component 6 (EXOC6), transcript variant 2, mRNA [NM_001013849] |
| 169 | A_23_P17021 | SCRN3 | GTCAAAGTTAGTTCTTAGTGATCATAATGGTCAGCTAATATTAGTTCTTAGTGATCAGTGG | SEQ ID NO: 1037 | Homo sapiens secernin 3 (SCRN3), mRNA [NM_024583] |
| 170 | A_23_P170233 | CSTA | AAGTGGTACTAGTCATGATCCTTGGTGATAATAAGGATCAATAAAGAAGCATTGT | SEQ ID NO: 1038 | Homo sapiens cystatin A (stefin A) (CSTA), mRNA [NM_005213] |
| 171 | A_23_P18325 | PDCD10 | CGAACCGAGTAATTGATCAAAGGCAGAACTTAATACTTCGAGCCTTGAAACCTGGCCTTG | SEQ ID NO: 1039 | Homo sapiens programmed cell death 10 (PDCD10), transcript variant 1, mRNA [NM_007217] |
| 172 | A_23_P18422 | MRPL3 | CAGTAGAAAACCATATGGGACTACAGTAGTGGAACCTATTTCGGTAAAGAAACCATTTGCTA | SEQ ID NO: 1040 | Homo sapiens mitochondrial ribosomal protein L3 (MRPL3), nuclear gene encoding mitochondrial protein, mRNA [NM_007208] |
| 173 | A_23_P18598 | PI4K2B | AGGCTTAAAACTGGTAAACTAGAAGTAAGTGCTTGGGGTTAACTGGGTAATTTGTGGTCTAGGCCTTT | SEQ ID NO: 1041 | Homo sapiens phosphatidylinositol 4-kinase type 2 beta (PI4K2B), mRNA [NM_018323] |
| 174 | A_23_P200030 | FPGT | TAAAATTGGTAAACTAGAAGTAAGTGCTGTCCAGAACCCTGAGTTATGATAGTTATGTGCG | SEQ ID NO: 1042 | Homo sapiens fucose-1-phosphate guanylyltransferase (FPGT), mRNA [NM_003838] |

Fig. 3-10

| No | Probe ID No. | Symbols of genes | Sequence | SEQ ID NO: | Descriptions of genes (letters and numbers within [ ] indicates GenBank accession No.) |
|---|---|---|---|---|---|
| 175 | A_23_P200298 | AGL | TAGATTTTAAGAGGTGTCATTTGACTAAAGGTTTCGGTAGAATGCTTCATACTTGAGTG | SEQ ID NO: 1043 | Homo sapiens amylo-1, 6-glucosidase, 4-alpha-glucanotransferase (glycogen debranching enzyme, glycogen storage disease type III) (AGL), transcript variant 4, mRNA [NM_000028] |
| 176 | A_23_P200493 | LBR | GAGCCCTTTATCAATACAGTGGTCCAATTCTGGATATCAGGTACAGTTGTTTTAAGT | SEQ ID NO: 1044 | Homo sapiens lamin B receptor (LBR), transcript variant 1, mRNA [NM_002296] |
| 177 | A_23_P200507 | CNIH4 | TGGTTGAAGTCAGCCTACACTAGAGGTGCACAGTTGAGGCAGCCAGAGACTTCTTAAATCAT | SEQ ID NO: 1045 | Homo sapiens cornichon homolog 4 (Drosophila) (CNIH4), mRNA [NM_014184] |
| 178 | A_23_P200955 | A_23_P200955 | AGACCATGATTGAACGTCACATTGATGTCAAGATACCGATGGTTATTTGTTTGATCTAG | SEQ ID NO: 1046 | |
| 179 | A_23_P201619 | NEK7 | TGAAGGCCAAGAGGAAGTCACTGTTAAAGGACTCGTGCCATGTTACAACGTTGGATGAA | SEQ ID NO: 1047 | Serine/threonine-protein kinase Nek7 (EC 2.7.11.1) (NimA-related protein kinase 7). [Source:Uniprot/SWISSPROT;Acc:Q8TDX7] [ENST00000367385] |
| 180 | A_23_P201918 | ABCB10 | CATGGATCAGGGTAGAGGTAAGAGTAATTAAGTCAATGTAAATCAAATGGAAGTTTTC | SEQ ID NO: 1048 | Homo sapiens ATP-binding cassette, sub-family B (MDR/TAP), member 10 (ABCB10), nuclear gene encoding mitochondrial protein, mRNA [NM_012089] |
| 181 | A_23_P201951 | ARID4B | ATGTTAGAGGTTTGAATTAGGGTAAGGTCTTGCAGTGGTTTTCATGGCCCTTGCAAA | SEQ ID NO: 1049 | Homo sapiens AT rich interactive domain 4B (RBP1-like) (ARID4B), transcript variant 1, mRNA [NM_016374] |
| 182 | A_23_P20225 | RRM2B | TGGTTCCTTGTTAAAAAGTTAAAGATTTGAAAGAGAATCTCATATTCCCGAGGCATTAGGA | SEQ ID NO: 1050 | Homo sapiens ribonucleotide reductase M2 B (TP53 inducible) (RRM2B), mRNA [NM_015713] |
| 183 | A_23_P202496 | NOC3L | ACACGTATTCGTAGTGCTGGAGTGGGCCTAAGAATGCGTGTTTCAGTGACTAGATTAT | SEQ ID NO: 1051 | Homo sapiens nucleolar complex associated 3 homolog (S. cerevisiae) (NOC3L), mRNA [NM_022451] |
| 184 | A_23_P202637 | SAPS3 | TGATTATTCGTACAAGTCAAACACTAGACTATTTGGAGTGTATAGGCTGTGTTTTGGG | SEQ ID NO: 1052 | Homo sapiens SAPS domain family, member 3 (SAPS3), mRNA [NM_018312] |
| 185 | A_23_P203498 | TRIM22 | GTACATAAGAATCTATCACTAAGTAATGATTCGTCAAGAATGTGTTGGTTTACCAGTGAC | SEQ ID NO: 1053 | Homo sapiens tripartite motif-containing 22 (TRIM22), mRNA [NM_006074] |
| 186 | A_23_P203645 | CREBZF | TCTCATTGGCAGTATTTTCTTCCTTACGTCAGTCAATACTTTTCTGGATTATTTGAAATTGGGG | SEQ ID NO: 1054 | Homo sapiens CREB/ATF bZIP transcription factor (CREBZF), mRNA [NM_001039618] |
| 187 | A_23_P204187 | FLJ22028 | GTATAAGGTTCTAGTGCTGGGAAAATAGAATGGACAGGGGTTAGGTTCAGAATCATGAATT | SEQ ID NO: 1055 | Homo sapiens hypothetical protein FLJ22028 (FLJ22028), mRNA [NM_024854] |
| 188 | A_23_P204269 | USP15 | GACGAGGATAAATCAGGTATGTTGATCATGAGGCTTTTGGTTTATATCTTGAATTTAAAGCTG | SEQ ID NO: 1056 | Homo sapiens ubiquitin specific peptidase 15 (USP15), mRNA [NM_006313] |
| 189 | A_23_P204564 | PPP1R12A | GTATAAGATGTTAGATTCGTAATCGTCAGATTCATTTTAGGAGGTACTGAGTGATGCTG | SEQ ID NO: 1057 | Homo sapiens protein phosphatase 1, regulatory (inhibitor) subunit 12A (PPP1R12A), mRNA [NM_002480] |
| 190 | A_23_P205027 | ABHD13 | ATTTGTGCAGAATGATAAAGAATGTTCCTTTTAGAGAGTGTGTTATGTGTATGGTCTG | SEQ ID NO: 1058 | Homo sapiens abhydrolase domain containing 13 (ABHD13), mRNA [NM_032859] |
| 191 | A_23_P205336 | C14orf129 | CAATTCATTGGCAGACTTCATTGGAATGGCTTGTTGATGATGTATGTTCATTCTCAGGT | SEQ ID NO: 1059 | Homo sapiens chromosome 14 open reading frame 129 (C14orf129), mRNA [NM_016472] |

Fig. 3-11

| No | Probe ID No. | Symbols of genes | Sequence | SEQ ID NO: | Descriptors of genes (letters and numbers within [ ] indicates GenBank accession No.) |
|---|---|---|---|---|---|
| 192 | A_23_P205646 | MAP4K5 | GTAATGTAGGAGGGGAAGTATTTAATTGCCCATGATATGTATT TTACTTATATGTATGCC | SEQ ID NO: 1060 | Homo sapiens mitogen-activated protein kinase kinase kinase kinase 5 (MAP4K5), transcript variant 2, mRNA [NM_198794] |
| 193 | A_23_P20606 | NIPSNAP3A | GTAAGTAGCACTTCAAAAAATAGTGTGTTTACTTTCTGGATGG TATTTCAGTGTCTGTC | SEQ ID NO: 1061 | Homo sapiens nipsnap homolog 3A (C. elegans) (NIPSNAP3A), mRNA [NM_015469] |
| 194 | A_23_P207299 | LOC51136 | CCAAAACAGGAATTTGAAATTAGAAGTAGTGGTTTTAGAGAACT CAGGTATTCTTCCTG | SEQ ID NO: 1062 | Homo sapiens PTD016 protein (LOC51136), mRNA [NM_016125] |
| 195 | A_23_P207999 | PMAIP1 | TTAGAGAATGTCTTCCAGTGTTTTGCCGAAGATTACCGGCTGGCC TACTGTGAAGGGAGAT | SEQ ID NO: 1063 | Homo sapiens phorbol-12-myristate-13-acetate-induced protein 1 (PMAIP1), mRNA [NM_021127] |
| 196 | A_23_P208238 | ZNF137 | CCATACTGGACATAAATGTTAGAAATGTGTTAAGTGTGGCAAGG TCTTCAGTGTCTGGGG | SEQ ID NO: 1064 | Homo sapiens zinc finger protein 137 (ZNF137), mRNA [NM_003438] |
| 197 | A_23_P209032 | ZNF302 | TCAGAAAAATGTATACTGGGGAAAAGTTGTATGAAGGTCGTGAA CATGGGAGACTTTTAG | SEQ ID NO: 1065 | Homo sapiens zinc finger protein 302 (ZNF302), transcript variant 1, mRNA [NM_018443] |
| 198 | A_23_P209879 | ATF2 | TCATGTAAAGGGTTAACAAGGTTACCAAGGTTAGGAAAAACTTTC ATTGTAAATCAGTGTG | SEQ ID NO: 1066 | Homo sapiens cDNA FLJ46399 fis, clone UTERU30222588, highly similar to Cyclic-AMP-dependent transcription factor ATF-2 [AK128731] |
| 199 | A_23_P210274 | PREI3 | GGATCAGTATGCGGTAGGATTTACAGAATATTTCAGATGGTTA TTTCATCATCGGCAG | SEQ ID NO: 1067 | Homo sapiens preimplantation protein 3 (PREI3), transcript variant 1, mRNA [NM_015387] |
| 200 | A_23_P210829 | PCMTD2 | TCCTGAGGACCTTATACGAGGAATTCAGTATATACACTACTTTG TGTTTTCAAACAGATA | SEQ ID NO: 1068 | Homo sapiens protein-L-isoaspartate (D-aspartate) O-methyltransferase domain containing 2 (PCMTD2), mRNA [NM_018257] |
| 201 | A_23_P211840 | UBE1C | GCCACGGTAGAGGGAAAAAATAGAACACTTTACAGTCGGT AAGCTCTATTGAAGAA | SEQ ID NO: 1069 | Homo sapiens ubiquitin-activating enzyme E1C (UBA3 homolog, yeast) (UBE1C), transcript variant 1, mRNA [NM_003968] |
| 202 | A_23_P212728 | TBC1D23 | TGTACCCTGTTAACAGGCAGCCAGTCATTTTGATTTAGTTATGGAAAT CAAGTGAATAAAAGGC | SEQ ID NO: 1070 | Homo sapiens TBC1 domain family, member 23, mRNA (cDNA clone MGC:8800 IMAGE:3847561), complete cds. [BC020955] |
| 203 | A_23_P2129 | TMEM126B | CATATGCATCATTGGCTACGCTACACTTCGCATTTTGCTAGTGTTGTT ACTGACAAGCTTTTG | SEQ ID NO: 1071 | Homo sapiens transmembrane protein 126B (TMEM126B), mRNA [NM_018480] |
| 204 | A_23_P213661 | HISPPD1 | GTATGTAAGTTTTCGTGTTTGTGAAAATAGTTAATGTACTGAC TGTGGAGGTCATAAGG | SEQ ID NO: 1072 | Homo sapiens histidine acid phosphatase domain containing 1 (HISPPD1), mRNA [NM_152161] |
| 205 | A_23_P215751 | NDUFA5 | TAAAAGTGGAGTCACTAAAATAGTTGGAGTACGTTTCTAATATA AGTGTAGGTGGGTATC | SEQ ID NO: 1073 | Homo sapiens NADH dehydrogenase (ubiquinone) 1 alpha subcomplex, 5, 13kDa (NDUFA5), nuclear gene encoding mitochondrial protein, mRNA [NM_005000] |
| 206 | A_23_P21734 | TAF9 | CATGGTTGTGATTTCTTCCCTGAACGGCTGGTTTCATATAGTTTT TGTGCTGAGAACAGAT | SEQ ID NO: 1074 | Homo sapiens TAF9 RNA polymerase II, TATA box binding protein (TBP)-associated factor, 32kDa (TAF9), transcript variant 3, mRNA [NM_001015891] |
| 207 | A_23_P217384 | AP1S2 | AAACGTGTTGTCTCTTGACAGTATTATGTGAAGTCATTGTT TAAAGCACGAATGTTC | SEQ ID NO: 1075 | Homo sapiens adaptor-related protein complex 1, sigma 2 subunit (AP1S2), mRNA [NM_003916] |
| 208 | A_23_P217564 | ACSL4 | GTTATAGGTGCTTTAGAAACACATAAGCACACTTAAGGTTGGG TGCTTGGTAATTCTTTG | SEQ ID NO: 1076 | Homo sapiens acyl-CoA synthetase long-chain family member 4 (ACSL4), transcript variant 1, mRNA [NM_004458] |

Fig. 3-12

| No. | Probe ID No. | Symbols of genes | Sequence | SEQ ID NO: | Descriptions of genes, letters and numbers without [ ] indicates GenBank accession No.) |
|---|---|---|---|---|---|
| 209 | A_23_P218928 | C4orf18 | CAGATGAGTTCATTGCTTCTGTAGAGTGTTTTCAGGAGCTAGGTACAGAGGAAATGTTTG | SEQ ID NO: 1077 | Homo sapiens chromosome 4 open reading frame 18 (C4orf18), transcript variant 2, mRNA [NM_016613] |
| 210 | A_23_P219072 | SAMD9 | AACCTACCTGCAGATTGTAGTAAAGCCAGTTGAAAAGTAAAAGATCAGCTTCAGAAGTCT | SEQ ID NO: 1078 | Homo sapiens sterile alpha motif domain containing 9 (SAMD9), mRNA [NM_017654] |
| 211 | A_23_P22671 | SYBL1 | CAAAGGAATACGGTGCAGCAGTGACAGCTGCAGGGTTGGGGTTGATTCCTGTTGAATAATA | SEQ ID NO: 1079 | Homo sapiens synaptobrevin-like 1 (SYBL1), mRNA [NM_005638] |
| 212 | A_23_P23765 | ITGB3BP | AGTATACAGGCTTGGAGGGCAGTAGAGAGGTTGAAAATCTCATTGGAATCTGGTGTGCA | SEQ ID NO: 1080 | Homo sapiens integrin beta 3 binding protein (beta3-endonexin) (ITGB3BP), mRNA [NM_014288] |
| 213 | A_23_P23960 | BLOC1S2 | GAGTAAAGGTGGAGGACTGGTGGCTATTCGTGAACCTTCTTGAGACAGAATCCCTGAGAAT | SEQ ID NO: 1081 | Homo sapiens biogenesis of lysosome-related organelles complex-1, subunit 2 (BLOC1S2), transcript variant 2, mRNA [NM_001042] |
| 214 | A_23_P24365 | ANKRD49 | GGGCAGTGCTTGTATAGTGTCTCAAGTTCACAAGGAAAGTTGAATTTTCTAAGGTCGTCAT | SEQ ID NO: 1082 | Homo sapiens ankyrin repeat domain 49 (ANKRD49), mRNA [NM_017704] |
| 215 | A_23_P250002 | HACE1 | TAAGCAGTCATGTGTTGTTGCCAGTAATGTTGAGAGACAGAAGTTGAAAGTTTTGCTA | SEQ ID NO: 1083 | Homo sapiens HECT domain and ankyrin repeat containing, E3 ubiquitin protein ligase 1 (HACE1), mRNA [NM_020771] |
| 216 | A_23_P250800 | ST3GAL6 | ATGTCACGAAGTTCACCTAGCTGGTTTAAATACAACGTTTGTGACCTCAAGAGTCCTT | SEQ ID NO: 1084 | Homo sapiens ST3 beta-galactoside alpha-2,3-sialyltransferase 6 (ST3GAL6), mRNA [NM_006100] |
| 217 | A_23_P250930 | CRBN | TGAGTATTGAGAAGTTCCCTTAAAATTCAGGCTCCTAAAATTGGCAGTGCTATCCAGCAGTTGGTGTTGA | SEQ ID NO: 1085 | Homo sapiens cereblon (CRBN), mRNA [NM_016302] |
| 218 | A_23_P250994 | ANAPC10 | GATTCATGTTCCTTAACTGACAATCATAAGAGAGCCAACTCGTACATTCATGATACAGAT | SEQ ID NO: 1086 | Homo sapiens anaphase promoting complex subunit 10 (ANAPC10), mRNA [NM_014885] |
| 219 | A_23_P251421 | CDCA7 | ATTAGTTGGATAATGTAAAGGATTGCTGTGCCATTCAATGTTATGCATAATTGGACCT | SEQ ID NO: 1087 | Homo sapiens cell division cycle associated 7 (CDCA7), transcript variant 1, mRNA [NM_031942] |
| 220 | A_23_P251937 | CPEB4 | GTATGTCAGTTAATTGTAGTACTGGGTGAATTTGATATAGTTTTACTGTGTATGGG | SEQ ID NO: 1088 | Homo sapiens cytoplasmic polyadenylation element binding protein 4 (CPEB4), mRNA [NM_030627] |
| 221 | A_23_P252145 | C1GALT1 | ATATGTCTATATATATGAGAACTTGTGTTTTTAAATGGTGCCAGGTAGGAAGTAG | SEQ ID NO: 1089 | Homo sapiens core 1 synthase, glycoprotein-N-acetylgalactosamine 3-beta-galactosyltransferase, 1 (C1GALT1), mRNA [NM_020156] |
| 222 | A_23_P252201 | EAF2 | CAGGGATTCCTGATATAGATAGCCAGTCATAATAGATTCGAGACAACAGTGCCTCTGAT | SEQ ID NO: 1090 | Homo sapiens ELL associated factor 2 (EAF2), mRNA [NM_018456] |
| 223 | A_23_P252371 | RBBP8 | GGCAAGAGAGGAGAAGACAAGAACGTTGAAAGAGAAGAGGATGAAGGACAGTTTTT | SEQ ID NO: 1091 | Homo sapiens retinoblastoma binding protein 8 (RBBP8), transcript variant 1, mRNA [NM_002894] |
| 224 | A_23_P253412 | MRPL50 | GAAAAGTTTTGAGAGGGCAGTGTCAACTGTGAAGGTTTAAGAGGAGGAGGCATTGCAAGTCA | SEQ ID NO: 1092 | Homo sapiens mitochondrial ribosomal protein L50 (MRPL50), nuclear gene encoding mitochondrial protein, mRNA [NM_019051] |
| 225 | A_23_P254472 | C6orf211 | TTGATTGCAATAGGTTGTTTCATTTGGCACGCGTTTGTATTTGATGACCTGTAGAATGG | SEQ ID NO: 1093 | Homo sapiens chromosome 6 open reading frame 211 (C6orf211), mRNA [NM_024573] |
| 226 | A_23_P254702 | DEK | TTTTTATTAACTGCTTTGGCCATAATAACATGCTGATATTTACTGGAAACCTAGGCAGG | SEQ ID NO: 1094 | Homo sapiens DEK oncogene (DNA binding) (DEK), mRNA [NM_003472] |
| 227 | A_23_P254733 | MLF1IP | GCTGTTAGGTTCTGAAAGTGTACCTTTATAAATCAATTGTTTTGCAAAGAAGTATGGGC | SEQ ID NO: 1095 | Homo sapiens MLF1 interacting protein (MLF1IP), mRNA [NM_024629] |

Fig. 3-13

| No. | Probe ID No. | Symbols of genes | Sequence | SEQ ID NO: | Descriptions of genes (letters and numbers within [ ] indicates GenBank accession No.) |
|---|---|---|---|---|---|
| 228 | A_23_P254756 | CD164 | TTAGTTTTAAGTGAGTGCTGTAGGATTAATTCGAAAATAGGCAG AATTCCATTGCTCCCA | SEQ ID NO: 1096 | Homo sapiens CD164 molecule, sialomucin (CD164), mRNA [NM_006016] |
| 229 | A_23_P25503 | FNDC3A | ATACTTGGCATTTGAGGCTCACTCGAAAATAGTGCAGGAGA AAAGAATTTTAATGT | SEQ ID NO: 1097 | Homo sapiens fibronectin type III domain containing 3A (FNDC3A), transcript variant 2, mRNA [NM_014923] |
| 230 | A_23_P255663 | MANEA | AAAGAGTCTGTACATGTTCAGAGTTTCAGTGGGCAATTTGTTGG CCATGGATGTAGAACC | SEQ ID NO: 1098 | Homo sapiens mannosidase, endo-alpha (MANEA), mRNA [NM_024641] |
| 231 | A_23_P256231 | FBXO30 | GGCTTTTAAAGTTTTGCTGAAGAATGTGTCTGTGGTTAGGATAG CACAAGCATTAACTTT | SEQ ID NO: 1099 | Homo sapiens F-box protein 30 (FBXO30), mRNA [NM_032145] |
| 232 | A_23_P256342 | SNX13 | ATTAGCCAGGTGAATGATCCTTGAAACATCTGTTTCAGGCTCTG AGAAGAGACAGAATG | SEQ ID NO: 1100 | Homo sapiens sorting nexin 13 (SNX13), mRNA [NM_015132] |
| 233 | A_23_P25638 | C13orf7 | CTTGCATTCCAGGGGAGGAGTTTTCTTTGAGTAGTATGTTTCTTGT TTGCATGTTCCTGTC | SEQ ID NO: 1101 | Homo sapiens chromosome 13 open reading frame 7 (C13orf7), mRNA [NM_024546] |
| 234 | A_23_P25735 | PSMA6 | TAGCAGAGAGAGCTAAACATGTCGTTAGTTTACCAGATGCGT GATGCCACTTACCTGT | SEQ ID NO: 1102 | Homo sapiens proteasome (prosome, macropain) subunit, alpha type, 6 (PSMA6), mRNA [NM_002791] |
| 235 | A_23_P257911 | USP16 | GTAGTTGTTGTTTAATATATGTGGGTAGTTTGGATGATCAGAACAGATG AATAAACTGACTTACC | SEQ ID NO: 1103 | Homo sapiens ubiquitin specific peptidase 16 (USP16), transcript variant 1, mRNA [NM_006447] |
| 236 | A_23_P256108 | LOC731224 | GTGAGGCCAGGTGTTGCTTGTTCAATATCCAAGCCCAGAAAGA TGAGTTCATCGTAAA | SEQ ID NO: 1104 | PREDICTED: Homo sapiens similar to 60S ribosomal protein L9 (LOC731224), mRNA [XR_015757] |
| 237 | A_23_P256054 | SNX14 | CATCAGACTTCTGTTTGATGGCTTACAGCAACCAGTACTCAACA AGCAGGTCACTTATGT | SEQ ID NO: 1105 | Homo sapiens sorting nexin 14 (SNX14), transcript variant 1, mRNA [NM_153816] |
| 238 | A_23_P255594 | AKAP7 | GAAGATAAGCTCGAGGTCTTATCGTATGCCTTGGGATCTGAACT TGTTTGGACTGCTTCT | SEQ ID NO: 1106 | Homo sapiens A kinase (PRKA) anchor protein 7 (AKAP7), transcript variant gamma, mRNA [NM_016377] |
| 239 | A_23_P26021 | COPS2 | TGCTTTTTGATCAACTGGTTCTGTGTTTGCTGCTGTGCATTATC CCAAGAAAAACAGCTT | SEQ ID NO: 1107 | Homo sapiens COP9 constitutive photomorphogenic homolog subunit 2 (Arabidopsis) (COPS2), mRNA [NM_004236] |
| 240 | A_23_P2705 | P2RY5 | TCTGTATTGCTAACTGGTTCCAACTGTTGTTTGTTTGACCCTATAGTTTAC TACTTTACATCGGACA | SEQ ID NO: 1108 | Homo sapiens purinergic receptor P2Y, G-protein coupled, 5 (P2RY5), mRNA [NM_005767] |
| 241 | A_23_P28169 | ARL6IP6 | GGAAAGCAAATAATGCCTACTACTCCGACTTTTATAGAAGCTAC TTTAAATCAGAATAT | SEQ ID NO: 1109 | Homo sapiens ADP-ribosylation-like factor 6 interacting protein 6 (ARL6IP6), mRNA [NM_152522] |
| 242 | A_23_P29005 | SAMSN1 | CTCTGGTTGCTATATCTCATGCAGAATTTCAGATAATAATGGCAAAG AGGATGGAGTCTGA | SEQ ID NO: 1110 | Homo sapiens SAM domain, SH3 domain and nuclear localization signals 1 (SAMSN1), mRNA [NM_022136] |
| 243 | A_23_P302550 | RGS18 | GAGTCTAAGGCCCTAGGAGATTGGGCATCTGGACATTGGTTCA TATTCAGAAAGTGTTA | SEQ ID NO: 1111 | Homo sapiens regulator of G-protein signalling 18 (RGS18), mRNA [NM_130782] |
| 244 | A_23_P30307 | CRSP9 | GAATTGTAGTGGACAAGAATGAAGATCAAAAGAGAAAATTCAGGTC ATAGGACAGATCAGAT | SEQ ID NO: 1112 | Homo sapiens cofactor required for Sp1 transcriptional activation, subunit 9, 33kDa (CRSP9), mRNA [NM_004270] |
| 245 | A_23_P303260 | STX7 | GTCTGAAGTTTACGGGGGGAGAGTGTAGTACTAAAATGTTTAA CATAATTTGGAAGAAG | SEQ ID NO: 1113 | Homo sapiens syntaxin 7 (STX7), mRNA [NM_003569] |
| 246 | A_23_P305060 | PBEF1 | TGGCTGTCGGCTGTAATATGACCTCAAGATTTTTAAGGAGATAAT GTTTTTAGAGAGAATT | SEQ ID NO: 1114 | Homo sapiens pre-B-cell colony enhancing factor 1 (PBEF1), mRNA [NM_005746] |

Fig. 3-14

| No. | Probe ID No. | Symbols of genes | Sequence | SEQ ID NO. | Descriptions of genes, letters and numbers within [ ] indicates GenBank accession No.; |
|---|---|---|---|---|---|
| 247 | A_23_P305723 | MIER1 | TGATGTATTTCAAATACAGTTCAGGATGTCGAATTCAGTTCAA GACAAGTTGTTGTGAGG | SEQ ID NO: 1115 | Homo sapiens mesoderm induction early response 1 homolog (Xenopus laevis) (MIER1), transcript variant 1, mRNA [NM_020948] |
| 248 | A_23_P306890 | POLI | TGAATAACGGAGTAAAGTGTTCCAGATAAAGCAAGAATAGTTGC AAGAAGTAAATTCTGG | SEQ ID NO: 1116 | Homo sapiens polymerase (DNA directed) iota (POLI), mRNA [NM_007195] |
| 249 | A_23_P307940 | CAPZA2 | CTACAAGATTGGCAAAGAAGAGGAGAATGGATAAGAATGAACAT GCATGACCGGATCATT | SEQ ID NO: 1117 | Homo sapiens capping protein (actin filament) muscle Z-line, alpha 2 (CAPZA2), mRNA [NM_006136] |
| 250 | A_23_P308800 | GLS | CGGAGAAGAAGATAAGATACTGCGAATAGGCGGCTCAAACTAAA AAGAAAAAAACTTTGC | SEQ ID NO: 1118 | Homo sapiens glutaminase C mRNA, complete cds. [AF158555] |
| 251 | A_23_P30955 | KIAA0776 | TTTCATTTGTCAAAATGCTTCTTTGTTGCCACAGTAAAGA ACAGTTTTATTGTTT | SEQ ID NO: 1119 | Homo sapiens KIAA0776 (KIAA0776), mRNA [NM_015323] |
| 252 | A_23_P31097 | OSTM1 | ACTGAAAATGTGCTGGGGTTGTTCTGTGGTCACTGTTTATGCT GGTGGAACTTAGCACT | SEQ ID NO: 1120 | Homo sapiens osteopetrosis associated transmembrane protein 1 (OSTM1), mRNA [NM_014028] |
| 253 | A_23_P312246 | CCDC82 | GGCTTTATAACAGATGACTGTCAAGTGAATGAGTCGTTGATATC CTGTCAGTTTAGTCAA | SEQ ID NO: 1121 | Homo sapiens coiled-coil domain containing 82 (CCDC82), mRNA [NM_024725] |
| 254 | A_23_P314191 | ZDHHC17 | TGGATACTTTAGGAAATAAGGAAGAACTTAAATTCTCAGCAGTGAACA TGAATTAGTTCGTG | SEQ ID NO: 1122 | Homo sapiens zinc finger, DHHC-type containing 17 (ZDHHC17), mRNA [NM_015336] |
| 255 | A_23_P314591 | NFYB | GGAGGCATTTACTAACCAGTTACCAGCTGGGTTAATGACGACAG ACGGTCAACAACAAAA | SEQ ID NO: 1123 | Homo sapiens nuclear transcription factor Y, beta (NFYB), mRNA [NM_006166] |
| 256 | A_23_P31671 | UQCRB | AAGCATAAGAAGAGACTTCCGAGAACCTTTATAATGACAGGATG TTTGGCATTAAGAGGG | SEQ ID NO: 1124 | Homo sapiens ubiquinol-cytochrome c reductase binding protein (UQCRB), mRNA [NM_006294] |
| 257 | A_23_P31702 | PXMP3 | CTTCTGTGGCATGGTTTTCTGAATTTGCTGATTTTTCTCTTACC ACTTATCAATGTCCAG | SEQ ID NO: 1125 | Homo sapiens peroxisomal membrane protein 3, 35kDa (Zellweger syndrome) (PXMP3), transcript variant 1, mRNA [NM_000318] |
| 258 | A_23_P317347 | ESCO1 | GGTAATTTTTAAAAGGCTGAACTATACTTGAAGAAAACGCGTA TAGAAAAGGAAAAGCTC | SEQ ID NO: 1126 | Homo sapiens establishment of cohesion 1 homolog 1 (S. cerevisiae) (ESCO1), mRNA [NM_052911] |
| 259 | A_23_P3204 | MAPK6 | AACGTGCTCACTGTGTATCCCTCGGATTCAGTGTGTAGAAATGTGTAA ATCTATCTACAAGAA | SEQ ID NO: 1127 | Homo sapiens mitogen-activated protein kinase 6 (MAPK6), mRNA [NM_002748] |
| 260 | A_23_P324633 | C9orf72 | TTTGTGGATTTAGTCCCTGGGATTGCTTTATTGGTCCATGTTTGTGTGCA TAGTTCTCTAGTGC | SEQ ID NO: 1128 | Homo sapiens chromosome 9 open reading frame 72 (C9orf72), transcript variant 1, mRNA [NM_018325] |
| 261 | A_23_P325501 | MORC3 | CATGGGTAAAAATACTACGTCTTTATTGGTCCCATGTTTTGTGCA ATTTAAAACAGATGGC | SEQ ID NO: 1129 | Homo sapiens MORC family CW-type zinc finger 3 (MORC3), mRNA [NM_015358] |
| 262 | A_23_P327022 | MDFIC | TTATGATTTCTTAATGTAAAATGTTTTGTTGAAGTATAGGGTA TCATGACTAAGTGGTA | SEQ ID NO: 1130 | Homo sapiens MyoD family inhibitor domain containing (MDFIC), mRNA [NM_199072] |
| 263 | A_23_P329198 | OBFC2A | ACATGTCATAAGTGGTACCCACACTTCCCCTTTTTACTGTAGGGTG GATAACGTCTTAGGATT | SEQ ID NO: 1131 | Homo sapiens oligonucleotide/oligosaccharide-binding fold containing 2A (OBFC2A), mRNA [NM_001031716] |
| 264 | A_23_P33045 | RPL26 | TACAAAGGTCAGGCAAAATTGGCAAAGTAGTCCAAAGTTACAGGAA GAAATAGTTATGTAC | SEQ ID NO: 1132 | Homo sapiens ribosomal protein L26 (RPL26), mRNA [NM_000987] |
| 265 | A_23_P332439 | NUPL1 | ATTGAAATCTTGAATGTATATGTCAAGATCTGTCAAGGTACAGAGGGT GCCTTTGTAAATGTTC | SEQ ID NO: 1133 | Homo sapiens KIAA0410 mRNA, partial cds. [AB007870] |
| 266 | A_23_P339460 | HAT1 | AACAGTAACAGCTGGAAGAGAGTTTCAGGAACTAGTGGAAGAT TACCGGCGTGTATTG | SEQ ID NO: 1134 | Homo sapiens histone acetyltransferase 1 (HAT1), transcript variant 1, mRNA [NM_003642] |

Fig. 3-15

| No. | Probe ID No. | Symbols of genes | Sequence | SEQ ID NO: | Descriptions of genes (letters and numbers within [ ] indicates GenBank accession No.) |
|---|---|---|---|---|---|
| 267 | A_23_P34307 | PIGK | ATTGATTCAGAGTCTTCTATTGTTGGAGCACTTACATTGTACC AAATGTTTTGCTTTGG | SEQ ID NO: 1135 | Homo sapiens phosphatidylinositol glycan anchor biosynthesis, class K (PIGK), mRNA [NM_005482] |
| 268 | A_23_P347059 | MOBKL1A | CTAGAAGGGGAAAAAATCATCTAAGTTATGAAATGCAACATAGGC GCTATATTACAAAGTG | SEQ ID NO: 1136 | Homo sapiens MOB1, Mps One Binder kinase activator-like 1A (yeast) (MOBKL1A), mRNA [NM_173468] |
| 269 | A_23_P347198 | SP3 | GAGGACCTCAAATTTAAAGGCTAGGTTATTGTAGGTTTAAAGTG TATTATAACAGTGTGG | SEQ ID NO: 1137 | Homo sapiens Sp3 transcription factor (SP3), transcript variant 1, mRNA [NM_003111] |
| 270 | A_23_P349083 | FCHO2 | GTGAAATGGTTAAGCTTCGGACGTTCGTTGTGTTAGTTACCACAGTGTCTT CATACCAAGTATTGGG | SEQ ID NO: 1138 | Homo sapiens FCH domain only 2 (FCHO2), mRNA [NM_138782] |
| 271 | A_23_P351467 | CMAH | GCTTACATTTGTGGATCACTACATAGGCAGAATTCAAAAATATT TACTTGTTCCATGGAC | SEQ ID NO: 1139 | Homo sapiens cytidine monophosphate-N-acetylneuraminic acid hydroxylase (CMP-N-acetylneuraminate monooxygenase) (CMAH) on chromosome 6 [NR_002174] |
| 272 | A_23_P353704 | RP5-1022P6.2 | TGTCTCAGTACCTATTAGAGACACGTGTTGGCTTGCTGGTTTGTT TTGTATGTCGGTGTGT | SEQ ID NO: 1140 | Homo sapiens hypothetical protein KIAA1434 (KIAA1434), mRNA [NM_019593] |
| 273 | A_23_P354894 | ZNF567 | ACCTAAGAGTTACGACTTCCGTTAGCCTATAACATCAAAACGTAG TTTTGCATGTTTCA | SEQ ID NO: 1141 | Homo sapiens zinc finger protein 567 (ZNF567), mRNA [NM_152603] |
| 274 | A_23_P355067 | TMCO1 | AAGTCAAGAAGTCTTTATTTCTATCGATTCTTTCTAGAGACACA CACATCAGACTGGCAA | SEQ ID NO: 1142 | Homo sapiens transmembrane and coiled-coil domains 1 (TMCO1), mRNA [NM_019026] |
| 275 | A_23_P355244 | SAMD9 | TCACTGGACGGAAGATTTTCCGTTGCTTGTGGCATAAAATTTAAG TCGATAAGTTATAAGG | SEQ ID NO: 1143 | Homo sapiens sterile alpha motif domain containing 9 (SAMD9), mRNA [NM_017654] |
| 276 | A_23_P356122 | ZNF451 | TTTTACCTGGTTAGAGCTTTTAATTACTGCTGTATATTGTTGATTTCGTGGT TAAAGGGAATGGTGTC | SEQ ID NO: 1144 | Homo sapiens zinc finger protein 451 (ZNF451), transcript variant 2, mRNA [NM_015555] |
| 277 | A_23_P356125 | KIAA1468 | GCACTGGTTGTTAATTACTGCTGTATTGTTGATTTGGAGTT ACAACTGGTGATAG | SEQ ID NO: 1145 | Homo sapiens KIAA1468 (KIAA1468), mRNA [NM_020854] |
| 278 | A_23_P357811 | MBNL1 | ATGGTTTCAAACCCTCATGACTGACTGAGAAAAACTGCATGGGGCGAA ATCTGCCTGAAGATCA | SEQ ID NO: 1146 | Homo sapiens muscleblind-like (Drosophila) (MBNL1), transcript variant 1, mRNA [NM_021038] |
| 279 | A_23_P358470 | CCDC111 | ATGAGGGTCTATGTAAAGCAGATTCTTAATGCTGATATATG GACTCTTGAATGGAA | SEQ ID NO: 1147 | Homo sapiens coiled-coil domain containing 111 (CCDC111), mRNA [NM_152663] |
| 280 | A_23_P364107 | C14orf106 | AGGAGACAGTTGTTTGTATTTCAAGTGGAGTACATGTATTTCT TTGTAAAGTAGGTCTC | SEQ ID NO: 1148 | Homo sapiens chromosome 14 open reading frame 106 (C14orf106), mRNA [NM_018353] |
| 281 | A_23_P36776 | PUS7L | GGGCTTGACTTTGGTTGTCAACATCGTAAAATGGCATGTTAACAGTTAAG CTACCTCATAGGATTA | SEQ ID NO: 1149 | Homo sapiens pseudouridylate synthase 7 homolog (S. cerevisiae)-like (PUS7L), mRNA [NM_031292] |
| 282 | A_23_P371266 | DNM3 | ACTGTCTTCTTGGCACTTTCAGGATTTCTTAATGCTGATATATG GACTCTTGAATGGAA | SEQ ID NO: 1150 | Homo sapiens dynamin 3 (DNM3), mRNA [NM_015569] |
| 283 | A_23_P37275 | CGRRF1 | GAGCAAGAGATAAAGCAAACGGAAGACTGTTTGAAGAGTACACT CACTGAAAAGTACACT | SEQ ID NO: 1151 | Homo sapiens cell growth regulator with ring finger domain 1 (CGRRF1), mRNA [NM_006568] |
| 284 | A_23_P37441 | B2M | TTGTTTTTCAGCAGGATAGTTAAGATTAAGAGGCATGTTACTACGAC TGAATTCAGCCCCACT | SEQ ID NO: 1152 | Homo sapiens beta-2-microglobulin (B2M), mRNA [NM_004048] |
| 285 | A_23_P37636 | FAM96A | CTTGAACCTGACTGATAGCTGTGTTTTAAGAGGCACTGGCCTGTAA TTGTTTGATATATTG | SEQ ID NO: 1153 | Homo sapiens family with sequence similarity 96, member A (FAM96A), transcript variant 1, mRNA [NM_032231] |

Fig. 3-16

| No. | Probe ID No | Symbols of genes | Sequence | SEQ ID NO: | Descriptions of genes (letters and numbers within [ ] indicates GenBank accession No.) |
|---|---|---|---|---|---|
| 286 | A_23_P38275 | THC2504576 | TCTGCGCAAATGAAGTTTAATCCTTGTGACTTCCGACGGAAGCAAGAATGGCAAAAG | SEQ ID NO: 1154 | RL26_BOVIN (P61257) 60S ribosomal protein L26, complete [THC2504576] |
| 287 | A_23_P384056 | CCDC14 | TAGCTCAGTATCATCTCCCTTCATGTAAGCAGCAGCAGTTTTAACTCTTAGAAGCTGAATG | SEQ ID NO: 1155 | Homo sapiens coiled-coil domain containing 14 (CCDC14), mRNA [NM_022757] |
| 288 | A_23_P390734 | FGFR1OP2 | CCACCACATACAGAAATGTGCTTAACATCAGTGAAACCTAAATTTTCTTATGTGTGG | SEQ ID NO: 1156 | Homo sapiens FGFR1 oncogene partner 2 (FGFR1OP2), mRNA [NM_015633] |
| 289 | A_23_P394276 | RWDD4A | TTGTTCAGGCTTATTATGGCTCATAGATTACAGAGAATGATGCTAGTTAGATGCAATGA | SEQ ID NO: 1157 | Homo sapiens RWD domain containing 4A (RWDD4A), mRNA [NM_152682] |
| 290 | A_23_P394605 | SEC24A | GATTTATTTCTTCTAATCAAAGATGCATAACAGGTATTATGTAGGGGACCAGCAAATGTG | SEQ ID NO: 1158 | Homo sapiens SEC24 related gene family, member A (S. cerevisiae) (SEC24A), mRNA [NM_021982] |
| 291 | A_23_P396353 | NIN | ATCTTGCAGGTCTAGTATTTTAATAATGACTATTACCCAGGGCAGATATTATGAGAAAG | SEQ ID NO: 1159 | Homo sapiens ninein (GSK3B interacting protein) (NIN), transcript variant 2, mRNA [NM_020921] |
| 292 | A_23_P398073 | PPM1B | GGTTCAGTAACTTTCATTTATAACATGGGCAGGTACAGAGTGATTGTCAGATAAGG | SEQ ID NO: 1160 | Homo sapiens protein phosphatase 1B (formerly 2C), magnesium-dependent, beta isoform (PPM1B), transcript variant 2, mRNA [NM_177968] |
| 293 | A_23_P40059 | PMS1 | GATCCTGTCTTAGCAGGGAATGGTTTCAAGATAAAATTGATACCAGGAGTTTCAATTACT | SEQ ID NO: 1161 | Homo sapiens PMS1 postmeiotic segregation increased 1 (S. cerevisiae) (PMS1), mRNA [NM_000534] |
| 294 | A_23_P405873 | C9orf72 | GAGAATGGAAGATCAGGGTCAGAGTATTATTCCAATGGTTAGTGGAGAAGTGATTCCTGT | SEQ ID NO: 1162 | Homo sapiens chromosome 9 open reading frame 72 (C9orf72), transcript variant 2, mRNA [NM_145005] |
| 295 | A_23_P408455 | SLC25A36 | GCATTAACCTACACACACTCATTTTTATGCTACTCCTTGTAGAAACAAATTCGTTTGAC | SEQ ID NO: 1163 | Homo sapiens mRNA; cDNA DKFZp564C053 (from clone DKFZp564C053) [AL049246] |
| 296 | A_23_P41114 | CSTA | AAACAAATGAGACTTATGGAAGAATGGAAGCGTGCAGTATAAAACTCAAGTTGTTGCTG | SEQ ID NO: 1164 | Homo sapiens cystatin A (stefin A) (CSTA), mRNA [NM_005213] |
| 297 | A_23_P413796 | CCDC5 | GCATGATGCTTCTGTGTCATCAGTCGTTAGTAGCACTATCAGAGAAACTGGCAAGAT | SEQ ID NO: 1165 | Homo sapiens coiled-coil domain containing 5 (spindle associated) (CCDC5), mRNA [NM_138443] |
| 298 | A_23_P41470 | FLJ20035 | TGTGGCTTAATGCCTATGCACTGGATTTCTACAAACATGGTTCCTTGATAGGATTAGTCC | SEQ ID NO: 1166 | Homo sapiens hypothetical protein FLJ20035 (FLJ20035), mRNA [NM_017631] |
| 299 | A_23_P41512 | C4orf15 | TAAGGCTGTTAGTCTTGAAGATTAGTGAAAACTGAATCTTTATTACGTGTCGT | SEQ ID NO: 1167 | Homo sapiens chromosome 4 open reading frame 15 (C4orf15), mRNA [NM_024511] |
| 300 | A_23_P41645 | ELL2 | TGTCTTTTCAAAGTGCTGCCAGTTGAAAAGGGAAAGCATTATGTTTACAAACTGTGTTTGA | SEQ ID NO: 1168 | Homo sapiens elongation factor, RNA polymerase II, 2 (ELL2), mRNA [NM_012081] |
| 301 | A_23_P41664 | ENST00000334994 | TGGCTTGGAGCAGATTCGACTTCATAAACAAATTGTTCCTGAAAATGAGGGCACAGGTCAT | SEQ ID NO: 1169 | Syntaurin (Q9LQ1891) [Source:Uniprot/SPTREMBL;Acc:Q72207] [ENST00000334994] |
| 302 | A_23_P421563 | LSM3 | CATAAGAGAAACCTGCATAGATTTGTATTAAGAATAATTCCGGGGATTCTTCCACTC | SEQ ID NO: 1170 | Homo sapiens LSM3 homolog, U6 small nuclear RNA associated (S. cerevisiae) (LSM3), mRNA [NM_014463] |
| 303 | A_23_P422083 | TMEM55A | AAATTTATGGAATCAGGTGTGGGAGTTGGGGATGTGGGCAGTTTGGAGTTTTGAAAAGAAATTGCTT | SEQ ID NO: 1171 | Homo sapiens transmembrane protein 55A (TMEM55A), mRNA [NM_018710] |
| 304 | A_23_P422794 | NSMCE2 | CATTGTTCGCATGATTGAGTCCAGGCAAAAGGGAAGAAAAAGGCCTATTCCCCTCAAAT | SEQ ID NO: 1172 | Homo sapiens non-SMC element 2, MMS21 homolog (S. cerevisiae) (NSMCE2), mRNA [NM_173685] |

Fig. 3-17

| No. | Probe ID No. | Symbols of genes | Sequence | SEQ ID NO: | Descriptions of genes (letters and numbers within [ ] indicates GenBank accession No.) |
|---|---|---|---|---|---|
| 305 | A_23_P428468 | ENST00000369577 | AAACCTACCGTCAGTCTGAAAAAACTTGAAGTAGATTGAAATGATCCAGATATGTCTGTT | SEQ ID NO: 1173 | Zinc finger protein 292. [Source:Uniprot/SWISSPROT:Acc:Q60281] [ENST00000369577] |
| 306 | A_23_P429491 | FLJ25416 | GGTTGGTCACGTGAATTGTTTCATAAAAAGTCACCTGAACCCAATTCGTGAACTATTTAA | SEQ ID NO: 1174 | Homo sapiens hypothetical protein FLJ25416 (FLJ25416), mRNA [NM_145018] |
| 307 | A_23_P42975 | PRKAR2B | GCCACATTTTTAGAAGCACTGTTTAAGACATTTTTGCAAAAACGTTCTTGTAGGAAAAGAGAGC | SEQ ID NO: 1175 | Homo sapiens protein kinase, cAMP-dependent, regulatory, type II, beta (PRKAR2B), mRNA [NM_002736] |
| 308 | A_23_P430161 | EXOC8 | AAGTACAGAGATTTTCTTCAGGTAAAATGTGTGTTCGAATTACAGTTGTAGTGAAGGA | SEQ ID NO: 1176 | Homo sapiens exocyst complex component 8 (EXOC8), mRNA [NM_175876] |
| 309 | A_23_P434809 | S100A8 | AAAGCCATGGAAGAAAAGCCACAAAGAGTAGGTGAGTTAGTAGGGCCCAGAAGAGTCGGGGGGT | SEQ ID NO: 1177 | Homo sapiens S100 calcium binding protein A8 (S100A8), mRNA [NM_002964] |
| 310 | A_23_P43946 | CIP29 | AAAGAGCAGAGCCCTTGGGATTGCCTGATGAAAAGTTCGTGATACTTTCTGTTCTGCAG | SEQ ID NO: 1178 | Homo sapiens cytokine induced protein 29 kDa (CIP29), mRNA [NM_033082] |
| 311 | A_23_P44257 | COMMD8 | AACATTTTACTTCTGCCGCTTCTATGTTTGGGAAACATTGGTGTGATAAGCTTCTCTATA | SEQ ID NO: 1179 | Homo sapiens COMM domain containing 8 (COMMD8), mRNA [NM_017845] |
| 312 | A_23_P4462 | A_23_P4462 | GGTCTGAAAAGCAGGGGAATACGATTATTTTGGGATTAAGGGTTACTGGGAAATATTTTA | SEQ ID NO: 1180 | |
| 313 | A_23_P44768 | TBK1 | TCTACTCTGAGTCGGGGCTAAATAAGTTATTTCTCTGACGCCCTACTGGAAATATTTTA | SEQ ID NO: 1181 | Homo sapiens TANK-binding kinase 1 (TBK1), mRNA [NM_013254] |
| 314 | A_23_P44974 | MRPL13 | ATGGAGTAAAACAAGTGGTAGAGTCAGCACCGTCTTTATGCCGGAATCACTCTGGGGGA | SEQ ID NO: 1182 | Homo sapiens mitochondrial ribosomal protein L13 (MRPL13), nuclear gene encoding mitochondrial protein, mRNA [NM_014078] |
| 315 | A_23_P46396 | PTBP2 | AACCAGGTTGGGAACCAAGTTTATGTGCCTTAGTGTTTAATTACCTTGCATTGTAATATT | SEQ ID NO: 1183 | Homo sapiens polypyrimidine tract binding protein 2 (PTBP2), mRNA [NM_021190] |
| 316 | A_23_P48166 | TWF1 | TGGAGCAGACCATAGCTGAAGCTGTTATTTTCAGTGAGCAGGAAGACTACCTGTCATGAAGGT | SEQ ID NO: 1184 | Homo sapiens twinfilin, actin-binding protein, homolog 1 (Drosophila) (TWF1), mRNA [NM_002822] |
| 317 | A_23_P48897 | CCPG1 | AACTTGCAGAAGAGCTCATATATATAATTCTAATGTCCACGTATGTCCATTCCATGTACA | SEQ ID NO: 1185 | Homo sapiens cell cycle progression restoration 8 protein (CCPG8) mRNA, complete cds. [AF011794] |
| 318 | A_23_P501080 | ZNF92 | GAATATTAAGTCGTACTTGAGGTACAGTTCAGAGTAAGCATTCTTTGCAGTATAGTGAG | SEQ ID NO: 1186 | Homo sapiens zinc finger protein 92 (ZNF92), transcript variant 1, mRNA [NM_007139] |
| 319 | A_23_P50195 | A_23_P50195 | CCTCACGAAGTGTGATGATTGTGGGCAAGAGTTTAGTTCATGTTGACACCGTCTTAGACATG | SEQ ID NO: 1187 | |
| 320 | A_23_P502425 | MRPL47 | GTTCCACATCGTTGCTGAAGCCCAAAAGTCAAGTCTGTCGTAAGATGTGAACTATTAA | SEQ ID NO: 1188 | Homo sapiens mitochondrial ribosomal protein L47 (MRPL47), nuclear gene encoding mitochondrial protein, transcript variant 1, mRNA [NM_020409] |
| 321 | A_23_P502797 | WDFY1 | GTAAGAGTTTACTTGGTTGTTCCATTCCTGAATATGCAGGGTAATTTGTAGATAGGGAT | SEQ ID NO: 1189 | Homo sapiens WD repeat and FYVE domain containing 1 (WDFY1), mRNA [NM_020830] |
| 322 | A_23_P502832 | RBM12 | CTGGACAGTTGTATAGTAGTCAGAGACTTTAGAAACCAAACACAAAAATGGCTTGTTGCC | SEQ ID NO: 1190 | Homo sapiens RNA binding motif protein 12 (RBM12), transcript variant 1, mRNA [NM_006047] |
| 323 | A_23_P50907 | ITGAV | AAAGAGTGATTAAGTAGAGGTTATTACCCTAAATGGTGGATTCTGCATTGTATTCAGG | SEQ ID NO: 1191 | Homo sapiens integrin, alpha V (vitronectin receptor, alpha polypeptide, antigen CD51) (ITGAV), mRNA [NM_002210] |

Fig. 3-18

| No. | Probe ID No. | Symbols of genes | Sequence | SEQ ID NO: | Descriptions of genes (letters and numbers within [ ] indicates GenBank accession No.) |
|---|---|---|---|---|---|
| 324 | A_23_P51009 | NDUFB3 | CGGCAATGAAGCTTGGAGATACATGGGTGGCTTTGGAAAGAGTGTTTCCTTTTGTGATGT | SEQ ID NO: 1192 | Homo sapiens NADH dehydrogenase (ubiquinone) 1 beta subcomplex, 3, 12kDa (NDUFB3), mRNA [NM_002491] |
| 325 | A_23_P51317 | CCDC76 | CCCTTGTTATAAGTTTATGTCAAGTAAGGTAGTTGTTTAAGTTAGTTAGGCATGTCCC | SEQ ID NO: 1193 | Homo sapiens coiled-coil domain containing 76 (CCDC76), mRNA [NM_019083] |
| 326 | A_23_P51487 | GBP3 | AATCCTAAAGCATAAGTTAGTTGTTTCTGATTCTTAAAGGTCATACTTGAAATCCTGCC | SEQ ID NO: 1194 | Homo sapiens guanylate binding protein 3 (GBP3), mRNA [NM_018284] |
| 327 | A_23_P53668 | NFYB | TGGGCTCATATTGTGGCATAGGATTTGTAAGCTGGTTTTTTCACTTAACAATATATTGGG | SEQ ID NO: 1195 | Homo sapiens nuclear transcription factor Y, beta (NFYB), mRNA [NM_006166] |
| 328 | A_23_P53957 | C14orf112 | TTATAGTTGCCAGCTATTCGGATCGTGGGATGAAAGTAACAATGTTGGGCACGTATATTT | SEQ ID NO: 1196 | Homo sapiens chromosome 14 open reading frame 112 (C14orf112), mRNA [NM_016468] |
| 329 | A_23_P5611 | RIF1 | ATGTATTCTTGGCTGCTATGCGTGGTGGTTTTCAGGAAATTTAATTATCTTACTGAGATGTGG | SEQ ID NO: 1197 | Homo sapiens RAP1 interacting factor homolog (yeast) (RIF1), mRNA [NM_018151] |
| 330 | A_23_P56380 | ZC3H15 | GTCCACCCAAGTAAGAAGTGTATGTGCCTTTCCATCTTTGGTTTCATTTGGGCATGTGTG | SEQ ID NO: 1198 | Homo sapiens zinc finger CCCH-type containing 15 (ZC3H15), mRNA [NM_018471] |
| 331 | A_23_P56734 | HNMT | CCTTTGTCGACCAATAGATATACTGACGTGGTTTATTGATGGTAATGAAAATGGAGAGGT | SEQ ID NO: 1199 | Homo sapiens histamine N-methyltransferase (HNMT), transcript variant 1, mRNA [NM_006895] |
| 332 | A_23_P56759 | KRCC1 | GATATCCGTGTTGTCATAGCCACAGTTTTCTTTATGTGAATAGGTTGTCTTAACTCTCTAACGAAAGGC | SEQ ID NO: 1200 | Homo sapiens lysine-rich coiled-coil 1 (KRCC1), mRNA [NM_016618] |
| 333 | A_23_P58877 | GOPC | AAGGTTTCATGTGATTCATGTGTAAGAATGCACAGTATTTGACATCCTGATTATGTAATCC | SEQ ID NO: 1201 | Homo sapiens golgi associated PDZ and coiled-coil motif containing (GOPC), transcript variant 1, mRNA [NM_020399] |
| 334 | A_23_P58898 | CASP8AP2 | ATCTATATTTGTTATTACTCAGTGAGTCTCTAATTTCACATGCAGCATGTTCAGGTTGTGC | SEQ ID NO: 1202 | Homo sapiens CASP8 associated protein 2 (CASP8AP2), mRNA [NM_012115] |
| 335 | A_23_P58912 | SLC35A1 | ATGATGAGTGCCGTTATGTGGAAAGACAACAAACAAACAAGAAGCTATCTGAGTGAAGTGG | SEQ ID NO: 1203 | Homo sapiens solute carrier family 35 (CMP-sialic acid transporter), member A1 (SLC35A1), mRNA [NM_006416] |
| 336 | A_23_P59637 | DOCK4 | TTTGGCAGTGAGGAGTAGTTGAATTTATCTTGAATTTATCATGTGTGTGTATTTCTGAAGCAG | SEQ ID NO: 1204 | Homo sapiens dedicator of cytokinesis 4 (DOCK4), mRNA [NM_014705] |
| 337 | A_23_P59921 | SUB1 | CAGATTGGGAAAATGAGGTAGGTTAGTGTTCGGCAGTTGTTAAGGCAAAGTGCTAATTGAT | SEQ ID NO: 1205 | Homo sapiens SUB1 homolog (S. cerevisiae) (SUB1), mRNA [NM_006713] |
| 338 | A_23_P60565 | ZNF354A | AAACGAAAGGTCATGAAGAATACATCCTTGACAGATTGTTAATAAAAATGTAATGGATGTG | SEQ ID NO: 1206 | Homo sapiens zinc finger protein 354A (ZNF354A), mRNA [NM_005649] |
| 339 | A_23_P61674 | CLK4 | GAAAGGCATGGCAGTTTGTCCATGTGACAGTTTGTTTAATAAACCCACATACAACTTTA | SEQ ID NO: 1207 | Homo sapiens CDC-like kinase 4 (CLK4), mRNA [NM_020666] |
| 340 | A_23_P62890 | GBP1 | CAAAGATGCATTACCTCTGTATCAACTCAGGAAATCTCATAAGCTGGTACCACTGAGGA | SEQ ID NO: 1208 | Homo sapiens guanylate binding protein 1, interferon-inducible, 67kDa (GBP1), mRNA [NM_002053] |
| 341 | A_23_P63190 | NRAS | ATGAATGCTGAGATACGCATTACGTGAGTTTATCACCATGAAGGA AAGGTATATGTTG | SEQ ID NO: 1209 | Homo sapiens neuroblastoma RAS viral (v-ras) oncogene homolog (NRAS), mRNA [NM_002524] |
| 342 | A_23_P63205 | DR1 | TCCAGTAGTAGGCCTAGAGTGCCAACATTAGGTTTGGAGATGACATTATTGTCCATA | SEQ ID NO: 1210 | Homo sapiens down-regulator of transcription 1, TBP-binding (negative cofactor 2) (DR1), mRNA [NM_001938] |

Fig. 3-19

| No. | Probe ID No. | Symbols of genes | Sequence | SEQ ID NO. | Descriptions of genes (letters and numbers within [ ] indicates GenBank accession No.) |
|---|---|---|---|---|---|
| 343 | A_23_P63343 | UTS2 | AGAATCGTGAAAACGATAGAAGAAAGGTGAGAACTCCTGATTGCTTCTGTGAAATACTGTGTC | SEQ ID NO: 1211 | Homo sapiens urotensin 2 (UTS2), transcript variant 1, mRNA [NM_021995] |
| 344 | A_23_P63655 | ATP5C1 | AGAGAGCTGAAACAGCTGGAATATATGATGGATCTTAGCTCTGTATGAAAAAGCT | SEQ ID NO: 1212 | Homo sapiens ATP synthase, H+ transporting, mitochondrial F1 complex, gamma polypeptide 1 (ATP5C1), nuclear gene encoding mitochondrial protein, transcript variant 2, mRNA [NM_001174] |
| 345 | A_23_P63789 | ZWINT | TCAAAGATTCAGAGATTGGCTTTTGTCATCCAGTATTGTATGTTTGTTTCATTGACCTC | SEQ ID NO: 1213 | Homo sapiens ZW10 interactor (ZWINT), transcript variant 4, mRNA [NM_001005414] |
| 346 | A_23_P63896 | FAS | ATGTCTATCCACAGAGGTAAGCCCACTCTATGAATCAATAGAAGAAGCTATGAGTTTTGC | SEQ ID NO: 1214 | Homo sapiens Fas (TNF receptor superfamily, member 6) (FAS), transcript variant 1, mRNA [NM_000043] |
| 347 | A_23_P65262 | RP11-298P3.3 | AGCCAAGACTTAAGAAGGACTGACTACGGTTCCCTTGAGCTACCATTATCACAAGGGTTT | SEQ ID NO: 1215 | Human BRCA2 region, mRNA sequence CG016. [U50529] |
| 348 | A_23_P65766 | C15orf15 | TCCTGCATTGCCATCTACAGTAATAATCAGATATTACGGATGTTAGATTGCATCTCAGTGTT | SEQ ID NO: 1216 | Homo sapiens chromosome 15 open reading frame 15 (C15orf15), mRNA [NM_016304] |
| 349 | A_23_P66260 | ZNF267 | TGTGATGAATGCTGGTAAAGCCTTGAGCTATAGGTGTATAGCCTCACTACAACATCGGGAAGAAGT | SEQ ID NO: 1217 | Homo sapiens zinc finger protein 267 (ZNF267), transcript variant 498723, mRNA [NM_003414] |
| 350 | A_23_P67992 | C1D | AATGAATAAGTCAGCCTTATGAAGGTATGCTATCGTAAGGCTGAAATTATAGGTACATCTGTT | SEQ ID NO: 1218 | Homo sapiens nuclear DNA-binding protein (C1D), transcript variant 1, mRNA [NM_006333] |
| 351 | A_23_P68472 | DPM1 | CTATTGGGACGGAAGGTTCCAATATCATTTGTGGATCGTGTTTATGGTGAATCAAGTTGGGAG | SEQ ID NO: 1219 | Homo sapiens dolichyl-phosphate mannosyltransferase polypeptide 1, catalytic subunit (DPM1), mRNA [NM_003859] |
| 352 | A_23_P69791 | C4orf16 | GGGCTCCATTCATTTGATTTTATTAAGGCCTTCCTTTTCACGTTCCATTGAGTACAAGGTCCTTTAATGGGAT | SEQ ID NO: 1220 | Homo sapiens chromosome 4 open reading frame 16 (C4orf16), mRNA [NM_018569] |
| 353 | A_23_P69908 | GLRX | CTGATAAAAGTTAGAGGCCGGGTACACCAAGAGTGTATCGTGAAAGAGCTCCTACACGTTT | SEQ ID NO: 1221 | Homo sapiens glutaredoxin (thioltransferase) (GLRX), mRNA [NM_002064] |
| 354 | A_23_P70047 | MATR3 | GCAAGACGAGAAGGTACTTTGTAGAGATTGACTTCCTAAGCTACTTAAGACAACTTGCAC | SEQ ID NO: 1222 | Homo sapiens matrin 3 (MATR3), transcript variant 1, mRNA 1991891 |
| 355 | A_23_P70318 | ENPP4 | TGTTTTGGGTGTCCTTCCTTCTTGTGCCATATCGTAAGATGAATAAGCTTTATGGATTATTTGCATTT | SEQ ID NO: 1223 | Homo sapiens ectonucleotide pyrophosphatase/phosphodiesterase 4 (putative function) (ENPP4), mRNA [NM_014936] |
| 356 | A_23_P70328 | CENPQ | GAATGCTACAGTTCTGTCTGGTGATGTGGAAGTTGAAAAATCCTCAAATGCCTTCAC | SEQ ID NO: 1224 | Homo sapiens centromere protein Q (CENPQ), mRNA [NM_018132] |
| 357 | A_23_P7066 | RPL9 | GGTCTCTTGTTGAAATCCGAAATTTCTTGGCTGAAAAATATATCCGCAGGGTTCGGATGA | SEQ ID NO: 1225 | Homo sapiens ribosomal protein L9 (RPL9), transcript variant 1, mRNA [NM_000661] |
| 358 | A_23_P70938 | STARD3NL | GGTTATGTATGCCTGAAGTGGACTTGCAAAAGGGGAAGAAAGGAATTTGCGAAT | SEQ ID NO: 1226 | Homo sapiens STARD3 N-terminal like (STARD3NL), mRNA [NM_032016] |
| 359 | A_23_P71433 | UBE2W | CATGAGCCCTACTGCCTAAAACACTATTTGATTTATTTATGTTGGAAACCCCCGTAAACAT | SEQ ID NO: 1227 | Homo sapiens ubiquitin-conjugating enzyme E2W (putative) (UBE2W), transcript variant 1, mRNA [NM_001001481] |
| 360 | A_23_P71727 | CKS2 | GATAAAAGTTCTTCCAGTCAGTTTTTCTGTTAAGTGCCTGTTTGAGTTTAGTGAAACAGT | SEQ ID NO: 1228 | Homo sapiens CDC28 protein kinase regulatory subunit 2 (CKS2), mRNA [NM_001827] |

Fig. 3-20

| No. | Probe ID No. | Symbols of genes | Sequence | SEQ ID NO: | Descriptions of genes (letters and numbers within [ ] indicates GenBank accession No.) |
|---|---|---|---|---|---|
| 361 | A_23_P72503 | KLHL2 | TTTTTGATATTAAGAATGGTTAACACTTTAAATGCCACTGTG AGGAATGGACCTGGTG | SEQ ID NO: 1229 | Homo sapiens kelch-like 2, Mayven (Drosophila) (KLHL2), mRNA [NM_007246] |
| 362 | A_23_P72568 | SNX4 | AAGCTGAGTAATGAGCGTAAATTTAGTCTGCTTGGCTGTCTAGA CATGGCATTTCAGGGT | SEQ ID NO: 1230 | Homo sapiens sorting nexin 4 (SNX4), mRNA [NM_003794] |
| 363 | A_23_P7282 | ELMOD2 | TTCAAGTAGCTTTCTCTGGGGAAAAAGTAGCACTTGGACACTT AAAGGAATTGGGATTT | SEQ ID NO: 1231 | ELMO domain-containing protein 2. [Source:Uniprot/SWISSPROT:Acc:Q8IZ81] [ENST00000323570] |
| 364 | A_23_P73114 | PROS1 | CCAGAACAAATTTAAGAAAAAGGACAACCACAGAGGGATATAGT GAATATGGTATCATTG | SEQ ID NO: 1232 | Homo sapiens protein S (alpha) (PROS1), mRNA [NM_000313] |
| 365 | A_23_P73577 | DYNLT3 | TGTTTCTTATGCTGGTGGCTTTGTGGCGTGAAGATCATAAT AGTGACCAAAATATAC | SEQ ID NO: 1233 | Dynein light chain Tctex-type 3 (T-complex-associated testis-expressed 1-like) (Protein 91/23). [Source:Uniprot/SWISSPROT:Acc:P51808] [ENST00000378578] |
| 366 | A_23_P73835 | MOSPD1 | TATGTGGAGATGATTTTTCACCTTTAAACTGTAAGCCAAGTGTA AGAAACTCTGATAGC | SEQ ID NO: 1234 | Homo sapiens motile sperm domain containing 1 (MOSPD1), mRNA [NM_019556] |
| 367 | A_23_P74001 | S100A12 | TGAAGGCTTTTAGGAGCAATGTCCTCAATGAGGGTCTTTCT TTCCCTCACGAAAAGC | SEQ ID NO: 1235 | Homo sapiens S100 calcium binding protein A12 (S100A12), mRNA [NM_005621] |
| 368 | A_23_P74799 | SLC25A24 | GATTGTGTATCTTTTGGAAAAAAGGCGGAGAGTTGAAGATAGTAT ATTTCGTAGTACTG | SEQ ID NO: 1236 | Homo sapiens solute carrier family 25 (mitochondrial carrier; phosphate carrier), member 24 (SLC25A24), transcript variant 2, mRNA [NM_213651] |
| 369 | A_23_P7543 | ZFYVE16 | TCTGCCTCAGCATTATCTAAATGATCTTGATAGTGCTCTGATAC CTGTCATCCATGGTGG | SEQ ID NO: 1237 | Homo sapiens zinc finger, FYVE domain containing 16 (ZFYVE16), mRNA [NM_014733] |
| 370 | A_23_P76159 | EEA1 | TATTGTTTTAGTACTTGTGATCATGTAGTGTGTGCCTTACTTG TGAAAAGGTTAGGTC | SEQ ID NO: 1238 | Homo sapiens early endosome antigen 1 (EEA1), mRNA [NM_003566] |
| 371 | A_23_P76480 | BF213738 | AAATCGAACAGGACGAATGGGTAGAGATGGAGCTAGATTTACCAAAT CGTTTCGGCATGACAGG | SEQ ID NO: 1239 | BF213738 601847628F1 NIH_MGC_55 Homo sapiens cDNA clone IMAGE:4078519 5', mRNA sequence [BF213738] |
| 372 | A_23_P76598 | EFHA1 | AAAGTACTTGAGACCAAGGCCAGGATCAATCCAGACATCTTA TGTTCGTAATAGGCTA | SEQ ID NO: 1240 | Homo sapiens EF-hand domain family, member A1 (EFHA1), mRNA [NM_152726] |
| 373 | A_23_P76799 | BAZ1A | TACACATGAATGAATCCAATCTTATAACCTTGAAGTGTGTAGC AGTGGTGGCTGCAGT | SEQ ID NO: 1241 | Homo sapiens bromodomain adjacent to zinc finger domain 1A (BAZ1A), transcript variant 1, mRNA [NM_013448] |
| 374 | A_23_P76951 | TXNDC1 | ATTTCGTAATGTCCCGTTCTTCTCTAGGGCTCGTGTTGCTGTGTGA ATCCATTAGATTTACA | SEQ ID NO: 1242 | Homo sapiens thioredoxin domain containing 1 (TXNDC1), mRNA [NM_030755] |
| 375 | A_23_P78018 | ABCA5 | ACTGGAGAACCAAGAACGGACTGAAATTTTGTAAGTCCTTA ATTGAAATGCTGTGGT | SEQ ID NO: 1243 | Homo sapiens ATP-binding cassette, sub-family A (ABC1), member 5 (ABCA5), transcript variant 1, mRNA [NM_018672] |
| 376 | A_23_P78092 | EVI2A | GCTGAATCAGAGACAGTTGAAAAAGAACAAAACAGCTCACAGGACC CAACCTAGTGATGGAA | SEQ ID NO: 1244 | Homo sapiens ecotropic viral integration site 2A (EVI2A), transcript variant 1, mRNA [NM_001003927] |

Fig. 3-21

| No. | Probe ID No. | Symbols of genes | Sequence | SEQ ID NO: | Descriptions of genes (letters and numbers within [ ] indicates GenBank accession No.) |
|---|---|---|---|---|---|
| 377 | A_23_P79199 | DBI | TGGTGAGCATACGGGCTCTAAGAGATTAGGGGCTAAAAGGATTACTGACTTCCTTGAGTA | SEQ ID NO: 1245 | Homo sapiens diazepam binding inhibitor (GABA receptor modulator, acyl-Coenzyme A binding protein) (DBI), transcript variant 1, mRNA [NM_020548] |
| 378 | A_23_P81212 | MRPS18C | ATGGGGTTTATGCCAGTTACATAGAAGGATCCTGCATATGTCAAGGACCCTAAAGTTTGT | SEQ ID NO: 1246 | Homo sapiens mitochondrial ribosomal protein S18C (MRPS18C), nuclear gene encoding mitochondrial protein, mRNA [NM_016067] |
| 379 | A_23_P81249 | TAF7 | TGCTAGTTTGCATATGTTTGGGATGCAATAGTTGTTTGCGAGTTATTCAAARGAAGTT | SEQ ID NO: 1247 | Homo sapiens TAF7 RNA polymerase II, TATA box binding protein (TBP)-associated factor, 55kDa (TAF7), mRNA [NM_005642] |
| 380 | A_23_P82047 | BU507302 | TCTGTTCGTTAATGTCAGGTGCCTGAAGATGCCAGCAGTTTATAAATTGGTTAATTGTG | SEQ ID NO: 1248 | AGENCOURT_10309688 NIH_MGC_71 Homo sapiens cDNA clone IMAGE:6501220 5', mRNA sequence [BU507302] |
| 381 | A_23_P8241 | FBXO5 | GATACCAACGAAGAATATCAACTTCTGAGTCTATTAAATGTGTTGTCAGCTTTCTAAAGC | SEQ ID NO: 1249 | Homo sapiens F-box protein 5 (FBX05), mRNA [NM_012177] |
| 382 | A_23_P83175 | PTPLAD2 | CATGCTTTTGTGGTGATCACCAGTCAAGAGAAGTCGAAGAGAAATATGGGTGTGT | SEQ ID NO: 1250 | Homo sapiens protein tyrosine phosphatase-like A domain containing 2 (PTPLAD2), mRNA [NM_001109915] |
| 383 | A_23_P83276 | CHMP5 | CATTGCTCTTTATTTTTTCGATTAAGGAGAATGCATTGGCTTGGGAAATGCTTCTTCGTAC | SEQ ID NO: 1251 | Homo sapiens chromatin modifying protein 5 (CHMP5), mRNA [NM_016410] |
| 384 | A_23_P84070 | LARP7 | TGATTTGCTAGCAAGGGGATACAGAATGCCATGCTAGATTTAAGACTCCTGAGGAGTCTCA | SEQ ID NO: 1252 | Homo sapiens La ribonucleoprotein domain family, member 7 (LARP7), transcript variant 1, mRNA [NM_016648] |
| 385 | A_23_P86653 | SRGN | ACGACTTGGGTGAACATGGATTAGAGAGAGGATTTATGTTATAAAAGAGGATTTCCCAC | SEQ ID NO: 1253 | Homo sapiens serglycin (SRGN), mRNA [NM_002727] |
| 386 | A_23_P87769 | C12orf48 | GTAAGAAATATCGTCAGTCGTCCTAATGCATATTGTGACTGTTGCATATATCTGTTT | SEQ ID NO: 1254 | Homo sapiens chromosome 12 open reading frame 48 (C12orf48), mRNA [NM_017915] |
| 387 | A_23_P87879 | CD69 | TGTGGAATATGTGATGTGGGAAATCTCTATTAGGAAAATATTCTGTAATCTTCAGAGCTAG | SEQ ID NO: 1255 | Homo sapiens CD69 molecule (CD69), mRNA [NM_001781] |
| 388 | A_23_P89145 | ZNF83 | GTATAATGAATGTAGCAGAGGCGTTAGTTTTTGTTCAAGGGTAATAACGGTTAGCTAGA | SEQ ID NO: 1256 | Homo sapiens zinc finger protein 83 (ZNF83), mRNA [NM_018300] |
| 389 | A_23_P89755 | RNF138 | GTAACCGTGATATAGTGAGAAGAGATTGTAGCGACCACTGTTTCACTAGTTTTAGTTAA | SEQ ID NO: 1257 | Homo sapiens ring finger protein 138 (RNF138), transcript variant 1, mRNA [NM_016271] |
| 390 | A_23_P89921 | ZNF180 | AGTGCATCATTTTAGTAGATGATATCTTCGGAATTAGATAGGCTTGTAATGTGTTCCTTACAGC | SEQ ID NO: 1258 | Homo sapiens zinc finger protein 180 (ZNF180), mRNA [NM_013256] |
| 391 | A_23_P9056 | RB1CC1 | TTGATTTTCTCAAAGGGGCATACCTTGTGTGCATTGTGCGTTATGATGAGGCATTAATTGC | SEQ ID NO: 1259 | Homo sapiens RB1-inducible coiled-coil 1 (RB1CC1), mRNA [NM_014781] |
| 392 | A_23_P91345 | BC008667 | GRGTTAGGAGTGAGATTTGTGGTCTACAGAAATGATGATGGTCATGAATTTGACATTT | SEQ ID NO: 1260 | Homo sapiens cDNA clone MGC:17708 IMAGE:3865595, complete cds. [BC008667] |
| 393 | A_23_P92410 | CASP3 | TGCACCAAGTCTCAGTGGTGTGTAGAGATTTCAGGGAGATTTGTTGTTCTCAAA | SEQ ID NO: 1261 | Homo sapiens caspase 3, apoptosis-related cysteine peptidase (CASP3), transcript variant alpha, mRNA [NM_004346] |
| 394 | A_23_P92441 | MAD2L1 | TGTAGGTGAAAAATGGAAGAGTCGGGACCACAGTTATTACCAATTCTGAGGAAGTCGG | SEQ ID NO: 1262 | Homo sapiens MAD2 mitotic arrest deficient-like 1 (yeast) (MAD2L1), mRNA [NM_002358] |

Fig. 3-22

| No | Probe ID No. | Symbols of genes | Sequence | SEQ ID NO: | Descriptions of genes (letters and numbers within [ ] indicates GenBank accession No.) |
|---|---|---|---|---|---|
| 395 | A_23_P92842 | SAR1B | TAATGTGACATCACCCAGGGGATTTGTAAAGAGAAGAAGTTTCC AGCAGTACATTTGAAG | SEQ ID NO: 1263 | Homo sapiens SAR1 gene homolog B (S. cerevisiae) (SAR1B), transcript variant 2, mRNA [NM_016103] |
| 396 | A_23_P933 | RWDD3 | GGAATCTTTTAGTAAATAGCAGTGTTTTTGTTGTTCTTTTTGCTTTG TGGATTTGGGAGTGG | SEQ ID NO: 1264 | Homo sapiens RWD domain containing 3 (RWDD3), mRNA [NM_015463] |
| 397 | A_23_P94230 | LY96 | TGAAGCTATTTCTGGGAGCCCAGAAGAAACATGGTCTCTTTTGCTTGG AGTTTGTCATCCTACA | SEQ ID NO: 1265 | Homo sapiens lymphocyte antigen 96 (LY96), mRNA [NM_015364] |
| 398 | A_23_P94501 | ANXA1 | GGCTCTTTGTTGTGGAGGAAACTAAAGATTGGCTTGATGGTCTCAAG CTATCATCAGAAGACT | SEQ ID NO: 1266 | Homo sapiens annexin A1 (ANXA1), mRNA [NM_000700] |
| 399 | A_23_P94546 | GKAP1 | TACCAGGGTGGCAGAAAAGGGAAAAAGAAAACTGAATGGAGCCA GTGTAGGTGATTATGAT | SEQ ID NO: 1267 | Homo sapiens G kinase anchoring protein 1 (GKAP1), mRNA [NM_025211] |
| 400 | A_23_P95130 | SLC37A3 | TTGAGGGATACGTTAATTTGCATTCGGTTAGGGGATATTTTTCAAA CCTCTTGCTTTATACT | SEQ ID NO: 1268 | Homo sapiens solute carrier family 37 (glycerol-3-phosphate transporter), member 3 (SLC37A3), transcript variant 1, mRNA [NM_207113] |
| 401 | A_23_P95594 | NAT1 | TCGTTGACAGAAAGGTTGTGCCGAAACATGGTGATAGATTTTT TACTATTTAGAATAAG | SEQ ID NO: 1269 | Homo sapiens N-acetyltransferase 1 (arylamine N-acetyltransferase) (NAT1), mRNA [NM_000662] |
| 402 | A_23_P9574 | ECT2 | TAATAGTTAACTGACTATAGATTTGTTTCATAGGATGGTTGCATATGTG CCAGTCTCGAGAGTAG | SEQ ID NO: 1270 | Homo sapiens epithelial cell transforming sequence 2 oncogene (ECT2), mRNA [NM_018098] |
| 403 | A_23_P98382 | TIMM8B | TTGTTACTACTAAGAGATTTAAGGAGTCAGTGGGGGAAGGCTATCAA CCCATTGTCAGATCAG | SEQ ID NO: 1271 | Homo sapiens translocase of inner mitochondrial membrane 8 homolog B (yeast) (TIMM8B), mRNA [NM_012459] |
| 404 | A_23_P98446 | SC5DL | TGTCAACACCAGGAGAGTTTAATCTTATGCTTAAAATGCCAGATGT TGTTGGGGGACAAGT | SEQ ID NO: 1272 | Homo sapiens sterol-C5-desaturase (ERG3 delta-5-desaturase homolog, S. cerevisiae)-like (SC5DL), transcript variant 2, mRNA [NM_001024956] |
| 405 | A_23_P99405 | ZMYM2 | GCTGGGTATTACCATGTAAATAATCTGTGAAAGTTGAAAGTTTTGCCAT TATTCTATGTAGTTGGT | SEQ ID NO: 1273 | Homo sapiens zinc finger, MYM-type 2 (ZMYM2), mRNA [NM_003453] |
| 406 | A_23_P99693 | ZBTB1 | TATTAGAGTCTAAAAACGGTAGAGATTACTCTCTTTGGGAACA TAAGAGGTATACAGA | SEQ ID NO: 1274 | Homo sapiens zinc finger and BTB domain containing 1 (ZBTB1), mRNA [NM_014950] |
| 407 | A_23_P99853 | KIAA1370 | CTTTTGTACTGTTGAAACCACTTCATTGTTTTATTTCAGAGCATGTTGCAATAG CAAAACGCCCAGTAG | SEQ ID NO: 1275 | Homo sapiens KIAA1370 (KIAA1370), mRNA [NM_019600] |
| 408 | A_23_P99960 | HMGB1 | GGATTCTTTCGATTTGGCATTGGTTGTTATTTCAGGAGGAAT AGTGAAGATCTCAGTC | SEQ ID NO: 1276 | Homo sapiens high-mobility group box 1 (HMGB1), mRNA [NM_002128] |
| 409 | A_23_P99985 | HMGB1 | TGGGCCAGCTTTTCAAACAAGATGCCACATTCAAAATAGGGTA TATTCCTATATTAC | SEQ ID NO: 1277 | Homo sapiens high-mobility group box 1 (HMGB1), mRNA [NM_002128] |
| 410 | A_24_P100387 | GK | TAAAAGTTCTGTTTTTGTTGGAATCAATGGTAGCTTTATTGAC TGTTCGATTGTGTG | SEQ ID NO: 1278 | Homo sapiens glycerol kinase (GK), transcript variant 1, mRNA [NM_203391] |
| 411 | A_24_P105648 | BX111927 | TTATGAGATGGTTCAGTTCAAATAACAGTGCAGTAATTCAGGTA TATGTAAAAGACTGTC | SEQ ID NO: 1279 | BX111927 Soares_multiple_sclerosis_2NbHMSP Homo sapiens cDNA clone IMAGp998G055619, mRNA sequence [BX111927] |
| 412 | A_24_P105913 | THC2606573 | CTGTTGGTCTAGGAAATGGACGAATACCAAAGGTCAATGGAAA TATGTTTGCC | SEQ ID NO: 1280 | AY151336 NAP1 [Homo sapiens] {exp=-1; wgp=0; cg=0}, partial (35%) [THC2606573] |
| 413 | A_24_P106306 | RPL26L1 | TGGAAGGTAGTCCAGGTGTAGAGAAGAAAATATGTCATCTACA TCGAGGGGGTGCAGCG | SEQ ID NO: 1281 | Homo sapiens ribosomal protein L26-like 1 (RPL26L1), mRNA [NM_016093] |

Fig. 3-23

| No. | Probe ID No. | Symbols of genes | Sequence | SEQ ID NO: | Descriptions of genes (letters and numbers within [ ] indicates GenBank accession No.) |
|---|---|---|---|---|---|
| 414 | A_24_P107257 | LIN7C | TATTAGTGTGGGACTGTGACTGAGGTGTTAAAGAGCTGAAAGAGT TGGGGTTCATTTCTG | SEQ ID NO: 1282 | Homo sapiens lin-7 homolog C (C. elegans) (LIN7C), mRNA [NM_018362] |
| 415 | A_24_P11045 | THC2785765 | CCAGGCAGAAACGTACAGCGTGATTTTCATGACAAATACGGTAGCA ACACAAGTCGGAATAG | SEQ ID NO: 1283 | COX7B_HUMAN (P24311) Cytochrome c oxidase polypeptide VIb, mitochondrial precursor , partial (78%) [THC2785765] |
| 416 | A_24_P114249 | GALNT3 | ATTTCAAATGCAGAATACTGACTCATTTAAAGGCTAAATTTTGT TAGTGATTCAATTATA | SEQ ID NO: 1284 | Homo sapiens UDP-N-acetyl-alpha-D-galactosamine:polypeptide N-acetylgalactosaminyltransferase 3 (GalNAc-T3) (GALNT3), mRNA [NM_004482] |
| 417 | A_24_P115774 | BIRC2 | GATAGGATTTGGTTAAAGGAAATGCTGGGGGGAAGATCTTCAA AAACTGTCTAAAAGAA | SEQ ID NO: 1285 | Homo sapiens baculoviral IAP repeat-containing 2 (BIRC2), mRNA [NM_001166] |
| 418 | A_24_P118766 | ZNF207 | TTCTCGAGAGCCACGTATACCAGTGCTGAAAATTAGCTCTGAGTAAA TTTCTAATTTATGCCC | SEQ ID NO: 1286 | Homo sapiens mRNA; cDNA DKFZp761N202 (from clone DKFZp761N202). [AL834501] |
| 419 | A_24_P123521 | CLK4 | CCCACACTGAAAAAGACAGATATCAAAGTTGTTGACTTTGGAAG TGCAACGTATGATGAT | SEQ ID NO: 1287 | Homo sapiens CDC-like kinase 4 (CLK4), mRNA [NM_020666] |
| 420 | A_24_P124325 | IKZF5 | GGTACAACTTCTTGAACTTCAAGTTAAGGCTAGACATTTACTTT GAAAAATTGCACTGG | SEQ ID NO: 1288 | Homo sapiens mRNA; cDNA DKFZp781B0249 (from clone DKFZp781B0249). [CR749800] |
| 421 | A_24_P124992 | PSMA4 | AAACGGTTCCCTTGGTGTTTCATTGCTGTACATTGGCTGGGATAA GCACTATGGGTTTCAG | SEQ ID NO: 1289 | Homo sapiens proteasome (prosome, macropain) subunit, alpha type, 4 (PSMA4), mRNA [NM_002789] |
| 422 | A_24_P126741 | ENST00000309178 | AGCCTCCAAGCACCACTAACAAGATTACTGAAGTACTTGCAACAGC TCACAGGAGCGAGAAT | SEQ ID NO: 1290 | |
| 423 | A_24_P127181 | LOC442237 | AACTGAAATGTTCCAGAAAAATCCAAGTCCAGCTAGTAGAGAATTG GAGAAAAAGTTCAGTG | SEQ ID NO: 1291 | PREDICTED: Homo sapiens similar to 40S ribosomal protein S7 (S8) (LOC442237), mRNA [XR_018963] |
| 424 | A_24_P127621 | A_24_P127621 | CAGGGTCAGAAGAATGATGGAATGTTTTTAGAATAAACTCCTGCTT ATAGTATAGTCAGAG | SEQ ID NO: 1292 | |
| 425 | A_24_P129232 | SERINC1 | TAAAAACCTCACATTCTAGTTGATTTACACGTTCGGTAGTCTACAT TACATGTGGTTGAAGG | SEQ ID NO: 1293 | Homo sapiens serine incorporator 1 (SERINC1), mRNA [NM_020755] |
| 426 | A_24_P132787 | RAB18 | TTTGAATGGAGTAGAGTATATGCGTGAAAAGGTTTTGGATTCAGAAAAG AAAAAGGATGGTTAGT | SEQ ID NO: 1294 | Homo sapiens RAB18, member RAS oncogene family (RAB18), mRNA [NM_021252] |
| 427 | A_24_P133991 | ANKRD12 | TGAGTAACTTATTTTGTATCAGGAATGTTTTGGTACTGTGTTTT CACTCAAAGCAGTGAC | SEQ ID NO: 1295 | Homo sapiens ankyrin repeat domain 12 (ANKRD12), mRNA [NM_015208] |
| 428 | A_24_P134392 | STCH | GATGGCAAGAAAAAACGCTGGCAAGCTAGTTTGTACCTGCAGAACCGA AAGTGGCATTTGTCAT | SEQ ID NO: 1296 | Homo sapiens stress 70 protein chaperone, microsome-associated, 60kDa (STCH), mRNA [NM_006948] |
| 429 | A_24_P135242 | A_24_P135242 | TAACAGCATAGCGTCCGTGTGGGCATTCACGCAAAGGTGGTTA TCACTAGAGTAAAACT | SEQ ID NO: 1297 | |
| 430 | A_24_P135551 | LOC130865 | TTTGAATGGAGTAGAGTATATGCGTGAAAAGGTTTTGGATTCAGAAAAG (see note) | SEQ ID NO: 1298 | PREDICTED: Homo sapiens similar to 60S ribosomal protein L26 (Silica-induced gene 20 protein) (SIG-20) (LOC130865), mRNA [XR_019454] |
| 431 | A_24_P139208 | USP25 | CAATATAGAGAAGGTGATTATTTGAAGAAGAATGCTAAGGAGTAGT TGAATAAGGCCTATTG | SEQ ID NO: 1299 | Homo sapiens ubiquitin specific peptidase 25 (USP25), mRNA [NM_013396] |
| 432 | A_24_P144383 | A_24_P144383 | GTGCGGTTGAGCCGCCAAAAGATGCTAAGAGAATGCTGGCTAAAAGAT GCAAGGCATTTTGAAGT | SEQ ID NO: 1300 | |

Fig. 3-24

| No. | Probe ID No. | Symbols of genes | Sequence | SEQ ID NO: | Descriptions of genes (letters and numbers within [ ] indicates GenBank accession No.) |
|---|---|---|---|---|---|
| 433 | A_24_P144866 | LOC401975 | TGTCGATGTCAAGACGTAATGATGGCTAGTTCTTAATCGTGTTGTGTGTTGGTTTTACTGA | SEQ ID NO: 1301 | PREDICTED: Homo sapiens similar to ribosomal protein S3a (LOC401975), mRNA [XR_017247] |
| 434 | A_24_P146151 | TSNAX | AAAGTTGAGTTATATAGTTGTAGATAGAATGGAAATGGTTTTAGTAGTGATTATTTAGCA | SEQ ID NO: 1302 | Homo sapiens translin-associated factor X (TSNAX), mRNA [NM_005999] |
| 435 | A_24_P152753 | LOC285260 | TGTGTGATACGGAATGCGGTGTGGGATTATGGAGAAAGATGAAAGATTCACCAAATAAGCT | SEQ ID NO: 1303 | PREDICTED: Homo sapiens similar to ribosomal protein L31 (LOC285260), mRNA [XR_019376] |
| 436 | A_24_P153324 | LOC390413 | GAAGGTTAACAACAAGGTTTGAATTAACATGGTGGGGATTGTAGAAGCATATATTGCAGGGTA | SEQ ID NO: 1304 | PREDICTED: Homo sapiens similar to 60S ribosomal protein L7 (LOC390413), mRNA [XR_018341] |
| 437 | A_24_P153511 | OSBPL8 | GGTTGTGCATATAACACAGAGAAATTTTGTGGAAGGCAGTTTTAACTTTCTGAAGATATC | SEQ ID NO: 1305 | Homo sapiens oxysterol binding protein-like 8 (OSBPL8), transcript variant 1, mRNA [NM_020841] |
| 438 | A_24_P15765 | AK098605 | TCCAAGTCTTGGCTAGTACGTGAGTTGGAGAAAAAGTTGGGAAGCATGTTGTCTTATTG | SEQ ID NO: 1306 | Homo sapiens cDNA FLJ25739 fis, clone TST05834. [AK098605] |
| 439 | A_24_P161914 | LOC130728 | CTATACGTGTTGGAAAACACACTTCAAAGAAATAACTTCCTGCGGCGATTCAAATTATGTTG | SEQ ID NO: 1307 | PREDICTED: Homo sapiens similar to 60S ribosomal protein L7 (LOC130728), mRNA [XR_019248] |
| 440 | A_24_P165816 | AK023645 | AAGATTGAATGGCTAGGAGTAATTCGTCTCGTATAGGCAACTTAAGTTCAGTGTGGAA | SEQ ID NO: 1308 | Homo sapiens cDNA FLJ13583 fis, clone PLACE1009050. [AK023645] |
| 441 | A_24_P167063 | ZNF518 | AAGAAAGGCCATACATAGAGCTTCAAGCTATCTTGCTATGCAGATTATAGTTGTAGTG | SEQ ID NO: 1309 | Homo sapiens zinc finger protein 518 (ZNF518), mRNA [NM_014803] |
| 442 | A_24_P169378 | RPS7 | AACTGAAAATTTCCAGAAAATCCAAATCCGGCTAGTAAGTGAATTGGAGAAAAAGTTGA | SEQ ID NO: 1310 | Homo sapiens ribosomal protein S7 (RPS7), mRNA [NM_001011] |
| 443 | A_24_P170025 | A_24_P170025 | TCCATGCTATTGTTGTCAGAGGAGTAGCTGTTATTAAAGTGGCCATTGATAATGCTC | SEQ ID NO: 1311 | |
| 444 | A_24_P171873 | FBXO4 | GATTGCAGAGATTGAAAAAGTGTGTGAAGTTGAGATGGGTCATCTATGTTGCAAATGC | SEQ ID NO: 1312 | Homo sapiens F-box protein 4 (FBXO4), transcript variant 1, mRNA [NM_012176] |
| 445 | A_24_P172481 | TRIM22 | TGGCCGTTAAAAGATTAAAGAAAGAGAAAGTTGTGAAGTTGATACAAGCGTTATCTCGTTATCTCGTCAGCTAGCA | SEQ ID NO: 1313 | Homo sapiens tripartite motif-containing 22 (TRIM22), mRNA [NM_006074] |
| 446 | A_24_P175059 | ATG5 | TTGGAGAAGAGAGGCTGGTCTGAATATGATTGTTGACATTAAGAGTGTTATCGTCGGTTC | SEQ ID NO: 1314 | Homo sapiens ATG5 autophagy related 5 homolog (S. cerevisiae) (ATG5), mRNA [NM_004849] |
| 447 | A_24_P175176 | PHTF2 | AGATTGAGGTTAACTTAACATAGAGTTGGAGTTGATTGATTATTAAGTAGAGTATACCTCTCAACAG | SEQ ID NO: 1315 | Homo sapiens putative homeodomain transcription factor 2 (PHTF2), mRNA [NM_020432] |
| 448 | A_24_P175187 | SAMD9 | CAACAGCGGATAGGATAATGCAAATGTAATTTCCCCTAATAAATTATGGATATGGGCAG | SEQ ID NO: 1316 | Homo sapiens sterile alpha motif domain containing 9 (SAMD9), mRNA [NM_017654] |
| 449 | A_24_P175188 | SAMD9 | TGCCAATGTACTGGCAGATTAACATACAACCTATGTTTTGAACAAAACAGACAGAGGATA | SEQ ID NO: 1317 | Homo sapiens sterile alpha motif domain containing 9 (SAMD9), mRNA [NM_017654] |
| 450 | A_24_P179351 | TPT1 | GAACAGAGACCAGAAAGAGAGTAAAACCTTTTATGACAGGGCTGCAGAACAAATCAAGCAG | SEQ ID NO: 1318 | Homo sapiens tumor protein, translationally-controlled 1 (TPT1), mRNA [NM_003295] |
| 451 | A_24_P180424 | TMEM30A | CAATGTGTATGCACATTCTCTTTAGTTAAGGACCACCAATTGTTTGGTTTGGTTTTCGTTAAG | SEQ ID NO: 1319 | Homo sapiens transmembrane protein 30A (TMEM30A), mRNA [NM_018247] |
| 452 | A_24_P183864 | IMPA1 | TCAGGCTTATCCTTGGCACGTAAACAGACTACACATCGTAGAACTCAGTCTAAGGTTCGTTTGAGCT | SEQ ID NO: 1320 | Homo sapiens inositol(myo)-1(or 4)-monophosphatase 1 (IMPA1), mRNA [NM_005536] |
| 453 | A_24_P186944 | LOC389404 | AGGAAGCCGTGCGGAGGGAGCTTCAATCACCATCGTAGAACTCAGTCTTCTTGGAAGAAAAA | SEQ ID NO: 1321 | PREDICTED: Homo sapiens similar to 60S ribosomal protein L9 (LOC389404), mRNA [XR_018133] |

Fig. 3-25

| No. | Probe ID No. | Symbols of genes | Sequence | SEQ ID NO | Descriptions of genes (letters and numbers within [ ] indicates GenBank accession No.) |
|---|---|---|---|---|---|
| 454 | A_24_P191417 | NAB1 | AAGTTTCCTTAAGTATCTTATGTTTCGAGTCTTTCAAGGTTAGTGATAAGGTGGAAGCAC | SEQ ID NO: 1322 | Homo sapiens NGFI-A binding protein 1 (NAB1), mRNA [NM_005966] |
| 455 | A_24_P191833 | SFRS12 | AAGGACTTAGGAGTATATGGGAAGGTTATTGGTTTAGTTAAGGATACGTTTACTTGAG | SEQ ID NO: 1323 | Homo sapiens splicing factor, arginine/serine-rich 12 (SFRS12), transcript variant 2, mRNA [NM_139168] |
| 456 | A_24_P192586 | DNAJA1 | TATAGGAAGGTGTTGTTTAGGTATGTTAGGAGGATTACTTAAACGATTGACTTTGACTC | SEQ ID NO: 1324 | Dnaj homolog subfamily A member 1 (Heat shock 40 kDa protein 4) (DnaJ protein homolog 2) (HSJ-2) (HSDJ). [Source:Uniprot/SWISSPROT:Acc:P31689] [ENST00000328899] |
| 457 | A_24_P194313 | C21orf66 | ATTTAAATTAACCGTCTCAGTTAATTGTCCCCTGTAAACGATGTGTGCAGTGTAAATTGT | SEQ ID NO: 1325 | Homo sapiens chromosome 21 open reading frame 66 (C21orf66), transcript variant 1, mRNA [NM_016631] |
| 458 | A_24_P195500 | RNF2 | AAAGTGGTTAGATTTGTTGATGAGATAGATAGTAGTTGCATTAAATAACTAAAATTCC | SEQ ID NO: 1326 | Homo sapiens ring finger protein 2 (RNF2), mRNA [NM_007212] |
| 459 | A_24_P201702 | CLEC2B | ATTGGAATTCAAGTAACACAAGTGTTCCACTCAACATGCGGAGCTAAGTATATTGACA | SEQ ID NO: 1327 | Homo sapiens C-type lectin domain family 2, member B (CLEC2B), mRNA [NM_005127] |
| 460 | A_24_P203909 | RPL34 | GAGGGGTTCGTGCTGTAAGGACTTAAGTTCTTATGAAATTGTCCAAAACAAAACAATG | SEQ ID NO: 1328 | Homo sapiens ribosomal protein L34 (RPL34), transcript variant 2, mRNA [NM_033625] |
| 461 | A_24_P208045 | EDEM3 | TTTTAGAGGGGGTAGAATTTAGTAAATATTCCAAGCGGGTCGTTTATGCACAAGGCTCA | SEQ ID NO: 1329 | Homo sapiens ER degradation enhancer, mannosidase alpha-like 3 (EDEM3), mRNA [NM_025191] |
| 462 | A_24_P20996 | BC043173 | CTGAAAATGTTCATATATATGTATATGAATGGTCTCTTTATGGTGAAGGGTGTGATTGG | SEQ ID NO: 1330 | Homo sapiens cDNA clone IMAGE:5287721. [BC043173] |
| 463 | A_24_P212864 | LOC646161 | ACAGAAGTACAAGCGTGCGATCCATGATCCGAAAGAATGATGAAGTTAGCGTGCAGAGG | SEQ ID NO: 1331 | PREDICTED: Homo sapiens similar to 60S ribosomal protein L26 (LOC646161), mRNA [XR_018048] |
| 464 | A_24_P213375 | A_24_P213375 | AAATGTCTCCATGATCAAAAATGGCAGACAATGATTGTTCATCTGTCTGTGTTGGTT | SEQ ID NO: 1332 | |
| 465 | A_24_P213783 | RPL31 | CTTTGTTACGTATGTACCTGTTACCACTGTTGAAAAATCTAAAGTATGCACAAGGCTCA | SEQ ID NO: 1333 | Homo sapiens ribosomal protein L31 (RPL31), mRNA [NM_000993] |
| 466 | A_24_P221375 | A_24_P221375 | TACTTGGTTACCGATGGTTACCCACTACCACTGTTCAAAAAATCTACAGAGAGTCAATGTGAGGA | SEQ ID NO: 1334 | |
| 467 | A_24_P222911 | SFRS7 | CAGAAATGTCAATGACAAGAGACTAAGATGGTTGTTGAAATTGTCAGGTAATCTCAGGTATATTAGGAACACTCC | SEQ ID NO: 1335 | Homo sapiens splicing factor, arginine/serine-rich 7, 35kDa (SFRS7), mRNA [NM_001031684] |
| 468 | A_24_P225308 | ARID4B | GTTGAAAATGCTTATTCAAGTTATTGCAGGAGTGTAAAGATTGTGAGAGCA | SEQ ID NO: 1336 | Homo sapiens AT rich interactive domain 4B (RBP1-like) (ARID4B), transcript variant 1, mRNA [NM_016374] |
| 469 | A_24_P225468 | ANP32E | TCATCTTACTGTGTGCAATCAAAATTAGAGTACTTGGTTTGAAAAGAACACTAGAGCTC | SEQ ID NO: 1337 | Homo sapiens acidic (leucine-rich) nuclear phosphoprotein 32 family, member E (ANP32E), mRNA [NM_030920] |
| 470 | A_24_P225719 | PRE13 | GAGTATTTCTTAGTGAATATTTATACTAAGGTAGTGAGTGAGATTTGGTGATCTGGCTG | SEQ ID NO: 1338 | Homo sapiens preimplantation protein 3 (PRE13), transcript variant 1, mRNA [NM_015387] |
| 471 | A_24_P229066 | ENST00000078131 | AAGAGAGCTCCAGAACAAGAGCAGGTTATGCACCCATCTGATGAAGGAGATTCAGAGA | SEQ ID NO: 1339 | OTTHUMPCO000016594 [Source:Uniprot/SPTREMBL:Acc:Q8NU98] [ENST00000078131] |

Fig. 3-26

| No. | Probe ID No. | Symbols of genes | Sequence | SEQ ID NO: | Descriptions of genes (letters and numbers within [ ] indicates GenBank accession No.) |
|---|---|---|---|---|---|
| 472 | A_24_P232856 | RPL9 | GAACCCTGCGGAGGACTTGAATCACATCAATGTAGAACTCAGCCTCTTGGAAAGAAAA | SEQ ID NO: 1340 | Homo sapiens ribosomal protein L9 (RPL9), transcript variant 1, mRNA [NM_000661] |
| 473 | A_24_P234792 | CSNK1G3 | GGGTTTTTTGGATTGTACAAGTGTTTATATGATCTGAACTCGTTATACATAACGAAGGTGTG | SEQ ID NO: 1341 | Homo sapiens casein kinase 1, gamma 3 (CSNK1G3), transcript variant 1, mRNA [NM_004384] |
| 474 | A_24_P235429 | ABCA1 | CCAAAGAGCCATGTGTCATGTAATACTGAACGACTTGATATTGAGACATTAATTTGTAC | SEQ ID NO: 1342 | Homo sapiens ATP-binding cassette, sub-family A (ABC1), member 1 (ABCA1), mRNA [NM_005502] |
| 475 | A_24_P236008 | SCYL2 | ATAGACTATGTAGTTGTCTGGTTTTGTTGTTGTTTTATTTTGGAATGCTATAAGCCTCG | SEQ ID NO: 1343 | Homo sapiens mRNA for KIAA1360 protein, partial cds. [AB037781] |
| 476 | A_24_P242299 | ZRANB2 | GAGTTTTTGAAAGTCTACCTTGCTAAATTGCCCGACGATCTAGATTGTACATGTTACCAT | SEQ ID NO: 1344 | Homo sapiens zinc finger, RAN-binding domain containing 2 (ZRANB2), transcript variant 2, mRNA [NM_005455] |
| 477 | A_24_P243749 | PDK4 | ATTTGACATTGTGTGTAATTTCATGGTGGCCTAGTGTTGTGGTGGTTCTGTGGTAATGGTA | SEQ ID NO: 1345 | Homo sapiens pyruvate dehydrogenase kinase, isozyme 4 (PDK4), mRNA [NM_002612] |
| 478 | A_24_P250922 | PTGS2 | TGAGATATTTAAGGTGAATGTTTGCTTAGGATAGGCCTATGTGGTAGCGGACAAAGA | SEQ ID NO: 1346 | Homo sapiens prostaglandin-endoperoxide synthase 2 (prostaglandin G/H synthase and cyclooxygenase) (PTGS2), mRNA [NM_000963] |
| 479 | A_24_P25326 | ZMYM6 | AGGACATTTAAATCAGTGTCTAACGTACGTGAGTTTGCATAAATGCAAAGACAAGTTAGGC | SEQ ID NO: 1347 | Homo sapiens zinc finger, MYM-type 6 (ZMYM6), mRNA [NM_007167] |
| 480 | A_24_P255252 | A_24_P255252 | TGGACTAGTCGAGGATGGTGGTACTGTGATATGGTGATTTGTTGAGGATGATTAGAAA | SEQ ID NO: 1348 | |
| 481 | A_24_P257151 | CLK1 | TATGGAGCTGTCTGAATTTTTGCAGAGTAATAAGTTGACTCACACAGACTTAAAGCCTG | SEQ ID NO: 1349 | Homo sapiens CDC-like kinase 1 (CLK1), transcript variant 1, mRNA [NM_004071] |
| 482 | A_24_P263524 | TXNDC9 | TGACTTCACGCACAGAAACTTAGAATATGGGCTCAGTGTTGTCTGAGATTCTTAATTACAG | SEQ ID NO: 1350 | Homo sapiens thioredoxin domain containing 9 (TXNDC9), mRNA [NM_005783] |
| 483 | A_24_P265856 | SENP7 | TTGTGTGTTGGGGGTACTTTAAAGGTGACTATTGTTTTGTACATGTAAATTTGGA | SEQ ID NO: 1351 | Homo sapiens SUMO1/sentrin specific peptidase 7 (SENP7), transcript variant 1, mRNA [NM_020654] |
| 484 | A_24_P268786 | MYNN | TGCAGAGGATCATACTTGAGTGAACAGGATTCCATACAAAAAGTCCTTTATCAGAAAC | SEQ ID NO: 1352 | Homo sapiens myoneurin (MYNN), mRNA [NM_018657] |
| 485 | A_24_P268917 | RAB33B | CCGAGAATCTAATGTAGTTCGGTATTAATAACAATGCATTATTGAAAGTATATTGGAAAT | SEQ ID NO: 1353 | Homo sapiens RAB33B, member RAS oncogene family (RAB33B), mRNA [NM_031296] |
| 486 | A_24_P276583 | TMCO1 | CCTTGATTTTGGTGTATATTCTGTACTATGTCGATGGAGCAGAACATTCAGAAGATTC | SEQ ID NO: 1354 | Homo sapiens transmembrane and coiled-coil domains 1 (TMCO1), mRNA [NM_019026] |
| 487 | A_24_P278008 | DCTN6 | CTATAAAGGAAGGCTCAACTCCAGTAAAGAAGACTAAGAACAGAGTGTATAACATGAAGATAAC | SEQ ID NO: 1355 | Homo sapiens dynactin 6 (DCTN6), mRNA [NM_006571] |
| 488 | A_24_P278460 | MLSTD2 | ACCGATGGAACAATATGGTTAGGATTGAACAGGAGCAGTGCTTACTTACACTTCTGTCTG | SEQ ID NO: 1356 | Homo sapiens male sterility domain containing 2 (MLSTD2), mRNA [NM_032228] |
| 489 | A_24_P280897 | LOC388532 | AGCACTCGAGACTGGAGCTGGATAGGTTCGTGAAATACATGAAGGAAAATGATCACAGAAAAAGA | SEQ ID NO: 1357 | PREDICTED: Homo sapiens similar to ribosomal protein L21 (LOC388532), mRNA [XM_380532] |
| 490 | A_24_P285179 | THC2649313 | AGTGGGAATTTGAAATGCCATGTCCATATATATGTGGATATTTGTTGGCACATTTGCA | SEQ ID NO: 1358 | |

Fig. 3-27

| No. | Probe ID No. | Symbols of genes | Sequence | SEQ ID NO: | Descriptions of genes (letters and numbers within [ ] indicates GenBank accession No.) |
|---|---|---|---|---|---|
| 491 | A_24_P280054 | ZFYVE16 | GTGTATGTATTCTGCCATGTAAGTAATTGAACAGTCTTAAAATA ACCAAATGGTAGAGGG | SEQ ID NO: 1359 | Zinc finger FYVE domain-containing protein 16 (Endofin) (Endosome-associated FYVE domain protein). [Source:Uniprot/SWISSPROT:Acc:Q7Z1R8] [ENST00000380248] |
| 492 | A_24_P287756 | NUDT21 | GCCATAGTTACTTCACTTGTTATACATCACTGATTATTTGGGTT AAACTGGACTCATTTC | SEQ ID NO: 1360 | Homo sapiens nudix (nucleoside diphosphate linked moiety X)-type motif 21 (NUDT21), mRNA [NM_007006] |
| 493 | A_24_P288754 | PIGA | CTTTCTGGATACCTTAATTGTAACTGTCAGTTTGCACTGGTCGG TATATGGAAAACACATT | SEQ ID NO: 1361 | Homo sapiens phosphatidylinositol glycan anchor biosynthesis, class A (paroxysmal nocturnal hemoglobinuria) (PIGA), transcript variant 1, mRNA [NM_002641] |
| 494 | A_24_P290257 | A_24_P290257 | CCAATTCATTCAACATAGAACAAGCCAATTATACCATCCAGTCA TTGAAGGACACCAAGA | SEQ ID NO: 1362 | |
| 495 | A_24_P295543 | BLOC1S2 | GTTTATTTCTATGTGAGTGACATTGACATGCGATCAGTTTGGG AAATGTGATGAAAACA | SEQ ID NO: 1363 | Homo sapiens biogenesis of lysosome-related organelles complex-1, subunit 2 (BLOC1S2), transcript variant 2, mRNA [NM_001001342] |
| 496 | A_24_P298238 | A_24_P298238 | ATCGTTGAAGGAAATGACATTGAGCTTGTTGTTTGAATTCAGCAAGC CACAACAGTTAAAAAC | SEQ ID NO: 1364 | |
| 497 | A_24_P298604 | LOC731599 | GATGGAAAATCATGACCAGAGGTGCGGCAAAATGACTTGAAAGAAT TGGTCAATAAAATGAT | SEQ ID NO: 1365 | PREDICTED: Homo sapiens hypothetical protein LOC731599 (LOC731599), mRNA [XR_015536] |
| 498 | A_24_P306527 | ENST00000308989 | ACGGATCCGTTGCGTGGTTATCCAGAGAAATGTAATGAGGATGAA GATTCACCAAATAAGT | SEQ ID NO: 1366 | PREDICTED: Homo sapiens similar to ribosomal protein L31 (LOC729305), mRNA [XM_001133428] |
| 499 | A_24_P306726 | TPT1 | GAGCCAGAAACAGTAAAAACCTTTATGACAGGGGCTGCAAAACAA ATCAAGGACATCCTTG | SEQ ID NO: 1367 | Homo sapiens tumor protein, translationally-controlled 1 (TPT1), mRNA [NM_003295] |
| 500 | A_24_P309415 | TMEM123 | GTTTCCTCTGCATTGGGTTTGAAGTAGTTAGTTATGTCTTTT CTGTATGTAAGTAG | SEQ ID NO: 1368 | Homo sapiens transmembrane protein 123 (TMEM123), mRNA [NM_052932] |
| 501 | A_24_P310894 | CAPZA1 | TGTATTATTTGTCCTTCATCATCCATGCATACCATACAGCACTATCT TCTGTATCAGGTAGTC | SEQ ID NO: 1369 | Homo sapiens capping protein (actin filament) muscle Z-line, alpha 1 (CAPZA1), mRNA [NM_006135] |
| 502 | A_24_P312417 | ZBTB26 | AGAGGAGGAAGATTTTTAAACCTTTATCATTCAGCATTCTGTAT TTTATGGATCCCGAGG | SEQ ID NO: 1370 | Zinc finger and BTB domain-containing protein 26 (Zinc finger protein 481) (Zinc finger protein Bioref). [Source:Uniprot/SWISSPROT:Acc:Q9H5K0] [ENST00000373656] |
| 503 | A_24_P315326 | LOC341412 | AAGTCTATACTTTGGTTACCAATGTAGGGGTTACGGCTTTGAA AAATACAAGGCAATG | SEQ ID NO: 1371 | AGENCOURT_10649955 NIH_MGC_126 Homo sapiens cDNA clone IMAGE:6723568 5', mRNA sequence [CA452253] |
| 504 | A_24_P316074 | LOC730902 | TATCAATGGTGTGAGCCGAAAAGGTCAAAGGTGTTGCAGCTTCTT CGGTTGGTCAAATCTT | SEQ ID NO: 1372 | PREDICTED: Homo sapiens similar to 60S ribosomal protein L7 (LOC730902), mRNA [XR_015500] |
| 505 | A_24_P320328 | SUB1 | CAGAAGAACCTGTAAAGAAACAAAAGACAGGTGAGAGACTTCAAGA GCCGTGTCATCTCTA | SEQ ID NO: 1373 | Homo sapiens SUB1 homolog (S. cerevisiae) (SUB1), mRNA [NM_006713] |
| 506 | A_24_P321511 | GOLT1B | TTAGAGCAAGAATAGTATCTGCTAATGTAAGGGACATCTCTATT TAAGTCGTTTGTAGAC | SEQ ID NO: 1374 | Homo sapiens golgi transport 1 homolog B (S. cerevisiae) (GOLT1B), mRNA [NM_016072] |
| 507 | A_24_P324224 | A_24_P324224 | AAAGCTGTCTGGGCAAGGAATAAGGAATTGCTATAGGCATGT GCGGTTGTCCACAAAA | SEQ ID NO: 1375 | |

Fig. 3-28

| No. | Probe ID No. | Symbols of genes | Sequence | SEQ ID NO: | Descriptions of genes (letters and numbers within [ ] indicates GenBank accession No.) |
|---|---|---|---|---|---|
| 508 | A_24_P324506 | A_24_P324506 | GCAATATAAGGCAGCTAATTGGAAATACAAGTATGGCTATTTGGTGTGGACATGTGTGT | SEQ ID NO: 1376 | |
| 509 | A_24_P324581 | KIAA1466 | ATAATAGCTCATAGAATGAATTGCTGTACCAACCAAGGCTAAAAAGAATTAAGTAGCCC | SEQ ID NO: 1377 | Homo sapiens mRNA for KIAA1466 protein, partial cds. [AB040899] |
| 510 | A_24_P330397 | STRN3 | ATGGTGTAACTAAAGATTTTGTTGTGTAATGCATGATTGATTAAGACAATAAAGTATTTTTC | SEQ ID NO: 1378 | Homo sapiens striatin, calmodulin binding protein 3 (STRN3), mRNA [NM_014574] |
| 511 | A_24_P33213 | A_24_P33213 | GACCATATATTACATGGGGGTACCCAAATCTGAAGTCAGTAAATGAACTTATGTACAGG | SEQ ID NO: 1379 | |
| 512 | A_24_P333112 | A_24_P333112 | GGTCATCAGAATCAGAGGTATCAAGTGTGTGAGCGCACAGGACCAAAGGTATTGCAACTT | SEQ ID NO: 1380 | |
| 513 | A_24_P334361 | FLJ20035 | GTGAAAATGAAGACGACAAGGTTGTCTTAGCCTTTGAAGAACTGAGTACAAGCTTTTTGGG | SEQ ID NO: 1381 | Homo sapiens hypothetical protein FLJ20035 (FLJ20035), mRNA [NM_017631] |
| 514 | A_24_P33607 | LOC652558 | TAAGAAAATAATTGCTTGACAGAGAACGCTTTGATTGCTGATCTCTGGTAAATATGG | SEQ ID NO: 1382 | PREDICTED: Homo sapiens similar to 60S ribosomal protein L7 (LOC652558), mRNA [XR_019386] |
| 515 | A_24_P349635 | LOC388401 | AGTTGGTTGGACAGATAACAGTTTGATTGCTCGATCTCTTGGTAAATATAGGATCAACTG | SEQ ID NO: 1383 | PREDICTED: Homo sapiens similar to 60S ribosomal protein L7 (LOC388401), mRNA [XR_016879] |
| 516 | A_24_P351435 | CRBN | GAAAGTGAAAGCAATTGAAGAACAAAAGTTCAAAGTCGTTGAGCTAAGAACAGAGTCAGA | SEQ ID NO: 1384 | Homo sapiens cereblon (CRBN), mRNA [NM_016302] |
| 517 | A_24_P352445 | MRPL42 | TTTTTAGTGCATGCACAATGAGAAAGGACGTGGTTTCTTTCACCCAAGCAATGTGGTTTGC | SEQ ID NO: 1385 | Homo sapiens mitochondrial ribosomal protein L42 (MRPL42), nuclear gene encoding mitochondrial protein, transcript variant 3, mRNA [NM_172178] |
| 518 | A_24_P354257 | AK025305 | GAAAACAGATCTTTTTCTTAAGTGAAAGCACCTTTAATTTGCTAACGGTAGATCCTG | SEQ ID NO: 1386 | Homo sapiens cDNA: FLJ21652 fis, clone COL08582 [AK025305] |
| 519 | A_24_P354412 | AK091335 | TGTAGACTGAAGGAGTCTTTCAAAACACGCCAGCATTAAATCCACTCTGCGCGTCTCT | SEQ ID NO: 1387 | Homo sapiens cDNA FLJ34016 fis, clone FCBBF2002541 [AK091335] |
| 520 | A_24_P354954 | CCDC126 | ATGGAAGCTGTTGAGGAGTTTAGCCAGGTGTATAATAAAGGTATACTGTTGGTCATT | SEQ ID NO: 1388 | Homo sapiens coiled-coil domain containing 126 (CCDC126), mRNA [NM_138771] |
| 521 | A_24_P357576 | KIAA1370 | TGCTGCATATGAACTGAAATCTTACACTGAATCACCAACAAACCCTCAGTTTTGCCACC | SEQ ID NO: 1389 | Homo sapiens KIAA1370 (KIAA1370), mRNA [NM_019600] |
| 522 | A_24_P362646 | TXNDC9 | CTCCAGATTCAGGTGTAAAATAGTAGACAGAGACATGGGCAATATGTCCAAGAAACAGAGT | SEQ ID NO: 1390 | Homo sapiens thioredoxin domain containing 9 (TXNDC9), mRNA [NM_005783] |
| 523 | A_24_P364807 | AYTL1 | TGTAAGCTGTTGTTCAGGTAATGTTCTCTCTCAACAAAGTGTCAAGCGCTGTGTAA | SEQ ID NO: 1391 | Homo sapiens mRNA; cDNA DKFZp686H22112 (from clone DKFZp686H22112) [BX641089] |
| 524 | A_24_P365048 | C17orf42 | CGGACTAGTGGAAAAGAAGGTAGTGAAGCAGTTTCTCTTGGATTCTATACTGAAGGGAT | SEQ ID NO: 1392 | Homo sapiens chromosome 17 open reading frame 42 (C17orf42), mRNA [NM_024663] |
| 525 | A_24_P366165 | LOC391126 | ACTTCCAAGCCAAATGAAACTGAAAAATAACCAAAAGGGATTTCAATGCACCTTGGGAGATTTCACAGG | SEQ ID NO: 1393 | PREDICTED: Homo sapiens similar to 60S ribosomal protein L26 (Silica-induced gene 20 protein) (SIG-20) (LOC391126), mRNA [XR_019504] |
| 526 | A_24_P366646 | RPL31P10 | CGGGTGTCCAGAAAACGTAATGAGAAATGAAGAATTCAAAATAAAGCCTATACTTTGGTTACGC | SEQ ID NO: 1394 | PREDICTED: Homo sapiens similar to ribosomal protein L31 (LOC390283), mRNA [XR_018695] |
| 527 | A_24_P367139 | A_24_P367139 | ACACCATGAAACTGCTCAGGGCATCAAGGGGTATACATAAAAGCCAAGAAGTATGTCAAAG | SEQ ID NO: 1395 | |

Fig. 3-29

| No. | Probe ID No. | Symbols of genes | Sequence | SEQ ID NO: | Descriptions of genes (letters and numbers within [ ] indicates GenBank accession No.) |
|---|---|---|---|---|---|
| 528 | A_24_P367191 | LOC652890 | AGTTAACATGGTGAGGAGTGTAGAGGCCATATATTGCCTGTGGGT ACCCAAATCTGAAGTC | SEQ ID NO: 1396 | PREDICTED: Homo sapiens similar to 60S ribosomal protein L7 (LOC652890), mRNA [XR_019544] |
| 529 | A_24_P367199 | A_24_P367199 | TCTTATGCTCAGCAGGTCAAGAGTGTGGGAAATCGAGAAGAAGGTG TAATGATGAGCTGAGA | SEQ ID NO: 1397 | |
| 530 | A_24_P367369 | A_24_P367369 | ATTTAAAGGTTTCGATGTAGATTCTCTGGTCGAGGATATCGAAG TGAACAAAGGCATCTAA | SEQ ID NO: 1398 | |
| 531 | A_24_P371303 | C3orf63 | GTCAGTGTCAAGAAATGAGAATTAGTTCTTATCTGGTTATACT GAAAACTTGGAATAGAG | SEQ ID NO: 1399 | Homo sapiens chromosome 3 open reading frame 63 (C3orf63), mRNA [NM_015224] |
| 532 | A_24_P374319 | RAP2C | ATTGTGTGTCGATGTTCAAATAAAGTGGTATCATCTACATTCATGTGA TTTATGGGTCACATG | SEQ ID NO: 1400 | Homo sapiens RAP2C, member of RAS oncogene family (RAP2C), mRNA [NM_021183] |
| 533 | A_24_P37519 | LZTFL1 | GGTAGGTAGAATTGTACTGTTTTCTTGGTAGCAGTTTGAAA TATTCTGTACAGTACG | SEQ ID NO: 1401 | Homo sapiens leucine zipper transcription factor-like 1 (LZTFL1), mRNA [NM_020347] |
| 534 | A_24_P375599 | LOC731681 | TGTATGTGCACTCGGGACGGATCAAGTGGTTATCCAGAAATGGGTGT CTTGTTGAAATCGAA | SEQ ID NO: 1402 | PREDICTED: Homo sapiens similar to 60S ribosomal protein L9 (LOC731681), mRNA [XR_015944] |
| 535 | A_24_P375849 | ENST00000359659 | AAGAAGCTCTGGAACAAGATAGAGGCTATGTCACACATGTGAT GAAGCGGGATTCAGAGA | SEQ ID NO: 1403 | Q8BI90_MOUSE (Q8BI90) 10, 11 days embryo whole body cDNA, RIKEN full-length enriched library, clone:2810021H19 product:ribosomal protein S17, full insert sequence (Fragment), partial (98%) [THC2555910] |
| 536 | A_24_P381625 | PSMC6 | ATGAAAGAGTCAGTCGAAAATGTGGCTGATTCTCAAGAAGCTGGAGTG TAAATTGGACTAGAAA | SEQ ID NO: 1404 | Homo sapiens proteasome (prosome, macropain) 26S subunit, ATPase, 6 (PSMC6), mRNA [NM_002806] |
| 537 | A_24_P383999 | RPS3A | TGGTTTTACTAAAAAAGGCAAGACAATCAGAGATACAAGAGAGACCTGT ATGCCAGCCAAGG | SEQ ID NO: 1405 | Homo sapiens ribosomal protein S3A (RPS3A), mRNA [NM_001006] |
| 538 | A_24_P384411 | A_24_P384411 | ATGGCAAAATCAATAAGAAGTGAAGCTTTGACAGATAATGCTTTG AGAGCTCGATGTGTTG | SEQ ID NO: 1406 | |
| 539 | A_24_P384539 | LOC730452 | CAAGAAAAGCTGGCAAGTTTCTATGTACCACAGACAAAAGCCAAATTG GCATTTGTCATCAGGA | SEQ ID NO: 1407 | PREDICTED: Homo sapiens similar to 60S ribosomal protein L7 (LOC730452), mRNA [XM_001125895] |
| 540 | A_24_P387869 | PKN2 | TTGTCCAGAAGATGATTTATATTACCTTGGAAATTGTTATTACC CAAGAATCCTTTGGGAG | SEQ ID NO: 1408 | Homo sapiens protein kinase N2 (PKN2), mRNA [NM_006256] |
| 541 | A_24_P389612 | ARL5B | ATTAATGCATTCAACATGATCAGTCTTGAAAATGGTCAAAGCA TGTTTCCTGATGGTG | SEQ ID NO: 1409 | ADP-ribosylation factor-like protein 5B (ADP-ribosylation factor-like protein 8). [Source:Uniprot/SWISSPROT;Acc:Q96KC2] [ENST00000377275] |
| 542 | A_24_P392231 | LOC641784 | CGATCAATATTGGATGGAATCGATGGAGTGGGCAAGAAGCGT GCCCCTGGGGAACTGA | SEQ ID NO: 1410 | xr55h07.x1 NCI_CGAP_Ov26 Homo sapiens cDNA clone IMAGE:2764093 3' similar to gb:X69181 60S RIBOSOMAL PROTEIN L31 (HUMAN), mRNA sequence [AW302767] |
| 543 | A_24_P39378 | CCPG1 | TAGTTTTTGTGGGTGGAACGGAACTTGATCAGTTCATCAATAAGT TTTTTCCTAAACGGTGT | SEQ ID NO: 1411 | Homo sapiens cell cycle progression 1 (CCPG1), transcript variant 1, mRNA [NM_004748] |
| 544 | A_24_P393611 | TMCO1 | AGATGACAACCAGACTGTTCCTTGCATTTCCTGTATATTCTGT GTAGTATGTGGATTCG | SEQ ID NO: 1412 | Homo sapiens transmembrane and coiled-coil domains 1 (TMCO1), mRNA [NM_019026] |

Fig. 3-30

| No. | Probe ID No. | Symbols of genes | Sequence | SEQ ID NO: | Descriptions of genes (letters and numbers within [ ] indicates GenBank accession No.) |
|---|---|---|---|---|---|
| 545 | A_24_P396720 | PPP1CB | TTTCTTCAACGACTACCTTCTACATTGGTTGACTTAGACGGTAA GGTTTTTAAGTTGTG | SEQ ID NO: 1413 | Homo sapiens protein phosphatase 1, catalytic subunit, beta isoform (PPP1CB), transcript variant 1, mRNA [NM_002709] |
| 546 | A_24_P399942 | ATP11C | TGAGGATGTACCTACTAAAGTGAAAACAATTCATTCCATATCTA CTTACAGATACAGCAG | SEQ ID NO: 1414 | Homo sapiens ATPase, Class VI, type 11C (ATP11C), transcript variant 1, mRNA [NM_173694] |
| 547 | A_24_P40417 | FMR1 | TCTGAGTTTGTTCTTTGAATTTTCATTTACATTGTACAGTAGTTTC CTTAGCATACAAAGAAG | SEQ ID NO: 1415 | Homo sapiens fragile X mental retardation 1 (FMR1), mRNA [NM_002024] |
| 548 | A_24_P405202 | PDIK1L | TGGTGGTAAGGGATACTTTGTCATTATGATGAAGTAAGTGTTAA GTGTCAGATAAATAGC | SEQ ID NO: 1416 | Homo sapiens PDLIM1 interacting kinase 1 like (PDIK1L), mRNA [NM_152835] |
| 549 | A_24_P405298 | PPP1CB | GTATTAGGTTAGGTGCAGAAAGTTTTATGTGAGGTGATTTAAAT AACTTCCTGATTGGAG | SEQ ID NO: 1417 | Homo sapiens protein phosphatase 1, catalytic subunit, beta isoform (PPP1CB), transcript variant 1, mRNA [NM_002709] |
| 550 | A_24_P405430 | TIA1 | GGATTTTCTCTCTGTTGTTAAATCACAAAAATGATAGTCCCCAATC GTTCTTTATAGGAGG | SEQ ID NO: 1418 | Homo sapiens cDNA FLJ36425 fis, clone THYMU2011482 [AK093744] |
| 551 | A_24_P406034 | SLC35A1 | ATGTACAGTATTTGTCCTAGCAGCATAAAGACCTAGCTCTTTT CTTACAAGAGGCAGAA | SEQ ID NO: 1419 | Homo sapiens solute carrier family 35 (CMP-sialic acid transporter), member A1 (SLC35A1), mRNA [NM_006416] |
| 552 | A_24_P409681 | A_24_P409681 | ACATGAGGTGTCCCTGGGGCATTGAGATGATTCTTGAAAAGGAA CAGATTGTTCATAAAC | SEQ ID NO: 1420 | |
| 553 | A_24_P414556 | TTC33 | TACTCAACATTTGGTATATGTTGTTTTGAGTAATGGATGTTGTTT TTTGTATAATTGTGA | SEQ ID NO: 1421 | Homo sapiens tetratricopeptide repeat domain 33 (TTC33), mRNA [NM_012382] |
| 554 | A_24_P414952 | TMEM168 | TTTCTACTGAAGGTCAGAGGATAGGAAACAACAAGTATTGTGTTC TGGTATACAATGTAATG | SEQ ID NO: 1422 | Homo sapiens transmembrane protein 168 (TMEM168), mRNA [NM_022484] |
| 555 | A_24_P41551 | LOC641790 | AAGGAGATGGGAACTCCTGATGTGCGATTGATATGAGGCACAA CAAAGTAGTGTCGAAA | SEQ ID NO: 1423 | PREDICTED: Homo sapiens similar to ribosomal protein L31 (LOC641790), mRNA [XR_018025] |
| 556 | A_24_P417281 | TXNDC10 | ATGAGTAGTGATTCTTGGGAAGATAAATGTAATGTTCCCAATA GTCAAGCTGTTTTTC | SEQ ID NO: 1424 | Homo sapiens thioredoxin domain containing 10 (TXNDC10), mRNA [NM_019022] |
| 557 | A_24_P418418 | RPS17 | GATGAAGTTCAAAATGCCGTCAGCGACCTGTTTGAATTTTTCTG CAGTGCTGTATATTT | SEQ ID NO: 1425 | Homo sapiens ribosomal protein S17 (RPS17), mRNA [NM_001021] |
| 558 | A_24_P418712 | A_24_P418712 | AGGCTGAACAACAAGCTGTCTGGGCCAAAGAAATAAGGAATATCGA TACCATATGTGTGTTA | SEQ ID NO: 1426 | |
| 559 | A_24_P450172 | AK095151 | TATGCCACTGAATAAAGCTACTTAAACCAGAGTAATTTGGGAT ATTAATCCTAGGGTAC | SEQ ID NO: 1427 | Homo sapiens cDNA FLJ37832 fis, clone BRSSN2009630. [AK095151] |
| 560 | A_24_P487736 | CXorf23 | TGCATAGTTAGTATGTGTAAGAGCAAATGGGATGGATTTTTAAA TGAAATTTTTAGGGCG | SEQ ID NO: 1428 | Homo sapiens chromosome X open reading frame 23 (CXorf23), mRNA [NM_198279] |
| 561 | A_24_P497226 | RPS6KB1 | TAAGATTATAGCACAGTATATCTCAGTGGATTATCCGGAATA ACATGTAAAGATGGG | SEQ ID NO: 1429 | Homo sapiens ribosomal protein S6 kinase, 70kDa, polypeptide 1 (RPS6KB1), mRNA [NM_003161] |
| 562 | A_24_P50437 | BC065737 | TGCAGAATGATGAAGTTGGCATTTAGAAAATTCCTGATTACTGAA GATGTTCAGGGCAAAA | SEQ ID NO: 1430 | Homo sapiens cDNA clone IMAGE:30404477, partial cds. [BC065737] |
| 563 | A_24_P50472 | LOC649839 | TAAAGTTACAAAGAAGAATTGTGGTGGGGCTTGAGTGCATTCAGG CCAACTGAGATCCAA | SEQ ID NO: 1431 | PREDICTED: Homo sapiens similar to large subunit ribosomal protein L36a (LOC649839), mRNA [XM_001129410] |

Fig. 3-31

| No. | Probe ID No | Symbols of genes | Sequence | SEQ ID NO: | Descriptions of genes (letters and numbers within [ ] indicates GenBank accession No.) |
|---|---|---|---|---|---|
| 564 | A_24_P50554 | LOC391655 | TGAAGGGTTTAGATGATGAGAATTCTCGGTGATTGAGTATAACCGAGTAAAGAAAGGAGGTA | SEQ ID NO: 1432 | PREDICTED: Homo sapiens similar to 60S ribosomal protein L17 (L23) (LOC391655), mRNA [XR_018405] |
| 565 | A_24_P50567 | A_24_P50567 | CCTTGGTAATTTCAAAAGTACGAGAACGATGAATGGAATGGCA TGGTTCTCTGGACTA | SEQ ID NO: 1433 | |
| 566 | A_24_P538403 | ROCK1 | TTAGAGGTTTGTTGGACTTTCATAAATTGAGTACAATCTTTGGA TCAAAGTACCTGCTAC | SEQ ID NO: 1434 | Homo sapiens Rho-associated, coiled-coil containing protein kinase 1 (ROCK1), mRNA [NM_005406] |
| 567 | A_24_P54178 | TMED5 | GCTCTGATATGCATTTGGATGATTAATGTTATGCTGTTCTTCA TGTGAATGTCAAGACA | SEQ ID NO: 1435 | Homo sapiens transmembrane emp24 protein transport domain containing 5 (TMED5), mRNA [NM_016040] |
| 568 | A_24_P551028 | LOC339745 | TGGAGTTGAAGAAATATTGAGTGGCTATCATATGGAAGAGTAAG TCCTACTAGGAATGA | SEQ ID NO: 1436 | Homo sapiens hypothetical protein LOC339745 (LOC339745), mRNA [NM_001001664] |
| 569 | A_24_P561223 | THC2697551 | TTATGCCAGTTACATACAAGGATCCTGCCATATTTCAGGAGCC CTAAAGTTATAAGAT | SEQ ID NO: 1437 | ALU1_HUMAN (P39188) Alu subfamily J sequence contamination warning entry, partial (8%) [THC2697551] |
| 570 | A_24_P55240 | CPNE8 | TACAACTATGTGACTTAGTGCACAACACATTTGGAAAATAACCT ACTCGTATACTGAAC | SEQ ID NO: 1438 | Homo sapiens copine VIII (CPNE8), mRNA [NM_153634] |
| 571 | A_24_P56252 | AF086032 | GTATCTAAAAACTGAACAGGTACTGTGCTATATGATTTGATTATTGG TAGTATTGAGCAGACC | SEQ ID NO: 1439 | Homo sapiens full length insert cDNA clone YW25609. [AF086032] |
| 572 | A_24_P57837 | THC2567891 | AGAAATCCGGAAGAACCTCTTATGCTCAGTACGACCGAAATCCGG AAGAAGATGAAGAA | SEQ ID NO: 1440 | Q6NXR8_HUMAN (Q6NXR8) Ribosomal protein S3a, partial (91%) [THC2567891] |
| 573 | A_24_P587938 | A_24_P587938 | CTTCAAAGACAAAAAGTGGAGAGTGGCAACAGGCAGGACC AGATTAACAGTCTTAT | SEQ ID NO: 1441 | |
| 574 | A_24_P606663 | LOC392030 | TGTGCGGTTGCCCAGAAAGTAATGCAGGTGAAGATTCACCAA ATAAGGTCCATACTTT | SEQ ID NO: 1442 | PREDICTED: Homo sapiens hypothetical LOC392030 (LOC392030), mRNA [XR_018063] |
| 575 | A_24_P62659 | TSPAN2 | CCGTTTTGGAGATAAGCTTTCCAAAATATGCGTATGAGTAAAAT TAGAGAATTGCACGAC | SEQ ID NO: 1443 | Homo sapiens tetraspanin 2 (TSPAN2), mRNA [NM_005725] |
| 576 | A_24_P62860 | STAM2 | GTCTATATGGTACTTGATGTACATTTAAGTGGAAAAATTAGCAG TATTGAAAGCTCAGT | SEQ ID NO: 1444 | Homo sapiens signal transducing adaptor molecule (SH3 domain and ITAM motif) 2 (STAM2), mRNA [NM_005843] |
| 577 | A_24_P630039 | AL049321 | AAGATGAGACAATACAAAGTTACATTTTTGGACCATATTAAAAC TGCAAGAAGACAGGGG | SEQ ID NO: 1445 | Homo sapiens mRNA; cDNA DKFZp564D156 (from clone DKFZp564D156). [AL049321] |
| 578 | A_24_P66125 | STAG2 | TAATCATTCCATGGCTTAATATGGTTGGAATACAAGAATATCT CAGATGGTGAATACC | SEQ ID NO: 1446 | Homo sapiens stromal antigen 2 (STAG2), transcript variant 4, mRNA [NM_006603] |
| 579 | A_24_P675947 | ENST00000389400 | CTTCATGGCCAAGATAGCAGTTCTGGAAAAAGTACTGGAGAAGA GACAAGGTCTAAAGTT | SEQ ID NO: 1447 | similar to 40S ribosomal protein S3a (V-fos transformation effector protein) (LOC391706), mRNA [Source:RefSeq_dna;Acc:XR_017186] [ENST00000389400] |
| 580 | A_24_P685729 | A_24_P685729 | TTGAAGGTTATGTTGATGTCAAGACTATCAGTGATTATTTCCTT TGTCTGTTTTGTGTGG | SEQ ID NO: 1448 | |
| 581 | A_24_P688133 | AK124299 | TAGCATATCTGCAGGAAAAATATCTTGTTTGTAGTGATGATTTC AATAGTAGTGATTC | SEQ ID NO: 1449 | Homo sapiens cDNA FLJ42306 fis, clone TRACH2001646. [AK124299] |

Fig. 3-32

| No. | Probe ID No. | Symbols of genes | Sequence | SEQ ID NO: | Descriptions of genes (letters and numbers within [ ] indicates GenBank accession No.) |
|---|---|---|---|---|---|
| 582 | A_24_P6975 | LOC342994 | GGAAGAGTTCGAGGGGTTGGTCGTGTAAGAGCGTAAAGTTCTTAT GAAATTGTCAAAAAGA | SEQ ID NO: 1450 | PREDICTED: Homo sapiens similar to ribosomal protein L34 (LOC342994), mRNA [XM_938484] |
| 583 | A_24_P703614 | A_24_P703614 | AAGAACATTACCGGATGGAGTGTGCACTGTAAGCATGAGTAG CAGCTTGTGTGTGTG | SEQ ID NO: 1451 | |
| 584 | A_24_P712350 | CHML | GTGTAGAAGAGTATAAAAAGGGGTTTATAAGTGATCTTTGACA TAGTGATCTTTAGTGA | SEQ ID NO: 1452 | Homo sapiens choroideremia-like (Rab escort protein 2) (CHML), mRNA [NM_001821] |
| 585 | A_24_P7181 | A_24_P7181 | TCATGGTCGGATTAAGTCACACGTGATGTGTGGCTGGCACATGA AAATGATCTTTAGTGA | SEQ ID NO: 1453 | |
| 586 | A_24_P75158 | PTAR1 | GCATTAGATTGTTCTTTATGTGACCATGTAGGAAGCAGGCTATA AAGTTATTGTATTCTG | SEQ ID NO: 1454 | Homo sapiens mRNA; cDNA DKFZp313P0917 (from clone DKFZp313P0917). [AL832683] |
| 587 | A_24_P755505 | A_24_P755505 | ATACAAGAAGACCTCTTTATGCTCAGGACCAACAGAGAAAAGTAAAAA TGCTGAAGAAGGGAA | SEQ ID NO: 1455 | |
| 588 | A_24_P76358 | LOC643981 | TTACTGAAGATGTTCAGGGCAAAAAACTGGCTAACTTCCGGCATG GATCTTATTCGTGACA | SEQ ID NO: 1456 | PREDICTED: Homo sapiens similar to 40S ribosomal protein S3a (V-fos transformation effector protein) (LOC643981), mRNA [XR_018444] |
| 589 | A_24_P77681 | PAIP1 | AGGTGATCCAGATTACCAAGAAGAATACCAAGAATTAGTTGAAA GAGAGAAGCTTTTTATGG | SEQ ID NO: 1457 | Homo sapiens poly(A) binding protein interacting protein 1 (PAIP1), transcript variant 1, mRNA [NM_006451] |
| 590 | A_24_P781846 | AK024092 | ACTTTTTATAGATACAAATGTATCTGTGGTAGTACAAGGACTT TGTTACTTTGGCGGTGC | SEQ ID NO: 1458 | Homo sapiens cDNA FLJ14030 fis, clone HEMBA1004086. [AK024092] |
| 591 | A_24_P792734 | PSMC6 | AGAAGGTTAACGGGAGTTACTGAATCAAATGGAATTGGATTT GATAC TCTGGATAAGAGTTAAA | SEQ ID NO: 1459 | Homo sapiens proteasome (prosome, macropain) 26S subunit, ATPase, 6 (PSMC6), mRNA [NM_002806] |
| 592 | A_24_P795230 | AK027541 | AGAAGTTCTAGGAGTTTGAAGTTCGGTCAAGATGTTGATTCCT TTTAAGTGCGAGGGT | SEQ ID NO: 1460 | Homo sapiens cDNA FLJ14635 fis, clone NT2RP2001196. [AK027541] |
| 593 | A_24_P80915 | BCLAF1 | AACTGTGTCAATGATGTAATGAGAGAGAGAAACTTGTACATTTAA TTAAGGGTACCAGTTC | SEQ ID NO: 1461 | Homo sapiens BCL2-associated transcription factor 1 (BCLAF1), transcript variant 1, mRNA [NM_014739] |
| 594 | A_24_P81965 | RAP2A | TTGTTTGATGTTGCAACTTTTGGGGTTCTTTTAAAGTGTGATAG TCAGTAACTGATGATGG | SEQ ID NO: 1462 | Homo sapiens RAP2A, member of RAS oncogene family (RAP2A), mRNA [NM_021033] |
| 595 | A_24_P82630 | SMCHD1 | TGTTTAATATGTAACAGGTAAGAACAATTGAAATTTCTCTAA GATTTCATACTAGTCT | SEQ ID NO: 1463 | Homo sapiens mRNA for KIAA0650 protein, partial cds. [AB014550] |
| 596 | A_24_P83968 | LOC730887 | ACAAAGCCCAGAACGACGTGGAAGAGAGAGAAACTTTTCT GGTGTCTCTAAGAAGC | SEQ ID NO: 1464 | PREDICTED: Homo sapiens similar to 40S ribosomal protein S7 (S8) (LOC730887), mRNA [XR_015607] |
| 597 | A_24_P84408 | A_24_P84408 | AAGGTACATCGAGCAGTGGTCATTGAGAAGTGATACCAGAGAAA AGATGGCGTGTTTCTT | SEQ ID NO: 1465 | |
| 598 | A_24_P84808 | LOC729449 | GAATTGTTTGACAGATAACGGTCGGATGTCTTGGAAAATAT GGCATCATCGTATGG | SEQ ID NO: 1466 | PREDICTED: Homo sapiens similar to 60S ribosomal protein L7 (LOC729449), mRNA [XR_015548] |
| 599 | A_24_P850187 | A_24_P850187 | TAAATGAACTAATCTACAAGGGTGCTTATGTGCAAAATGAATTG ACTTGCACTTTGGTAG | SEQ ID NO: 1467 | |
| 600 | A_24_P859859 | THC2553238 | TTTAAGGAGGAGCTGCGACGGGTTTTTCCTGATATAGTGAGGACA CTCGGTCTCTAGGCAAT | SEQ ID NO: 1468 | T305349A cystic fibrosis antigen [Homo sapiens] (exp=0; wgp=0; cg=0), partial (65%) [THC2553238] |
| 601 | A_24_P867201 | AK022997 | CTGACATGTGATAAATATTTCAGTGACTTTTGAGATTATTCT TGTTAGCCGCTGTGTC | SEQ ID NO: 1469 | Homo sapiens cDNA FLJ12935 fis, clone NT2RP2004982. [AK022997] |

Fig. 3-33

| No. | Probe ID No. | Symbols of genes | Sequence | SEQ ID NO: | Descriptions of genes (letters and numbers within [ ] indicates GenBank accession No.) |
|---|---|---|---|---|---|
| 602 | A_24_P886040 | DCP2 | CATTGGAACAGGTTTCATTCTGTTTGTAGAATTATGTTTGT AGTTGAACAGCAACTG | SEQ ID NO: 1470 | Homo sapiens DCP2 decapping enzyme homolog (S. cerevisiae) (DCP2), mRNA [NM_152624] |
| 603 | A_24_P890536 | CR627148 | AATTGCCTTCTTGTAACCCAAGTATGGTGAAGCAGAGAATTGAAT TCTACAAAGTCTTC | SEQ ID NO: 1471 | Homo sapiens mRNA; cDNA DKFZp779F2127 (from clone DKFZp779F2127). [CR627148] |
| 604 | A_24_P91852 | DYNLT3 | ATACATATAGAAGAGCGGAAGCAATAACTCATTGAAATTTGGAGAG GAATAAGCTTAGCGTT | SEQ ID NO: 1472 | Homo sapiens dynein, light chain, Tctex-type 3 (DYNLT3), mRNA [NM_006520] |
| 605 | A_24_P91916 | NXT2 | ACCATGGTTTCTTGTAGTACTGATTGAAAGTTACAGGTTTTAT TCTACTCATAGTGAGC | SEQ ID NO: 1473 | Homo sapiens nuclear transport factor 2-like export factor 2 (NXT2), mRNA [NM_018698] |
| 606 | A_24_P931282 | THC2726401 | GGAAATATTTCTCCTCTAAATGCATGAAATCATGTTGAGGTAAT CTACTGGAGATTACAC | SEQ ID NO: 1474 | Q26195 PVAI (Q26195) Pval protein, partial (14%) [THC2726401] |
| 607 | A_24_P935986 | BCAT1 | ATGCTCTGAAGTTTGTAGAAGGACACAATTAAACATGTAAAATG GGTTGTTACACCAGA | SEQ ID NO: 1475 | Homo sapiens branched chain aminotransferase 1, cytosolic (BCAT1), mRNA [NM_005504] |
| 608 | A_24_P937095 | SLC30A1 | TTTGATGTAGGTCTACCGATACTATGTGGTAATGGTATTTTGTT TTAGTAACAAGTCTG | SEQ ID NO: 1476 | Zinc transporter 1 (ZnT-1) (Solute carrier family 30 member 1). [Source:Uniprot/SWISSPROT:Acc:Q9Y6M5] [ENST00000367000] |
| 609 | A_24_P940426 | QKI | AAGCTGTTGAATGAGTCTTAAAAAATATAGTACTGTTAAGTGGA CCAAGTTTGGTGAAGC | SEQ ID NO: 1477 | Homo sapiens quaking homolog (mouse) (QKI), transcript variant 4, mRNA [NM_206855] |
| 610 | A_24_P940725 | C6orf111 | AATTATGATTGAGTGRTCTAAGCAGTTTAAGGGATTGATAAC TTACAGTAGAGTGGG | SEQ ID NO: 1478 | Splicing factor, arginine/serine-rich 130 (Serine-arginine-rich-splicing regulatory protein 130) (SRrp130) (SR-rich protein) (SR-related protein). [Source:Uniprot/SWISSPROT:Acc:Q8IF01] [ENST00000369239] |
| 611 | A_24_P940776 | BDP1 | TCGGAGGCGGAAATTGTCCTATAAGTAGGCATTTATTTGATGATTG ATATGTCACAGAAATC | SEQ ID NO: 1479 | Homo sapiens B double prime 1, subunit of RNA polymerase III transcription initiation factor IIIB (BDP1), mRNA [NM_018429] |
| 612 | A_24_P941643 | PLCB1 | ATGAGTGCAGTTTGTGGGTTTAGTATTTGGCTTGTGTCTTG TCGAATGTGTGAAATT | SEQ ID NO: 1480 | Homo sapiens phospholipase C, beta 1 (phosphoinositide-specific) (PLCB1), transcript variant 2, mRNA [NM_182734] |
| 613 | A_24_P941699 | PCGF5 | TGGTATATCAACTACAGCTTTCTAAGGATAGGACACTTCAT GTCTAGTAATACACTG | SEQ ID NO: 1481 | Homo sapiens polycomb group ring finger 5 (PCGF5), mRNA [NM_032373] |
| 614 | A_24_P944458 | INSIG2 | ATGTATTCGTGTATCCATTAGTGAAGTTCAAGTCTGTTAAG AGTGTATTGAGATGGC | SEQ ID NO: 1482 | Homo sapiens insulin induced gene 2 (INSIG2), mRNA [NM_016133] |
| 615 | A_24_P95029 | TAX1BP1 | TGCTTTGAATTCCAGCTTGATGTTCACAAGAAGTCCGGTCG TGAGTTAATGTTTCCT | SEQ ID NO: 1483 | Homo sapiens Tax1 (human T-cell leukemia virus type I) binding protein 1 (TAX1BP1), transcript variant 1, mRNA [NM_006024] |
| 616 | A_24_P99046 | STK38L | GCTATGTGTCTTTTGCTGATCTACAAATAATGATTGAGAATT TAGTACATAGAGGTCC | SEQ ID NO: 1484 | Homo sapiens serine/threonine kinase 38 like (STK38L), mRNA [NM_015000] |
| 617 | A_32_P10100 | A_32_P10100 | TATGAGGAAATAGTATCATGTTAGAAGCCTGGAATGAGTA TAAATAATGGCTGGTG | SEQ ID NO: 1485 | |

Fig. 3-34

| No. | Probe ID No. | Symbols of genes | Sequence | SEQ ID NO: | Descriptions of genes (letters and numbers within { } indicates GenBank accession No.) |
|---|---|---|---|---|---|
| 618 | A_32_P10424 | AX721252 | AAATTGTCAGGAAGGAAGAAGTGGGAAGTCTAGATGTGCACAAGTGATACCAGGGTCAACAA | SEQ ID NO: 1486 | Sequence 212 from Patent WO220754. [AX721252] |
| 619 | A_32_P105397 | THC2642694 | TAAAATGGTACTACAGATATTCTACGATGCAGGGTGAATGTATATTACAGTAATTGTGTGG | SEQ ID NO: 1487 | Q6TDT1_HUMAN (Q6TDT1) Protein transactivated by hepatitis B virus E antigen, partial (11%) [THC2642694] |
| 620 | A_32_P106732 | FANCM | AATCAAGCTGCTCAAGATGGGGTTTCAAAGAGCTCTCAACAATATTAAATGACTTCAAT | SEQ ID NO: 1488 | Homo sapiens Fanconi anemia, complementation group M (FANCM), mRNA [NM_020937] |
| 621 | A_32_P107372 | GBP1 | GGTAGTGAGCAGAGTCTTAGGTAAAAGTGTTGGAAAATATTTGGGCATTGGTCTGGGCAA | SEQ ID NO: 1489 | Homo sapiens guanylate binding protein 1, interferon-inducible, 67kDa (GBP1), mRNA [NM_002053] |
| 622 | A_32_P109522 | C6orf113 | TAGAGGGTGCTGTCTTTCTCTAGAGGAGAAAGTTGCCAGGAGACAAGCTCTCAAGTCTTA | SEQ ID NO: 1490 | Homo sapiens chromosome 6 open reading frame 113 (C6orf113), mRNA [NM_145062] |
| 623 | A_32_P113154 | LOC730861 | ACCACGAGTCCAAGAACTGTCTTAAAGTTCAGAGTTAAAACAGTACCAAATAAAAAGTCC | SEQ ID NO: 1491 | PREDICTED: Homo sapiens similar to 40S ribosomal protein S3a (V-fos transformation effector protein) (LOC730861), mRNA [XR_015591] |
| 624 | A_32_P113584 | ZNF292 | GGGGCTTTGGGTTTTATTGAATAGTTCATTTCACCTGTTAAGACTTACTACCAATAAAG | SEQ ID NO: 1492 | Zinc finger protein 292. [Source:Uniprot/SWISSPROT;Acc:O60281] [ENST00000339907] |
| 625 | A_32_P14215 | COMMD6 | AATTTGTATCATTCTAAAGTCATGGACTTCACTTTCGGCAACAAACTAAATAAGGATGG | SEQ ID NO: 1493 | Homo sapiens COMM domain containing 6 (COMMD6), transcript variant 2, mRNA [NM_203495] |
| 626 | A_32_P1144 | AK091357 | GGGACTTATAATATTTTACATCTTACTAGGCAATGTCAATAGGTTTTAAGTGTTTAATGGGG | SEQ ID NO: 1494 | Homo sapiens cDNA FLJ34038 fis, clone FCBBF2005645. [AK091357] |
| 627 | A_32_P11451 | NMD3 | CAGTTAGGGCAGTAGGTGCTGCTTTTGTCATAAAATATCTTCCTACGAGATCAAAATGCGC | SEQ ID NO: 1495 | Homo sapiens NMD3 homolog (S. cerevisiae) (NMD3), mRNA [NM_015938] |
| 628 | A_32_P115505 | ZNF294 | TGTGTCTCAGAGGATTATAGTTGAGAGTGAAGTACTATGTGTGAGTTATAGATGTCTCGAA | SEQ ID NO: 1496 | Homo sapiens zinc finger protein 294 (ZNF294), mRNA [NM_015565] |
| 629 | A_32_P11931 | LOC441073 | GTGTGATGCATGCCATCCGAAAAGGATGATGAAGTTCACGGTGTACGTGGAGACTATAAG | SEQ ID NO: 1497 | PREDICTED: Homo sapiens similar to 60S ribosomal protein L26 (Silica-induced gene 20 protein) (SIG-20) (LOC441073), mRNA [XR_016376] |
| 630 | A_32_P12430 | SPG20 | TCAGGGTAAAGAATAATCGAAAAACGGTTAGACGTAATGCATCGATGGAGAATAGGCATTATGGTTTC | SEQ ID NO: 1498 | Homo sapiens spastic paraplegia 20, spartin (Troyer syndrome) (SPG20), mRNA [NM_015087] |
| 631 | A_32_P124580 | THC2610143 | ATTAGCTGGGAGTAAAACGGACATGTTTGTTTGTGAATTCTACGTAAATGTGTGTCTA | SEQ ID NO: 1499 | AA490192 aa43f10.r1 Soares_NhHMPu_S1 Homo sapiens cDNA clone IMAGE:823723 5', mRNA sequence [AA490192] |
| 632 | A_32_P125549 | RPL31P4 | TGTAGACAGTCGAATGAATGGAAGAAGTAATCCCTGATGGTCAGATACGATCAAATAAAG | SEQ ID NO: 1500 | PREDICTED: Homo sapiens ribosomal protein L31 pseudogene 4 (RPL31P4), mRNA [XR_018222] |
| 633 | A_32_P125917 | THC2753798 | GCTTATAAAGTGTAAAGTGGAGAGGGCTAAATTGTGAGTACAAAGTTTCTTTTTCACACACAG | SEQ ID NO: 1501 | BF238843 601904455F1 NIH_MGC_54 Homo sapiens cDNA clone IMAGE:4132429 5', mRNA sequence [BF238843] |
| 634 | A_32_P128781 | A_32_P128781 | CATATATTGCATGGGGTAGCCCAATCGAAGTAGCAGTAAATGAACTAATCTACAAGAGTG | SEQ ID NO: 1502 | |
| 635 | A_32_P128980 | BC062780 | AGATGGGAGAACAGAAGGAGTAGTGACGAGTAAGAGGTAGAAGCACGTGTAGAGGTTTCCATATCAT | SEQ ID NO: 1503 | Homo sapiens cDNA clone IMAGE:4700531, partial cds. [BC062780] |

Fig. 3-35

| No. | Probe ID No. | Symbols of genes | Sequence | SEQ ID NO: | Descriptions of genes (letters and numbers within [ ] indicates GenBank accession No.) |
|---|---|---|---|---|---|
| 636 | A_32_P135818 | RPS3A | CTTGTTCATCTGTTCTGTGTTGGTTTAATAAAAAGGCAACAATCAGATATGGAAGAC | SEQ ID NO: 1504 | Homo sapiens ribosomal protein S3A (RPS3A), mRNA [NM_001006] |
| 637 | A_32_P136319 | RPL36A | AAGTGATCCAGTTGTAAGTGTCATGTTTTATCATGAAGAGAATAAAATGTTGAGTTTATG | SEQ ID NO: 1505 | Homo sapiens ribosomal protein L36a (RPL36A), mRNA [NM_021029] |
| 638 | A_32_P137266 | KIAA1799 | AAGTGGGACCCGAAATGTCAATGGTACATGTGTCAACATGTAATGGCTTGAATGAACGACAAG | SEQ ID NO: 1506 | Homo sapiens KIAA1799 protein (KIAA1799), mRNA [NM_032437] |
| 639 | A_32_P143323 | CR613267 | AGAGAGGTGAAACAATGGGGTTTATGCCAGATTAGATACAACGGATCCTCCATATTTCAGGG | SEQ ID NO: 1507 | full-length cDNA clone CS0DL011YP14 of B cells (Ramos cell line) Cot 25-normalized of Homo sapiens (human) [CR613267] |
| 640 | A_32_P145153 | RPL31 | ATCCTGTGCACGTGTCCAGAAAAACGTAATGAGGATGAAGATTCAGCAAATAAGGCATAT | SEQ ID NO: 1508 | Homo sapiens ribosomal protein L31 (RPL31), mRNA [NM_000993] |
| 641 | A_32_P145159 | | CATACATTGGGCGTGTCGTACATAAACGTTTGTGGGAAAAACGTTAGTTGTGTGATTATTCTCTTG | SEQ ID NO: 1509 | |
| 642 | A_32_P147747 | THC2575761 | TTGATAGGTCTGATTCCTGATGAGAAACGGCCAATTGGGGTTCTGCAGGTACATAGAAGTTG | SEQ ID NO: 1510 | HUMRPL7Y ribosomal protein L7 [Homo sapiens] (exp=-1; wgp=0; cg=0), partial (40%) [THC2575761] |
| 643 | A_32_P148824 | C1orf27 | GAAAAACAGATGTTATCCTCAGGACAAATTCAGTGAAAGAGACTACAAAAGGATGATCTC | SEQ ID NO: 1511 | Homo sapiens chromosome 1 open reading frame 27 (C1orf27), mRNA [NM_017847] |
| 644 | A_32_P151516 | AA714537 | CTGAGGCATAAAGAGGTCTTCCGTATCTGATTTTTCGGTTTTTTAGTAAAAACAACAGAA | SEQ ID NO: 1512 | nw20g12.s1 NCI_CGAP_RGB0 Homo sapiens cDNA clone IMAGE:1241062 3' similar to gb:M84711 40S RIBOSOMAL PROTEIN S3A (HUMAN), mRNA sequence [AA714537] |
| 645 | A_32_P153725 | KIAA1033 | TTTTGTAAAAGATGGGAAGTTGTTACCTCACTTGAGTGGGGTTTCCTTTCCCGGAAT | SEQ ID NO: 1513 | Homo sapiens KIAA1033 (KIAA1033), mRNA [NM_015275] |
| 646 | A_32_P155364 | RPL7 | CAACAGGGTTATTAGAAGAATTGAAGCAAGGTGTCACCAGGTCATTTTGTAAGCTGG | SEQ ID NO: 1514 | Homo sapiens ribosomal protein L7 (RPL7), mRNA [NM_000971] |
| 647 | A_32_P155811 | CD2AP | AAACATGGTCTGTGTCAAAAAGAAAATTAAAGAGATTTATTGCCAGTGGTGTCAGTC | SEQ ID NO: 1515 | Homo sapiens CD2-associated protein (CD2AP), mRNA [NM_012120] |
| 648 | A_32_P158746 | RPL17 | TTTTGCTGCACATGCTAAAAAATGAAGAATCATGATGAGAGTAATGGTGAACTTAAGGGTTTAGATGTAG | SEQ ID NO: 1516 | Homo sapiens ribosomal protein L17 (RPL17), transcript variant 1, mRNA [NM_000985] |
| 649 | A_32_P159651 | PCAF | GAGTGGTGTCTAGATTCTAATGAAGAATCATGATACAGTTGGATTAAGTATCTTGGAC | SEQ ID NO: 1517 | Homo sapiens p300/CBP-associated factor (PCAF), mRNA [NM_003884] |
| 650 | A_32_P162150 | MAP3K7IP3 | AGGCATAGAAGAATTGTCCTCTAAAAATATCAATGATGTATCCTGGAATGTGAAGATGTC | SEQ ID NO: 1518 | Homo sapiens mitogen-activated protein kinase kinase kinase 7 interacting protein 3 (MAP3K7IP3), mRNA [NM_152787] |
| 651 | A_32_P164203 | THC2683448 | TTGATGGTCATTGTACGAGGTATTGTATGGATTAGTGTGGAGTGCTGTTTACCACAGATGAT | SEQ ID NO: 1519 | Q7WZG3_PASP1 (Q7WZG3) Ferric uptake regulator, partial (8%) [THC2683448] |
| 652 | A_32_P167122 | RCOR3 | GTATCGAGGGATGGTGTGTAATCTGATTACATGATTAGAGCACACAGTAGAAAAAGT | SEQ ID NO: 1520 | Homo sapiens REST corepressor 3 (RCOR3), mRNA [NM_018254] |
| 653 | A_32_P170444 | SUB1 | TAGGTATCTCTCCTGAAATTCTTTGCAGTTGTCATTTTTATCGGCAGTTAATGGAGTGAAAC | SEQ ID NO: 1521 | Activated RNA polymerase II transcriptional coactivator p15 (SUB1 homolog) (Positive cofactor 4) (PC4) (p14). [Source:Uniprot/SWISSPROT;Acc:P53999] [ENST00000265073] |

Fig. 3-36

| No | Probe ID No | Symbols of genes | Sequence | SEQ ID NO: | Descriptions of genes (letters and numbers within [ ] indicates GenBank accession No.) |
|---|---|---|---|---|---|
| 654 | A_32_P170736 | AK098422 | ACGTCATAATTGTTGAGGGGAAGCTCATTGTTGATAGTGCAAAGTGTGGCTGTGTTGAT | SEQ ID NO: 1522 | Homo sapiens cDNA FLJ25556 fis, clone JTH02629. [AK098422] |
| 655 | A_32_P172578 | THC2661509 | ACTTAATCAATGCTCAAACATTGTAGGGATTGTCTCCATCTCAGGATCCTTGTGTTGG | SEQ ID NO: 1523 | |
| 656 | A_32_P173385 | ENST00000334663 | AAATGCAGAGAGGATGCTGAACTTAAGGGTTCAGAGTAGAGATTCTGTGTCATTGAGCA | SEQ ID NO: 1524 | PREDICTED: Homo sapiens similar to 60S ribosomal protein L17 (L23) (LOC650848), mRNA [XR_019013] |
| 657 | A_32_P176619 | CMAH | GATTATATATGCTAGGTGTCGATTCTGAAGATAGAAGAATTCAATGGTGGAATTTGTCTCC | SEQ ID NO: 1525 | Homo sapiens cytidine monophosphate-N-acetylneuraminic acid hydroxylase (CMP-N-acetylneuraminate monooxygenase) (CMAH) on chromosome 6 [NR_002174] |
| 658 | A_32_P177040 | WBSCR19 | AATCTTGTATCTATTATTAGAGGTGTTGGTGAAGGGAGGAGCATGGTTTTATGTGTCATAC | SEQ ID NO: 1526 | Homo sapiens Williams Beuren syndrome chromosome region 19 (WBSCR19), mRNA [NM_175064] |
| 659 | A_32_P177953 | GCLM | ATTATTGTATGTTGGCTAGGAGTCATCGTTCTCTGCAAAATATGGATTCAGAGAAATGTG | SEQ ID NO: 1527 | Glutamate—cysteine ligase regulatory subunit (EC 6.3.2.2) (Gamma-glutamylcysteine synthetase) (Gamma-ECS) (GCS light chain) (Glutamate—cysteine ligase modifier subunit). [Source:Uniprot/SWISSPROT;Acc:P48507] [ENST00000370233] |
| 660 | A_32_P178966 | ENST00000379426 | GTAATATACAGAGGGTGAAACTCTTACTGATACACAAGACAAGTGTTAAAAAGTGAATCC | SEQ ID NO: 1528 | Novel protein. [Source:Uniprot/SPTREMBL;Acc:Q5T4T1] [ENST00000379426] |
| 661 | A_32_P180435 | WBSCR19 | CTTTGAATCTTTGTATCTATTATTACAGGTGCTGGTGAAGGGAGCATGTTTTATCTATG | SEQ ID NO: 1529 | Homo sapiens Williams Beuren syndrome chromosome region 19 (WBSCR19), mRNA [NM_175064] |
| 662 | A_32_P186961 | RPL17 | CATGAGGAGATGATCCTTACGGAAAAGGAACAGATTGTTGCTAACCAGAAGAGGAGGTTGC | SEQ ID NO: 1530 | Homo sapiens ribosomal protein L17 (RPL17), transcript variant 1, mRNA [NM_000985] |
| 663 | A_32_P191488 | hCG_26523 | CCCAGTGAAGGTGGTTATCAGTCAGGGCTAAAACTGGAGAAGAGACGGCAAAAGATCCTTGAA | SEQ ID NO: 1531 | PREDICTED: Homo sapiens similar to 60S ribosomal protein L26 (LOC646161), mRNA [XR_018048] |
| 664 | A_32_P193322 | RICTOR | ACCACATGAGTTCTTCTTTTTTATTAGTAATACGCTGCTACATATTCTGGAAGGTTCTGG | SEQ ID NO: 1532 | Homo sapiens rapamycin-insensitive companion of mTOR (RICTOR), mRNA [NM_152756] |
| 665 | A_32_P195387 | DKFZP779L1066 | ATAAACCTTGGAATTCTATTCTAATTATGTTGTTGGCTGGTTGTAGTATCAGTTCGC | SEQ ID NO: 1533 | Homo sapiens cDNA clone IMAGE:5555490. [BC110326] |
| 666 | A_32_P198463 | RPS3A | GGGGCCAAGAAGAAGAAATGGTTGATCCATTTTTGATGAAAGATTGAAGAGAAGATTGGTATGCATGTGAAAGCA | SEQ ID NO: 1534 | Homo sapiens ribosomal protein S3A (RPS3A), mRNA [NM_001006] |
| 667 | A_32_P19752 | FAM76B | TTGTGCTTTTAGCCTGTCTTTTGCACTCATATTAATTAGGCATTTACCAGTAAGGGTCATTTTGAC | SEQ ID NO: 1535 | Homo sapiens family with sequence similarity 76, member B (FAM76B), mRNA [NM_144664] |
| 668 | A_32_P20240 | SP3 | GTTAGGCTGTGTTAATTGTAGTTAATTCAGTACTGCCTACTCAGACCCAAAAGTTTTTGT | SEQ ID NO: 1536 | Homo sapiens mRNA; cDNA DKFZp686N17231 (from clone DKFZp686N17231). [BX648357] |
| 669 | A_32_P202488 | RPL21 | AAGAAGGAGGCAGCGACCGGATATGTCTGTAGGGCGTTTTTAGAAAACATGGCAATGGGTAC | SEQ ID NO: 1537 | Homo sapiens ribosomal protein L21, mRNA (cDNA clone IMAGE:6605332), complete cds. [BC104478] |
| 670 | A_32_P203320 | ROCK1 | AACGGGCATCACTACGATCACGCCATGGAAGGAGTAAGAAAATATGCTAAAATGAG | SEQ ID NO: 1538 | Homo sapiens Rho-associated, coiled-coil containing protein kinase 1, mRNA (cDNA clone IMAGE:5269982), complete cds. [BC041849] |

Fig. 3-37

| No. | Probe ID No. | Symbols of genes | Sequence | SEQ ID NO: | Descriptions of genes (letters and numbers within [ ] indicates GenBank accession No.) |
|---|---|---|---|---|---|
| 671 | A_32_P20367 | RPS7 | ATGGTTGAGGAGTTGGTCTTGACAAGGAAAATTGTGGGCAAGAG AATCCGGGGTGAAAGTA | SEQ ID NO: 1539 | Homo sapiens ribosomal protein S7 (RPS7), mRNA [NM_001011] |
| 672 | A_32_P204330 | AK093982 | AAACCGTGAGCTTTTTGCTCGTCTTGGTAGAGATATGTGTAAA AACGTACCAGAATTG | SEQ ID NO: 1540 | Homo sapiens cDNA FLJ36663 fis, clone UTERU2002826. [AK093982] |
| 673 | A_32_P205550 | RPL26L1 | AGGTAGTTCAGAGGACTAGAAAGGTAGCAGCAAATTGGCAAGTA ATCCAGGTGTACAGAA | SEQ ID NO: 1541 | Homo sapiens ribosomal protein L26-like 1 (RPL26L1), mRNA [NM_016093] |
| 674 | A_32_P205553 | RPL26L1 | TTCGGAATGTCGGAACATTCATTCCTGTTTTGTTGTACGTGTG GCTCTGTAAATCTACT | SEQ ID NO: 1542 | Homo sapiens ribosomal protein L26-like 1 (RPL26L1), mRNA [NM_016093] |
| 675 | A_32_P207231 | AI630435 | TTCCTCGGTTTTCTTAAGGGTTTCTCTGGAACAGCAGGAAGCTC CTGTTCTTCTGTCT | SEQ ID NO: 1543 | AI630435 ad10b05.y1 Hembase: Erythroid Progenitor Cells (LCB:ad library) Homo sapiens cDNA clone ad10b05 random, mRNA sequence [AI630435] |
| 676 | A_32_P208178 | RPS3A | GGAAAGACGTAGAAAAGGTTGCCAATCTATTTATCCTCGGA TGATGTCTCGTTAGA | SEQ ID NO: 1544 | Homo sapiens ribosomal protein S3A (RPS3A), mRNA [NM_001006] |
| 677 | A_32_P21384 | RPL17 | AGATGTCACTTTACAGAACAGTGTGTATGGATTCCGAGCATTACA ACGGTGAGTTGGCAG | SEQ ID NO: 1545 | Homo sapiens ribosomal protein L17 (RPL17), transcript variant 1, mRNA [NM_000985] |
| 678 | A_32_P220127 | RPL34 | CAAAACTAGGGTGTCCTGAAGCCCTGGTAATAGATGTTCAGG TTTATACCAAGAAGGT | SEQ ID NO: 1546 | Homo sapiens ribosomal protein L34 (RPL34), transcript variant 2, mRNA [NM_033625] |
| 679 | A_32_P223319 | ESCO1 | ATGCCGTGATTAGTGAGACTTCATTTGATAGTGTCTATCCTC ATAGTGGCTGCTACTT | SEQ ID NO: 1547 | Homo sapiens establishment of cohesion 1 homolog 1 (S. cerevisiae) (ESCO1), mRNA [NM_052911] |
| 680 | A_32_P224666 | CAPZA2 | AATTGCTGTTTTTGAGATTGTGAAATAAATGAAAATACTTATTTC AGAAATGCATTTAATG | SEQ ID NO: 1548 | Homo sapiens capping protein (actin filament) muscle Z-line, alpha 2 (CAPZA2), mRNA [NM_006136] |
| 681 | A_32_P22539 | hCG_26525 | AGTACGAAGGTCAGCAAATTGGCAAATGGTCCAGGTTTACAGG AAGAATATGTTATC | SEQ ID NO: 1549 | PREDICTED: Homo sapiens similar to 60S ribosomal protein L26 (Silica-induced gene 20 protein) (SIG-20) (LOC400055), mRNA [XM_374987] |
| 682 | A_32_P226786 | BC045174 | TTATTGGTGCAGTGTAAGGCATTATCCTGTCTTAATGAACCGATT AATGCTGTTGATTGTT | SEQ ID NO: 1550 | Homo sapiens cDNA clone IMAGE:5273745. [BC045174] |
| 683 | A_32_P2333 | SUB1 | AGGAAGACAAAAGGTATTTCTTAAATCCAGAAGAATGCAGCCAGC TGACAGAACAGATTTC | SEQ ID NO: 1551 | Homo sapiens SUB1 homolog (S. cerevisiae) (SUB1), mRNA [NM_006713] |
| 684 | A_32_P233304 | LIN9 | AAAGGTTCCGTATTCTTTGTTGGTATTGTGCCACTGCAGAACT TTAGTGCAGAGTTTAT | SEQ ID NO: 1552 | Homo sapiens lin-9 homolog (C. elegans) (LIN9), mRNA [NM_173083] |
| 685 | A_32_P233314 | EXOC8 | AGGATTGGAAGCTTTGGAGCATGAGATGTACTAAAGTCAGTC TATGTACATAGTGCTT | SEQ ID NO: 1553 | Homo sapiens exocyst complex component 8 (EXOC8), mRNA [NM_175876] |
| 686 | A_32_P234738 | RPL21 | GTTGTAAACAAACAAGTTAAGGGCAAGATTCTTGGCAAGAGAAT TAATGTGGTATTGAG | SEQ ID NO: 1554 | Homo sapiens ribosomal protein L21 (RPL21), mRNA [NM_000982] |
| 687 | A_32_P28895 | KIAA1600 | AATTCTTGGTCCCTCCGTGGAGAAACTTCAGATGGTCATTGT GTACCTACTGTCTCTT | SEQ ID NO: 1555 | KIAA1600 (KIAA1600), mRNA [Source:RefSeq_dna;Acc:NM_020940] [ENST00000369248] |
| 688 | A_32_P30710 | RPL23 | ACGAAAGTGATACCGTAGAGAAAGAAGGTGGGGTGTTCCTTAAG AAGATAATGGAGGAG | SEQ ID NO: 1556 | Homo sapiens ribosomal protein L23 (RPL23), mRNA [NM_000978] |
| 689 | A_32_P31182 | RPL7 | GTAGAAGAGAAGAAGTTCCTGGTGTGCCAGAAACCCTTAA GAAAAAGCCAAGGAAT | SEQ ID NO: 1557 | Homo sapiens ribosomal protein L7 (RPL7), mRNA [NM_000971] |

Fig. 3-38

| No. | Probe ID No. | Symbols of genes | Sequence | SEQ ID NO: | Descriptions of genes (letters and numbers within [ ] indicate GenBank accession No.) |
|---|---|---|---|---|---|
| 690 | A_32_P3742 | RFX3 | GGTCTCAAAATTGGGAGGAGGCTAAATAATAGTTTGTGGGGGATT TGTATTGTTGTACTGTA | SEQ ID NO: 1558 | Transcription factor RFX3 [Source:Uniprot/SWISSPROT;Acc:P48380] [ENST00000382004] |
| 691 | A_32_P43217 | PSMA6 | TTGTGTTAGTTTACCAGAATCGGTGATGCCACTTACCTGTGT TTGGTAACAACAAACA | SEQ ID NO: 1559 | Homo sapiens proteasome (prosome, macropain) subunit, alpha type, 6 (PSMA6), mRNA [NM_002791] |
| 692 | A_32_P43932 | LOC643932 | GATTCGAGAGCAGCATTGGAAAAGACATAGAAAAAGGGTTGGCAAT CTATCCTCTCCATGAT | SEQ ID NO: 1560 | PREDICTED: Homo sapiens similar to 40S ribosomal protein S3a (V-fos transformation effector protein) (LOC643932), mRNA [XR_017289] |
| 693 | A_32_P46765 | C12orf29 | TTTAGAATAGGCAGTGATGATCACTAGCTAATTCTGTATATCCATGCC TTTTGTCCTGTTTAG | SEQ ID NO: 1561 | Homo sapiens chromosome 12 open reading frame 29 (C12orf29), mRNA [NM_001009894] |
| 694 | A_32_P49164 | AV714556 | AAATGCAGACTTTGTTATTTGGCAAAAAGATGATGGAAATGATGATTCC TCCTTTCTTTTTCCC | SEQ ID NO: 1562 | AV714556 AV714556 DCB Homo sapiens cDNA clone DCBADG06 5', mRNA sequence [AV714556] |
| 695 | A_32_P49392 | A_32_P49392 | AATTCTGCAAATGTGGAAGAAGAAGATGGAAATGATGACCGAA GAGGTGCAGAAAATG | SEQ ID NO: 1563 | |
| 696 | A_32_P50417 | LOC649314 | AATCAGGGTGAATTTGTAAATGCAACTTCATGCATTCTGCAAAT CAGGAAGAGTCAGTTC | SEQ ID NO: 1564 | Homo sapiens cDNA FLJ35212 fis, clone PROST1000136. [AK092531] |
| 697 | A_32_P54305 | LOC401397 | AGAATCTTAGGAAATCACCACTGTGGTTATAATCAGTCAGTGCTC CTGAATGTTGAGGAG | SEQ ID NO: 1565 | Homo sapiens hypothetical LOC401397, mRNA (cDNA clone IMAGE:4244115), complete cds. [BC107360] |
| 698 | A_32_P58074 | RPS3A | GTTGGTTTTACTAAAAAACGCAAAATCAGATACGGAAGAGCTC TTATGCTCAGCACCAA | SEQ ID NO: 1566 | Homo sapiens ribosomal protein S3A (RPS3A), mRNA [NM_001006] |
| 699 | A_32_P61857 | KIAA1468 | CAGTGTACAGTTCACTGGAATTGACAGTGTGTCTCACAGTC ATGCAACTCGAAGTAG | SEQ ID NO: 1567 | Homo sapiens KIAA1468 (KIAA1468), mRNA [NM_020854] |
| 700 | A_32_P62342 | GLT8D3 | GTGATGTAAGTGATGTAACCATTGAGAATCTATGTGTGGGTTT ATACATTTGATCTCTG | SEQ ID NO: 1568 | Homo sapiens glycosyltransferase 8 domain containing 3, mRNA (cDNA clone MGC:21651 IMAGE:4508300), complete cds. [BC039145] |
| 701 | A_32_P68586 | ARL1 | TTGGTTACCTGCCTTGAAGGACCGAAAATGGGAGATATTCAAA ACGTCAGCAACCAAAG | SEQ ID NO: 1569 | Homo sapiens ADP-ribosylation factor-like 1 (ARL1), mRNA [NM_001177] |
| 702 | A_32_P71118 | PSMC6 | AGGAGACCTGAGAAATGTTTGTACTGAAGGCAGGTATGTGTGGAA TTCGTGGTGATCATGA | SEQ ID NO: 1570 | Homo sapiens proteasome (prosome, macropain) 26S subunit, ATPase, 6 (PSMC6), mRNA [NM_002806] |
| 703 | A_32_P77571 | AK024584 | GTCATCCTCTTAATGAAGCATTATGGAGCTGTTAAAGATGATAC AGTAAAGGTTATGAG | SEQ ID NO: 1571 | Homo sapiens cDNA: FLJ20931 fis, clone ADSE01282. [AK024584] |
| 704 | A_32_P81768 | TMEM167 | CCTCAGTACTGTCAGTAGAATTACATTCTGGAAATGTTATTC TGTTGTATCAGATACG | SEQ ID NO: 1572 | Homo sapiens transmembrane protein 167 (TMEM167), mRNA [NM_174909] |
| 705 | A_32_P83784 | CENTD1 | ACAGGGGATACTTCAGTCAGTCAATGATCAGATACAGATGTG GTGGTAGATGTATGA | SEQ ID NO: 1573 | Homo sapiens centaurin, delta 1 (CENTD1), transcript variant 1, mRNA [NM_015230] |
| 706 | A_32_P86400 | LYSMD3 | AAATGTTGCTCAGGTAATCAGTATATTTCTTCCACGTATGTGCAT ATTGCACTGTTAGATC | SEQ ID NO: 1574 | Homo sapiens LysM, putative peptidoglycan-binding, domain containing 3 (LYSMD3), mRNA [NM_198273] |
| 707 | A_32_P88494 | A_32_P88494 | TGAGGCTTGCGTGCCACATTGAGATGATGCGTTAGTGAAAGGAA CAGATTGTTCCTAAAC | SEQ ID NO: 1575 | |
| 708 | A_32_P8857 | A_32_P8857 | AATGTCGGAATGGTACACACTGTTGTGTAAAGTAGAGATGTTT CAGAATAGTTCGTGGCT | SEQ ID NO: 1576 | |

Fig. 3-39

| No. | Probe ID No. | Symbols of genes | Sequence | SEQ ID NO: | Descriptions of genes (letters and numbers within [ ] indicates GenBank accession No.) |
|---|---|---|---|---|---|
| 709 | A_32_P88679 | THC2643265 | TTATAGGTCAGAAAAATGAGGTCCAGACTAATTTTGCCTCTTCCACAGGGAGATAGATTC | SEQ ID NO: 1577 | ALU1_HUMAN (P39188) Alu subfamily J sequence contamination warning entry, partial (5%) [THC2643265] |
| 710 | A_32_P93782 | RPL26 | AGGTTGTACATGGACAGTACTAAAGGTCAGGAAATTGGCAAAGTAGTCCAGGTTTACAGGA | SEQ ID NO: 1578 | Homo sapiens ribosomal protein L26 (RPL26), mRNA [NM_000987] |
| 711 | A_32_P9382 | RP11-11C5.2 | AAGAAAGCAGCAGTAATATATTCAGGAAGGGATGGTGTTTACAGAGGAGTTGTTTAAAGTGT | SEQ ID NO: 1579 | Homo sapiens similar to RIKEN cDNA 2410129H14 (LOC440145), mRNA [NM_001071775] |
| 712 | A_32_P96213 | TPT1 | GAAAGCACAGTAATCACTGCTCTCAGATGTTGTCATGAACCATCACCTGCAGGAAACAAGT | SEQ ID NO: 1580 | Homo sapiens tumor protein, translationally-controlled 1 (TPT1), mRNA [NM_003295] |
| 713 | A_32_P98313 | NDUFA4 | AGCCGTGGAACAAGTGGGTGCCAATGATCAATACAAGTTGTGCTCAGTGAATGTGGATT | SEQ ID NO: 1581 | Homo sapiens NADH dehydrogenase (ubiquinone) 1 alpha subcomplex, 4, 9kDa (NDUFA4), nuclear gene encoding mitochondrial protein, mRNA [NM_002489] |

Fig. 4-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_32_P184330 | AK130741 | TGTGACCGTTTGTGACGAGTTATCTCAGTCGTCACATGAGTTGCTTACATGAGTCGGTCTA | SEQ ID NO: 923 | Homo sapiens cDNA FLJ27231 fis, clone SYN06240. [AK130741] |
| 2 | A_32_P209582 | THC2663167 | CAATGTAAAGGCCAGAATCAACGTCCTTTTGTCAAGATTTTCAAACCTATTTGGGTGAT | SEQ ID NO: 927 | ALU1_HUMAN (P39188) Alu subfamily J sequence contamination warning entry, partial (5%) [THC2663167] |
| 3 | A_32_P213509 | THC2663555 | GATTTGTTCGAGTGTTGGAGCCGTTTTTAATGAAAATTCTGAACACCTACACTGGAAAAA | SEQ ID NO: 929 | |
| 4 | A_32_P227110 | THC2512148 | TAAAACAAATCGTTTTGATTCAGCCACTGTGTATTGATAATGGCTTATTTATTACAATCA | SEQ ID NO: 932 | |
| 5 | A_32_P71171 | A_32_P71171 | TCTAGATAGTAATAGGAAAACCAAGAATCCAGCCTGGTGATGGGTGGAGGGAGTGGATTGAA | SEQ ID NO: 946 | |
| 6 | A_32_P98940 | THC2745859 | AAGAGTATTCCAAGATAAGAAAAAGGTGTGTTGTTTTAGGAGGTGTATTTCAGGTAGTTA | SEQ ID NO: 952 | |
| 7 | A_23_P128930 | PSMC6 | GAACAAGCAAGATTAGACATACTGAAAATCGATGCAGGTGCCATTACAAAGCATGGTGAA | SEQ ID NO: 986 | Homo sapiens proteasome (prosome, macropain) 26S subunit, ATPase, 6 (PSMC6), mRNA [NM_002806] |
| 8 | A_23_P143958 | RPL22L1 | ATTGGCTTCAGTGCTTGCATCTGAGAAGGAGACCTACGAAGCTCGTTACTTCCAGATTA | SEQ ID NO: 998 | Homo sapiens ribosomal protein L22-like 1, mRNA (cDNA clone IMAGE:4865906) [BC049823] |
| 9 | A_23_P144497 | RPS3A | CCAAATCGGAAGAAGATGATGGAAATCATGACCGAGAGGTTGCAGAGAATGACTTGAA | SEQ ID NO: 1000 | Homo sapiens ribosomal protein S3A (RPS3A), mRNA [NM_001006] |
| 10 | A_23_P14708 | SUHW4 | TCTTTGTACCTCCATACAAGTGTTAGCCTGCCTGGCCAGGCTGTAAGGTACCTTAATTAAAGTT | SEQ ID NO: 1006 | Homo sapiens suppressor of hairy wing homolog 4 (Drosophila) (SUHW4), transcript variant 1, mRNA [NM_017661] |
| 11 | A_23_P14734 | RPS27L | TACAAGATGACCAGGGTTTCAGGCATGCTCAGACAGTGGTTGTTTGTGTAGGTTGTTCA | SEQ ID NO: 1007 | Homo sapiens ribosomal protein S27-like (RPS27L), mRNA [NM_015920] |
| 12 | A_23_P152002 | BCL2A1 | ATAAGCCATATTTGCATTTTGAAGGTATTCTCATCAAGAAACTTCTACGAACAGCAAATGGC | SEQ ID NO: 1013 | Homo sapiens BCL2-related protein A1 (BCL2A1), mRNA [NM_004049] |
| 13 | A_23_P156842 | EEF1E1 | AAGAAAAGACATGGTTCAGGAGGTTAGAATACAGAGGTCAGTCAAGTAGAATGGGCACT | SEQ ID NO: 1019 | Homo sapiens eukaryotic translation elongation factor 1 epsilon 1 (EEF1E1), mRNA [NM_004280] |
| 14 | A_23_P157449 | POLR2K | GGTCTCTCTTGGTTCAAAATATGTCTTGTACAGTACTCAGGATTTAGATGTGGTTGAC | SEQ ID NO: 1020 | Homo sapiens polymerase (RNA) II (DNA directed) polypeptide K, 7.0kDa (POLR2K), mRNA [NM_005034] |
| 15 | A_23_P159650 | COX7B | CAAATACGGTAATGCTGTATTAGGTAGTGGAGCCACTTTCTGTATTGTTACGATGGACATA | SEQ ID NO: 1022 | Homo sapiens cytochrome c oxidase subunit VIIb (COX7B), nuclear gene encoding mitochondrial protein, mRNA [NM_001866] |
| 16 | A_23_P162596 | ACTR6 | TTAACGGCTTCACTGGACAGTTTCCTTAGAAGGTAGTTTGTGTGACTGTGACTAAAGT | SEQ ID NO: 1027 | Homo sapiens ARP6 actin-related protein 6 homolog (yeast) (ACTR6), mRNA [NM_022496] |
| 17 | A_23_P18325 | PDCD10 | CCAATCGAGTAATTCATCAAACCAACTTAATACTTCAGAGCCTTCAAAACTGTGGGTGAA | SEQ ID NO: 1039 | Homo sapiens programmed cell death 10 (PDCD10), transcript variant 1, mRNA [NM_007217] |
| 18 | A_23_P200955 | A_23_P200955 | AGAGACATGATTGAACCTCACATTGAATGTCAAGAGTACCATGGTTATTGTTCATCTAC | SEQ ID NO: 1046 | |

Fig. 4-2

| No. | Probe ID No. | Symbols of genes | Sequence | SEQ ID NO: | Descriptions of genes (letters and numbers within [ ] indicates GenBank accession No.) |
|---|---|---|---|---|---|
| 19 | A_23_P215751 | NDUFA5 | TAAAAGTGGAGTCACTACTAAAATAGTTTGCAGTACGTTTGTAATATAAGTGTAGGTGGTATC | SEQ ID NO: 1075 | Homo sapiens NADH dehydrogenase (ubiquinone) 1 alpha subcomplex, 5, 13kDa (NDUFA5), nuclear gene encoding mitochondrial protein, mRNA [NM_005000] |
| 20 | A_23_P252201 | EAF2 | CAGGATTCCTGATATAGAGATGCCAGTGCATAATAGATTCGGAGACAACAGTGGCTTCTGAT | SEQ ID NO: 1090 | Homo sapiens ELL associated factor 2 (EAF2), mRNA [NM_018456] |
| 21 | A_23_P26021 | COPS2 | TGCTTTTTGATCAACTGGTTTGTGTTTTGGTGCTGCATTTATCCCAAGAAAAACAGCTT | SEQ ID NO: 1107 | Homo sapiens COP9 constitutive photomorphogenic homolog subunit 2 (Arabidopsis) (COPS2), mRNA [NM_004236] |
| 22 | A_23_P2705 | P2RY5 | TCTGTATTGTCTGTTTGTTGGAACGTGTTTGTTTGTTGAGCGTATAAGTTTACTACTTTACATCGGACA | SEQ ID NO: 1108 | Homo sapiens purinergic receptor P2Y, G-protein coupled, 5 (P2RY5), mRNA [NM_005767] |
| 23 | A_23_P307940 | CAPZA2 | CTACAAGATTGGGAAAGAAGAGAATGCAGATAAAGAATGAACATTGCATGACCGGATCATT | SEQ ID NO: 1117 | Homo sapiens capping protein (actin filament) muscle Z-line, alpha 2 (CAPZA2), mRNA [NM_006136] |
| 24 | A_23_P312246 | CCDC82 | GGCTTATAACAGATGACTGTCAAGTGAATGAGCTGTGATATCCTGTCAGTTTAGTCAA | SEQ ID NO: 1121 | Homo sapiens coiled-coil domain containing 82 (CCDC82), mRNA [NM_024725] |
| 25 | A_23_P33045 | RPL26 | TACAAAGGTCAGGACAAATTGGCAAAGAGTCCAGGTTACAGGAAGAAATATGTTATCTAC | SEQ ID NO: 1132 | Homo sapiens ribosomal protein L26 (RPL26), mRNA [NM_000987] |
| 26 | A_23_P339480 | HAT1 | AACATGAACAGCTGGAAGAGAGTTTCAGGAAGAAGTAGTAGTCAGGAAGATTACCGGCGTGTTATTC | SEQ ID NO: 1134 | Homo sapiens histone acetyltransferase 1 (HAT1), transcript variant 1, mRNA [NM_003642] |
| 27 | A_23_P38275 | THC2504576 | TCTCGCCAAAATGCAAAATGAAGTTTAATCCCTTTGTGACTTCCGACCGAAGCAAGAATCGCAAAAG | SEQ ID NO: 1154 | RL26_BOVIN (P61257) 60S ribosomal protein L26, complete [THC2504576] |
| 28 | A_23_P405873 | C9orf72 | GAGAATGCAAGATCAGGGTCAGATAATCCAATGCTGGAGAAGTGATTCCTGT | SEQ ID NO: 1162 | Homo sapiens chromosome 9 open reading frame 72 (C9orf72), transcript variant 2, mRNA [NM_145005] |
| 29 | A_23_P44257 | COMMD8 | AACATTTTACTTCTGCGGTCTATATGTTGTTTGGGAAACATTGGTCTCATAAAAAATAGCTGTC | SEQ ID NO: 1179 | Homo sapiens COMM domain containing 8 (COMMD8), mRNA [NM_017845] |
| 30 | A_23_P46396 | PTBP2 | AAGCAGGGTGGGACCAAGTTTAGTCTTAATTAGCTTGGCATTGTAATATT | SEQ ID NO: 1183 | Homo sapiens polypyrimidine tract binding protein 2 (PTBP2), mRNA [NM_021190] |
| 31 | A_23_P50907 | ITGAV | AAAGAGTGATTAAGTGAGGTTATTACCCCTAAAATGGTCCATTCTGCATTGTATTTCAGG | SEQ ID NO: 1191 | Homo sapiens integrin, alpha V (vitronectin receptor, alpha polypeptide, antigen CD51) (ITGAV), mRNA [NM_002210] |
| 32 | A_23_P59921 | SUB1 | CAGATTGGGAAAATGAGGTAGTGTTGGGGATTTTAAAGGCAAAGTGCTAATTGAT | SEQ ID NO: 1205 | Homo sapiens SUB1 homolog (S. cerevisiae) (SUB1), mRNA [NM_006713] |
| 33 | A_23_P61674 | CLK4 | GAAAGGCATGGCAGTTTGTCCATTGTGACAGTTGTTTAATAAAAGCACATACACACTTTA | SEQ ID NO: 1207 | Homo sapiens CDC-like kinase 4 (CLK4), mRNA [NM_020666] |
| 34 | A_23_P63343 | UTS2 | AGATCTGGGAAAGGATACACAAGAAAAGTGAGAGTCCTGATTGCTTCTGGAAATAGCTGTGTC | SEQ ID NO: 1211 | Homo sapiens urotensin 2 (UTS2), transcript variant 1, mRNA [NM_021995] |
| 35 | A_23_P65768 | C15orf15 | TGTGCATTGCCATCAGATATATAACGATATTACGGAGATGTTAGAATTGCATCTGCAGTGTT | SEQ ID NO: 1216 | Homo sapiens chromosome 15 open reading frame 15 (C15orf15), mRNA [NM_016304] |
| 36 | A_23_P66260 | ZNF267 | TGTGATGAATGTGGTAAAAGCCTTCAGCTATAGGTCATAGGTCACTACAGATCGGAGAAGT | SEQ ID NO: 1217 | Homo sapiens zinc finger protein 267 (ZNF267), transcript variant 498723, mRNA [NM_003414] |
| 37 | A_23_P70328 | CENPQ | CAATGGCTTAGAGTTCTGTGTGGTCATCTGGAAGTTGAAAAATCGTCAAATGGCTTCAC | SEQ ID NO: 1224 | Homo sapiens centromere protein Q (CENPQ), mRNA [NM_018132] |

Fig. 4-3

| No. | Probe ID No. | Symbols of genes | Sequence | SEQ ID NO: | Descriptions of genes (letters and numbers within [ ] indicates GenBank accession No.) |
|---|---|---|---|---|---|
| 38 | A_23_P76480 | BF213738 | AAATCGAACAGGACAATGGGTAGATGGAGCTACATTTACCAAATCGTTTGGCATGAGAGG | SEQ ID NO: 1239 | BF213738 601847628F1 NIH_MGC_55 Homo sapiens cDNA clone IMAGE:4078519 5. mRNA sequence [BF213738] |
| 39 | A_23_P78092 | EVI2A | GCTGAATCAGACACAGTTGGAAAAGAACAAAAACAGGTCACAGGACCCAACCTAGTGATGGAA | SEQ ID NO: 1244 | Homo sapiens ecotropic viral integration site 2A (EVI2A), transcript variant 1, mRNA [NM_001003927] |
| 40 | A_23_P83278 | CHMP5 | CATTGCTGTCTTTATTTTTCGATTAAGAGACTCATTGCTTGGGAAATGCTTCTTCGTAC | SEQ ID NO: 1251 | Homo sapiens chromatin modifying protein 5 (CHMP5), mRNA [NM_016410] |
| 41 | A_23_P97769 | C12orf48 | GTAAGAAATATCGTGAGTCCTAATGCATATGTAATATGTGAGTGTTGCATATACTTCTGTTT | SEQ ID NO: 1254 | Homo sapiens chromosome 12 open reading frame 48 (C12orf48), mRNA [NM_017915] |
| 42 | A_23_P87879 | CD69 | TGTGCAATATGTGATGTGGCAAATCTCTATTAGGAAAATATCTGTAATCTTCAGACCTAG | SEQ ID NO: 1255 | Homo sapiens CD69 molecule (CD69), mRNA [NM_001781] |
| 43 | A_23_P11045 | THC2785765 | CCACGAGAAACGTACAGCGTGATTTTCATGACAAATAGGGTAGCAACACAAGTCGGAATAG | SEQ ID NO: 1263 | COX7B_HUMAN (P24311) Cytochrome c oxidase polypeptide VIIb, mitochondrial precursor, partial (78%) [THC2785765] |
| 44 | A_24_P115774 | BIRC2 | GATACCATTTGGTTAAAGGAAATGCTGCGGGCAACATGTTCAAAACTGTCTAAAAGAA | SEQ ID NO: 1265 | Homo sapiens baculoviral IAP repeat-containing 2 (BIRC2), mRNA [NM_001166] |
| 45 | A_24_P144666 | LOC401975 | TGTCGATGTCAAGACTAATGATGGCTACTCTCTTTAATCTGTTCTGTGTTTTACTGA | SEQ ID NO: 1301 | PREDICTED: Homo sapiens similar to ribosomal protein S3a (LOC401975), mRNA [XR_017247] |
| 46 | A_24_P153324 | LOC390413 | GAAGCTTAACAAGGTTTGCAATTAACATGCTGGGATTGTAGAACCATATATTGCAGGGTA | SEQ ID NO: 1304 | PREDICTED: Homo sapiens similar to 60S ribosomal protein L7 (LOC390413), mRNA [XR_018341] |
| 47 | A_24_P175187 | SAMD9 | CAACCAGGGATACGTAATGAATCAAAATGTAATTTCCCTAATAAATTATGGATATGGAGG | SEQ ID NO: 1316 | Homo sapiens sterile alpha motif domain containing 9 (SAMD9), mRNA [NM_017654] |
| 48 | A_24_P175186 | SAMD9 | TGCCAATGTACTGCCAGATTAACATACAACCTATGTTTTGAACAAAACAACCAGGATA | SEQ ID NO: 1317 | Homo sapiens sterile alpha motif domain containing 9 (SAMD9), mRNA [NM_017654] |
| 49 | A_24_P201702 | CLEC2B | ATTGGAATTCAAGTAACACACTGTTCCACTCAACATGCGCAGCCTAACTATAATTGACA | SEQ ID NO: 1327 | Homo sapiens C-type lectin domain family 2, member B (CLEC2B), mRNA [NM_005127] |
| 50 | A_24_P203909 | RPL34 | GAGGGGTTCGTGCTGTAAGAGTTAAAGTTCTTATGAAATGTCCAAACAAAGATG | SEQ ID NO: 1328 | Homo sapiens ribosomal protein L34 (RPL34), transcript variant 2, mRNA [NM_033625] |
| 51 | A_24_P212864 | LOC646161 | ACAGAAGTACAAGTGGATCCATGATCCGAAAGAAATGATGAAGTTAGGCTTGTAGCGAGG | SEQ ID NO: 1331 | PREDICTED: Homo sapiens similar to 60S ribosomal protein L26 (LOC646161), mRNA [XR_019048] |
| 52 | A_24_P221375 | A_24_P221375 | TACTTTGGTTAGCCATGGTGTACCACTTGTCAAAATCTACAGAGAGTCAATGGGTA | SEQ ID NO: 1332 | |
| 53 | A_24_P243749 | PDK4 | ATTTGACATTTGTGTGTAATTTTCATGGTGGGCTAGTGTTGTGGTGGTTCTGTAATGGTA | SEQ ID NO: 1345 | Homo sapiens pyruvate dehydrogenase kinase, isozyme 4 (PDK4), mRNA [NM_002612] |
| 54 | A_24_P266054 | ZFYVE16 | GTGTATGTATTCGTGCCATGTAAGTAATTGAAGAGTCTTAAAATAACCAAATGGTAGAGGG | SEQ ID NO: 1359 | Zinc finger FYVE domain-containing protein 16 (Endofin) (Endosome-associated FYVE domain protein). [Source:Uniprot/SWISSPROT;Acc:Q7Z3T8] [ENST00000380248] |
| 55 | A_24_P298604 | LOC731599 | GATGCAAATCATGACCAGAGGGTGCGGCAACAAATGACTTGAAAGAATTGGTCAATAAAATGAT | SEQ ID NO: 1365 | PREDICTED: Homo sapiens hypothetical protein LOC731599 (LOC731599), mRNA [XR_015536] |
| 56 | A_24_P306527 | ENST00000308989 | ACCGGATCGCGTGGTTATCCAGAGAAAATGTAATGAGGATGAAGATTCACCAAATAAGT | SEQ ID NO: 1366 | PREDICTED: Homo sapiens similar to ribosomal protein L31 (LOC729005), mRNA [XM_001134428] |

Fig. 4-4

| No. | Probe ID No. | Symbols of genes | Sequence | SEQ ID NO: | Descriptors of genes (letters and numbers within [ ] indicates GenBank accession No.) |
|---|---|---|---|---|---|
| 57 | A_24_P316074 | LOC730902 | TATCAATGGTGTGAGCCCAAAGGTGAAAGGTGTTGCAGGCTCTTGCCTTCGTCAAATCTT | SEQ ID NO: 1372 | PREDICTED: Homo sapiens similar to 60S ribosomal protein L7 (LOC730902), mRNA [XR_015600] |
| 58 | A_24_P320328 | SUB1 | CAGAAAAACCTGTAAAGAAACAAAGACGAGGTGAGACTTGAGAAGCCCTGTCATCTCTA | SEQ ID NO: 1373 | Homo sapiens SUB1 homolog (S. cerevisiae) (SUB1), mRNA [NM_006713] |
| 59 | A_24_P324224 | A_24_P324224 | AAAGCTGTCTGTGGGGCAAAGGAATAAGGAGGCATTCCTATAGGCATGTGCGGTTGTCCAGAAAA | SEQ ID NO: 1375 | |
| 60 | A_24_P33213 | A_24_P33213 | GAGCATATATTACATGGAGGGTACCCAAATCTGAAGTCAGTAAATGAACTTATCTACAAGG | SEQ ID NO: 1379 | |
| 61 | A_24_P333112 | A_24_P333112 | GGTCATCAGAATCAGAGGTATCAATGTGTGAGCCCAGAGGACCAAAAGGTATTGGAAGTT | SEQ ID NO: 1380 | |
| 62 | A_24_P33607 | LOC652558 | TAAGAAAATAATTGCTTTGACAGAGACAACGCTTTGATTGCTGGATCTCTTGGTAAATATGG | SEQ ID NO: 1382 | PREDICTED: Homo sapiens similar to 60S ribosomal protein L7 (LOC652558), mRNA [XR_019386] |
| 63 | A_24_P349636 | LOC388401 | AGTTGCTTCGACAGATAACACAGTTTGATTGTGTCGATCTGTTGGTAAATATAGCATGAAGTG | SEQ ID NO: 1383 | PREDICTED: Homo sapiens similar to 60S ribosomal protein L7 (LOC388401), mRNA [XR_016879] |
| 64 | A_24_P366165 | LOC391126 | ACTTCCAAGCAAATCAAAAATCAAAAGGCATTCAATGCACCTTCCAGATTCACAGG | SEQ ID NO: 1393 | PREDICTED: Homo sapiens similar to 60S ribosomal protein L26 (Silica-induced gene 20 protein) (SIG-20) (LOC391126), mRNA [XR_019504] |
| 65 | A_24_P366546 | RPL31P10 | CGGCTGTCCAGAAAAGTCAATGAGGATGAAGATTCAAATAAGGTCTATACTTTGGTTACC | SEQ ID NO: 1394 | PREDICTED: Homo sapiens similar to ribosomal protein L31 (LOC390283), mRNA [XR_018695] |
| 66 | A_24_P367191 | LOC652890 | AGTTAAGATGCTGAGGACTGTAGAGCCATATATTGTGTGGGTACCCAAATGTGAAGTG | SEQ ID NO: 1396 | PREDICTED: Homo sapiens similar to 60S ribosomal protein L7 (LOC652890), mRNA [XR_019144] |
| 67 | A_24_P367199 | A_24_P367199 | TCTTATGCTCAGCCACCCAACAGTCCTGCCAAATCAGAAGAAGAAGGTGTAATCATGACTGAGA | SEQ ID NO: 1397 | |
| 68 | A_24_P38.1625 | PSMC6 | ATGAAAGCAGTCAGAAAACGTCAGAATTGCATTGTAAGAAGGCTGGAGTCTAAATTGACTACAA | SEQ ID NO: 1404 | Homo sapiens proteasome (prosome, macropain) 26S subunit, ATPase, 6 (PSMC6), mRNA [NM_002806] |
| 69 | A_24_P383399 | RPS3A | TGGTTTTACTAAAAAACGGCAACAATCAGATACAGAAGAAGAGCTGTTATGCCCAGCACCAACG | SEQ ID NO: 1405 | Homo sapiens ribosomal protein S3A (RPS3A), mRNA [NM_001006] |
| 70 | A_24_P384411 | A_24_P384411 | ATGGCAAAATCAATAAGAGTGAAGCTTTGAGAGTAATGCTTTGACAGCTGATCTCTTG | SEQ ID NO: 1406 | |
| 71 | A_24_P384539 | LOC730452 | CAAGAAAAGGTGGCAACTTCTATGTACCCACAAACCCAAATTGGCATTGTCATCAGGA | SEQ ID NO: 1407 | PREDICTED: Homo sapiens similar to 60S ribosomal protein L7 (LOC730452), mRNA [XM_001125895] |
| 72 | A_24_P414556 | TTC33 | TACTCAACATTTGGTATCTGTATATTTTGAGTAATGGATGTTGTTTTTGTGTAATTTGTGA | SEQ ID NO: 1421 | Homo sapiens tetratricopeptide repeat domain 33 (TTC33), mRNA [NM_012382] |
| 73 | A_24_P41551 | LOC641790 | AAGGAGATGGAACCTGTGATGTGCGGCATTGATATGAGGCACAACAAGTAGTCTCAGGAA | SEQ ID NO: 1423 | PREDICTED: Homo sapiens similar to ribosomal protein L31 (LOC641790), mRNA [XR_018025] |
| 74 | A_24_P418712 | A_24_P418712 | AAGGCTCAAGAAAGGCTGTCTGTGGGGCAAAGAAAATAAGGAATATGGATACCATATCTGTGTTA | SEQ ID NO: 1426 | |
| 75 | A_24_P50437 | BC065737 | TGCAGAATGATGAAGTTGCATTTAGAAAATTGCTGATTACTGAAGAATGTTCAGGGCAAAA | SEQ ID NO: 1430 | Homo sapiens cDNA clone IMAGE:30404477, partial cds. [BC065737] |
| 76 | A_24_P57837 | THC2567891 | AGAAATCCGGAAGACCTCTTATGCTCAGTCAGTACCAGCCAAATCCGGAAGAAGATGAGGAAA | SEQ ID NO: 1440 | Q6NXR8_HUMAN (Q6NXR8) Ribosomal protein S3a, partial (91%) [THC2567891] |

Fig. 4-5

| No. | Probe ID No. | Symbols of genes | Sequence | SEQ ID NO: | Descriptions of genes (letters and numbers within [ ] indicates GenBank accession No.) |
|---|---|---|---|---|---|
| 77 | A_24_P587938 |  | CTTCAAAGAAGCAAAAGGTGGAAGATGGTGGCAACAGGGAGGACCAGATTAACAGTCTTAT | SEQ ID NO: 1441 |  |
| 78 | A_24_P606663 | LOC392030 | TGTGCGGTTGCCGAGAAAACGTAATGCGGGTGAAGATTCACGAAATAAGCTCGATACTTT | SEQ ID NO: 1442 | PREDICTED: Homo sapiens hypothetical LOC392030 (LOC392030), mRNA [XR_018063] |
| 79 | A_24_P685729 |  | TTGAAGGTTATGTGTGAGTCGAAGACTATCAGTGATTATTTGTTTGTCTGTTTTGTGTGG | SEQ ID NO: 1448 |  |
| 80 | A_24_P6975 | LOC342994 | GGAAGACTTCGAGGGGGTTCGTGGTGTAAGAACCTAAAGTTCTTATGAAATTGTCAAAAGA | SEQ ID NO: 1450 | PREDICTED: Homo sapiens similar to ribosomal protein L34 (LOC342994), mRNA [XM_938484] |
| 81 | A_24_P75158 | PTAR1 | CCATTAGATTTGTTCTTTATGTGACCATGTGACCAAGCCAGCTATAAAGTATGTATTTCTG | SEQ ID NO: 1454 | Homo sapiens mRNA; cDNA DKFZp313P0917 (from clone DKFZp313P0917). [AL832683] |
| 82 | A_24_P755505 |  | ATACAGAGAACCTCTTATGCTCAGCACCAACAAGAGAAAGTAAAAATGCTGAAGAAGCCCAA | SEQ ID NO: 1455 |  |
| 83 | A_24_P76358 | LOC643981 | TTACTGAAGATGTTCAGGGCAAAAACTGCCTAACTTCCGGCATGGATCTTATTCGTGACA | SEQ ID NO: 1456 | PREDICTED: Homo sapiens similar to 40S ribosomal protein S3a (V-fos transformation effector protein) (LOC643981), mRNA [XR_018444] |
| 84 | A_24_P792734 | PSMC6 | AGAAGCTTAACGGAGTTACTGAATGAACATGAAATGGATTTGATTTGATACTCTGCATAGAGTAAA | SEQ ID NO: 1459 | Homo sapiens proteasome (prosome, macropain) 26S subunit, ATPase, 6 (PSMC6), mRNA [NM_002806] |
| 85 | A_24_P84808 | LOC729449 | GAATTGCTTGACAGATAACGGCTTGGGATCTCTTGGAAATCAATTTGGCATCATCTGTATGG | SEQ ID NO: 1466 | PREDICTED: Homo sapiens similar to 60S ribosomal protein L7 (LOC729449), mRNA [XR_015549] |
| 86 | A_24_P850187 |  | TAAATGAACTAATCTACAAGCGTGCTTATGGCAAAATCAATTTGACTTGCACTTCGTAC | SEQ ID NO: 1467 |  |
| 87 | A_32_P113154 | LOC730861 | ACCACAGCAGTCGAAGAATCTGTTTAAAGTTCAGACTTAAAAACAGTACCAAATAAAAGTCC | SEQ ID NO: 1491 | PREDICTED: Homo sapiens similar to 40S ribosomal protein S3a (V-fos transformation effector protein) (LOC730861), mRNA [XR_015591] |
| 88 | A_32_P11931 | LOC441073 | GTGTGATCCATGCCATCCGAAAGGATGATGAAGTTCAGGTTGTAGGTGGAGACTATAAA | SEQ ID NO: 1497 | PREDICTED: Homo sapiens similar to 60S ribosomal protein L26 (Silica-induced gene 20 protein) (SIG-20) (LOC441073), mRNA [XR_016376] |
| 89 | A_32_P125549 | RPL31P4 | TCTACAGACAGTCAATGTGGATGAGAACTAATCCCTGATCGTCAGATACATCAAATAAAG | SEQ ID NO: 1500 | PREDICTED: Homo sapiens ribosomal protein L31 pseudogene 4 (RPL31P4), mRNA [XR_018222] |
| 90 | A_32_P128781 |  | CATATATTGCATGGGGGGTACCCCAATCTGAAGTCAGTCAGTAAATGAACTAATCTACAAGAGTG | SEQ ID NO: 1502 |  |
| 91 | A_32_P135818 | RPS3A | CTTGTTCATGTGTTGTTGTGTGTTGGTTTTTAATAAAAAGGCAAGAATCAGATATGGAAGAC | SEQ ID NO: 1504 | Homo sapiens ribosomal protein S3A (RPS3A), mRNA [NM_001006] |
| 92 | A_32_P146153 | RPL3 | ATCCGTGTGCAGCTGTCGAGAAAACGTAATGAGGATGAAGATTCACCAAATAAGCCATAT | SEQ ID NO: 1508 | Homo sapiens ribosomal protein L31 (RPL31), mRNA [NM_000993] |
| 93 | A_32_P153725 | KIAA1033 | TTTTGTAAAAGATGGCAAGTTTGTTACCTGCACTCAGTGAGTGGGGTTTCCTTTCCCCAAT | SEQ ID NO: 1513 | Homo sapiens KIAA1033 (KIAA1033), mRNA [NM_015275] |
| 94 | A_32_P155364 | RPL7 | TCAACAGGGTTTATTAGAAAATGAACCAAGGTGTCTACCATGGATTATTTCTAAGCTGG | SEQ ID NO: 1514 | Homo sapiens ribosomal protein L7 (RPL7), mRNA [NM_000971] |
| 95 | A_32_P164203 | THC2683448 | TTGATGGTCATTGTGACGAGCTATTGTATGGATTACTGTGGAGTGCTGTTTACCACATGAT | SEQ ID NO: 1519 | Q7WZG3_PASP1 (Q7WZG3) Ferric uptake regulator, partial (8%) [THC2683448] |

Fig. 4-6

| No. | Probe ID No. | Symbols of genes | Sequence | SEQ ID NO: | Descriptions of genes (letters and numbers within [ ] indicates GenBank accession No.) |
|---|---|---|---|---|---|
| 96 | A_32_P190488 | hCG_26523 | CCCAGCAAGGTGGTTATCACTAGGCTAAAACTGGACAAAGACCGCAAAAAGATCCTTGAA | SEQ ID NO: 1531 | PREDICTED: Homo sapiens similar to 60S ribosomal protein L26 (LOC646161), mRNA [XR_018048] |
| 97 | A_32_P196483 | RPS3A | GGGGCCAAGGAAGAAAGTGGTTGATCCATTTTCTAAGGATGATTGGTATGATGTGAAAGCA | SEQ ID NO: 1534 | Homo sapiens ribosomal protein S3A (RPS3A), mRNA [NM_001006] |
| 98 | A_32_P208178 | RPS3A | GGAAAAGACGTAGAAAAGGGCTTGGGAATGGTTATTTATCCTCTCCATGATGTCTTCGTTAGA | SEQ ID NO: 1544 | Homo sapiens ribosomal protein S3A (RPS3A), mRNA [NM_001006] |
| 99 | A_32_P220127 | RPL34 | CAAAACTAGGCTGTCCTGAACCCCTGGTAATAGAATTGTTCACCTTTATAGCAAGAAGGT | SEQ ID NO: 1546 | Homo sapiens ribosomal protein L34 (RPL34), transcript variant 2, mRNA [NM_033625] |
| 100 | A_32_P22539 | hCG_26523 | ACTACGAAGGTCAGCAATTGGCAAAGTGGTCCAGGTTTACAGGAAGAAATATGTTATCT | SEQ ID NO: 1549 | PREDICTED: Homo sapiens similar to 60S ribosomal protein L26 (Silica-induced gene 20 protein) (SIG-20) (LOC400055), mRNA [XM_374987] |
| 101 | A_32_P2333 | SUB1 | AGGAAGAAAAGGTATTCTGTTAAATCCAGAACAATGGAGGCAGGTGACAGAACAGATTTC | SEQ ID NO: 1551 | Homo sapiens SUB1 homolog (S. cerevisiae) (SUB1), mRNA [NM_006713] |
| 102 | A_32_P4532 | LOC643932 | GATTCCAGACAGGATTGGAAAAGACATAAGAAAAGGCTTGCCAATCTATCCTCTCCATGAT | SEQ ID NO: 1560 | PREDICTED: Homo sapiens similar to 40S ribosomal protein S3a (V-fos transformation effector protein) (LOC643932), mRNA [XR_017789] |
| 103 | A_32_P49392 | A_32_P49392 | AATTGTTGCCAAATCTGGAAGAAGAAGTGATGGAAATCATGACGAAGAGGTGCAGACAAATG | SEQ ID NO: 1563 | |
| 104 | A_32_P58974 | RPS3A | GTTGGTTTTACTAAAAAACGCAAAAATGAGATACGGAAGAGACCTCTTATGCTCAGCACGAA | SEQ ID NO: 1566 | Homo sapiens ribosomal protein S3A (RPS3A), mRNA [NM_001006] |
| 105 | A_32_P7118 | PSMC6 | AGGAGACGTGAGAAATGTTGTAGTGAAGCAGGATATGTTCGGAATTCGTGCTGATCATGA | SEQ ID NO: 1570 | Homo sapiens proteasome (prosome, macropain) 26S subunit, ATPase, 6 (PSMC6), mRNA [NM_002806] |
| 106 | A_32_P77571 | AK024584 | GTCATCCTCGTTAATGAAGCATTATGCAGGGTGTTAAAGATGATAGATGTAAAGGTTATGAG | SEQ ID NO: 1571 | Homo sapiens cDNA: FLJ20931 fis, clone ADSE01282. [AK024584] |
| 107 | A_32_P93782 | RPL26 | AGGTTGTACATGGACACTATAAAGGTCAGCAAATTGGCAAAGTAGTCCAGGTTTACAGGA | SEQ ID NO: 1578 | Homo sapiens ribosomal protein L26 (RPL26), mRNA [NM_000987] |

Fig. 5-1

| No. | Probe ID No. | Symbols of genes | Sequence | SEQ ID NO: | Description of genes (letters and numbers within [ ] indicates GenBank accession No.) |
|---|---|---|---|---|---|
| 1 | A_23_P141415 | MYCBPAP | TCTGCAGGTGACTCTCGGCCCCAAGGCAACCTTCTGGAAAACGGGTTAATAAATAAATCAA | SEQ ID NO: 1582 | Homo sapiens MYCBP associated protein (MYCBPAP), mRNA [NM_032133] |
| 2 | A_23_P143247 | TSHZ2 | GGCACAAGAGGGTATGCAAATCTGTAAGTTTACGGAGGAGTGTGAATGACCACTATCAGTCA | SEQ ID NO: 1583 | Homo sapiens teashirt family zinc finger 2 (TSHZ2), mRNA [NM_173485] |
| 3 | A_23_P146325 | DDEFIIT1 | TGGAAAGTGAAGTGAAGAGCATTTTTGTCATACAAGCCAGTAAGTGCGAGAACTGACTTGAAC | SEQ ID NO: 1584 | Homo sapiens DDEF1 intronic transcript 1 (DDEFIIT1) on chromosome 8 [NR_002765] |
| 4 | A_23_P151426 | FOXO1 | GAGGGTTAGTGAGGAGGTTAGACTTAAAAGTAGTTCAGATTGTCTGAACAGGGAAGCTGA | SEQ ID NO: 1585 | Homo sapiens forkhead box O1A (FOXO1A), mRNA [NM_002015] |
| 5 | A_23_P151805 | FBLN5 | GGGAACCCTGGGAGTTAGCTAGTTTGGTTTTGGGTACGAGAGAAAGGCTATGTAAACAAA | SEQ ID NO: 1586 | Homo sapiens fibulin 5 (FBLN5), mRNA [NM_006329] |
| 6 | A_23_P153616 | MADCAM1 | CTTTCTGGACGGAACGCAGGTAGTTTTTACATACAGATTGATTCATGTCTCACGTCTCCGTAA | SEQ ID NO: 1587 | Homo sapiens mucosal vascular addressin cell adhesion molecule 1 (MADCAM1), transcript variant 1, mRNA [NM_130760] |
| 7 | A_23_P154627 | TSHZ2 | GTATTGGGGTTCTTGTAGCTTGTTAAAAATTGTCTGCTCCAATCCAGGGTCTACCAAGAGC | SEQ ID NO: 1588 | Teashirt homolog 2 (Zinc finger protein 218) (Ovarian cancer-related protein 10-2) (OVC10-2). [Source:Uniprot/SWISSPROT;Acc:Q9NRE2] [ENST00000371497] |
| 8 | A_23_P157299 | AEBP1 | ACAGTAGAGACCTACAGAGTGAACTTTGGGRAGTTCTGAGATCAGGGCTCTACCAAGAGC | SEQ ID NO: 1589 | Homo sapiens AE binding protein 1 (AEBP1), mRNA [NM_001129] |
| 9 | A_23_P157333 | EPHA1 | TATGGGGAGAGTAAGCAATCAGGAGGTTATGAAGAGCATTGAAGATGGGGTACCGGTTGCCC | SEQ ID NO: 1590 | Homo sapiens EPH receptor A1 (EPHA1), mRNA [NM_005232] |
| 10 | A_23_P163492 | BAIAP3 | GACGCATTTTGTAATCACAGCTGGGAGGTGAAAGGAAGGTGCCACTGGGATGGGCCTG | SEQ ID NO: 1591 | Homo sapiens BAI1-associated protein 3 (BAIAP3), mRNA [NM_003933] |
| 11 | A_23_P16496 | A_23_P16496 | GGAGATGTGGGGCCTGGGAGCTGGGAAGAGAATCTAAAGCAACCTAAAACAGTAATTTAAGAATGGAGA | SEQ ID NO: 1592 | |
| 12 | A_23_P202520 | ABLIM1 | TCACTGGACTCCTTTGTCATATACTCTGGATGAGTGTCATAGTCACAACTCGTGAATAA | SEQ ID NO: 1593 | Homo sapiens actin binding LIM protein 1 (ABLIM1), transcript variant 3, mRNA [NM_001003407] |
| 13 | A_23_P209055 | CD22 | GCCTCAGGACAAGAAGAAAAATGTGGACTATGTGATCCTCAAACATTGACAGTGGAATGGGCTG | SEQ ID NO: 1594 | Homo sapiens CD22 molecule (CD22), mRNA [NM_001771] |
| 14 | A_23_P214821 | EDN1 | AGGGAGCCTTGGCCTAGCAATTCAGGGAGAAAAGTCCAAAGTCGAAGCAAAGATTTTCCTAAGGAAT | SEQ ID NO: 1595 | Homo sapiens endothelin 1 (EDN1), mRNA [NM_001955] |
| 15 | A_23_P250212 | DKFZp761P0423 | GAACTGAATGGAGGGTGGACAGTGGGCTGAATACCTTGTTTAGGATTTCTTCACCCTTTT | SEQ ID NO: 1596 | Tyrosine-protein kinase SgK223 (Sugen kinase 223) [Source:Uniprot/SWISSPROT;Acc:Q86YV5] [ENST00000330777] |
| 16 | A_23_P255896 | ENST00000335459 | GCAAGGGGTCTACGCAGAGTACCTCTGAATGGTATTGCGGGAAACTGGGAGCGCAAGA | SEQ ID NO: 1597 | Homo sapiens hypothetical protein LOC128293 (cDNA clone IMAGE:5762496), partial cds. [BC051789] |
| 17 | A_23_P315378 | ATG16L1 | CTGTCTTTCCAGTTTATACTCTTTGTCGAAAAGTCAGTTTCAAAATATTTGGAATGGGAC | SEQ ID NO: 1598 | Homo sapiens cDNA FLJ10035 fis, clone HEMBA1000919. [AK000897] |
| 18 | A_23_P315386 | RHPN1 | CAGGCTGGCCTGAAGGAGGAGGCCGACTACAGTGTGTGAATGGGCAGGCCATGCAGGTGGT | SEQ ID NO: 1599 | Homo sapiens rhophilin, Rho GTPase binding protein 1 (RHPN1), mRNA [NM_052924] |

Fig. 5-2

| No. | Probe ID No. | Symbols of genes | Sequence | SEQ ID NO: | Descriptions of genes (letters and numbers within [ ] indicate GenBank accession No.) |
|---|---|---|---|---|---|
| 19 | A_23_P338919 | SPEG | GCAGGGGCCACTGTAGTGAGGGTGGAGAAATTTGGAAACACCT ATTTGTTAACTGAAAT | SEQ ID NO: 1600 | Homo sapiens cDNA FLJ30825 fis, clone FEBRA2001706, highly similar to Human APEG-1 mRNA. [AK055387] |
| 20 | A_23_P341938 | NOG | GCAAGAGGCGTGGGGCTGGATTCCCATCCAGTAGGCGATGATTGC GAGTGCAAGTGCTCGT | SEQ ID NO: 1601 | Homo sapiens noggin (NOG), mRNA [NM_005450] |
| 21 | A_23_P343398 | CCR7 | AAGAGAGGCAAGATTTTACCCACACACAGAGATAAAGTTTGGGTTG AGGAAACAACAGTTT | SEQ ID NO: 1602 | Homo sapiens chemokine (C-C motif) receptor 7 (CCR7), mRNA [NM_001838] |
| 22 | A_23_P344531 | SYNPO | TCCTGCTGCTGTGAAGATGAGAGGTGCTCTTACTCAGTTAATG ATGAGTGACTATATTT | SEQ ID NO: 1603 | Synaptopodin [Source:Uniprot/SWISSPROT;Acc:Q8N3V7] [ENST00000307662] |
| 23 | A_23_P357504 | AL834280 | CCCACAGCGGCAATCAAGACGGTTCGTGAATAAATAAAAGTT ATGATTGGGTACAAAC | SEQ ID NO: 1604 | |
| 24 | A_23_P359670 | C8orf16 | CTGAGGTTATAATTTTCAGTTAAGATTGTCGAGTTGGCATTTG GTTTAGTCGAATGGT | SEQ ID NO: 1605 | Homo sapiens mRNA for hypothetical protein (C8ORF16). [AJ312026] |
| 25 | A_23_P391275 | DSCR1L2 | TAAATTATGATTTACTCTGTGCTGTTCCAAATTGGGACCAGGA GAGAAATAATGAACTTC | SEQ ID NO: 1606 | Homo sapiens Down syndrome critical region gene 1-like 2 (DSCR1L2), mRNA [NM_013441] |
| 26 | A_23_P3921 | FLJ11710 | CCTGCTCATGATTGAAGTACCATTACAGAAGTCTCTCGTTTATA CATGCATTGGATGTTA | SEQ ID NO: 1607 | Homo sapiens cDNA FLJ11710 fis, clone HEMBA1005149. [AK021772] |
| 27 | A_23_P420873 | NR1D1 | CCGTTCTAGAGAATCGAACTCGAGACTTCTGCGTCTCGTTTACGAG ACGAAAGGAAAAGCA | SEQ ID NO: 1608 | Homo sapiens nuclear receptor subfamily 1, group D, member 1 (NR1D1), mRNA [NM_021724] |
| 28 | A_23_P48585 | SALL2 | CTAGTAAAATGTCAAGAACAGAGCGGGAGATATTAGTGTTTCC CTCTATCATTAAAGGT | SEQ ID NO: 1609 | Homo sapiens sal-like 2 (Drosophila) (SALL2), mRNA [NM_005407] |
| 29 | A_23_P49638 | GRAP | CCAGGAGCAGACAGAAAGTTGGGGCAGAGTAGGTTTTTAGAG ATCCTACAAGGATCCA | SEQ ID NO: 1610 | Homo sapiens GRB2-related adaptor protein (GRAP), mRNA [NM_006613] |
| 30 | A_23_P500130 | ANKRD15 | TTTAGGTGTGTGACATTTACTTGGTCCTCTATGTATTAAATGT TTGAAGTGCCTTAGAG | SEQ ID NO: 1611 | Homo sapiens ankyrin repeat domain 15 (ANKRD15), transcript variant 2, mRNA [NM_153186] |
| 31 | A_23_P7582 | TCF7 | CCCAGAAAAGCTCCAGTAGTGGACAACAGAGGTTTTCACCATAGGC TACGGTAAGCGATTT | SEQ ID NO: 1612 | Homo sapiens transcription factor 7 (T-cell specific, HMG-box) (TCF7), transcript variant 1, mRNA [NM_003202] |
| 32 | A_23_P83368 | EPPK1 | GTTTTTGGTGTGTTTTCTGGGTTGGGTCATGTGTGTCATATGGTTT TACTTTGTGCCGGAA | SEQ ID NO: 1613 | Homo sapiens epiplakin 1 (EPPK1), mRNA [NM_031308] |
| 33 | A_23_P84399 | CNTNAP2 | GTTGAGCAGCATCGTTAAAATATCAGGCAGCAAGTTGGGGGAGGGCAG GCAATGGAATATAATG | SEQ ID NO: 1614 | Homo sapiens contactin associated protein-like 2 (CNTNAP2), mRNA [NM_014141] |
| 34 | A_24_P128057 | MBNL1 | AGAATATTGCTGCAACACTACTGTGATTGGTTATGTGTGTATC ATGCATTGGTTCACAA | SEQ ID NO: 1615 | Homo sapiens muscleblind-like (Drosophila), mRNA (cDNA clone IMAGE:3938312), partial cds. [BC005296] |
| 35 | A_24_P252945 | BLR1 | TTTTCTTTTAATAAAAAGGAGCAGCTATAAAACAGGTCAATACAG TACAGGCAGCAGAGAG | SEQ ID NO: 1616 | Homo sapiens Burkitt lymphoma receptor 1, GTP binding protein (chemokine (C-X-C motif) receptor 5) (BLR1), transcript variant 2, mRNA [NM_032966] |
| 36 | A_24_P290751 | DTX1 | TCCGAAATTTGAGACCCAAAGGCCTTCGTGAGTCAGGAG CGAAAGGAGGAGGCCT | SEQ ID NO: 1617 | Homo sapiens deltex homolog 1 (Drosophila) (DTX1), mRNA [NM_004416] |
| 37 | A_24_P298360 | LTBP3 | CTGGTGTTGGGGAAGCCCCAAGAGATGAGGAGAGTTCAGAGGA GGATTCAGAGTGT | SEQ ID NO: 1618 | Homo sapiens latent transforming growth factor beta binding protein 3 (LTBP3), mRNA [NM_021070] |

Fig. 5-3

| No. | Probe ID No | Symbols of genes | Sequence | SEQ ID NO: | Descriptions of genes (letters and numbers within [ ] indicates GenBank accession No.) |
|---|---|---|---|---|---|
| 38 | A_24_P312325 | C8orf15 | CTTGTTCAATGTGAAGTACTTTAGTTGCCTGTGAAATGAAGTA GAAAAGGAGATTTCTG | SEQ ID NO: 1619 | Homo sapiens chromosome 8 open reading frame 15 (C8orf15), mRNA [NM_001033662] |
| 39 | A_24_P316414 | BC014346 | TAACCTTGGGGTCTTGGGAGTAGAAGCTTTAGCTTTGAATAATTT AAGGGCTTGGCCTGTA | SEQ ID NO: 1620 | Homo sapiens, clone IMAGE:4042988, mRNA, partial cds. [BC014346] |
| 40 | A_24_P340112 | THC2683124 | TGCAATTTGTAAGTGTTGAGTGCAGTGAGTGTAGAAGTCTGAGT TGTAACCATTGATCC | SEQ ID NO: 1621 | |
| 41 | A_24_P360499 | DDEF1IT1 | TGTTCGTTTAATGTAGCGCAGGTGGTATACTTCAGATTTAAGT TTGAAGTAGACATAG | SEQ ID NO: 1622 | Homo sapiens DDEF1 intronic transcript 1 (DDEF1IT1) on chromosome 8 [NR_002765] |
| 42 | A_24_P360722 | DIP2C | GGCTTAGGTTGGCAAATAGCACTGTTTTCTTAGCTGCAAGAAT TCATTGCAGAATGTTT | SEQ ID NO: 1623 | Homo sapiens DIP2 disco-interacting protein 2 homolog C (Drosophila) (DIP2C), mRNA [NM_014974] |
| 43 | A_24_P37020 | THC2690931 | TGCTTCTACGTCCAAGTAAAAGGGAAAAGAGGGTTGAAGGTCAGG CATGTTAGCTATGAGA | SEQ ID NO: 1624 | AF235005 suppression of tumorigenicity 16 protein [Homo sapiens] (exp=-1; wgp=0; cg=0), partial (13%) [THC2690931] |
| 44 | A_24_P413126 | TMEPAI | AAGAAACTGGTTGTTGTGTATCAGTAATCATTAGTGGCAATGAT GAGATTCTGAAAAGCT | SEQ ID NO: 1625 | Homo sapiens transmembrane, prostate androgen induced RNA (TMEPAI), transcript variant 1, mRNA [NM_020182] |
| 45 | A_24_P417352 | ENST00000390559 | TGAGCACGTATGACAGGGTGAAGGATGTCCTGGACCCGGCCAGAAT GCCGAAGCTGTGAAAA | SEQ ID NO: 1626 | Immunoglobulin heavy chain G gene segment [Source:IMGT/GENE_DB;Acc:IGHM] [ENST00000390559] |
| 46 | A_24_P460763 | AK022443 | GTGAGTTAGCAGGCTACTTAAGATGCCTAGGTAGGGTCTAAATGTGA AATGCTATTGGCAGAT | SEQ ID NO: 1627 | Homo sapiens cDNA FLJ12391 fis, clone MAMMA1002666. [AK022443] |
| 47 | A_24_P491923 | THC2491622 | CTTCTGTTGTTTCCAATAAAGTAGACAAGTGCATCTGATGGGT GTTAGTAGGGTATGA | SEQ ID NO: 1628 | |
| 48 | A_24_P548264 | AL512741 | AAGAATTGAGTTAGAAGTTGCCCTATAATGTAATGCAGAATATTT CCCAATAATGCCTAGG | SEQ ID NO: 1629 | Homo sapiens mRNA; cDNA DKFZp667N064 (from clone DKFZp667N064) [AL512741] |
| 49 | A_24_P642771 | AK024956 | ATTCTTGTTCCCATATATTTTAGTGTTGTCTTATTGGGTAGAAAGACAA AAGAAGGGGAATCTGG | SEQ ID NO: 1630 | Homo sapiens cDNA: FLJ21303 fis, clone COL02107. [AK024956] |
| 50 | A_24_P662177 | THC2666469 | GGGCAGGTAGGATTTCAATGATGTTAGATAACCATCTCTAA AGGGACAGAATGTCA | SEQ ID NO: 1631 | |
| 51 | A_24_P713312 | THC2639056 | TTTATATGGTCCGATGCTGCATGTTAGGATTAAGGGGTAATTAA TAGTAATGTATGTGGA | SEQ ID NO: 1632 | ALU8_HUMAN (P39195) Alu subfamily SX sequence contamination warning entry, partial (10%) [THC2639056] |
| 52 | A_24_P728115 | AK024937 | ACTGCATAGTCAGTCAGTTTTAGTGAGTTTGAAATCTGTTTGGAG AGCTATGTAAGTACCA | SEQ ID NO: 1633 | Homo sapiens cDNA: FLJ21284 fis, clone COL01911. [AK024937] |
| 53 | A_24_P792389 | THC2671169 | ATGCTAACGGTGGAGCATAAGGCATACAAGTATGACTAGAATTG CCAAGCTACACATTAGA | SEQ ID NO: 1634 | |
| 54 | A_24_P7974 | SLC26A6 | GTTTGGTTTATGTAGCAAATTCTCCGTTTGGAGCTTTTAAAATAG GATTATTTGGCAGAAG | SEQ ID NO: 1635 | Homo sapiens HSPC106 mRNA, partial cds. [AF161369] |
| 55 | A_24_P79855 | ENST00000390643 | AAACCATTGGTCCCTTTTACCCAGGGAAGGACTCAAGAAGCCGA ACGTGATAGGAGATGG | SEQ ID NO: 1636 | Homo sapiens hypothetical protein DKFZp566H0824, mRNA (cDNA clone MGC:129790 IMAGE:40021976), complete cds. [BC104430] |
| 56 | A_24_P910490 | BX099367 | AGGGCAGAGAGTTCAGAGACCAGGTTGGGCTACACAGTGAGAGGGT GTCTGTACAAAAGTA | SEQ ID NO: 1637 | BX099367 Soares_fetal_liver_spleen_1NFLS_S1 Homo sapiens cDNA clone IMAGp998O05977, mRNA sequence [BX099367] |

Fig. 5-4

| No. | Probe ID No. | Symbols of genes | Sequence | SEQ ID NO: | Descriptions of genes (letters and numbers within [ ] indicates GenBank accession No.) |
|---|---|---|---|---|---|
| 57 | A_24_P914102 | A_24_P914102 | TTAGTAGAGCGCTAGATTTTCTGTAGAAATGTAAAATGTTATTTTACTGTTGAAAATCAG | SEQ ID NO:1638 | |
| 58 | A_24_P915361 | AF086536 | AGTTGACTCCAGAAGGTTGAGAGCTCTGCAAACTGAGGGGCTGCGAGCTCTGTGTTACGGAAGGAA | SEQ ID NO:1639 | Homo sapiens full length insert cDNA clone ZE08A03. [AF086536] |
| 59 | A_24_P928025 | DKFZp547E087 | TGTTATAGAACGATAGTTCATAGTTAAGCTCTCCATTTAAATACAACCTGAAATACCAAAGTTA | SEQ ID NO:1640 | Homo sapiens cDNA FLJ30147 fis, clone BRACE2000266. [AK054709] |
| 60 | A_24_P927090 | AF116678 | TGTGGTTTCTCTTTAACGAGATTCAGGGGCGTCATCCTTTGACTCGGAACCAGGAAGGAATT | SEQ ID NO:1641 | Homo sapiens cDNA PR01995 mRNA, complete cds. [AF116678] |
| 61 | A_24_P930337 | THC2503773 | AGGAAGTGGAACGAGACGAGACCCAAAATAGACTGAAGAATGTAATTAAAATGTAAGCATAG | SEQ ID NO:1642 | |
| 62 | A_24_P930391 | AK022351 | AAGTGGGTTTATTTGCTTTCATGAAAGGAAAGATTAGGTTTCATGCAAACACTTGGTC | SEQ ID NO:1643 | Homo sapiens cDNA FLJ12289 fis, clone MAMMA1001783. [AK022351] |
| 63 | A_24_P930963 | LOC650392 | GCCCCATTTCAAGTATAAGCAGAGGGAGGGGAAAATGGTGGTTAGTTGAAATAAGCATGCCACAAAGG | SEQ ID NO:1644 | Homo sapiens cDNA clone IMAGE:5264670. [BC036550] |
| 64 | A_24_P933548 | A_24_P933548 | CACGTCCACTTTATAGTTACTGCTTTATACCTGCAGAAGTATAACCTAAGGAAGGAAATG | SEQ ID NO:1645 | |
| 65 | A_24_P934661 | A_24_P934661 | GGAAGGTATCAAGCAGGAAAATTCCAGTTCTGGGAAATAGTGGACCAGATCGTCTCCATGG | SEQ ID NO:1646 | |
| 66 | A_24_P935682 | AY358248 | AGTCAGTAATCAGCATTCAATCAATAGAGCTCTAACAATGATGGCTTGACAGTTATGAAGC | SEQ ID NO:1647 | Homo sapiens clone DNA166629 MRSS6228 (UNQ6228) mRNA, complete cds. [AY358248] |
| 67 | A_24_P945096 | CACNA1I | CTTAGAGCTGGTCTTTAGCCAGATACAGACATACTCTTTTTGTCTTTGTGTAATAATCA | SEQ ID NO:1648 | Homo sapiens calcium channel, voltage-dependent, T type, alpha 1I subunit (CACNA1I), transcript variant 1, mRNA [NM_021096] |
| 68 | A_24_P910002 | CA433167 | CTGTGAACTTGTCAAAGATCATGCAAGCTGAACTATTTAAATTCTACTCAGGAGAGATTTC | SEQ ID NO:1649 | UI-H-C00-ark-e-04-0-U1.s1 NCI_CGAP_Sub9 Homo sapiens cDNA clone UI-H-C00-ark-e-04-0-U1 3′, mRNA sequence [CA433167] |
| 69 | A_32_P105940 | A_32_P105940 | GTGCCAAGGTAAGCTACCACCAGTTTTGGTTTTATTTCAAGCAGCAACATGAAATAAGGCATTC | SEQ ID NO:1650 | |
| 70 | A_32_P111394 | THC2643957 | GAATACAGGTGTCGTTTCATCCGCATATTTGACTGAAGGTAAGACACATGAAATTATAAGG | SEQ ID NO:1651 | |
| 71 | A_32_P112546 | LOC649344 | AGGGAGGTGAGTATGCAGGGTAGGCACTGGGAAGAGGAGGAGACCCAGCTGAGGGCTCAGGCGTA | SEQ ID NO:1652 | PREDICTED: Homo sapiens similar to Keratin, type II cytoskeletal 8 (Cytokeratin-8) (K8) (Keratin-8) (LOC649344), mRNA [XR_018597] |
| 72 | A_32_P116997 | THC2719256 | AAACATTAGGTAGGAGCAGGTTGCTAGAGGAATATATTTAGGGTCATGAATGTCTTCTGTTGGC | SEQ ID NO:1653 | BE147120 PM2-HT0224-221099-001-b10 HT0224 Homo sapiens cDNA, mRNA sequence [BE147120] |
| 73 | A_32_P121978 | A_32_P121978 | CAGATTAGAACCACCTCATAATGAGTTCTTGATTGCAGTTCAGATTGTTCTTGATGGGGAC | SEQ ID NO:1654 | |
| 74 | A_32_P125589 | THC2649341 | CGGCTCTATCCGTTGCTTTAGCCTTTGAATGAAATGAAGTGAGATGTCTCACAGGTCAGATAG | SEQ ID NO:1655 | |
| 75 | A_32_P12703 | THC2697162 | TTGAAAAGGAAAAAGGTTTGTTCCTTAATTAGGGGGGAAGTGCCAGAGTAAAAGGAATCCTAAGTAAATAGGGT | SEQ ID NO:1656 | |
| 76 | A_32_P131294 | BM854107 | AGTTGGACATAAAAGGTTTGTTGCTTTAATTAGAGGTAGTCTGGGAAATGGTAGCACTTGTGC | SEQ ID NO:1657 | K-EST0136406 S22SNU16n1 Homo sapiens cDNA clone S22SNU16n1-145-F11 5′, mRNA sequence [BM854107] |

Fig. 5-5

| No. | Probe ID No. | Symbols of genes | Sequence | SEQ ID NO: | Descriptions of genes (letters and numbers within { } indicates GenBank accession No.) |
|---|---|---|---|---|---|
| 77 | A_32_P132936 | THC2673686 | AAATGGAAGTATTGACCAGATTAAGAGAGTGGTTAAGTCATGGGCATGAATGAATTTACCA | SEQ ID NO: 1658 | Q65549_9ALPH (Q65549) Glycoprotein C, partial (4%) [THC2673688] |
| 78 | A_32_P136033 | AK090477 | AGCCTCGGTCTAGAGTCTCATGTCCTTCGTGTCAGGTGGTTGACTTGAATATTGATCAA | SEQ ID NO: 1659 | Homo sapiens mRNA for FLJ00399 protein. [AK090477] |
| 79 | A_32_P136597 | THC2714184 | CGGGACTGTTTTGCCCGAGAAATAGAATAGTGAAGATTGTGCCATATTCGTACTA | SEQ ID NO: 1660 | |
| 80 | A_32_P146826 | THC2652700 | ACCCTGTAGGAGGAGTTGGAAAGTTGTGAAGGTTTGAATTGTCTGGAGGATGTGGTTC | SEQ ID NO: 1661 | |
| 81 | A_32_P148844 | THC2639689 | CCTGTGGGCTGATTCCAGACTGAGAGTTGAAGTTTTGTGTGCATCATCATGTGCCATTAA | SEQ ID NO: 1662 | |
| 82 | A_32_P147969 | AL080232 | TAATGAGCTCTTTTGGGCATGAAGGCAAGGAACTGTCGAGAAGACCTCTGAGAATTCTT | SEQ ID NO: 1663 | Homo sapiens mRNA; cDNA DKFZp586A061 (from clone DKFZp586A061). [AL080232] |
| 83 | A_32_P155841 | AL079294 | CCTTCCTGTTATATAGGTGGAGTTAGGATGTGTGTTAAGGAAGAATGGCAAATGCAAA | SEQ ID NO: 1664 | Homo sapiens mRNA full length insert cDNA clone EUROIMAGE 362780. [AL079294] |
| 84 | A_32_P156062 | THC2681718 | CTGGAGGTTGTTGGCATTGGTTCAGTGTGTCAGGGAGGAGGTCAGGGCTCAGTTGACTGTTC | SEQ ID NO: 1665 | |
| 85 | A_32_P164573 | THC2611661 | AGGTGTTTCTATTAACAGTCGAAGTACTCTGAGAGCTTGGAAATTTTCAAGTGCAAATC | SEQ ID NO: 1666 | RR12_SPIMX (P42344) Chloroplast 30S ribosomal protein S12, partial (1%) [THC2611661] |
| 86 | A_32_P165407 | AK024826 | AAAGGAGGAGGATCCCTGGACCAGGACTTCACAGGAACCAACATGATTCATGAAAAA | SEQ ID NO: 1667 | Homo sapiens cDNA: FLJ21273 fis, clone COL01778. [AK024826] |
| 87 | A_32_P171253 | THC2674306 | GGGCTCAGACGTTAAGACGTGATGGTCTTTTCTTTTACTCTACACAAAGTCAAGCAGT | SEQ ID NO: 1668 | Q9F8M7_CARHY (Q9F8M7) DTDP-glucose 4,6-dehydratase (Fragment), partial (1%) [AK024826] |
| 88 | A_32_P179526 | ZBTB20 | TTGAAGTTGGAAATCAAGGGCAATCTAAAACGGACCAGATGTTTCTGCTGCTGGGAAAGG | SEQ ID NO: 1669 | Homo sapiens zinc finger and BTB domain containing 20, mRNA (cDNA clone IMAGE:4291354), partial cds. [BC010934] |
| 89 | A_32_P179998 | DMRTC1 | ATATGCCAGAGTTTTTATTCGTCTTGTTGATTGCTGACATACCTGTGCACTCATGTGTATA | SEQ ID NO: 1670 | Homo sapiens DMRT-like family C1 (DMRTC1), mRNA [NM_033053] |
| 90 | A_32_P182458 | A_32_P182458 | ACCTAGGCACAGTGGAGTGAAAGACTTTAAATAGCACTTGTTCCTTGAGTATATATGGAAA | SEQ ID NO: 1671 | |
| 91 | A_32_P185398 | THC2750143 | AAATATCTGATACTTTAGCATATCTGCAATTATAAGAATTAAATATGCAAATATACCAT | SEQ ID NO: 1672 | ALU1_HUMAN (P39188) Alu subfamily J sequence contamination warning entry, partial (11%) [THC2750143] |
| 92 | A_32_P194372 | AK129547 | AGACCACAGAAAACATAGAGCCATGATATTTGGACCAAGGATAGGTTAAACATAGGGGAGG | SEQ ID NO: 1673 | Homo sapiens cDNA FLJ26036 fis, clone PRS00145. [AK129547] |
| 93 | A_32_P198287 | THC2652486 | CCTTTCACAAGACGTGTAGGCTTACCGAAGCTTAATTTGCTGCATAGGCGGGCCTGTT | SEQ ID NO: 1674 | Q9BHM3_PARTE (Q9BHM3) Cyclophilin-RNA interacting protein, partial (4%) [THC2652466] |
| 94 | A_32_P208039 | AL049390 | TTTCATGTTTGAGCATTCAGATTGGGCTTATTTCTCAAGGCATGTTCGAAAGCTCACAA | SEQ ID NO: 1675 | Homo sapiens mRNA; cDNA DKFZp586O1318 (from clone DKFZp586O1318). [AL049390] |
| 95 | A_32_P208200 | THC2659414 | GACATTAAAATGAGTGGAGAAGAAACCTGAAAGGCGGCCGCAGAGAATAAGACTAAAATTTG | SEQ ID NO: 1676 | |
| 96 | A_32_P20912 | AK025669 | ACAAGTACGTGTAGGCTGGGAGGAAGCATCTTCACAGTGCCCATAAAGTCGAATTTGGCAAA | SEQ ID NO: 1677 | Homo sapiens cDNA: FLJ22016 fis, clone HEP07422. [AK025669] |

Fig. 5-6

| No. | Probe ID No. | Symbols of genes | Sequence | SEQ ID NO. | Descriptions of genes (letters and numbers within [ ] indicates GenBank accession No.) |
|---|---|---|---|---|---|
| 97 | A_32_P209582 | THC2663167 | CAATGTAAAGCCAGAATATCAAGGTCGTTTTGTCAAGAATTTCAAACCTATTTGGCTGAT | SEQ ID NO: 1678 | ALU1_HUMAN (P39188) Alu subfamily J sequence contamination warning entry, partial (5%) [THC2663167] |
| 98 | A_32_P211048 | A_32_P211048 | GTTCAGAAAAACACGTAGTAGGTATTGAGGTCATATTGGAATGAATGAGAAATGAGCAG | SEQ ID NO: 1679 | |
| 99 | A_32_P213509 | THC2663555 | GATTGTTCCAGTGTGGAGCCCTTTTAATGAAAATTCTCAACACCTACAGTGGAAAAA | SEQ ID NO: 1680 | |
| 100 | A_32_P214054 | THC2755661 | GGCTTATCTCGTTGTTTAACAGTTGGGAGCTTTGGCTTCGATAGCAATGATTTGCAAAT | SEQ ID NO: 1681 | |
| 101 | A_32_P216122 | AK130891 | TTCTTCGTCTATATGTTTGGGAGGCATTCATGAAGAATTGAGTAGACATATATATGGGTC | SEQ ID NO: 1682 | Homo sapiens cDNA FLJ27381 fis, clone UBA07680. [AK130891] |
| 102 | A_32_P225301 | THC2727302 | GGGCTCAATGACGATTGTGATGGCAACAAAATTTACCAAGGATTTTGCTAAGCTGAAGAA | SEQ ID NO: 1683 | ALU6_HUMAN (P39193) Alu subfamily SP sequence contamination warning entry, partial (9%) [THC2727302] |
| 103 | A_32_P227110 | THC2512148 | TAAAACAAATGGTTTTGATTCAGCAGTGTATTGATAATGGGTTATTTATTACAATCA | SEQ ID NO: 1684 | |
| 104 | A_32_P232851 | THC2645586 | GTTGAAAAGGATATCCTTGACATTCGTTCTTGGAGAAAATTGAGGTCACTGACTTATTTC | SEQ ID NO: 1685 | Q9P3E1_NEUGR (Q9P3E1) Related to rna-binding protein fus/tls, partial (5%) [THC2645586] |
| 105 | A_32_P34926 | AL833696 | CTGGGCAGAGAGTGAAGTGCCAAGCGTTCCCCAGTGCCTAGTGCTTGTTTGAGTGTGGGTTCTTGTGATAA | SEQ ID NO: 1686 | Homo sapiens mRNA; cDNA DKFZp667D139 (from clone DKFZp667D139). [AL833696] |
| 106 | A_32_P40673 | A_32_P40673 | CATCACACTTGATATTAGGAGAGGCCTACTGTTGTTGAGTGTCACAGGGTGATATGTA | SEQ ID NO: 1687 | |
| 107 | A_32_P41099 | THC2658419 | AGGGGCAGAAATATTTGGGTTCGTCCGTTTATTAGTAAAGTGTCCTATGCTATGTCTC | SEQ ID NO: 1688 | |
| 108 | A_32_P42976 | THC2713076 | CTTATGGTTTCCTTTGTGTGTCAAGGTGCCAACATTGTGTGGCTCATTCTTTCTGGGTA | SEQ ID NO: 1689 | |
| 109 | A_32_P43878 | DB111455 | ATGTGAGAAAGTTCTTAAGGTTAATGACCAAGTTCCATGTGAGGTCTTACTTGGGA | SEQ ID NO: 1690 | DB111455 THYMU2 Homo sapiens cDNA clone THYMU2015028 5', mRNA sequence [DB111455] |
| 110 | A_32_P46404 | AK092468 | CTCTATGCCAACCTCTTTTTGCATAAATACTTATGGATTCAGCGAAGAGGAAAAGGACT | SEQ ID NO: 1691 | Homo sapiens cDNA FLJ35149 fis, clone PLACE6010485. [AK092468] |
| 111 | A_32_P5542 | AF131782 | GAGGCCTTACGATCTAACTTCCACTGGAGGAAATCTTATAAATAAACAACAG | SEQ ID NO: 1692 | Homo sapiens clone 24941 mRNA sequence. [AF131782] |
| 112 | A_32_P55427 | THC2701763 | GACTTTTATCGTATCCGTAAAACAAACAGCAAAATTGAGAGAGTACATTGGTATAGCTTGG | SEQ ID NO: 1693 | Q9F8M7_CARHY (Q9F8M7) DTDP-glucose 4, 6-dehydratase (Fragment), partial (11%) |
| 113 | A_32_P55438 | A_32_P55438 | GTTGCTTGGTCAAACCTGGTGAGGTTTGTACTATGTTAGTGTCACTACATGCAGCAG | SEQ ID NO: 1694 | |
| 114 | A_32_P61708 | A_32_P61708 | AGGAGGCAAGTGATTGTTCTCTACAAGCGGAGACATAGTATACCTTCCAAGGACCAT | SEQ ID NO: 1695 | |
| 115 | A_32_P64570 | ANKRD15 | AGAGCTTCTGTTGACTCGGACAAAGTCCTACAGAAGGCAGGTGTGTGGTTCTGAGTCAGAGACGTTTTAAGATTT | SEQ ID NO: 1696 | Homo sapiens ankyrin repeat domain 15 (ANKRD15), transcript variant 2, mRNA [NM_153186] |
| 116 | A_32_P65067 | THC2618074 | CCCGAAAGTGAATTTAAACTTGAGTCTATTATGGGTTCTCATAGCAACAGGAAAACT | SEQ ID NO: 1697 | |

Fig. 5-7

| No. | Probe ID No. | Symbols of genes | Sequence | SEQ ID NO: | Descriptions of genes (letters and numbers within [ ] indicates GenBank accession No.) |
|---|---|---|---|---|---|
| 117 | A_32_P67209 | BU726029 | CTCACTCTATATTTATTCTGTGGAGCTACGTGGACGTGACTCTG GTATTGTTCAGAAGAAG | SEQ ID NO: 1698 | UI-E-C1O-aac-g-02-0-UI.s1 UI-E-C1O Homo sapiens cDNA clone UI-E-C1O-aac-g-02-0-UI 3', mRNA sequence [BU726029] |
| 118 | A_32_P70875 | CD239706 | GTTCTTTGAGAAGTTCCTAATGCAGTAGGAGGAGAAAGTGACA GTTTCTTATTTACTG | SEQ ID NO: 1699 | FNP8XF03 FNP Homo sapiens cDNA, mRNA sequence [CD239706] |
| 119 | A_32_P71171 | A_32_P71171 | TGTAGATAGTAATAGGAAAACCAAGAATCCAGGCTGGTGATGGGT GGAGGGAGTGATTGAA | SEQ ID NO: 1700 | |
| 120 | A_32_P79103 | BM932034 | GTGGTACAAGAATGAAAATAGGCATTTTAGGAAGGGTTGAGTCAGAG GTGCAGTGGGGCATA | SEQ ID NO: 1701 | UI-E-EJ1-ajl-k-24-0-UI.r1 UI-E-EJ1 Homo sapiens cDNA clone UI-E-EJ1-ajl-k-24-0-UI 5', mRNA sequence [BM932034] |
| 121 | A_32_P88987 | AK022345 | ATGGAAGTTACTACCCAGGGTTACCAAAAGGTCAGGTTTATAT AAAGTGGGGTTCGTTT | SEQ ID NO: 1702 | Homo sapiens cDNA FLJ12284 fis, clone MAMMA1001757 [AK022346] |
| 122 | A_32_P89987 | AL134462 | TTCATGGAGCTTCTAGTCAAGCAGGAGACGGCACTAAACAGTAAAGG GACAAATAGGATTACT | SEQ ID NO: 1703 | DKFZp547J065 r1 547 (synonym: hfbr1) Homo sapiens cDNA clone DKFZp547J065 5', mRNA sequence [AL134462] |
| 123 | A_32_P91328 | THC2641595 | GTTAGGGGAATAAATGTCATTGAAGTCTTTAACTCTAGGCTGAGT CTAAGGCCAAGGTTCA | SEQ ID NO: 1704 | |
| 124 | A_32_P97305 | THC2681839 | AATATGGAGACAGAAAACTAAAGAAGATGTCAGTTGAGGAGA CAGCTTGCTGCGCCT | SEQ ID NO: 1705 | |
| 125 | A_32_P98940 | THC2745859 | AAGAGTATTCGGAAGATAGGAAAGGTGTGTTGTTTTTAGGAGGT GTATTTCAGCTAGTTA | SEQ ID NO: 1706 | |
| 126 | A_23_P102235 | SNRPG | ACACAGAAGAACAATATTGGGAATGGGTAATACGAGGAAATAGTA TGATATGTTAGAAGC | SEQ ID NO: 1707 | Homo sapiens small nuclear ribonucleoprotein polypeptide G (SNRPG), mRNA [NM_003096] |
| 127 | A_23_P104054 | C1orf9 | TAAATTCTTCCTGTCTGCACAATTAGGTATTCAGAGCAAGAAG GGGCTTGCTGATTTATAGA | SEQ ID NO: 1708 | Homo sapiens chromosome 1 open reading frame 9 (C1orf9), transcript variant 2, mRNA [NM_016227] |
| 128 | A_23_P106131 | KTN1 | ATGTTTCACCCTTTCACTTTGTCAGAAACACTGAAACAGAGTT TTGTGTTTCTAATCC | SEQ ID NO: 1709 | Homo sapiens kinectin 1 (kinesin receptor) (KTN1), transcript variant 1, mRNA [NM_182926] |
| 129 | A_23_P108751 | FHL2 | TTTACAGCTCTGTAACCTCCCGTTGGGTCAAGTCTAAACCAAGA TTATGTGACTTGCAAT | SEQ ID NO: 1710 | Homo sapiens four and a half LIM domains 2 (FHL2), transcript variant 2, mRNA [NM_201555] |
| 130 | A_23_P110362 | MAP2K1IP1 | AGTAGAGACAGAGTTGTGGAAGTTTCTTAACTGACAGTGGTTTCGA GTGTAGCCTTATCTT | SEQ ID NO: 1711 | Homo sapiens mitogen-activated protein kinase kinase 1 interacting protein 1 (MAP2K1IP1), mRNA [NM_021970] |
| 131 | A_23_P110611 | ZH2C2 | CTCTGAAAAGCAGAGTTTGGAAGTCTGTTGGACTCTTCAAACCAG GTTGTTGAATAGTTAA | SEQ ID NO: 1712 | Homo sapiens zinc finger, H2C2 domain containing (ZH2C2), mRNA [NM_017676] |
| 132 | A_23_P110811 | COX7C | AGCCCTCTGGAAGTGGATGAGAAAGTAGAAGTGATATGCCATACTAG ATATGTTTGTCAATAA | SEQ ID NO: 1713 | Homo sapiens cytochrome c oxidase subunit VIIc (COX7C), nuclear gene encoding mitochondrial protein, mRNA [NM_001867] |
| 133 | A_23_P111583 | CD36 | CTTTGGGTTAATGAGACTGGGACCATTGGTGATGAGAAGGGAAA CATGTTCAGAAGGTCAA | SEQ ID NO: 1714 | Homo sapiens CD36 molecule (thrombospondin receptor) (CD36), transcript variant 2, mRNA [NM_001001547] |
| 134 | A_23_P114662 | CRYZ | AACATGCTAGTTCAAAAATAAGAGTGGTCAGTTTCCAAGGGTTT CAAGGTAGTTAGCTT | SEQ ID NO: 1715 | Homo sapiens crystallin, zeta (quinone reductase) (CRYZ), mRNA [NM_001889] |

Fig. 5-8

| No. | Probe ID No. | Symbols of genes | Sequence | SEQ ID NO: | Description of genes (letters and numbers within [ ] indicates GenBank accession No.) |
|---|---|---|---|---|---|
| 135 | A_23_P11652 | USP1 | TTGCGCATGGAGTAATTGTATCTGTTTAAGTCATATCTGCAACGATGTGTATATAGTAC | SEQ ID NO: 1716 | Homo sapiens ubiquitin specific peptidase 1 (USP1), transcript variant 1, mRNA [NM_003368] |
| 136 | A_23_P11685 | PLA2G4A | GAAATGGCAGCAGTTTCTGATGCTGAGGCAGTTTGCAATGCCATGACAACTGGATTTAAA | SEQ ID NO: 1717 | Homo sapiens phospholipase A2, group IVA (cytosolic, calcium-dependent) (PLA2G4A), mRNA [NM_024420] |
| 137 | A_23_P117721 | RPS17 | AATTATGTTCTGAGGTCTGAGCCTTGAATCAGGAGGAGTATTGAAGTGATCTGCACAC | SEQ ID NO: 1718 | Homo sapiens ribosomal protein S17 (RPS17), mRNA [NM_001021] |
| 138 | A_23_P117852 | KIAA0101 | TACTGTCGGCATTTTATTGGTGTTGATTATTGGAATGGTGCCATATTGTCACTCCTTC | SEQ ID NO: 1719 | Homo sapiens KIAA0101 (KIAA0101), transcript variant 1, mRNA [NM_014736] |
| 139 | A_23_P118516 | FAM18B | TATTCTGTAGAATTGTTTCAGGAGAAAGTTTTGTTCTATGGTAAAGTGAGCACTTTG | SEQ ID NO: 1720 | Homo sapiens family with sequence similarity 18, member B (FAM18B), mRNA [NM_016078] |
| 140 | A_23_P120048 | BAZ2B | TATTTCGGTCTGAAGGTAATGATAGCTATACAGTGTGTACAGTAAATTATCCTACGGAAC | SEQ ID NO: 1721 | Homo sapiens bromodomain adjacent to zinc finger domain, 2B (BAZ2B), mRNA [NM_013450] |
| 141 | A_23_P120316 | MTHFD2 | AGGATTATTCCTGGTATTAGTAGTAGTCATTTTATGTATGTTACCCTTCAGTAAGTTCTCC | SEQ ID NO: 1722 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 142 | A_23_P1206 | RPS24 | TTTGGATTCAGAGTCATTTTGTTGGTGGCAAGAGAACTGGCTTTGCATGATTATGAT | SEQ ID NO: 1723 | Homo sapiens ribosomal protein S24 (RPS24), transcript variant 2, mRNA [NM_001026] |
| 143 | A_23_P120902 | LGALS2 | CTGAAGTACCTCGAGCGTAAGGGAGGCGGGTTCAACATGTCGGTCTTCAAGTTAAAAGAATAA | SEQ ID NO: 1724 | Homo sapiens lectin, galactoside-binding, soluble, 2 (LGALS2), mRNA [NM_006498] |
| 144 | A_23_P121386 | IFT57 | TGGAACACACACTACTGCAATGGAATGAAAGCTGAAGCTGAAGGAAGAAGTGAAGATGACTAGGAACATGC | SEQ ID NO: 1725 | Homo sapiens intraflagellar transport 57 homolog (Chlamydomonas) (IFT57), mRNA [NM_018010] |
| 145 | A_23_P121622 | SULT1B1 | GAAATAGAGTTGTCTGGCTGGGTGTAGTTGATTGAAAAGAAAACTTCTCTGATGTAATCACACAATTAGTTATGAGCAAG | SEQ ID NO: 1726 | Homo sapiens mRNA for ST1B2, complete cds. [D89479] |
| 146 | A_23_P121925 | FLJ13611 | CATGTGTTACTGTTAGTAGAAAACTTTCTCTGATGTAATCACACTTAGTTATGAGCAAG | SEQ ID NO: 1727 | Homo sapiens hypothetical protein FLJ13611 (FLJ13611), mRNA [NM_024941] |
| 147 | A_23_P122174 | XRCC4 | AAACGAAACTGATCCTCTGGGTTGGGAGGGGGTGGAATACATCCTCATTAAGTAAAGATGATTCGATTAT | SEQ ID NO: 1728 | Homo sapiens X-ray repair complementing defective repair in Chinese hamster cells 4 (XRCC4), transcript variant 3, mRNA [NM_022550] |
| 148 | A_23_P123315 | BC067244 | CTTCCAAATCACTGGTTTGGGAGGGGGGTGGAATACATCCTCATTTCTGTACATCATGCAT | SEQ ID NO: 1729 | Homo sapiens cDNA clone IMAGE:4807381, partial cds. [BC067244] |
| 149 | A_23_P123343 | NUDCD1 | TTGGCCTCTTTGTACTGGAAAAGTTATTCAGTGGTACGTCGGAGGTCTGAGAGTTATCTG | SEQ ID NO: 1730 | Homo sapiens NudC domain containing 1 (NUDCD1), mRNA [NM_032869] |
| 150 | A_23_P123608 | JAK2 | GGATAAGAGTTTGTTGGCTTGAAGAAATGAACCTCATTCTGAGACCAAGTAGATTTTAGAGA | SEQ ID NO: 1731 | Homo sapiens Janus kinase 2 (a protein tyrosine kinase) (JAK2), mRNA [NM_004972] |
| 151 | A_23_P127279 | FAM35A | TGTACATTCCAGCCATTGGTACTAAGTATGGGAACCACAGAGAACAATTCCCTCAGAA | SEQ ID NO: 1732 | Homo sapiens family with sequence similarity 35, member A (FAM35A), mRNA [NM_019054] |
| 152 | A_23_P127579 | PTS | GTGGTTTATAAAGGAGAATAGGTATTGGGGTTAGCATTGGAGAAGCCCAGTTTGTTTCT | SEQ ID NO: 1733 | Homo sapiens 6-pyruvoyltetrahydropterin synthase (PTS), mRNA [NM_000317] |
| 153 | A_23_P128192 | PFDN5 | CACGGTCCATTGCTCAGGTCAAGTCAGTGGTACGAGACCAAGTAGTATGTGGAAGGCAAGGACTGTGT | SEQ ID NO: 1734 | Homo sapiens prefoldin subunit 5 (PFDN5), transcript variant 1, mRNA [NM_002624] |

Fig. 5-9

| No. | Probe ID No. | Symbols of genes | Sequence | SEQ ID NO: | Descriptions of genes (letters and numbers within [ ] indicates GenBank accession No.) |
|---|---|---|---|---|---|
| 154 | A_23_P126384 | VPS29 | GAGGTAATTGGAGATGATGTGAAAGTAGAACGAATGGAATACAAAAAACCTTAAAGGCAG | SEQ ID NO: 1735 | Homo sapiens vacuolar protein sorting 29 homolog (S. cerevisiae) (VPS29), transcript variant 2, mRNA [NM_057180] |
| 155 | A_23_P126470 | CLEC12A | CCACCAAATTATGTCGTGAGCTATATAGCAAAGAACAAGAGGCACAAATGTAAGGGTTGTC | SEQ ID NO: 1736 | Homo sapiens C-type lectin domain family 12, member A (CLEC12A), transcript variant 1, mRNA [NM_138337] |
| 156 | A_23_P128930 | PSMC6 | CAACAAGGAAGATTAGAACATAGTGAAAATCGATGCAGGTCCCATTACAAAGCATGGTGAA | SEQ ID NO: 1737 | Homo sapiens proteasome (prosome, macropain) 26S subunit, ATPase, 6 (PSMC6), mRNA [NM_002806] |
| 157 | A_23_P130444 | ZNF701 | CTCCTTGCAGAATATCATAAGGTTGATTTTTGAGGTAATAGTTACAAATGCGGTGAGCAC | SEQ ID NO: 1738 | Homo sapiens zinc finger protein 701 (ZNF701), mRNA [NM_018260] |
| 158 | A_23_P132863 | ENST00000306024 | AGGTAAATGGTATTTCATTTTTCTCAAGCTGTCCAATAAATATGACCACCAAGAATGCAG | SEQ ID NO: 1739 | U6 snRNA-associated Sm-like protein LSm3. [Source:Uniprot/SWISSPROT;Acc:P62310] [ENST00000306024] |
| 159 | A_23_P132936 | SPCS3 | GAATGTCAGTTTTGACCCTGTCGTTGAAGGTCGTACCAAATGGTGGAATGTCTACCCTCTGT | SEQ ID NO: 1740 | Homo sapiens signal peptidase complex subunit 3 homolog (S. cerevisiae) (SPCS3), mRNA [NM_021928] |
| 160 | A_23_P133293 | MCTP1 | AGCAACCCAGTAAGTACAGTTATCAAAGAATACTAGGAAACTATATCCATATGGGTTTGG | SEQ ID NO: 1741 | Homo sapiens cDNA: FLJ22344 fis, clone HRC06080. [AK025997] |
| 161 | A_23_P133445 | GZMA | GAATGAATATGGTTTGTGCTGGAAGCCTCCGAGGTGGGAAAAAACTCGTGGAATGGAGATT | SEQ ID NO: 1742 | Homo sapiens granzyme A (granzyme 1, cytotoxic T-lymphocyte-associated serine esterase 3) (GZMA), mRNA [NM_006144] |
| 162 | A_23_P133648 | FAM8A1 | ACTTGGCCGGAATTACAAATGAGTGTTTTTAGATTCAAGTGAGCGGTAAAAGGATTGTT | SEQ ID NO: 1743 | Homo sapiens family with sequence similarity 8, member A1 (FAM8A1), mRNA [NM_016255] |
| 163 | A_23_P134714 | HRSP12 | TAAATTACACCGTGTGTGCAGGTGTATTACTGAATATAGGAAAGAGATACCGATTAGAATAC | SEQ ID NO: 1744 | Homo sapiens heat-responsive protein 12 (HRSP12), mRNA [NM_005836] |
| 164 | A_23_P134786 | PHF20L1 | AGTGTATGTGCCCCAGTGCTACATACATCGGCAGGTAATGCGGTAAGTGTGTATGCTTGTTTA | SEQ ID NO: 1745 | Homo sapiens PHD finger protein 20-like 1 (PHF20L1) transcript variant 1, mRNA [NM_016018] |
| 165 | A_23_P134925 | BNIP3L | ATTGGGACGACAAAAAGGACAGGCTTCATTTTTGATATGTTTGATGAAAGTGGCTCAAGAT | SEQ ID NO: 1746 | Homo sapiens BCL2/adenovirus E1B 19kDa interacting protein 3-like (BNIP3L), mRNA |
| 166 | A_23_P135123 | BG216229 | CTGGTCTGAAGGGTACCGGGGTGTCAACAGGTGTTCGTTACTGATAATTGATTATTCAA | SEQ ID NO: 1747 | BG216229 RST35603 Athersys RAGE Library Homo sapiens cDNA, mRNA sequence [BG216229] |
| 167 | A_23_P135494 | CLIC4 | CTCCTCAAGCGGTAATGTTGAACAGAATTGGAGTATATTCTTTATAATTCTTGAAGCAGG | SEQ ID NO: 1748 | Homo sapiens chloride intracellular channel 4 (CLIC4), mRNA [NM_013943] |
| 168 | A_23_P135499 | CLIC4 | CTTGCGTTTTTTGATGTAGATAGATGCAGATATTCTATAGAGTTCGTTGTCTTTTTACTAGGAC | SEQ ID NO: 1749 | Homo sapiens chloride intracellular channel 4 (CLIC4), mRNA [NM_013943] |
| 169 | A_23_P137366 | C1QB | CACCGGACAAGGAACTACTACTGGGCATGGGCATGAGGTGCCAACAGCATCTTTTCCGGGTTCCT | SEQ ID NO: 1750 | Homo sapiens complement component 1, q subcomponent, B chain (C1QB), mRNA [NM_000491] |
| 170 | A_23_P137434 | RNF11 | TGTAGTATCCATATGTTGCTTAAATTTCGTTATGAGGCCCATGATGGAAAGAGACTTAAAGA | SEQ ID NO: 1751 | Homo sapiens ring finger protein 11 (RNF11), mRNA [NM_014372] |
| 171 | A_23_P138308 | CD58 | AACCTGTATGGGAAGCACGCCGGTCATTGAAGACAAGAATATGCAGTTATACCATACCATT | SEQ ID NO: 1752 | Homo sapiens CD58 molecule (CD58), mRNA [NM_001779] |
| 172 | A_23_P138541 | AKR1C3 | TTTTTGAGTTCCAGTTGAGTGCAGAGGACATGAAAGGCAGATATGGCCTAGAACAAGAAATCT | SEQ ID NO: 1753 | Homo sapiens aldo-keto reductase family 1, member C3 (3-alpha hydroxysteroid dehydrogenase, type II) (AKR1C3), mRNA [NM_003739] |

Fig. 5-10

| No. | Probe ID No. | Symbols of genes | Sequence | SEQ ID NO: | Descriptions of genes (letters and numbers within [ ] indicates GenBank accession No.) |
|---|---|---|---|---|---|
| 173 | A_23_P140301 | PSMA3 | TCAAGTAGAACTCAGCTGGGTTGGTGAATTAACTAATGGAAGAGATGAAATTGTTCCAAA | SEQ ID NO: 1754 | Homo sapiens proteasome (prosome, macropain) subunit, alpha type, 3 (PSMA3), transcript variant 1, mRNA [NM_002788] |
| 174 | A_23_P141549 | RPS7 | GTCAAAGTAGATGGCAGCGGCCTCATAAAGGTTCATTTGGACAAAAGGACAGCAGAAGAAT | SEQ ID NO: 1755 | Homo sapiens ribosomal protein S7 (RPS7), mRNA [NM_001011] |
| 175 | A_23_P142560 | ZEB2 | CTTTTAATCTGTGTTTCTGCAAGTGCATCCTTGTACAGTGTTAAGAGGGTAACATGGGT | SEQ ID NO: 1756 | Homo sapiens zinc finger E-box binding homeobox 2 (ZEB2), mRNA [NM_014795] |
| 176 | A_23_P143958 | RPL22L1 | ATTGGCTTCAGAGTGGTTGCATCTGACAAGGAGACCTACGAAGTTCGTTAGTGCCAGATTA | SEQ ID NO: 1757 | Homo sapiens ribosomal protein L22-like 1, mRNA (cDNA clone IMAGE:4865966), [BC049823] |
| 177 | A_23_P144145 | DCUN1D1 | TCTTAGTGAATACATGTGCATATCTCGTAAGTTCAATTGTGTTTCTTACAGTCGCTG | SEQ ID NO: 1758 | Homo sapiens RP42 protein mRNA, complete cds. [AF292100] |
| 178 | A_23_P144151 | DCUN1D1 | TATGCTGTGTTTTCTTTAAAAGTCATATGGTTCGTTGGGTAATGCCTTGGATTTTACAT | SEQ ID NO: 1759 | Homo sapiens RP42 protein mRNA, complete cds. [AF292100] |
| 179 | A_23_P144497 | RPS3A | GAAAATCCGGAAGAACATGATGGAAATCATGACGCGAGAGGTGCAGAGCAAATGACTTGAA | SEQ ID NO: 1760 | Homo sapiens ribosomal protein S3A (RPS3A), mRNA [NM_001006] |
| 180 | A_23_P145114 | GCLC | AGAATGGGTGGTTTTCGGTTTGCAATTGGTTGCAATTGGTTGTGTGTAAATCAGGTGTAAAAGGGCAGATA | SEQ ID NO: 1761 | Homo sapiens glutamate-cysteine ligase, catalytic subunit (GCLC), mRNA [NM_001498] |
| 181 | A_23_P145397 | CCNC | TAGTGGACCACTTGGAAATAAACCATTGGACAGATGGACAGATTCAGTAATGTCTTCAGTGGAACAC | SEQ ID NO: 1762 | Homo sapiens cyclin C (CCNC), transcript variant 1, mRNA [NM_005190] |
| 182 | A_23_P14564 | GPR65 | AACAAGTTTAAATGTGTTGCTGATCGAATCGTGTAGTGTTTGTAACCGAAACAGGAAG | SEQ ID NO: 1763 | Homo sapiens G protein-coupled receptor 65 (GPR65), mRNA [NM_003608] |
| 183 | A_23_P145777 | NDUFA4 | ACGGTGCTTTAGAATGAAGATGAAGTCTTCCAGAAGGCCACATCCGACAATTTGCAGTTAACCA | SEQ ID NO: 1764 | Homo sapiens NADH dehydrogenase (ubiquinone) 1 alpha subcomplex, 4, 9kDa (NDUFA4), nuclear gene encoding mitochondrial protein, mRNA [NM_002489] |
| 184 | A_23_P14708 | SUHW4 | TCTTTGTACCTCCATACAAGTGTTTCAGGCATGGTCAGGAGTGGCTGTAAGGCTACCTTAATTAAACTT | SEQ ID NO: 1765 | Homo sapiens suppressor of hairy wing homolog 4 (Drosophila) (SUHW4), transcript variant 1, mRNA [NM_017661] |
| 185 | A_23_P14734 | RPS27L | TACAAGATCACCACGGTTTCAGGCATGGTGTTCATTGTTGGATGGTGAGGATTGTAGGTTGTTCA | SEQ ID NO: 1766 | Homo sapiens ribosomal protein S27-like (RPS27L), mRNA [NM_015920] |
| 186 | A_23_P147404 | A_23_P147404 | TGGGGTGAACATGAAATTGATTAGATTTGTTGGATGGTGAGGAGGCTGCCTCTCATGTG | SEQ ID NO: 1767 | |
| 187 | A_23_P148969 | LRRC40 | GCATGTATATCAATTTATATAGATAGGTAGATAGCTTTTGGATGATGGAGCATGCTAT | SEQ ID NO: 1768 | Homo sapiens leucine rich repeat containing 40 (LRRC40), mRNA [NM_017768] |
| 188 | A_23_P149775 | ARHGAP12 | TGTATAATAAAACACAGGGTTTGGAAGGTTTGTTACAGGGAGCATGCGTGTTGAAGAT | SEQ ID NO: 1769 | Homo sapiens Rho GTPase activating protein 12 (ARHGAP12), mRNA [NM_018287] |
| 189 | A_23_P149892 | GALNACT-2 | CATGGTGGTTCAGAATGAATAGATGAAGGATAGCATGGTTTTGTTTGTT | SEQ ID NO: 1770 | Homo sapiens chondroitin sulfate GalNAcT-2 (GALNACT-2), mRNA [NM_018590] |
| 190 | A_23_P151018 | LEMD3 | CCCCATTGTTAACCTGTTGCAAGAGTGAATGTAAAAATAGTTGTGGCATTTTAAAAGG | SEQ ID NO: 1771 | Homo sapiens LEM domain containing 3 (LEMD3), mRNA [NM_014319] |
| 191 | A_23_P151637 | RNASE2 | GTTGGTAACCCAAATATGACCTGTCCTAGTAAGAAAAACTCGGAAAAATTGTCACCACAGTG | SEQ ID NO: 1772 | Homo sapiens ribonuclease, RNase A family, 2 (liver, eosinophil-derived neurotoxin) (RNASE2), mRNA [NM_002934] |

Fig. 5-11

| No. | Probe ID No. | Symbols of genes | Sequence | SEQ ID NO: | Descriptions of genes letters and numbers within [ ] indicates GenBank accession No.) |
|---|---|---|---|---|---|
| 192 | A_23_P152002 | BCL2A1 | TGTAAGGATATTTGCATTTGAAGGTATTGTCATCAAGAAAGTTC TACGCAGCAGCAAATTGC | SEQ ID NO:1773 | Homo sapiens BCL2-related protein A1 (BCL2A1), mRNA [NM_004049] |
| 193 | A_23_P154330 | TXNDC9 | CTCAGTTGTTAAATTATCTGGGAAGGCTGGATTGCATTCTCTATTTT TCAGATTGACTTTATC | SEQ ID NO:1774 | Homo sapiens thioredoxin domain containing 9 (TXNDC9), mRNA [NM_005783] |
| 194 | A_23_P155765 | HMGB2 | TAAAAAATGGAGGTTGTAGCTTTTGATGGGCTAGTCATGATACAGT TAGATTTACAGCTTG | SEQ ID NO:1775 | Homo sapiens high-mobility group box 2 (HMGB2), mRNA [NM_002129] |
| 195 | A_23_P155815 | NCAPG | AAGTTAGGAAAGACGATGGAGGTGGAATCGTTAAGATTATGTC CAGTTATTTGCTTTAA | SEQ ID NO:1776 | Homo sapiens non-SMC condensin I complex, subunit G (NCAPG), mRNA [NM_022346] |
| 196 | A_23_P156355 | TMEM161B | AGGTTTGGACCTGCCATATTTTGTTTATTCTGTGATCCTAAGCT AGTTCGTTTAATAGG | SEQ ID NO:1777 | Homo sapiens transmembrane protein 161B (TMEM161B), mRNA [NM_153354] |
| 197 | A_23_P156842 | EEF1E1 | AAGAAAAGGAATCGTTCAGCAGTGGTTAGAATACAGAGGTCACT CAAGTAGATGGGCACT | SEQ ID NO:1778 | Homo sapiens eukaryotic translation elongation factor 1 epsilon 1 (EEF1E1), mRNA [NM_004280] |
| 198 | A_23_P157449 | POLR2K | GGTCTCTCTTGGTTCAAAATATCTTCTTGTACAGTAGACAGGCCAT TTTAGATGTGGTTGAC | SEQ ID NO:1779 | Homo sapiens polymerase (RNA) II (DNA directed) polypeptide K, 7.0kDa (POLR2K), mRNA [NM_005034] |
| 199 | A_23_P157452 | POLR2K | GGAATGCTCACTTATAGTTGGATTTGCTCTCTCTCCCATTTGT GATTGTTGTATAGGTT | SEQ ID NO:1780 | Homo sapiens polymerase (RNA) II (DNA directed) polypeptide K, 7.0kDa (POLR2K), mRNA [NM_005034] |
| 200 | A_23_P157795 | CTNNAL1 | GGATAGTAAAACTTGAAGGCTTTTGGGCTCAGATCTAGGAAG ATCATGTGATGAAGCT | SEQ ID NO:1781 | Homo sapiens catenin (cadherin-associated protein), alpha-like 1 (CTNNAL1), mRNA |
| 201 | A_23_P159650 | COX7B | CAAAATAGGGTAATGCTGTATTAGCTAGTAGTGGAGCCACTTTCTGTA TTGTTACATGGACATA | SEQ ID NO:1782 | Homo sapiens cytochrome c oxidase subunit VIIb (COX7B), nuclear gene encoding mitochondrial protein, mRNA [NM_001866] |
| 202 | A_23_P159839 | C1GALT1C1 | TCCAAATCAGATGCATGTGATGATGTATGGGGTATACCGCGTTA GGGCATTTGGGGATAT | SEQ ID NO:1783 | Homo sapiens C1GALT1-specific chaperone 1 (C1GALT1C1), transcript variant 1, mRNA [NM_152692] |
| 203 | A_23_P160406 | KCTD3 | TTGTAGGAGTGCAGTTCTGAATTTTGGGTTAAAGGTTTTGGCTG CTGTAAGAATGTGAAT | SEQ ID NO:1784 | Homo sapiens potassium channel tetramerisation domain containing 3 (KCTD3), mRNA [NM_016121] |
| 204 | A_23_P160466 | SLC19A2 | CTTGGTATGTGGCCATATTTATAGAATGCTGAAGCAATGTGCA AGTTGTACTGTATGCA | SEQ ID NO:1785 | Homo sapiens solute carrier family 19 (thiamine transporter), member 2 (SLC19A2), mRNA |
| 205 | A_23_P161091 | ZMYM1 | GAAGGTATTTTGCTAAGTGGTATTGTACGGGTGTATAGTGTCTT CAGCTTGCTCTCTCTG | SEQ ID NO:1786 | Homo sapiens zinc finger, MYM-type 1 (ZMYM1), mRNA [NM_024772] |
| 206 | A_23_P162596 | ACTR6 | TACTGTAGGGGGAAAATGTCAATTAGTAGCTTACCAGAGATAC TGTTCCTACGGATTTA | SEQ ID NO:1787 | Homo sapiens ARP6 actin-related protein 6 homolog (yeast) (ACTR6), mRNA [NM_022496] |
| 207 | A_23_P163113 | PRPF39 | GAGGATGCCTGGAAACAAGCTGGAGGTAGAATGAGTCTTTGTTCCA AGAAAATGGATGACTTG | SEQ ID NO:1788 | Homo sapiens PRP39 pre-mRNA processing factor 39 homolog (S. cerevisiae) (PRPF39), mRNA |
| 208 | A_23_P167828 | RWDD1 | AGAAATGGATGACTTG | SEQ ID NO:1789 | Homo sapiens RWD domain containing 1 (RWDD1), transcript variant 2, mRNA [NM_016104] |
| 209 | A_23_P16817 | CLK1 | AATTTGGGATTTCTGATAGAAGTGTTCTACTGAGCACCATG AAAGCATGGTGTTACT | SEQ ID NO:1790 | Homo sapiens CDC-like kinase 1 (CLK1), transcript variant 1, mRNA [NM_004071] |
| 210 | A_23_P168656 | GTPBP10 | AATTTGGGATTTCTGATAGAAGTGTTCTACTGAGCACCATG AAAGCATGGTGTTACT | SEQ ID NO:1791 | Homo sapiens GTP-binding protein 10 (putative) (GTPBP10), transcript variant 2, mRNA [NM_033107] |
| 211 | A_23_P169050 | MRPS28 | GAGGAAGAAGAGATACAAACTGTACTAGAGAGGGTAATGGAGTTCTC TTGGGAATCCAGGAGA | SEQ ID NO:1792 | Homo sapiens mitochondrial ribosomal protein S28 (MRPS28), nuclear gene encoding mitochondrial protein, mRNA [NM_014018] |

Fig. 5-12

| No. | Probe ID No. | Symbols of genes | Sequence | SEQ ID NO: | Descriptions of genes (letters and numbers within [ ] indicates GenBank accession No.) |
|---|---|---|---|---|---|
| 212 | A_23_P17021 | SCRN3 | GTCAAAGTTAGTTGTTAGTGATGATGCATATGGTCAGCTAATATTAGTTCTTAGTGATCAGTGG | SEQ ID NO: 1793 | Homo sapiens secernin 3 (SCRN3), mRNA [NM_024583] |
| 213 | A_23_P170233 | CSTA | AAGTGGGTAGTGAGTGATGATGATCCTTGCTGATAAATATAAGCATCAATAAACAAGCCATCT | SEQ ID NO: 1794 | Homo sapiens cystatin A (stefin A) (CSTA), mRNA [NM_005213] |
| 214 | A_23_P18325 | PDCD10 | CCAAGCGGAGTAATTGATCAAACGAAGCTAATACTTCAGACGTTGAAAACTGTGGCCTGAA | SEQ ID NO: 1795 | Homo sapiens programmed cell death 10 (PDCD10), transcript variant 1, mRNA [NM_007217] |
| 215 | A_23_P18422 | MRPL3 | CAGTAGAAAACCATATGGGAGTATAGTGGAAGGTATTTGGGTAAAGAAACCATTTGGTA | SEQ ID NO: 1796 | Homo sapiens mitochondrial ribosomal protein L3 (MRPL3), nuclear gene encoding mitochondrial protein, mRNA [NM_007208] |
| 216 | A_23_P18598 | PI4K2B | AGGCTTAAAACCAATGTCACCACTGTGGGCTTAAGTGGGTAATTTGTGGTCAGGCTTTT | SEQ ID NO: 1797 | Homo sapiens phosphatidylinositol 4-kinase type 2 beta (PI4K2B), mRNA [NM_018323] |
| 217 | A_23_P19291 | TUBB2A | ACTTCTCAGATCAATCGTGCATCCTTGATGAACTTCTGTTGTCCTCAAGGATGGTCTTTC | SEQ ID NO: 1798 | Homo sapiens tubulin, beta 2A (TUBB2A), mRNA [NM_001069] |
| 218 | A_23_P200030 | FPGT | TAAAAATTGTAAACTAGAAGTAACTTGTCCACAAGCCTCAGTTATGATACTTATGTGCG | SEQ ID NO: 1799 | Homo sapiens fucose-1-phosphate guanylyltransferase (FPGT), mRNA [NM_003838] |
| 219 | A_23_P200298 | AGL | TAGAATTTTAACAGGTGTCATTGACTAAAGGTTTCGGTAGAATGGTCATACTTGAGTTG | SEQ ID NO: 1800 | Homo sapiens amylo-1, 6-glucosidase, 4-alpha-glucanotransferase (glycogen debranching enzyme, glycogen storage disease type III) (AGL), transcript variant 4, mRNA [NM_000028] |
| 220 | A_23_P200507 | CNIH4 | TGGTTGAAGTCAGGCTACACTACAGTGCACAGTTGAGGAGGCAGAGACTTCTTAAATCAT | SEQ ID NO: 1801 | Homo sapiens cornichon homolog 4 (Drosophila) (CNIH4), mRNA [NM_014184] |
| 221 | A_23_P200955 | A_23_P200955 | AGACCATGATTGAAGCTGAGATTGATGTCAAGACTACCGATGGTTATTGTTCATCTAC | SEQ ID NO: 1802 | |
| 222 | A_23_P201619 | NEK7 | TGAAGGCCAAGAGGAAGTCACGTGTTAAAGGAGTCTGTGCGATCTTACAACGTTGGATGAA | SEQ ID NO: 1803 | Serine/threonine-protein kinase Nek7 (EC 2.7.11.1) (NimA-related protein kinase 7). [Source:Uniprot/SWISSPROT;Acc:Q8TDX7] [ENST00000367385] |
| 223 | A_23_P201918 | ABCB10 | CATGGATGAGGCTAGAGCCTAAGAAGAAGTAATTAAGTCAATGTAAATCAAATCGGAAGTTTTC | SEQ ID NO: 1804 | Homo sapiens ATP-binding cassette, sub-family B (MDR/TAP), member 10 (ABCB10), nuclear gene encoding mitochondrial protein, mRNA [NM_012089] |
| 224 | A_23_P202587 | KIAA1598 | GTAATAATTCCAGTAGTTGTGTATTGTATTTTGGCAGGTGTGGTAAGGATAGGGTTG | SEQ ID NO: 1805 | Homo sapiens KIAA1598 (KIAA1598), mRNA [NM_018330] |
| 225 | A_23_P203376 | MS4A6A | ACGGGGCTGTAAATTACGATTTACTAGATTAGCCAAATAGTCTGAATTCGAGAAAACAA | SEQ ID NO: 1806 | Homo sapiens membrane-spanning 4-domains, subfamily A, member 6A (MS4A6A), transcript variant 1, mRNA [NM_152852] |
| 226 | A_23_P203498 | TRIM22 | GTACATAAGAATGTATGACTAAGTAATGTATCCTTCAGAATGTGTTGGTTACCAGTGAC | SEQ ID NO: 1807 | Homo sapiens tripartite motif-containing 22 (TRIM22), mRNA [NM_006074] |
| 227 | A_23_P203845 | CREBZF | TCTGTTGGAGTATTTTGTTGGTTACGTCAATACTTTCCTGGATTATTTGAAATTGTGGG | SEQ ID NO: 1808 | Homo sapiens CREB/ATF BZIP transcription factor (CREBZF), mRNA [NM_001039618] |
| 228 | A_23_P204187 | FLJ22028 | CTATAAGGTTGTAGTGGTGGGAAAATAGAAATGCACAGGGCTTAGGTCAGATCATGAATT | SEQ ID NO: 1809 | Homo sapiens hypothetical protein FLJ22028 (FLJ22028), mRNA [NM_024854] |
| 229 | A_23_P204269 | USP15 | GACCAAGGATAAATGAGGTATGTTGATCATGGCTTGCTTTATATCTTGATTATTAAAGCTG | SEQ ID NO: 1810 | Homo sapiens ubiquitin specific peptidase 15 (USP15), mRNA [NM_006313] |

Fig. 5-13

| No. | Probe ID No. | Symbols of genes | Sequence | SEQ ID NO: | Descriptions of genes (letters and numbers within [ ] indicates GenBank accession No.) |
|---|---|---|---|---|---|
| 230 | A_23_P205027 | ABHD13 | ATTGTGGAGAATGATAAAGAATGTTCGTTTAGAAGTGTGTTATGTGTGTACCTGTGTG | SEQ ID NO: 1811 | Homo sapiens abhydrolase domain containing 13 (ABHD13), mRNA [NM_032859] |
| 231 | A_23_P205336 | C14orf129 | CAATTCATTGGCAGACTTGATTGGAATGGTTGTTTGATGATGTATGTTCATTCTCAGCT | SEQ ID NO: 1812 | Homo sapiens chromosome 14 open reading frame 129 (C14orf129), mRNA [NM_016472] |
| 232 | A_23_P205846 | MAP4K5 | CTATGTGAGCAGGGAGGAAGTATTTAATTGCCCAATGATATGTTTTACTTATACTATGCC | SEQ ID NO: 1813 | Homo sapiens mitogen-activated protein kinase kinase kinase kinase 5 (MAP4K5), transcript variant 2, mRNA [NM_198794] |
| 233 | A_23_P20606 | NIPSNAP3A | GTAAGTAGCACTTCAAAAAATAGTTGTGTTTACTTCTGCATGGTATTTCAGTGTGTGTC | SEQ ID NO: 1814 | Homo sapiens nipsnap homolog 3A (C. elegans) (NIPSNAP3A), mRNA [NM_015469] |
| 234 | A_23_P206228 | VPS13C | GGGATGCATTATCAGTAATTCATAGCAACGTTCTAGTGTTTGTGTTTTTAAAACAGAA | SEQ ID NO: 1815 | Homo sapiens vacuolar protein sorting 13 homolog C (S. cerevisiae) (VPS13C), transcript variant 1A, mRNA [NM_017684] |
| 235 | A_23_P207299 | LOC51136 | CCAAAACAGGAATTTGAAATTAGAACTAGTGGTTTAGAGAACTCAGGTATTGTTCCTG | SEQ ID NO: 1816 | Homo sapiens PT0G16 protein (LOC51136), mRNA [NM_016125] |
| 236 | A_23_P209032 | ZNF302 | TCAGAAAAATGTATAGTGGGGAAAAGTTGTATGAAGGTGGTGAACATGGGAAGACTTTTTAG | SEQ ID NO: 1817 | Homo sapiens zinc finger protein 302 (ZNF302), transcript variant 1, mRNA [NM_018443] |
| 237 | A_23_P209232 | CLIP4 | GCTTATGAAAGTCATTTAAAGTTCACTTGTCTGAGCATGAACAATAAAAAGGAAGGTGTGTG | SEQ ID NO: 1818 | Homo sapiens CAP-GLY domain containing linker protein family, member 4 (CLIP4), mRNA [NM_024692] |
| 238 | A_23_P209625 | CYP1B1 | CTGTGTTTAATGAGAAGAAAGTAAGGTGCTTAGGTGGAGTTTAGGTCTGTAGCTTATTAATGTGTT | SEQ ID NO: 1819 | Homo sapiens cytochrome P450 family 1, subfamily B, polypeptide 1 (CYP1B1), mRNA [NM_000104] |
| 239 | A_23_P210001 | PAX8 | CAAGCTTCCTCTTTTCTAACCCCCAGACTTTGGGCCTCTGAGTGAAATGCTCTGTTTGCC | SEQ ID NO: 1820 | Homo sapiens paired box gene 8 (PAX8), transcript variant PAX8A, mRNA [NM_003466] |
| 240 | A_23_P210274 | PREI3 | GGATAGTATGCGGTAGGAATTTAGAGAATATTTCACATGGTTATTTCATCATGGGCAG | SEQ ID NO: 1821 | Homo sapiens preimplantation protein 3 (PREI3), transcript variant 1, mRNA [NM_015387] |
| 241 | A_23_P210829 | PCMTD2 | TGCTGGGCACCTTATAGCCAGAATTCAGTATAATACAGTACTTCTGTTTTGAAACAGATA | SEQ ID NO: 1822 | Homo sapiens protein-L-isoaspartate (D-aspartate) O-methyltransferase domain containing 2 (PCMTD2), mRNA [NM_018257] |
| 242 | A_23_P211840 | UBE1C | GCCACGCTAGAGGGGTCTGTTGTTCTAGATTCATATTGCACTCGGTAACCTCTATTGAAGAA | SEQ ID NO: 1823 | Homo sapiens ubiquitin-activating enzyme E1C (UBA3 homolog, yeast) (UBE1C), transcript variant 1, mRNA [NM_003968] |
| 243 | A_23_P212383 | SACM1L | GCCTCTGAGAGGGTCTGTTGTTCTAGATTTCATATTGCACTGGAGGGTAACAGGTGCTTT | SEQ ID NO: 1824 | Homo sapiens SAC1 suppressor of actin mutations 1-like (yeast) (SACM1L), mRNA [NM_014016] |
| 244 | A_23_P2129 | TMEM126B | CATATAGGCATCATTGGCTACACTTCCATTTTGTCTACTGTTGTTACTGACAAGGTTTTG | SEQ ID NO: 1825 | Homo sapiens transmembrane protein 126B (TMEM126B), mRNA [NM_018480] |
| 245 | A_23_P213838 | PANK3 | TGTATATTGGCAGTGTTAAATCCTTAAATGCAATAGAGCCTCTGATTATTGAGCTTCGTC | SEQ ID NO: 1826 | Homo sapiens pantothenate kinase 3 (PANK3), mRNA [NM_024594] |
| 246 | A_23_P213661 | HISPPD1 | GTATGTAAGTTTTGTGTTTTGTGAAAATGTAGTTAATGTAGTGACGTGGAAGGTCATAAGG | SEQ ID NO: 1827 | Homo sapiens histidine acid phosphatase domain containing 1 (HISPPD1), mRNA [NM_015216] |
| 247 | A_23_P213718 | UQCRQ | TTGGGTGTCTCTGAAAAGACGTTTCTCTGAAGAGGAGTGTGCATTGTAGTGTCTCAAAGA | SEQ ID NO: 1828 | Homo sapiens ubiquinol-cytochrome c reductase, complex III subunit VII, 9.5kDa (UQCRQ), nuclear gene encoding mitochondrial protein, mRNA [NM_014402] |

Fig. 5-14

| No. | Probe ID No. | Symbols of genes | Sequence | SEQ ID NO: | Descriptions of genes (letters and numbers within [ ] indicates GenBank accession No.) |
|---|---|---|---|---|---|
| 248 | A_23_P214108 | TPMT | GGTTGATGATCTTTTGAAGAACGACATAAAAGTTGGGGAATTGACT GTGTTTTTGAAAAGTT | SEQ ID NO: 1829 | Homo sapiens thiopurine S-methyltransferase (TPMT), mRNA [NM_000367] |
| 249 | A_23_P215051 | ECHDC1 | TTTTTGAGAGGTAAACTGTAGATTACTGTGTCAACCGAATAGT ATTGGCGATAGATGT | SEQ ID NO: 1830 | Homo sapiens enoyl Coenzyme A hydratase domain containing 1 (ECHDC1), mRNA [NM_018479] |
| 250 | A_23_P215751 | NDUFA5 | TAAAAGTGGAGTCACTAAATAGTTGGCAGTAGTTTCTAATATA AGTGTAGGTGGGTATC | SEQ ID NO: 1831 | Homo sapiens NADH dehydrogenase (ubiquinone) 1 alpha subcomplex, 5, 13kDa (NDUFA5), nuclear gene encoding mitochondrial protein, mRNA [NM_005000] |
| 251 | A_23_P216708 | RFK | ACTCAGAAAAACATGTAAAGCTGTTGGAGAAGAGGAGTGCATAT AAATAGTTGGATTGGG | SEQ ID NO: 1832 | Homo sapiens riboflavin kinase (RFK), mRNA [NM_018339] |
| 252 | A_23_P21734 | TAF9 | CATGGTGTGATTTCTCCCTGAACGCTGGTTTCATATAGTTT TGTGCTGAGAACAGAT | SEQ ID NO: 1833 | Homo sapiens TAF9 RNA polymerase II, TATA box binding protein (TBP)-associated factor, 32kDa (TAF9), transcript variant 3, mRNA [NM_001015091] |
| 253 | A_23_P217384 | AP1S2 | AAAGTGTTGCTGTCTTCACAGTATTATGTGTAAAGTCATTGTT TAAAGCACGAATGTTC | SEQ ID NO: 1834 | Homo sapiens adaptor-related protein complex 1, sigma 2 subunit (AP1S2), mRNA [NM_003916] |
| 254 | A_23_P217564 | ACSL4 | GTTATATAGGTCGTTTAGAAAGACATAATTAACACAAGTTAAGGTTGGG TGTGCTAATTCTTG | SEQ ID NO: 1835 | Homo sapiens acyl-CoA synthetase long-chain family member 4 (ACSL4), transcript variant 1, mRNA [NM_004458] |
| 255 | A_23_P217797 | DDX3Y | CACTGATAGGAAGGTCCACATGCACAAAGTTTCTCTTGAGTTT GTTATGTGTTTGCTG | SEQ ID NO: 1836 | Homo sapiens DEAD (Asp-Glu-Ala-Asp) box polypeptide 3, Y-linked (DDX3Y), mRNA [NM_004660] |
| 256 | A_23_P218928 | C4orf16 | CAGATGAGTTGCATTTGCTTCTGTAGATGTGTTTCAGAGGCTAGG TACAGACTTGATAC | SEQ ID NO: 1837 | Homo sapiens chromosome 4 open reading frame 18 (C4orf18), transcript variant 2, mRNA [NM_016613] |
| 257 | A_23_P219072 | SAMD9 | AACCTACCTCCAGATTAGTAAGGCCAGTTGAAAAACTAAAAGAT CAGCTTCGAGAAGTC | SEQ ID NO: 1838 | Homo sapiens sterile alpha motif domain containing 9 (SAMD9), mRNA [NM_017654] |
| 258 | A_23_P219161 | OLFM1 | GGGCTAACTTAAAAGAGTTTTTCAATGCTGCAGTGACTGAAGAA AGCAGTTCCAGTCGCAT | SEQ ID NO: 1839 | Homo sapiens olfactomedin 1 (OLFM1), transcript variant 2, mRNA [NM_006334] |
| 259 | A_23_P22433 | RP2 | TATTTGTCTTGCATTAATAGTAGTGGTGTTTTGTTTTTGGTTC TTTATATTTATCTCTA | SEQ ID NO: 1840 | Homo sapiens retinitis pigmentosa 2 (X-linked recessive) (RP2), mRNA [NM_006915] |
| 260 | A_23_P2262 | SURB7 | ATGTGGCTGAGAAAAGACAGTAGAGAGCTTGAAAATTGCTG CATCAGACTCTGTGTGA | SEQ ID NO: 1841 | Homo sapiens SRB7 suppressor of RNA polymerase B homolog (yeast) (SURB7), mRNA [NM_004264] |
| 261 | A_23_P22671 | SYBL1 | GAAAACGGAATACGGTCAGGACTGAGCAGTCAAGTCCAAGGTTGGGGTTGA TTCCTGTTGAATAATA | SEQ ID NO: 1842 | Homo sapiens synaptobrevin-like 1 (SYBL1), mRNA [NM_005638] |
| 262 | A_23_P2356 | NUDT4 | CATCAGTGTGTGGTTATTTGTCATCAGATTACTGTGGGGTAT ACCTACCCAAAATTG | SEQ ID NO: 1843 | Homo sapiens nudix (nucleoside diphosphate linked moiety X)-type motif 4 (NUDT4), transcript variant 2, mRNA [NM_199040] |
| 263 | A_23_P23765 | ITGB3BP | AGTATACAAGGGTTTGGAGGGCAGTAGAGAGCTTGAAACTCAT TGGAATCTCCTGTGA | SEQ ID NO: 1844 | Homo sapiens integrin beta 3 binding protein (beta3-endonexin) (ITGB3BP), mRNA [NM_014288] |
| 264 | A_23_P23860 | BLOC1S2 | GAGTAAACTGGAGGACTGTGGGTATTCCTGGAACCTTGTTGAGA CAGAATCTGCTCAGAAT | SEQ ID NO: 1845 | Homo sapiens biogenesis of lysosome-related organelles complex-1, subunit 2 (BLOC1S2), transcript variant 2, mRNA [NM_001001342] |
| 265 | A_23_P24365 | ANKRD49 | GGGCACTGCTTGTATAGTCTCCAAGTTGACACGGAAAGTTGCAT TTTCTAAGGTCCTCAT | SEQ ID NO: 1846 | Homo sapiens ankyrin repeat domain 49 (ANKRD49), mRNA [NM_017704] |

Fig. 5-15

| No. | Probe ID No. | Symbols of genes | Sequence | SEQ ID NO.: | Descriptions of genes (letters and numbers within [ ] indicates GenBank accession No.) |
|---|---|---|---|---|---|
| 266 | A_23_P250602 | HACE1 | TAAGGAGTCATTGTGTTTGCCAGTAATGTTTGAGAGACATGTAAGTTGAAAGTTTTGCTA | SEQ ID NO: 1847 | Homo sapiens HECT domain and ankyrin repeat containing, E3 ubiquitin protein ligase 1 (HACE1), mRNA [NM_020771] |
| 267 | A_23_P250800 | ST3GAL6 | ATGTCACGAAGTTCACCTAGGTGGTTTTAAATACAACGTTCTGACCTCAAGAGTCGTTT | SEQ ID NO: 1848 | Homo sapiens ST3 beta-galactoside alpha-2,3-sialyltransferase 6 (ST3GAL6), mRNA [NM_006100] |
| 268 | A_23_P250930 | CRBN | TGATGTATTGAGAATTCAGGTGGTTAAAATTGGCAGTGGTATCCAGCGACTTCGCTGTGA | SEQ ID NO: 1849 | Homo sapiens cereblon (CRBN), mRNA [NM_016302] |
| 269 | A_23_P250994 | ANAPC10 | GATTCATGTTCGGTTAAGTCACAATCATAAGAAAGCCAAGTCGTACATTCATGATACAGAT | SEQ ID NO: 1850 | Homo sapiens anaphase promoting complex subunit 10 (ANAPC10), mRNA [NM_014885] |
| 270 | A_23_P251937 | CPEB4 | GTATGTCAGTTAATTGTACTACTTGGCTGAATTTGCATATAGTTTTTAGTGTGTATGGGG | SEQ ID NO: 1851 | Homo sapiens cytoplasmic polyadenylation element binding protein 4 (CPEB4), mRNA [NM_030627] |
| 271 | A_23_P252145 | C1GALT1 | ATATGTCTATATATGAGGAACTTGTGTTTTTAAATGGTGGCCAGGTAGAGGAACTAG | SEQ ID NO: 1852 | Homo sapiens core 1 synthase, glycoprotein-N-acetylgalactosamine 3-beta-galactosyltransferase, 1 (C1GALT1), mRNA [NM_020156] |
| 272 | A_23_P252201 | EAF2 | CAGGATTCCTGATATAGATGCCAGTCATAATAAGATTTCGAGACAACAGTGGCCTTCTGAT | SEQ ID NO: 1853 | Homo sapiens ELL associated factor 2 (EAF2), mRNA [NM_018456] |
| 273 | A_23_P252235 | CLEC4D | CATTTAACCGACGGAGAGTATTCTGGCATAAGAATGAACCCGACAAGTCTCAGGGAGAAA | SEQ ID NO: 1854 | Homo sapiens C-type lectin domain family 4, member D (CLEC4D), mRNA [NM_080387] |
| 274 | A_23_P252371 | RBBP8 | GGCAAGAGGAGCAAAGACATAGAGGTTGAAAGAGAAACAGAGAAGGATGAAGGACAGTTTTT | SEQ ID NO: 1855 | Homo sapiens retinoblastoma binding protein 8 (RBBP8), transcript variant 1, mRNA [NM_002894] |
| 275 | A_23_P252403 | COMMD10 | GCGTCATGGATACAAGATAAGATGTGTACCTTAGTAGAATACAGAGCTTGGTAATTAC | SEQ ID NO: 1856 | Homo sapiens COMM domain containing 10 (COMMD10), mRNA [NM_016144] |
| 276 | A_23_P253412 | MRPL50 | GAAAAGTTTTGAGAGGGCACTGTCAACTTGGGTTAAGACAGGAGGACATTGCAAGTTCA | SEQ ID NO: 1857 | Homo sapiens mitochondrial ribosomal protein L50 (MRPL50), nuclear gene encoding mitochondrial protein, mRNA [NM_019051] |
| 277 | A_23_P254472 | C6orf211 | TTCATTTGAATAGCTTGTTTCATTTGCACGCGTTTGTATTTTGATTGACGTCTAGAATGG | SEQ ID NO: 1858 | Homo sapiens chromosome 6 open reading frame 211 (C6orf211), mRNA [NM_024573] |
| 278 | A_23_P254702 | DEK | TTTTTTATTAACTGCTTTTGCCCATATAACATGCTGATATTACTGGAAACGTAGGCAGC | SEQ ID NO: 1859 | Homo sapiens DEK oncogene (DNA binding) (DEK), mRNA [NM_003472] |
| 279 | A_23_P255503 | FNDC3A | ATAGTTGCCATTTGAGCCTCACTGACAAAATTAGTGCAGGAGAAAACAATTTTAATGT | SEQ ID NO: 1860 | Homo sapiens fibronectin type III domain containing 3A (FNDC3A), transcript variant 2, mRNA [NM_014923] |
| 280 | A_23_P255663 | MANEA | AAAGAGTCTGTACATCTTCAGAGTTTCAGTCGGCAATTCTGGCCATGGATGTAGAACC | SEQ ID NO: 1861 | Homo sapiens mannosidase, endo-alpha (MANEA), mRNA [NM_024641] |
| 281 | A_23_P255827 | FKSG2 | ACTACGGTAAGGATGGTCAGTAGATGACCCATATGATTTTTTAAGGAATGGTTTAGAAA | SEQ ID NO: 1862 | Homo sapiens apoptosis inhibitor (FKSG2), mRNA [NM_021631] |
| 282 | A_23_P255638 | C13orf7 | CTTGGATTCCAGGGAGGAGTTTTGTTTGAGTAGTAGTATGTTTGTGTTTGCATGTTCGTGTTC | SEQ ID NO: 1863 | Homo sapiens chromosome 13 open reading frame 7 (C13orf7), mRNA [NM_024546] |
| 283 | A_23_P25735 | PSMA6 | TAGGAGAGAGACTAAACATTGTGGTTAGTTTACGAGATGCGTGATGCCACTTACCTGT | SEQ ID NO: 1864 | Homo sapiens proteasome (prosome, macropain) subunit, alpha type, 6 (PSMA6), mRNA [NM_002791] |
| 284 | A_23_P257911 | USP16 | GTAGTTTGTGTTTAATATATCTGGGTGATGAATCACACAACATCAATAAACTCACTTACC | SEQ ID NO: 1865 | Homo sapiens ubiquitin specific peptidase 16 (USP16), transcript variant 1, mRNA [NM_006447] |

Fig. 5-16

| No. | Probe ID No. | Symbols of genes | Sequence | SEQ ID NO: | Descriptions of genes (letters and numbers within [ ] indicate GenBank accession No.) |
|---|---|---|---|---|---|
| 285 | A_23_P258108 | LOC731224 | GTGAGCCCAGGTGTTGCTTGTTCAATATCCAAGCCCAGAAAGATCAGTTCATGTTAAA | SEQ ID NO:1866 | PREDICTED: Homo sapiens similar to 60S ribosomal protein 19 (LOC731224), mRNA [XR_015767] |
| 286 | A_23_P258582 | GK5 | ATGCCATTTGGAGACAGATATGATAGAAGTAGAAATTAAGATTCATTGTTGCAAGTGC | SEQ ID NO:1867 | Homo sapiens glycerol kinase 5 (putative) (GK5), mRNA [NM_001039547] |
| 287 | A_23_P259054 | SNX14 | CATCAGACTTCTGTTTTGATGGCTTAGAGCAACCAGTACTCAACAAGCAGCTCAGTATGT | SEQ ID NO:1868 | Homo sapiens sorting nexin 14 (SNX14), transcript variant 1, mRNA [NM_153816] |
| 288 | A_23_P26021 | COPS2 | TGGTTTTTGATCAACTGGTTGGTTTGTGTTTGCTGCTGATTATCCCAAGAAAAACAAGCTT | SEQ ID NO:1869 | Homo sapiens COP9 constitutive photomorphogenic homolog subunit 2 (Arabidopsis) (COPS2), mRNA [NM_004236] |
| 289 | A_23_P26713 | RPL23 | TGGCCCCGGATTGCATCCAATGCTGGCAGCAATGGATGATCTGCCAGTATATTGTAAAA | SEQ ID NO:1870 | Homo sapiens ribosomal protein L23 (RPL23), mRNA [NM_000978] |
| 290 | A_23_P2705 | P2RY5 | TCTGTATTGCTTCCAACTGTTGTTTTGACCCTATAGTTTACTACATCGGACA | SEQ ID NO:1871 | Homo sapiens purinergic receptor P2Y, G-protein coupled, 5 (P2RY5), mRNA [NM_005767] |
| 291 | A_23_P29005 | SAMSN1 | CTCTGGTTGCTATATCTCATCAGGAAATTCAGATAATGGCAAAGAGGATCTGGAGTCTGA | SEQ ID NO:1872 | Homo sapiens SAM domain, SH3 domain and nuclear localization signals 1 (SAMSN1), mRNA [NM_022136] |
| 292 | A_23_P302550 | RGS18 | GAGTGTAAGGCCCTAGGGATTGGCATCTGGGACATGGAATTGGTCATGTTTA | SEQ ID NO:1873 | Homo sapiens regulator of G-protein signalling 18 (RGS18), mRNA [NM_130782] |
| 293 | A_23_P30307 | CRSP9 | CAATTGTACGTGGACAGAATGAAGAATGAAAGACAAAATTGAGGTCATAGGAGAGATCAGAT | SEQ ID NO:1874 | Homo sapiens cofactor required for Sp1 transcriptional activation, subunit 9, 33kDa (CRSP9), mRNA [NM_004270] |
| 294 | A_23_P305140 | C10orf32 | AAATGGACTCTATATTGTTGTAGTTCAGGTGTTCATTGACTAGGAGATGAGAGAAATC | SEQ ID NO:1875 | Homo sapiens chromosome 10 open reading frame 32 (C10orf32), mRNA [NM_144591] |
| 295 | A_23_P307940 | CAPZA2 | CTACAAGATTAAGCAAAGATGACTGTCAAGTGAATGAGTGTGTGATATGCATGAGAACATT | SEQ ID NO:1876 | Homo sapiens capping protein (actin filament) muscle Z-line, alpha 2 (CAPZA2), mRNA [NM_006136] |
| 296 | A_23_P308600 | GLS | CCGAAGAGAGATTAAGATATACTGGAAATAGGCCCTCAAAGTTAAAAAGAAAAAACTTTG | SEQ ID NO:1877 | Homo sapiens glutaminase C mRNA, complete cds. [AF158555] |
| 297 | A_23_P30956 | KIAA0776 | TTTTTCATTTGTCAAAATGGTCTTCTTTTGTTGCCAGAGTAAAGAACAGTTTTATTGTTT | SEQ ID NO:1878 | Homo sapiens KIAA0776 (KIAA0776), mRNA [NM_015323] |
| 298 | A_23_P31097 | OSTM1 | ACTGAAAATGTGCTGGGTTTGTTCTGCAGTGTTAGCTGCTGGAACTTAGCACT | SEQ ID NO:1879 | Homo sapiens osteopetrosis associated transmembrane protein 1 (OSTM1), mRNA [NM_014028] |
| 299 | A_23_P312246 | CCDC82 | GGCTTATAACAGATGACTGTCAAGTGAATGAGTGTGATATCCTGTCAGTTTAGCAA | SEQ ID NO:1880 | Homo sapiens coiled-coil domain containing 82 (CCDC82), mRNA [NM_024725] |
| 300 | A_23_P314191 | ZDHHC17 | TGGATACTTTTAGCAAATAGGAAGTTAATTCTCAGGACAGGAGTAATAACCACAGTGAATTACTTCCTTGG | SEQ ID NO:1881 | Homo sapiens zinc finger, DHHC-type containing 17 (ZDHHC17), mRNA [NM_015336] |
| 301 | A_23_P314591 | NFYB | GGAGGCATTTACTAACCAGTTACCAGCTGGCTTAATAATGACACGATCACGGTCAACAACAAA | SEQ ID NO:1882 | Homo sapiens nuclear transcription factor Y, beta (NFYB), mRNA [NM_006166] |
| 302 | A_23_P31671 | UQCRB | AAGGCATAAGAAGACTTCCTGAGAACCTTTATAATGACACGGATGTTTGGCATTAAGAGGG | SEQ ID NO:1883 | Homo sapiens ubiquinol-cytochrome c reductase binding protein (UQCRB), mRNA [NM_006294] |
| 303 | A_23_P31702 | PXMP3 | CTTCTCTGGCATGGTTTGGAATTCTGAATTTCTGATTTTTCTGTTACCAGTTATCAATGTCCAG | SEQ ID NO:1884 | Homo sapiens peroxisomal membrane protein 3, 35kDa (Zellweger syndrome) (PXMP3), transcript variant 1, mRNA [NM_000318] |
| 304 | A_23_P317347 | ESCO1 | GGTAATTTTAAAAGGCCTGAAACTATAGTTTGAAGAAACCCTATAGAAAGGAAAGCTC | SEQ ID NO:1885 | Homo sapiens establishment of cohesion 1 homolog 1 (S. cerevisiae) (ESCO1), mRNA [NM_052911] |

Fig. 5-17

| No. | Probe ID No. | Symbols of genes | Sequence | SEQ ID NO. | Descriptions of genes (letters and numbers within [ ] indicates GenBank accession No.) |
|---|---|---|---|---|---|
| 305 | A_23_P319133 | DNAJC10 | TCTAGGAAAGGGATCTTCTAGTTCTGTCGTTGTTAGACTCAAA GAATGAGAAATTTGTG | SEQ ID NO: 1886 | Homo sapiens DnaJ (Hsp40) homolog, subfamily C, member 10 (DNAJC10), mRNA [NM_018981] |
| 306 | A_23_P3204 | MAPK6 | AACGTGCTCACTGTGATAGGCAGTGATATACGGAATTTGTATTTGGAAGGTGCTTG ATCTATCAGAAAGAA | SEQ ID NO: 1887 | Homo sapiens mitogen-activated protein kinase 6 (MAPK6), mRNA [NM_002748] |
| 307 | A_23_P324633 | C9orf72 | TTTGTGGATTTAGTGCGTGGGATTCAGTCGTGTAGAAAATGTGCTAA TAGTTCTCTATGTCG | SEQ ID NO: 1888 | Homo sapiens chromosome 9 open reading frame 72 (C9orf72), transcript variant 1, mRNA [NM_018325] |
| 308 | A_23_P327022 | MDFIC | TTATGATTCTTAATGTAATGTAAAATGTTTGTTGGAAGTATATGGCTA TCATGACTAAGTGCTA | SEQ ID NO: 1889 | Homo sapiens MyoD family inhibitor domain containing (MDFIC), mRNA [NM_199072] |
| 309 | A_23_P33045 | RPL26 | TACAAAGGTCAGGAAATTGGCAAAGTAGTCCAGGTTTACAGGAA GAAATATGTTTATCTAC | SEQ ID NO: 1890 | Homo sapiens ribosomal protein L26 (RPL26), mRNA [NM_000987] |
| 310 | A_23_P332439 | NUPL1 | ATTGAAATCTTGAATGTTGAATCTGTGAAGGTACACAGCGGT GCCTTGTAAATGTTC | SEQ ID NO: 1891 | Homo sapiens KIAA0410 mRNA, partial cds. [AB007870] |
| 311 | A_23_P339480 | HAT1 | AAGAATGAACAGCGTGGAAGAGAGTTTCAGGAACTAGTGGAAGAT TACGGGGGTGTGTATTG | SEQ ID NO: 1892 | Homo sapiens histone acetyltransferase 1 (HAT1), transcript variant 1, mRNA [NM_003642] |
| 312 | A_23_P341416 | ZDHHC20 | TGTGAGTTAATGTTGATGCTTGGTTTGTCTTTGTGGGGCTA ACCTACATTGACATGT | SEQ ID NO: 1893 | Homo sapiens cDNA FLJ25952 fis, clone SYN00911. [AK098818] |
| 313 | A_23_P34307 | PIGK | ATTCATTCAGAGTCTTCTATTGTTGGACGACTTACAGTTGTACC AAATGTTTTGGCTTGG | SEQ ID NO: 1894 | Homo sapiens phosphatidylinositol glycan anchor biosynthesis, class K (PIGK), mRNA [NM_005482] |
| 314 | A_23_P345591 | PSMA2 | GCCTGGAAAGCTACAGGAGTAGTCCAGGTTTACAGGGAA GACTTTCGTTGAGAAA | SEQ ID NO: 1895 | Homo sapiens proteasome (prosome, macropain) subunit, alpha type, 2 (PSMA2), mRNA [NM_002787] |
| 315 | A_23_P347059 | MOBKL1A | CTAGAAGGGAAAAATCATCTAAGTTATGAAATCCAACATAGGC GGTATATTAGAAACTG | SEQ ID NO: 1896 | Homo sapiens MOB1, Mps One Binder kinase activator-like 1A (yeast) (MOBKL1A), mRNA [NM_173468] |
| 316 | A_23_P347198 | SP3 | GACCACCTGCAAATTTAAAGGGTACCTTATTGTACGTTAAAGTG TATTAAACAGTGTGG | SEQ ID NO: 1897 | Homo sapiens Sp3 transcription factor (SP3), transcript variant 1, mRNA [NM_003111] |
| 317 | A_23_P349083 | FCHO2 | TGTGAAATGGTTAAACTTCTGCACTTCTCTTAGTTACCAGTCTT GATACCAAGTATTGGG | SEQ ID NO: 1898 | Homo sapiens FCH domain only 2 (FCHO2), mRNA [NM_138782] |
| 318 | A_23_P351467 | CMAH | GCTTAGACATTGTGGATGACTACATAGGCAGATTCAAAATATT TAGTTGTTCGATCCAC | SEQ ID NO: 1899 | Homo sapiens cytidine monophosphate-N-acetylneuraminic acid hydroxylase (CMP-N-acetylneuraminate monooxygenase) (CMAH) on chromosome 6 [NR_002174] |
| 319 | A_23_P351903 | TMEM167 | AAAGTTGGATGTTGGGTATATTTTGGAAGTGTGGGAGAATTGG GAACGGAAGAGTCCTT | SEQ ID NO: 1900 | Homo sapiens transmembrane protein 167 (TMEM167), mRNA [NM_174909] |
| 320 | A_23_P353704 | RP5-1022P6.2 | TGTCTCCACTACCTATTAGACACTGTTGCTTGGTTTGGTGGTTTGTT TTGTATGTGTGTGT | SEQ ID NO: 1901 | Homo sapiens hypothetical protein KIAA1434 (KIAA1434), mRNA [NM_019593] |
| 321 | A_23_P354894 | ZNF567 | ACGTAAGAAGTTACCACTTCGGTAGCCTATAACATCAAAAGGTAG TTTTTGCATGTTTCA | SEQ ID NO: 1902 | Homo sapiens zinc finger protein 567 (ZNF567), mRNA [NM_152603] |
| 322 | A_23_P355067 | TMCO1 | AAGTCAAGAACTCTTTATTTCTATGATTCTTTCTAGACACACA CACATCAGACTGGCAA | SEQ ID NO: 1903 | Homo sapiens transmembrane and coiled-coil domains 1 (TMCO1), mRNA [NM_019026] |
| 323 | A_23_P355244 | SAMD9 | TGCATTGGAGGAAGAATTTGGCTTGGCTGTGGAATAAATTTTAAG TCGATAACTTATAAGC | SEQ ID NO: 1904 | Homo sapiens sterile alpha motif domain containing 9 (SAMD9), mRNA [NM_017654] |
| 324 | A_23_P356122 | ZNF451 | TTTTAAAGTCTTAGAGTTTTATGTGACTGTATGGTCTCCTGGT TAAAGGGAATGTGTC | SEQ ID NO: 1905 | Homo sapiens zinc finger protein 451 (ZNF451), transcript variant 2, mRNA [NM_015555] |

Fig. 5-18

| No. | Probe ID No. | Symbols of genes | Sequence | SEQ ID NO: | Descriptions of genes (letters and numbers within [ ] indicates GenBank accession No.) |
|---|---|---|---|---|---|
| 325 | A_23_P358470 | CCDC111 | ATGACCGTGTATGTAAAGGAGAAAACTTCAAATCGAGTGTTTGCCATTACCTGCTGAAG | SEQ ID NO: 1906 | Homo sapiens coiled-coil domain containing 111 (CCDC111), mRNA [NM_152683] |
| 326 | A_23_P358628 | DPY19L1 | ATATAAATTAGGTTTTTTCAGAAGGATCCTTTGTAGGCAGTGTTTATGAATGTAACCCCC | SEQ ID NO: 1907 | Homo sapiens DPY-19-like protein 1 (DPY19L1) mRNA, complete cds. [DQ287932] |
| 327 | A_23_P361448 | SESN3 | AAGGAGAAGAAGAAAGTGTTTTTGTCGTCTGGAGTACTTTTCATTCATTTCCTCAT | SEQ ID NO: 1908 | Homo sapiens sestrin 3 (SESN3), mRNA [NM_144665] |
| 328 | A_23_P364107 | C14orf106 | AAGCAGAGAGTGTTTGATTTTCAACTGGAGTACATGTATTTCTTTGTAAAGTAGCTTCC | SEQ ID NO: 1909 | Homo sapiens chromosome 14 open reading frame 106 (C14orf106), mRNA [NM_018353] |
| 329 | A_23_P36776 | PUS7L | GGGCTTGAGTTTGAACATGTGTAAAATGGCATGTTAACATTGCCTACCTCATAGGATTA | SEQ ID NO: 1910 | Homo sapiens pseudouridylate synthase 7 homolog (S. cerevisiae)-like (PUS7L), mRNA [NM_031292] |
| 330 | A_23_P3681 | NETO2 | AGAGGTTGGAAATGTGGAGATAAGGCTCTTTCTTCCTTTTGTTA | SEQ ID NO: 1911 | Homo sapiens neuropilin (NRP) and tolloid (TLL)-like 2 (NETO2), mRNA [NM_018092] |
| 331 | A_23_P368581 | GIMAP2 | ATGAGCAAGTGAAGGAAGTAGTGGACTGTATTGAGGATGTGTTGATGGAGAAAATGGTG | SEQ ID NO: 1912 | Homo sapiens GTPase, IMAP family member 2 (GIMAP2), mRNA [NM_015660] |
| 332 | A_23_P371266 | DNM3 | ACTGTGTTCTTTGGGCAGTTTGGAGATTTCTTAATGCTGATATGGGACTCTTAGAATGGAA | SEQ ID NO: 1913 | Homo sapiens dynamin 3 (DNM3), mRNA [NM_015569] |
| 333 | A_23_P37275 | CGRRF1 | GAAGAAGATAAAGACAAAATGGAAGACTCTTTGAAGACATCGTAACACTGAAAAGTACACT | SEQ ID NO: 1914 | Homo sapiens cell growth regulator with ring finger domain 1 (CGRRF1), mRNA [NM_006568] |
| 334 | A_23_P37441 | B2M | TTGCTTTCAGCAAGGACTGGTCTTTCTATCTCTTGTACTACACTGAATTCACCCCCACT | SEQ ID NO: 1915 | Homo sapiens beta-2-microglobulin (B2M), mRNA [NM_004048] |
| 335 | A_23_P37636 | FAM96A | CTTGAACCTGACTGATAGAGTGTGTTTAAGAGGCAGTGGGGTGTAATTGTTTGATATTTG | SEQ ID NO: 1916 | Homo sapiens family with sequence similarity 96, member A (FAM96A), transcript variant 1, mRNA [NM_032231] |
| 336 | A_23_P380848 | TXNL5 | GTGTGTGGAAATGTTGTTCTCTGAAGATTAAGATTTAGGATGGCAATCATGTCTTGATGT | SEQ ID NO: 1917 | Homo sapiens thioredoxin-like 5 (TXNL5), mRNA [NM_032731] |
| 337 | A_23_P38275 | THC2504576 | TCTGCCAAAATGAAGTTTAATCCCTTTGTGACTTCCGACGGAAGCAAGAATCGGAAAAG | SEQ ID NO: 1918 | RL26_BOVIN (P61257) 60S ribosomal protein L26, complete [THC2504576] |
| 338 | A_23_P384056 | CCDC14 | AGCTAGCAGTATCATCTCGCGTTCATGTAAGCAGCACGTTTTAACTCTTAGGAACGTGAATG | SEQ ID NO: 1919 | Homo sapiens coiled-coil domain containing 14 (CCDC14), mRNA [NM_022757] |
| 339 | A_23_P390734 | FGFR1OP2 | CCACCAGATACAAAGTGCTTTAACATCAGTTGAAACCTAAATTTCTTATGTGTGG | SEQ ID NO: 1920 | Homo sapiens FGFR1 oncogene partner 2 (FGFR1OP2), mRNA [NM_015633] |
| 340 | A_23_P394276 | RWDD4A | TTGTTCAGGCTTATTATGGCTCATAGATTACAGAGAATGATGCTAGTTACATGCCAATGA | SEQ ID NO: 1921 | Homo sapiens RWD domain containing 4A (RWDD4A), mRNA [NM_152682] |
| 341 | A_23_P394605 | SEC24A | GATTTATTTTCTTCTAATCAAAGAATGGATAACAGCTATTATCTAGGGACCACCAAATGTG | SEQ ID NO: 1922 | Homo sapiens SEC24 related gene family, member A (S. cerevisiae) (SEC24A), mRNA [NM_021982] |
| 342 | A_23_P397999 | FZD5 | GGGCTTAGAATGCTAAGGTTGGGGTTGTAATGAAGTTCCACTTGGTTCAGGTTTCTTT | SEQ ID NO: 1923 | Homo sapiens frizzled homolog 5 (Drosophila) (FZD5), mRNA [NM_003468] |
| 343 | A_23_P410017 | TBCEL | ATACAGTTGCATGTAAAGGGAGGTTCTTCATTTAATTCAGCGGATGTGGGTATTTTAGGG | SEQ ID NO: 1924 | Homo sapiens leucine rich repeat containing 35, mRNA (cDNA clone IMAGE:3913004), [BC025011] |
| 344 | A_23_P41114 | CSTA | AAACAAAATGAGAGTTTATGGAAAATTGGAAGCTGTGCATGATAAAAGTCAAGTTGTGCTG | SEQ ID NO: 1925 | Homo sapiens cystatin A (stefin A) (CSTA), mRNA [NM_005213] |
| 345 | A_23_P413796 | CCDC5 | GCATGGATGTTGTGTGTCATCAGTCCTTAGTAGCACTATCAGAGAAACTGCCAAGAT | SEQ ID NO: 1926 | Homo sapiens coiled-coil domain containing 5 (spindle associated) (CCDC5), mRNA [NM_138443] |

Fig. 5-19

| No | Probe ID No. | Symbols of genes | Sequence | SEQ ID NO. | Descriptions of genes (letters and numbers within [ ] indicates GenBank accession No.) |
|---|---|---|---|---|---|
| 346 | A_23_P41512 | C4orf15 | TAAGGCTGTTAGTCTTGAAGATTGAAGATTGAAAATTACTGAAAACTGAATCTTTATTACGTCGTCGT | SEQ ID NO: 1927 | Homo sapiens chromosome 4 open reading frame 15 (C4orf15), mRNA [NM_024511] |
| 347 | A_23_P41645 | ELL2 | TGTGTTTCAAAGTGCTGGCAGTGAAGTGCACAGCTGAATAGTT TACAAATCTGTTTTGA | SEQ ID NO: 1928 | Homo sapiens elongation factor, RNA polymerase II, 2 (ELL2), mRNA [NM_012081] |
| 348 | A_23_P41664 | ENST00000334994 | TGGGTTGGAGCAGATTCGACTTGACTTAACAAATTGTTCCTGAAA ATGAGGGACAGGTCAT | SEQ ID NO: 1929 | Syrieurin (CGL01891). [Source:Uniprot/SPTREMBL;Acc:Q72207] [ENST00000334994] |
| 349 | A_23_P421563 | LSM3 | GATAAGAGAAAGGTGCATAGATTTGTATATTAAGAAATAATTCC GGGGATTGTTCCACTC | SEQ ID NO: 1930 | Homo sapiens LSM3 homolog, U6 small nuclear RNA associated (S. cerevisiae) (LSM3), mRNA [NM_014463] |
| 350 | A_23_P422794 | NSMCE2 | CATTGTGGACTGATTGAGTGCAGGTCCAAAGCAAAAGCGAAGAAAAGG CCTATCGGCTCAAAT | SEQ ID NO: 1931 | Homo sapiens non-SMC element 2, MMS21 homolog (S. cerevisiae) (NSMCE2), mRNA [NM_173685] |
| 351 | A_23_P42718 | NFE2L3 | CAGGCATCCTTTTAAGAGTAAGTTGGTTACTTCAAAAGAGACA AACACTGGGATGAAA | SEQ ID NO: 1932 | Homo sapiens nuclear factor (erythroid-derived 2)-like 3 (NFE2L3), mRNA [NM_004289] |
| 352 | A_23_P428468 | ENST00000369577 | AAACCTACCGTCAGTCTGAAAAAACTTGAAGTACATTCAAATGA TCCAGATATGTCTGTT | SEQ ID NO: 1933 | Zinc finger protein 292. [Source:Uniprot/SWISSPROT;Acc:Q62081] [ENST00000369577] |
| 353 | A_23_P429491 | FLJ25416 | GCTTGGCTCACCTGAATTGTTTCATAAAAGTCACCTGAAGCCAA ATTCCTGAAGTTTTAA | SEQ ID NO: 1934 | Homo sapiens hypothetical protein FLJ25416 (FLJ25416), mRNA [NM_145018] |
| 354 | A_23_P42975 | PRKAR2B | GCCACATATTAGAAACACTGTTTAAGCATTTTCGAAAACCTGTT TGTAGGAAAAGAGAGC | SEQ ID NO: 1935 | Homo sapiens protein kinase, cAMP-dependent, regulatory, type II, beta (PRKAR2B), mRNA [NM_002736] |
| 355 | A_23_P43049 | DCTN6 | AAATACATTGAAGTCATCCCTGAGAATACGGTCGATCTATGGTG CAGAGTCCCTTGTCTC | SEQ ID NO: 1936 | Homo sapiens dynactin 6 (DCTN6), mRNA [NM_006571] |
| 356 | A_23_P43150 | ZHX1 | TTTGTAAAGACTGGTGCTGTTCATTCATATTGGAAGACCCTTT CTTTGTGTGACCATAGG | SEQ ID NO: 1937 | Homo sapiens zinc fingers and homeoboxes 1 (ZHX1), transcript variant 1, mRNA [NM_001017926] |
| 357 | A_23_P43157 | MYBL1 | ATACATATATTGGGTTGGTACTGGTTGAATCCTTCAGTTAACTGC TTTGTTGCTTTTTGCA | SEQ ID NO: 1938 | Homo sapiens v-myb myeloblastosis viral oncogene homolog (avian)-like 1 (MYBL1), mRNA [NM_001080416] |
| 358 | A_23_P43175 | SEPT10 | AAATGCAGATAATTCATATATTTCAGTGGTATTTCAGTTCAGTTGC CTTACTGCAGTTCTCA | SEQ ID NO: 1939 | Homo sapiens septin 10 (SEPT10), transcript variant 1, mRNA [NM_144710] |
| 359 | A_23_P433111 | C5orf35 | GTTCCAATGCAGAGCAGGCTAATGCTGTTGCGTTATGAGGAT GTGCCTGGAGTTTCG | SEQ ID NO: 1940 | Homo sapiens chromosome 5 open reading frame 35 (C5orf35), mRNA [NM_153706] |
| 360 | A_23_P434809 | S100A8 | AAAGGCATGAAGAAACCACAAAGAGTGAGTTACTGGGGCC CAGAGGGTGGGCCCT | SEQ ID NO: 1941 | Homo sapiens S100 calcium binding protein A8 (S100A8), mRNA [NM_002964] |
| 361 | A_23_P44257 | COMMD8 | AACATTTTAGTTCTGCGGTTCTATGTTGGGAAGAATTGTCTG ATAAAAATAGGTGTC | SEQ ID NO: 1942 | Homo sapiens COMM domain containing 8 (COMMD8), mRNA [NM_017845] |
| 362 | A_23_P44974 | MRPL13 | ATGGAGTAAAACAACTTGCTACAGTTCAGGACCGTGTTTATGTGC CGAATCACGTGTGGGA | SEQ ID NO: 1943 | Homo sapiens mitochondrial ribosomal protein L13 (MRPL13), nuclear gene encoding mitochondrial protein, mRNA [NM_014078] |
| 363 | A_23_P45180 | GYPA | AGGTGCCTAAGTTGTACAATTTGAGAATGGAATTTGATTATAA TGAGTTCCAGTGACTC | SEQ ID NO: 1944 | Homo sapiens glycophorin A (MNS blood group) (GYPA), mRNA [NM_002099] |

Fig. 5-20

| No. | Probe ID No. | Symbols of genes | Sequence | SEQ ID NO: | Descriptions of genes (letters and numbers within [ ] indicates GenBank accession No.) |
|---|---|---|---|---|---|
| 364 | A_23_P45248 | SH2D1A | TTGTAAAGCCATTGTAGTCCGTGTAATGGAAGCATCTAGGATGTCGTCAAAGCTGAAATGG | SEQ ID NO: 1945 | Homo sapiens SH2 domain protein 1A, Duncan's disease (lymphoproliferative syndrome) (SH2D1A), mRNA [NM_002351] |
| 365 | A_23_P45934 | SRP9 | TATAGGCATTGTCATGGGAACTGTGTGTTAAAGTAACGATGATTAGTTTGTTTGGTG | SEQ ID NO: 1946 | Homo sapiens signal recognition particle 9kDa (SRP9), mRNA [NM_003133] |
| 366 | A_23_P48396 | PTBP2 | AACCAGGTGGGACCAAAGTTTATGTGCCTTTAGTCTTAATTACCTTGGATTGTAATATT | SEQ ID NO: 1947 | Homo sapiens polypyrimidine tract binding protein 2 (PTBP2), mRNA [NM_021190] |
| 367 | A_23_P48166 | TWF1 | TGGACCAGACCATAGGCTGAAGCTGTTATTTCAGTCAGGAAGACTACCTGTCATGAAGGT | SEQ ID NO: 1948 | Homo sapiens twinfilin, actin-binding protein, homolog 1 (Drosophila) (TWF1), mRNA [NM_002822] |
| 368 | A_23_P501080 | ZNF92 | GAATATTAAGTGCTACTTGAGGTACAATGTCAGAGTAAGATGTTTTGACATTAGTGAG | SEQ ID NO: 1949 | Homo sapiens zinc finger protein 92 (ZNF92), transcript variant 1, mRNA [NM_007139] |
| 369 | A_23_P501276 | TUBB2A | GTGGAGGAGCAGATGCTCAAGGTGGAGAACAGAACAGGAGGTACTTCGTGGAGTGGATC | SEQ ID NO: 1950 | Homo sapiens tubulin, beta 2A (TUBB2A), mRNA [NM_001069] |
| 370 | A_23_P502425 | MRPL47 | GTTCCACATCTGGTGAAGCCCAAAAGTCAAGTCTTGTCTAAGATGTGAACTATTAA | SEQ ID NO: 1951 | Homo sapiens mitochondrial ribosomal protein L47 (MRPL47), nuclear gene encoding mitochondrial protein, transcript variant 1, mRNA [NM_020409] |
| 371 | A_23_P502797 | WDFY1 | GTAACAGTTTACTGGTTGTTGGAATTCCTGAATATGCAGGGTAATTGTACAGATAGGGAT | SEQ ID NO: 1952 | Homo sapiens WD repeat and FYVE domain containing 1 (WDFY1), mRNA [NM_020830] |
| 372 | A_23_P50907 | ITGAV | AAAGAGTTGATTAAGTGAGGTTATTTACGCGTAAATGGTCCATTCTGGATTGTATTTCAGG | SEQ ID NO: 1953 | Homo sapiens integrin, alpha V (vitronectin receptor, alpha polypeptide, antigen CD51) (ITGAV), mRNA [NM_002210] |
| 373 | A_23_P51009 | NDUFB3 | CCGCAATGAAGCTTGGAGATACATGGGTGGCTTGGACAGAGTGTTTGCTTTCGAGTGT | SEQ ID NO: 1954 | Homo sapiens NADH dehydrogenase (ubiquinone) 1 beta subcomplex, 3, 12kDa (NDUFB3), mRNA [NM_002491] |
| 374 | A_23_P51317 | CCDC76 | CCCTTGTTATAAGTTTATGTCAAGTAAGGTAGGTTAGTTGTTAAGTTAGTTACCCATGTCCC | SEQ ID NO: 1955 | Homo sapiens coiled-coil domain containing 76 (CCDC76), mRNA [NM_019083] |
| 375 | A_23_P51487 | GBP3 | AATGCTAAAGCATAAGGTTGCTTGCTGATTCTTAAAGGTCATACTTGAAATGGTGCC | SEQ ID NO: 1956 | Homo sapiens guanylate binding protein 3 (GBP3), mRNA [NM_018284] |
| 376 | A_23_P53668 | NFYB | TGGGCTCATATTGGCATAGCCATTTCCATCTGCTTTTCAGCTTAACAATATATTGGG | SEQ ID NO: 1957 | Homo sapiens nuclear transcription factor Y, beta (NFYB), mRNA [NM_006166] |
| 377 | A_23_P53957 | C14orf112 | TTATACTTCCAGCTATTCCATCTGTGGATGAAAGTAACAATGTTGGCCACGTATATTT | SEQ ID NO: 1958 | Homo sapiens chromosome 14 open reading frame 112 (C14orf112), mRNA [NM_016468] |
| 378 | A_23_P56050 | TNNT1 | TCCGAGCGTAAGAAGGCCTCTGGACATTGACTACATGGGGGAGGAACAGGCTCCGGGAGAA | SEQ ID NO: 1959 | Homo sapiens troponin T type 1 (skeletal, slow), mRNA (cDNA clone MGC:104241 IMAGE:4247379), complete cds. [BC107798] |
| 379 | A_23_P5611 | RIF1 | ATGTAATTCCTGCCTGCTATGCGTGGGTGGTTTTCAGGAAATTTAATTATCTTACTGAGATGTG | SEQ ID NO: 1960 | Homo sapiens RAP1 interacting factor homolog (yeast) (RIF1), mRNA [NM_018151] |
| 380 | A_23_P56380 | ZC3H15 | GTCACGGCAAGTAAGAAGTGTATCGCCTTGCCTTCCATCTTTTGGTTTCATTGGGCAGTGTG | SEQ ID NO: 1961 | Homo sapiens zinc finger CCCH-type containing 15 (ZC3H15), mRNA [NM_018471] |
| 381 | A_23_P56734 | HNMT | CCTTTGTCCACCATGGAATATATCTGACTGCTGTTTATTGATTGTAATGAAAATGCAGACCT | SEQ ID NO: 1962 | Homo sapiens histamine N-methyltransferase (HNMT), transcript variant 1, mRNA [NM_006895] |
| 382 | A_23_P56759 | KRCC1 | GATATCCGTGTTCATACCACTTTCTTATTGTGAATAGGTTCTTAAGTTCTAACAAAGGC | SEQ ID NO: 1963 | Homo sapiens lysine-rich coiled-coil 1 (KRCC1), mRNA [NM_016618] |

Fig. 5-21

| No. | Probe ID No. | Symbols of genes | Sequence | SEQ ID NO. | Descriptions of genes (letters and numbers within [ ] indicates GenBank accession No.) |
|---|---|---|---|---|---|
| 383 | A_23_P57277 | C21orf7 | CCAGCTCTAGCTTGAGAGAAGGGATATTTTAAATGAGATCATT AACGTGAAACTATTAG | SEQ ID NO: 1964 | Homo sapiens chromosome 21 open reading frame 7 (C21orf7), mRNA [NM_020152] |
| 384 | A_23_P58390 | C4orf32 | TAATACTAACTATTTAGTACATGTCAGTAGTGTACATGTTGCAC ACTGTGTTAATAGGG | SEQ ID NO: 1965 | Homo sapiens chromosome 4 open reading frame 32 (C4orf32), mRNA [NM_152400] |
| 385 | A_23_P58396 | PDGFC | CATGGATATTTTATGTACAGAAGTATGTGTCTTAACCAGTTGA CTTATTGTACTCGGC | SEQ ID NO: 1966 | Homo sapiens platelet derived growth factor C (PDGFC), mRNA [NM_016205] |
| 386 | A_23_P58877 | GOPC | AAGGTTCATGTGATTCATCGTAAGATGCACAGTATTTGACAT CCTGATTATGTAATCC | SEQ ID NO: 1967 | Homo sapiens golgi associated PDZ and coiled-coil motif containing (GOPC), transcript variant 1, mRNA [NM_020399] |
| 387 | A_23_P58912 | SLC35A1 | ATGATCAGTGGGGTTATGTGGAAAGAACAACAAACAAACGAAGC TATGTGAGTGAAGTGG | SEQ ID NO: 1968 | Homo sapiens solute carrier family 35 (CMP-sialic acid transporter), member A1 (SLC35A1), mRNA [NM_006416] |
| 388 | A_23_P59637 | DOCK4 | TTTGGGAGTGAGGCAGTTGAATTTATCTTGAATTTATCATGTGTG TGTATTCTGAAGCAG | SEQ ID NO: 1969 | Homo sapiens dedicator of cytokinesis 4 (DOCK4), mRNA [NM_014705] |
| 389 | A_23_P59921 | SUB1 | CAGATATTTTTATGAGGTACGTTAGTGTTCGGCATTTTAAAGG CAAAGTGCTAATTGAT | SEQ ID NO: 1970 | Homo sapiens SUB1 homolog (S. cerevisiae) (SUB1), mRNA [NM_006713] |
| 390 | A_23_P60248 | TXN | GGACAAAAGGTGGGTGAATTTCGTAAGGCCAATAAGGAAAAGCT TGAAGGCAGCATTAAT | SEQ ID NO: 1971 | Homo sapiens thioredoxin (TXN), mRNA [NM_003329] |
| 391 | A_23_P61674 | CLK4 | GAAAGGCATGCAGTTTGTCATTGCGACAGTTGTTGTTAATAAAA CCACATACAGATTTA | SEQ ID NO: 1972 | Homo sapiens CDC-like kinase 4 (CLK4), mRNA [NM_020666] |
| 392 | A_23_P63655 | ATP5C1 | AGAGAGGTGAAACGACCAGCTGAATATATGGATTGGATCTTAGC TCTGATGAAAAAGCT | SEQ ID NO: 1973 | Homo sapiens ATP synthase, H+ transporting, mitochondrial F1 complex, gamma polypeptide 1 (ATP5C1), nuclear gene encoding mitochondrial protein, transcript variant 2, mRNA [NM_005174] |
| 393 | A_23_P63668 | IFIT5 | AAGATACGATCCAGAAAAATGGAGAATTCCTGACTGCTCCTGTGA GCTCCGAGTTTGGATT | SEQ ID NO: 1974 | Homo sapiens interferon-induced protein with tetratricopeptide repeats 5 (IFIT5), mRNA [NM_012420] |
| 394 | A_23_P63896 | FAS | ATGTCTATGCAGAGGCTAAGCGACCCAGTCTATGAATGAATAGAAGA AGCTATGACCTTTGC | SEQ ID NO: 1975 | Homo sapiens Fas (TNF receptor superfamily, member 6) (FAS), transcript variant 1, mRNA [NM_000043] |
| 395 | A_23_P65230 | TMTC4 | AGAAGGGCAACACATCTGTGTAAGCTGCTGTTTTTAGTGTGTTATC TGAAGGGCGTTTTTCCA | SEQ ID NO: 1976 | Homo sapiens transmembrane and tetratricopeptide repeat containing 4 (TMTC4), transcript variant 1, mRNA [NM_028313] |
| 396 | A_23_P65768 | C15orf15 | TCCTGCATTGGGATCTACAATAATATCAGATATTACAGAAGTTGA ATTGGATGTCAGTGTT | SEQ ID NO: 1977 | Homo sapiens chromosome 15 open reading frame 15 (C15orf15), mRNA [NM_016304] |
| 397 | A_23_P66260 | ZNF267 | TGTGATGAATGTGGTAAAGCCTTCAGGTATAGTGATACGTCAC TACACATGGAGAAGT | SEQ ID NO: 1978 | Homo sapiens zinc finger protein 267 (ZNF267), transcript variant 493723, mRNA [NM_003414] |
| 398 | A_23_P68472 | DPM1 | GTATTGGCGAGGTCTTACAGTCTATCCTTCCTAGAAAATGGTAATTGAG GAATGGAAGTTGGGAG | SEQ ID NO: 1979 | Homo sapiens dolichyl-phosphate mannosyltransferase polypeptide 1, catalytic subunit (DPM1), mRNA [NM_003859] |
| 399 | A_23_P69109 | PLSCR1 | GTTTAGGTCTTACAGTCTATCCTTCCTAGAAAATGGTAATTGAG ATTACTCAGATATTAA | SEQ ID NO: 1980 | Homo sapiens phospholipid scramblase 1 (PLSCR1), mRNA [NM_021105] |
| 400 | A_23_P69695 | ZCD2 | ATTTGTGTCTTACTAAGGAGCTTATTGTAGGGTTGGGGGTTCT AAAAGGTTTCCTGCCT | SEQ ID NO: 1981 | Homo sapiens zinc finger, CDGSH-type domain 2 (ZCD2), mRNA [NM_001008388] |

Fig. 5-22

| No. | Probe ID No. | Symbols of genes | Sequence | SEQ ID NO: | Descriptions of genes (letters and numbers within [ ] indicates GenBank accession No.) |
|---|---|---|---|---|---|
| 401 | A_23_P69908 | GLRX | CTGATAAAGTTACAGCCCCTAGACCAAGAGTGTATCTGAAAGAGGTCCTACACTTT | SEQ ID NO: 1982 | Homo sapiens glutaredoxin (thioltransferase) (GLRX), mRNA [NM_002064] |
| 402 | A_23_P70290 | TMEM30A | ATCTTCTGCCTGAACTGTAAACCACATGTAAGTTGGTTAATGAAGACTGTTTCATTCTG | SEQ ID NO: 1983 | Homo sapiens transmembrane protein 30A (TMEM30A), mRNA [NM_018247] |
| 403 | A_23_P70318 | ENPP4 | TGTTTTTGGGTGTCTCCTTCTGTGTGCCCATATCTGATAAGCTTTATGGATTATTGCATTT | SEQ ID NO: 1984 | Homo sapiens ectonucleotide pyrophosphatase/phosphodiesterase 4 (putative function) (ENPP4), mRNA [NM_014936] |
| 404 | A_23_P70328 | CENPQ | CAATGGCTTACAGTTTGTGTCTGGTCATGTGGAACTTGAAAAATCCTAAATGCGTTCAC | SEQ ID NO: 1985 | Homo sapiens centromere protein Q (CENPQ), mRNA [NM_018132] |
| 405 | A_23_P7066 | RPL9 | GGTCTCTTTGAAGTCGGAAATTTCTTGGGTGAAAAATATACCGGCAAGGGTTCGGATGA | SEQ ID NO: 1986 | Homo sapiens ribosomal protein L9 (RPL9), transcript variant 1, mRNA [NM_000661] |
| 406 | A_23_P70938 | STARD3NL | GCATTATGTGTATGGCCTGAAGTGTTGGACTTGGAAAGGGGAAGAAAGGAATTGCCAAT | SEQ ID NO: 1987 | Homo sapiens STARD3 N-terminal like (STARD3NL), mRNA [NM_032016] |
| 407 | A_23_P71433 | UBE2W | CATGAGGGCCTACTGCGTAAACACTATTTCATTTATTATGTTTGGAAACCCGTAAACAT | SEQ ID NO: 1988 | Homo sapiens ubiquitin-conjugating enzyme E2W (putative) (UBE2W), transcript variant 1, mRNA [NM_001001481] |
| 408 | A_23_P72117 | SMPDL3A | TTTGTGGGAATTTACATAAATCTTGTTAATTACTGAGTGGGCAAGTAGAGCTTGGTGTC | SEQ ID NO: 1989 | Homo sapiens sphingomyelin phosphodiesterase, acid-like 3A (SMPDL3A), mRNA [NM_006714] |
| 409 | A_23_P7221 | RPL34 | CGAGGAGCAGAAAATGGTTGTGAAAGTGTTGAAGGAGCAAGAGCAGAAAGCTAA | SEQ ID NO: 1990 | Homo sapiens ribosomal protein L34 (RPL34), transcript variant 2, mRNA [NM_033625] |
| 410 | A_23_P7229 | RPL34 | CGAACCCGTGGTAAATGAATTGTTACCTTTATAGCAAGAAGGTTGGAAAGCACCAAA | SEQ ID NO: 1991 | Homo sapiens ribosomal protein L34 (RPL34), transcript variant 2, mRNA [NM_033625] |
| 411 | A_23_P72568 | SNX4 | AACCTTCAGTAATGAGCCTAAATTTACTCTGCTTGGCTCTCTACACATGGCATTCAGGGT | SEQ ID NO: 1992 | Homo sapiens sorting nexin 4 (SNX4), mRNA [NM_003794] |
| 412 | A_23_P7262 | MARCH1 | GATATGTGTTCTTTGGATATTCATGTAAACTGATGTGTGAATGACATTGCAGTGAGC | SEQ ID NO: 1993 | Homo sapiens cDNA FLJ20668 fis, clone KAIA5565. [AK000675] |
| 413 | A_23_P7282 | ELMOD2 | TTCAAGTAGGTTCTCTGGGGGAAAAAGTACCAGTTGGACACTTAAAGGAATTTGGGATTT | SEQ ID NO: 1994 | ELMO domain-containing protein 2. [Source:Uniprot/SWISSPROT;Acc:Q6IZ81] [ENST00000323570] |
| 414 | A_23_P73577 | DYNLT3 | TGTTTCTTTATGCTGGCTTTTGTGCCCTGGAAGATCATAATAGTGACCAAAATATAC | SEQ ID NO: 1995 | Dynein light chain Tctex-type 3 (T-complex-associated testis-expressed 1-like) (Protein 91/23). [Source:Uniprot/SWISSPROT;Acc:P51808] [ENST00000378578] |
| 415 | A_23_P74001 | S100A12 | TGAAGGTTTTACCGAGCAATGTGCTCAATGAGGGTGTTTTCTTCCCTCACGAAAACC | SEQ ID NO: 1996 | Homo sapiens S100 calcium binding protein A12 (S100A12), mRNA [NM_005621] |
| 416 | A_23_P74799 | SLC25A24 | GATTCGTGTATCTTTGGAAAAAGCGAGAGTTGAAGATAGTATATTCTGGTAGTACTG | SEQ ID NO: 1997 | Homo sapiens solute carrier family 25 (mitochondrial carrier; phosphate carrier), member 24 (SLC25A24), transcript variant 2, mRNA [NM_213651] |
| 417 | A_23_P75028 | REEP3 | AGAAACGACCAAGTGTATTTTAGTCATCTACAGGTCAAATACCCAAGACAGATTAT | SEQ ID NO: 1998 | Homo sapiens receptor accessory protein 3 (REEP3), mRNA [NM_001001330] |
| 418 | A_23_P7543 | ZFYVE16 | TGTGCCTGACATTATGTAAATGATCTTGATGATGATGGTGATAGCTGTGATACCTGTGATCATGGTGG | SEQ ID NO: 1999 | Homo sapiens zinc finger, FYVE domain containing 16 (ZFYVE16), mRNA [NM_014733] |

Fig. 5-23

| No. | Probe ID No. | Symbols of genes | Sequence | SEQ ID NO: | Descriptions of genes (letters and numbers within [ ] indicates GenBank accession No.) |
|---|---|---|---|---|---|
| 419 | A_23_P75769 | MS4A4A | CACCAAAAGATCAACAGAAGAAATGCTCAGAAATCTATGCTGACTGTGACAAGAGGCT | SEQ ID NO: 2000 | Homo sapiens membrane-spanning 4-domains, subfamily A, member 4 (MS4A4A), transcript variant 1, mRNA [NM_024021] |
| 420 | A_23_P76159 | EEA1 | TATTGTGTTTAGTACTTGTGATCATGTAGTGTGCTTACTTTGTGAGAAAGTTAGCTC | SEQ ID NO: 2001 | Homo sapiens early endosome antigen 1 (EEA1), mRNA [NM_003566] |
| 421 | A_23_P76480 | BF213738 | AAATGGAACAGGACAACATGGGTAGATGGAGCTAGAATTACCAAATCGTTTGGCATGACAGG | SEQ ID NO: 2002 | BF213738 601847628F1 NIH_MGC_55 Homo sapiens cDNA clone IMAGE:4078519 5', mRNA sequence [BF213738] |
| 422 | A_23_P76951 | TXNDC1 | ATTTCTGTAATGTCCCTTCTTCTAGGCTCTGTTGCTGTGTGAATCCATTAGATTTACA | SEQ ID NO: 2003 | Homo sapiens thioredoxin domain containing 1 (TXNDC1), mRNA [NM_030755] |
| 423 | A_23_P78092 | EVI2A | GCTGAATCAGAACTTGGAAGACTTGGAAAAGAAGAAAAAACAGCTCACACGACCGAAGCTAGTGATGCAA | SEQ ID NO: 2004 | Homo sapiens ecotropic viral integration site 2A (EVI2A), transcript variant 1, mRNA |
| 424 | A_23_P79199 | DBI | TGCTCACCATACGGCTCTAACAGATTAGGGGCTAAAAACGGATTACTGAGTTTCCTTGAGTA | SEQ ID NO: 2005 | Homo sapiens diazepam binding inhibitor (GABA receptor modulator, acyl-Coenzyme A binding protein) (DBI), transcript variant 1, mRNA [NM_020548] |
| 425 | A_23_P81212 | MRPS18C | ATGGGGTTTATGCCAGTTACATACAAGAAGGATCCTGACATGTCAAGGACGGTAAAGTTTGT | SEQ ID NO: 2006 | Homo sapiens mitochondrial ribosomal protein S18C (MRPS18C), nuclear gene encoding mitochondrial protein, mRNA [NM_016067] |
| 426 | A_23_P83278 | CHMP5 | CATTGCTGTCTTTATTTTTTGGATTAAGAGAGTGATTGCTTGGGAAATGCTTTCTGGTAC | SEQ ID NO: 2007 | Homo sapiens chromatin modifying protein 5 (CHMP5), mRNA [NM_016410] |
| 427 | A_23_P84070 | LARP7 | TGATTTGTAGAAGGGATACAGAATGCCATGCTAGATTAAGACTCCTGAGGATGCTCA | SEQ ID NO: 2008 | Homo sapiens La ribonucleoprotein domain family, member 7 (LARP7), transcript variant 1, mRNA [NM_016648] |
| 428 | A_23_P8640 | GPR30 | AACAGGTCGGGACAACGTGGGTGAGTCAGATGATGTAAAAACCTTCCATAAAATGTAAGAAAAGC | SEQ ID NO: 2009 | Homo sapiens G protein-coupled receptor 30 (GPR30), transcript variant 2, mRNA [NM_001505] |
| 429 | A_23_P86653 | SRGN | AGGACTTGGGTCAACATGGAGATTAGAAGAAGGATTTTATGTTATAAAACAGGATTTCCCAC | SEQ ID NO: 2010 | Homo sapiens serglycin (SRGN), mRNA [NM_002727] |
| 430 | A_23_P87879 | CD69 | TTGCAATATGATGGATGTGGCAAATGTGTATTAGGAAATATCTGTAATCTTCAGACCTAG | SEQ ID NO: 2011 | Homo sapiens CD69 molecule (CD69), mRNA [NM_001781] |
| 431 | A_23_P89145 | ZNF83 | GTATAATGAAATGTAGCAGAGCCTTTAGTTTTTGTTCAAGGGTTAATAACCGTTAGTAGA | SEQ ID NO: 2012 | Homo sapiens zinc finger protein 83 (ZNF83), mRNA [NM_018300] |
| 432 | A_23_P9056 | RB1CC1 | TTCATTTTCTCAAAGGCACATACCTTGTGGCATTGTGGCTTATGATGACCCATATTAATTGC | SEQ ID NO: 2013 | Homo sapiens RB1-inducible coiled-coil 1 (RB1CC1), mRNA [NM_014781] |
| 433 | A_23_P91346 | BC008667 | GGGCTAGGAGTGAGATTTCTGGTTCTACAGAAATGATCATGTCATGAATTTTGACATTT | SEQ ID NO: 2014 | Homo sapiens cDNA clone MGC:17708 IMAGE:3868595, complete cds, [BC008667] |
| 434 | A_23_P92410 | CASP3 | TGCACCAAGTCACTGGCTGTCAGTATGACATTTGACGGGAGATTTCTGTTGCTCAAA | SEQ ID NO: 2015 | Homo sapiens caspase 3, apoptosis-related cysteine peptidase (CASP3), transcript variant alpha, mRNA [NM_004346] |
| 435 | A_23_P92842 | SAR1B | TAATCTGACATCACCCCAGGGCCATTGTAAAGAGGAACTTCCAGGAGTACATTTGAAG | SEQ ID NO: 2016 | Homo sapiens SAR1 gene homolog B (S. cerevisiae) (SAR1B), transcript variant 2, mRNA [NM_016103] |
| 436 | A_23_P933 | RWDD3 | GGAATCTTTTAGTAAAATAGGAGTGTTTTTGTGTTTCCAAGTTGAATTGGGGAGTGG | SEQ ID NO: 2017 | Homo sapiens RWD domain containing 3 (RWDD3), mRNA [NM_015485] |

Fig. 5-24

| No | Probe ID No. | Symbols of genes | Sequence | SEQ ID NO: | Descriptions of genes (letters and numbers within [ ] indicates GenBank accession No.) |
|---|---|---|---|---|---|
| 437 | A_23_P94230 | LY96 | TGAAGCTATTTCTGGGAGCCCAGAAGAAATGCTCTTTTGCTTGG AGTTGTCATCCTACA | SEQ ID NO: 2018 | Homo sapiens lymphocyte antigen 96 (LY96), mRNA [NM_015364] |
| 438 | A_23_P94501 | ANXA1 | GGCTCTTGTGGAGGAAACTAAAGATTCCCTTGATGGCTCCAAG GTATGATCAGAAGAGT | SEQ ID NO: 2019 | Homo sapiens annexin A1 (ANXA1), mRNA [NM_000700] |
| 439 | A_23_P94533 | CTSL1 | AAGACATGGATCAGTTGGTTGGTGGTCGTTGGCTAGGGATTGAA AGGAGAATCAGATA | SEQ ID NO: 2020 | Homo sapiens cathepsin L1 (CTSL1), transcript variant 1, mRNA [NM_001912] |
| 440 | A_23_P95594 | NAT1 | TGCTTGCAGAGAAAGCTTGTGCCCAAACATGGTGATAGAATTTT TACTATTTAGAATAAG | SEQ ID NO: 2021 | Homo sapiens N-acetyltransferase 1 (arylamine N-acetyltransferase) (NAT1), mRNA [NM_000662] |
| 441 | A_23_P9574 | ECT2 | TAATAGTTAACTGACTATAGATTGTTTTGTATGCCATGTATGTG CCACTTCTGAGAGTAG | SEQ ID NO: 2022 | Homo sapiens epithelial cell transforming sequence 2 oncogene (ECT2), mRNA [NM_018098] |
| 442 | A_23_P96658 | C9orf15B | ATGCCCTAAAGTTAATACCAGCAGTCATATTTTATCAGATGTAA ATCTGGATGTAAGCTC | SEQ ID NO: 2023 | lipopolysaccharide-specific response 5-like protein [Source:RefSeq_peptide;Acc:NP_115965] [ENST00000362832] |
| 443 | A_23_P98382 | TIMM8B | TTGTTAGTAAGCAGATTTAAGGGTCAGTGGGAGGAAGGCTATCAA CCCATTGTCAGATCAG | SEQ ID NO: 2024 | Homo sapiens translocase of inner mitochondrial membrane 8 homolog B (yeast) (TIMM8B), mRNA [NM_012459] |
| 444 | A_23_P98446 | SC5DL | TGTGAAGAGGAGGACTTAATGTTATGCTTAAAATGCCAGATGT TGTCGGGGGACAAGT | SEQ ID NO: 2025 | Homo sapiens sterol-C5-desaturase (ERG3 delta-5-desaturase homolog, S. cerevisiae)-like (SC5DL), transcript variant 2, mRNA [NM_001024956] |
| 445 | A_23_P99980 | HMGB1 | GGATTCTTTCCATTTGCATTTGTTTATGTAATTTCAGTAGGAAGAAT ACTGAACATGTGAGTC | SEQ ID NO: 2026 | Homo sapiens high-mobility group box 1 (HMGB1), mRNA [NM_002128] |
| 446 | A_23_P99985 | HMGB1 | TGGGCCAGCTTTCAAACAAAGATGCCACATTCAAAATAGGTA TATTTTCCTATATTAG | SEQ ID NO: 2027 | Homo sapiens high-mobility group box 1 (HMGB1), mRNA [NM_002128] |
| 447 | A_24_P105648 | BX111927 | TTATAGATGGTCAGTTCAAATAACAGTGCAGTAATTCAGGTA TATCTAAAAGACTGCC | SEQ ID NO: 2028 | BX111927 Soares_multiple_sclerosis_2NbHMSP Homo sapiens cDNA clone IMAGp998G05619, mRNA sequence [BX111927] |
| 448 | A_24_P105794 | RPL31 | CAGACCCGTCTACAAAAGGTTTTTGAGAGTTGAAATATGAAATGT GATGTGGGTATGGAAA | SEQ ID NO: 2029 | Homo sapiens ribosomal protein L31, mRNA (cDNA clone MGC:69191 IMAGE:4714258), complete cds. [BC070210] |
| 449 | A_24_P105913 | THC2606573 | CTGTGCTGTATGGAGAAATGCACCAATACCAAAGGTCAATGTGGAAA TATGGAGCATGTTTGGC | SEQ ID NO: 2030 | AY151386 NAP1 [Homo sapiens] {exp=-1; wgp=0; cg=0}, partial (35%) [THC2606573] |
| 450 | A_24_P107257 | LIN7C | TATTAGTGTGGGACGTGTGACTGAGGTCTTAAAGACTGAAAGAGT TGGGGTTCATTTTCTG | SEQ ID NO: 2031 | Homo sapiens lin-7 homolog C (C. elegans) (LIN7C), mRNA [NM_018362] |
| 451 | A_24_P11045 | THC2785765 | CCACCAGAAACGTACACGTGATTTTCATGACAAATACGTAGGA ACACAAGTCGGAATAG | SEQ ID NO: 2032 | COX7B_HUMAN (P24311) Cytochrome c oxidase polypeptide VIIb, mitochondrial precursor, partial (78%) [THC2785765] |
| 452 | A_24_P114249 | GALNT3 | ATTTCAAATGCAGAATACTTCAGCTCATTTAAAGGTAAATTTTGT TAGTGATTCAATTATA | SEQ ID NO: 2033 | Homo sapiens UDP-N-acetyl-alpha-D-galactosamine:polypeptide N-acetylgalactosaminyltransferase 3 (GalNAc-T3) (GALNT3), mRNA [NM_004482] |
| 453 | A_24_P115774 | BIRC2 | GATACCATTTTGGTTAAAGGAAATGCTGGGGCCAACATCTTCAA AAAGTGTCTAAAAGAA | SEQ ID NO: 2034 | Homo sapiens baculoviral IAP repeat-containing 2 (BIRC2), mRNA [NM_001166] |

Fig. 5-25

| No. | Probe ID No. | Symbols of genes | Sequence | SEQ ID NO: | Descriptions of genes (letters and numbers within [ ] indicates GenBank accession No.) |
|---|---|---|---|---|---|
| 454 | A_24_P116766 | ZNF267 | TTTCTGAGACCACAGTATACCAGTGTGAAATTAGGTTCTGAGTAAATTTCTAATTTATGCCC | SEQ ID NO: 2035 | Homo sapiens mRNA; cDNA DKFZp761N202 (from clone DKFZp761N202). [AL834501] |
| 455 | A_24_P118855 | ENST00000329784 | GCTATGGTGGGCAGACTAAGCCCATTTCCAGAAAAAGGGTAAAACTACAAAGAATACTG | SEQ ID NO: 2036 | PREDICTED: Homo sapiens similar to large subunit ribosomal protein L36a (LOC284230), mRNA [XM_208135] |
| 456 | A_24_P124992 | PSMA4 | AAAGCTGCGTTGGTGTGTTTCATTGCTGATGACATGGGCTGGGATAAGGAGTATGGGTTTCAG | SEQ ID NO: 2037 | Homo sapiens proteasome (prosome, macropain) subunit, alpha type, 4 (PSMA4), mRNA [NM_002789] |
| 457 | A_24_P126741 | ENST00000309178 | AGCCTCGAACGCAGACTAACAAGATTCAAGATTACTGCAAGACAGTCACAGGAGCGAGAAT | SEQ ID NO: 2038 | |
| 458 | A_24_P126890 | RPL9 | GGTGTTGCTTGTCAGTATGTCAAACGGAGAAAAGATGAAATAAT CCTGAAGGAAATGAC | SEQ ID NO: 2039 | Homo sapiens ribosomal protein L9 (RPL9), transcript variant 1, mRNA [NM_000661] |
| 459 | A_24_P127181 | LOC442237 | AACTGAAATCTTTCAGAGAAAATCGAAGTCGAGTAGTAGAATTGGAGAAAAATTCAGTG | SEQ ID NO: 2040 | PREDICTED: Homo sapiens similar to 40S ribosomal protein S7 (S8) (LOC442237), mRNA [XR_018963] |
| 460 | A_24_P127621 | A_24_P127621 | TCGAAGCAAGTACCACAAAAGGCATTTGAATGCAGTTCCCAGATTCTCAGAAATATTAG | SEQ ID NO: 2041 | |
| 461 | A_24_P132787 | RAB18 | TAAAAGGTGACATTGCACTTGATTTACACGTTGCTAGTGTCATTACATGTGGTTGAAGG | SEQ ID NO: 2042 | Homo sapiens RAB18, member RAS oncogene family (RAB18), mRNA [NM_021252] |
| 462 | A_24_P133991 | ANKRD12 | AACTGAAATCTTTGAGAATGGCTGAAAATGGTGAAATGGTAGTAAAAAGGATGGTAGT | SEQ ID NO: 2043 | Homo sapiens ankyrin repeat domain 12 (ANKRD12), mRNA [NM_015208] |
| 463 | A_24_P134392 | STCH | TGAGTAACTTATTTGATGAGGAAAAGTTTGGTAGTGTGTTTTCACTGAAAGCACTGAG | SEQ ID NO: 2044 | Homo sapiens stress 70 protein chaperone, microsome-associated, 60kDa (STCH), mRNA [NM_006948] |
| 464 | A_24_P135242 | A_24_P135242 | GATGGGAAGAAAAAGCTGGCAAGCTACTTGTACCTGCAGAACCCAAACTGGCATTTGTCAT | SEQ ID NO: 2045 | |
| 465 | A_24_P135551 | LOC130865 | TAACAGGATAGCTGTGGCTGTGGGGATTCAGCGAAAGGTGTTACAGTAGACTAAAACT | SEQ ID NO: 2046 | PREDICTED: Homo sapiens similar to 60S ribosomal protein L26 (Silica-induced gene 20 protein) (SIG-20) (LOC130865), mRNA [XR_019454] |
| 466 | A_24_P139208 | USP25 | CAATATACAGCAAGGTGATTATTTGAAGAGAATGCCAAAGTACTTGAATAAGGGCTATTG | SEQ ID NO: 2047 | Homo sapiens ubiquitin specific peptidase 25 (USP25), mRNA [NM_013396] |
| 467 | A_24_P141214 | STOM | GGGTTGAGCATTTAACATTGGTCTTTGAGACGTCTGAGTTGACCTAGAGAACAAGCA | SEQ ID NO: 2048 | Homo sapiens stomatin (STOM), transcript variant 2, mRNA [NM_198194] |
| 468 | A_24_P144383 | A_24_P144383 | GTCGGTTGAGCCGAAAAGATCTAAGAGAATGGTGGCTAAAAGATGGAAGCATTTGAACT | SEQ ID NO: 2049 | |
| 469 | A_24_P144666 | LOC401975 | GTGTGGGTGTGAAGCTAATGATGCATGGCTACTTCTTTAACTGTGTCTGTGTGGGTTTACGTGA | SEQ ID NO: 2050 | PREDICTED: Homo sapiens similar to ribosomal protein S3a (LOC401975), mRNA [XR_017247] |
| 470 | A_24_P148151 | TSNAX | AAAGTTGAGTTATATCTCGTACATGAAGAATGGTTTTAGAGTAGATTATTAGCA | SEQ ID NO: 2051 | Homo sapiens translin-associated factor X (TSNAX), mRNA [NM_005999] |
| 471 | A_24_P152753 | LOC285260 | TGTCTGACATGGAATCGGTGTGAGGAGATCGCCATTATCGAGAAAGGATGAAGATTCACGAAATAAGGT | SEQ ID NO: 2052 | PREDICTED: Homo sapiens similar to ribosomal protein L31 (LOC285260), mRNA [XR_019376] |
| 472 | A_24_P152775 | LOC442195 | ACACAAGCAAGGTGTGTGAGGAGATCGCCATTATCGAGGAAG AGGCTCCACAACAGGA | SEQ ID NO: 2053 | PREDICTED: Homo sapiens hypothetical LOC442195 (LOC442195), mRNA [XR_019264] |
| 473 | A_24_P153324 | LOC390413 | GAAGCTTAACAAGGTTTCAATTAACATGCTGGGATTGTAGAAACCATATATTGCAGGGTA | SEQ ID NO: 2054 | PREDICTED: Homo sapiens similar to 60S ribosomal protein L7 (LOC390413), mRNA [XR_018341] |

Fig. 5-26

| No. | Probe ID No. | Symbols of genes | Sequence | SEQ ID NO: | Descriptions of genes (letters and numbers within [ ] indicates GenBank accession No.) |
|---|---|---|---|---|---|
| 474 | A_24_P153511 | OSBPL8 | CGTTGTGCCATATACACACAAAATTTGTGGAAGGCAGTTTTAA CTTTCTGAAGAATATC | SEQ ID NO: 2055 | Homo sapiens oxysterol binding protein-like 8 (OSBPL8), transcript variant 1, mRNA [NM_020841] |
| 475 | A_24_P15765 | AK098605 | TCCAAGTCTGGCTAGTACGTGAATTGGAGAGAAAAAGTTTGGGAAG CATGTGTCTTTATTG | SEQ ID NO: 2056 | Homo sapiens cDNA FLJ25739 fis, clone TST05834. [AK098605] |
| 476 | A_24_P161914 | LOC130728 | CTATAGTGTTGGAAAACACTTCAAACGAAAATAACTTCCTGCAGGG CATTCAAATTATGTTC | SEQ ID NO: 2057 | PREDICTED: Homo sapiens similar to 60S ribosomal protein L7 (LOC130728), mRNA [XR_019248] |
| 477 | A_24_P165595 | ARL5A | GAAGTAACTTGCACCGAAAACAGCTTTTATGTTGCTTAGGGTAT ATTTTTCAGTGTGTG | SEQ ID NO: 2058 | Homo sapiens ADP-ribosylation factor-like 5A (ARL5A), transcript variant 1, mRNA [NM_012097] |
| 478 | A_24_P165864 | P2RY14 | TTTTTCTGGAAAACAGAGACGGATTTTACTTCTGGAGACATGGCAT ACGGTTACTGACTTAT | SEQ ID NO: 2059 | Homo sapiens purinergic receptor P2Y, G-protein coupled, 14 (P2RY14), transcript variant 2, mRNA [NM_014879] |
| 479 | A_24_P167063 | ZNF518 | AAAGAAAGGCATACATAGAATGGTTCAAGGTATCTTGGTATGCA CATTATACTTGTACTG | SEQ ID NO: 2060 | Homo sapiens zinc finger protein 518 (ZNF518), mRNA [NM_014803] |
| 480 | A_24_P169378 | RPS7 | AACTGAAATCTTTCCAGAAAAATCCAAATCCGGGTAGTAAGTGAA TTGGAGAAAAGTTGA | SEQ ID NO: 2061 | Homo sapiens ribosomal protein S7 (RPS7), mRNA [NM_001011] |
| 481 | A_24_P171873 | FBXO4 | GATTCCACAGATTCAAAAGTGTGTAGAAGTTGTAGATGGGTTCA TCTATGTTGCAAATGC | SEQ ID NO: 2062 | Homo sapiens F-box protein 4 (FBXO4), transcript variant 1, mRNA [NM_012176] |
| 482 | A_24_P172481 | TRIM22 | TGCCCCTTAAAGATTGAAGAAGAAGAAAGTTGTCAACTCATAT CGACGGTTATCTAGCAA | SEQ ID NO: 2063 | Homo sapiens tripartite motif-containing 22 (TRIM22), mRNA [NM_006074] |
| 483 | A_24_P175059 | ATG5 | TTGCACAAGAGGCTGGTCTGAATATGAATTCACATTAAGAGT GTTATTGTCTGGGTTC | SEQ ID NO: 2064 | Homo sapiens ATG5 autophagy related 5 homolog (S. cerevisiae) (ATG5), mRNA [NM_004849] |
| 484 | A_24_P175176 | PHTF2 | AGATTGAGGTTAAGTTAGAGTTGGGAGTTGATTATTAAGTACA GTATACGCTCAACAG | SEQ ID NO: 2065 | Homo sapiens putative homeodomain transcription factor 2 (PHTF2), mRNA [NM_020422] |
| 485 | A_24_P175187 | SAMD9 | CAACAGCAGGATACGTAATGCAAATGTAATTTTCGGCTAATAAAA TTATGGATATGGGAG | SEQ ID NO: 2066 | Homo sapiens sterile alpha motif domain containing 9 (SAMD9), mRNA [NM_017654] |
| 486 | A_24_P175188 | SAMD9 | TGCCAATTGACTGGCAGATTAACATACAACCTATGTTTTTGAACA AAACAACCAGCGATA | SEQ ID NO: 2067 | Homo sapiens sterile alpha motif domain containing 9 (SAMD9), mRNA [NM_017654] |
| 487 | A_24_P175519 | TXN | AAGTAGATGTGTGGATGACTGTCAAGATGTTGTTCAGAGTGTGAA GTCAAATGGCACGCCAA | SEQ ID NO: 2068 | Homo sapiens thioredoxin (TXN), mRNA [NM_003329] |
| 488 | A_24_P175989 | VPS29 | GAGAGGAGACTTCGATGAGAGAATCTGAATTATCCAGAACAGAAAG TTGTGACTGTTGGACA | SEQ ID NO: 2069 | Homo sapiens vacuolar protein sorting 29 homolog (S. cerevisiae) (VPS29), transcript variant 2, mRNA [NM_057180] |
| 489 | A_24_P178602 | ZNF600 | ATAAGATAATTCACACCCGAGAGAACAGTAAAACGTTTATGAGGGCTGC TGTGAAAAGCCTTTG | SEQ ID NO: 2070 | Homo sapiens zinc finger protein 600 (ZNF600), mRNA [NM_198457] |
| 490 | A_24_P179351 | TPT1 | GAACAGAGACAGAGCAGAAGAGTAAAAAGGTTTTATGACAGGGGCTGTT AGAAGCAAATCAAGCAG | SEQ ID NO: 2071 | Homo sapiens tumor protein, translationally-controlled 1 (TPT1), mRNA [NM_003295] |
| 491 | A_24_P180424 | TMEM30A | CAATTGTGTATGCACATTGTCTTAGTTAAGCGACCAATTGTTT GGTTGGGTTTTGGTAAG | SEQ ID NO: 2072 | Homo sapiens transmembrane protein 30A (TMEM30A), mRNA [NM_018247] |
| 492 | A_24_P181120 | PFDN5 | CACGGCATGAAACAAGGCCGTCATGAAATGAGTCAGAAGAT TCAGACTGTCAGAGCC | SEQ ID NO: 2073 | Homo sapiens prefoldin subunit 5 (PFDN5), transcript variant 1, mRNA [NM_002624] |
| 493 | A_24_P183864 | IMPA1 | TCAGGCTTATCCCTTGGCACGTAAACAGACTACTAGACTTATTG TAGGTTCGTTTGAGCT | SEQ ID NO: 2074 | Homo sapiens inositol (myo)-1 (or 4)-monophosphatase 1 (IMPA1), mRNA [NM_005536] |

Fig. 5-27

| No. | Probe ID No. | Symbols of genes | Sequence | SEQ ID NO: | Descriptions of genes (letters and numbers within [ ] indicates GenBank accession No.) |
|---|---|---|---|---|---|
| 494 | A_24_P186844 | LOC389404 | AGGAACGCTGCGGAGGGACTTCAATCACATCGTAGAAGTGAGTCTTCTTGGAAAGAAAA | SEQ ID NO: 2075 | PREDICTED: Homo sapiens similar to 60S ribosomal protein L9 (LOC389404), mRNA [XR_018133] |
| 495 | A_24_P188800 | MARCH1 | GTCACGAAAAAGATTTTCAGAAAATGTTCGGATATAATTAGGTCTGTTAAATACCCACAG | SEQ ID NO: 2076 | Homo sapiens membrane-associated ring finger (C3HC4) 1 (MARCH1), mRNA [NM_017923] |
| 496 | A_24_P188878 | RPL34 | TGTTTACCTTTATACCAAGCAAGGTTGGGAAAAGCACCAAAATGTCCATGTCGTCGTGCC | SEQ ID NO: 2077 | Homo sapiens ribosomal protein L34 (RPL34), transcript variant 2, mRNA [NM_033625] |
| 497 | A_24_P190904 | AP1S2 | GGTGGAAGACTGTAAGGAGTGCTTCATGTAGTCTTCATTAAAAATAACATGGATAGTG | SEQ ID NO: 2078 | Homo sapiens adaptor-related protein complex 1, sigma 2 subunit (AP1S2), mRNA [NM_003916] |
| 498 | A_24_P191417 | NAB1 | AAGTTCCTTAACTATCTTATGTTTGTAGTCTTTCAAGCTTAGTGATAAGGTGGAAGGAC | SEQ ID NO: 2079 | Homo sapiens NGFI-A binding protein 1 (EGR1 binding protein 1) (NAB1), mRNA [NM_005966] |
| 499 | A_24_P191833 | SFRS12 | AAGGACTTAGGAGTATATGGGAGGTTATTGGTTTTATGTTTAAGGATACGTTTACTTGAG | SEQ ID NO: 2080 | Homo sapiens splicing factor, arginine/serine-rich 12 (SFRS12), transcript variant 2, mRNA [NM_139168] |
| 500 | A_24_P194313 | C21orf66 | ATTTAAATTAAGGCTCAGTTAATTGTCCCGTGTAAACGATGTGTCAGTGTAAATGT | SEQ ID NO: 2081 | Homo sapiens chromosome 21 open reading frame 66 (C21orf66), transcript variant 1, mRNA [NM_007021] |
| 501 | A_24_P199500 | RNF2 | AAACTGCTTAGATTTTGATGACATTAGATTAGTAGTTGGATTAAATAACTAAATTGG | SEQ ID NO: 2082 | Homo sapiens ring finger protein 2 (RNF2), mRNA [NM_007212] |
| 502 | A_24_P20120 | KIAA1212 | TTGGAGAATGAAAATGCCTAAGATTAGGACATGAGTCGTGTTGTCAAGCCTGCACTTATATAAGACGC | SEQ ID NO: 2083 | Homo sapiens KIAA1212 (KIAA1212), mRNA [NM_018064] |
| 503 | A_24_P201353 | C10orf32 | AATATGTTTTAAATGACATTAGGACATGAGTCGTGTTGTCAACAAATATGTTGTTGA | SEQ ID NO: 2084 | Homo sapiens chromosome 10 open reading frame 32 (C10orf32), mRNA [NM_144591] |
| 504 | A_24_P201702 | CLEC2B | ATTGCGAATTCAAGTAAATACAGAGTGTTCGACTCAACATGCCGAGCTAACTATAATTGACGA | SEQ ID NO: 2085 | Homo sapiens C-type lectin domain family 2, member B (CLEC2B), mRNA [NM_005127] |
| 505 | A_24_P203103 | SH2D1A | AAGGGTAAGGTTCACTGTGTAAAATAATAACTGGAATTGTGGATTGTGTATGGGTGTTGGT | SEQ ID NO: 2086 | Homo sapiens SH2 domain protein 1A, Duncan's disease (lymphoproliferative syndrome) (SH2D1A), mRNA [NM_002351] |
| 506 | A_24_P203327 | LOC730647 | CTTGCTTTGATGACACTTCCCCTCAAGCACCAAGACAGGTTTCTGTTGATATCGAAAAAA | SEQ ID NO: 2087 | PREDICTED: Homo sapiens similar to Histidine triad nucleotide-binding protein 1 (Adenosine 5'-monophosphoramidase) (Protein kinase C inhibitor 1) (Protein kinase C-interacting protein 1) (PKCI-1) (LOC730647), mRNA [XM_001126674] |
| 507 | A_24_P203909 | RPL34 | GAGGGGTTGGTGCTGTAAGACTTAAAGTTCTTATGAAATTGTCCAAAACAAACAACATG | SEQ ID NO: 2088 | Homo sapiens ribosomal protein L34 (RPL34), transcript variant 2, mRNA [NM_033625] |
| 508 | A_24_P206045 | EDEM3 | TTTAGAGGGGGGTAGAATTTAGTAAATTTAGTAAAATTTCAGCAGGTGGTTTATGCACAAGGCTTCA | SEQ ID NO: 2089 | Homo sapiens ER degradation enhancer, mannosidase alpha-like 3 (EDEM3), mRNA [NM_025191] |
| 509 | A_24_P20996 | BC043173 | CTGAAAAATGTTCATATATGAGTATATATATATATGAATGTGTCTTTATGGTGAAGGGCTCTCATTGC | SEQ ID NO: 2090 | Homo sapiens cDNA clone IMAGE:5287121. [BC043173] |
| 510 | A_24_P212864 | LOC646161 | ACAGAAGTACAACGTGCGATCCATGATGATCGGAAAGAATGAAGAATGATGAAGTTAGGCTTGTACGAGG | SEQ ID NO: 2091 | PREDICTED: Homo sapiens similar to 60S ribosomal protein L26 (LOC646161), mRNA [XR_018048] |
| 511 | A_24_P213354 | LOC731048 | CACGTGCTTAAAAACACAGAGTAAATGTGAACTTAAGGGTGATCTGTGGTCATTGAG | SEQ ID NO: 2092 | PREDICTED: Homo sapiens similar to 60S ribosomal protein L17 (L23) (LOC731048), mRNA [XR_015710] |
| 512 | A_24_P213375 | A_24_P213375 | AAATGTGTTCCATGATCAAAAAATGGCAGACAATGATTCTTCAT CTGTCTGTGTTGGTT | SEQ ID NO: 2093 | |

Fig. 5-28

| No. | Probe ID No. | Symbols of genes | Sequence | SEQ ID NO: | Descriptions of genes (letters and numbers within [ ] indicates GenBank accession No.) |
|---|---|---|---|---|---|
| 513 | A_24_P213783 | RPL31 | CTTTGGTTAGCTATGTACCTGTTAGGACTTTGAAAAATGTAGAG ACAGTCAATGTGGATG | SEQ ID NO: 2094 | Homo sapiens ribosomal protein L31 (RPL31), mRNA [NM_000993] |
| 514 | A_24_P221375 | A_24_P221375 | TAGTTTGGTTAGGCATGTAGGTACCACTTTGAAAAATGTACACAG GAGTCAATGTGGAGGA | SEQ ID NO: 2095 | |
| 515 | A_24_P222655 | C1QA | GGGTGACCAGGCTCTGGGTTGAAAAGAGCCCAAAAGGGTCACA TTTACCAGGGCTCTGA | SEQ ID NO: 2096 | Homo sapiens complement component 1, q subcomponent, A chain (C1QA), mRNA [NM_015591] |
| 516 | A_24_P222911 | SFRS7 | CAGAAATGTCAATGAGACTAAAGTGGTTTTGTAAATCTAAGGCTA TATTTAGGAACACTCC | SEQ ID NO: 2097 | Homo sapiens splicing factor, arginine/serine-rich 7, 35kDa (SFRS7), mRNA [NM_001031684] |
| 517 | A_24_P225308 | ARID4B | GTTGAAAATGGTTTGAAGTTATTGAAATTTGTAGAGGACTGTAA AGATTTGTTGACAGCA | SEQ ID NO: 2098 | Homo sapiens AT rich interactive domain 4B (RBP1-like) (ARID4B), transcript variant 1, mRNA [NM_016374] |
| 518 | A_24_P225468 | ANP32E | TCATCTTACTGTGCAATCAAAATTAGAGTACTTTGGTTTGAAAA CAACACTTAGAGCCTC | SEQ ID NO: 2099 | Homo sapiens acidic (leucine-rich) nuclear phosphoprotein 32 family, member E (ANP32E), mRNA [NM_030920] |
| 519 | A_24_P225749 | PREI3 | GACTATTTTCTAGTGAATATTTATACTAAGGTAGTGACTGAGGA TTTGGTGATCTGGCTG | SEQ ID NO: 2100 | Homo sapiens preimplantation protein 3 (PREI3), transcript variant 1, mRNA [NM_015387] |
| 520 | A_24_P229066 | ENST00000078131 | AAGAAGTCCACAACAAGAACAGGCAGGTTATGTCACCCATCTGAT GAAGCAGAGTTCAGAGA | SEQ ID NO: 2101 | OTTHUMP00000016594. [Source:Uniprot/SPTREMBL;Acc:Q9NU98] [ENST00000078131] |
| 521 | A_24_P232856 | RPL9 | GAACCCTGCGGAGGGACGTTCAATCACACATCAAGTAGAACTCAGC CTTCTTGGAAAGAAAA | SEQ ID NO: 2102 | Homo sapiens ribosomal protein L9 (RPL9), transcript variant 1, mRNA [NM_000661] |
| 522 | A_24_P254429 | ABCA1 | CCAAAGAGCCATGTGTCATGATGTAATACGAACCAGTTGATATG AGACATTAATTTGTAC | SEQ ID NO: 2103 | Homo sapiens ATP-binding cassette, sub-family A (ABC1), member 1 (ABCA1), mRNA [NM_005502] |
| 523 | A_24_P236008 | SCYL2 | ATAGACTATGTAGTTGTCTGTCTGGGTTTTTGTTTGTTTTATTTTTGGA ATGCTTATAAGCTCC | SEQ ID NO: 2104 | Homo sapiens mRNA for KIAA1360 protein, partial cds. [AB037781] |
| 524 | A_24_P237511 | EIF1AY | GTTTCAGTTACTTAGATGGTCCATAAGGTTTCATAACAATTT GAAGACAGAAATCTGC | SEQ ID NO: 2105 | Homo sapiens eukaryotic translation initiation factor 1A, Y-linked (EIF1AY), mRNA [NM_004681] |
| 525 | A_24_P242298 | ZRANB2 | GACTTTTTGAAAGTCTACCTTCTAAATTGCCCGACGATCTAGA TTCTACATGTTACCAT | SEQ ID NO: 2106 | Homo sapiens zinc finger, RAN-binding domain containing 2 (ZRANB2), transcript variant 2, mRNA [NM_005455] |
| 526 | A_24_P25326 | ZMYM6 | AGGACTATTTAAATCAGTGTGTGTGAGCTCAGTTTTGGATAAATG CAAAGACAAGTTACCC | SEQ ID NO: 2107 | Homo sapiens zinc finger, MYM-type 6 (ZMYM6), mRNA [NM_007167] |
| 527 | A_24_P255252 | A_24_P255252 | TGGACTAGTGGAAGGATGGGTGTGAGTCAGTTGATTGATTTGTTT GAGGATGATTAGAAGA | SEQ ID NO: 2108 | |
| 528 | A_24_P263524 | TXNDC9 | TGAGTTCACCAGAAACTTTAGATATGGGGGCTGCAGTTGTGTCTG ACATCTTAATTACAG | SEQ ID NO: 2109 | Homo sapiens thioredoxin domain containing 9 (TXNDC9), mRNA [NM_005783] |
| 529 | A_24_P264549 | A_24_P264549 | ATTCATAGTAGCATAGAAGACATGATCAAAGGTGTTACACTGGA CTTCGATTACAATATG | SEQ ID NO: 2110 | |
| 530 | A_24_P265856 | SENP7 | TTGTGTGTGTTGGGGGGTACTTTTAAAGGTGACTATGTTTTGT AGATCTAATTTTGGA | SEQ ID NO: 2111 | Homo sapiens SUMO1/sentrin specific peptidase 7 (SENP7), transcript variant 1, mRNA [NM_020654] |
| 531 | A_24_P268736 | MYNN | TGGAGAGGATCAATACTTGAGTGAACAGGAATCGCATACAAAAAA GTGCTTTATCAGAAAC | SEQ ID NO: 2112 | Homo sapiens myoneurin (MYNN), mRNA [NM_018657] |

Fig. 5-29

| No. | Probe ID No. | Symbols of genes | Sequence | SEQ ID NO: | Descriptions of genes (letters and numbers within [ ] indicates GenBank accession No.) |
|---|---|---|---|---|---|
| 532 | A_24_P268917 | RAB33B | CCCAGAATCTAATGTAGTTCGCTATTAATAACAATGGATTATTG AAAGTATATTGGAAAT | SEQ ID NO: 2113 | Homo sapiens RAB33B, member RAS oncogene family (RAB33B), mRNA [NM_031296] |
| 533 | A_24_P276683 | TMCO1 | CCTTCATTTCCTGGTATATTCTGTGTACTATGTCGATTCGACAG AAGATTCAGAAGATTC | SEQ ID NO: 2114 | Homo sapiens transmembrane and coiled-coil domains 1 (TMCO1), mRNA [NM_019026] |
| 534 | A_24_P278008 | DCTN6 | CTATGAAAGGAAGCTCAACCCAGTAAAGAACTAAGAACAGTGT ATAACATGAAGATAAG | SEQ ID NO: 2115 | Homo sapiens dynactin 6 (DCTN6), mRNA [NM_006571] |
| 535 | A_24_P278460 | MLSTD2 | ACCCATGGAACAATAGGTTAGGATACAGGAAGCAGTCCTTAC TTACAGTTGTTGTCTG | SEQ ID NO: 2116 | Homo sapiens male sterility domain containing 2 (MLSTD2), mRNA [NM_032228] |
| 536 | A_24_P280897 | LOC388532 | AGCACTGTGAGAGGCTGGGATAGCTTCCTGAAATACAATGAAGGAA AATGACATAGAAAAAGA | SEQ ID NO: 2117 | PREDICTED: Homo sapiens similar to ribosomal protein L21 (LOC388532), mRNA [XM_001127035] |
| 537 | A_24_P281304 | A_24_P281304 | GAGGAGAAGGCACCGGATATATGGTTCTAAGGCGTTTTAGAAAAC AAGTTTTTCCTTTGGC | SEQ ID NO: 2118 | |
| 538 | A_24_P285179 | THC2649313 | AGTTGGGAATTTTGAAATGGCATGTCGTATATATGTGGCATAAT TGTTGGCACATTTGCA | SEQ ID NO: 2119 | |
| 539 | A_24_P288064 | ZFYVE16 | GTGTATGGTATTCTGCCATGTAAGTAATTGAACAGTCTTAAAATA AGCAAATGGTAGAGGG | SEQ ID NO: 2120 | Zinc finger FYVE domain-containing protein 16 (Endofin) (Endosome-associated FYVE domain protein) [Source:Uniprot/SWISSPROT;Acc:Q7Z3T8] [ENST00000380248] |
| 540 | A_24_P287756 | NUDT21 | CCCATAGTTAGTTGAGTTGTTATACACGTGATTATTTGGGTT AAACTGGACTCATTTC | SEQ ID NO: 2121 | Homo sapiens nudix (nucleoside diphosphate linked moiety X)-type motif 21 (NUDT21), mRNA |
| 541 | A_24_P28901 | LSM3 | CCGTCCACTAGTGAGGAGTTGGCTGAAAACAACAAGCCAATTGTGCTGTATG GAAAACGGGAGACTTT | SEQ ID NO: 2122 | Homo sapiens LSM3 homolog, U6 small nuclear RNA associated (S. cerevisiae) (LSM3), mRNA [NM_014463] |
| 542 | A_24_P290257 | A_24_P290257 | CCAATTCATTCAACATAGAACCAAGCCAATTATACCATCCAGTCA TTGAAGGACACCAAGA | SEQ ID NO: 2123 | |
| 543 | A_24_P295543 | BLOC1S2 | GTTTATTTCATGTGAGTGACCACAGGGTTGATGACAGCAGTTGGG AAATGTGATGAAAACA | SEQ ID NO: 2124 | Homo sapiens biogenesis of lysosome-related organelles complex-1, subunit 2 (BLOC1S2), transcript variant 2, mRNA [NM_001013421] |
| 544 | A_24_P298238 | A_24_P298238 | ATCCTTGAAGGAAATGACATTGAGGTTGTTCAATTCAGGAAGC GACAACAGTTAAAAG | SEQ ID NO: 2125 | |
| 545 | A_24_P298604 | LOC731599 | GATGAAATCAATGACCACAGGGTTGCGGCAAATGACTTGAAAGAAT TGGTCAATAAAATGAT | SEQ ID NO: 2126 | PREDICTED: Homo sapiens hypothetical protein LOC731599 (LOC731599), mRNA [XR_015536] |
| 546 | A_24_P30194 | IFIT5 | AATGTGGCTTCTCTAATGTAGTTTCTTGATTACGGACTACACA ATTATGTACGATCACA | SEQ ID NO: 2127 | Homo sapiens interferon-induced protein with tetratricopeptide repeats 5 (IFIT5), mRNA [NM_012420] |
| 547 | A_24_P303118 | RPL34 | CGAGGAGCAGAAAATGGTTGTGTAAAGTGTTGAAGGACAAGGAC AGAGTACGAAAGGCTAA | SEQ ID NO: 2128 | Homo sapiens ribosomal protein L34 (RPL34), transcript variant 2, mRNA [NM_033625] |
| 548 | A_24_P303127 | C5orf29 | CCCAAATGCGTAGAAACATCACATAAGGACTAAATGGCTCATGT TACTGACGGGAATT | SEQ ID NO: 2129 | Homo sapiens chromosome 5 open reading frame 29 (C5orf29), mRNA [NM_152687] |
| 549 | A_24_P305570 | RIN2 | TATGCAGTGAGGAGTTTGGCAAAAATGCATTGGGAAAATGTCATTGATTGCT GTGTAGAAACAATTTG | SEQ ID NO: 2130 | Homo sapiens Ras and Rab interactor 2 (RIN2), mRNA [NM_018993] |
| 550 | A_24_P306469 | LOC257039 | AGAGAAAACAGAGACAATATTGTCCGGAGATCTCAGTCTGGA TCAGGAGAGCGGTTGAA | SEQ ID NO: 2131 | PREDICTED: Homo sapiens similar to 40S ribosomal protein S17 (LOC257039), mRNA [XM_172230] |

Fig. 5-30

| No. | Probe ID No. | Symbols of genes | Sequence | SEQ ID NO: | Description of genes (letters and numbers within [ ] indicates GenBank accession No.) |
|---|---|---|---|---|---|
| 551 | A_24_P306527 | ENST00000308989 | ACCGCATCCGTCCGTGGTTATCCAGAAAATGTAATGAGGATGAAGATTCAGCAAATAAGT | SEQ ID NO: 2132 | PREDICTED: Homo sapiens similar to ribosomal protein L31 (LOC729905), mRNA [XM_011334281] |
| 552 | A_24_P306726 | TPT1 | GACCAGAAACAGTAAAAGGTTTATGACAGGGGGCTGCAAAAGAAATCAAGGAGACATCCTTG | SEQ ID NO: 2133 | Homo sapiens tumor protein, translationally-controlled 1 (TPT1), mRNA [NM_003295] |
| 553 | A_24_P310894 | CAPZA1 | TGTATTATTTGTCCTTCATAGTATCCATCCATACCACAGTATGTTCTGTATGAGGTAGTC | SEQ ID NO: 2134 | Homo sapiens capping protein (actin filament) muscle Z-line, alpha 1 (CAPZA1), mRNA [NM_006135] |
| 554 | A_24_P312417 | ZBTB26 | AGAGGAGGAAGATTTTTAAAACCTTTATCATTCAGCATTTGTATTTTATGGATCCCAGG | SEQ ID NO: 2135 | Zinc finger and BTB domain-containing protein 26 (Zinc finger protein 481) (Zinc finger protein Bioref). [Source:Uniprot/SWISSPROT;Acc:Q9HCK0] [ENST00000373656] |
| 555 | A_24_P315326 | LOC341412 | AAGCTCTATACTTTGGTTACGAAGTGTACCCGTTACCGCTTTCAAAAATCTACAGGCAATG | SEQ ID NO: 2136 | AGENCOURT_10640955 NIH_MGC_126 Homo sapiens cDNA clone IMAGE:6723568 5', mRNA sequence [CA455253] |
| 556 | A_24_P316074 | LOC730902 | TATGAATGGTGTGAGCCCGAAAGGTCAAAGGTCGTTGGCAGCTTCTTCCCTTCGTCAAATCTT | SEQ ID NO: 2137 | PREDICTED: Homo sapiens similar to 60S ribosomal protein L7 (LOC730902), mRNA [XR_015600] |
| 557 | A_24_P320326 | SUB1 | CAGAAAAAACTGTAAGCAAAACAAAAGAGACAAGGTGAGACTTCGAGAGCCCTGTCATCTCTA | SEQ ID NO: 2138 | Homo sapiens SUB1 homolog (S. cerevisiae) (SUB1), mRNA [NM_006713] |
| 558 | A_24_P321511 | GOLT1B | TTAGAGGAAGAATAGTATCTGGTAATGTGAAGGAGCATCGTATTTAACTCCTTTGTAGAG | SEQ ID NO: 2139 | Homo sapiens golgi transport 1 homolog B (S. cerevisiae) (GOLT1B), mRNA [NM_016072] |
| 559 | A_24_P324224 | A_24_P324224 | AAAGGTCTGTGGGCCAAGAATTGGATAAGGAAATCCATAGGCATGTGCGGTTGTCCAGAAAA | SEQ ID NO: 2140 | |
| 560 | A_24_P324506 | A_24_P324506 | GCAATAAAGGCAGCTAATTGAAATACAAGTATGGCTATTTCCTGTGGACATGCTGTGT | SEQ ID NO: 2141 | |
| 561 | A_24_P32790 | YOD1 | CTAGGAGTCTAATTAAGGACATTAAGATACAATTCTTGAGGTACTAACATCCAGCTCTTC | SEQ ID NO: 2142 | Homo sapiens YOD1 OTU deubiquinating enzyme 1 homolog (S. cerevisiae) (YOD1), mRNA [NM_018566] |
| 562 | A_24_P33213 | A_24_P33213 | GACCATATTACATGGGGGTAAAGGTACGGAAATCTGAAGTCAGATAAATGAAGTTATGTACAAGG | SEQ ID NO: 2143 | |
| 563 | A_24_P333112 | A_24_P333112 | GGTCATCAGAATCAGAAGTATGAATGTGTGAGCCACAGGACGAAAGGTATTGCAACTT | SEQ ID NO: 2144 | |
| 564 | A_24_P33607 | LOC652558 | TAAGAAATAATTGCTTTGACGAGACAACCGTTGATTGCTGGATCTCTTGGTAAATATGG | SEQ ID NO: 2145 | PREDICTED: Homo sapiens similar to 60S ribosomal protein L7 (LOC652558), mRNA [XR_019386] |
| 565 | A_24_P339869 | ZNF295 | TCATATGCCTTAGCAGAGTAAGTCATTTTCATTTTAGTTCGAATAAGCTTTTCGAA | SEQ ID NO: 2146 | Homo sapiens zinc finger protein 295 (ZNF295), transcript variant 3, mRNA [NM_020727] |
| 566 | A_24_P349636 | LOC388401 | AGTTGCTGGAAGCATAACAACGTTTCAGTTCAGTTGCTCATCTCTCTTGGTAAATATAGGCATCAACTG | SEQ ID NO: 2147 | PREDICTED: Homo sapiens similar to 60S ribosomal protein L7 (LOC388401), mRNA [XR_016879] |
| 567 | A_24_P351435 | CRBN | GAAAGTTGAAACGAATTCGAAGCAGACAAAAGGTTCAAAGTCCTTGAGCTAAGAACACAGTGAGA | SEQ ID NO: 2148 | Homo sapiens cereblon (CRBN), mRNA [NM_016302] |
| 568 | A_24_P352445 | MRPL42 | TTTTTAGTGCATGCAATCAGAATGACAAAGGGGTGGTTTTCTTCACCCAAGAATGCTTTTCC | SEQ ID NO: 2149 | Homo sapiens mitochondrial ribosomal protein L42 (MRPL42), nuclear gene encoding mitochondrial protein, transcript variant 3, mRNA [NM_172178] |
| 569 | A_24_P354412 | AK091335 | TGTAGACTGAAGGAGTCTTGAGGACTTTAGGGAAACACCCAGGATTAAATCTCACTCTGCGGTGCTTGT | SEQ ID NO: 2150 | Homo sapiens cDNA FLJ34016 fis, clone FCBBF2002541, [AK091335] |
| 570 | A_24_P354954 | CCDC126 | AATGGAACTCTTGAGGACTTTAGCCAGGTGTATATAAAGGTACTTTGTGTGCATT | SEQ ID NO: 2151 | Homo sapiens coiled-coil domain containing 126 (CCDC126), mRNA [NM_138771] |

Fig. 5-31

| No. | Probe ID No. | Symbols of genes | Sequence | SEQ ID NO | Descriptions of genes (letters and numbers within [ ] indicates GenBank accession No.) |
|---|---|---|---|---|---|
| 571 | A_24_P357518 | RPL21 | GGGCAGATATATGGTAATCTATAAGAAAGGTGATATTGCAGAGATCAAGGGAAGGGGTAC | SEQ ID NO: 2152 | Homo sapiens ribosomal protein L21 (RPL21), mRNA [NM_000982] |
| 572 | A_24_P358205 | A_24_P358205 | TGTTCAAAAAGAATGCCCAAGTGTTACCATGGCTAAATGAAGAGTGTGCAGTGTTGC | SEQ ID NO: 2153 | |
| 573 | A_24_P362646 | TXNDC9 | CTCCACATTCCAGGTGTGTAAAATACTAGACAGACATCTGGCAATATGTCCAAGAAACACCT | SEQ ID NO: 2154 | Homo sapiens thioredoxin domain containing 9 (TXNDC9), mRNA [NM_005783] |
| 574 | A_24_P364025 | UBE2D1 | ATGTGATGGGTGAGTCATTAGCAAAGCATTAAATCAGTCAGAATTGATTGCATGTC | SEQ ID NO: 2155 | Homo sapiens ubiquitin-conjugating enzyme E2D 1 (UBC4/5 homolog, yeast) (UBE2D1), mRNA [NM_003338] |
| 575 | A_24_P364807 | AYTL1 | TGTAACTTCTGTTTCTTAGGTAATGCTTCTCTCTCAACAAGTTCTCAAGCGTCTGTGTAA | SEQ ID NO: 2156 | Homo sapiens cDNA DKFZp686H22112 (from clone DKFZp686H22112), [BX641069] |
| 576 | A_24_P366165 | LOC391126 | ACTTCCAACCAAATCAAAATAGCAAAAATAGCAAAAGGCATTCAATGCACCTTGGACATTCAGAGG | SEQ ID NO: 2157 | PREDICTED: Homo sapiens similar to 60S ribosomal protein L26 (Silica-induced gene 20 protein) (SIG-20) (LOC391126), mRNA [XR_019504] |
| 577 | A_24_P366546 | RPL31P10 | CGGATGTCCAGAAAGTGTAATGAAGGATGAAGAATTGAAATAAGGTCTATACTTTGGTTACC | SEQ ID NO: 2158 | PREDICTED: Homo sapiens similar to ribosomal protein L31 (LOC390283), mRNA [XR_018695] |
| 578 | A_24_P367139 | A_24_P367139 | ACACAATGAAACTGCTCAGGCCATCAGAGGGTATACATAAAGCCAAGAAGTATCTGAAAG | SEQ ID NO: 2159 | |
| 579 | A_24_P367191 | LOC652890 | AGTTAACATGCTGAGGACTGTTGAGAGCCATATATTGCCTGTGGGTACCCAAATCTGAAGTC | SEQ ID NO: 2160 | PREDICTED: Homo sapiens similar to ribosomal protein L7 (LOC652890), mRNA [XR_015544] |
| 580 | A_24_P367199 | A_24_P367199 | TGTTATGCTCAGCACCAAGAGTCTGCCAAATCCAGAAGAAGGTGTAATGAACCTGAGA | SEQ ID NO: 2161 | |
| 581 | A_24_P367369 | A_24_P367369 | ATTTAAAGGTTCGATGTAGATTCTCTGGTCAGGATATCCAAGTGAACAAAGGATCTAA | SEQ ID NO: 2162 | |
| 582 | A_24_P368575 | SLC4A7 | TTTTTAATGACATTTTTGCACACTGATTAGTTTTGTGTTGGCTTTTGTTGCTTTAT | SEQ ID NO: 2163 | Homo sapiens solute carrier family 4, sodium bicarbonate cotransporter, member 7 (SLC4A7), mRNA [NM_003615] |
| 583 | A_24_P370096 | ZNF230 | GAAACTTATATTGTGAGAAATGTGGAGGGCCTTCATTCACGATTTAAAGCTCAGAA | SEQ ID NO: 2164 | Homo sapiens zinc finger protein 230 (ZNF230), mRNA [NM_006300] |
| 584 | A_24_P371053 | ORMDL1 | GAATGAAAAGAGTTAGAGACGAACTAAACATGAATCAGTGTGTCAGTAAAGTACTTTGG | SEQ ID NO: 2165 | Homo sapiens ORM1-like 1 (S. cerevisiae) (ORMDL1), mRNA [NM_016467] |
| 585 | A_24_P371303 | C3orf63 | GTCAGTGTCAAGAAAATGAAGAATTACTTCTATCGCTATAGGAAAGCTTGGATACAG | SEQ ID NO: 2166 | Homo sapiens chromosome 3 open reading frame 63 (C3orf63), mRNA [NM_152241] |
| 586 | A_24_P371399 | C3orf58 | TAAAATAGTTGATTCCGGTTAATTTTTACGAGTAGTTGATTGCGTATATGAACTGGCGC | SEQ ID NO: 2167 | Homo sapiens chromosome 3 open reading frame 58 (C3orf58), mRNA [NM_173552] |
| 587 | A_24_P374319 | RAP2C | ATTGGTGTGATGTTCAAATAAAGTGGATACTACATTCAGAAATCATGTGATTATGGGTGAGGAAG | SEQ ID NO: 2168 | Homo sapiens RAP2C, member of RAS oncogene family (RAP2C), mRNA [NM_021183] |
| 588 | A_24_P375599 | LOC731681 | TGTATGCTTGCCCATCAAGCGTTATCCAGAATGGGTCTCTGTTGGAAATCCGAA | SEQ ID NO: 2169 | PREDICTED: Homo sapiens similar to 60S ribosomal protein L9 (LOC731681), mRNA [XR_015944] |
| 589 | A_24_P375849 | ENST00000359659 | AAGAAGGTCTGGAACAAGAATAGCAGGCTATGTCACAGATCTGATGAAGCGGATTCAGAGA | SEQ ID NO: 2170 | Q8BTV0_MOUSE (Q8BTV0) 10, 11 days embryo whole body cDNA, RIKEN full-length enriched library, clone:2810021H19 product:ribosomal protein S17, full insert sequence, (Fragment), partial (98%) [TH2555910] |

Fig. 5-32

| No. | Probe ID No. | Symbols of genes | Sequence | SEQ ID NO: | Descriptions of genes (letters and numbers within [ ] indicates GenBank accession No.) |
|---|---|---|---|---|---|
| 590 | A_24_P375932 | A_24_P375932 | ATGGTTAAAAATGCAGAGAGGAATGCAGAAGTTAAGGGTTTAGATGTAGATTCTCTGGTC | SEQ ID NO: 2171 | |
| 591 | A_24_P379379 | CAPZA1 | ACCAGTTTCAGCGTAAAAAGTTCTGGAATGGTGGTTGGAGATCAGAGTGGAAGTTCACCA | SEQ ID NO: 2172 | Homo sapiens capping protein (actin filament) muscle Z-line, alpha 1 (CAPZA1), mRNA [NM_006135] |
| 592 | A_24_P381625 | PSMC6 | ATGAAAGGAGTCAGAAAAAGTGGGTGATTCGTAAGAAGCTGGAGTCTAAATTGGACTACAAA | SEQ ID NO: 2173 | Homo sapiens proteasome (prosome, macropain) 26S subunit, ATPase, 6 (PSMC6), mRNA [NM_002806] |
| 593 | A_24_P383569 | LOC391130 | ATGCATCTGGTGAAGTGGATTCAGAGGGGTAAGATACCAGTAAGAGGTATCGTCATCAAG | SEQ ID NO: 2174 | PREDICTED: Homo sapiens similar to 40S ribosomal protein S17 (LOC391130), mRNA [XR_019508] |
| 594 | A_24_P383999 | RPS3A | TGGTTTTACTAAAAAACGCAACAATCACAGATACAGAAGACCCTCTTATGCCCAGCACCAAG | SEQ ID NO: 2175 | Homo sapiens ribosomal protein S3A (RPS3A), mRNA [NM_001006] |
| 595 | A_24_P384411 | A_24_P384411 | ATGCAAAATCAATAAGAGTGAAGGTTGACAGATAATGCTTTGACAGGTGGATCTCTTG | SEQ ID NO: 2176 | |
| 596 | A_24_P384539 | LOC730452 | CAAGAAAAGCTGGCAACTTCTATGTACCCACAAAACCGAAATTGGGATTTGTCATGAGGA | SEQ ID NO: 2177 | PREDICTED: Homo sapiens similar to 60S ribosomal protein L7 (LOC730452), mRNA [XM_001125895] |
| 597 | A_24_P387869 | PKN2 | TTGTGCAAGAGATCATTTATATATAGTTCCAAATTGTTATTACCCAAGATCGTTTGGAG | SEQ ID NO: 2178 | Homo sapiens protein kinase N2 (PKN2), mRNA [NM_006256] |
| 598 | A_24_P392231 | LOC641784 | CGATCAATATTCAGAAGTGCATGAGTGTGGGCAAGAAGCGTGCCCGTGGGAGAACTCA | SEQ ID NO: 2179 | xr55h07.x1 NCI_CGAP_Ov26 Homo sapiens cDNA clone IMAGE:2764093 3' similar to gb:X69181 60S RIBOSOMAL PROTEIN L31 (HUMAN); mRNA sequence [AW302767] |
| 599 | A_24_P392900 | A_24_P392900 | GTCTGTTTCTGTTCTTGGTTTTCCTAAAAACAATGTAACAATCCGAAAAGCTTTTATGCTC | SEQ ID NO: 2180 | |
| 600 | A_24_P39378 | CCPG1 | TAGTTTTGTGGGTGGAAGGAAGTTGATCAGTTCATCAATAAGTTTTTGCTAAACGGTGT | SEQ ID NO: 2181 | Homo sapiens cell cycle progression 1 (CCPG1), transcript variant 1, mRNA [NM_004748] |
| 601 | A_24_P393811 | TMCO1 | AGATGAAGCAGCACAGAGTGTTCCTTGATTTCTGTATATTCTGTACTATGTCGATTCG | SEQ ID NO: 2182 | Homo sapiens transmembrane and coiled-coil domains 1 (TMCO1), mRNA [NM_019026] |
| 602 | A_24_P399942 | ATP11C | TGAGGATGTTAGGTAGCTAACTGAAAACATTCATTCCATATGTACTTACAGATACACCAG | SEQ ID NO: 2183 | Homo sapiens ATPase, Class VI, type 11C (ATP11C), transcript variant 1, mRNA [NM_173694] |
| 603 | A_24_P40417 | FMR1 | TTGTGAGTTGTTCTTTGAATTTCATTTTAGAGTAGTTTGCTTGCATACAAACAAG | SEQ ID NO: 2184 | Homo sapiens fragile X mental retardation 1 (FMR1), mRNA [NM_002024] |
| 604 | A_24_P405002 | PDIK1L | TGGTGCTAAGGGATAGTTTTGTCATTTATGATGAAGTAAGTGTTAAGTGCAGATAAATAGC | SEQ ID NO: 2185 | Homo sapiens PDLIM1 interacting kinase 1 like (PDIK1L), mRNA [NM_152835] |
| 605 | A_24_P405298 | PPP1CB | GTATTAGGTAGGTGACAAAGGTTTATCGGAGGTGATTTAAATAAGTTCCTGATTGGAG | SEQ ID NO: 2186 | Homo sapiens protein phosphatase 1, catalytic subunit, beta isoform (PPP1CB), transcript variant 1, mRNA [NM_002709] |
| 606 | A_24_P405430 | TIA1 | GGATTTCTCTGTTGTTAAATGAGAAAAATGATAGTCCCGAATGGTTCTTTATAGGAGG | SEQ ID NO: 2187 | Homo sapiens cDNA FLJ36425 fis, clone THYMU2011492. [AK093744] |
| 607 | A_24_P406034 | SLC35A1 | ATGTAGAGTATTTTGTGGTAGCAGGATAAAGACCTAGTCTTTCTTGTTATAAGGCAGAA | SEQ ID NO: 2188 | Homo sapiens solute carrier family 35 (CMP-sialic acid transporter), member A1 (SLC35A1), mRNA [NM_006416] |
| 608 | A_24_P409681 | A_24_P409681 | ACATGAGGTCTCCCTGCCGGATTGAGATGATTCTTGAAAAGGAAGAGATTGTTGATAAAC | SEQ ID NO: 2189 | |

Fig. 5-33

| No. | Probe ID No | Symbols of genes | Sequence | SEQ ID NO: | Descriptions of genes (letters and numbers within [ ] indicates GenBank accession No.) |
|---|---|---|---|---|---|
| 609 | A_24_P414256 | CCDC72 | TCTTTGGTCCTTGTTCTACCCTAAAGTTTGTATCACCTGAAATT AAACCAACTCATTTGA | SEQ ID NO:2190 | Homo sapiens KSPC330 mRNA, partial cds. [AF161448] |
| 610 | A_24_P414556 | TTC33 | ACTCAAGCATTTGGTATATTGTTTGAGTAATGGATGTTTTGTTT TTTGTGTAATTTGTGA | SEQ ID NO:2191 | Homo sapiens tetratricopeptide repeat domain 33 (TTC33), mRNA [NM_012232] |
| 611 | A_24_P414952 | TMEM168 | TTTCTACTGAAGGTCAGGAGATAGGAACACAGTATTTGTTC TGGTATACATGTAATG | SEQ ID NO:2192 | Homo sapiens transmembrane protein 168 (TMEM168), mRNA [NM_022484] |
| 612 | A_24_P41551 | LOC641790 | AAGGAGATGGGAAGTCCTGATGTGGGCATTGATATGAGGGACAA CAAAGTAGTCTGGAAA | SEQ ID NO:2193 | PREDICTED: Homo sapiens similar to ribosomal protein L31 (LOC641790), mRNA [XR_018025] |
| 613 | A_24_P417281 | TXNDC10 | ATGATGAGTGATTCTTGGGAAGATAAATGTTAATGTTCCCAATA GTCAAGCTTGTTTTGC | SEQ ID NO:2194 | Homo sapiens thioredoxin domain containing 10 (TXNDC10), mRNA [NM_019022] |
| 614 | A_24_P418418 | RPS17 | GATGAACTTCAAAATGCCTGGGGGACCTGTTTGAATTTTTCTG CAGTGCTGTATTATTT | SEQ ID NO:2195 | Homo sapiens ribosomal protein S17 (RPS17), mRNA [NM_031021] |
| 615 | A_24_P418712 | A_24_P418712 | AGGTCAACAAAGCTGTCTGGGCAAAGAAAATAAGGAATATGGA TACCATATCTGTGTTA | SEQ ID NO:2196 | |
| 616 | A_24_P487736 | CXorf23 | TGGATACCTAGTATGTGTAAGAGGAAATGGATTTTTAAA TGAAATTTTTAGGCCG | SEQ ID NO:2197 | Homo sapiens chromosome X open reading frame 23 (CXorf23), mRNA [NM_198279] |
| 617 | A_24_P50437 | BC065737 | TGGAGAATGATGAAGTTGCATTTAGAAGAATTCCTGATTACTGAA GATGTTCAGGGCAAAA | SEQ ID NO:2198 | Homo sapiens cDNA clone IMAGE:30404477, partial cds. [BC065737] |
| 618 | A_24_P50472 | LOC649839 | TAAAACTACAAAGAAGAATTGTGCTGGGGCTTGCAGTGCATTCAGC CCAAGTGGAGATCCAA | SEQ ID NO:2199 | PREDICTED: Homo sapiens similar to large subunit ribosomal protein L36a (LOC649839), mRNA [XM_001129410] |
| 619 | A_24_P50554 | LOC391655 | TCAAGGGTTTAGAATGTAGATCTCTGGTCATTGAGTATAACCGA GTAAACAAAGAGGTA | SEQ ID NO:2200 | PREDICTED: Homo sapiens similar to 60S ribosomal protein L17 (L23), (LOC391655), mRNA [XR_018405] |
| 620 | A_24_P50567 | A_24_P50567 | CCTTGCTAATTTCAAAAACTACCAGAACATGAATCCAGATGGCA TGGTTGCTCTGGACTA | SEQ ID NO:2201 | |
| 621 | A_24_P538403 | ROCK1 | TTAGAGGTTGTTGGACTTTCATCATAAATTGAGTACAATCTTGGCA TGAAACTACCTGCTAC | SEQ ID NO:2202 | Homo sapiens Rho-associated, coiled-coil containing protein kinase 1 (ROCK1), mRNA [NM_005406] |
| 622 | A_24_P54178 | TMED5 | GCTCTGATATGCATTTGGATGATTAATGTTATGCCTGTTCTTTCA TGTGAATGTCAAGACA | SEQ ID NO:2203 | Homo sapiens transmembrane emp24 protein transport domain containing 5 (TMED5), mRNA [NM_016040] |
| 623 | A_24_P561223 | THC2697551 | TTATGCGCAGTTACATAGAAGGATCCTGGCCATATTTCAGGGACC GTAAAGTTTATAAGAT | SEQ ID NO:2204 | ALU1_HUMAN (P39188) Alu subfamily J sequence contamination warning entry, partial (8%) [THC2697551] |
| 624 | A_24_P56240 | CPNE8 | TACAACTATGTGAGTTAGTCGTCACAAGACATTGTGAAATAAGCT ACTCCTATATACTGAC | SEQ ID NO:2205 | Homo sapiens copine VIII (CPNE8), mRNA [NM_153634] |
| 625 | A_24_P56252 | AF086032 | GTATCTAAACTGAACAGGTACTGTGCTATATTGATTTATTGG TAGTATTGAGGAGACC | SEQ ID NO:2206 | Homo sapiens full length insert cDNA clone YW25G09. [AF086032] |
| 626 | A_24_P57837 | THC2667891 | AGAAAATCGGGAGACCTGTTATGCTCAGTAGGAGGCAAATCCGG AAGAAGATGATGGAAA | SEQ ID NO:2207 | G6NXR3_HUMAN (G6NXR3) Ribosomal protein S3a, partial (91%) [THC2667891] |
| 627 | A_24_P587938 | A_24_P587938 | CTTCAAGAAGAAGCAAAAGGTGGAGATGGCAACACGCGAGGACC AGATTAAGAGTCTTAT | SEQ ID NO:2208 | |
| 628 | A_24_P606663 | LOC392030 | TGTGCGGTTGCGGAGAAAACGTAATGCGGGGTGAAGATTGCACCAA ATAAGGTGCATACTTT | SEQ ID NO:2209 | PREDICTED: Homo sapiens hypothetical LOC392030 (LOC392030), mRNA [XR_018063] |

Fig. 5-34

| No. | Probe ID No. | Symbols of genes | Sequence | SEQ ID NO: | Descriptions of genes, letters and numbers within [ ] indicates GenBank accession No. |
|---|---|---|---|---|---|
| 629 | A_24_P62530 | RHOU | GGCTGAAGTACAAGTGTAGGCGCACCATTATAATTTATAAATACAGCATAGTTCAAAACTG | SEQ ID NO: 2210 | Homo sapiens ras homolog gene family, member U (RHOU), mRNA [NM_021205] |
| 630 | A_24_P62860 | STAM2 | GTCTATATGGTACTTGATGTCTAGATTTAAGTGGAAAAATTAGCAGTATTTGAAAGGTGAGT | SEQ ID NO: 2211 | Homo sapiens signal transducing adaptor molecule (SH3 domain and ITAM motif) 2 (STAM2), mRNA [NM_005843] |
| 631 | A_24_P830039 | AL049321 | AACATGAGAGAATACAAAGTTACATTTTTGGACCATATATTAAAACTGCAAGAAGAAGGGG | SEQ ID NO: 2212 | Homo sapiens mRNA; cDNA DKFZp564D156 (from clone DKFZp564D156). [AL049321] |
| 632 | A_24_P63347 | PF4V1 | CTACATATTTAGTTGAAATGTTACAATTAGCTTGGCAATAAATATTAGTAGCTCTTAAGC | SEQ ID NO: 2213 | Homo sapiens platelet factor 4 variant 1 (PF4V1), mRNA [NM_002620] |
| 633 | A_24_P62786 | THC2533996 | TGCTTGTTGGTATGTCAGGCCGAAGATGATTATCCTTGAGGAATGACATTGAGCTGTTT | SEQ ID NO: 2214 | HSU09954 ribosomal protein L9 [Homo sapiens] (exp=-1; wgp=0; cg=0), partial (42%) [THC2533996] |
| 634 | A_24_P67100 | LOC646949 | AGTCATAGGGAGAAAAGATGGGCTCTTTCTTTATTTGAAGATAATCCAGGGGTCACAG | SEQ ID NO: 2215 | PREDICTED: Homo sapiens similar to ribosomal protein L23 (LOC646949), mRNA [XR_017294] |
| 635 | A_24_P675947 | ENST00000389400 | CTTCATGCGCGAAGGTAGCAGTTGTGGAAAAAGCTACTGGAGAAGAGACAGGTTCTAAAGTT | SEQ ID NO: 2216 | similar to 40S ribosomal protein S3a (V-fos transformation effector protein) (LOC391706), mRNA [Source:RefSeq_dna;Acc:XR_017186] [ENST00000389400] |
| 636 | A_24_P685729 | ENST00000331306 | TTGAAGCTTATTGTTGATGTCAAGAACTATCAGTGATTATTTGCTTGTCTGTTTTGTGTGG | SEQ ID NO: 2217 | |
| 637 | A_24_P6975 | LOC342994 | GGGAAGACTTCGAGCGGGGTTCGTGCTCGTAAGAGCTAAAGTCTTAGAAATTGTCAAAAGA | SEQ ID NO: 2218 | PREDICTED: Homo sapiens similar to large subunit protein L34 (LOC342994), mRNA [XM_936484] |
| 638 | A_24_P703614 | A_24_P703614 | AAGAACATTACCGGAATGGATGTGTGCACGTAAGTCATCAGTAGCAGCTTTGTGTGTGTG | SEQ ID NO: 2219 | |
| 639 | A_24_P7181 | A_24_P7181 | TCATGGTCGGATTAACTCACGATGCATGATCTCCGTGCCACATCGAAATGATCTTTAGTGA | SEQ ID NO: 2220 | |
| 640 | A_24_P71938 | SMAD1 | TGTATTCACTTATGCTCTCGTACATTGAGTAGCTTTATTCCAAAACTAGTGRRTTTTGTC | SEQ ID NO: 2221 | Homo sapiens SMAD family member 1 (SMAD1), transcript variant 1, mRNA [NM_005900] |
| 641 | A_24_P75158 | PTAR1 | GCATTAGATTTGTTCTTATGTGACGAGTACCAAGCCAGCTATAAAGTATTATTTCTG | SEQ ID NO: 2222 | Homo sapiens mRNA; cDNA DKFZp313P0917 (from clone DKFZp313P0917). [AL832683] |
| 642 | A_24_P755505 | A_24_P755505 | ATACAGAAGACCTCTTATGGTCAGCAGAGACTGAAGAAGTAAAATGCTGAAGAAGCCAA | SEQ ID NO: 2223 | |
| 643 | A_24_P76169 | ENST00000331306 | TTCCTAAAATTGAGTGGAGTTTCTCTAAGAAGTGTGGCAAGCATCAACCCCACAAAGTGA | SEQ ID NO: 2224 | PREDICTED: Homo sapiens similar to large subunit ribosomal protein L36a (LOC728202), mRNA [XM_001129191] |
| 644 | A_24_P76358 | LOC643981 | TTACTGAAGATGTTCAGGGCAAAAAGTGGGTAACTTCCGGCATGGATCTTATTGGTGAGA | SEQ ID NO: 2225 | PREDICTED: Homo sapiens v-fos transformation effector protein S3a (v-fos transformation effector protein) (LOC643981), mRNA [XR_018444] |
| 645 | A_24_P77681 | PAIP1 | AGTCTGATGCGAGATTACGAAGAGAAGAAATACCAAGAATTACTTGAAAGAGAGGACTTTTTCC | SEQ ID NO: 2226 | Homo sapiens poly(A) binding protein interacting protein 1 (PAIP1), transcript variant 1, mRNA [NM_006451] |
| 646 | A_24_P792734 | PSMC6 | AGAAACGTTAACGGAGTTAGTGAATGAAATGGATGGATTTGATACTCTGATAGAGTTAAA | SEQ ID NO: 2227 | Homo sapiens proteasome (prosome, macropain) 26S subunit, ATPase, 6 (PSMC6), mRNA [NM_002806] |

Fig. 5-35

| No. | Probe ID No. | Symbols of genes | Sequence | SEQ ID NO. | Descriptions of genes (letters and numbers within [ ] indicates GenBank accession No.) |
|---|---|---|---|---|---|
| 647 | A_24_P813147 | TUBB8 | TACCTAACGGTGGCTGCCATTTTCAGRGGTCGGCATGCCCATGAGGGAGGTGGATGAACAA | SEQ ID NO: 2228 | Homo sapiens tubulin, beta 8 (TUBB8), mRNA [NM_177987] |
| 648 | A_24_P810965 | RAP2A | TTCTTTGATGTTGCAACGTTTTGGGTGTTCTTTTAAACTGTGATAGTGATGGTAACTGATGC | SEQ ID NO: 2229 | Homo sapiens RAP2A, member of RAS oncogene family (RAP2A), mRNA [NM_021033] |
| 649 | A_24_P830667 | RPL21 | GTGTTCCTTTGGCGACGTATATGGGAATGCTATATAAGAAAGGTGAATATTGTAGAGATGAAGG | SEQ ID NO: 2230 | Homo sapiens ribosomal protein L21 (RPL21), mRNA [NM_000982] |
| 650 | A_24_P83968 | LOC730887 | ACAAAGCCCAGCAGAGAAGAACGTGGAACACAGAGAAACTTTTCTGGTGTCTCTAAGAAGG | SEQ ID NO: 2231 | PREDICTED: Homo sapiens similar to 40S ribosomal protein S7 (S8) (LOC730887), mRNA [XR_015607] |
| 651 | A_24_P84408 | A_24_P84408 | AAGGTACATCCAGCAGTGGTCATTGACAAGTCATAGCAGAGAAAAGATGGCGTGTTCTT | SEQ ID NO: 2232 | |
| 652 | A_24_P84908 | LOC729449 | GAATTGCTTTGACAGATAACGCTTGCGATCTCTTGGAAAATATGGGATCATCTGATGG | SEQ ID NO: 2233 | PREDICTED: Homo sapiens similar to 60S ribosomal protein L7 (LOC729449), mRNA [XR_015548] |
| 653 | A_24_P867201 | AK022997 | CTGACATGTATAAATATTTCAGTGACTTTTCAGATTTATTCTTGTTAGCCCGCTGTGTC | SEQ ID NO: 2234 | Homo sapiens cDNA FLJ12935 fis, clone NT2RP2004982. [AK022997] |
| 654 | A_24_P879895 | BC043357 | ACATACGTTGAAGTGCAGAACGTCAGTTTTATGACAGGTGAATAAAACAAAAGTGGCAG | SEQ ID NO: 2235 | Homo sapiens, clone IMAGE:3883659, mRNA. [BC043357] |
| 655 | A_24_P886040 | DCP2 | CATTGAAGCAGGTTCATTCGTTTCTAGATTTATGTTGTGTAGTGAACAGGAACTG | SEQ ID NO: 2236 | Homo sapiens DCP2 decapping enzyme homolog (S. cerevisiae) (DCP2), mRNA [NM_152624] |
| 656 | A_24_P890536 | CR627148 | AATTGCCTTCGTGTAACCCTAAGTATGGTGAAGCAGAATTGAATTCTACAAAAGTCTTTC | SEQ ID NO: 2237 | Homo sapiens mRNA; cDNA DKFZp779F2127 (from clone DKFZp779F2127). [CR627148] |
| 657 | A_24_P915806 | HNMT | GGACAAGAAGCTGCCAGGCATAATAGGAAGACATACCACGAATTTTGGAGAGGTTAACAAATAAAATA | SEQ ID NO: 2238 | Homo sapiens histamine N-methyltransferase (HNMT), transcript variant 2, mRNA [NM_001024074] |
| 658 | A_24_P91852 | DYNLT3 | ATACATATAGAGAGCGGAACCATAACTCATTGCAATTTGAATTTTGGAGAGGAATACATATAGAGCGTT | SEQ ID NO: 2239 | Homo sapiens dynein, light chain, Tctex-type 3 (DYNLT3), mRNA [NM_006520] |
| 659 | A_24_P91916 | NXT2 | AAGCAGTGCTTTCTTGCTAGTAGTGATTGAATGAAACTTACACGTTTATTCTACTCATAGTGAAGC | SEQ ID NO: 2240 | Homo sapiens nuclear transport factor 2-like export factor 2 (NXT2), mRNA [NM_018698] |
| 660 | A_24_P925505 | CD36 | GGTACCCTGTAGTACGACAGAGTTGGTCTGTGTTTTATCCTGTAAGTACCAAATATGAATGGC | SEQ ID NO: 2241 | CD36-collagen type I/thrombospondin receptor (one exon) [human, mRNA Partial, 369 nt] [S67044] |
| 661 | A_24_P931282 | THC2726401 | GGAAAATATTTCTCCTGTAAATGCATGAAATCATGTTGAGGTAATCTACTGCGAGATTACAC | SEQ ID NO: 2242 | Q26195_PLAVI (Q26195) Pval protein, partial (14%) [THC2726401] |
| 662 | A_24_P935986 | BCAT1 | ATGCTGTGAAGGTTTTTGTAGAAGCACGAAATAAACATGTAAAATGGGTTTGTTACACCAGA | SEQ ID NO: 2243 | Homo sapiens branched chain aminotransferase 1, cytosolic (BCAT1), mRNA [NM_005504] |
| 663 | A_24_P937095 | SLC30A1 | TTTGATGTACCTCTACACGGATACTATGTGGTAATGCTATTTTGTTTTAGTAACGAAGGTGTG | SEQ ID NO: 2244 | Zinc transporter 1 (ZnT-1) (Solute carrier family 30 member 1). [Source:Uniprot/SWISSPROT;Acc:Q9Y6M5] [ENST00000367000] |
| 664 | A_24_P940426 | QKI | AAGCTGTTGAATGAGTCTTAAAAATTATACTACTGTTAAGTGGACCAAGTTTGGTGAAGC | SEQ ID NO: 2245 | Homo sapiens quaking homolog, KH domain RNA binding (mouse) (QKI), transcript variant 4, mRNA [NM_206855] |
| 665 | A_24_P940776 | BDP1 | TCGGAGGGGAAATTGTCTATAAGTAGGCATTTATTTCATGATTCATATGTCACAGAAATC | SEQ ID NO: 2246 | Homo sapiens B double prime 1, subunit of RNA polymerase III transcription initiation factor IIIB (BDP1), mRNA [NM_018429] |

Fig. 5-36

| No. | Probe ID No. | Symbols of genes | Sequence | SEQ ID NO: | Descriptions of genes (notes and numbers within [ ] indicates GenBank accession No.) |
|---|---|---|---|---|---|
| 666 | A_24_P941643 | PLCB1 | ATGATGTGCAGTTTTTGTGCCTTTATGTATTTGCCTGTCTTG TCAATGTGTGAAATT | SEQ ID NO: 2247 | Homo sapiens phospholipase C, beta 1 (phosphoinositide-specific) (PLCB1), transcript variant 2, mRNA [NM_182734] |
| 667 | A_24_P941699 | PCGF5 | TGGTATATTGAACACAGACCTTTGTCAAGGATAAGGAGTACTTCAT GTCTAGTAATACATG | SEQ ID NO: 2248 | Homo sapiens polycomb group ring finger 5 (PCGF5), mRNA [NM_032373] |
| 668 | A_24_P98210 | TFEC | ACATGGGGCTTAGAAGTGTTGTCCAAGTAGTGTACCAATG AAAAGAGAAATTAGAG | SEQ ID NO: 2249 | Homo sapiens transcription factor EC (TFEC), transcript variant 1, mRNA [NM_012252] |
| 669 | A_24_P99046 | STK38L | GCTATCGTCTTGCTCATCTACAAATAAATGAATTGAGAATT AGTCCATAGAGGTCG | SEQ ID NO: 2250 | Homo sapiens serine/threonine kinase 38 like (STK38L), mRNA [NM_015000] |
| 670 | A_32_P10100 | A_32_P10100 | TATGAGGAAATAGTATCATCATATGTTAGAAGCCTTGGAATGAATGAGTA TAAATAATGGCTGGTC | SEQ ID NO: 2251 | |
| 671 | A_32_P105397 | THC2642694 | AAAATGTACTACAGATATTCTACGAATGCAGGGTGAATGTATAT TACAGTAATTCTCTGG | SEQ ID NO: 2252 | Q6TDT1_HUMAN (Q6TDT1) Protein transactivated by hepatitis B virus E antigen, partial (11%) [THC2642694] |
| 672 | A_32_P106732 | FANCM | AATCAAGGTGCTCAAGATGGGGTTTTCAAAGAGCCTCACAACAATA TTAAATGCAGTTCAAT | SEQ ID NO: 2253 | Homo sapiens Fanconi anemia, complementation group M (FANCM), mRNA [NM_020937] |
| 673 | A_32_P107372 | GBP1 | GGTACTGAGGAGAGTGTTAGGTAAAAGTGTTCGGGAAATATTGG GCATTGGTGTGGCCAA | SEQ ID NO: 2254 | Homo sapiens guanylate binding protein 1, interferon-inducible, 67kDa (GBP1), mRNA [NM_002053] |
| 674 | A_32_P107717 | BX100535 | TCTTGTGCAGCCAAGATCTGCTCTCTGTTGTAAATCCTGTTGAG ACCTGGTCTAAATTGGT | SEQ ID NO: 2255 | BX100535 Soares_testis_NHT Homo sapiens cDNA clone IMAGp998J094457, mRNA sequence [BX100535] |
| 675 | A_32_P109495 | THC2618720 | AAAGATATATCAGGCAACACTGCAAGTGCTCACCATGAATTTTT GGTTTGTTCATAAGAA | SEQ ID NO: 2256 | |
| 676 | A_32_P109653 | THC2669092 | TGTTGGTTTGGTATTCCAAGTGGGGTGTTTTTCAGAATGTCTGCA CTAGTGTAGAGATGAA | SEQ ID NO: 2257 | |
| 677 | A_32_P113154 | LOC730861 | ACCACCAGTCCAAGAATCTGTTTAAAGTTCAGACTTAAAACAGT AGGAAATAAAAAGTGC | SEQ ID NO: 2258 | PREDICTED: Homo sapiens similar to 40S ribosomal protein S3a (V-fos transformation effector protein) (LOC730861), mRNA [XR_015591] |
| 678 | A_32_P113584 | ZNF292 | GGGGCTTTTGGGTTTTATGAATAGTTCATTCAGCTGTTAAG ACTTACTACCAATAAG | SEQ ID NO: 2259 | Zinc finger protein 292 [Source:Uniprot/SWISSPROT:Acc:Q9P2R1] [ENST00000339907] |
| 679 | A_32_P113742 | RPL21 | ATGTCTCTGTAGGCCTTTTAGAAAAACATGGAGGAATGGGTAGTGT TCAAAAAGGAATTGCCC | SEQ ID NO: 2260 | Homo sapiens ribosomal protein L21, mRNA (cDNA clone IMAGE:6605832), complete cds. [BC104478] |
| 680 | A_32_P114215 | COMMD6 | AATTGCTATCATTGTAAGTCATGGAGTTCAGTTCGGGAACAA AACTAAATAAGGATGG | SEQ ID NO: 2261 | Homo sapiens COMM domain containing 6 (COMMD6), transcript variant 2, mRNA [NM_203495] |
| 681 | A_32_P1144 | AK091357 | GGGGACTTAATATTTTACATCTTACTAGCCATGTCATAGGTTTTA AGTGCTTTTAATGGG | SEQ ID NO: 2262 | Homo sapiens cDNA FLJ34038 fis, clone FCBBF2005645. [AK091357] |
| 682 | A_32_P11451 | NMD3 | CAGTTTAGGGCAGTAGGATTATAGTTGAGAGTGCATAAATATCTACC ACATCAAAAATGCTGC | SEQ ID NO: 2263 | Homo sapiens NMD3 homolog (S. cerevisiae) (NMD3), mRNA [NM_015938] |
| 683 | A_32_P115505 | ZNF294 | TGTGGTGAGGAGGATTATAGTTGAGAGTGCTACTAGTGAGTGTGAG TTATAGATCTCTGGAA | SEQ ID NO: 2264 | Homo sapiens zinc finger protein 294 (ZNF294), mRNA [NM_015565] |

Fig. 5-37

| No. | Probe ID No. | Symbols of genes | Sequence | SEQ ID NO: | Descriptions of genes (letters and numbers within [ ] indicates GenBank accession No.) |
|---|---|---|---|---|---|
| 684 | A_32_P11931 | LOC441073 | GTGTGATCCATGCCATCCGAAAGGATGATGAAGTTCAGGTTGTACGTGGAGACTATAAA | SEQ ID NO: 2265 | PREDICTED: Homo sapiens similar to 60S ribosomal protein L26 (Silica-induced gene 20 protein) (SIG-20) (LOC441073), mRNA [XR_016376] |
| 685 | A_32_P125549 | RPL31P4 | TCTACAGAGAGTCAATGTGGATGAGAGTAATGCCTGATGGTGAGATACATCAATAAAG | SEQ ID NO: 2266 | PREDICTED: Homo sapiens ribosomal protein L31 pseudogene 4 (RPL31P4), mRNA [XR_018222] |
| 686 | A_32_P125917 | THC2753798 | GCTTATAAAGTGTAAGTGGAGACGCTAAATTGTGAGTACAAAGTTTCTTTTCACAACAG | SEQ ID NO: 2267 | BF238843 601904455F1 NIH_MGC_54 Homo sapiens cDNA clone IMAGE:4132429 5', mRNA sequence [BF238843] |
| 687 | A_32_P128781 | A_32_P128781 | GATATATTGCATGGGGGTACCGCAATGTCGAAGTCAGTAAATGAACTAATGCAAGAGTG | SEQ ID NO: 2268 | |
| 688 | A_32_P135818 | RPS3A | CTTGCTTGATCTGTTCTGTGTTGGTTTTAATAAAAACGGAAACAATGAGATATGGAAGAC | SEQ ID NO: 2269 | Homo sapiens ribosomal protein S3A (RPS3A), mRNA [NM_001006] |
| 689 | A_32_P136319 | RPL36A | AAGTGATGGCAGTTCTAAGTGTGTCATCTTTTATGATGAAGACAATAAAATCTGAGTTATG | SEQ ID NO: 2270 | Homo sapiens ribosomal protein L36a (RPL36A), mRNA [NM_021029] |
| 690 | A_32_P137266 | KIAA1799 | AAGTGGGACCCAAATCTACAATGGTTTGTCAACATGTAATGCCTTTGAATGAACGACAG | SEQ ID NO: 2271 | Homo sapiens KIAA1799 protein (KIAA1799), mRNA [NM_032437] |
| 691 | A_32_P143323 | CR613267 | AGAGAGCTGAAACAATGGGGTTTATGGCAGTTACACATACAAGGACCGTGCATATTTCAGGG | SEQ ID NO: 2272 | full-length cDNA clone CS0DL011YP14 of B cells (Ramos cell line) Cot 25-normalized of Homo sapiens (human) [CR613267] |
| 692 | A_32_P145153 | RPL31 | ATCCGTGTGCAGCTGTGCAGAAAAACGTAATGAGGATGAAGATTCAGGAAATAAGCCATAT | SEQ ID NO: 2273 | Homo sapiens ribosomal protein L31 (RPL31), mRNA [NM_000993] |
| 693 | A_32_P145159 | A_32_P145159 | CATAGATGGCGGTGTACAATAAACGTTTGTGTGGAAAACTTAGTGTGTGATTATTCTTTG | SEQ ID NO: 2274 | |
| 694 | A_32_P145477 | BX350256 | TGGCAACCATGCTAAGAAGAAGCGGAAACCAAGGGAAACAGATGTCTACATAGGAGCTGTA | SEQ ID NO: 2275 | BX350256 BX350256 Homo sapiens PLACENTA COT 25-NORMALIZED Homo sapiens cDNA clone CSODI081YM16 3-PRIME, mRNA sequence [BX350256] |
| 695 | A_32_P147747 | THC2575761 | TGATACCCTGATTCTGATGACAAACGCCAAATTGGGTCTGCAGGTACATAGAAGTTG | SEQ ID NO: 2276 | HUMRPL7Y ribosomal protein L7 [Homo sapiens] (exp=-1; wgp=0; cg=0), partial (40%) [THC2575761] |
| 696 | A_32_P148824 | C1orf27 | GAAAAACAGATGTTATCCTGAGGAGAAAATTCAGTAAGAGACTACAAAGGATGATCTTC | SEQ ID NO: 2277 | Homo sapiens chromosome 1 open reading frame 27 (C1orf27), mRNA [NM_017847] |
| 697 | A_32_P151516 | AA714537 | CTGAGCATAAGAGGTCTTCCGTATCTGATTTTGGGTTTTTAGTAAACCAACACAGAA | SEQ ID NO: 2278 | nw20g12.s1 NCI_CGAP_GCB0 Homo sapiens cDNA clone IMAGE:1241062 3' similar to gb:M84711 40S RIBOSOMAL PROTEIN S3A (HUMAN), mRNA sequence [AA714537] |
| 698 | A_32_P153725 | KIAA1033 | TTTTGTAAAAGATGGGAAGTTTGTTAGGTCACTTCAGTGAGTGGGGTTTTCTTTGCCCCAAT | SEQ ID NO: 2279 | Homo sapiens KIAA1033 (KIAA1033), mRNA [NM_015275] |
| 699 | A_32_P155364 | RPL7 | TGAACAGGCTTATTCTCTCTGTGAAAAGAAAATGAACCAAGGTGTGTACCATGATTATTTTCTTAAGCTGG | SEQ ID NO: 2280 | Homo sapiens ribosomal protein L7 (RPL7), mRNA [NM_000971] |
| 700 | A_32_P155811 | CD2AP | AAAGCATGCTTCTCTCTGTGAAAAGAAAATGAACCAAGGATTTTATTGGCAGTCGTGTCAGTC | SEQ ID NO: 2281 | Homo sapiens CD2-associated protein (CD2AP), mRNA [NM_012120] |
| 701 | A_32_P158746 | RPL17 | TTTGGCTGCACATGCTAAAATGGAGAGAGAATGCAGATGATTGGGAACTTAAGGGTTTAGATGTAG | SEQ ID NO: 2282 | Homo sapiens ribosomal protein L17 (RPL17), mRNA [NM_000985] |
| 702 | A_32_P158966 | KLRF1 | TACGTGATAGTAAAACCAATGTGAGTTCATGATGATATCCAGGATTTTATTCGTCG | SEQ ID NO: 2283 | Homo sapiens killer cell lectin-like receptor subfamily F, member 1 (KLRF1), mRNA [NM_016523] |

Fig. 5-38

| No. | Probe ID No. | Symbols of genes | Sequence | SEQ ID NO. | Descriptions of genes (letters and numbers within; [ ] indicates GenBank accession No.) |
|---|---|---|---|---|---|
| 703 | A_32_P159651 | PCAF | GAGTGGTGTCTAGATTTCTAAGAAGAATCATGATACAGTTTGGATTAAGTAGTCTTGGAC | SEQ ID NO: 2284 | Homo sapiens p300/CBP-associated factor (PCAF), mRNA [NM_003884] |
| 704 | A_32_P162250 | ARHGAP18 | AAGTCCTGAATAAGTCTACTGGAAGAATTATCTCTGGGTGAAAAAGCTTTGTTTGTG | SEQ ID NO: 2285 | Homo sapiens Rho GTPase activating protein 18 (ARHGAP18), mRNA [NM_033515] |
| 705 | A_32_P164203 | THC2683448 | TTGATGGTCATTGTACGAGCTATTGTATGGATTAGTAGTGGATGCTGTTTACCAGATGAT | SEQ ID NO: 2286 | Q7WZG3_PASPI (Q7WZG3) Ferric uptake regulator, partial (8%) [THC2683448] |
| 706 | A_32_P165340 | SRP9 | ACATTGAAATATGTTTTGTATAAATTTGTCATGTTGAACAACATTTTAGCATGGTAAGTT | SEQ ID NO: 2287 | Homo sapiens signal recognition particle 9kDa (SRP9), mRNA [NM_003133] |
| 707 | A_32_P167122 | RCOR3 | GTATCTGAGGGATCTGCTGTGTAATCTGATTAGATGCATTAGAGCAGACAGATAGAAAAACT | SEQ ID NO: 2288 | Homo sapiens REST corepressor 3 (RCOR3), mRNA [NM_018254] |
| 708 | A_32_P170444 | SUB1 | TACGGTATGTCTCCTGAAATTCTTGGAGTTCATTTTTATGGGAGTTAATCCAGTGAAAC | SEQ ID NO: 2289 | Activated RNA polymerase II transcriptional coactivator p15 (SUB1 homolog) (Positive cofactor 4) (PC4). [Source:Uniprot/SWISSPROT;Acc:P53999] [ENST00000265073] |
| 709 | A_32_P170736 | AK098422 | ACGTCATAATTGTGAGGGAGGCAAGCTTCATTGTTGATAAGTGCAAAGTGTCGCTGTTGTGAT | SEQ ID NO: 2290 | Homo sapiens cDNA FLJ25556 fis, clone JTH02629. [AK098422] |
| 710 | A_32_P17163 | ENST00000368149 | TCGTTAGTGAGTTTAAATCTGAGGCTAGAATTTATTTGTTTTCTGTGTGTGATGAG | SEQ ID NO: 2291 | Rho GTPase-activating protein 18 (MacGAP). [Source:Uniprot/SWISSPROT;Acc:Q8N392] [ENST00000368149] |
| 711 | A_32_P173385 | ENST00000334683 | AAATGCAGAGAGTGATGCTGAACCTTAAGGCGTTCAGATGGTAGATTCTCGGTCATTGAGCA | SEQ ID NO: 2292 | PREDICTED: Homo sapiens similar to 60S ribosomal protein L17 (L23) (LOC650848), mRNA [XR_019013] |
| 712 | A_32_P17504 | THC2698682 | ATGTCTAGCTGGTTTTCACTATGGTGCAAATATTCCCAGGTTTTCCGCTTGATGGCGCAAA | SEQ ID NO: 2293 | |
| 713 | A_32_P176819 | CMAH | GATTTATATGCTAGGTCTGATTCTGAACGATACAAGAATTCAATGGTGGAATTTGTGTCC | SEQ ID NO: 2294 | Homo sapiens cytidine monophosphate-N-acetylneuraminic acid hydroxylase (CMP-N-acetylneuraminate monooxygenase) (CMAH) on chromosome 6 [NR_002174] |
| 714 | A_32_P177685 | THC2632286 | TTTGACTGAGTATTTGTAGGCTTAATGACTGAATGAAATTGGAGGCACTGATGAAAAG | SEQ ID NO: 2295 | AA665072 nu76b01.s1 NCI_CGAP_Aiv1 Homo sapiens cDNA clone IMAGE:1216585, mRNA sequence |
| 715 | A_32_P178945 | YOD1 | TTGCCAGTATTTTTGAAGTAATACAGTGCTGGTACGTGGAAGATGTCTAAGGTTCATTTTT | SEQ ID NO: 2296 | Homo sapiens YOD1 OTU deubiquinating enzyme 1 homolog (S. cerevisiae) (YOD1), mRNA [NM_018566] |
| 716 | A_32_P178966 | ENST00000379426 | GTAAATATAGGGGTGAAGTCTTTAGTGATACAGACAGAACACAAGTGTTAAAAGTGAATCC | SEQ ID NO: 2297 | Novel protein. [Source:Uniprot/SPTREMBL;Acc:Q5T4T1] [ENST00000379426] |
| 717 | A_32_P180435 | WBSCR19 | CTTTCAATCTTTGTATGTATTATTAGACGGTGGTGCTGGTGAAGGGAGCATGTTTTATGTATG | SEQ ID NO: 2298 | Homo sapiens Williams Beuren syndrome chromosome region 19 (WBSCR19), mRNA [NM_175064] |
| 718 | A_32_P186981 | RPL17 | CATTGACAATGATCCTTACGACAAAAGGAACAAGATTGTTCCTAAACGAGAAGAGGAGGTTGC | SEQ ID NO: 2299 | Homo sapiens ribosomal protein L17 (RPL17), transcript variant 1, mRNA [NM_000985] |
| 719 | A_32_P190488 | hCG_26523 | CCCAGCAAGGTGGTATCACTAGGGTAAAACTGGACAAAGACCGCAAAAAGATCCTTGAA | SEQ ID NO: 2300 | PREDICTED: Homo sapiens similar to 60S ribosomal protein L26 (LOC646161), mRNA [XR_018048] |

Fig. 5-39

| No | Probe ID No. | Symbols of genes | Sequence | SEQ ID NO: | Descriptions of genes (letters and numbers within [ ] indicates GenBank accession No.) |
|---|---|---|---|---|---|
| 720 | A_32_P192480 | ENST00000370857 | TAGTGCTGTAGTGCTTGTTTATGTTTAAAAGTGCAGATTATGCAGGTCATTTTAGTATGG | SEQ ID NO: 2301 | Muscleblind-like X-linked protein (Muscleblind-like protein 3) (Cys3His CCG1-required protein) (Protein MBXL) [Source:Uniprot/SWISSPROT;Acc:Q9NUK0] [ENST00000370857] |
| 721 | A_32_P193322 | RICTOR | ACCGATGAGTTGCTTCTTTTTTATTTAGTAATAGGCTGGTACATATTTGAGGTTCTCG | SEQ ID NO: 2302 | Homo sapiens rapamycin-insensitive companion of mTOR (RICTOR), mRNA [NM_152756] |
| 722 | A_32_P194821 | RPL21 | GAACACAAAGAGAGAAAGGCACGGCGATATATGTTCTTTAGGGTTTTAGAAAACA | SEQ ID NO: 2303 | Homo sapiens ribosomal protein L21 (RPL21), mRNA [NM_000982] |
| 723 | A_32_P195387 | DKFZP779L1068 | ATATAACCTTGGAATTGTATCTAATTATGTTGTTCTGGGTGCTGTAGTATCAGTCGG | SEQ ID NO: 2304 | Homo sapiens cDNA clone IMAGE:5555490 [BC110326] |
| 724 | A_32_P196047 | DPY19L4 | ATATTAAGATAGTTGCAGGCAGTGTACCTCAGGTTGACGTCTGTAGATCTGAATAGTGAGT | SEQ ID NO: 2305 | Homo sapiens dpy-19-like 4 (C. elegans) (DPY19L4), mRNA [NM_181787] |
| 725 | A_32_P196483 | RPS3A | GGGGCCAAGAAGAAAGTTGGTTGATGGATTTCTAAGAAAGATTGGTATGTGAAAGCA | SEQ ID NO: 2306 | Homo sapiens ribosomal protein S3A (RPS3A), mRNA [NM_001006] |
| 726 | A_32_P19752 | FAM76B | TTGTCTTTTAGGCTGTTTCCACGTATTAATTAGGACTGCCTACTGAAGGGTCATTTTGAC | SEQ ID NO: 2307 | Homo sapiens family with sequence similarity 76, member B (FAM76B), mRNA [NM_144664] |
| 727 | A_32_P20240 | SP3 | GTTAGGCTCTTAATTGTAGTTTAAATTCAGTCTCTAGGGCTTTAGAAGACCGAAAAGTTTTGT | SEQ ID NO: 2308 | Homo sapiens mRNA; cDNA DKFZp686N17231 (from clone DKFZp686N17231). [BX648857] |
| 728 | A_32_P202488 | RPL21 | AAGGAGAGAGGCCACCCGATATATGTTCTCAGGGCTTTAGAAACATGGGAATGGGTAG | SEQ ID NO: 2309 | Homo sapiens ribosomal protein L21, mRNA (cDNA clone IMAGE:6605832), complete cds. [BC104478] |
| 729 | A_32_P203154 | RPL21 | CTTTGGGCAGGTGTATGTGAATGTATAAGAAAAGGTATATTGTAGACATCAAGGAATGG | SEQ ID NO: 2310 | Homo sapiens ribosomal protein L21 (RPL21), mRNA [NM_000982] |
| 730 | A_32_P203320 | ROCK1 | AACGGCCATCACTACTGAAGATCAGCTGATGGAAGGAGTAAAGAAAATATCTGAAAATGAG | SEQ ID NO: 2311 | Homo sapiens Rho-associated, coiled-coil containing protein kinase 1, mRNA (cDNA clone IMAGE:5269982), complete cds. [BC041849] |
| 731 | A_32_P20367 | RPS7 | ATCCTTGAGGACTTGGTCTTCAAAGGCAAAATGTGGGAAGAGAATCCCGTGAAACTA | SEQ ID NO: 2312 | Homo sapiens ribosomal protein S7 (RPS7), mRNA [NM_001011] |
| 732 | A_32_P204330 | AK093982 | AAACCCTGAGCTTTCTTGGTCCTGTCTGGTAGCAGATATCGTAAAACCTAGCGAGAATTG | SEQ ID NO: 2313 | Homo sapiens cDNA FLJ36663 fis, clone UTERU2002826. [AK093982] |
| 733 | A_32_P205550 | RPL26L1 | AGGTAGTTCGAGGAGACGTACAAAGGTGAGCAAATTCGCAAGGTAATCCAGGTGTACAGAA | SEQ ID NO: 2314 | Homo sapiens ribosomal protein L26-like 1 (RPL26L1), mRNA [NM_016093] |
| 734 | A_32_P205553 | RPL26L1 | TTCGGAATGCTGGAACATTTCATTTCCTGTTTTGTTACGTGTGGCTGTGTAAATCTACT | SEQ ID NO: 2315 | Homo sapiens ribosomal protein L26-like 1 (RPL26L1), mRNA [NM_016093] |
| 735 | A_32_P207231 | AI630435 | TTCCTTCGCTTTTCTTAAGGTTTCTGAACAGCAGGAACCTCCTCTGTCTGTTCTCT | SEQ ID NO: 2316 | Homo sapiens Rho-associated, Erythroid Progenitor Cells (LCB:ad library) Homo sapiens cDNA clone IMAGE:ad10b05.y1 Hembase. Erythroid Progenitor Cells (LCB:ad library) Homo sapiens cDNA clone ad10b05 random, mRNA sequence [AI630435] |
| 736 | A_32_P208178 | RPS3A | GGAAAAGAGGTTAGAAAAGGGTTGGCAATCTATTTATCGTCTCCATCATGTCTTCGTTAGA | SEQ ID NO: 2317 | Homo sapiens ribosomal protein S3A (RPS3A), mRNA [NM_001006] |
| 737 | A_32_P21384 | RPL17 | AGATGTGAGTTACAGAAACAGTGTGTACCATTCGAGAGATTACAACGGTGAGTTGGCAG | SEQ ID NO: 2318 | Homo sapiens ribosomal protein L17 (RPL17), transcript variant 1, mRNA [NM_000985] |
| 738 | A_32_P219031 | RPL21 | AGAGGCACCCGATATATGTTCTCTAGGCCTTTAGAAAACATGGGAAGGGTAGTGTTCA | SEQ ID NO: 2319 | Homo sapiens ribosomal protein L21, mRNA (cDNA clone IMAGE:6605832), complete cds. [BC104478] |

Fig. 5-40

| No. | Probe ID No. | Symbols of genes | Sequence | SEQ ID NO: | Descriptions of genes (letters and numbers within [ ] indicates GenBank accession No.) |
|---|---|---|---|---|---|
| 739 | A_32_P220127 | RPL34 | GAAAACTAGGCTGTGGTGAAGCGCGTGGTAATAGAATTGTTGACCTTTATACGAAGAAGGT | SEQ ID NO: 2320 | Homo sapiens ribosomal protein L34 (RPL34), transcript variant 2, mRNA [NM_033625] |
| 740 | A_32_P223319 | ESCO1 | ATGCCTGATTACTGGACTTCATTTTGATACTTGTCTATCGTTCATAGTGCCTCTAGTT | SEQ ID NO: 2321 | Homo sapiens establishment of cohesion 1 homolog 1 (S. cerevisiae) (ESCO1), mRNA [NM_052911] |
| 741 | A_32_P224666 | CAPZA2 | AATGTGTTTGAGATTGTGAAATTAAATGAAAATACTTATTTCAGAAATGCATTTAATG | SEQ ID NO: 2322 | Homo sapiens capping protein (actin filament) muscle Z-line, alpha 2 (CAPZA2), mRNA [NM_006136] |
| 742 | A_32_P22539 | hCG_26523 | ACTACGAAGGTCAGCAAATTGGCAAAGTGGTCCAGGTTTACAGGAAGAAATATGTATCT | SEQ ID NO: 2323 | PREDICTED: Homo sapiens similar to 60S ribosomal protein L26 (Silica-induced gene 20 protein) (SIG-20) (LOC400055), mRNA [XM_374987] |
| 743 | A_32_P226786 | BC045174 | TTATTGGTCATGTAAGCCATTATCCTGTCTTAATGAAGCGATTAATCGTGTTGATTGTT | SEQ ID NO: 2324 | Homo sapiens cDNA clone IMAGE:5273245. [BC045174] |
| 744 | A_32_P2333 | SUB1 | AGGAAGAAAAGGTATTTCTTTAAATGCAGAACAATGGAGCCAGCTGACAGAACAGATTTC | SEQ ID NO: 2325 | Homo sapiens SUB1 homolog (S. cerevisiae) (SUB1), mRNA [NM_006713] |
| 745 | A_32_P26695 | KIAA1600 | AATTCTTTGGTCCCTCCGTGGAGAGAAACTCTTCAGATGGTCATTGTGTACCTACTGTGTCTT | SEQ ID NO: 2326 | KIAA1600 (KIAA1600), mRNA [Source:RefSeq_dna;Acc:NM_020940] [ENST00000369248] |
| 746 | A_32_P30710 | RPL23 | ACGAAAGTCATACGGTAGAAGATGGGTGTTGTTCTTTATTTTGAAGATAATGCAGGAGT | SEQ ID NO: 2327 | Homo sapiens ribosomal protein L23 (RPL23), mRNA [NM_000978] |
| 747 | A_32_P31182 | RPL7 | GTAGAAGAGAAGAAGAAGGTTCCTGCTGTGTGGCAGAAACCCTTAAGAAAAAGGGAAGGAAT | SEQ ID NO: 2328 | Homo sapiens ribosomal protein L7 (RPL7), mRNA [NM_000971] |
| 748 | A_32_P336445 | HINT1 | GTGATACCCAAGAAACATATATGCCAGATTCTGTGGCAGAAGAGATCATGATAAAGTCTT | SEQ ID NO: 2329 | Homo sapiens histidine triad nucleotide binding protein 1 (HINT1), mRNA [NM_005340] |
| 749 | A_32_P36101 | ARL1 | GTATCAAACAACAGATGCAGTCATTTATATGTAGTAGACAGTTGTGACCGGAACGGAATTGG | SEQ ID NO: 2330 | Homo sapiens ADP-ribosylation factor-like 1 (ARL1), mRNA [NM_001177] |
| 750 | A_32_P43217 | PSMA6 | TTGGTTTAGTTTACCAGATCCGTCATGCCAGTTAGCGTGTGTGTTTGGTAACACAAAGA | SEQ ID NO: 2331 | Homo sapiens proteasome (prosome, macropain) subunit, alpha type, 6 (PSMA6), mRNA [NM_002791] |
| 751 | A_32_P4532 | LOC643932 | GATTCCAGACAGCAGGATTGGAAAGAGAGATAGAAAAGGCTTGCCAATCTATGGTGTCATGAT | SEQ ID NO: 2332 | PREDICTED: Homo sapiens similar to 40S ribosomal protein (LOC643932), mRNA [XR_017289] |
| 752 | A_32_P49164 | AV714556 | AAAATGCAGAGACTTGTTATTGCCAAGAAGAATTCATCATGTTCCTTCCTTTCTTTCCC | SEQ ID NO: 2333 | AV714556 AV714556 DCB Homo sapiens cDNA clone DCBAD606 5', mRNA sequence [AV714556] |
| 753 | A_32_P49392 | A_32_P49392 | AATTCTGCCAAATGTGGAAGGAAGATGATGGAAAATCATGACCCAAGAGGTGCAGAGAAATG | SEQ ID NO: 2334 | |
| 754 | A_32_P54305 | LOC401397 | AGAATCTTAGGAAATGACCACTGTTGGGTTATAATGACGTCCTGAATGCGTTAGGAG | SEQ ID NO: 2335 | Homo sapiens hypothetical LOC401397, mRNA (cDNA clone IMAGE:4244115), complete cds. [BC107860] |
| 755 | A_32_P58074 | RPS3A | GTTGGTTTACTAGTAAAAAGCGGCCAAAATCAGATACGGAAGAGGGCTGTTATGCTGAGGAA | SEQ ID NO: 2336 | Homo sapiens ribosomal protein S3A (RPS3A), mRNA [NM_001006] |
| 756 | A_32_P61857 | KIAA1468 | TCAGTGTACAGTTCCACTGGAAATTTGACAGTTGTCGTGACGTCATGCAAGTGGAAGTAG | SEQ ID NO: 2337 | Homo sapiens KIAA1468 (KIAA1468), mRNA [NM_020854] |
| 757 | A_32_P68586 | ARL1 | TTGGGTTACCTGGTTGAAGGACCGAAAATGGCAGATATTCAAAACGTCAGGAACCAAAG | SEQ ID NO: 2338 | Homo sapiens ADP-ribosylation factor-like 1 (ARL1), mRNA [NM_001177] |
| 758 | A_32_P7118 | PSMC6 | AGCAGAGGTGAGGAAATGTTGTACTGAAGCAGGGATGTGTTCGGCAATCGTGGTCGATCATGA | SEQ ID NO: 2339 | Homo sapiens proteasome (prosome, macropain) 26S subunit, ATPase, 6 (PSMC6), mRNA [NM_002806] |

Fig. 5-41

| No. | Probe ID No. | Symbols of genes | Sequence | SEQ ID NO: | Descriptors of genes (letters and numbers within [ ] indicates GenBank accession No.) |
|---|---|---|---|---|---|
| 759 | A_32_P73222 | AA631847 | TTCTTTGTTTGGAATCTCATAAGAACTTAGGTCTTACAGCACGAACCCGTGAAG | SEQ ID NO: 2340 | np61b02.s1 NCI_CGAP_Br2 Homo sapiens cDNA clone IMAGE:1130763 3' similar to TR:Q971838 Q971838 60S RIBOSOMAL PROTEIN L34 ; mRNA sequence |
| 760 | A_32_P77102 | BC042469 | AAATGTGAAGTCTGGCTTTGAAGAGGGTGTATAACACACATAATTTAGTGTGCATCAGTG | SEQ ID NO: 2341 | Homo sapiens, clone IMAGE:5198554, mRNA [BC042469] |
| 761 | A_32_P81768 | TMEM167 | CCTCAGTACTGTCACTACAATATTACATTCTGCAAATGTTATTCTGTTGTATCAGATACG | SEQ ID NO: 2342 | Homo sapiens transmembrane protein 167 (TMEM167), mRNA [NM_174909] |
| 762 | A_32_P83784 | CENTD1 | ACAGGGCGATACTTCAGTCAGTCCAATCATAGTACAGTAGTGATGTGGTGGTAGATGGTATGA | SEQ ID NO: 2343 | Homo sapiens centaurin, delta 1 (CENTD1), transcript variant 1, mRNA [NM_152230] |
| 763 | A_32_P86400 | LYSMD3 | AAATGTTGCTCAGGTAATCAGTATTTTCTTCCAGTAGTGTGCATATTGCACTGTTAGATC | SEQ ID NO: 2344 | Homo sapiens LysM, putative peptidoglycan-binding domain containing 3 (LYSMD3), mRNA |
| 764 | A_32_P86494 | A_32_P86494 | TGAGGCTTCCGTGCCACATTGAGATGATCCTTACTGAAAAGGAACAGATTGTTCCTAAAC | SEQ ID NO: 2345 | |
| 765 | A_32_P8857 | A_32_P8857 | TAATGTCGGAATGGTAGACAGTGTTTCTGTAAAGTGACATCTTTCAGATACTTGGTGGCT | SEQ ID NO: 2346 | |
| 766 | A_32_P93782 | RPL26 | AGGTTGACATGGACACTATAAAGGTCAGCAAATTGGCAAAGTAGTCCAGGTTTACAGGA | SEQ ID NO: 2347 | Homo sapiens ribosomal protein L26 (RPL26), mRNA [NM_000987] |
| 767 | A_32_P9382 | RP11-11C5.2 | AACAAAGAGGAAAATATATTGAGAAGGATGCGTGTTTACAGAGGACTCTTTAAAGTGT | SEQ ID NO: 2348 | Homo sapiens similar to RIKEN cDNA 2410129H14 (LOC440145), mRNA [XM_001071775] |
| 768 | A_32_P96134 | DPY19L1 | ATAAGTGCTTCATTTGCTGGGAAGCCATTACAAGTAGTAAATTAGGTTTTCGAGAAGG | SEQ ID NO: 2349 | Homo sapiens DPY-19-like protein 1 (DPY19L1) mRNA, complete cds. [DQ287932] |
| 769 | A_32_P96213 | TPT1 | GAAAGGACAGTAATCACTGCTGCGATGTTGTCATGAACCATGCACCCTGCAGGAAACAAGT | SEQ ID NO: 2350 | Homo sapiens tumor protein, translationally-controlled 1 (TPT1), mRNA [NM_003295] |
| 770 | A_32_P96933 | AL571926 | GAGGCTGACAAATGTCTGAATGTAACAGTATGAACACCTATGAGCTGGGACTACTTCTG | SEQ ID NO: 2351 | AL571926 Homo sapiens PLACENTA COT 25-NORMALIZED Homo sapiens cDNA clone CS0DI029YJ06 3-PRIME, mRNA sequence [AL571926] |
| 771 | A_32_P98313 | NDUFA4 | AGCCGTGGAACAAACTGGGTCCAATGATCAATACAAGTTCTGCTCAGTGAATGTGATT | SEQ ID NO: 2352 | Homo sapiens NADH dehydrogenase (ubiquinone) 1 alpha subcomplex, 4, 9kDa (NDUFA4), nuclear gene encoding mitochondrial protein, mRNA [NM_002489] |

Fig. 6-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P143247 | TSHZ2 | CCCACAAGAGGGTATGGAAATGTCTAAGTTTACGGGGACTGTCAA TGACCACTATCAGTCA | SEQ ID NO: 1583 | Homo sapiens teashirt family zinc finger 2 (TSHZ2), mRNA [NM_173485] |
| 2 | A_23_P341938 | NOG | GCGAGGCGTGCGCTGATTCGAATCCAGTAGCCACATGATTTGC GAGTGCAAGTGCTCGT | SEQ ID NO: 1601 | Homo sapiens noggin (NOG), mRNA [NM_005450] |
| 3 | A_23_P500130 | ANKRD15 | TTTACGGTGTCAGATTTACTTTGGTCTCTATGTATTTAAATGT TTGAAGTGCCTTAGAC | SEQ ID NO: 1611 | Homo sapiens ankyrin repeat domain 15 (ANKRD15), transcript variant 2, mRNA [NM_153186] |
| 4 | A_23_P84399 | CNTNAP2 | CTTGAGCAGAATCCTAAAATATCAGGACAAGTTGGGGAGGCAG GGAATGGAATATAATG | SEQ ID NO: 1614 | Homo sapiens contactin associated protein-like 2 (CNTNAP2), mRNA [NM_014141] |
| 5 | A_24_P930963 | LOC650392 | GCCCCATTTCAAGTATAACCAGGAGGGAAAATGGCTGCTTGAAAT AAGCATGGCACAAAGG | SEQ ID NO: 1644 | Homo sapiens cDNA clone IMAGE:5264670 [BC036550] |
| 6 | A_32_P111394 | THC2643957 | GAATAGAGTGTTCCTTTTCATCCCATATTTGACTGAACCTAAGA CACATCAATTATAAGG | SEQ ID NO: 1651 | |
| 7 | A_32_P209562 | THC2663167 | CAATGTAAAGCCAGAATATGAACGTCCTTTTGTCAAGATTTTCA AAGCTATTTGGCTGAT | SEQ ID NO: 1678 | ALU1_HUMAN (P39188) Alu subfamily J sequence contamination warning entry, partial (5%) [THC2663167] |
| 8 | A_23_P213509 | THC2663555 | GATTTGTTCCAGTGTGTTGGAGGCGCTTTTAATGAAAATTCGAAC ACGTACAGTGGAAAAA | SEQ ID NO: 1680 | |
| 9 | A_32_P227110 | THC2512143 | TAAAACAAATCCTTTCAGGCACTGTGTATTGATAATGGC TTATTATTACAATCA | SEQ ID NO: 1684 | |
| 10 | A_23_P128930 | PSMC6 | GAACAAGGAAGATTAGACATACTGAAAATCGATGCGAGGTCCAT TACAAAGGCATGGTGAA | SEQ ID NO: 1737 | Homo sapiens proteasome (prosome, macropain) 26S subunit, ATPase, 6 (PSMC6), mRNA [NM_002806] |
| 11 | A_23_P134925 | BNIP3L | ATTTGGGGACAAAAAAGGCAGGGTTCATTTTTCATATGTTTGATG AAAACTGGGTCAAGAT | SEQ ID NO: 1746 | Homo sapiens BCL2/adenovirus E1B 19kDa interacting protein 3-like (BNIP3L), mRNA [NM_004331] |
| 12 | A_23_P137366 | C1QB | CACCGGACAAGAACTCACTACTGCCATGGGCATGGAGGTGCCAACAGCA TCTTTCGGGGTTCCT | SEQ ID NO: 1750 | Homo sapiens complement component 1, q subcomponent, B chain (C1QB), mRNA [NM_000491] |
| 13 | A_23_P137434 | RNF11 | TGTAGTATCCATATGTTGCTTAAATTTCCTTATGAGCCCCATGA TGGAAAGACTTAAAGA | SEQ ID NO: 1751 | Homo sapiens ring finger protein 11 (RNF11), mRNA [NM_014372] |
| 14 | A_23_P143958 | RPL22L1 | ATTGGCTTCGAGTCGTTGGCATCGACAAGGAGGACCTAGGAACTT CGTTACTTCCAGATTA | SEQ ID NO: 1757 | Homo sapiens ribosomal protein L22-like 1, mRNA (cDNA clone IMAGE:4865966), [BC049623] |
| 15 | A_23_P144497 | RPS3A | CCAAATCCGGAAGAAGATGATGGAAAATGATGCCGAGAGGTGC AGAGCAAATGACTTGAA | SEQ ID NO: 1560 | Homo sapiens ribosomal protein S3A (RPS3A), mRNA [NM_001006] |
| 16 | A_23_P14708 | SUHW4 | TCTTTGTACCTCGATCGATACAGTGTTAGGCTGCCAAGGCTGTAAGCT TACCTTAATTAAACTT | SEQ ID NO: 1765 | Homo sapiens suppressor of hairy wing homolog 4 (Drosophila) (SUHW4), transcript variant 1, mRNA [NM_017661] |
| 17 | A_23_P14734 | RPS27L | TACAAGATCAGCACGGGTTTCAGGCCATGCTCAGAGAGTGGTTCT TTGTGTAGGTTGTTGA | SEQ ID NO: 1766 | Homo sapiens ribosomal protein S27-like (RPS27L), mRNA [NM_015920] |
| 18 | A_23_P152202 | BCL2A1 | TGTAAGCATATTTGGATTGAAGGTATCGTCATCAAGAAACTTC TAGGACAGGAAATTGC | SEQ ID NO: 1773 | Homo sapiens BCL2-related protein A1 (BCL2A1), mRNA [NM_004049] |
| 19 | A_23_P156842 | EEF1E1 | AAGAAAAAGAATGCTTCAGCAGTAGTTAGAATACAGGGTCACT CAAGTAGAATGGGCACT | SEQ ID NO: 1778 | Homo sapiens eukaryotic translation elongation factor 1 epsilon 1 (EEF1E1), mRNA [NM_004280] |

Fig. 6-2

| No. | Probe ID No. | Symbols of genes | Sequence | SEQ ID NO. | Descriptions of genes, letters and numbers within [ ] indicates GenBank accession No.) |
|---|---|---|---|---|---|
| 20 | A_23_P157449 | POLR2K | GGTCTCTCTTGCTTCAAAATATGTTCTTGTACAGTACTGACCAT TTTAGATGTGGTTGAC | SEQ ID NO: 1779 | Homo sapiens polymerase (RNA) II (DNA directed) polypeptide K, 7.0kDa (POLR2K), mRNA [NM_005034] |
| 21 | A_23_P157452 | POLR2K | GGAATGTCTTCACTCATATAGTTCGATTTGGATTTGCTCTGTCTTCCATTTGT GATTGTTGTATAGCTT | SEQ ID NO: 1780 | Homo sapiens polymerase (RNA) II (DNA directed) polypeptide K, 7.0kDa (POLR2K), mRNA [NM_005034] |
| 22 | A_23_P159650 | COX7B | CAAATACGGTAATGCTGTATTAGCTAGTGGAGCCACTTCTGTA TTGTTACATGGACATA | SEQ ID NO: 1782 | Homo sapiens cytochrome c oxidase subunit VIIb (COX7B), nuclear gene encoding mitochondrial protein, mRNA [NM_001866] |
| 23 | A_23_P162596 | ACTR6 | TTAACGGCTTCACTGGACAGTTTTGCTTAGAAGGTAGTTTTGTG TGAGTGTGACTAAACT | SEQ ID NO: 1787 | Homo sapiens ARP6 actin-related protein 6 homolog (yeast) (ACTR6), mRNA [NM_022496] |
| 24 | A_23_P170233 | CSTA | AACTGGCTACTGAGTCATGATCCTTGGTGATAAATATAACCATC AATAAGAGACATTCT | SEQ ID NO: 1794 | Homo sapiens cystatin A (stefin A) (CSTA), mRNA [NM_005213] |
| 25 | A_23_P18325 | PDCD10 | CCAACCGACTAATTCATCAAACCAAGCTTAATACTTCAGACCTTC AAAGTGTGGCGTGAA | SEQ ID NO: 1795 | Homo sapiens programmed cell death 10 (PDCD10), transcript variant 1, mRNA [NM_007217] |
| 26 | A_23_P19291 | TUBB2A | ACTGTCAGATGAATGCTGGTGCATGCTTAGTGAACTTCTGTTGTCC TCAAGGCATGTCTTTC | SEQ ID NO: 1798 | Homo sapiens tubulin, beta 2A (TUBB2A), mRNA [NM_001069] |
| 27 | A_23_P200955 | A_23_P200955 | AGACCATGATTGAACCTCACATTGATGTCAAGAGTACGGATGGT TATTGTTTCATCTAC | SEQ ID NO: 1802 | |
| 28 | A_23_P215751 | NDUFA5 | TAAAAGTGGAGTCACTAAATAGTTGCAGTAGCTTCTAATATA AGTGTAGGTGGGTATC | SEQ ID NO: 1831 | Homo sapiens NADH dehydrogenase (ubiquinone) 1 alpha subcomplex, 5, 13kDa (NDUFA5), nuclear gene encoding mitochondrial protein, mRNA [NM_005000] |
| 29 | A_23_P217797 | DDX3Y | CAGTGATAGGAAGGTCCACATCCACAAAGTTTCTCTCTGAGTTT GTTATGTGTTTGCTG | SEQ ID NO: 1836 | Homo sapiens DEAD (Asp-Glu-Ala-Asp) box polypeptide 3, Y-linked (DDX3Y), mRNA [NM_004660] |
| 30 | A_23_P218928 | C4orf18 | CAGATGAGTTCATTTGCTTCTGTAGATGTGTTTCTGAGAGGTAGG TACAGAGGAATGTTTG | SEQ ID NO: 1837 | Homo sapiens chromosome 4 open reading frame 18 (C4orf18), transcript variant 2, mRNA [NM_016613] |
| 31 | A_23_P252201 | EAF2 | CAGGATTCCTGATATAGATAGCAGTCATAATAGATTTCGAGACA ACAGTGGCCTTGTGAT | SEQ ID NO: 1853 | Homo sapiens ELL associated factor 2 (EAF2), mRNA [NM_018456] |
| 32 | A_23_P26235 | CLEC4D | CATTTAAGCACGAGGAGTATTCTGGCATAAGAATGAACCCGAC AACTCTCAGGGAGAAA | SEQ ID NO: 1854 | Homo sapiens C-type lectin domain family 4, member D (CLEC4D), mRNA [NM_080387] |
| 33 | A_23_P26821 | COPS2 | TGCTTTTTTGATCAAGTCGGTTTGTTGTTTTGCTGGTCCATTTATC CCAAGAAAACACGTT | SEQ ID NO: 1869 | Homo sapiens COP9 constitutive photomorphogenic homolog subunit 2 (Arabidopsis) (COPS2), mRNA [NM_004236] |
| 34 | A_23_P2705 | P2RY5 | TCTGTATTGTGTCTTCGAACGTGTGTTTTGAACCGTATAGTTTAT TAGTTTACATCGGACA | SEQ ID NO: 1871 | Homo sapiens purinergic receptor P2Y, G-protein coupled, 5 (P2RY5), mRNA [NM_005767] |
| 35 | A_23_P302560 | RGS18 | GAGTCTAAGGGCTAGGCGATTTGGGCATCGTGCCACATGGTTCA TATTCAGAAAGTGTTA | SEQ ID NO: 1873 | Homo sapiens regulator of G-protein signalling 18 (RGS18), mRNA [NM_130782] |
| 36 | A_23_P307940 | CAPZA2 | CTACAAGATTTGGCAAAAGAGATGCAGAAATGCATAAGATGAACATT GCATGACCGATCATT | SEQ ID NO: 1876 | Homo sapiens capping protein (actin filament) muscle Z-line, alpha 2 (CAPZA2), mRNA [NM_006136] |
| 37 | A_23_P312246 | CCDC82 | GGCTTTATAACGATGACGTGTCAAGTGAATGAATGAGCTGTTGATATC CTGTCAGTTTAGTCAA | SEQ ID NO: 1880 | Homo sapiens coiled-coil domain containing 82 (CCDC82), mRNA [NM_024725] |
| 38 | A_23_P33045 | RPL26 | TACAAAGGTCAGCAAATTGGCAAAGTAGTCCAAGGTTTACAGGAA GAAATATGTTATCTAC | SEQ ID NO: 1890 | Homo sapiens ribosomal protein L26 (RPL26), mRNA [NM_000987] |

Fig. 6-3

| No. | Probe ID No. | Symbols of genes | Sequence | SEQ ID NO: | Descriptions of genes (letters and numbers within [ ] indicates GenBank accession No.) |
|---|---|---|---|---|---|
| 39 | A_23_P339480 | HAT1 | AACATGAACAGCTGGAAGAGAGTTTTCAGGAACTAGTGGAAGATTACGGGCGTGTTATTG | SEQ ID NO: 1892 | Homo sapiens histone acetyltransferase 1 (HAT1), transcript variant 1, mRNA [NM_003642] |
| 40 | A_23_P347059 | MOBKL1A | CTAGAAGGGGAAAAATCATCTAAGTTATGAAATCCAAGATAGGCGCTATATTACAAAGTG | SEQ ID NO: 1896 | Homo sapiens MOB1, Mps One Binder kinase activator-like 1A (yeast) (MOBKL1A), mRNA [NM_173468] |
| 41 | A_23_P41114 | CSTA | AAAGAAATGAGAGTTATGGAAAATTGGAAGGTGTGCAGTATAAAACTCAAGTTGTTGCTG | SEQ ID NO: 1925 | Homo sapiens cystatin A (stefin A) (CSTA), mRNA [NM_005213] |
| 42 | A_23_P44257 | COMMD8 | AAGATTTAGTTCTGCGGGTTCATGTTTGGAAACATTGCTCTGATAAAAATAGCTGTC | SEQ ID NO: 1942 | Homo sapiens COMM domain containing 8 (COMMD8), mRNA [NM_017845] |
| 43 | A_23_P501276 | TUBB2A | GTGACGAGGCAGATGCTCAACGTGCAGAAGAAGAACAGCAGCTACTTCGTGGAGTGGATC | SEQ ID NO: 1950 | Homo sapiens tubulin, beta 2A (TUBB2A), mRNA [NM_001069] |
| 44 | A_23_P50907 | ITGAV | AAAGAGTGATTAAGTGAGGTTATTACCGCTAAATGGTCCATTCTGCATTGTATTTCAGG | SEQ ID NO: 1953 | Homo sapiens integrin, alpha V (vitronectin receptor, alpha polypeptide, antigen CD51) (ITGAV), mRNA [NM_002210] |
| 45 | A_23_P56734 | HNMT | CCTTTTGTCCACCATGGATATATCTGACTGCTTATTGATGGTAATGAAAATGGAGACCT | SEQ ID NO: 1962 | Homo sapiens histamine N-methyltransferase (HNMT), transcript variant 1, mRNA [NM_006895] |
| 46 | A_23_P59921 | SUB1 | CAGAATTGGGAAAATGAGGTACGTTAGTTGTTCGGCGAATTTTAAAGGCAAAGTGCTAATTGAT | SEQ ID NO: 1970 | Homo sapiens SUB1 homolog (S. cerevisiae) (SUB1), mRNA [NM_006713] |
| 47 | A_23_P65768 | C15orf15 | TCCTGCATTGCCATCTACAATAATATCAGATATTACGGATGTTAGATTGCGTCAGTGTT | SEQ ID NO: 1977 | Homo sapiens chromosome 15 open reading frame 15 (C15orf15), mRNA [NM_016304] |
| 48 | A_23_P66260 | ZNF267 | TGTGATGAATGTGAAAGCCTCAGGTATAGGTCATAGGCCTCACTACAGATCGGAGAAGT | SEQ ID NO: 1978 | Homo sapiens zinc finger protein 267 (ZNF267), transcript variant 498723, mRNA [NM_003414] |
| 49 | A_23_P70328 | CENPQ | CAATGGCTTAGAGTTCTGTCTGGTCATCTGGAACTTGAAAATCCTCAAATGCCTTCAG | SEQ ID NO: 1985 | Homo sapiens centromere protein Q (CENPQ), mRNA [NM_018132] |
| 50 | A_23_P7221 | RPL34 | GAGGAGCAGAGAAATGGTTGTGAAAGTGTTGAAGGGACGAAGACAGAGTCAGAAAGGTAA | SEQ ID NO: 1990 | Homo sapiens ribosomal protein L34 (RPL34), transcript variant 2, mRNA [NM_033625] |
| 51 | A_23_P7229 | RPL34 | CGAACCCCTGGTAATAGAATTGTTTACCTTTATACCAAGAAGGTTGGGAAAGGACCAAAA | SEQ ID NO: 1991 | Homo sapiens ribosomal protein L34 (RPL34), transcript variant 2, mRNA [NM_033625] |
| 52 | A_23_P75769 | MS4A4A | CACCAAAAGATCAACAGACAAGACAAATGCTCCAGAAATGTCCAGAAATATGCTGACTGTCACAGAAGGCCT | SEQ ID NO: 2000 | Homo sapiens membrane-spanning 4-domains, subfamily A, member 4 (MS4A4A), transcript variant 1, mRNA [NM_024021] |
| 53 | A_23_P78092 | EVI2A | GCTAATACAGACACTTGGAAAAGAGACAAAAACAGGTCACACGGACGCAACCTAGTGATGCAA | SEQ ID NO: 2004 | Homo sapiens ecotropic viral integration site 2A (EVI2A), transcript variant 1, mRNA [NM_001003927] |
| 54 | A_23_P83278 | CHMP5 | CATTGCTCTCTTTATTTTTCATTAAGAGAGTCATTGCTTGGGAAATGCTTTCTTCGGTAC | SEQ ID NO: 2007 | Homo sapiens chromatin modifying protein 5 (CHMP5), mRNA [NM_016410] |
| 55 | A_23_P87879 | CD69 | TGTGCAATATGTGATGTGGCAAATGTCTATTAGGAAATATTCTGTAATCTTCAGACCTAG | SEQ ID NO: 2011 | Homo sapiens CD69 molecule (CD69), mRNA [NM_001781] |
| 56 | A_23_P94230 | LY96 | TGAAGCTATTTCTGGGAGCCCAGAAGAAGAAATGCTCTTTTGGTTGGAGTTGTCATCCTACA | SEQ ID NO: 2018 | Homo sapiens lymphocyte antigen 96 (LY96), mRNA [NM_015364] |
| 57 | A_23_P94501 | ANXA1 | GGCTCTTTGTGGAGGAAACTAAACATTCCTTGATGATGAAGACTCTATGATGAAGAGACT | SEQ ID NO: 2019 | Homo sapiens annexin A1 (ANXA1), mRNA [NM_000700] |

Fig. 6-4

| No. | Probe ID No. | Symbols of genes | Sequence | SEQ ID NO. | Descriptions of genes (letters and numbers within [ ] indicates GenBank accession No.) |
|---|---|---|---|---|---|
| 58 | A_23_P96658 | C1orf115B | ATGCCCTAAAGTTAATACCAGGAGTCATATTTTATCAGATGTAAATCTGGATGTAAGCTC | SEQ ID NO: 2023 | lipopolysaccharide-specific response 5-like protein [Source:RefSeq_peptide;Acc:NP_115965] [ENST00000382322] |
| 59 | A_24_P11045 | THC2785765 | CCACCAGAAACGTACACCTGATTTTCATGACAAATACGGTAGGAACACAAGTCGGAATAG | SEQ ID NO: 2032 | COX7B_HUMAN (P24311) Cytochrome c oxidase polypeptide VIIb, mitochondrial precursor, partial (78%) [THC2785765] |
| 60 | A_24_P135551 | LOC130865 | TAACAGCATAGCTGTCCCTGTGGGATTCACCCAAAGTGGTTATCAGTAGACTAAAACT | SEQ ID NO: 2046 | PREDICTED: Homo sapiens similar to 60S ribosomal protein L26 (Silica-induced gene 20 protein) (SIG-20), (LOC130865), mRNA [XR_019454] |
| 61 | A_24_P144666 | LOC401975 | TGTCGATGTCAAGACTAATAATGATGGCTACTTCTTTAATCTGTTCTGTGTTGGTTTTACTGA | SEQ ID NO: 2050 | PREDICTED: Homo sapiens similar to ribosomal protein S3a (LOC401975), mRNA [XR_017247] |
| 62 | A_24_P153324 | LOC390413 | GAAGCTTAACAAGGTTTCAATTAACATGCTGGGGATTGTAGAACCATATATTGCAGGGTA | SEQ ID NO: 2054 | PREDICTED: Homo sapiens similar to 60S ribosomal protein L7 (LOC390413), mRNA [XR_018341] |
| 63 | A_24_P188878 | RPL34 | TGTTTAGCTTTATACCAAGAAGGTTGGAAAGCACCAAAATCTGCATGTGGTGTGTGCCC | SEQ ID NO: 2077 | Homo sapiens ribosomal protein L34 (RPL34), transcript variant 2, mRNA [NM_033625] |
| 64 | A_24_P201702 | CLEC2B | ATTGGAATTGACAAGGTTTCAGTAAATACAAGAACGTTGCACTCAACGATGCGAACCTAACTATAATTGACA | SEQ ID NO: 2085 | Homo sapiens C-type lectin domain family 2, member B (CLEC2B), mRNA [NM_005127] |
| 65 | A_24_P203909 | RPL34 | GAGGGGTTCGTGCTGTAAGTAAATACGTTAAGAGTTACCACACTTTCAAAAATGTACAGAAAAACAAACATG | SEQ ID NO: 2088 | Homo sapiens ribosomal protein L34 (RPL34), transcript variant 2, mRNA [NM_033625] |
| 66 | A_24_P221375 | A_24_P221375 | TACTTTGGTTACCATGTACCTACCACTTCAAGGTTTCTGATACAATTGAAGACAGAAATCTGC | SEQ ID NO: 2095 | |
| 67 | A_24_P237511 | EIF1AY | GTTTCAGTTACTTAGATGGTCATCATAAGGTTTCGTCATACAATTTGAAGACAGAAATCTGC | SEQ ID NO: 2105 | Homo sapiens eukaryotic translation initiation factor 1A, Y-linked (EIF1AY), mRNA [NM_004681] |
| 68 | A_24_P298604 | LOC731599 | GATGGAAATCATGACCAGAGGTGCGGCAAATGACTTGAAAGATTGGTCAATAAATGAT | SEQ ID NO: 2126 | PREDICTED: Homo sapiens hypothetical protein LOC731599 (LOC731599), mRNA [XR_015536] |
| 69 | A_24_P303118 | RPL34 | CGAGGACGAGAAATCGTTGTGAAATGTTGAAGGCACAAGCACAGAGTCAGAAAGCTAA | SEQ ID NO: 2128 | Homo sapiens ribosomal protein L34 (RPL34), transcript variant 2, mRNA [NM_033625] |
| 70 | A_24_P306527 | ENST00000308989 | ACCGATCCGTGGGTGGTTATCCAGAAAATGTAATGAGGATGAAGATTCACCAAATAAGT | SEQ ID NO: 2132 | PREDICTED: Homo sapiens similar to ribosomal protein L31 (LOC729005), mRNA [XM_001133428] |
| 71 | A_24_P320328 | SUB1 | CAGAAAAACGTGTAAAGAAACAAAGAAACAGGTGAGACTTCGAGAGCCCTGTCATCTTCTA | SEQ ID NO: 2138 | Homo sapiens SUB1 homolog (S. cerevisiae) (SUB1), mRNA [NM_006713] |
| 72 | A_24_P324224 | A_24_P324224 | AAAGCTGTCTGGGCCAAAGGAATAGGAATTCCTATAGGCATGTGCAGTTGTCCAGAAAA | SEQ ID NO: 2140 | |
| 73 | A_24_P33213 | A_24_P33213 | GACCATATATTACATGGGGTACCCAAATCTGAAGTCAGTAAATGAACTTATCTACAAGG | SEQ ID NO: 2143 | |
| 74 | A_24_P333112 | A_24_P333112 | GGTTCATCAGAATCAGAGGTATCAATGTGTGAGCGACAGGACGAAAAGGTATTGCAACTT | SEQ ID NO: 2144 | |
| 75 | A_24_P33607 | LOC652558 | TAAGAAAATAATTGCTTTGACAGACAACAAGGTTTGATTGGTCCATCTCTTGGTAATATGG | SEQ ID NO: 2145 | PREDICTED: Homo sapiens similar to 60S ribosomal protein L7 (LOC652558), mRNA [XR_019336] |
| 76 | A_24_P349636 | LOC388401 | AGTTGCTTCGACAGATAAGACTTTGATTGCTGATCTCTTGGTAAATATAGCAACTG | SEQ ID NO: 2147 | PREDICTED: Homo sapiens similar to 60S ribosomal protein L7 (LOC388401), mRNA [XR_016879] |

Fig. 6-5

| No. | Probe ID No. | Symbols of genes | Sequence | SEQ ID NO: | Descriptions of genes (letters and numbers within [ ] indicates GenBank accession No.) |
|---|---|---|---|---|---|
| 77 | A_24_P366546 | RPL31P10 | CGGCTGTCGCAGAAAACGTAATGAGGATGAAGATTCAAATAAGGTCTATAGTTTGGTTACC | SEQ ID NO: 2158 | PREDICTED: Homo sapiens similar to ribosomal protein L31 (LOC390283), mRNA [XR_018695] |
| 78 | A_24_P367191 | LOC652890 | AGTTAACATGCTGAGGACTGTAGAGGCCATATATTGCCTGTGGGTACCAAATCTGAAGTC | SEQ ID NO: 2160 | PREDICTED: Homo sapiens similar to 60S ribosomal protein L7 (LOC652890), mRNA [XR_019544] |
| 79 | A_24_P367199 | A_24_P367199 | TCTTATGCTCAGGACCCAAGAGTCTGCCAAATCGAAGAAGAAGGTCTAATCATGACCTGAGA | SEQ ID NO: 2161 | |
| 80 | A_24_P381625 | PSMC6 | ATGAAAGCAGTCAGAAAAGTGGCTGATTCTAAGAAGCGTGGAGTCTAAATTGGACTACAAA | SEQ ID NO: 2173 | Homo sapiens proteasome (prosome, macropain) 26S subunit, ATPase, 6 (PSMC6), mRNA [NM_002806] |
| 81 | A_24_P383999 | RPS3A | TGGTTTACTAAAAACGCAACAATCAGATACAGAAGACCTGTTATGCCGCAGCAACG | SEQ ID NO: 2175 | Homo sapiens ribosomal protein S3A (RPS3A), mRNA [NM_001006] |
| 82 | A_24_P384411 | A_24_P384411 | ATGGCAAATCAATAAGAGTGAAGCTTGAGAGATAATGCTTTGACAGCTCGATCTCTTG | SEQ ID NO: 2176 | |
| 83 | A_24_P392900 | A_24_P392900 | GTGTGTTCTGTCTGTTGGTTTTCCTAAAACAATGTAACAATGGGAAAAGGTTTTATGGTC | SEQ ID NO: 2180 | |
| 84 | A_24_P414556 | TTC33 | TACTGAACATTTGGTATATTGTTTTGAGTAATGGATGTGTTTTTGTGTAATTTGTGTA | SEQ ID NO: 2191 | Homo sapiens tetratricopeptide repeat domain 33 (TTC33), mRNA [NM_012382] |
| 85 | A_24_P41561 | LOC641790 | AAGGAGATGGGAACTCCTGATGTGGCATTGATATGAGGCACAACAAAGTAGTCTGAAAA | SEQ ID NO: 2193 | PREDICTED: Homo sapiens similar to ribosomal protein L31 (LOC641790), mRNA [XR_018025] |
| 86 | A_24_P50437 | BC065737 | TGCAGAATGATGAAGTTGAAATTGGAAAAATGCTGATTACTGAAGATGTCAGGGCAAAA | SEQ ID NO: 2198 | Homo sapiens cDNA clone IMAGE:30404477, partial cds. [BC065737] |
| 87 | A_24_P57837 | THC2567891 | AGAAATGCGGAAGAGCTCTTATGCTCAGCACGAAAATCCGGAAGAGATGATGGAAA | SEQ ID NO: 2207 | Q6NXR8_HUMAN (Q6NXR8) Ribosomal protein S3a, partial (91%) [THC2567891] |
| 88 | A_24_P606663 | LOC392030 | TGTGCGGTTGCCCAGAAAACGTAATGCGGGGTGAAGATTGACCAAATAAGCTCCATACTTT | SEQ ID NO: 2209 | PREDICTED: Homo sapiens hypothetical LOC392030 (LOC392030), mRNA [XR_018063] |
| 89 | A_24_P63347 | PF4V1 | CTACATATTTACCTTGAATGTTACAATGGGGATTAGCTTGGCAATAAATATTAGTAGTCTTAAGC | SEQ ID NO: 2213 | Homo sapiens platelet factor 4 variant 1 (PF4V1), mRNA [NM_002620] |
| 90 | A_24_P685729 | A_24_P685729 | TTGAAGTTATGTTGATGTCAAGACTATCAGTGATTATTGCTTGTCTGTTTTGTGTGG | SEQ ID NO: 2217 | |
| 91 | A_24_P6975 | LOC342994 | GGAAGACTTCGAGGGGTTCGTGCTGTAAGACCTAAAGTTCTTATGAAATTGTCAAAAGA | SEQ ID NO: 2218 | PREDICTED: Homo sapiens similar to ribosomal protein L34 (LOC342994), mRNA [XM_938484] |
| 92 | A_24_P755505 | A_24_P755505 | ATACAGAAGACCTGTTATGCTGAGCACCAAGAAGAGTAAAATGTGAAGAAGCCCAA | SEQ ID NO: 2223 | |
| 93 | A_24_P792734 | PSMC6 | AGAACGTTAACGGAGTTACTGAATCAAATCAAATGGATTGGATTACTCTGACAGATAGAITAA | SEQ ID NO: 2227 | Homo sapiens proteasome (prosome, macropain) 26S subunit, ATPase, 6 (PSMC6), mRNA [NM_002806] |
| 94 | A_24_P84908 | LOC729449 | GAATTGCTTTGACAGATAACGCTTGGCATCTCTTTGGAAAATATGGGCATGATCTGATATGG | SEQ ID NO: 2233 | PREDICTED: Homo sapiens similar to 60S ribosomal protein L7 (LOC729449), mRNA [XR_015548] |
| 95 | A_24_P941643 | PLCB1 | ATGATGTGCACCCAAGATCTGTCCTTTATGTGTATTTGGCCTGTTGTTCTTTGTCGAATGTCTAATTT | SEQ ID NO: 2247 | Homo sapiens phospholipase C, beta 1 (phosphoinositide-specific) (PLCB1), transcript variant 2, mRNA [NM_182734] |
| 96 | A_32_P107717 | BX100535 | TCTTGTGCACCCAAGATCTGTCTCTGTTGTAAATCCTGTTCAGACCTGGTCTAATTGGT | SEQ ID NO: 2255 | BX100535 Soares_testis_NHT Homo sapiens cDNA clone IMAGp998I094457, mRNA sequence [BX100535] |

Fig. 6-6

| No. | Probe ID No. | Symbols of genes | Sequence | SEQ ID NO: | Descriptions of genes (letters and numbers within [ ] indicates GenBank accession No.) |
|---|---|---|---|---|---|
| 97 | A_32_P109653 | THC2669092 | TGTGGTTGGTATTCGAAGTGGGGTCTTTTCGAGAATCTGTGCACTAGTGTGAGATGCAA | SEQ ID NO: 2257 | |
| 98 | A_32_P113154 | LOC730861 | ACCACCAGTCCAAGAATCTGTTTAAAGTTCAGAGACTTAAAACAGTAACAAATAAAAGTCC | SEQ ID NO: 2259 | PREDICTED: Homo sapiens similar to 40S ribosomal protein S3a (V-fos transformation effector protein) (LOC730861), mRNA [XR_015591] |
| 99 | A_32_P114215 | COMMD6 | AATTGCTATCATTCTAAAGTCATGGACTTCACTTTCGGCAACAAAACTAAATAAGGATGG | SEQ ID NO: 2261 | Homo sapiens COMM domain containing 6 (COMMD6), transcript variant 2, mRNA [NM_203495] |
| 100 | A_32_P125549 | RPL31P4 | TCTACAGACAGTCAATGTGGATGGAGAGAACTAATCCCTGATCGTCAGATACGAAATAAAG | SEQ ID NO: 2266 | PREDICTED: Homo sapiens ribosomal protein L31 pseudogene 4 (RPL31P4), mRNA [XR_018222] |
| 101 | A_32_P128781 | THC2683448 | CATATATTGCATGGGGGTACCCCAATCTGAAGTCAGTAAATGAACTAATCTACAAGAGTG | SEQ ID NO: 2268 | |
| 102 | A_32_P135818 | RPS3A | CTTGCTCATCTGTCTGTGTTGGTTTGGTTTAATAAAAAACGGAACAATCAGATATGGAAGAG | SEQ ID NO: 2269 | Homo sapiens ribosomal protein S3A (RPS3A), mRNA [NM_001006] |
| 103 | A_32_P145153 | RPL31 | ATCGGTGTGCAGCTGTCGAGAAAACGTAATGAGGATGAAGATTCACCAAATAAGCCATAT | SEQ ID NO: 2273 | Homo sapiens ribosomal protein L31 (RPL31), mRNA [NM_000993] |
| 104 | A_32_P155364 | RPL7 | TGAACAGGCTTATTAGAAAAATGAACCAAGTGTCTACCATGATTATTTTCTAAGGTGG | SEQ ID NO: 2280 | Homo sapiens ribosomal protein L7 (RPL7), mRNA [NM_000971] |
| 105 | A_32_P164203 | THC2683448 | TTGATGTCATTGTACGGAGCTATTGTATGGATTACTGTGGAGTGCTGTTTACCACAGAT | SEQ ID NO: 2286 | Q7WZG3_PASPI (Q7WZG3) Ferric uptake regulator, partial (8%) [THC2683448] |
| 106 | A_32_P178945 | YOD1 | TTGCCAGCATTTTTGAAGTATAATACACTGCTGCTACCGTGGAAGATGTCTAACTTCATTTT | SEQ ID NO: 2296 | Homo sapiens YOD1 OTU deubiquinating enzyme 1 homolog (S. cerevisiae) (YOD1), mRNA [NM_018566] |
| 107 | A_32_P198483 | RPS3A | GGGGCCAAGAACAAAGTTGGATCCATTTTCTAAGAAGATTGGTATGATGTGAAAGCA | SEQ ID NO: 2306 | Homo sapiens ribosomal protein S3A (RPS3A), mRNA [NM_001006] |
| 108 | A_32_P208178 | RPS3A | GGAAATGACAGGTAGAAAAGGCTTGCCATCTATATTATGCTCTCGAGATGTCTTGGTTAGA | SEQ ID NO: 2317 | Homo sapiens ribosomal protein S3A (RPS3A), mRNA [NM_001006] |
| 109 | A_32_P220127 | RPL34 | CAAAACTGACTGTCCTGAACCGCGTGGTAATGAAGAATTGTTCACCTTTATACCAAGAAGGT | SEQ ID NO: 2320 | Homo sapiens ribosomal protein L34 (RPL34), mRNA [NM_033625] |
| 110 | A_32_P224666 | CAPZA2 | AATGCTTTTGAGATTCTGAAATTCAGAAATTAAATGAAAATACTTATTCAGAAATGCATTTAATG | SEQ ID NO: 2322 | Homo sapiens capping protein (actin filament) muscle Z-line, alpha 2 (CAPZA2), mRNA [NM_006136] |
| 111 | A_32_P2333 | SUB1 | AGGAAGAAAAGGTATTTCTTTAAATCCAGAACAATGGAGCCAGCTGACAGAACAGAATTC | SEQ ID NO: 2325 | Homo sapiens SUB1 homolog (S. cerevisiae) (SUB1), mRNA [NM_006713] |
| 112 | A_32_P4532 | LOC643932 | GATTGCAGAGACAGCATTGGAAAAGAACATAGAAAAAGGGCTTGCCAATCTATCGCTCGATGAT | SEQ ID NO: 2332 | PREDICTED: Homo sapiens similar to 40S ribosomal protein S3a (V-fos transformation effector protein) (LOC643932), mRNA [XR_017289] |
| 113 | A_32_P49392 | A_32_P49392 | AATTCTGCCAAATCTGGAAGAAGAAGATGATGGAAATCAGATACGGAAGACCTCGAGGTCAGAACAAAATG | SEQ ID NO: 2334 | |
| 114 | A_32_P58074 | RPS3A | GTTGGTTTTGATGCTCAGGACCAA | SEQ ID NO: 2336 | Homo sapiens ribosomal protein S3A (RPS3A), mRNA [NM_001006] |
| 115 | A_32_P7118 | PSMC6 | AGCAGACGCTGAGAAATGTTTGTACTGAAGGCAGGTATGTTCGCAATTCGTTGCTGATCATGA | SEQ ID NO: 2339 | Homo sapiens proteasome (prosome, macropain) 26S subunit, ATPase, 6 (PSMC6), mRNA [NM_002806] |

Fig. 6-7

| No. | Probe ID No. | Symbols of genes | Sequence | SEQ ID NO. | Descriptions of genes (letters and numbers within [ ] indicates GenBank accession No.) |
|---|---|---|---|---|---|
| 116 | A_32_P73222 | AA631847 | TTTCTTTGTTTTGGACAATCTCATAAGAACTTTACGTCTTACAG CACGAACCCCTCGAAG | SEQ ID NO: 2340 | np61b02.s1 NCI_CGAP_Br2 Homo sapiens cDNA clone IMAGE:1130763 3' similar to TR:G971838 G971838 60S RIBOSOMAL PROTEIN L34 ;. mRNA sequence [AA631847] |

Fig. 7-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P105803 | FGF9 | CAAAGGAGTGTGCGGCCTGATGGATGGTGGAAAAAGACACGGCTTTTCATTGTGATCAGTT | SEQ ID NO: 2353 | Homo sapiens fibroblast growth factor 9 (glia-activating factor) (FGF9), mRNA [NM_002010] |
| 2 | A_23_P123172 | OR2A9P | GAGGGTCAGTTGTCAGTGGACTCTTGATGCGAATTATTGCCTCAATCCAGAAAAGTTT | SEQ ID NO: 2354 | Homo sapiens olfactory receptor, family 2, subfamily A, member 9 pseudogene (OR2A9P) on chromosome 7 [NR_021577] |
| 3 | A_23_P153676 | TLE2 | CGTGGTCAGTCCTGAGTTGTGACATCCCAGAAATAAGAAATACATTGTGACAGGGTCGG | SEQ ID NO: 2355 | Homo sapiens transducin-like enhancer of split 2 (E(sp1) homolog, Drosophila) (TLE2), mRNA [NM_003260] |
| 4 | A_23_P157299 | AEBP1 | ACAGTAGAGACSTACACAGTGAAGTTTGGGGACTTCTGAGATCAGGGTGGTACCAAGACC | SEQ ID NO: 2356 | Homo sapiens AE binding protein 1 (AEBP1), mRNA [NM_001129] |
| 5 | A_23_P159907 | MAGED4 | GGAGGGTGTGGATGATGGCTTTCAAGAGAATGGATGTGGATATGGCCGAGGAACATGCCAG | SEQ ID NO: 2357 | Homo sapiens melanoma antigen family D, 4 (MAGED4), transcript variant 1, mRNA [NM_030801] |
| 6 | A_23_P166280 | THC2614148 | GTCAGGGGAGTTCTGAGGTTGGACCCTTATCTCGGCAGAATCCTGGAACGTGCTCCTCT | SEQ ID NO: 2358 | Q59G86_HUMAN (Q59G86) Androgen-regulated short-chain dehydrogenase/reductase 1 variant (Fragment), partial (7%) [THC2614148] |
| 7 | A_23_P166371 | VPREB3 | TGCCGTCTGGATATCTCCTCAGTACGCTCGGAGGAGGATCACGACCGGGCGTGCTGACAT | SEQ ID NO: 2359 | Homo sapiens pre-B lymphocyte gene 3 (VPREB3), mRNA [NM_013378] |
| 8 | A_23_P200015 | AK5 | AATGGAGAGGGAACACAGGAGGACGTTTTCTTCAACTCTGCCGACGCTATTGAGTCTATT | SEQ ID NO: 2360 | Homo sapiens adenylate kinase 5 (AK5), transcript variant 1, mRNA [NM_174858] |
| 9 | A_23_P202520 | ABLIM1 | TCACTGCACTCGTTTGTCCATAATACTGCATCACTGTCATAGTCAGAACTTCGTGAATAA | SEQ ID NO: 2361 | Homo sapiens actin binding LIM protein 1 (ABLIM1), transcript variant 3, mRNA [NM_001003408] |
| 10 | A_23_P202881 | FEZ1 | TGCTGACAAACATTCTGTCTTTGGCATGAAGGAGGATAATGAGAAGGTGCCTACTTGGTAA | SEQ ID NO: 2362 | Homo sapiens fasciculation and elongation protein zeta 1 (zygin I) (FEZ1), transcript variant 1, mRNA [NM_005103] |
| 11 | A_23_P209055 | ENST00000335459 | GCCTCAGGAGAAGAAAATGTGGAGTATGTGATCCTCAAAGATTGACAGTGGATGGCTG | SEQ ID NO: 2363 | Homo sapiens CD22 molecule (CD22), mRNA [NM_001771] |
| 12 | A_23_P21495 | CD22 | TCAGTCATCCACGCAGGGAACGGAAGATTCCTGAAGAAGACCTGGTCCCTCTGGAGGTTGGG | SEQ ID NO: 2364 | Homo sapiens Fc fragment of IgG binding protein (FCGBP), mRNA [NM_003890] |
| 13 | A_23_P250212 | DKFZp761P0423 | GAACTGAATGGCAGCCTGGACACTGGGCGTCAATACCTTGTTAGGATTTGTGTCAGCCTTT | SEQ ID NO: 2365 | tyrosine-protein kinase SgK223 (EC 2.7.10.2) (Sugen kinase 223) [Source:Uniprot/SWISSPROT;Acc:Q86YV5] [ENST00000330777] |
| 14 | A_23_P25060 | FLJ13769 | CAGAGTTCTTGGAGGATTCTGAGGTAGAGAGTAGCATAATTGCATTTGTGTTTTTATTCT | SEQ ID NO: 2366 | Homo sapiens cDNA FLJ13769 fis, clone PLACE4000222. [AK023831] |
| 15 | A_23_P255896 | ENST00000335459 | GGAAAGGGGCTCTACGGCAAGAGTACCTGTTCAAGTGTATTGCCGGAAACTGGGAGGGCAAGA | SEQ ID NO: 2367 | Homo sapiens hypothetical protein LOC129293, (cDNA clone IMAGE:5762496), partial cds. [BC051789] |
| 16 | A_23_P30634 | BACH2 | CCCTGTGTAGGTCTCATAACTGGTCAAGGACTGTAACAGGTTACATCAGGTGTTTTCTA | SEQ ID NO: 2368 | Homo sapiens BTB and CNC homology 1, basic leucine zipper transcription factor 2 (BACH2), mRNA [NM_021813] |
| 17 | A_23_P315378 | ATG16L1 | CTGTGTTTGCAGTTTATACTCTTTGTCCAAAACTCAGTTTCAAAATATTTGCAATGGGAC | SEQ ID NO: 2369 | Homo sapiens cDNA FLJ10035 fis, clone HEMBA1000919. [AK000897] |

Fig. 7-2

| No. | Probe ID No. | Symbols of genes | Sequence | SEQ ID NO: | Descriptions of genes (letters and numbers within [ ] indicates GenBank accession No.) |
|---|---|---|---|---|---|
| 18 | A_23_P316472 | DNHD1 | TAAGCTGCAGAGGAGGAACATGTGATGCATCTGCCTTTACCCACCAAGCTCAACCCCAA | SEQ ID NO: 2370 | Homo sapiens dynein heavy chain domain 1 (DNHD1), mRNA [NM_144666] |
| 19 | A_23_P325212 | ETS1 | GTCAACCCAGCGTATGGAGAATCCGGTATACCTCGGATTAGTTCATTAGCTATGGTATT | SEQ ID NO: 2371 | Homo sapiens v-ets erythroblastosis virus E26 oncogene homolog 1 (avian) (ETS1), mRNA [NM_005238] |
| 20 | A_23_P329375 | POU6F1 | GTTCCTTTGGGGGCAGAAATTGCACTAAAACAGAAGCTTTCTTAATCCATGTTGGAAGGA | SEQ ID NO: 2372 | Homo sapiens POU domain, class 6, transcription factor 1 (POU6F1), mRNA [NM_002702] |
| 21 | A_23_P341938 | NOG | CCCAGCGTGCGGCCTGGATTCCCATCCAGTACCCATCATTCCGAGTGCAAGTGCTCGT | SEQ ID NO: 2373 | Homo sapiens noggin (NOG), mRNA [NM_005450] |
| 22 | A_23_P343398 | CCR7 | AAGAGAGCAACATTTACCACACAGAGATAAAGTTTGGTTGAGGAAACAACAGCTTT | SEQ ID NO: 2374 | Homo sapiens chemokine (C-C motif) receptor 7 (CCR7), mRNA [NM_001838] |
| 23 | A_23_P344531 | SYNPO | TCCTCTGTGTCTGTGAAGATGAAGAGTGCTCTTACTGAGTTAATGATGAGTGACTATATT | SEQ ID NO: 2375 | Synaptopodin. [Source:Uniprot/SWISSPROT;Acc:Q8N3V7] ENST00000307662] |
| 24 | A_23_P344884 | KIAA1394 | ACCGAAATTCTAGGATAGGCTCTGAAGCCTGCTGGAAAGTTGGTTGG CATGCAACTGCCTC | SEQ ID NO: 2376 | Homo sapiens KIAA1394 protein, mRNA (cDNA clone IMAGE:4310128), complete cds. [BC036557] |
| 25 | A_23_P356681 | ROBO3 | GGGCTAGCTGAACGCCCATTGGTTCGAACGATTTCAATGGCTGAGAAGGCAGAGGTAG | SEQ ID NO: 2377 | Homo sapiens roundabout, axon guidance receptor, homolog 3 (Drosophila) (ROBO3), mRNA [NM_022370] |
| 26 | A_23_P357104 | ANXA6 | CTGGTCAACATCCGGAGGAATTCATTGAGAAATATGACAAGTGCTCTCAGGCAAGGCATT | SEQ ID NO: 2378 | Homo sapiens annexin A6 (ANXA6), transcript variant 1, mRNA [NM_001155] |
| 27 | A_23_P357717 | TCL1A | CTGCCCCCTTTATAGATGGTCAACGACGTGGGTGTTGGAGGTTACAAGTT GTATGTGGCATGAAT | SEQ ID NO: 2379 | Homo sapiens T-cell leukemia/lymphoma 1A (TCL1A), mRNA [NM_021966] |
| 28 | A_23_P358870 | C8orf16 | CTGAGGTTATAATTTCACTTAACATTGTCGGAGTTGGGAGTTTTTGG TTTAGTCCAATCGT | SEQ ID NO: 2380 | Homo sapiens mRNA for hypothetical protein (C8ORF16). [AJ312026] |
| 29 | A_23_P368996 | LRRC56 | CAAACGAACATTTCCAGGTCTGCAGGTGTACAGGTGTACAGAGAAATGGGGTTTAC TTTGTAGGCCACGTT | SEQ ID NO: 2381 | Homo sapiens leucine rich repeat containing 56 (LRRC56), mRNA [NM_198075] |
| 30 | A_23_P39067 | SPIB | CCTGTCCAAGGTTCCCTCTTGTCAGATCGTGAGATTCCTAGTATGTCTGGGGGCGTCTG | SEQ ID NO: 2382 | Homo sapiens Spi-B transcription factor (Spi-1/PU.1 related) (SPIB), mRNA [NM_003121] |
| 31 | A_23_P39356 | FFAR1 | GAGGGTTACTTGGAAGGGCGTCCTGGCGTGAAGACAGCTGTGCGGCAAGAACGGCAAGG | SEQ ID NO: 2383 | Homo sapiens free fatty acid receptor 1 (FFAR1), mRNA [NM_005303] |
| 32 | A_23_P398294 | HIP1R | GTTAGCATTTCCCTGAAGTCTTCTGTTGGCAATAAAATGCACTTTGACTGTTTGTTGT | SEQ ID NO: 2384 | Homo sapiens huntingtin interacting protein 1 related (HIP1R), mRNA [NM_003959] |
| 33 | A_23_P407601 | C8orf6 | GTGTTCCTAGGTTAGTGTGAGCAGAGATTCTATTCTGAGATAAGACT TCGGTGTCGGCTGAA | SEQ ID NO: 2385 | Homo sapiens mRNA for hypothetical protein (C8orf6 gene). [AJ307469] |
| 34 | A_23_P40989 | USP13 | TGAATGGAAGATAATGCCAATGCAAACATTATTCTGAGGGCAAGCCCGAAGGGCTAG | SEQ ID NO: 2386 | Homo sapiens ubiquitin specific peptidase 13 (isopeptidase T-3) (USP13), mRNA [NM_003940] |
| 35 | A_23_P420873 | NR1D1 | GGCTTGTACAGAATGGAACTCTGCACTGTCTCCTTAGGAGAGAGCCGAAAAGGAAAGCA | SEQ ID NO: 2387 | Homo sapiens nuclear receptor subfamily 1, group D, member 1 (NR1D1), mRNA [NM_021724] |
| 36 | A_23_P48585 | SALL2 | CTAGTAAATGTCAAGAACACGGAGATATTAGTGTCTTTCCCTGTATCATTAAAGGT | SEQ ID NO: 2388 | Homo sapiens sal-like 2 (Drosophila) (SALL2), mRNA [NM_005407] |
| 37 | A_23_P49643 | GRAP | CTCTGGCAGGGAAGGTTGAGGAGTCCCAGGTTTCAGCCACTGGAGGCTCAACCTAAGGAA | SEQ ID NO: 2389 | Homo sapiens GRB2-related adaptor protein (GRAP), mRNA [NM_006613] |

Fig. 7-3

| No. | Probe ID No. | Symbols of genes | Sequence | SEQ ID NO: | Descriptions of genes (letters and numbers within [ ] indicates GenBank accession No.) |
|---|---|---|---|---|---|
| 38 | A_23_P57236 | GGTL3 | CGAAGGAGGAACAAGTTCATCATCGCTGTTAAGGACGGTGGGAGC CCAGATGCAGCTGGA | SEQ ID NO: 2390 | Homo sapiens gamma-glutamyltransferase-like 3 (GGTL3), mRNA [NM_178026] |
| 39 | A_23_P63388 | EPPK1 | GTTTTTGGTGTGTTTTTCTGGTCGTCGTCTATGTCGTCATGGTTTT ACTTTCTCCCGGAA | SEQ ID NO: 2391 | Homo sapiens epiplakin 1 (EPPK1), mRNA [NM_031308] |
| 40 | A_23_P85269 | TTN | CTGACAACCCTGATCATCATGGACGTACAGAAACAACAGATGGTGGA GTTTATACCCTGAGT | SEQ ID NO: 2392 | Homo sapiens titin (TTN), transcript variant N2-A, mRNA [NM_133378] |
| 41 | A_23_P88222 | PLD4 | TGAAGTCTTCATCGTGCCAGTGGGGGAACCATTCCAACATCCAACAT TCAAGAGGGTGAACC | SEQ ID NO: 2393 | Homo sapiens phospholipase D family, member 4 (PLD4), mRNA [NM_138790] |
| 42 | A_24_P102512 | CABIN1 | CTCCTGTGGGTGATATTTCTGGGGAGATAAATCCAAGAAGGGG TAAAAGGAAGAAGA | SEQ ID NO: 2394 | Homo sapiens calcineurin binding protein 1 (CABIN1), mRNA [NM_012295] |
| 43 | A_24_P134816 | BCL9L | TGCTCCTACCCAGGAGAGGCTGGGTATCGGCCTTTGGTCAGAGGCTG AAGGCATATAGGACT | SEQ ID NO: 2395 | Homo sapiens B-cell CLL/lymphoma 9-like (BCL9L), mRNA [NM_182557] |
| 44 | A_24_P229164 | HIP1R | CCTGAGCCTCAACTGTTCAGAAAATAGTGTTTTAATATTCCTCT TCAGAAAATAGTGTT | SEQ ID NO: 2396 | Homo sapiens huntingtin interacting protein 1 related (HIP1R), mRNA [NM_003959] |
| 45 | A_24_P288360 | LTBP3 | CTGCTGTTGGGGAAGGCCGCAAGAATGAGACAGTCAGAGGAG GATTCAGAGAGTGT | SEQ ID NO: 2397 | Homo sapiens latent transforming growth factor beta binding protein 3 (LTBP3), mRNA [NM_021070] |
| 46 | A_24_P302506 | AMIGO1 | AATTGAGAATTGAATAATCAGCATATGTAAGGCACTAGAACCC TGTGTGAAAAGTGC | SEQ ID NO: 2398 | Amphoterin-induced protein 1 precursor (AMIGO-1) (Alivin-2). [Source:Uniprot/SWISSPROT;Acc:Q86WK6] [ENST00000369584] |
| 47 | A_24_P312325 | C8orf15 | CTTGTTCAAGTGAGTACTTTAGTTGCGTGTCCAATATGAAGTAG AAAGACAGATTTCTG | SEQ ID NO: 2399 | Homo sapiens chromosome 8 open reading frame 15 (C8orf15), mRNA [NM_001033662] |
| 48 | A_24_P324838 | IGHD | AGATGGTGCAGTTGGTTAGAGCTGAGGGTTATCCACAGAGAACC TGGGCGCTTGGTCAA | SEQ ID NO: 2400 | Homo sapiens mRNA for FLJ00382 protein. [AK094611] |
| 49 | A_24_P354715 | NT5E | TCTGCCTCCAAATCTGAACAGTCACTGTAAATCATTCTTAAGCCC AGATATGAGAAGTTC | SEQ ID NO: 2401 | Homo sapiens 5'-nucleotidase, ecto (CD73) (NT5E), mRNA [NM_002526] |
| 50 | A_24_P37020 | THC2690931 |  TGCTTCACGTCCAACTAAAAGGAATAAAGAGAGGGTTGAAGGTCAGCC ATGTTAGGTATGAGA | SEQ ID NO: 2402 | AF235005 suppression of tumorigenicity 16 protein [Homo sapiens] (exp=-1; wgp=0; cg=0), partial (13%) [THC2650931] |
| 51 | A_24_P385012 | BC030084 | TCGGGGGTTCACTGTGTGGGTGAAATAGTGTTTATCGTTTAGTACT AAATTAAAAGTTAG | SEQ ID NO: 2403 | Homo sapiens cDNA clone IMAGE:4791887. [BC030084] |
| 52 | A_24_P413126 | TMEPAI | AAGAAACTGCTGTTGTGTATCAGTAATCATTAGTGGCAATGATG ACAGTCTGAAAAGCT | SEQ ID NO: 2404 | Homo sapiens transmembrane, prostate androgen induced RNA (TMEPAI), transcript variant 1, mRNA [NM_020182] |
| 53 | A_24_P419028 | MOP-1 | ACCCCCCTCACTTTTTCAGAGCTATAGTTGTCCTTTTGATTCTC CAGTGAAAAGCTACAA | SEQ ID NO: 2405 | Homo sapiens mRNA for MOP-1, complete cds. [AB014711] |
| 54 | A_24_P525144 | A_24_P525144 | GCTGATGACAACTGTATTGGGCACCTTCCAACCTTC CTATCAAATATTCTT | SEQ ID NO: 2406 | |
| 55 | A_24_P62505 | GLT25D2 | ABCATTTAGACTAGGACTGTTCTAGTGTGAAGAAAGTTCTGTCT CCTTTAGCCGGGTTT | SEQ ID NO: 2407 | Homo sapiens glycosyltransferase 25 domain containing 2 (GLT25D2), mRNA [NM_015101] |
| 56 | A_24_P682177 | THC2686469 | GGGGACAGGTAGGATTCAATGCATGTTACATAACCATGGTCTAAA GGGACAGAATGTACA | SEQ ID NO: 2408 | |
| 57 | A_24_P8257 | BC009036 | GTGGGTACATGAGAAAGTAAGCCTCAAGACTCAGGTCGTGTGA TTTTTCTGAAGATTTT | SEQ ID NO: 2409 | Homo sapiens cDNA clone IMAGE:4155841, partial cds. [BC009036] |

Fig. 7-4

| No | Probe ID No. | Symbols of genes | Sequence | SEQ ID NO: | Descriptions of genes (letters and numbers within { } indicates GenBank accession No.) |
|---|---|---|---|---|---|
| 58 | A_24_P910490 | BX099367 | AGGCCCAGAGTTGGCAGAGACCACCTTGGGCTAGACAGTGACAGGCTGTCTGTAGAAAAACTA | SEQ ID NO: 2410 | BX099367 Soares_fetal_liver_spleen_1NFLS_S1 Homo sapiens cDNA clone IMAGp998O05977, mRNA sequence [BX099367] |
| 59 | A_24_P922809 | AF272377 | AAGAAAAAGCAGCCTCGACCACGAGAATCAGGTCTAGAGCGGAAGCTGGAGTGGTGGCGT | SEQ ID NO: 2411 | Homo sapiens clone 1370-48 MLL protein mRNA, partial cds [AF272377] |
| 60 | A_24_P924462 | PRKCZ | GGATGAGATGAAAGATGAATATTCTATCATTGAGGCATAGTCTTTCAACACACC | SEQ ID NO: 2412 | Homo sapiens mRNA, chromosome 1 specific transcript KIAA0505 [AB007974] |
| 61 | A_24_P930963 | LOC650392 | GCCCCATTTGAATGTAAGTATAACCAGGAGGGAAAATGGTGCTTGAAATAAGCATGGCACAAGG | SEQ ID NO: 2413 | Homo sapiens cDNA clone IMAGE:5264670. [BC036550] |
| 62 | A_24_P933492 | ZDHHC21 | GCGAGCCAGGGGGACGGAATGAAGAAGTTTTTCACTTACTGCAGGATTTTCAGCTTCAGG | SEQ ID NO: 2414 | Homo sapiens zinc finger, DHHC-type containing 21 (ZDHHC21), mRNA [NM_178566] |
| 63 | A_24_P940348 | FAM129C | AGACAAGCTTTTACGGACTTCGTCTCTGCCAGGAAGTCATCTGCTAACTGGATATTG | SEQ ID NO: 2415 | Homo sapiens family with sequence similarity 129, member C (FAM129C), mRNA [NM_173544] |
| 64 | A_24_P943263 | RASA4 | TCCTGGATAGTCATCTTTGTATATCTTGAAGTTTTCAAGAGATAAAAAAGCTTAAAAG | SEQ ID NO: 2416 | Homo sapiens RAS p21 protein activator 4 (RASA4), transcript variant 1, mRNA [NM_006989] |
| 65 | A_24_P945396 | SF3B3 | ATCCAGTTTTGTCGGATCCAATTGAGAAAACATTCATGAACAACTACTTGTGGGATGCAT | SEQ ID NO: 2417 | Homo sapiens cDNA clone KIAA0017 mRNA, complete cds. [D13642] |
| 66 | A_32_P111394 | THC2643957 | GAATACAGTGTTCGTTTTTCATCCCATATTTGACTGAACCTAAGACACTTGTGGAATAAGG | SEQ ID NO: 2418 |  |
| 67 | A_32_P125589 | THC2649341 | CGGCTATCCCTTGGTTTAGCGTTTGAATGAAAGTGAGATGTGTCATCAGCTCAGATAG | SEQ ID NO: 2419 |  |
| 68 | A_32_P131294 | BM854107 | AGTAGGGAAAAGGTTTGTTCGTTAATTAGAGGTAGTCTGGGAAATGCTAGCACTTGTGG | SEQ ID NO: 2420 | K-ES-013640S S22SNU16n1 Homo sapiens cDNA clone S22SNU16n1-145-F11 5', mRNA sequence [BMC54107] |
| 69 | A_32_P133767 | C12orf42 | AAGGGCTCAGATGACTGGTTCCACAGAACCAATGCCATATAAATGTTGTGAAGGATTTTT | SEQ ID NO: 2421 | Homo sapiens chromosome 12 open reading frame 42 (C12orf42), mRNA [NM_198521] |
| 70 | A_32_P145764 | BC043547 | GGTCCCCGTGCCTCTCTGTAACCAATAACGAATCCAATATAAATGGAAAAGTATAAAGAA | SEQ ID NO: 2422 | Homo sapiens, clone IMAGE:5171873, mRNA [BC043547] |
| 71 | A_32_P146659 | LOC401431 | AGGTCTGATGCAGTAGCTTTACTATTGGTGGAAATCGATGTTTTCCTTGAAAGTGTA | SEQ ID NO: 2423 | Homo sapiens hypothetical gene LOC401431 (LOC401431), mRNA [NM_001008745] |
| 72 | A_32_P146844 | THC2639689 | CCTGTGTGGGCTGATTCCAGAGTGAGAGTGAAGTTTGTGTGCATCATCATGTGGCATTAA | SEQ ID NO: 2424 |  |
| 73 | A_32_P15829 | AW389914 | TGATGTCGAAGTTCTGAGGTGTGAGGTGTAAGTCCAGAGAGCCAGACACTACA | SEQ ID NO: 2425 | AW389914 RC4-ST0173-191099-032-f06 ST0173 Homo sapiens cDNA, mRNA sequence [AW389914] |
| 74 | A_32_P164378 | THC2703271 | GAAAGAACATGAAAGGCATTGGAATTGAAGGAAAAGCCACCTGGTTTAGAGTTTAATTTTG | SEQ ID NO: 2426 |  |
| 75 | A_32_P164573 | THC2611661 | AGCTGTTTCTATTAAGACTGAAGTAGTCGTAGAGCTTGGAAATTTGAAGTGCAAAATC | SEQ ID NO: 2427 | RR12_SPINX (P42344) Chloroplast 30S ribosomal protein S12, partial (11%) [THC2611661] |
| 76 | A_32_P169222 | THC2673977 | GATAGGGTCTGAGGGAGGAGAGAGAAAAAGCAGCATAGTCGGAATTTAGTTTCTCAAAAACGATAG | SEQ ID NO: 2428 | ALU1_HUMAN (P39188) Alu subfamily J sequence contamination warning entry, partial (14%) [THC2673977] |
| 77 | A_32_P170397 | ENST00000309874 | CTGTTTGGCAGGAGAGTGATTGCAGCCGGTGGTGAAATGAGAAGCGTGTGGGGTGGGAACAA | SEQ ID NO: 2429 | Homo sapiens cDNA FLJ33063 fis, clone TRACH2000047. [AK057625] |

Fig. 7-5

| No. | Probe ID No. | Symbols of genes | Sequence | SEQ ID NO: | Descriptions of genes, letters and numbers within [ ] indicates GenBank accession No.) |
|---|---|---|---|---|---|
| 78 | A_32_P179998 | DMRTC1 | ATATGGCAGAGTTTTATTCGTCTGTGATTGCTGACATACCTGTGCACTCATGTGTATA | SEQ ID NO: 2430 | Homo sapiens DMRT-like family C1 (DMRTC1), mRNA [NM_033053] |
| 79 | A_32_P184039 | A_32_P184039 | ATCATTGTTAGTCTTGGCCCAAAAATAGTTGTTATGTATCATGCGTAATAACTGACCAGC | SEQ ID NO: 2431 | |
| 80 | A_32_P190682 | THC2739159 | TCAATAGGTTTTTATTTGCTCCGGTTTACCTAGATGAAAAATGAAGACCCAGAATGCATGC | SEQ ID NO: 2432 | ALU6_HUMAN (P39195) Alu subfamily SX sequence contamination warning entry, partial (8%) [THC2739159] |
| 81 | A_32_P196287 | THC2652456 | CGTTTCACAAAGACTGTAAGACGTCCTTTAGGGAAGCATTAATTTTGGTGCATAGGCGGCTGTT | SEQ ID NO: 2433 | Q9BHM3_PARTE (Q9BHM3) Cyclophilin-RNA interacting protein, partial (4%) [THC2652456] |
| 82 | A_32_P209382 | THC2663167 | CAATGTAAAGGGAGAATATCAACGTCCTTTGTCAAGATTTCAAAGGTATTTGGCTGAT | SEQ ID NO: 2434 | ALU1_HUMAN (P39138) Alu subfamily J sequence contamination warning entry, partial (5%) [THC2663167] |
| 83 | A_32_P22254 | COL6A1 | ATAGTGATGTGTTCGACGTTTATCAAAGGCGCCCCTTCTATGTTCATGTTAGTTTTGCT | SEQ ID NO: 2435 | Homo sapiens collagen, type VI, alpha 1 (COL6A1), mRNA [NM_001848] |
| 84 | A_32_P3342 | THC2676548 | TATAGCATTTTCTGAAGATCATGTTGTACTCTCTTCGTCTTCTAGATGATTTGGTCAACAG | SEQ ID NO: 2436 | ALU7_HUMAN (P39194) Alu subfamily SQ sequence contamination warning entry, partial (19%) [THC2676548] |
| 85 | A_32_P356316 | HLA-DOA | TGGAAAGRTGTTGTTGCATCTCGTCCTAAGGTTGCATAAAGTCATTAAAATGTGTTC | SEQ ID NO: 2437 | Homo sapiens major histocompatibility complex, class II, DO alpha (HLA-DOA), mRNA [NM_002119] |
| 86 | A_32_P40673 | A_32_P40673 | CATCAGACATTGATATTAGGACAGCCTACCTACTTGTTTGAGTGTCACAGCCTCATATGTA | SEQ ID NO: 2438 | |
| 87 | A_32_P62371 | THC2674900 | GTCTTGCCTGAAGTATTTCTCGAGTCTTAGGAAAACAGTGAACTGACTCATCTGTC | SEQ ID NO: 2439 | |
| 88 | A_32_P71171 | A_32_P71171 | TCTAGATAGTAATAGGAAAACCAAGAATCCAGCCTGGTGATGGGTGGAGGGAGTGATTGAA | SEQ ID NO: 2440 | |
| 89 | A_32_P79103 | BM932034 | GTTGCTACGAATGAAAATAGGACATTTTAGGAAGGTTGAGTCAGGTGCCGAGTGGGGAGCTATGGGGCATA | SEQ ID NO: 2441 | U1-E-EJ1-ajl-k-24-0-U1 r1 U1-E-EJ1-ajl-k-24-0-U1 5', Homo sapiens cDNA clone U1-E-EJ1-ajl-k-24-0-U1 5', mRNA sequence [BM932034] |
| 90 | A_32_P93468 | LRFN2 | ATGGCGGACTGAGCGCCTGAGTGTTTGGAAAAGGGAGAGCTCCGGCGCTCTAATCACAAATG | SEQ ID NO: 2442 | Homo sapiens leucine rich repeat and fibronectin type III domain containing 2 (LRFN2), mRNA [NM_020737] |
| 91 | A_32_P88987 | AK022346 | ATGGGAAGTTACTACCGAGGCTTACCAAGAGGTCAGGTTTATATAAGTGGCGTTCCTTT | SEQ ID NO: 2443 | Homo sapiens cDNA FLJ12284 fis, clone MAMMA1001757. [AK022346] |
| 92 | A_32_P90346 | THC2662291 | TACAGGGATTAGATGGAGGCCAGATACCCAGATTATGGCTAGAATGGTCTGTCAGGAACA | SEQ ID NO: 2444 | |
| 93 | A_32_P90468 | A_32_P90468 | AAGCCAGGAATAATTTTCTATCTCATGCTAGCTAAGTGGTGGAAGTTATCATGAGACCCT | SEQ ID NO: 2445 | |
| 94 | A_32_P91328 | THC2641595 | GTTAGCGCAATAATGTCATTGAAGTCTTAAGTCTAGGCTGAGCCAAGGCAGGGTTCA | SEQ ID NO: 2446 | |
| 95 | A_32_P91743 | THC2724906 | TTCAAAGGATTCTGGAAGGGGTCAGTGATTCTGAAAGATTAAGAGCCACTAATTTAAGCC | SEQ ID NO: 2447 | Q96HL9_HUMAN (Q96HL9) CHP protein, partial (39%) [THC2724906] |
| 96 | A_32_P98940 | THC2745659 | AAGAGTATTCCCAAGATAGCAAAGGTGTGTTGTTTTTAGCAGGTGTATTTCAGGTAGTTA | SEQ ID NO: 2448 | |

Fig. 7-6

| No. | Probe ID No. | Symbols of genes | Sequence | SEQ ID NO. | Descriptions of genes (letters and numbers within [ ] indicates GenBank accession No.) |
|---|---|---|---|---|---|
| 97 | A_23_P102060 | SSFA2 | GTATCATCCAAATAATGGGGCCTATGACTTGAATGAATAGAAATGAATAAGTGGTGTT | SEQ ID NO: 2449 | Homo sapiens sperm specific antigen 2 (SSFA2), mRNA [NM_006751] |
| 98 | A_23_P102160 | FAM82A | GGGTATTGTGCTTAGATTTGAAGGTAAAGCCATGTTGTGCAAGAATGCATTCCAGTAGTA | SEQ ID NO: 2450 | Homo sapiens unknown mRNA. [AF435956] |
| 99 | A_23_P102235 | SNRPG | ACAACAGAACAATATTGGAATGGTGGTAATACGAGGAAATAGTATCATCATGTTAGAAGG | SEQ ID NO: 2451 | Homo sapiens small nuclear ribonucleoprotein polypeptide G (SNRPG), mRNA [NM_003096] |
| 100 | A_23_P102391 | SLC40A1 | CTCATGTGTTATCATCATTAGTAGTCTGTGTTAGAAGATGAGGGTGTAAGGTTCAGGGT | SEQ ID NO: 2452 | Homo sapiens solute carrier family 40 (iron-regulated transporter), member 1 (SLC40A1), mRNA [NM_014585] |
| 101 | A_23_P104054 | C1orf9 | TAAATTCTTCGTGTCTGGACAATTAGCTATTCAGAGAGAAGAGGCCCTCATTTTATAGA | SEQ ID NO: 2453 | Homo sapiens chromosome 1 open reading frame 9 (C1orf9), transcript variant 2, mRNA [NM_016227] |
| 102 | A_23_P104471 | DUSP13 | GATTTGGGTGAGGGAATTCAGAGATTCTTTATGCAAAAGTGAGTTCAGTCCATCTCTATA | SEQ ID NO: 2454 | Homo sapiens dual specificity phosphatase 13 (DUSP13), transcript variant 1, mRNA [NM_001007271] |
| 103 | A_23_P107847 | LILRA5 | CCAGTGACCTCCTGGAGATTCCGGTCTCAGGAGCAGCTGATAACGTCAGTGGGTCAGAAA | SEQ ID NO: 2455 | Homo sapiens leukocyte immunoglobulin-like receptor, subfamily A (with TM domain), member 5 (LILRA5), transcript variant 2, mRNA [NM_181985] |
| 104 | A_23_P108394 | THC2783023 | ATTCAGAAAGTTGCTTGTGTGATAGATAAGTCTCTCATTTATTACTGCTCTGCTG | SEQ ID NO: 2456 | Q81UM9_HUMAN (Q81UM9) ACSL3 protein, complete [THC2467888] |
| 105 | A_23_P110362 | MAP2K1IP1 | ACTGAGACAAGTTGTGGAAGTTCTTAATCTGACAGTGGTTCAGTGTGTACCTTATCTT | SEQ ID NO: 2457 | Homo sapiens mitogen-activated protein kinase 1 interacting protein 1 (MAP2K1IP1), mRNA [NM_021970] |
| 106 | A_23_P110611 | ZH2C2 | CTCTTGAAAAGCAGAGCTTCAGTCTGTTGGACTGTCTTCAAACAGAGGTTCTTGAATACTTAA | SEQ ID NO: 2458 | Homo sapiens zinc finger, H2C2 domain containing (ZH2C2), mRNA [NM_017676] |
| 107 | A_23_P111321 | ARG1 | TGGAATCAGGAGACAAAGCTACCACATGTGGAAAGTAGTATGTGTCCATGTCATTGAAA | SEQ ID NO: 2459 | Homo sapiens arginase, liver (ARG1), mRNA [NM_000045] |
| 108 | A_23_P111583 | CD36 | GTTTGGCTTAATGAGACTGGGACCCATTGGTGATGAGAAGCAAAAATGTTCAGAAGTGAA | SEQ ID NO: 2460 | Homo sapiens CD36 molecule (thrombospondin receptor) (CD36), transcript variant 2, mRNA [NM_001001547] |
| 109 | A_23_P11201 | GPR34 | AGTAGGAGTGAAAGAGCAGTTCAGAATTTAAACCAGGATAGTCCCTGCATGATACATCTGTG | SEQ ID NO: 2461 | Homo sapiens G protein-coupled receptor 34 (GPR34), transcript variant 1, mRNA [NM_005300] |
| 110 | A_23_P112251 | LOC552891 | AGAATTCTTAAGTTCAGAAGTGTTTTAGTTGGACGATGCCTTTGATTTAATTTGGGAC | SEQ ID NO: 2462 | Homo sapiens hypothetical protein LOC552891 (LOC552891), mRNA [NM_001125] |
| 111 | A_23_P113972 | EXOC1 | CGTGGCAGGGCATTAAGGAGGAGGAAGTAAGTTACCAACTTGCATTTAACAAACAAGA | SEQ ID NO: 2463 | Homo sapiens exocyst complex component 1 (EXOC1), transcript variant 1, mRNA [NM_018261] |
| 112 | A_23_P114947 | RGS2 | TAGATCTGGGATTATGTGGGGTTAGGTAGGTGGTTGTACATCTTCCCTAAATCGATCCA | SEQ ID NO: 2464 | Homo sapiens regulator of G-protein signalling 2, 24kDa (RGS2), mRNA [NM_002923] |
| 113 | A_23_P11685 | PLA2G4A | GAAATGGCAGGAGTTGTGATGCTGAAGGCAGTTTGCAATCCCATGACAACTGGATTTAAA | SEQ ID NO: 2465 | Homo sapiens phospholipase A2, group IVA (cytosolic, calcium-dependent) (PLA2G4A), mRNA [NM_024420] |
| 114 | A_23_P118061 | CKLF | GGCACAAGCCCTGAACCATATATTGTTATTGGATTTGAAGTGACGGTTATGTTATTT | SEQ ID NO: 2466 | Homo sapiens chemokine-like factor (CKLF), transcript variant 4, mRNA [NM_181641] |

Fig. 7-7

| No. | Probe ID No. | Symbols of genes | Sequence | SEQ ID NO. | Descriptions of genes (letters and numbers within [ ] indicates GenBank accession No.) |
|---|---|---|---|---|---|
| 115 | A_23_P118246 | GINS2 | TGTGTGATGGTGCAAGGAATGGATTCAGGATGTTGTTGGAGAAAC AAGTTTGTGATTAGT | SEQ ID NO: 2467 | Homo sapiens GINS complex subunit 2 (Psf2 homolog) (GINS2), mRNA [NM_016095] |
| 116 | A_23_P118516 | FAM18B | TATTCGTGTAGATTGTTTTCACGGAGAAGTTTCTCTATCGTA AGAGTGAGCACTTTG | SEQ ID NO: 2468 | Homo sapiens family with sequence similarity 18, member B (FAM18B), mRNA [NM_016078] |
| 117 | A_23_P119222 | RETN | CAATAACAACAGATTGGCCTGGAGTGGCCAAGAGCGTCACCTCCAGGA GGGACCTGGGTACTT | SEQ ID NO: 2469 | Homo sapiens resistin (RETN), mRNA [NM_020415] |
| 118 | A_23_P120048 | BAZ2B | TATTTTGGTCTGAAGGTAATGATAAGGTATACAGTCGTACAGATAA TTATCCTACGAAG | SEQ ID NO: 2470 | Homo sapiens bromodomain adjacent to zinc finger domain, 2B (BAZ2B), mRNA [NM_013450] |
| 119 | A_23_P120316 | MTHFD2 | AGGGATTATTCCTTGCTATTAGTAGTAGTCATTTTATGTAGTTAGGCT TCAGTAAGTTCTGTGGG | SEQ ID NO: 2471 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 120 | A_23_P120345 | PELI1 | CTTCCACAGCGTTTTTCAAAGGGACAGGAGGAGTATAGACAAGTTGGA CTACATGAAATCTT | SEQ ID NO: 2472 | Homo sapiens pellino homolog 1 (Drosophila) (PELI1), mRNA [NM_020651] |
| 121 | A_23_P121253 | TNFSF10 | GGAACAATCGATCTCTGAAGTAGTGTATGACAGAGTAGTAGGCTCCA GGGTTCGTTAAGGGA | SEQ ID NO: 2473 | Homo sapiens tumor necrosis factor (ligand) superfamily, member 10 (TNFSF10), mRNA [NM_003810] |
| 122 | A_23_P121622 | SULT1B1 | GAAATAGAGATGTCTGTAGTTGATTGAAACGAGGCAGTTATGA ATTGATTGGGCAAT | SEQ ID NO: 2474 | Homo sapiens mRNA for ST1B2, complete cds. [D89479] |
| 123 | A_23_P121716 | ANXA3 | TGGACATTGGAACAGAGTTCAAGAAGCAGTTATGGCTATTCCGTAT ATTCAGCAATTAAAT | SEQ ID NO: 2475 | Homo sapiens annexin A3 (ANXA3), mRNA [NM_005139] |
| 124 | A_23_P121825 | FLJ13611 | CATGTTACTGTTACAAAGTTCTCTCCATGTAATCACACT TAGTATGAGCAAAG | SEQ ID NO: 2476 | Homo sapiens hypothetical protein FLJ13611 (FLJ13611), mRNA [NM_024941] |
| 125 | A_23_P122007 | C5orf30 | ATCAGATTTCTCGTTGGGCTGGAAATGTTTCGGTGTTGTATATTT TAAAGTAAATTGCAC | SEQ ID NO: 2477 | Homo sapiens chromosome 5 open reading frame 30 (C5orf30), mRNA [NM_033211] |
| 126 | A_23_P122174 | XRCC4 | AAAACCAAAACTGATCTGTCTGTGGGTTGGGCTTGAGCTGCTGTAAGTAA ACATGATTCCATTAT | SEQ ID NO: 2478 | Homo sapiens X-ray repair complementing defective repair in Chinese hamster cells 4 (XRCC4), transcript variant 3, mRNA [NM_022550] |
| 127 | A_23_P122724 | VNN2 | AAAGAGCCTGGGTGTTTGGGTCAGATAAAATGAAGATCAAACTCCA GCTCCAGGGTCATTT | SEQ ID NO: 2479 | Homo sapiens vanin 2 (VNN2), transcript variant 1, mRNA [NM_004665] |
| 128 | A_23_P123608 | JAK2 | GGATAACAATGGCTGGATGAAAAGAGAATGAGCTTGATTGTGAGACCA AAGTAGATTTACAGA | SEQ ID NO: 2480 | Homo sapiens Janus kinase 2 (a protein tyrosine kinase) (JAK2), mRNA [NM_004972] |
| 129 | A_23_P123727 | ZCCHC6 | TTGAAGAGGGGAAATTATACTTATTGTTTACTGAATCGTGGT GTGAAAGGATATCAG | SEQ ID NO: 2481 | Homo sapiens zinc finger, CCHC domain containing 6 (ZCCHC6), mRNA [NM_024617] |
| 130 | A_23_P128384 | VPS29 | CAGGTAATTGGAGATGATGATGTGAAAGTAGAACGAATCGAATACAAA AAACGTTAAAGCCAG | SEQ ID NO: 2482 | Homo sapiens vacuolar protein sorting 29 homolog (S. cerevisiae) (VPS29), transcript variant 2, mRNA [NM_057180] |
| 131 | A_23_P128447 | LRRK2 | GCGAGAAAGAGATAGAATGTTCCTTGACCGTTTGGGAGATCAATCT TCCAGATGAAGTGCA | SEQ ID NO: 2483 | Homo sapiens leucine-rich repeat kinase 2 (LRRK2), mRNA [NM_198578] |
| 132 | A_23_P128930 | PSMC6 | GAACAAGCAAGATTAGACATACTGAAAATCCATGCAGGTGCCATT ACAAAGCATGGTGAA | SEQ ID NO: 2484 | Homo sapiens proteasome (prosome, macropain) 26S subunit, ATPase, 6 (PSMC6), mRNA [NM_002806] |

Fig. 7-8

| No. | Probe ID No. | Symbols of genes | Sequence | SEQ ID NO: | Descriptions of genes (letters and numbers within [ ] indicates GenBank accession No.) |
|---|---|---|---|---|---|
| 133 | A_23_P128940 | C14orf138 | TTGGTATTGAGGGGGAGGCTGAAATCTGTGAAAAACAGGGAAGATGATTTGACTGGACCTT | SEQ ID NO: 2485 | Homo sapiens chromosome 14 open reading frame 138 (C14orf138), transcript variant 1, mRNA [NM_024558] |
| 134 | A_23_P129935 | TMEM49 | CACAGGGACAGAAAAACTGGTTGTCCTGCATGTTTGAAAAGTTGGTCGTTGTCATGGTGTGTT | SEQ ID NO: 2486 | Homo sapiens transmembrane protein 49 (TMEM49), mRNA [NM_030938] |
| 135 | A_23_P132910 | FLJ20273 | CACGGGATTTTTTGATGGCTGAATTGTTGTGGATTCATAAGAGGATCATGGGCTTAGC | SEQ ID NO: 2487 | Homo sapiens RNA-binding protein (FLJ20273), mRNA [NM_019027] |
| 136 | A_23_P133470 | PJA2 | GTTGTTGTTTTTAGTAGTCTGATCAGTTGTGACACTTACTGGTTAAACTTACGTTG | SEQ ID NO: 2488 | Homo sapiens praja 2, RING-H2 motif containing (PJA2), mRNA [NM_014819] |
| 137 | A_23_P133648 | FAM8A1 | ACTTCGGCGGGAATTACAAAATGAGTGTTTTTAGATTCAAGTGACGGTAAAGGATTGTT | SEQ ID NO: 2489 | Homo sapiens family with sequence similarity 8, member A1 (FAM8A1), mRNA [NM_016255] |
| 138 | A_23_P133691 | RRAGD | GCTGTGATATGATAGATGTGGTTATTGACATCTCTGTATTTATGGTCAAAGAAGA | SEQ ID NO: 2490 | Homo sapiens Ras-related GTP binding D (RRAGD), mRNA [NM_021244] |
| 139 | A_23_P134786 | PHF20L1 | AGTTGTATGTGCCGCCAGTGCTACATAGGCAGGTATGGGTAAGTCTGTATGTTGTTTTA | SEQ ID NO: 2491 | Homo sapiens PHD finger protein 20-like 1 (PHF20L1), transcript variant 1, mRNA [NM_016018] |
| 140 | A_23_P134910 | GGH | GGAGGTGAATTGCACAGGAGAAGTTCCAGAATTTCCTACTGAGTTGTTGCTGTCATTA | SEQ ID NO: 2492 | Homo sapiens gamma-glutamyl hydrolase (conjugase, folylpolygammaglutamyl hydrolase) (GGH), mRNA [NM_003878] |
| 141 | A_23_P135494 | CLIC4 | CTCCTCAAGCGGTAATGTTGAACAGAATGGAGTATATTTCTTTATAATTCTTCAACAGG | SEQ ID NO: 2493 | Homo sapiens chloride intracellular channel 4 (CLIC4), mRNA [NM_013943] |
| 142 | A_23_P135499 | CLIC4 | CTTCCCTTTTTGCTGTATGAGATGGAGATTCTATAGAGTCTGTTGTGTTTTTACTAGGAG | SEQ ID NO: 2494 | Homo sapiens chloride intracellular channel 4 (CLIC4), mRNA [NM_013943] |
| 143 | A_23_P136964 | RPGR | GAGCAGAACCACAGATGAGTCAGAATCATGAGAAAAGTCCAGAGAACAAATAGAGAAGAAGA | SEQ ID NO: 2495 | Homo sapiens retinitis pigmentosa GTPase regulator (RPGR), transcript variant A, mRNA [NM_000328] |
| 144 | A_23_P13701 | TMBIM4 | TGCACATGGAATGGCCCTTTGTGAGAAAGTCTAGAGCATTCTTCTCTGCAGGTCTCT | SEQ ID NO: 2496 | Homo sapiens transmembrane BAX inhibitor motif containing 4 (TMBIM4), mRNA [NM_016056] |
| 145 | A_23_P137016 | SAT1 | GAAATAATAGAATGAGCACACCCATTCGAAAGGTTTATTACCAGTGGCGTTGTTGGAATGTTT | SEQ ID NO: 2497 | Homo sapiens spermidine/spermine N1-acetyltransferase 1 (SAT1), mRNA [NM_002970] |
| 146 | A_23_P138262 | PADI4 | AAGAGACATTCTGTCAAACAAGACATTGAGAGAACATAATTGATTTGTGGGAGAGTGGATC | SEQ ID NO: 2498 | Homo sapiens peptidyl arginine deiminase, type IV (PADI4), mRNA [NM_012387] |
| 147 | A_23_P138308 | CD58 | AACCTGTATGTCGAAGCAGCAGGGGTGATTCAAGACAGATATGGACTTATACCATACCATT | SEQ ID NO: 2499 | Homo sapiens CD58 molecule (CD58), mRNA [NM_001779] |
| 148 | A_23_P140069 | FBXL3 | TAACCCCAGTGGAATACATTAATTCTTAAAGCGGGTCTTTCAGTAGTGTGACTTTTAGA | SEQ ID NO: 2500 | Homo sapiens F-box and leucine-rich repeat protein 3 (FBXL3), mRNA [NM_012158] |
| 149 | A_23_P14105 | RCBTB2 | TGACTTTCATGTCACTCACTATAAAAATAGGTCTCTTAACCTGGCACCAGTATAAGTATAA | SEQ ID NO: 2501 | Homo sapiens regulator of chromosome condensation (RCC1) and BTB (POZ) domain containing protein 2 (RCBTB2), mRNA [NM_001268] |
| 150 | A_23_P143858 | RPL22L1 | ATTGGCTTGGAGTGGTTGGACATGCGACAAGGAGACCTAGAAGTTCGTTACTTCCAGATTA | SEQ ID NO: 2502 | Homo sapiens ribosomal protein L22-like 1, mRNA (cDNA clone IMAGE:4865966) [BC049823] |
| 151 | A_23_P144145 | DCUN1D1 | TGTTTAGTGAATACATCTGCATATGTGTGAAGTTCAATTGTGTTTCTTACAGTCCCTG | SEQ ID NO: 2503 | Homo sapiens RP42 protein mRNA, complete cds. [AF292100] |

Fig. 7-9

| No. | Probe ID No. | Symbols of genes | Sequence | SEQ ID NO. | Descriptions of genes (letters and numbers within [ ] indicates GenBank accession No.) |
|---|---|---|---|---|---|
| 152 | A_23_P144384 | GALNT7 | TACTGTAGGTGCTTGCTTGGAAATAATTCCGATATCCTTGCTTTGTAAGTTGGTAATATGAG | SEQ ID NO: 2504 | Homo sapiens UDP-N-acetyl-alpha-D-galactosamine:polypeptide N-acetylgalactosaminyltransferase 7 (GalNAc-T7) (GALNT7), mRNA [NM_017423] |
| 153 | A_23_P144684 | ANKRD32 | AAACTTGTAGAAAACTCTAGTATGGGTGTGACTTTTGGAGGGTGTAGAATTTGACTC | SEQ ID NO: 2505 | Homo sapiens ankyrin repeat domain 32 (ANKRD32), mRNA [NM_032290] |
| 154 | A_23_P14564 | GPR65 | AAGAAGTTTAAATTGTGTGGTGATCGAATTCTGTACTGTTTGTAACCGAAAGAGGAAG | SEQ ID NO: 2506 | Homo sapiens G protein-coupled receptor 65 (GPR65), mRNA [NM_003608] |
| 155 | A_23_P14708 | SUHW4 | TCTTGTAGCTCCATACAAGTTAGCCTGGCAGGCTGTAAGTTAGCTTAATTAAACTT | SEQ ID NO: 2507 | Homo sapiens suppressor of hairy wing homolog 4 (Drosophila) (SUHW4), transcript variant 1, mRNA [NM_017661] |
| 156 | A_23_P14734 | RPS27L | TACAAGATACACCACGGTTTTCAGCCATGCTCAGACAGTGGTTGTTTGTGTAGGTTGTTCA | SEQ ID NO: 2508 | Homo sapiens ribosomal protein S27-like (RPS27L), mRNA [NM_015920] |
| 157 | A_23_P148584 | DOCK11 | TGCACCACTGTGTTGTTTGGTTTTGTACTTTTTAGGTAAATGATATGCTGAAAAGTAGAGC | SEQ ID NO: 2509 | Homo sapiens dedicator of cytokinesis 11 (DOCK11), mRNA [NM_144658] |
| 158 | A_23_P149775 | ARHGAP12 | TGTATAATAAAACAGAGAGGTTTGGAAGGTTTTGTTACAGGGAGGATGGTCGTGTGAAGAT | SEQ ID NO: 2510 | Homo sapiens Rho GTPase activating protein 12 (ARHGAP12), mRNA [NM_018287] |
| 159 | A_23_P149892 | GALNACT-2 | CATGGTGGTTCAGAATAGATGAGCATAGAACGAATGAACATTTGTGTTGTTTGTTCAATTTTC | SEQ ID NO: 2511 | Homo sapiens chondroitin sulfate GalNAcT-2 (GALNACT-2), mRNA [NM_018590] |
| 160 | A_23_P150129 | SAPS3 | TACCTGTTAACAAGCATCACCAATGAACATTTTGAGAGGAATCTGCATATTTTAACAGAG | SEQ ID NO: 2512 | Homo sapiens SAPS domain family, member 3 (SAPS3), mRNA [NM_018312] |
| 161 | A_23_P151018 | LEMD3 | GCAGATCTTGTAAGCGTTGTTGGCAAGAGTGGTGAAGTAAAAATAGTTTGGCATTTTAAAAGG | SEQ ID NO: 2513 | Homo sapiens LEM domain containing 3 (LEMD3), mRNA [NM_014319] |
| 162 | A_23_P151637 | RNASE2 | GTGGTAACCCAAATATGACCTGTCCTAGTAACAAAACTCGCAAAAATTGTCACCACAGTG | SEQ ID NO: 2514 | Homo sapiens ribonuclease, RNase A family, 2 (liver, eosinophil-derived neurotoxin) (RNASE2), mRNA [NM_002934] |
| 163 | A_23_P152002 | BCL2A1 | AGGAGCAGCAAATTGCATTTGAAGGTATTGTCATCAAGAAAGTTCTAGGAGCAGCAAATTGG | SEQ ID NO: 2515 | Homo sapiens BCL2-related protein A1 (BCL2A1), mRNA [NM_004049] |
| 164 | A_23_P154235 | NMI | CCATGTTTCTGAATCTCTTCTTTTGTTTGAAATGGTGCTGCATGTTTGAACTACATAAGTG | SEQ ID NO: 2516 | Homo sapiens N-myc (and STAT) interactor (NMI), mRNA [NM_004688] |
| 165 | A_23_P154330 | TXNDC9 | CTCAGTGTCTTAATTATCTGGGAAGGGTGTGGATTCTGTATTTTGAGATTGACTTTATC | SEQ ID NO: 2517 | Homo sapiens thioredoxin domain containing 9 (TXNDC9), mRNA [NM_005783] |
| 166 | A_23_P154367 | STK17B | TACCCAATGGCATGGAATGCTTGCTCTGTTAGGACTTTTTCTTTAGACTCA | SEQ ID NO: 2518 | Homo sapiens serine/threonine kinase 17b (STK17B), mRNA [NM_004226] |
| 167 | A_23_P155765 | HMGB2 | AAAAAATGCAGGTTGTAGCTTGTATGGGCTAGTGACATACAGATTAGAATTTACAAGGTTC | SEQ ID NO: 2519 | Homo sapiens high-mobility group box 2 (HMGB2), mRNA [NM_002129] |
| 168 | A_23_P155815 | NCAPG | AAGTTAGGAAGACGAATGGAAGTGGAATCGTTTAAGAATTAAGTTAATATGCCAGTTATTTGCTTAA | SEQ ID NO: 2520 | Homo sapiens non-SMC condensin I complex, subunit G (NCAPG), mRNA [NM_022346] |
| 169 | A_23_P156609 | A_23_P156609 | TTCACGTGTTTAGTAGGTCGGGTTTAGAATACGAGGGTCAGTGACGCCCTTCAT | SEQ ID NO: 2521 |  |
| 170 | A_23_P156842 | EEF1E1 | AAGAAAAGCAATGTTCAGCAGTGGTTAGAATACAGAGGGTCAGTGAAGTAGATGGCCACT | SEQ ID NO: 2522 | Homo sapiens eukaryotic translation elongation factor 1 epsilon 1 (EEF1E1), mRNA [NM_004280] |

Fig. 7-10

| No. | Probe ID No. | Symbols of genes | Sequence | SEQ ID NO: | Descriptions of genes (letters and numbers within [ ] indicates GenBank accession No.) |
|---|---|---|---|---|---|
| 171 | A_23_P157449 | POLR2K | GGTGTCTTGTTCAAATATGTTCTGTACAGTACTCACCATTTAGATGGTTGAC | SEQ ID NO: 2523 | Homo sapiens polymerase (RNA) II (DNA directed) polypeptide K, 7.0kDa (POLR2K), mRNA [NM_005034] |
| 172 | A_23_P157452 | POLR2K | GGAATGTTCACTTATAGTTGGATTTGGTGCTGTTCCCATTTGTGATTGTGTATAGGTT | SEQ ID NO: 2524 | Homo sapiens polymerase (RNA) II (DNA directed) polypeptide K, 7.0kDa (POLR2K), mRNA [NM_005034] |
| 173 | A_23_P159850 | COX7B | CAAATACGGTAATGCTGTATTAGCTAGTAGTGGAGCCACTTTCTGTATTGTTACATGGACATA | SEQ ID NO: 2525 | Homo sapiens cytochrome c oxidase subunit VIIb (COX7B), nuclear gene encoding mitochondrial protein, mRNA [NM_001866] |
| 174 | A_23_P159839 | C1GALT1C1 | TGCAAATCAGATGCATGTGATGATGTATGGGGTATACCGCCTTAGGGCATTTGGGCATAT | SEQ ID NO: 2526 | Homo sapiens C1GALT1-specific chaperone 1 (C1GALT1C1), transcript variant 1, mRNA [NM_152692] |
| 175 | A_23_P160406 | KCTD3 | TTGTAGGACTGCAGTTCTGAATTTTGGGTAAAGGTTTTGCCTGCTGTAAGAAATGTGAAT | SEQ ID NO: 2527 | Homo sapiens potassium channel tetramerisation domain containing 3 (KCTD3), mRNA [NM_016121] |
| 176 | A_23_P160466 | SLC19A2 | CTTGGTATGTGGGCATATTTATAGAATGCTGAACTCAATGTGGAAGTTGTAGTGTATGCA | SEQ ID NO: 2528 | Homo sapiens solute carrier family 19 (thiamine transporter), member 2 (SLC19A2), mRNA [NM_006996] |
| 177 | A_23_P162300 | IRAK3 | TTGTGTGATGACCAAATCACGGCTGAATTAGAGACGATTCAAAATTCCTTAAGATCATGGG | SEQ ID NO: 2529 | Homo sapiens interleukin-1 receptor-associated kinase 3 (IRAK3), mRNA [NM_007199] |
| 178 | A_23_P162596 | ACTR6 | TTAAGGGCTTACTGCGACAGTTTTGCTTAGAAGGTAGTTGTTGTGTGACTGTGACTAAACT | SEQ ID NO: 2530 | Homo sapiens ARP6 actin-related protein 6 homolog (yeast) (ACTR6), mRNA [NM_022496] |
| 179 | A_23_P163216 | ATP8B4 | ATCAGTGTATTTCCATAAAAGTGATTCGGGTCATATTTGTGTGAAAACCTCAGTTCTGTCA | SEQ ID NO: 2531 | Homo sapiens ATPase, Class I, type 8B, member 4 (ATP8B4), mRNA [NM_024837] |
| 180 | A_23_P165824 | TNFAIP6 | AAATGAGATACGGAAGATAAGGAAATCTGGTACTGGGACATTAGACTCAAGTATGGTCAGCG | SEQ ID NO: 2532 | Homo sapiens tumor necrosis factor, alpha-induced protein 6 (TNFAIP6), mRNA [NM_007115] |
| 181 | A_23_P167005 | GPR160 | AGGCACAAGATCCTTATTCTGGTCACTGTCCTTCTATGTGAGGATTCAGAAGTTACTGGC | SEQ ID NO: 2533 | Homo sapiens G protein-coupled receptor 160 (GPR160), mRNA [NM_014373] |
| 182 | A_23_P167863 | HIST1H2AC | GCATTATGCAAATGCATTATATTTTATGTAACCTGTCGCACTGTTGGTAGGCACTTGAGTT | SEQ ID NO: 2534 | Histone H2A type 1-C [Source:Uniprot/SWISSPROT;Acc:Q93077] [ENST00000314088] |
| 183 | A_23_P16817 | CLK1 | ATGGAAAGGATTCTTGGAGGGTGTAGGAAAAACATATGATACAGAAACCAGGAAAACGTAAA | SEQ ID NO: 2535 | Homo sapiens CDC-like kinase 1 (CLK1), transcript variant 1, mRNA [NM_004071] |
| 184 | A_23_P168656 | GTPBP10 | AATTTGTGGATTTCTGATACAAATGTCTTCTACTGAGCGACCATCAAAGCATGGTGTTACT | SEQ ID NO: 2536 | Homo sapiens GTP-binding protein 10 (putative) (GTPBP10), transcript variant 2, mRNA [NM_033107] |
| 185 | A_23_P168882 | TP53INP1 | GGGAGGTTAGATGTGTTTCAGGCTTGGAGTGTATGAGTGGTTTTGCTTGTATTTTCCT | SEQ ID NO: 2537 | Homo sapiens tumor protein p53 inducible nuclear protein 1 (TP53INP1), mRNA [NM_033285] |
| 186 | A_23_P168974 | SDCBP | GGAAAGGAACAAGCAAGTTCACTTGAGAATTCATGAGAAGGTTTATGACAGACTGGTGCGAGAAAGCATCCTCAG | SEQ ID NO: 2538 | Homo sapiens cDNA FLJ46804 fis, clone TRACH3032570, highly similar to Homo sapiens syndecan binding protein (syntenin) (SDCBP). [AK128645] |
| 187 | A_23_P16915 | QPCT | CATATTCATTTTAAGAGAAGGAGGTGTTCCAGTTCTGCATGTGATACCGGTCTCGCTTTCCCT | SEQ ID NO: 2539 | Homo sapiens glutaminyl-peptide cyclotransferase (glutaminyl cyclase) (QPCT), mRNA [NM_012413] |
| 188 | A_23_P169278 | AGTPBP1 | AAACCTGAGTATCATTGGATGAATTTTATCTCCCTATGGTTATATGCTGCATCAAGTGG | SEQ ID NO: 2540 | Homo sapiens ATP/GTP binding protein 1 (AGTPBP1), mRNA [NM_015239] |

Fig. 7-11

| No. | Probe ID No | Symbols of genes | Sequence | SEQ ID NO: | Descriptions of genes letters and numbers within [ ] indicates GenBank accession No.) |
|---|---|---|---|---|---|
| 189 | A_23_P169576 | EXOC6 | ATGGTGAAATCTTCCGTTTGGGTTTTCAGGATTAGGGCTGTAAGAAAGTATGCCTGATTC | SEQ ID NO: 2541 | Homo sapiens exocyst complex component 6 (EXOC6), transcript variant 2, mRNA [NM_001013848] |
| 190 | A_23_P17021 | SCRN3 | GTCAAAGTTAGTTCTTAGTGATCATATGGTCAGCTAATATAGTTCTTAGTGATCAGTGG | SEQ ID NO: 2542 | Homo sapiens secernin 3 (SCRN3), mRNA [NM_024583] |
| 191 | A_23_P170233 | CSTA | AACTGGCTACGTAGTGCATGATCATCCTTGGTGATAAATAAGGATCAATAAAGAAGCATTCT | SEQ ID NO: 2543 | Homo sapiens cystatin A (stefin A) (CSTA), mRNA [NM_005213] |
| 192 | A_23_P18325 | PDCD10 | CCAACGCGACTAATTCATGAAACGAACTAATAGTTCAGACCTTCAAAACTGTGGGCTGAA | SEQ ID NO: 2544 | Homo sapiens programmed cell death 10 (PDCD10), transcript variant 1, mRNA [NM_007217] |
| 193 | A_23_P18372 | B3GNT5 | AAATGTCAACAAACGGGAAAATAAACTATGCAGCTTGGATGGTCACTTGAATAGAAGATGGT | SEQ ID NO: 2545 | Homo sapiens UDP-GlcNAc:betaGal beta-1,3-N-acetylglucosaminyltransferase 5 (B3GNT5), mRNA [NM_032047] |
| 194 | A_23_P19543 | SRPK1 | CTGTCAAATTGCCACGATCTCACTAAAGGATTCTATTTGCTGTCAGTTAAAAATAAAGC | SEQ ID NO: 2546 | Homo sapiens SFRS protein kinase 1 (SRPK1), mRNA [NM_003137] |
| 195 | A_23_P200030 | FPGT | TAAAAATTGTAAACTAGAAGTAACTTGTGTAGACAAGGTCAGTTATGATACTTATGTGGG | SEQ ID NO: 2547 | Homo sapiens fucose-1-phosphate guanylyltransferase (FPGT), mRNA [NM_003838] |
| 196 | A_23_P200493 | LBR | GAGCCCTTATCAATACAGCGTGGAATTCTGGATATCAGGTACACTTTGTTTTAAGT | SEQ ID NO: 2548 | Homo sapiens lamin B receptor (LBR), transcript variant 1, mRNA [NM_002296] |
| 197 | A_23_P200507 | CNIH4 | TGGTTGAAGTGAGGGTACGACTACAGTGGAAGAGTTGAGGAGGAAGAGACTTCTTAAATCAT | SEQ ID NO: 2549 | Homo sapiens cornichon homolog 4 (Drosophila) (CNIH4), mRNA [NM_014184] |
| 198 | A_23_P201619 | NEK7 | TGAAGGCCAAGAGGAAGGAAGTCACTGTTAAAAGGACTCTGTGGCATGTTACAAGGTTGGATGAA | SEQ ID NO: 2550 | Serine/threonine-protein kinase Nek7 (EC 2.7.11.1) (NimA-related protein kinase 7) [Source:Uniprot/SWISSPROT;Acc:Q8TDX7] [ENST00000367385] |
| 199 | A_23_P201758 | CD46 | CTCATGAGTGAAGTGTGCCTTAGGTAATATTGCAATGTGGGTTGAATGTAGGTAGCATC | SEQ ID NO: 2551 | Homo sapiens CD46 molecule, complement regulatory protein (CD46), transcript variant a, mRNA [NM_002389] |
| 200 | A_23_P201951 | ARID4B | ATGTTTACAGGTTTGAATTAGGGTAAAAGGGTCTTGCAGTGGCTTTCATGGCCCTTCAAA | SEQ ID NO: 2552 | Homo sapiens AT rich interactive domain 4B (RBP1-like) (ARID4B), transcript variant 1, mRNA [NM_016374] |
| 201 | A_23_P20225 | RRM2B | TGCTGTTTGTAAAAGTTAAAGATTTGAAAGAAGAATCTCATATTCCCGAGGCATTAGGA | SEQ ID NO: 2553 | Homo sapiens ribonucleotide reductase M2 B (TP53 inducible) (RRM2B), mRNA [NM_015713] |
| 202 | A_23_P202637 | SAPS3 | TGATTATTCCTACAAGTGAAACACTAGACTATTGGAGTGTATATGGCTGTGTTTTGGG | SEQ ID NO: 2554 | Homo sapiens SAPS domain family, member 3 (SAPS3), mRNA [NM_018312] |
| 203 | A_23_P202978 | CASP1 | CTGTTGTGTGATGAGTGGAGGAAATTTTCCGCAAGGTTCGATTTCATTTGAGCAGGCAGA | SEQ ID NO: 2555 | Homo sapiens caspase 1, apoptosis-related cysteine peptidase (interleukin 1, beta, convertase) (CASP1), transcript variant alpha, mRNA [NM_033292] |
| 204 | A_23_P203376 | MS4A6A | ACGAGGGTGTAAATTACCATTTACTAGAATTAGGCAAATAGTCTGAATTCCAGAAAACAA | SEQ ID NO: 2556 | Homo sapiens membrane-spanning 4-domains, subfamily A, member 6A (MS4A6A), transcript variant 1, mRNA [NM_152852] |
| 205 | A_23_P203498 | TRIM22 | GTACATAAGGATGTATCACTAAGTAATGTATCCTTCAGAATGTGTTGGTTTACGAGTGAC | SEQ ID NO: 2557 | Homo sapiens tripartite motif-containing 22 (TRIM22), mRNA [NM_006074] |

Fig. 7-12

| No. | Probe ID No. | Symbols of genes | Sequence | SEQ ID NO: | Descriptions of genes (letters and numbers within [ ] indicates GenBank accession No.) |
|---|---|---|---|---|---|
| 206 | A_23_P204269 | USP15 | GACCAAGATAAATGAGGTATGTTGATCATGGCTTGCTTATATCTTGATATTAAAGCTG | SEQ ID NO: 2558 | Homo sapiens ubiquitin specific peptidase 15 (USP15), mRNA [NM_006313] |
| 207 | A_23_P204564 | PPP1R12A | GTATAAGATGTTAGATTCTGTAATCTCAGATTCATTTAGGCAGGTACTGAGTGATGCTG | SEQ ID NO: 2559 | Homo sapiens protein phosphatase 1, regulatory (inhibitor) subunit 12A (PPP1R12A), mRNA [NM_002480] |
| 208 | A_23_P205027 | ABHD13 | ATTGTGGAGAATGATAAAGAATGTTCCTTTAGAAGTGTGTTATGTCTGTAGCTGTCTG | SEQ ID NO: 2560 | Homo sapiens abhydrolase domain containing 13 (ABHD13), mRNA [NM_032859] |
| 209 | A_23_P205336 | C14orf129 | CAATTCATTGCCAGACTTGATTGGAATGCTTTGTTGATGATGTATGTTCATTCTCAGCT | SEQ ID NO: 2561 | Homo sapiens chromosome 14 open reading frame 129 (C14orf129), mRNA [NM_016472] |
| 210 | A_23_P20606 | NIPSNAP3A | GTAAGTAGCACTTCAAAAAATAGTTCTGTTTACTTCTGCATGGTATTTGCAGTGTCGTG | SEQ ID NO: 2562 | Homo sapiens nipsnap homolog 3A (C. elegans) (NIPSNAP3A), mRNA [NM_015469] |
| 211 | A_23_P205396 | CKLF | ATTATACTTGACTTGGTAAGAACAGATTCATGGTCATGCTATCTGTGTTGGCACTGATA | SEQ ID NO: 2563 | Homo sapiens chemokine-like factor (CKLF), transcript variant 1, mRNA [NM_016951] |
| 212 | A_23_P207299 | LOC51136 | CCAAAACAGCAATTTGAAATTAGAACTAGTGGTTTTAGAAGAACTGAGGTATTGTTCCTG | SEQ ID NO: 2564 | Homo sapiens PTD016 protein (LOC51136), mRNA [NM_016125] |
| 213 | A_23_P207666 | USP6 | TCCATTACCGTTCTTCCTCATAGGTAGTAATTACCAATGTAAGTAAGGATTTGTTCT | SEQ ID NO: 2565 | Homo sapiens ubiquitin specific peptidase 6 (Tre-2 oncogene), (USP6), mRNA [NM_004505] |
| 214 | A_23_P207999 | PMAIP1 | AGAGAATGTTCTAGTGTTTTGCCGAAGAATTACCGGTTACTGGGCTAGTGTGAAGGAGAT | SEQ ID NO: 2566 | Homo sapiens phorbol-12-myristate-13-acetate-induced protein 1 (PMAIP1), mRNA [NM_021127] |
| 215 | A_23_P208119 | PSTPIP2 | AATTAGGTTTCAAGCATGGGAAGCATGGAAAGATCCACATTCTGGATTGGAGGATCCACTTGA | SEQ ID NO: 2567 | Homo sapiens proline-serine-threonine phosphatase interacting protein 2 (PSTPIP2), mRNA [NM_024430] |
| 216 | A_23_P209116 | CYP4F3 | GTTGAAATTTGGGTGGATAAATTTCTGGAGTTTCTATCTATTCCATGTGGAGGAATACC | SEQ ID NO: 2568 | Homo sapiens mRNA for leukotriene B4 omega-hydroxylase, complete cds. [AB002454] |
| 217 | A_23_P209625 | CYP1B1 | GTGTGTTTATGAAGAAGTAAGCGCTTGAGAGTTTACCGGGCTTATTAAATAGCTT | SEQ ID NO: 2569 | Homo sapiens cytochrome P450, family 1, subfamily B, polypeptide 1 (CYP1B1), mRNA [NM_000104] |
| 218 | A_23_P210274 | PREI3 | GGATCAGTATGCCGTAGGATTTACAGAGAATATTTCACATAGCTTATTTTCATCAGGCAG | SEQ ID NO: 2570 | Homo sapiens preimplantation protein 3 (PREI3), transcript variant 1, mRNA [NM_015387] |
| 219 | A_23_P211047 | BACH1 | ATGTTAGATGCAGTAGACGATAGAACAGGTTGCATGTGGACACTCAGTCACATTAAGAACTTG | SEQ ID NO: 2571 | Homo sapiens BTB and CNC homology 1, basic leucine zipper transcription factor 1 (BACH1), transcript variant 1, mRNA [NM_206866] |
| 220 | A_23_P211840 | UBE1C | GCCACCCTAGAGGGAAAAATAGAACACTTACTTACAGTCGCTAACCTGTATGTGAAGAA | SEQ ID NO: 2572 | Homo sapiens ubiquitin-activating enzyme E1C (UBA3 homolog, yeast) (UBE1C), transcript variant 1, mRNA [NM_003968] |
| 221 | A_23_P211899 | THC2522889 | AAACAAAGATTCGTTAAAGATGTTAAGGTTGGCATAAGGTCGGGTGTTCTACTGATGGTTG | SEQ ID NO: 2573 | GPR27_HUMAN (Q9NS67) Probable G-protein coupled receptor 27 (Super conserved receptor expressed in brain 1), complete [THC2522889] |
| 222 | A_23_P212061 | MME | TTATTACTGCCAGAACAACAGAACGATATCCTGACTTCTAATATCATTCACTAGCTTTGCCTG | SEQ ID NO: 2574 | Homo sapiens membrane metallo-endopeptidase (MME), transcript variant 2b, mRNA [NM_007289] |
| 223 | A_23_P212728 | TBC1D23 | TGTACCCTGTTAACAGCCAGTCATTTGAATTACTTATGGAAATCAAGTGAATAAAAGGC | SEQ ID NO: 2575 | Homo sapiens clone MGC:8830 IMAGE:3847561, complete cds. [BC020955] |

Fig. 7-13

| No. | Probe ID No. | Symbols of genes | Sequence | SEQ ID NO: | Descriptions of genes (letters and numbers within [ ] indicates GenBank accession No.) |
|---|---|---|---|---|---|
| 224 | A_23_P213247 | FBXL5 | ATGGAGGTGATTGGTTCTCTTAGACATTAAGACGTAGCAAGCTTTGCAGATCTTTCG | SEQ ID NO: 2576 | Homo sapiens F-box and leucine-rich repeat protein 5 (FBXL5), transcript variant 2, mRNA [NM_033535] |
| 225 | A_23_P213661 | HISPPD1 | GTATGTAAGTTTCTGTTTGTGAAAATGTAGTTAAGTACTCACTGTGGAGGTCATAAGG | SEQ ID NO: 2577 | Homo sapiens histidine acid phosphatase domain containing 1 (HISPPD1), mRNA [NM_015216] |
| 226 | A_23_P215751 | NDUFA5 | TAAAAGTGGAGTGAGTCACTAAAATAGTTTGCAGTACGTTTCTAATATAAGTGTAGGTGGGTATG | SEQ ID NO: 2578 | Homo sapiens NADH dehydrogenase (ubiquinone) 1 alpha subcomplex, 5, 13kDa (NDUFA5), nuclear gene encoding mitochondrial protein, mRNA [NM_005000] |
| 227 | A_23_P216325 | ASAH1 | ATGAAGTGATGGTAAGGAGGGTAGATGGTATGGTGGTACAAACAAATTATGACGGTGGA | SEQ ID NO: 2579 | Homo sapiens N-acylsphingosine amidohydrolase (acid ceramidase) 1 (ASAH1), transcript variant 2, mRNA [NM_004315] |
| 228 | A_23_P217384 | AP1S2 | AAAGGTGTTGCTGTGTTCAGAGTATTATGTGTAAAGTCATTGTTTAAAGCACGAAAGTTC | SEQ ID NO: 2580 | Homo sapiens adaptor-related protein complex 1, sigma 2 subunit (AP1S2), mRNA [NM_003916] |
| 229 | A_23_P217564 | ACSL4 | GTTATAGGTCGTTTAGAAAACACATAATTAACACTTAAGGTTGGGTGGTGGTAATTCTTTG | SEQ ID NO: 2581 | Homo sapiens acyl-CoA synthetase long-chain family member 4 (ACSL4), transcript variant 1, mRNA [NM_004458] |
| 230 | A_23_P217737 | ENST00000341514 | CACGAAGGATGAGTTCTTCTGTTCTTCCAGTTAAAAGAGGTGTTGTTCACAGTGTTGATAAGCAAA | SEQ ID NO: 2582 | Copper-transporting ATPase 1 (EC 3.6.3.4) (Copper pump 1) (Menkes disease-associated protein). [Source:Uniprot/SWISSPROT:Acc:Q04656] [ENST00000341514] |
| 231 | A_23_P218928 | C4orf18 | CAGAGTAGGTTCATTTGCTTCTGCTAGATGTGTTTCAGAAGCTAGGTACAGAAGGAATGTTTG | SEQ ID NO: 2583 | Homo sapiens chromosome 4 open reading frame 18 (C4orf18), transcript variant 2, mRNA [NM_016613] |
| 232 | A_23_P219072 | SAMD9 | AACCTACCTCCAGATTAGTAAGCCAGTTGAAAAGTAAAAGATCAGCTTCGAGAAGTCT | SEQ ID NO: 2584 | Homo sapiens sterile alpha motif domain containing 9 (SAMD9), mRNA [NM_017654] |
| 233 | A_23_P22433 | RP2 | TTATTCTCTTTGCATTAATAGTACTGCTGTTTTTGCTTCTTTATATTATGTCTA | SEQ ID NO: 2585 | Homo sapiens retinitis pigmentosa 2 (X-linked recessive) (RP2), mRNA [NM_006915] |
| 234 | A_23_P22048 | S100A9 | GAGCTGGTGCGAAAAGATGTGAAAAATTTCTCAAGAAGGAGAATAAGAATGAAAAGGTC | SEQ ID NO: 2586 | Homo sapiens S100 calcium binding protein A9 (S100A9), mRNA [NM_002965] |
| 235 | A_23_P23705 | SPATA6 | CATCTTTGGTAAGTGTGTGATTATCTTCTATCCCTAGGAGGAAAGAGTGGTCCATGTTG | SEQ ID NO: 2587 | Spermatogenesis-associated protein 6 precursor. [Source:Uniprot/SWISSPROT:Acc:Q9NWH7] |
| 236 | A_23_P23960 | BLOC1S2 | GAGTAAAGTGGAGGACTGTGGCTATTCCTGAAGCTTGTTTGAGACAGAATCCCTCAGAAT | SEQ ID NO: 2588 | Homo sapiens biogenesis of lysosome-related organelles complex-1, subunit 2 (BLOC1S2), transcript variant 2, mRNA [NM_001001342] |
| 237 | A_23_P24404 | IFIT2 | AGCTGACCCAGCATCAGCCACACTCTGGGTTGGAAAAATGTTTGCCTGTTGGAATTAATTT | SEQ ID NO: 2589 | Homo sapiens interferon-induced protein with tetratricopeptide repeats 2 (IFIT2), mRNA [NM_001547] |
| 238 | A_23_P24260 | ENST00000371207 | AAGGCACATCTTATTTTTCCAAGGTTTAATTAGTGAGAGGGCAGCATTAGTGTGGAGTG | SEQ ID NO: 2590 | Ectonucleoside triphosphate diphosphohydrolase 1 (EC 3.6.1.5) (NTPDase 1) (Ecto-ATP diphosphohydrolase) (ATPDase) (Lymphoid cell activation antigen) (Ecto-apyrase) (CD39 antigen). [Source:Uniprot/SWISSPROT:Acc:P49961] [ENST00000371207] |

Fig. 7-14

| No. | Probe ID No. | Symbols of genes | Sequence | SEQ ID NO: | Descriptions of genes (letters and numbers within [ ] indicates GenBank accession No.: |
|---|---|---|---|---|---|
| 239 | A_23_P24365 | ANKRD49 | GGGCACTGCTTGTATAGTCTCTCAAGTTCAGGAAATGTTGATTTTCTAAGGTGGTCAT | SEQ ID NO: 2591 | Homo sapiens ankyrin repeat domain 49 (ANKRD49), mRNA [NM_017704] |
| 240 | A_23_P250002 | HACE1 | TAAGCAGTCATTGTGTTTGGCAGTAATGTTTGAGAGACATGTAAGTTGAAGTTTTGGTA | SEQ ID NO: 2592 | Homo sapiens HECT domain and ankyrin repeat containing, E3 ubiquitin protein ligase 1 (HACE1), mRNA [NM_020771] |
| 241 | A_23_P250800 | ST3GAL6 | AGTCAGGAAGTCAGGTCAGGTAGGTGGTTTAAATAGAAGTTTCTGACCTCAAGAGTCCTTT | SEQ ID NO: 2593 | Homo sapiens ST3 beta-galactoside alpha-2,3-sialyltransferase 6 (ST3GAL6), mRNA [NM_006100] |
| 242 | A_23_P251002 | A_23_P251002 | GGTGATGGATGTGAGAGATGGACGTGGAGTGGAAAATGTGTCTGATTAGTTTTGACTG | SEQ ID NO: 2594 | |
| 243 | A_23_P251480 | NBN | AAGGAAGAAACGTGAAGTCAGGAAGGAGACTCACTATGGTCAGGTAAAGAAATATGTAACA | SEQ ID NO: 2595 | Homo sapiens nibrin (NBN), transcript variant 1, mRNA [NM_002485] |
| 244 | A_23_P251625 | IFRD1 | GTATGACACGTTAAGGAGGTTCTTGGATCAGGAGTGCAGTAGCCAGTGCAGTCAAAAT | SEQ ID NO: 2596 | Homo sapiens interferon-related developmental regulator 1 (IFRD1), transcript variant 2, mRNA [NM_001007245] |
| 245 | A_23_P251937 | CPEB4 | GTATGTCAGTTAATTGTACTAGTGGCTGAATTCCATATAGTTTTAGTGTGTATGGGG | SEQ ID NO: 2597 | Homo sapiens cytoplasmic polyadenylation element binding protein 4 (CPEB4), mRNA [NM_030627] |
| 246 | A_23_P252145 | C1GALT1 | ATATGTATATATGAGGAACTTGTGTTTTTTAAATGGTGGGAGGTAGAGGAAGTAG | SEQ ID NO: 2598 | Homo sapiens core 1 synthase, glycoprotein-N-acetylgalactosamine 3-beta-galactosyltransferase, 1 (C1GALT1), mRNA [NM_020156] |
| 247 | A_23_P252201 | EAF2 | CAGGATTCCTGATATGCCAGTCAGTCATAGATTTCGAGACAACAGTGGCCTTCTGAT | SEQ ID NO: 2599 | Homo sapiens ELL associated factor 2 (EAF2), mRNA [NM_018456] |
| 248 | A_23_P25235 | CLEC4D | CATTTAAGCCACCAGAGTATTCTGGCATAAGAATGAACCCGACAACTGTCAGGGAGAA | SEQ ID NO: 2600 | Homo sapiens C-type lectin domain family 4, member D (CLEC4D), mRNA [NM_080387] |
| 249 | A_23_P252371 | RBBP8 | GCAAGGAGGAAGAAGACATAGACGTTGAAACAGAAGAAATCAGAAGGATGAAGGAGAGTTTT | SEQ ID NO: 2601 | Homo sapiens retinoblastoma binding protein 8 (RBBP8), transcript variant 1, mRNA [NM_002894] |
| 250 | A_23_P253012 | GRAMD1C | GAATTCCAACGAAGCAAGCTACCTAGGGGTAACAGTGAAGCTTACCTGGGTTTGTTTGTTTG | SEQ ID NO: 2602 | Homo sapiens GRAM domain containing 1C (GRAMD1C), mRNA [NM_017577] |
| 251 | A_23_P253602 | BMX | TTATGGTGGTCCTGATATAACGTTCCAGCCTATAGCAGAAGACATTTCAGACTGGA | SEQ ID NO: 2603 | Homo sapiens BMX non-receptor tyrosine kinase (BMX), mRNA [NM_001721] |
| 252 | A_23_P254472 | C6orf211 | TGCATTTCAATAGCTTGTTTCAATTGCATCGGCTTTGTAATTTGATTGACCTGTAGAATGG | SEQ ID NO: 2604 | Homo sapiens chromosome 6 open reading frame 211 (C6orf211), mRNA [NM_024573] |
| 253 | A_23_P254702 | DEK | TTTTTTAAAGTTTTGCCTAGAACTGGTTTCTGTGAAGAATGTGTCTGTGGTTAAGGATAGCACAAGCTAGCCAGC | SEQ ID NO: 2605 | Homo sapiens DEK oncogene (DNA binding) (DEK), mRNA [NM_003472] |
| 254 | A_23_P25503 | FNDC3A | ATACTTGGGCATTTGAGGGTCAGTGCAAAATTAGTGCAGAGGAGAAACAATTTAATGT | SEQ ID NO: 2606 | Homo sapiens fibronectin type III domain containing 3A (FNDC3A), transcript variant 2, mRNA [NM_014923] |
| 255 | A_23_P255444 | DAPP1 | AGAAGAATGAGATACTGATGTCGACAGTTCATTGGCAGAATGAATTTGTAATTTGATCCCGTTCGTGTTATGT | SEQ ID NO: 2607 | Homo sapiens dual adaptor of phosphotyrosine and 3-phosphoinositides (DAPP1), mRNA [NM_014395] |
| 256 | A_23_P256231 | FBXO30 | GCCTTTTAAAGTTTTGCCTGAAGAATGTGTCTGTGGTTAAGGATAGCACAAGCATTAAGTTT | SEQ ID NO: 2608 | Homo sapiens F-box protein 30 (FBXO30), mRNA [NM_032145] |
| 257 | A_23_P256342 | SNX13 | ATTAGCCAGGTGAATGATCCTTGAAACATCTCTTTGAGGTCTGGAGAAAGAGACAGAATG | SEQ ID NO: 2609 | Homo sapiens sorting nexin 13 (SNX13), mRNA [NM_015132] |

Fig. 7-15

| No | Probe ID No. | Symbols of genes | Sequence | SEQ ID NO: | Descriptions of genes (letters and numbers within [ ] indicates GenBank accession No.) |
|---|---|---|---|---|---|
| 258 | A_23_P256432 | PPP2R5A | TTGGTGAAGTATTCTGACATCGTTTGTTATCAGAGTACCATTCC AATGTCTTAACTTGC | SEQ ID NO: 2610 | Homo sapiens protein phosphatase 2, regulatory subunit B', alpha isoform (PPP2R5A), mRNA [NM_006243] |
| 259 | A_23_P25735 | PSMA6 | TAGCAGAGAGACTAAACATTGTCGTTAGTTAGTTGACGAGATGCGTG ATGCCAGTTACCTGT | SEQ ID NO: 2611 | Homo sapiens proteasome (prosome, macropain) subunit, alpha type, 6 (PSMA6), mRNA [NM_002791] |
| 260 | A_23_P259054 | SNX14 | CATCAGAGCTGTGTTTGATGGGTTACAGGAACCAGTACTCAACAA GCAGCTGACTTATGT | SEQ ID NO: 2612 | Homo sapiens sorting nexin 14 (SNX14), transcript variant 1, mRNA [NM_153816] |
| 261 | A_23_P26021 | COPS2 | TGGTTTTTTGATGAACTGGTTTGTGTTTGGTGCTGCATTTATCC CAAGAAAAACAGCTT | SEQ ID NO: 2613 | Homo sapiens COP9 constitutive photomorphogenic homolog subunit 2 (Arabidopsis) (COPS2), mRNA [NM_004236] |
| 262 | A_23_P2765 | P2RY5 | TCTGTATTGCTGTTCGAACTGTTGTTTGACCCTATAGTTACT ACTTACATCGGACA | SEQ ID NO: 2614 | Homo sapiens purinergic receptor P2Y, G-protein coupled, 5 (P2RY5), mRNA [NM_005767] |
| 263 | A_23_P28169 | ARL6IP6 | GGAAAGGAAATAATGGCTACTACTCCGAGTTTTATAGAAGGCTACT TTTAAATCAGAATAT | SEQ ID NO: 2615 | Homo sapiens ADP-ribosylation-like factor 6 interacting protein 6 (ARL6IP6), mRNA [NM_152522] |
| 264 | A_23_P28485 | GCA | TGGTGGTGTTTGAGGAGTTGGCTAGAAATGAAAGCCTGGATTTGT GCCATGTTGTAATA | SEQ ID NO: 2616 | Homo sapiens grancalcin, EF-hand calcium binding protein (GCA), mRNA [NM_012198] |
| 265 | A_23_P29005 | SAMSN1 | CTCTGGTTGCTATATCCACATCAGGAAAATCAGATAATGGAAAGA GGATCTGGAGTCTGA | SEQ ID NO: 2617 | Homo sapiens SAM domain, SH3 domain and nuclear localization signals 1 (SAMSN1), mRNA [NM_022136] |
| 266 | A_23_P30069 | FLJ31033 | AGATTGTTAAGTCCCTACAGTTGTTATTCTAAATGAATGAA GAGTACACTTGCTGG | SEQ ID NO: 2618 | Homo sapiens cDNA FLJ13691 fis, clone PLACE2000014, weakly similar to HYPOTHETICAL HELICASE C28H8.3 IN CHROMOSOME III. [AK023743] |
| 267 | A_23_P30175 | ERBB2IP | TAGTTGAGCTAGTCTGGAAACCTTCATTAGAGGCAATATTTGGTT ATTGCAGTTCATTTT | SEQ ID NO: 2619 | Homo sapiens erbb2 interacting protein (ERBB2IP), transcript variant 2, mRNA [NM_018695] |
| 268 | A_23_P302470 | SULT1B1 | TGTCTAAGTCACAAATCTGAAGAAATAAGAGATGTGTGTAGTG ATTGAAAAGAGGGCA | SEQ ID NO: 2620 | Homo sapiens sulfotransferase family, cytosolic, 1B, member 1 (SULT1B1), mRNA [NM_014465] |
| 269 | A_23_P302550 | RGS18 | GAGTCTAAGGCCCTAGCCATTTGGGCATGTGGCAGATTGGTTCAT ATTCAGAGAAGTGTTA | SEQ ID NO: 2621 | Homo sapiens regulator of G-protein signalling 18 (RGS18), mRNA [NM_130782] |
| 270 | A_23_P30307 | CRSP9 | CAATTGTACTGCACACAATGAACATCAAAGAGAAAAATTCAGGTCA TAGGAGAGATAGAT | SEQ ID NO: 2622 | Homo sapiens cofactor required for Sp1 transcriptional activation, subunit 9, 33kDa (CRSP9), mRNA [NM_004270] |
| 271 | A_23_P303210 | IKIP | TTTAGGTTCCAACTGTGTTAGACATGAGTTTGGCTAGATCGATGGT GCTAGATGTTTAC | SEQ ID NO: 2623 | Homo sapiens IKK interacting protein (IKIP), transcript variant 1, mRNA [NM_153687] |
| 272 | A_23_P303260 | STX7 | GTCTGATGTTTACCGGGGAGAGTGTAGTTAGTAAGATAAATGTTTAAC ATAATTTGGAAGAAAG | SEQ ID NO: 2624 | Homo sapiens syntaxin 7 (STX7), mRNA [NM_003569] |
| 273 | A_23_P305060 | PBEF1 | TGCGTGTGGCTCTATATGCACCTCAAGATTTAAGGAGATAATG TTTTTAGAGAGAATT | SEQ ID NO: 2625 | Homo sapiens pre-B-cell colony enhancing factor 1 (PBEF1), mRNA [NM_005746] |
| 274 | A_23_P305723 | MIER1 | TGATGTATTTCAAATAGAGTTCAGGATGTCGCAGATTCAGTTCAAG ACAAGTTGTTGAGC | SEQ ID NO: 2626 | Homo sapiens mesoderm induction early response 1 homolog (Xenopus laevis) (MIER1), transcript variant 1, mRNA [NM_020948] |
| 275 | A_23_P305759 | ABHD3 | AGTCCTAGACTGAAGTCAGTCAGTAGGAATTCAGTATGTGTGTAAAT TCTGTGGATGATGTT | SEQ ID NO: 2627 | Homo sapiens abhydrolase domain containing 3 (ABHD3), mRNA [NM_138340] |
| 276 | A_23_P307940 | CAPZA2 | CTACAAGATTGGCAAAGAATGCAGAATGCATAAGATGAACATTG CATGACCGGATCATT | SEQ ID NO: 2628 | Homo sapiens capping protein (actin filament) muscle Z-line, alpha 2 (CAPZA2), mRNA [NM_006136] |

Fig. 7-16

| No. | Probe ID No. | Symbols of genes | Sequence | SEQ ID NO: | Descriptions of genes (letters and numbers within [ ] indicates GenBank accession No.) |
|---|---|---|---|---|---|
| 277 | A_23_P308800 | GLS | CGGAGAAGAGATAAGATACTGCGAATAGGCCCTCAAACTTAAAAAAGAAAAAACTTTGC | SEQ ID NO: 2629 | Homo sapiens glutaminase C mRNA, complete cds. [AF158555] |
| 278 | A_23_P30995 | CYB5R4 | TGCATTTGTGGACCAGTGCCATTTGCCATTACAGAACAAGGAGTAAGGTTGGTGCATGATCTCAAC | SEQ ID NO: 2630 | Homo sapiens cytochrome b5 reductase 4 (CYB5R4), mRNA [NM_016230] |
| 279 | A_23_P31097 | OSTM1 | ACTGAAAATGTGCTGGGGTTTGTTCTGCTGTCACTGTTTATGCTGCTGGAACTTAGCAGT | SEQ ID NO: 2631 | Homo sapiens osteopetrosis associated transmembrane protein 1 (OSTM1), mRNA [NM_014028] |
| 280 | A_23_P312246 | CCDC82 | GGCTTTATAAGCAATGAGTGAAGTGTCAAGTGAATGAATGAGGTGTTGATATCCTGTCAGTTTAGTCAA | SEQ ID NO: 2632 | Homo sapiens coiled-coil domain containing 82 (CCDC82), mRNA [NM_024725] |
| 281 | A_23_P312932 | KRTAP8-1 | GGCTATGGCTTCGGCTATGGCTACACAGGGTGTGGGGCTTTCGGCTACAGGAGATAGTCG | SEQ ID NO: 2633 | Homo sapiens keratin associated protein 8-1 (KRTAP8-1), mRNA [NM_175857] |
| 282 | A_23_P314191 | ZDHHC17 | TGGATACTTTTAGCAGAACTTAATCTCAGGACTGAACATGAATTAGTTCCTTGG | SEQ ID NO: 2634 | Homo sapiens zinc finger, DHHC-type containing 17 (ZDHHC17), mRNA [NM_015336] |
| 283 | A_23_P314591 | NFYB | GGAGGCATTTACTAACCAGTTACCAGCTGGCTTAATAACCACAGACGGTCAACAAGAAAA | SEQ ID NO: 2635 | Homo sapiens nuclear transcription factor Y, beta (NFYB), mRNA [NM_006166] |
| 284 | A_23_P317001 | BNIP2 | TTGAACCCGGTAGTTGTTTGACCTAGTAGAATGTGGTGTTTATTCAAGTTTGAAATCA | SEQ ID NO: 2636 | Homo sapiens BCL2/adenovirus E1B 19kDa interacting protein 2 (BNIP2), mRNA [NM_004330] |
| 285 | A_23_P317347 | ESCO1 | GGTAATTTTTAAAAGGCGTGAACTATAGTTTGAAGAAATGGCCTATAGAAAAGGAAAGCTC | SEQ ID NO: 2637 | Homo sapiens establishment of cohesion 1 homolog 1 (S. cerevisiae) (ESCO1), mRNA [NM_052911] |
| 286 | A_23_P317465 | RAB8B | CCTTGATATAGAAGGCACCTAGACGGACAGCAGGATATGCTAAAATAATTTCAAATTCTAGGAC | SEQ ID NO: 2638 | Homo sapiens RAB8B, member RAS oncogene family (RAB8B), mRNA [NM_016530] |
| 287 | A_23_P321354 | TMEM71 | AACCAGTTCTAAACCAAGTTTTAATCTTGTTGGGCTCTGTAATTACGTTCACTTTAA | SEQ ID NO: 2639 | Homo sapiens transmembrane protein 71 (TMEM71), mRNA [NM_144649] |
| 288 | A_23_P324633 | C9orf72 | TTGTGGATTAGTCCTGGGATTCAGTCTGTGAGAAATGTCTAATAGTTCTGTATAGTCG | SEQ ID NO: 2640 | Homo sapiens chromosome 9 open reading frame 72 (C9orf72), transcript variant 1, mRNA [NM_018325] |
| 289 | A_23_P325501 | MORC3 | CATGCCATAAAATACTATGCTTATTGGTCCGATGTTTTGTGCAATTTAAAGAGAATGGC | SEQ ID NO: 2641 | Homo sapiens MORC family CW-type zinc finger 3 (MORC3), mRNA [NM_015358] |
| 290 | A_23_P329198 | OBFC2A | AGATGTCATAAGTGGTACCCACACTTCCCGTTTTTACTGTAGGGTGGATAAATGTCTTAGGATT | SEQ ID NO: 2642 | Homo sapiens oligonucleotide/oligosaccharide-binding fold containing 2A (OBFC2A), mRNA [NM_001031716] |
| 291 | A_23_P330561 | C19orf59 | CTGTCTCCCTGTTTGTGTAAACATACTAGAGTATGTGCGCGTGTTTCTGTCAGCCA | SEQ ID NO: 2643 | Homo sapiens chromosome 19 open reading frame 59 (C19orf59), mRNA [NM_174918] |
| 292 | A_23_P332439 | NUPL1 | ATTGAAATGTCTTGAATGTATTATTGAATCTCTCAAGGTACACAGGGGTGGCTTTGTAAATGTTC | SEQ ID NO: 2644 | Homo sapiens KIAA0410 mRNA, partial cds. [AB007870] |
| 293 | A_23_P339480 | HAT1 | AACATGAACAGGTGGAAGAGAGTTTTCAGGAACTAGTGGAAGATTAGCGGGCGTGTTATTG | SEQ ID NO: 2645 | Homo sapiens histone acetyltransferase 1 (HAT1), transcript variant 1, mRNA [NM_003642] |
| 294 | A_23_P339554 | MLSTD2 | CAATAAGTCGTCTTGACAGAGTATGGTGTTTCTTAGAATATTGACAAGTATTTGCTTGGG | SEQ ID NO: 2646 | Homo sapiens male sterility domain containing 2 (MLSTD2), mRNA [NM_032228] |
| 295 | A_23_P34307 | PIGK | ATTGATTTCACAGTTCTTGTATTGTTGGACCACTTACCATTGAATCTTGAAATAGAA | SEQ ID NO: 2647 | Homo sapiens phosphatidylinositol glycan anchor biosynthesis, class K (PIGK), mRNA [NM_005482] |
| 296 | A_23_P346006 | CCPG1 | TATGGTCGGACTAATGGAAGACAACAATGGCAAATCTTGAAATAGAATTGGGGGGAATTACCT | SEQ ID NO: 2648 | Homo sapiens cell cycle progression 1 (CCPG1), transcript variant 2, mRNA [NM_020739] |

Fig. 7-17

| No. | Probe ID No. | Symbols of genes | Sequence | SEQ ID NO: | Descriptions of genes (letters and numbers within [ ] indicates GenBank accession No.) |
|---|---|---|---|---|---|
| 297 | A_23_P347059 | MOBKL1A | CTAGAAGGGAAAAATCATCTAAGTTATGAAATCCAACATAGGCGCTATATTACAAACTG | SEQ ID NO: 2649 | Homo sapiens MOB1, Mps One Binder kinase activator-like 1A (yeast) (MOBKL1A), mRNA [NM_173468] |
| 298 | A_23_P34710 | EGLN1 | TGATTGTCAAAATGTACAGCCACAGGCGTTTAATTGGGAGGCCCTGTTGTCATTCAAAT | SEQ ID NO: 2650 | Egl nine homolog 1 (EC 1.14.11.-) (Hypoxia-inducible factor prolyl hydroxylase 2) (HIF-prolyl hydroxylase 2) (HIF-PH2) (HPH-2) (Prolyl hydroxylase domain-containing protein 2) (PHD2) (SM-20). [Source:Uniprot/SWISSPROT;Acc:Q9GZT9] [ENST00000357180] |
| 299 | A_23_P347198 | SP3 | GACCAGGTCGAAATTTAAAGGCTACCTTATTGTAGGTTAAAGTGTATTATAACAGTGTGG | SEQ ID NO: 2651 | Homo sapiens Sp3 transcription factor (SP3), transcript variant 1, mRNA [NM_031111] |
| 300 | A_23_P349083 | FCHO2 | GTGAAATGGTTAAACGTTCTGCACTTTCTTAGTTAGGACAGTCTTCATACCAAGTATTGGG | SEQ ID NO: 2652 | Homo sapiens FCH domain only 2 (FCHO2), mRNA [NM_138782] |
| 301 | A_23_P350187 | ENST00000265149 | TTGCTAATATAGGAATATCAGGTTGACTATATAAGGATAGTTGAAAATGCTTCAGTGG | SEQ ID NO: 2653 | Homo sapiens mRNA for KIAA1546 protein, partial cds. [AB046766] |
| 302 | A_23_P353704 | RP5-1022P6.2 | TGTCTCTCAGTAGGTATTACACACTGTTGCTTGTGGGTTTGTTTGTATGTGGGTGTGT | SEQ ID NO: 2654 | Homo sapiens hypothetical protein KIAA1434 (KIAA1434), mRNA [NM_019593] |
| 303 | A_23_P354074 | LYST | GTGCATGTTGTAGCAAACATTTCGTAAATTATCACAAGGTCTGTTACCTTTATATAGGG | SEQ ID NO: 2655 | Homo sapiens lysosomal trafficking regulator (LYST), transcript variant 1, mRNA [NM_000081] |
| 304 | A_23_P355067 | TMCO1 | AACTCAAGACTCTTTATTTTGTATCATTCTTCTCAGACACACACATCAGAGTGGCAA | SEQ ID NO: 2656 | Homo sapiens transmembrane and coiled-coil domains 1 (TMCO1), mRNA [NM_019026] |
| 305 | A_23_P355244 | SAMD9 | TCACTCGAGGAAGAATTTCCTTGCTTCTGCCATAAAATTTAACTCCATAACTTATAAGC | SEQ ID NO: 2657 | Homo sapiens sterile alpha motif domain containing 9 (SAMD9), mRNA [NM_017654] |
| 306 | A_23_P356125 | KIAA1468 | GCACTGCTTTAATTACTGTGTATATTGTTGATTTGAGTTACAACTGTGTGGTGATAG | SEQ ID NO: 2658 | Homo sapiens KIAA1468 (KIAA1468), mRNA [NM_020854] |
| 307 | A_23_P364107 | C14orf106 | AGGAGACAGTGTTTGTATTTGAAGTGGAGTACATGTATTTCTTTGTAAAGTAGGCTTCC | SEQ ID NO: 2659 | Homo sapiens chromosome 14 open reading frame 106 (C14orf106), mRNA [NM_018353] |
| 308 | A_23_P371266 | DNM3 | ACTGTCTTCTTTGGACTTCAGGATTCTTCAATGCTGCATATATGG | SEQ ID NO: 2660 | Homo sapiens dynamin 3 (DNM3), mRNA [NM_015569] |
| 309 | A_23_P37275 | CGRRF1 | GAGCAAGATAAAGACAAACCGAAGACTCTTCGAACAACATGGTAACAGTGAAAAGTACACT | SEQ ID NO: 2661 | Homo sapiens cell growth regulator with ring finger domain 1 (CGRRF1), mRNA [NM_006568] |
| 310 | A_23_P37441 | B2M | TTGTCTTTCAGGAAGGAGCTGCTTTATCTGTTGTAGTACACTGAATTCACCCCCACT | SEQ ID NO: 2662 | Homo sapiens beta-2-microglobulin (B2M), mRNA [NM_004048] |
| 311 | A_23_P378722 | SAT1 | CCATGTACTATTTTACCTATGACCCGTGGAATTGGTGAAATTGGTGAATTATGTAGTACT ATCTGAGGACTTCT | SEQ ID NO: 2663 | Homo sapiens spermidine/spermine N1-acetyltransferase 1 (SAT1), mRNA [NM_002970] |
| 312 | A_23_P383764 | OR52K3P | TCCATCTCTGAGTTGTTGTGGAAATTGGTGAATTATGCGTCAGAT TGCCGAGTTAGGACC | SEQ ID NO: 2664 | Homo sapiens clone IMAGE:110749 mRNA sequence. [AF143328] |
| 313 | A_23_P38723 | SMCHD1 | ACAAGTACCTGGGCATGAATTTCCATTTCGATTCAGATGGACTGGAAACAACGATTCAA | SEQ ID NO: 2665 | Homo sapiens cDNA FLJ44350 fis, clone TRACH3006228. [AK126324] |
| 314 | A_23_P388900 | SLC22A15 | AGGCTAGGCTGGCCATCAGTTGCTTATTCAGATGTCACGTAAATTTTGTTCGTAGATG | SEQ ID NO: 2666 | Homo sapiens solute carrier family 22 (organic cation transporter), member 15 (SLC22A15), mRNA [NM_018420] |

Fig. 7-18

| No. | Probe ID No. | Symbols of genes | Sequence | SEQ ID NO: | Descriptions of genes (letters and numbers within [ ] indicates GenBank accession No.) |
|---|---|---|---|---|---|
| 315 | A_23_P380734 | FGFR1OP2 | GGAGCAGAATACAGAAATGTGCTTAAGATGAGTTGAAGAGTAAAT TTTCTTAGTGTGTGG | SEQ ID NO: 2667 | Homo sapiens FGFR1 oncogene partner 2 (FGFR1OP2), mRNA [NM_015633] |
| 316 | A_23_P394545 | KIAA1033 | AGCATTTGAATACATATTAATAATGCTTAGTTGCTAATGAATTCAATTC GAACACATGGCACCG | SEQ ID NO: 2668 | Homo sapiens KIAA1033 (KIAA1033), mRNA [NM_015275] |
| 317 | A_23_P394605 | SEC24A | GATTTATTGTGTGTAATGAAGATGGATAACAGAGCTATATGCAGG GGACCACCAAATGTG | SEQ ID NO: 2669 | Homo sapiens SEC24 related gene family, member A (S. cerevisiae) (SEC24A), mRNA [NM_021982] |
| 318 | A_23_P396353 | NIN | ATCTTGGAGGTCTAGTATTTAATAATGCACTATTACCGACAGGGCA GATATTATGAGAAAC | SEQ ID NO: 2670 | Homo sapiens ninein (GSK3B interacting protein) (NIN), transcript variant 2, mRNA [NM_020921] |
| 319 | A_23_P398073 | PPM1B | GGTTGAGTAAGTTTTCATTTTATAACATTGGGAGGGGTAGAGAGT GATTGTCACATAAGG | SEQ ID NO: 2671 | Homo sapiens protein phosphatase 1B (formerly 2C), magnesium-dependent, beta isoform (PPM1B), transcript variant 2, mRNA [NM_177968] |
| 320 | A_23_P398449 | VNN3 | AGATATCATTGTGACGCGAGAAGAATGGAATGTATGGTTGGATGTT CACCAGGAGAGCAT | SEQ ID NO: 2672 | Homo sapiens vanin 3 (VNN3), transcript variant 2, mRNA [NM_078625] |
| 321 | A_23_P40108 | COL9A3 | TCAAAAGGCGCTAGGTAATAAACGTGAAGGTGAAGCATTTGAGAG AAGTAGCGTGTGTA | SEQ ID NO: 2673 | Homo sapiens collagen, type IX, alpha 3 (COL9A3), mRNA [NM_001853] |
| 322 | A_23_P405873 | C9orf72 | GAGAATGAAGATCAGGGTCAGAGTATTATTGGAATGGCTTAGTGG AGAAGTGATTCCTGT | SEQ ID NO: 2674 | Homo sapiens chromosome 9 open reading frame 72 (C9orf72), transcript variant 2, mRNA [NM_145005] |
| 323 | A_23_P406966 | MOSPD2 | TTAGTATTCTGAAGGGTAGGTAGTGTTGTTGGTTTTCATGTTGAAGAAG TTGATTCCAAAACTG | SEQ ID NO: 2675 | Homo sapiens motile sperm domain containing 2 (MOSPD2), mRNA [NM_152581] |
| 324 | A_23_P4096 | CA4 | TAATATCGGCAAACCTGAGATGCGACACTAGGATGGCAGAGAGCAG CCTCTCGACCTGCC | SEQ ID NO: 2676 | Homo sapiens carbonic anhydrase IV (CA4), mRNA [NM_000717] |
| 325 | A_23_P41114 | CSTA | AAACAAATGAGACTTATGGAAAATGGGAAGCTGTGCAGAGTATAAA CTCAAGTGTTGCTG | SEQ ID NO: 2677 | Homo sapiens cystatin A (stefin A) (CSTA), mRNA [NM_005213] |
| 326 | A_23_P412980 | SNX13 | CCCATCTCAAGCAAGAATGGCCTTGGTTTCTTCCATTTCAAACT AATCAGACATTGCGA | SEQ ID NO: 2678 | Homo sapiens sorting nexin 13 (SNX13), mRNA [NM_015132] |
| 327 | A_23_P41645 | ELL2 | TGTCTTTTCAAGTGCTGCTCCCAGTTGAACTTCATAAACAAATTGTTCCTGAAAA AGAAATCTGTTTTGA | SEQ ID NO: 2679 | Homo sapiens elongation factor, RNA polymerase II, 2 (ELL2), mRNA [NM_012081] |
| 328 | A_23_P41664 | ENST00000334994 | TGGCTTCGAGGCAGATTCGACTTGCATAAACAAATTCGTGAAAA TGAGGCACAGGTCAT | SEQ ID NO: 2680 | Syntaurin [Source:Uniprot/SPTREMBL;Acc:Q7Z097] [ENST00000334994] |
| 329 | A_23_P420431 | XKR3 | CAGAGGTTGGGCCATAGAAATCGACGACTACAGATTTCAGTTTTT AGAAAATGTGATAAT | SEQ ID NO: 2681 | Homo sapiens XK, Kell blood group complex subunit-related family, member 3 (XKR3), mRNA [NM_175878] |
| 330 | A_23_P422083 | TMEM55A | AAATTTATGAGGAATCAGCTCTCGCACTGCCCATCTCTTTGCAGTTTG AAAAGAAAATTGCTT | SEQ ID NO: 2682 | Homo sapiens transmembrane protein 55A (TMEM55A), mRNA [NM_018710] |
| 331 | A_23_P424080 | YIPF4 | AAAGGTTGTCCAAAGCACCTGTGTTTTTAAGATTGTGCGATATTCACGTAAAAACT TGTCCAAAACCACC | SEQ ID NO: 2683 | Homo sapiens Yip1 domain family, member 4 (YIPF4), mRNA [NM_032312] |
| 332 | A_23_P427217 | JMJD1C | TCCAGAACATCTGTGAGAGTGCATTTCATTTAACACAGGAACTGAG ACTTTTCAAGGAAGA | SEQ ID NO: 2684 | Homo sapiens jumonji domain containing 1C (JMJD1C), transcript variant 2, mRNA [NM_004241] |
| 333 | A_23_P429491 | FLJ25416 | GCTTGGTCACTGAATTGTTTCATAAAAAGTCAGCGTGAACGAA TTCCTGAACTTTTAA | SEQ ID NO: 2685 | Homo sapiens hypothetical protein FLJ25416 (FLJ25416), mRNA [NM_145018] |
| 334 | A_23_P429689 | FAM44A | AGCAATACTGTTCGATATTAGTTCTTTTCAGTGAAGAGAAATGCA TTCAAGATTAGTCC | SEQ ID NO: 2686 | Homo sapiens family with sequence similarity 44, member A (FAM44A), mRNA [NM_148994] |

Fig. 7-19

| No | Probe ID No. | Symbols of genes | Sequence | SEQ ID NO: | Descriptions of genes (letters and numbers within [ ] indicates GenBank accession No.) |
|---|---|---|---|---|---|
| 335 | A_23_P42969 | FGL2 | TTCAGGACTGGTGGTTTGATGAATGTCTTCTGCAAACTTAAATGG GAAATATTATCACCA | SEQ ID NO: 2687 | Homo sapiens fibrinogen-like 2 (FGL2), mRNA [NM_006682] |
| 336 | A_23_P42975 | PRKAR2B | GCCACATTTTTAGAACACGTGTTTAACATTTTTGGAAAAACGTTCTT GTAGGAAAAGAGACC | SEQ ID NO: 2688 | Homo sapiens protein kinase, cAMP-dependent, regulatory, type II, beta (PRKAR2B), mRNA [NM_002736] |
| 337 | A_23_P430161 | EXOC8 | AAGTAGGAGATTTCTTCAGGCTAAAATCTGTGTGTTCCAATTACA GTTGTAGCTGAAGGA | SEQ ID NO: 2689 | Homo sapiens exocyst complex component 8 (EXOC8), mRNA [NM_175876] |
| 338 | A_23_P431630 | USP32 | GGACTACCCTTCTTCCTCATACATAGTAATTACCAATGTAACTA AGTATTTGTGTCTG | SEQ ID NO: 2690 | Homo sapiens ubiquitin specific peptidase 32 (USP32), mRNA [NM_032582] |
| 339 | A_23_P434809 | S100A8 | AAAGCCATGAAGAAGCCACAAAGAGTAGCGAGTACTGGGAGCC AGAGGCTGGGGCCCT | SEQ ID NO: 2691 | Homo sapiens S100 calcium binding protein A8 (S100A8), mRNA [NM_002964] |
| 340 | A_23_P44257 | COMMD8 | AAGATTTAGTCTGCGCTTCATGTTGGGAAAAACATTGCTCTGA TAAAAATAGTCGTC | SEQ ID NO: 2692 | Homo sapiens COMM domain containing 8 (COMMD8), mRNA [NM_017845] |
| 341 | A_23_P44768 | TBK1 | TGTAGTCTGAGTGGGGCTTGCCTTCTAAATAAGTATTTTCTGACGGCTA CTGGAAATATTTTA | SEQ ID NO: 2693 | Homo sapiens TANK-binding kinase 1 (TBK1), mRNA [NM_013254] |
| 342 | A_23_P46141 | CTSS | TCTGTTGGTGTAGATGCCGTCATCCTTCTTCTTCGTCTAGAGA AGTGGTGTCTACTAT | SEQ ID NO: 2694 | Homo sapiens cathepsin S (CTSS), mRNA [NM_004079] |
| 343 | A_23_P46396 | PTBP2 | AACCAGTGGGACCCAAAGTTTATGTGCTTAGTCTTAATTAGC TTGCATTGTAATATT | SEQ ID NO: 2695 | Homo sapiens polypyrimidine tract binding protein 2 (PTBP2), mRNA [NM_021190] |
| 344 | A_23_P48186 | TWF1 | TGGAGGAGACCATAGCTCGAAGCTGTTATTTCAGTCAGGAAGACT ACCTGTCATGAAGGT | SEQ ID NO: 2696 | Homo sapiens twinfilin, actin-binding protein, homolog 1 (Drosophila) (TWF1), mRNA [NM_002822] |
| 345 | A_23_P48897 | CCPG1 | AAGTCAGAAGAGCCTCATATATATAATCTAATGTCCCACGTATGT CCAATTCCAATGTACCA | SEQ ID NO: 2697 | Homo sapiens cell cycle progression restoration 8 protein (CPR8) mRNA, complete cds. [AF011794] |
| 346 | A_23_P50105 | NDC80 | AAAGTGGGAAATAACTTGGAACGTCTGTTAGAGATGGTTGGTACA CATGTTGGGTCTGTA | SEQ ID NO: 2698 | Homo sapiens NDC80 homolog, kinetochore complex component (S. cerevisiae) (NDC80), mRNA [NM_006101] |
| 347 | A_23_P502797 | WDFY1 | GTAACAGTTTACTGTTGTTGCATTGGTGAATATGGAGGCTAATT TGTACAGATAGGGAT | SEQ ID NO: 2699 | Homo sapiens WD repeat and FYVE domain containing 1 (WDFY1), mRNA [NM_020830] |
| 348 | A_23_P50907 | ITGAV | AAAGAGTGATTAAGTGAGGTTATTTACCGCTAAATGGTGCATTCT GCATTGTATTTCAGG | SEQ ID NO: 2700 | Homo sapiens integrin, alpha V (vitronectin receptor, alpha polypeptide, antigen CD51) (ITGAV), mRNA [NM_002210] |
| 349 | A_23_P50974 | HECW2 | GACAAAGATGAACGCATACAGATCAGCAGCTCCACGGTAATTTTTAG GGACTCAGGAGAATC | SEQ ID NO: 2701 | Homo sapiens HECT, C2 and WW domain containing E3 ubiquitin protein ligase 2 (HECW2), mRNA [NM_020760] |
| 350 | A_23_P51009 | NDUFB3 | GCGCAATGAAGCTTGGAGATACAIGGGTGGCTTTGCAAAGAGTGT TTCCTTTTCTGATGT | SEQ ID NO: 2702 | Homo sapiens NADH dehydrogenase (ubiquinone) 1 beta subcomplex, 3, 12kDa (NDUFB3), mRNA [NM_002491] |
| 351 | A_23_P51996 | STXBP3 | ATTCAGTCATTAATAGAAATGGAGTGATTTCACAGGTGTACTGT TGCACACATACTTC | SEQ ID NO: 2703 | Homo sapiens syntaxin binding protein 3 (STXBP3), mRNA [NM_007269] |
| 352 | A_23_P53467 | IKIP | GTTTAGAACGATTAGTAAATGATTTAACACTACGCATTGGGAGAT TGGTTACGGACTTAG | SEQ ID NO: 2704 | Homo sapiens IKK interacting protein (IKIP), transcript variant 2, mRNA [NM_201612] |
| 353 | A_23_P53668 | NFYB | TGGGCTCATATTGCATACCATTTGTAAGCTGCTTTTTCAGT TAACAATATATTTGGG | SEQ ID NO: 2705 | Homo sapiens nuclear transcription factor Y, beta (NFYB), mRNA [NM_006166] |

Fig. 7-20

| No. | Probe ID No. | Symbols of genes | Sequence | SEQ ID NO: | Descriptions of genes (letters and numbers within [ ] indicates GenBank accession No.) |
|---|---|---|---|---|---|
| 354 | A_23_P53891 | KLF5 | CGTTGAATTGCATGATGCCAGTTTTCATATATGGAGATGTTCGGTCG TGCAGTACTGTTGGT | SEQ ID NO: 2706 | Homo sapiens Kruppel-like factor 5 (intestinal) (KLF5), mRNA [NM_001730] |
| 355 | A_23_P5611 | RIF1 | ATGTATTCTTGGCTGCTATGCCTGGTTTTCAGGAAAATTTAATTA TGTTAGTAGATGTG | SEQ ID NO: 2707 | Homo sapiens RAP1 interacting factor homolog (yeast) (RIF1), mRNA [NM_018151] |
| 356 | A_23_P56734 | HNMT | CCTTTGTCCACCATGGATATATCGACTGCTTTATTGATGGTAA TGAAAATGGAGAGCT | SEQ ID NO: 2708 | Homo sapiens histamine N-methyltransferase (HNMT), transcript variant 1, mRNA [NM_006895] |
| 357 | A_23_P56759 | KRCC1 | GATATCCGTGTTCATCACCACTTTCTTATGTGAATAGGTTGTTA AGTTCTAACAAAGGC | SEQ ID NO: 2709 | Homo sapiens lysine-rich coiled-coil 1 (KRCC1), mRNA [NM_016618] |
| 358 | A_23_P57658 | HRASLS | TTGGGAGGGAAAAGAAAACCTGGGGTGAATAGTTATTTTCAGTG CATCATTACTGTTC | SEQ ID NO: 2710 | Homo sapiens HRAS-like suppressor (HRASLS), mRNA [NM_020386] |
| 359 | A_23_P57856 | BCL6 | CTGCGTAAAGCCTCATTTGTATCTGAGGCAGACACGGATGT GAGAATCTTTATTGA | SEQ ID NO: 2711 | Homo sapiens B-cell CLL/lymphoma 6 (BCL6), transcript variant 2, mRNA [NM_138931] |
| 360 | A_23_P58390 | C4orf32 | TAATACTAACTAACTATTTAGTATACTGTCAGTACATGTGACA CTGGTGTTAATAGGG | SEQ ID NO: 2712 | Homo sapiens chromosome 4 open reading frame 32 (C4orf32), mRNA [NM_152400] |
| 361 | A_23_P58912 | SLC35A1 | ATCATCACTCCGTTATGTGAAACAAGAAGAAGAAGAAGAAGT ATCTGAGTGAACTGC | SEQ ID NO: 2713 | Homo sapiens solute carrier family 35 (CMP-sialic acid transporter), member A1 (SLC35A1), mRNA [NM_006416] |
| 362 | A_23_P59637 | DOCK4 | TTTGGCAGTGCAGCAGTTGAATTTATCTTGAATTTATCTATGTGTGT GTATTTGTGAAGCAG | SEQ ID NO: 2714 | Homo sapiens dedicator of cytokinesis 4 (DOCK4), mRNA [NM_014705] |
| 363 | A_23_P59921 | SUB1 | CAGATTGGGAAAATCAGGTAGGTAGTGTTCGGGATTTAAAGGG AAAGTGCTAATTGAT | SEQ ID NO: 2715 | Homo sapiens SUB1 homolog (S. cerevisiae) (SUB1), mRNA [NM_006713] |
| 364 | A_23_P60565 | ZNF354A | AAACCAAGCTCATCGAAGAATAGCATCCTTGAGAGATGTAATA AATGAATGGATGTG | SEQ ID NO: 2716 | Homo sapiens zinc finger protein 354A (ZNF354A), mRNA [NM_005649] |
| 365 | A_23_P61674 | CLK4 | GAAAGGCATGCAGTTTGTCCATTGTGCATTTATTCTGAGAATGTGGACGGAGGGGTTA CACATACACACTTTA | SEQ ID NO: 2717 | Homo sapiens CDC-like kinase 4 (CLK4), mRNA [NM_020666] |
| 366 | A_23_P62227 | CXorf21 | AGCAAGACTTTATGCAATTTATTCTGAGAATGTGGACGGAGGGGTTA GTGAAGCGGAATTAA | SEQ ID NO: 2718 | Homo sapiens chromosome X open reading frame 21 (CXorf21), mRNA [NM_025159] |
| 367 | A_23_P63343 | UTS2 | AGAATCTGGAAAACAACATAACACCCACTCTATGAATCAAATAGAAGAA TGGAAATACTGTGTC | SEQ ID NO: 2719 | Homo sapiens urotensin 2 (UTS2), transcript variant 1, mRNA [NM_021995] |
| 368 | A_23_P63655 | ATP5C1 | AGAGAGGCTGAAACCAGCTCGAATATATGGGATCTTTAGGT CTGTATGAAAAAGCT | SEQ ID NO: 2720 | Homo sapiens ATP synthase, H+ transporting, mitochondrial F1 complex, gamma polypeptide 1 (ATP5C1), nuclear gene encoding mitochondrial protein, transcript variant 2, mRNA [NM_005174] |
| 369 | A_23_P63896 | FAS | ATGTCTATCCACAGGCTAACCCCACTGCTATGAATCAAATAGAAGAA GCTGAGCCTTTTGC | SEQ ID NO: 2721 | Homo sapiens Fas (TNF receptor superfamily, member 6) (FAS), transcript variant 1, mRNA [NM_000043] |
| 370 | A_23_P65262 | RP11-298P3.3 | AGGGAAGAGTTAAGAAGCAGTGACTACGGTTCCCTTGAGGTACCA TTATCACAAGGGTTT | SEQ ID NO: 2722 | Human BRCA2 region, mRNA sequence CG016 [U50529] |
| 371 | A_23_P65768 | C15orf15 | TCCTTGCATTGCCATCTGTAGATAATAATATCAGATATTACGGATGTTAGA TTGCATCTCAGTGTT | SEQ ID NO: 2723 | Homo sapiens chromosome 15 open reading frame 15 (C15orf15), mRNA [NM_016304] |
| 372 | A_23_P66260 | ZNF267 | TGTGATGAATGCTGGTAAGGCCTTCAGGTCATAGGTCATAGGTCACT AGACAATGGGAGAAGT | SEQ ID NO: 2724 | Homo sapiens zinc finger protein 267 (ZNF267), mRNA [NM_003414], transcript variant 499723. |

Fig. 7-21

| No. | Probe ID No. | Symbols of genes | SEQ ID NO: | Sequence | Descriptions of genes (letters and numbers within [ ] indicates GenBank accession No.) |
|---|---|---|---|---|---|
| 373 | A_23_P68472 | DPM1 | SEQ ID NO:2725 | CTATTGGCGAGGTTCCAATATCATTTGTGGATCGTGTTTATGGTGAATCCAAGTTGGGAG | Homo sapiens dolichyl-phosphate mannosyltransferase polypeptide 1, catalytic subunit (DPM1), mRNA [NM_003859] |
| 374 | A_23_P69109 | PLSCR1 | SEQ ID NO:2726 | GTTTAGCTCTTACAGTCTATCCTTGCTAGAAAATGGTAATTGAGATTAGTCAGATATTAA | Homo sapiens phospholipid scramblase 1 (PLSCR1), mRNA [NM_021105] |
| 375 | A_23_P6914 | OSBPL11 | SEQ ID NO:2727 | GGTCTTCCAATCAGTGTGTGTGTAAGATACCTGTTGTTTATCAGCCATTGTAGGTGCTGTG | Homo sapiens oxysterol binding protein-like 11 (OSBPL11), mRNA [NM_022776] |
| 376 | A_23_P68908 | GLRX | SEQ ID NO:2728 | CTGATAAAACTAGAGCCCGTACACCAAGAGTGTATCTGTGAAAGAGGTCCTACAGTTT | Homo sapiens glutaredoxin (thioltransferase) (GLRX), mRNA [NM_002064] |
| 377 | A_23_P70290 | TMEM30A | SEQ ID NO:2729 | ATCTTCTGCGTCAAGTCTAAAGCACAGTGTAAGTGCTTAATGGAGACTGTTTCATTCTTG | Homo sapiens transmembrane protein 30A (TMEM30A), mRNA [NM_018247] |
| 378 | A_23_P70297 | ANKRD6 | SEQ ID NO:2730 | CCTGTTGTGGAGTCAAGTGTTGATATACTTGAGGCATGTTATGTGTCTTCTAATTAAT | Homo sapiens mRNA for KIAA0957 protein, partial cds. [AB023174] |
| 379 | A_23_P70328 | CENPQ | SEQ ID NO:2731 | CAATGGCTTAGAGTTTGTGTCTGGTCATCTGGAACTTGAAAAATCCTGAAATGCTTCAC | Homo sapiens centromere protein Q (CENPQ), mRNA [NM_018132] |
| 380 | A_23_P70938 | STARD3NL | SEQ ID NO:2732 | GCATTAGTGTATGCCTGAAGTGTTGGACTTGCAAAGAGGAAGAAAGGAATTGGGAAT | Homo sapiens STARD3 N-terminal like (STARD3NL), mRNA [NM_032016] |
| 381 | A_23_P71430 | UBE2W | SEQ ID NO:2733 | AAATTGTTGAAAAGGTCCAGTTCTCAGTAGTACCATGTGAGTTAATGATACTACAGTAAGTTC | Homo sapiens ubiquitin-conjugating enzyme E2W (putative) (UBE2W), transcript variant 1, mRNA [NM_001014311] |
| 382 | A_23_P71433 | UBE2W | SEQ ID NO:2734 | CATGAGCCCTACTGCCTAAAACACTATTTCATTTATTTATGTTTGGAAACCCGTAAACAT | Homo sapiens ubiquitin-conjugating enzyme E2W (putative) (UBE2W), transcript variant 1, mRNA [NM_001014311] |
| 383 | A_23_P72503 | KLHL2 | SEQ ID NO:2735 | TTTTTGATATTTAACAATGCTTAAGACTTTAAATGCACTTCGAGGAATGGACTGGTG | Homo sapiens kelch-like 2, Mayven (Drosophila) (KLHL2), mRNA [NM_007246] |
| 384 | A_23_P7262 | MARCH1 | SEQ ID NO:2736 | GATTATTGTGTTGTTTTTGCATATTCATGTAAAAGTGATGTGTGAATGACATTGCAGTGAGC | Homo sapiens cDNA FLJ20668 fis, clone KAIA5S5. [AK000675] |
| 385 | A_23_P7282 | ELMOD2 | SEQ ID NO:2737 | TTCAAGTAGCTTGTCTGGGGGAAAAAGTACCACTTGGAGAGTTAAAGGAATTGGGATTT | ELMO domain-containing protein 2 [Source:Uniprot/SWISSPROT Acc:Q812Z1] [ENST00000323570] |
| 386 | A_23_P74001 | S100A12 | SEQ ID NO:2738 | TGAAGGCTTTTTTAGCCAGGAATGCCTCAATGAGGGTCTTTCTTCCCTCAGCAAAACC | Homo sapiens S100 calcium binding protein A12 (S100A12), mRNA [NM_005621] |
| 387 | A_23_P75028 | REEP3 | SEQ ID NO:2739 | AGAAACGAGGACGAAGTGTATTTTAGTCATGCATGAACAGGTGAAATATCCCAAGACAGATTAT | Homo sapiens receptor accessory protein 3 (REEP3), mRNA [NM_001001330] |
| 388 | A_23_P7543 | ZFYVE16 | SEQ ID NO:2740 | TCTGGTCAGCATTATCTAAATCATGTTGATAGTGCTCTGATACCTGTGATCCATGGTGG | Homo sapiens zinc finger, FYVE domain containing 16 (ZFYVE16), mRNA [NM_014733] |
| 389 | A_23_P75769 | MS4A4A | SEQ ID NO:2741 | GACCAAAAGATCAACAGACAGAACAAAATGCTCCAGAAATGTATGCTGACTGTGACAAGAGGCT | Homo sapiens membrane-spanning 4-domains, subfamily A, member 4 (MS4A4A), transcript variant 1, mRNA [NM_024021] |
| 390 | A_23_P76480 | BF213738 | SEQ ID NO:2742 | AAATCGAACAGGAGAATGGGTACAGTGGACCTAGATTTACGAAATCGTTGGCATGACAGG | BF213738 601847628F1 NIH_MCC_55 Homo sapiens cDNA clone IMAGE:4078519 5', mRNA sequence [BF213738] |

Fig. 7-22

| No. | Probe ID No. | Symbols of genes | Sequence | SEQ ID NO: | Descriptions of genes (letters and numbers within [ ] indicates GenBank accession No.) |
|---|---|---|---|---|---|
| 391 | A_23_P76799 | BAZ1A | TACACATGAATGAATCCAATGTTATAAGCTTGAAGTGCTGTACCAGTGCTGGCTGGAGGT | SEQ ID NO: 2743 | Homo sapiens bromodomain adjacent to zinc finger domain, 1A (BAZ1A), transcript variant 1, mRNA [NM_013448] |
| 392 | A_23_P76951 | TXNDC1 | ATTTCGTAATGTGCCCTTGTTCTGAGGCTCTGTTGCTGTGTGAATCCATTAGATTTACA | SEQ ID NO: 2744 | Homo sapiens thioredoxin domain containing 1 (TXNDC1), mRNA [NM_030755] |
| 393 | A_23_P77286 | C15orf29 | TGGTTTACAGTTAATGCTGTGATCTGTGTATTTTAAATTCGAACGTTTGTGTCACTAGCTCC | SEQ ID NO: 2745 | Homo sapiens chromosome 15 open reading frame 29 (C15orf29), mRNA [NM_024713] |
| 394 | A_23_P78092 | EVI2A | GCTGAATGCAGACACGTTGGAAAAACAAACAGCTCACGAGGACCGAAGGTAGTGATGCAA | SEQ ID NO: 2746 | Homo sapiens ecotropic viral integration site 2A (EVI2A), transcript variant 1, mRNA [NM_001003927] |
| 395 | A_23_P81248 | TAF7 | TGCTAGTTTGCATATGTTTCCTATGGAATAGTGTTTCGCAGTTATTCAAAGGCAGCTT | SEQ ID NO: 2747 | Homo sapiens TAF7 RNA polymerase II, TATA box binding protein (TBP)-associated factor, 55kDa (TAF7), mRNA [NM_005642] |
| 396 | A_23_P82047 | BU507302 | TCTGTTTCGTTAATGTCAGTGCCTGAACATTCAGCAGTTTATAAAATTGCTAATTTGTG | SEQ ID NO: 2748 | AGENCOURT_10309688 NIH_MGC_71 Homo sapiens cDNA clone IMAGE:6501220 5', mRNA sequence [BU507302] |
| 397 | A_23_P8281 | IFNGR1 | GTTTACATCGAGATAGGTTACAGTAAGGAACAGTATCCAGTAGTGCTGGTTGCGTAGGT | SEQ ID NO: 2749 | Homo sapiens interferon gamma receptor 1 (IFNGR1), mRNA [NM_000416] |
| 398 | A_23_P83073 | HIATL1 | AAACAACTCAAGACATTCTGGTGGCAACATAGAGATTGTAGGCTGCTTCTAAGAAGTTAT | SEQ ID NO: 2750 | Homo sapiens hippocampus abundant transcript-like 1 (HIATL1), mRNA [NM_032558] |
| 399 | A_23_P83094 | TLE4 | ACCTGCGTCTGAAAACACAGAATGGACTCTGTCCTGGGATGAGGACTTGCTTCTTT | SEQ ID NO: 2751 | Homo sapiens transducin-like enhancer of split 4 (E(sp1) homolog, Drosophila) (TLE4), mRNA [NM_007005] |
| 400 | A_23_P83175 | PTPLAD2 | CATGCTTTTTGTTGTGATCACCAGTCAAGAGGAAGTGCAAGAGAAATATGGGTGTGTGT | SEQ ID NO: 2752 | Homo sapiens protein tyrosine phosphatase-like A domain containing 2 (PTPLAD2), mRNA [NM_001010915] |
| 401 | A_23_P83278 | CHMP5 | CATTGCTGTTTTATTTTTCCATTAAGAGACTCATTGGTTGGGAAAATGGTTCTTCGTAC | SEQ ID NO: 2753 | Homo sapiens chromatin modifying protein 5 (CHMP5), mRNA [NM_016410] |
| 402 | A_23_P84070 | LARP7 | TGATTGCTAGAAGGGGATACAGAATGCCATGGTAGAATTAAGACTCCTGAGGATGCTCA | SEQ ID NO: 2754 | Homo sapiens La ribonucleoprotein domain family, member 7 (LARP7), transcript variant 1, mRNA [NM_016648] |
| 403 | A_23_P8513 | SNX10 | TTTAAGAGGGATCCTGACATGGATTAGAAGAGGATTTATGTTATTTGAGTTCACACTATTCTGTTT | SEQ ID NO: 2755 | Homo sapiens sorting nexin 10 (SNX10), mRNA [NM_013322] |
| 404 | A_23_P86653 | SRGN | AGGACTTGGGCTCAACATGGATTAGAAGAGAGACAGAGGATTTCCCAG | SEQ ID NO: 2756 | Homo sapiens serglycin (SRGN), mRNA [NM_002727] |
| 405 | A_23_P87879 | CD69 | TGTGCAATATGTGATGTGGCAAATGTCTCATTAGGAAAATATCTGTAATCTCAGAGCTAG | SEQ ID NO: 2757 | Homo sapiens CD69 molecule (CD69), mRNA [NM_001781] |
| 406 | A_23_P89755 | RNF138 | GTGACGGTCATAAGTAGAAGGCATAACACCTTGTGGATTGGCTTATGATGCTACTTTTAGTTAA | SEQ ID NO: 2758 | Homo sapiens ring finger protein 138 (RNF138), transcript variant 1, mRNA [NM_016271] |
| 407 | A_23_P9056 | RB1CC1 | TTGATTTCTGAAAGGGCATAAGTGATGGCTTATGATGAGGATATTAATTCC | SEQ ID NO: 2759 | Homo sapiens RB1-inducible coiled-coil 1 (RB1CC1), mRNA [NM_014781] |
| 408 | A_23_P91346 | BC008667 | GGGCTTAGGAGTGAGATTCTGGTGTACAGAATGATGCTCATGAATTTTGACATTT | SEQ ID NO: 2760 | Homo sapiens cDNA clone MGC:17708 IMAGE:3968595, complete cds. [BC008667] |

Fig. 7-23

| No. | Probe ID No. | Symbols of genes | Sequence | SEQ ID NO. | Descriptions of genes (letters and numbers within [ ] indicates GenBank accession No.) |
|---|---|---|---|---|---|
| 409 | A_23_P92410 | CASP3 | TGCACCAAGTCTCAGTGGGTGTCAGTATGACATTGACGGGAGATTTCTTGTTGGTCAAA | SEQ ID NO: 2761 | Homo sapiens caspase 3, apoptosis-related cysteine peptidase (CASP3), transcript variant alpha, mRNA [NM_004346] |
| 410 | A_23_P94216 | LONRF1 | GGGTCATTTATTGCCCAAGTTTAGAAGAGTAGGCGATACAAGTTTTGCAAATGAATTTG | SEQ ID NO: 2762 | Homo sapiens LON peptidase N-terminal domain and ring finger 1 (LONRF1), mRNA [NM_152271] |
| 411 | A_23_P94230 | LY96 | GTAAGGTATTTCTGGGAGGCGAGAAGAAATGGTCTGTTTTTGCTTGGAGTTTGTCATCCTACA | SEQ ID NO: 2763 | Homo sapiens lymphocyte antigen 96 (LY96), mRNA [NM_015364] |
| 412 | A_23_P94501 | ANXA1 | GGCTCTTGTGGAGGAAAGTAAACATTCCGTTGATGGTCTCAAGCTATGATCAGAAGACT | SEQ ID NO: 2764 | Homo sapiens annexin A1 (ANXA1), mRNA [NM_000700] |
| 413 | A_23_P95130 | SLC37A3 | TTGAGGGATACCTAATTTGCATTGGTTACGGGGATATTTTTCAAGCTCTTGCTTTATGT | SEQ ID NO: 2765 | Homo sapiens solute carrier family 37 (glycerol-3-phosphate transporter), member 3 (SLC37A3), transcript variant 1, mRNA [NM_207113] |
| 414 | A_23_P95594 | NAT1 | TCCTTGCAGAGAAAGCTGTGCCCAAACATGGTGATGATGAAGATTTTTACTATTAGAATAAG | SEQ ID NO: 2766 | Homo sapiens N-acetyltransferase 1 (arylamine N-acetyltransferase) (NAT1), mRNA [NM_000662] |
| 415 | A_23_P9574 | ECT2 | TAATAGTTAACTGAGTATAGATTGTTTCTATGGGATGTATGCCACTGTGAGAGTAG | SEQ ID NO: 2767 | Homo sapiens epithelial cell transforming sequence 2 oncogene (ECT2), mRNA [NM_018098] |
| 416 | A_23_P96085 | PTEN | ACAGAAGAATGACTTAGCAATCAAAGTGGACGCTATGAACAAAGAATGGGGTTGAAAA | SEQ ID NO: 2768 | Homo sapiens phosphatase and tensin homolog (mutated in multiple advanced cancers 1) (PTEN), mRNA [NM_000314] |
| 417 | A_23_P96382 | TIMM8B | TTGTTACTAAGGAGAGATTTAAGGGTCAGTGGGGGAAGGGTATCAACCCATTGTCAGATCAG | SEQ ID NO: 2769 | Homo sapiens translocase of inner mitochondrial membrane 8 homolog B (yeast) (TIMM8B), mRNA [NM_012459] |
| 418 | A_23_P98930 | C12orf35 | CCCATCTGAGGGAGGACGGTTCGTCAGTTAAGGACTTGTTTATTTAAATGGGACTGTAA | SEQ ID NO: 2770 | Homo sapiens chromosome 12 open reading frame 35 (C12orf35), mRNA [NM_018169] |
| 419 | A_23_P99163 | DRAM | CGTCAGGATGGAGTTTACCAGTGTACTTCATTTTCAGATCTCTGACAAATAAGCTGGAGCT | SEQ ID NO: 2771 | Homo sapiens damage-regulated autophagy modulator (DRAM), mRNA [NM_018370] |
| 420 | A_23_P99405 | ZMYM2 | GCTGGGTATTACGAGTGTAAATATCTGTGAGTGAAAGTTGCCATTATTGTAGTGGT | SEQ ID NO: 2772 | Homo sapiens zinc finger, MYM-type 2 (ZMYM2), mRNA [NM_003453] |
| 421 | A_23_P99442 | FLT3 | CGTTCTCGTTTACTCTTGTTTCAAAGGGACTTTTGTAAAATCAAATCATCCTGTCAGAA | SEQ ID NO: 2773 | Homo sapiens fms-related tyrosine kinase 3 (FLT3), mRNA [NM_004119] |
| 422 | A_23_P98853 | KIAA1370 | CTTTTTAGTGTTGAAGCAGTTCATTGGTTTATGTAATTTCAGGAGGAATAAAAACCCCAGTTAG | SEQ ID NO: 2774 | Homo sapiens KIAA1370 (KIAA1370), mRNA [NM_019600] |
| 423 | A_23_P99980 | HMGB1 | GGATTCTTGTTGCATTTGACATTTGTTTATGTAATTTCAGGAGGAATAGTGAACATCTGAGTC | SEQ ID NO: 2775 | Homo sapiens high-mobility group box 1 (HMGB1), mRNA [NM_002128] |
| 424 | A_23_P99985 | HMGB1 | TGGGGCAGTTTCTCAAACAAAGATGCAGATCAAAATAGGGTATATTTCCTATATAG | SEQ ID NO: 2776 | Homo sapiens high-mobility group box 1 (HMGB1), mRNA [NM_002128] |
| 425 | A_23_P100387 | GK | TAAAAGGTTCTGTTTTTGTTTGGAATCAATGGTAGCTTTATTGACTGTTCTGATTTGCTG | SEQ ID NO: 2777 | Homo sapiens glycerol kinase (GK), transcript variant 1, mRNA [NM_203391] |
| 426 | A_24_P105646 | BX111927 | TTATGAGATGCTTAGGAAATGCAGCAATAACAGTGCAGTAATTGACCTATATCTAAAAGACTGCC | SEQ ID NO: 2778 | BX111927 Soares multiple sclerosis 2NbMSP Homo sapiens cDNA clone IMAGp998G05619, mRNA sequence [BX111927] |
| 427 | A_24_P105913 | THC2606573 | CTGTGCCTGTAGGAAATGCAGCAAATACCAAAGGTCAATGTGAAATATGGGCATGTTTGCC | SEQ ID NO: 2779 | AV151386 NAP1 (Homo sapiens) (exp=-1; wgp=0; cg=0) partial (35%) [THC2606573] |

Fig. 7-24

| No. | Probe ID No. | Symbols of genes | Sequence | SEQ ID NO: | Descriptions of genes (letters and numbers within [ ] indicates GenBank accession No.) |
|---|---|---|---|---|---|
| 428 | A_24_P107257 | LIN7C | TATTAGTGTGGGACTGTGTGACTGAGGTCTTAAAGAGTGAAAGAGTTGGGGTTCATTTCTG | SEQ ID NO: 2780 | Homo sapiens lin-7 homolog C (C. elegans) (LIN7C), mRNA [NM_018362] |
| 429 | A_24_P11045 | THC2785765 | CCACCAGAAACGTACACGTGATTTTCATGAGAAATACGGTAGCAACACAAGTCGGAATAG | SEQ ID NO: 2781 | COX7B_HUMAN (P24311) Cytochrome c oxidase polypeptide VIIb, mitochondrial precursor, partial (78%) [THC2785765] |
| 430 | A_24_P114249 | GALNT3 | ATTTCAAATGCAGAATACTTGACTCATTTAAAGCTAAATTTTGTTACTGATTGAATTATA | SEQ ID NO: 2782 | Homo sapiens UDP-N-acetyl-alpha-D-galactosamine:polypeptide N-acetylgalactosaminyltransferase 3 (GalNAc-T3) (GALNT3), mRNA [NM_004482] |
| 431 | A_24_P115774 | BIRC2 | GATACCATTTTGGTTAAAGGAAATGCTGCGGGCCAACATCTTCAAAAACTGTAAAAGAA | SEQ ID NO: 2783 | Homo sapiens baculoviral IAP repeat-containing 2 (BIRC2), mRNA [NM_001166] |
| 432 | A_24_P116766 | ZNF207 | TTTCTGAGACCCAGGTATACCAGTGAAAATTAGGTTCTGAGTAAATTTCTAATTTATGCC | SEQ ID NO: 2784 | Homo sapiens mRNA; cDNA DKFZp761N202 (from clone DKFZp761N202). [AL834501] |
| 433 | A_24_P123521 | CLK4 | CCCACACGTGAAAAACACAGAGATATCAAGTTGACTTTGAAGTGCAACGTATGATGAT | SEQ ID NO: 2785 | Homo sapiens CDC-like kinase 4 (CLK4), mRNA [NM_020666] |
| 434 | A_24_P124325 | IKZF5 | GCTACAACTCTCAACTTCAAGTTAAGGCTAGAGATTACTTTGAAAAATTGCACTCGG | SEQ ID NO: 2786 | Homo sapiens mRNA; cDNA DKFZp781B0249 (from clone DKFZp781B0249). [CR749800] |
| 435 | A_24_P124992 | PSMA4 | AAAGTCGCTTTGGTGTTCATTGCTGTACATTGGGTGGGGATAAGCACTATGGCTTTCAG | SEQ ID NO: 2787 | Homo sapiens proteasome (prosome, macropain) subunit, alpha type 4 (PSMA4), mRNA [NM_002789] |
| 436 | A_24_P126060 | DDX3X | TGTGAAGGAGCAGCTTGTCTGTCTAGGAAGGGACTAGATTGTAAAATTTATTTGGGACGG | SEQ ID NO: 2788 | Homo sapiens DEAD (Asp-Glu-Ala-Asp) box polypeptide 3, X-linked (DDX3X), mRNA [NM_001356] |
| 437 | A_24_P126741 | ENST00000309178 | AGCCTCAACCTCAAGCACTAACAAGATTCAAGATTACTTGCAACAGCTGACGAGGAGAAT | SEQ ID NO: 2789 | |
| 438 | A_24_P129232 | SERINC1 | CAGGTCAGAGAAATGATGGAATGTTTTAGAATAAACTCCTGCTTATAGTATACTACACAG | SEQ ID NO: 2790 | Homo sapiens serine incorporator 1 (SERINC1), mRNA [NM_020755] |
| 439 | A_24_P132787 | RAB18 | TAAAACGTCACATTCTACGTTGATTACAGCTTGGTACGTGTAGATTACATGTCGTTGAAGG | SEQ ID NO: 2791 | Homo sapiens RAB18, member RAS oncogene family (RAB18), mRNA [NM_021252] |
| 440 | A_24_P133991 | ANKRD12 | TTTGGAATGGAGTATATGGCCGAAAAGGTTTTGGATTCAGAAAGAAAAAGGATGGTTAGT | SEQ ID NO: 2792 | Homo sapiens ankyrin repeat domain 12 (ANKRD12), mRNA [NM_015208] |
| 441 | A_24_P137897 | IFRD1 | AACCAAAGGTAGAAGCAAGTCGAGAATCCAAAGTGGAGAATTCTTCTAGAT | SEQ ID NO: 2793 | Homo sapiens interferon-related developmental regulator 1 (IFRD1), transcript variant 2, mRNA [NM_001007245] |
| 442 | A_24_P139208 | USP25 | CAATATACAGGCAAGGTGATTATTTCAAGAGAATCCCAAAGTAGTTGAATAAGGGCTATTG | SEQ ID NO: 2794 | Homo sapiens ubiquitin specific peptidase 25 (USP25), mRNA [NM_013396] |
| 443 | A_24_P148151 | TSNAX | AAAGTTGAGTTATATAGTTGTAGATACAACATGGCTGTTTAGTAGTGATTATTTAGCA | SEQ ID NO: 2795 | Homo sapiens translin-associated factor X (TSNAX), mRNA [NM_005999] |
| 444 | A_24_P150874 | BX647930 | GTATATTTGTAATAACCCGTAGATACTGTACCTAAGCAAACATGACTCGTATTAGGTC | SEQ ID NO: 2796 | Homo sapiens mRNA; cDNA DKFZp686I20201 (from clone DKFZp686I20201). [BX647930] |
| 445 | A_24_P153511 | OSBPL8 | CGTTGTGTCCATATACACACAAAATTTGTGGAAGGCAGTTTAACTTTGTGAAGAATATC | SEQ ID NO: 2797 | Homo sapiens oxysterol binding protein-like 8 (OSBPL8), transcript variant 1, mRNA [NM_020841] |
| 446 | A_24_P157415 | ATP11B | CTGTACTGTAACACAGGCTGTAAAGTTAGGCAATATAAAATGGAAGGGTATATCATATAC | SEQ ID NO: 2798 | Homo sapiens ATPase, Class VI, type 11B (ATP11B), mRNA [NM_014616] |

Fig. 7-25

| No. | Probe ID No. | Symbols of genes | Sequence | SEQ ID NO: | Descriptions of genes (letters and numbers within [ ] indicates GenBank accession No.) |
|---|---|---|---|---|---|
| 447 | A_24_P165616 | AK023645 | AAGATTGAATGGCTAGGAGTAATTGTGTTGTCGTATAGGCAACTT AACTTCACTGTGGAA | SEQ ID NO: 2799 | Homo sapiens cDNA FLJ13563 fis, clone PLACE1009050. [AK023645] |
| 448 | A_24_P166094 | ARFIP1 | TCATTCCTTCCTGTATATTTGTACTCAGAGAGGCTTATTTTATC TTCCAGCAGAATTAC | SEQ ID NO: 2800 | Homo sapiens ADP-ribosylation factor interacting protein 1 (arfaptin 1) (ARFIP1), transcript variant 1, mRNA [NM_001025595] |
| 449 | A_24_P166794 | BC047111 | AGCTTACAGTGTTTCAAGGTGTGATTTATTTCAAAATGGAGTG AGTCTGAACATCACT | SEQ ID NO: 2801 | Homo sapiens cDNA clone IMAGE:5314178. [BC047111] |
| 450 | A_24_P167063 | ZNF518 | AAAGAAAGGCATACATAGAATCGTCAAGTATCTTGGTATGCAC ATTATACTTGTACTG | SEQ ID NO: 2802 | Homo sapiens zinc finger protein 518 (ZNF518), mRNA [NM_014803] |
| 451 | A_24_P172481 | TRIM22 | TGGCCCTTAAAAGATTGAAGAAGAGAAACTTGTCAAGTCATATC CACGTTATCTAGCAA | SEQ ID NO: 2803 | Homo sapiens tripartite motif-containing 22 (TRIM22), mRNA [NM_006074] |
| 452 | A_24_P175059 | ATG5 | TTGACAAGAGGGTCGTCTCAAATATGATTGTTCAGATTAAGAGTG TTTATTCGTCGGTTC | SEQ ID NO: 2804 | Homo sapiens ATG5 autophagy related 5 homolog (S. cerevisiae) (ATG5), mRNA [NM_004849] |
| 453 | A_24_P175176 | PHTF2 | AGATTGAGGTTAACTTAGACTGGGAGTTGATTATTAAGTACAG TATACCTCAACAG | SEQ ID NO: 2805 | Homo sapiens putative homeodomain transcription factor 2 (PHTF2), mRNA [NM_020432] |
| 454 | A_24_P175167 | SAMD9 | CAACAGCGATACGTAATCAAAATGTAATTTTCGCGTAATAAAAT TATGGATATGGGCAG | SEQ ID NO: 2806 | Homo sapiens sterile alpha motif domain containing 9 (SAMD9), mRNA [NM_017654] |
| 455 | A_24_P175188 | SAMD9 | TGGCAATGTACTGGCAGATTAACATACAACCTATGTTTTGAACAA AAACAACCACGGATA | SEQ ID NO: 2807 | Homo sapiens sterile alpha motif domain containing 9 (SAMD9), mRNA [NM_017654] |
| 456 | A_24_P180424 | TMEM30A | CAATGTGTATGCACATTCGTTTAGTTAAGGCACCAATTGTTTTG GTTGGTTTTTCGTAAG | SEQ ID NO: 2808 | Homo sapiens transmembrane protein 30A (TMEM30A), mRNA [NM_018247] |
| 457 | A_24_P18105 | ASPH | GGTCTCTTGAAATAATCCTTTGTCAGAAAGAGGTAGGTACCA CATCATTTTGAAAGG | SEQ ID NO: 2809 | Homo sapiens aspartate beta-hydroxylase (ASPH), transcript variant 3, mRNA [NM_032466] |
| 458 | A_24_P183864 | IMPA1 | TCAGCCTTATCCTTTGGCACGTAAACAGAGTACTAGAGTTATTGT AGGTTCGTTTGAGCT | SEQ ID NO: 2810 | Homo sapiens inositol(myo)-1(or 4)-monophosphatase 1 (IMPA1), mRNA [NM_005536] |
| 459 | A_24_P190804 | AP1S2 | GGTGAAGATCTAAGGAGTCTGTCATGTACTTCATTAAAAATAAC ATGGAGCATACTG | SEQ ID NO: 2811 | Homo sapiens adaptor-related protein complex 1, sigma 2 subunit (AP1S2), mRNA [NM_003916] |
| 460 | A_24_P191417 | NAB1 | AAGTTTGCTTAACTATATCTTATGTTTGTAGTGTCTTCAAGCTTAGTG ATAAGGTGGAGCAC | SEQ ID NO: 2812 | Homo sapiens NGFI-A binding protein 1 (EGR1 binding protein 1) (NAB1), mRNA [NM_005966] |
| 461 | A_24_P196351 | PLXNC1 | ACCTCAAACAACAAAACAAAACTACCAAATAGAATGACAGATCAGAATAA AGGTGAGAGGTCTGG | SEQ ID NO: 2813 | Homo sapiens mRNA for plexin C1 variant protein. [AB208934] |
| 462 | A_24_P20120 | KIAA1212 | TTGGAGAATGAAAATGCCTTAAAAGGAATGCATATGGATAAAGTT GCACTTATAACACCC | SEQ ID NO: 2814 | Homo sapiens KIAA1212 (KIAA1212), mRNA [NM_018084] |
| 463 | A_24_P201702 | CLEC2B | ATTGAATCGAAGTAAGTAAATACAACGTTCCACTCAAGATGCGGACC TAACTATAATTGACA | SEQ ID NO: 2815 | Homo sapiens C-type lectin domain family 2, member B (CLEC2B), mRNA [NM_005127] |
| 464 | A_24_P208045 | EDEM3 | TTTAGAACGGGGGTAGAATTTAGTAAATATTGGACAGGGGCTGGTTT ATGCACAAGGCTTCA | SEQ ID NO: 2816 | Homo sapiens ER degradation enhancer, mannosidase alpha-like 3 (EDEM3), mRNA [NM_025191] |
| 465 | A_24_P208867 | IL18R1 | GGGAGCCTCTTGATGATCTCAAAAAATAATAGGTATTGAAGAAA TCACCAAGTGACTGT | SEQ ID NO: 2817 | Homo sapiens interleukin 18 receptor 1 (IL18R1), mRNA [NM_003855] |
| 466 | A_24_P20996 | BC043173 | CTTGGAAAATGTTCATATATATAGTATATGAATGTCGTTTATGTGTC AAGGGCTGATTGG | SEQ ID NO: 2818 | Homo sapiens cDNA clone IMAGE:5287121 [BC043173] |

Fig. 7-26

| No. | Probe ID No. | Symbols of genes | Sequence | SEQ ID NO: | Descriptions of genes (letters and numbers within [ ] indicates GenBank accession No.) |
|---|---|---|---|---|---|
| 467 | A_24_P216654 | SOAT1 | GGCAGTAATGTCTGGGACAACAGAGTATTGTAATTGTAATGGAATCATAACCTGGTAAGTAG | SEQ ID NO: 2819 | Homo sapiens sterol O-acyltransferase (acyl-Coenzyme A: cholesterol acyltransferase) 1 (SOAT1), transcript variant 688113, mRNA [NM_003101] |
| 468 | A_24_P223124 | FNDC3B | CTCACTGTTGGACATACATTCCAAGCTTTCAACTCTAGGAGAAAAAGAAAATCATGTTT | SEQ ID NO: 2820 | Homo sapiens fibronectin type III domain containing 3B (FNDC3B), mRNA [NM_022763] |
| 469 | A_24_P225308 | ARID4B | GTTGAAAATGGTTTCAAGTTATTCAAATTGTACAGGAGTGTAAAGATTTGTTGACAGCA | SEQ ID NO: 2821 | Homo sapiens AT rich interactive domain 4B (RBP1-like) (ARID4B), transcript variant 1, mRNA [NM_016374] |
| 470 | A_24_P225719 | PREI3 | GACTATTTTGTTAGTGAATATTTATAGTAAGGTAGTGACTGAGATTTGGTGATCTGGCTG | SEQ ID NO: 2822 | Homo sapiens preimplantation protein 3 (PREI3), transcript variant 1, mRNA [NM_015387] |
| 471 | A_24_P235429 | ABCA1 | CCAAAGAGCCATGTCATGTCAATACTGAACCACTTGATATTGAGACATTAATTTGTAC | SEQ ID NO: 2823 | Homo sapiens ATP-binding cassette, sub-family A (ABC1), member 1 (ABCA1), mRNA [NM_005502] |
| 472 | A_24_P235988 | CLEC7A | TTTTTCCAGTAATTACGTGTAAAATGCTATTATTGGAATGAAACTATATTCCTCATGT | SEQ ID NO: 2824 | Homo sapiens C-type lectin domain family 7, member A (CLEC7A), transcript variant 1, mRNA [NM_197947] |
| 473 | A_24_P236008 | SCYL2 | ATAGACTATGTACTTGTCTCTGGTTTTTTGTTTGTTTTATTTTGAATGGTTATAAGCCTCC | SEQ ID NO: 2825 | Homo sapiens mRNA for KIAA1360 protein, partial cds. [AB037781] |
| 474 | A_24_P236799 | RAB31 | ATTAAAGAGCTGAACTGTATTCAGACCGACTGGGTATGTAGGTACTGTTTAACATC | SEQ ID NO: 2826 | Homo sapiens RAB31, member RAS oncogene family (RAB31), mRNA [NM_006868] |
| 475 | A_24_P242299 | ZRANB2 | GACTTTTGAAAGTGTACGTTCTAAATTGCCCGACGATGCGAGATTCTACATGTTACCAT | SEQ ID NO: 2827 | Homo sapiens zinc finger, RAN-binding domain containing 2 (ZRANB2), transcript variant 1, mRNA [NM_005455] |
| 476 | A_24_P248606 | ACSL3 | GTATTTGATGATAGGACATTGCAGTAAGACACATGAAGAATTTAAGTTTATAACGCGGGTGAG | SEQ ID NO: 2828 | Homo sapiens acyl-CoA synthetase long-chain family member 3 (ACSL3), transcript variant 1, mRNA [NM_004457] |
| 477 | A_24_P250922 | PTGS2 | TGAGATATTTAAGGTTGAATGTTTCCTTAGGATAGGCCTATGTGCTAGGGCACAAAGA | SEQ ID NO: 2829 | Homo sapiens prostaglandin-endoperoxide synthase 2 (prostaglandin G/H synthase and cyclooxygenase) (PTGS2), mRNA [NM_000963] |
| 478 | A_24_P251221 | PPP2R5A | TGAATTCTTCTTTGATTGTGTTGCACATAGATATGTAGTCTGCTGTGTATATTTCCC | SEQ ID NO: 2830 | Homo sapiens protein phosphatase 2, regulatory subunit B', alpha isoform (PPP2R5A), mRNA [NM_006243] |
| 479 | A_24_P251326 | ZMYM6 | AGCACTATTTAAATACAGTGTGTGTAACTCAGTTTTGGATAAATGCAAAGAGACAAGTTACCC | SEQ ID NO: 2831 | Homo sapiens zinc finger, MYM-type 6 (ZMYM6), mRNA [NM_007167] |
| 480 | A_24_P257151 | CLK1 | TATGCAGTCGTGTGAATTTTGACACAGTAATAAGTTGAGTGACACAGACTTAAAGGCTG | SEQ ID NO: 2832 | Homo sapiens CDC-like kinase 1 (CLK1), transcript variant 1, mRNA [NM_004071] |
| 481 | A_24_P263144 | BMX | CAGACTGCAGGAGGTGTTTCATTACTGTCAAATACAGAGCAAGTCAGACGTATGGCATTTG | SEQ ID NO: 2833 | Homo sapiens BMX non-receptor tyrosine kinase (BMX), mRNA [NM_001721] |
| 482 | A_24_P263524 | TXNDC9 | TGACTCAGCACAGAAAACTTTAGAATGGGGGGCTAGGTGTTCTGACATTCTTAATTACAG | SEQ ID NO: 2834 | Homo sapiens thioredoxin domain containing 9 (TXNDC9), mRNA [NM_005783] |
| 483 | A_24_P265856 | SENP7 | TTGTGTGTTGGGGGTACTTTTAAAGGTGAGTATTGTTTTGTACATCTAATTTGTTGGGA | SEQ ID NO: 2835 | Homo sapiens SUMO1/sentrin specific peptidase 7 (SENP7), transcript variant 1, mRNA [NM_020654] |

Fig. 7-27

| No. | Probe ID No | Symbols of genes | Sequence | SEQ ID NO: | Descriptions of genes (letters and numbers within [ ] indicates GenBank accession No.) |
|---|---|---|---|---|---|
| 484 | A_24_P268786 | MYNN | TGGAGAGGATCATAGTTGAGTGAAGAGGATTGCATAGAAAAAGTCCTTTATCAGAAAC | SEQ ID NO: 2836 | Homo sapiens myoneurin (MYNN), mRNA [NM_018657] |
| 485 | A_24_P268917 | RAB33B | CCCAGAATCTAATGTAGTTCGCTATTAATAACAATGCATTATTGAAGTATATTGCAAAT | SEQ ID NO: 2837 | Homo sapiens RAB33B, member RAS oncogene family (RAB33B), mRNA [NM_031296] |
| 486 | A_24_P274615 | ARRDC3 | AGCAAAACAAAGTGCAATATAAATGTTTGGTTTAATAGATTATATTCTATGGCTGTTTGT | SEQ ID NO: 2838 | Homo sapiens arrestin domain containing 3 (ARRDC3), mRNA [NM_020801] |
| 487 | A_24_P276583 | TMCO1 | CCCTCATTTCCTGTATATTGTGTGTAGTATGTCGATTCGACAGAAGATTGAGAAGAATTC | SEQ ID NO: 2839 | Homo sapiens transmembrane and coiled-coil domains 1 (TMCO1), mRNA [NM_019026] |
| 488 | A_24_P278460 | MLSTD2 | ACCATGGAACAATAGGTTAGGAATTAGAGGAAGCCAGTCCTTACTTACAGTTCTGTCTG | SEQ ID NO: 2840 | Homo sapiens male sterility domain containing 2 (MLSTD2), mRNA [NM_032228] |
| 489 | A_24_P285501 | ZNF650 | CATGGTATAATGTATTCAGAGTTTGATTACTACTTATTTAAAATGGAATGTTTTATGTT | SEQ ID NO: 2841 | Homo sapiens zinc finger protein 650 (ZNF650), mRNA [NM_172070] |
| 490 | A_24_P286054 | ZFYVE16 | GTGTATGTATTGTGCCATGCTAAGCTAAGTAATTGAACAGTGTTAAAATAACCAAATGGTAGGGG | SEQ ID NO: 2842 | Zinc finger FYVE domain-containing protein 16 (Endofin) (Endosome- associated FYVE domain protein). [Source:Uniprot/SWISSPROT;Acc:Q7Z3T8] [ENST00000380248] |
| 491 | A_24_P28657 | AHCTF1 | AACAGACGCCTGTTGCTACAGACAAGTGTGTCGAATTAAGGAAATGTACTTGATGTA | SEQ ID NO: 2843 | Homo sapiens AT hook containing transcription factor 1 (AHCTF1), mRNA [NM_015446] |
| 492 | A_24_P287756 | NUDT21 | CCCATAGTTAGTTCAGTTGTGTTATACATCACTGATTATTTGGGTTAAACTGGACTCATTTC | SEQ ID NO: 2844 | Homo sapiens nudix (nucleoside diphosphate linked moiety X)-type motif 21 (NUDT21), mRNA [NM_007006] |
| 493 | A_24_P290257 | A_24_P290257 | CCAATTCATTCAACATAGAACAAGCCAATTATACCATCCAGTCATTGAAGGACAGGAAGA | SEQ ID NO: 2845 | |
| 494 | A_24_P29277 | COL4A3BP | TTAAAGTACCTTGGGAGTGTGTAGAGTAAGTTCTATAATAGCTTTATGATCGTGATATG | SEQ ID NO: 2846 | Goodpasture antigen-binding protein (EC 2.7.11.9) (GPBP) (Collagen type IV alpha-3-binding protein) (StAR-related lipid transfer protein 11) (StARD11) (START domain-containing protein 11). [Source:Uniprot/SWISSPROT;Acc:Q9Y5P4] [ENST00000380494] |
| 495 | A_24_P295543 | BLOC1S2 | GTTTATTTCTATGTGAGTCACATTGACATGGGATCAGTTTGGGAAATGTGATGAAAACA | SEQ ID NO: 2847 | Homo sapiens biogenesis of lysosome-related organelles complex-1, subunit 2 (BLOC1S2), transcript variant 2, mRNA [NM_001001342] |
| 496 | A_24_P2995 | PUM2 | TTTTTGAATAGCTACTTCCCAAGTAAGAGCAAAATGTATGATAACATTTTCCTGTGG | SEQ ID NO: 2848 | Homo sapiens pumilio homolog 2 (Drosophila) (PUM2), mRNA [NM_015317] |
| 497 | A_24_P30194 | IFIT5 | AATGGGCTCTCTAAGTAATGTATAGTTCTTTGATTACCGACATCACGAATTATGTAGGACAGA | SEQ ID NO: 2849 | Homo sapiens interferon-induced protein with tetratricopeptide repeats 5 (IFIT5), mRNA [NM_012420] |
| 498 | A_24_P303454 | TIAM2 | GCAGAATTGAGTGTGTCCAGAGTTAACATGTGTGTGAGTGAGGAGTGTTTTATGAAAAC | SEQ ID NO: 2850 | Homo sapiens T-cell lymphoma invasion and metastasis 2 (TIAM2), transcript variant 1, mRNA [NM_012454] |
| 499 | A_24_P303647 | FLJ31818 | ACTGTATGGGTACTCCTAAGAATATTCATTTTGGATATAAAGAAGTTATGAGGGCTGC | SEQ ID NO: 2851 | Homo sapiens hypothetical protein FLJ31818 (FLJ31818), mRNA [NM_152556] |

Fig. 7-28

| No. | Probe ID No. | Symbols of genes | Sequence | SEQ ID NO. | Descriptions of genes (letters and numbers within [ ] indicates GenBank accession No.) |
|---|---|---|---|---|---|
| 500 | A_24_P303852 | GNAQ | GCTTTTGGTAGAAGACAGAAAAAAACAGAAGAAGGTATTCGTTGGTAGAAAC ATTTTAAGTTCAGG | SEQ ID NO: 2852 | Guanine nucleotide-binding protein G(q) subunit alpha (guanine nucleotide-binding protein alpha-q). [Source:Uniprot/SWISSPROT:Acc:P50148] [ENST00000376611] |
| 501 | A_24_P307395 | A_24_P307395 | CTCCCTGTTTATGTGGACATGATTGAACTCCAACTTAAATTGCA GGGGTGTGTTTCCAT | SEQ ID NO: 2853 | |
| 502 | A_24_P310894 | CAPZA1 | TGTATATATTGTCCTTCATACAGTACATGGATGCATACCAGCATGTT GTGATGCAGGTAGTC | SEQ ID NO: 2854 | Homo sapiens capping protein (actin filament) muscle Z-line, alpha 1 (CAPZA1), mRNA [NM_006135] |
| 503 | A_24_P312417 | ZBTB26 | AGAGGAGGAAGATTTTTAAAACCTTTATCATTGAGGATTGTATT TTATGGATCCCAGG | SEQ ID NO: 2855 | Zinc finger and BTB domain-containing protein 26 (Zinc finger protein 481) (Zinc finger protein Biorex). [Source:Uniprot/SWISSPROT:Acc:Q9HCK0] [ENST00000373656] |
| 504 | A_24_P317604 | SLC37A3 | CCCGGCTGTCTTTGTTGGGCTATTGAGGTTTAGGCTTTTAACGTTA ACTGTGTTTTGGAC | SEQ ID NO: 2856 | Homo sapiens solute carrier family 37 (glycerol-3-phosphate transporter), member 3 (SLC37A3), transcript variant 1 mRNA [NM_207113] |
| 505 | A_24_P320328 | SUB1 | CAGAAAAAGGTGTAAAGAACAAAAGACAAGTGAGGTTGAGAG CCGTGTCATCTTCTA | SEQ ID NO: 2857 | Homo sapiens SUB1 homolog (S. cerevisiae) (SUB1), mRNA [NM_006713] |
| 506 | A_24_P322353 | PSTPIP2 | AGAATCTTCCCTTGCTAGACGCCAGAATTTAAATGCATCGTC TTACAGTTTCACAAA | SEQ ID NO: 2858 | Homo sapiens proline-serine-threonine phosphatase interacting protein 2 (PSTPIP2), mRNA [NM_024430] |
| 507 | A_24_P324506 | A_24_P324506 | GCAATAAGGCAGCTAATACGAAATACAAGTATGGCTATTCCT GTGACATGCTGTGT | SEQ ID NO: 2859 | |
| 508 | A_24_P324577 | KIAA1466 | AAGAATTTAAGTAGCCCCCCTGAAGTTAGAGTTAAAGAAGGATAT TAAGTGCCAGTGCCA | SEQ ID NO: 2860 | Homo sapiens mRNA for KIAA1466 protein, partial cds. [AB040899] |
| 509 | A_24_P324581 | KIAA1466 | ATAATAGCTCATAGAATGAATTGCTGTACCAACCAAGCAGCTAAAA GAATTTAAGTAGCCC | SEQ ID NO: 2861 | Homo sapiens mRNA for KIAA1466 protein, partial cds. [AB040899] |
| 510 | A_24_P324886 | DOCK4 | ATTTTCCCTCTTTGTTGGGAAGGTCATTTTAGTTAGTTAACCATGTT TGTTTGTTGGTAGC | SEQ ID NO: 2862 | Homo sapiens dedicator of cytokinesis 4 (DOCK4), mRNA [NM_014705] |
| 511 | A_24_P325176 | KIAA1109 | TTGATCCAGTAGGGTCGTTGATTATATTCTTCAAAAATTGGGCTTTC ATGATGGTAGGACTA | SEQ ID NO: 2863 | Homo sapiens KIAA1109, mRNA (cDNA clone IMAGE:3924663), complete cds. [BC108274] |
| 512 | A_24_P330397 | STRN3 | ATGTGTAACTAAAGATTTTGTTTGTGTAATGCATGATTAAGACA ATAAAGTATTTTTC | SEQ ID NO: 2864 | Homo sapiens striatin, calmodulin binding protein 3 (STRN3), mRNA [NM_014574] |
| 513 | A_24_P333213 | A_24_P333213 | GACCATATATCAGAATCAGAAGGTACGCAAATCTGAAGTCAGTAAATG AAGTGATACAAGG | SEQ ID NO: 2865 | |
| 514 | A_24_P333112 | A_24_P333112 | GGTCATCAGAATGAGAAGGTATGTAAGTGTGAGCCCACAGGAGCAA AAGGTATTGGAACTT | SEQ ID NO: 2866 | |
| 515 | A_24_P336728 | LPGAT1 | ATATCCCGTGGATTTCACTTGCATTGTGCAATAAGGAAAAAGGAGACA CATATGTGAATGGG | SEQ ID NO: 2867 | Homo sapiens lysophosphatidylglycerol acyltransferase 1 (LPGAT1), mRNA [NM_014873] |
| 516 | A_24_P351906 | STEAP4 | ATATCCCGTGGATTTCACTTGCATTGTGCAATAAGGAAAAAGGAGACA GTTGATAAAAGTTCT | SEQ ID NO: 2868 | Homo sapiens STEAP family member 4 (STEAP4), mRNA [NM_024636] |
| 517 | A_24_P354412 | AK091335 | TGTAGAGTGAAGGAGTCTTCAAAACACCCAGGCATTAAATGTCA CTCTGCGGCTGCTTCT | SEQ ID NO: 2869 | Homo sapiens cDNA FLJ34016 fis, clone FCBBF2002541 [AK091335] |
| 518 | A_24_P354854 | CCDC126 | AATGGAAGTCTTGACGGACTTAGCGACTTAGTGTATATAAAGGTA CTTTGTGCTGCATT | SEQ ID NO: 2870 | Homo sapiens coiled-coil domain containing 126 (CCDC126), mRNA [NM_138771] |

Fig. 7-29

| No. | Probe ID No. | Symbols of genes | Sequence | SEQ ID NO: | Descriptions of genes (letters and numbers within [ ] indicates GenBank accession No.) |
|---|---|---|---|---|---|
| 519 | A_24_P355816 | DRAM | ATAATATAGAATGGAATTTAGTGTGCTTTACCAGTTAGTTTCATAATAAACAAATAGTCT | SEQ ID NO: 2871 | Homo sapiens damage-regulated autophagy modulator (DRAM), mRNA [NM_018370] |
| 520 | A_24_P357576 | KIAA1370 | TGCTGCATATGAACTCAAATGTTACACTGAATCACGAACAAACCCTCAGTTTTCACCAAG | SEQ ID NO: 2872 | Homo sapiens KIAA1370 (KIAA1370), mRNA [NM_019600] |
| 521 | A_24_P362646 | TXNDC9 | GTCCACATTCAGGTGTGAAAATAGTAGAGAGAGATCTGGCAATATTGTCCAAGAAACACCT | SEQ ID NO: 2873 | Homo sapiens thioredoxin domain containing 9 (TXNDC9), mRNA [NM_005783] |
| 522 | A_24_P364025 | UBE2D1 | ATGTATGGGTGTAGTCATTAGGAAAGCATTAAATCACTTGAGTATTTTGTCATGGTTC | SEQ ID NO: 2874 | Homo sapiens ubiquitin-conjugating enzyme E2D 1 (UBC4/5 homolog, yeast) (UBE2D1), mRNA [NM_003338] |
| 523 | A_24_P364066 | BC030112 | AATGTCTATTACGGTTTGGGATAGTATATTTCTCTCAGTTCTGAGTGATTTAAATGTGACC | SEQ ID NO: 2875 | Homo sapiens cDNA clone IMAGE:4799578 [BC030112] |
| 524 | A_24_P364807 | AYTL1 | TGTAACTCTTGTTTGTAGGTAATCGTTCTCTCTCAAGAAAGTGTCAAGGGTCTGTGTAA | SEQ ID NO: 2876 | Homo sapiens mRNA; cDNA DKFZp686H22112 (from clone DKFZp686H22112) [BX641069] |
| 525 | A_24_P370096 | ZNF230 | GAAAACCTATATTTGTGAGAAATGTGGAGGGCTTGATTCACGATTTAAAGCTTCAGAA | SEQ ID NO: 2877 | Homo sapiens zinc finger protein 230 (ZNF230), mRNA [NM_006300] |
| 526 | A_24_P370172 | LILRA5 | AGGCAGAGGAGGTGGATGCTCAGATGTATGGCTGCGAGGCATATCCTGCAGGTATGGTCA | SEQ ID NO: 2878 | Homo sapiens leukocyte immunoglobulin-like receptor, subfamily A (with TM domain), member 5 (LILRA5), transcript variant 3, mRNA [NM_181879] |
| 527 | A_24_P371053 | ORMDL1 | GAATGAAAAGAGTTACAGAGGAAGTTAAACATCAATTCAATCAATTGTGTGAGTAAAGTGAGTTTTGG | SEQ ID NO: 2879 | Homo sapiens ORM1-like 1 (S. cerevisiae) (ORMDL1), mRNA [NM_016467] |
| 528 | A_24_P372625 | RNF141 | CTATGTAGTGGAATTTAGAGGTTGAGAATAAAAGTGGATGTGTGTTATTGTTAGTAGCCACTG | SEQ ID NO: 2880 | Homo sapiens ring finger protein 141 (RNF141), mRNA [NM_016422] |
| 529 | A_24_P374319 | RAP2C | ATTGTGTGATGTTCAAATAAAGTGCTACATTCATGATGATTTATGGGTCAGGATG | SEQ ID NO: 2881 | Homo sapiens RAP2C, member of RAS oncogene family (RAP2C), mRNA [NM_021183] |
| 530 | A_24_P379379 | CAPZA1 | ACCAGTTCAGCCTAAAAAGTTCTGGAATGGTCGTTGGAGATCAGAGTGGAAGTCACCA | SEQ ID NO: 2882 | Homo sapiens capping protein (actin filament) muscle Z-line, alpha 1 (CAPZA1), mRNA [NM_006135] |
| 531 | A_24_P380679 | FLJ39575 | GAACCTGGATTAGTTCCAGCAATGAAAGTAAGACAGACAAGGCATAAAGACATAAGACACAGT | SEQ ID NO: 2883 | Homo sapiens hypothetical protein FLJ39575 (FLJ39575), mRNA [NM_182597] |
| 532 | A_24_P381625 | PSMC6 | ATGAAGGAGTCAGAAAGTCAGAAAGGTGGCTGATTCGTAAGAAGGTGGAGTCTAAATTGGACTAGAAA | SEQ ID NO: 2884 | Homo sapiens proteasome (prosome, macropain) 26S subunit, ATPase, 6 (PSMC6), mRNA [NM_002806] |
| 533 | A_24_P387866 | PKN2 | TTGTCGAGAGATCATTTTATATCCTTCGAAATTGTTATTACCAAGATCCTTTGGGAG | SEQ ID NO: 2885 | Homo sapiens protein kinase N2 (PKN2), mRNA [NM_006256] |
| 534 | A_24_P39378 | CCPG1 | TACTTTTGTCGGGTGGAACGAAGTTGATCAGTTCAATAAGTTTTTTCCTAAACGGTGT | SEQ ID NO: 2886 | Homo sapiens cell cycle progression 1 (CCPG1), transcript variant 1, mRNA [NM_004749] |
| 535 | A_24_P393811 | TMCO1 | AGATGACACCACAGACTGTGCCTTGCAGTTCATCCTGTATATCTCTGTACTATGTGATTCG | SEQ ID NO: 2887 | Homo sapiens transmembrane and coiled-coil domains 1 (TMCO1), mRNA [NM_019026] |
| 536 | A_24_P396231 | BC040653 | GGATGTATGGATTTAGAGAAGGAATTAATACCTGCAAAATAAAGCATACTGTGGTAGTTC | SEQ ID NO: 2888 | Homo sapiens cDNA clone IMAGE:4797120 [BC040653] |
| 537 | A_24_P396702 | CD302 | GCATTCTTGTAGTGAAGCAGTGTATGGCTCTTTTGTTCAGAATTTAAAAGTGATAACCAA | SEQ ID NO: 2889 | Homo sapiens CD302 molecule (CD302), mRNA [NM_014880] |
| 538 | A_24_P398940 | CASC4 | CACTTGGTTGGTTGTATTGTAGGTATTACTTCTTATACAGGAACAGATTTGTTGAATTAGGAGTC | SEQ ID NO: 2890 | Homo sapiens cancer susceptibility candidate 4 (CASC4), transcript variant 1, mRNA [NM_138423] |

Fig. 7-30

| No. | Probe ID No. | Symbols of genes | Sequence | SEQ ID NO: | Descriptions of genes (letters and numbers within [ ] indicates GenBank accession No.) |
|---|---|---|---|---|---|
| 539 | A_24_P399942 | ATP11C | TGAGGATGTTAGGTACGTAGTAAAGTGAAAACATTCATTCGATATGTACTTACACATACACCAG | SEQ ID NO: 2891 | Homo sapiens ATPase, Class VI, type 11C (ATP11C), transcript variant 1, mRNA [NM_173694] |
| 540 | A_24_P40417 | FMR1 | TTGTGGAGTTTGTTCTTGAATTTTGCATTTTAGAGTTAGTTTTGTTCGCATAGAAACAAG | SEQ ID NO: 2892 | Homo sapiens fragile X mental retardation 1 (FMR1), mRNA [NM_002024] |
| 541 | A_24_P465298 | PPP1CB | GTATTAGGTTAGGTCAGAAAGGTTTTATGTGAGGTGATTAAATAACTTCCTGATTGGAG | SEQ ID NO: 2893 | Homo sapiens protein phosphatase 1, catalytic subunit, beta isoform (PPP1CB), transcript variant 1, mRNA [NM_002709] |
| 542 | A_24_P465430 | TIA1 | GGATTTTCTCGTTGTTAAATCACAAAAATGATAGTCCCAATCGTTTCTTTATAGGAGG | SEQ ID NO: 2894 | Homo sapiens cDNA FLJ36425 fis, clone THYMU2011482 [AK093744] |
| 543 | A_24_P466034 | SLC35A1 | ATGTACGAGTATTTTGTCCTAGCAGCATAAAGACCTAGGTCTTTTCTTACAAGAGGCAGAA | SEQ ID NO: 2895 | Homo sapiens solute carrier family 35 (CMP-sialic acid transporter), member A1 (SLC35A1), mRNA [NM_006416] |
| 544 | A_24_P466360 | IBRDC2 | CTTATCCAGGTTGGAAATGTACATGTTCATTTGAATGTAAATCACCATTTCTTGGAACC | SEQ ID NO: 2896 | Homo sapiens IBR domain containing 2 (IBRDC2), mRNA [NM_182757] |
| 545 | A_24_P407311 | ERO1L | TAACATGTTGAAATGTCACATTAGTAGTAAAGTGGGGTTTATTATATAGTGGTTAAGAA | SEQ ID NO: 2897 | Homo sapiens ERO1-like (S. cerevisiae) (ERO1L), mRNA [NM_014584] |
| 546 | A_24_P413669 | PFKFB2 | TCAAATGGTCTTTATAGTGTGGATGATACAGGACTCTGTACCTAAGATGTGATAAGC | SEQ ID NO: 2898 | Homo sapiens 6-phosphofructo-2-kinase/fructose-2,6-biphosphatase 2 (PFKFB2), transcript variant 2, mRNA [NM_001018053] |
| 547 | A_24_P414556 | TTC33 | TACTCAACATTTGGTATATTCTTTCGACTAATGGATGTGTTTTTGTGTAATTTGTGA | SEQ ID NO: 2899 | Homo sapiens tetratricopeptide repeat domain 33 (TTC33), mRNA [NM_012382] |
| 548 | A_24_P417281 | TXNDC10 | ATGATGAGTGATTCTTCGGGAAGATAAATGTTAAGTGTTCCCAATAGTCAAGGTTGTTTGC | SEQ ID NO: 2900 | Homo sapiens thioredoxin domain containing 10 (TXNDC10), mRNA [NM_019022] |
| 549 | A_24_P419211 | MTMR6 | AGAAAGAAAAAGATAAAAACGGAAAAGTACTTAAGCAAATTGCTTCAGTTGGAATTAGCAATATCACCCAACTGG | SEQ ID NO: 2901 | Homo sapiens myotubularin related protein 6 (MTMR6), mRNA [NM_004685] |
| 550 | A_24_P450172 | AK095151 | TATGCCAGTGAATAAAGCTAGTTAAACGCAAGAGATCCTAACATTTTACTGTTAATCCTAGGGTAC | SEQ ID NO: 2902 | Homo sapiens cDNA FLJ37832 fis, clone BRSSN2009630 [AK095151] |
| 551 | A_24_P45620 | UTS2 | AGAAAGTTCAGGATTCTGTGGAGAAGATCGTAACATTTTACTGAGTCATCTTTTGGCC | SEQ ID NO: 2903 | Homo sapiens urotensin 2 (UTS2), transcript variant 1, mRNA [NM_021995] |
| 552 | A_24_P467736 | CXorf23 | TGCATACCTACTATGTGTAAGAGCAAATGGATGGGATTTTTAAATGAAATTTTTAGGGCC | SEQ ID NO: 2904 | Homo sapiens chromosome X open reading frame 23 (CXorf23), mRNA [NM_192279] |
| 553 | A_24_P514678 | DB728175 | ATCACACAGTGTCTGTCAATTAAGGAATTGCTCATATTCTCGTCAATAAAGAGCAAACTCG | SEQ ID NO: 2905 | DB728175 RIKEN full-length enriched human cDNA library, hypothalamus Homo sapiens cDNA clone HO33001B22_3, mRNA sequence [DB728175] |
| 554 | A_24_P532232 | CREB5 | TCGTGAACACATTATTGTTACCAATGGACAATGAGTTCATTAAGACTGTTCAACTAGGT | SEQ ID NO: 2906 | Homo sapiens cAMP responsive element binding protein 5 (CREB5), transcript variant 1, mRNA [NM_182898] |
| 555 | A_24_P538403 | ROCK1 | TTAGAGGTTGTTGGACTTTCATAAATTGAGTACAATGTTGGATGAAAGTAGGTGGTAC | SEQ ID NO: 2907 | Homo sapiens Rho-associated, coiled-coil containing protein kinase 1 (ROCK1), mRNA [NM_005406] |
| 556 | A_24_P54178 | TMED5 | GGTCTGATATGGATTGGATGATTAATGTATGCTGTGTTTCATGTGAATGTCAAGACA | SEQ ID NO: 2908 | Homo sapiens transmembrane emp24 protein transport domain containing 5 (TMED5), mRNA [NM_016040] |

Fig. 7-31

| No. | Probe ID No. | Symbols of genes | Sequence | SEQ ID NO: | Descriptions of genes (letters and numbers within [ ] indicates GenBank accession No.) |
|---|---|---|---|---|---|
| 557 | A_24_P551028 | LOC339745 | TCCAGTTGAACAAATATTGAGTGGCTATCATATGAAGAGTAACT CCTTAGTAGGAATGA | SEQ ID NO: 2909 | Homo sapiens hypothetical protein LOC339745 (LOC339745), mRNA [NM_001091664] |
| 558 | A_24_P56240 | CPNE8 | TACAAGTACATGTGACTTAGTGCAACAGACATTTGTGAAATAACCTA GTCCTATATACTGAC | SEQ ID NO: 2910 | Homo sapiens copine VIII (CPNE8), mRNA [NM_153634] |
| 559 | A_24_P56252 | AF086032 | GTATGCTAAAACTGAACAACAGGTACTGTGCTATATGATTTTATTGGT AGTATTGAGCAGAGAC | SEQ ID NO: 2911 | Homo sapiens full length insert cDNA clone YW25G09 [AF086032] |
| 560 | A_24_P592591 | A_24_P592591 | GAATTTTGTTACACTGGAGGTGGAGGAAGGGAGACCTTGAGGAATAAGGT CAGGATGTGTCTCCAT | SEQ ID NO: 2912 |  |
| 561 | A_24_P605190 | THC2615064 | CAGTGGTGTAACTCAATACAATGGTCATTGTTTATTCTCATATTTC AGGTAAGTGAAAGGG | SEQ ID NO: 2913 | BX491310 DKFZp686K2197_r1 686 (synonym: hicc3) Homo sapiens cDNA clone DKFZp686K2197 5', mRNA sequence [BX491310] |
| 562 | A_24_P62860 | STAM2 | GTCTATATGGTACTTGATGTACAATTTAAGTGGAAAAATTAGCAGT ATTTGAAAGGTCAGT | SEQ ID NO: 2914 | Homo sapiens signal transducing adaptor molecule (SH3 domain and ITAM motif) 2 (STAM2), mRNA [NM_005843] |
| 563 | A_24_P630039 | AL049321 | AAGATGAGAATACAAAGGTTACATTTTTGGACGATATTAAAAGT GGAAGAAGAGAGGGG | SEQ ID NO: 2915 | Homo sapiens mRNA; cDNA DKFZp564D156 (from clone DKFZp564D156). [AL049321] |
| 564 | A_24_P66027 | APOBEC3B | GGTGCCGGCATCTATGATTACGACCCCCTATATAAGGAGGAGGCGGTG CAAATGCTGCGGGAT | SEQ ID NO: 2916 | Homo sapiens apolipoprotein B mRNA editing enzyme, catalytic polypeptide-like 3B (APOBEC3B), mRNA [NM_004900] |
| 565 | A_24_P66125 | STAG2 | TAATCATTCCATGCCTTAATATGCTTGAAATACAAGAATATGTTC AGATGGGTGAATACG | SEQ ID NO: 2917 | Homo sapiens stromal antigen 2 (STAG2), transcript variant 4, mRNA [NM_006603] |
| 566 | A_24_P675947 | ENST00000389400 | GTTCATGGGAAGGTAGCAGTTCTGGAAAAAGGTACTGGAGAAGAG ACAGGTTCTAAAGTT | SEQ ID NO: 2918 | similar to 40S ribosomal protein S3a (V-fos transformation effector protein) (LOC391706), mRNA [Source:RefSeq_dna;Acc:XR_017186] [ENST00000389400] |
| 567 | A_24_P681266 | A_24_P681266 | TAAGGAAGAAAAGGCACGATGATATTATGGTTCCTGAGTTGGTGA TTCAGCTCGGCTTTCG | SEQ ID NO: 2919 |  |
| 568 | A_24_P68133 | AK124299 | TAGGATAGATTCTCCAGGAGAAAAATATCTTGTTTGTAGTGATATGCGGA ATAGTGATTGATTTC | SEQ ID NO: 2920 | Homo sapiens cDNA FLJ42306 fis, clone TRACH2001646 [AK124299] |
| 569 | A_24_P703614 | A_24_P703614 | AAGAACATTACGCAGAATGGAGTGTGGACTGTAAGTCATGCAGTAGC AAGTTTGTCTGTGTG | SEQ ID NO: 2921 |  |
| 570 | A_24_P71468 | QPCT | GTGTGGAAACATCTATCCTATAGACATCCTATTCTTATGTGTGT TTGGTTATCAGATCA | SEQ ID NO: 2922 | Homo sapiens glutaminyl-peptide cyclotransferase (glutaminyl cyclase) (QPCT), mRNA [NM_012413] |
| 571 | A_24_P71938 | SMAD1 | TGATTCGACTTATGCTGTCGGTAGATTGAGATGTTTTTATTCCAAAA GTAGTGGGTTTGTC | SEQ ID NO: 2923 | Homo sapiens SMAD family member 1 (SMAD1), transcript variant 1, mRNA [NM_005900] |
| 572 | A_24_P725998 | THC2706471 | GTCTGCACATTACTGACTTGAACAAGAGGACCATCATTGGTGTT TGTCAGAATTTCG | SEQ ID NO: 2924 |  |
| 573 | A_24_P75158 | PTAR1 | GGATTAGATTTGTTCTTATGTAGGATGTACCAAGGCAGCTATAA AGTATTGTATTTCTG | SEQ ID NO: 2925 | Homo sapiens mRNA; cDNA DKFZp313P0917 (from clone DKFZp313P0917). [AL832683] |
| 574 | A_24_P781846 | AK024092 | ACTTTTTATAGATACAAATGTATCTGTGGTATTTGGTAGTACAAGGACTTT GTTACTTTGGGGTGC | SEQ ID NO: 2926 | Homo sapiens cDNA FLJ14030 fis, clone HEMBA1004086. [AK024092] |
| 575 | A_24_P791829 | THC2543120 | TTTTGGGTTTTGCTAAATGGTTAGGTATTTGGTATAGGTGTTTGT GATGTCATGGATTGT | SEQ ID NO: 2927 |  |

Fig. 7-32

| No. | Probe ID No. | Symbols of genes | Sequence | SEQ ID NO: | Descriptions of genes (letters and numbers within [ ] indicates GenBank accession No.) |
|---|---|---|---|---|---|
| 576 | A_24_P792734 | PSMC6 | AGAAGGTTAACGGAGTTACTGAATCAAATGGAATGGATTTGATACTCTGCATAGAGTTAAA | SEQ ID NO: 2926 | Homo sapiens proteasome (prosome, macropain) 26S subunit, ATPase, 6 (PSMC6), mRNA [NM_002806] |
| 577 | A_24_P80915 | BCLAF1 | AAGTTGTGTCAATGATGGTAATGAGACCAAACTTGTAGATTTAATTAAGGTAGGAGTTC | SEQ ID NO: 2929 | Homo sapiens BCL2-associated transcription factor 1 (BCLAF1), transcript variant 1, mRNA [NM_014739] |
| 578 | A_24_P82630 | SMCHD1 | TGTTTAATATGTAACGACGTAAGAACAATTGAAATTTCTTCAAGATTTAATAGTACTCT | SEQ ID NO: 2930 | Homo sapiens mRNA for KIAA0650 protein, partial cds. [AB014550] |
| 579 | A_24_P858859 | THC2553238 | TTTTACCAGAGGTCTGCACCCTTTTCCTGATATACTGAGGACACTCGGTCTCTAGCAAT | SEQ ID NO: 2931 | 1305349A cystic fibrosis antigen. [Homo sapiens] (exp=-1; wgp=0; cg=0), partial (65%) [THC2553238] |
| 580 | A_24_P867201 | AK022997 | GTGACATGTGATAAATATTTCAGTGACTTTGAGATTTATTTCTTGTTACCGCTGTGTG | SEQ ID NO: 2932 | Homo sapiens cDNA FLJ12935 fis, clone NT2RP2004982. [AK022997] |
| 581 | A_24_P886040 | DCP2 | CATTTGGAAGAGGTTCATTCGTTCTAGATTTATGTGTTGTAGTTGAACAGCAAGTG | SEQ ID NO: 2933 | Homo sapiens DCP2 decapping enzyme homolog (S. cerevisiae) (DCP2), mRNA [NM_152624] |
| 582 | A_24_P890536 | CR627148 | AATTGGCTTGTTGTAAGCGTAAGTATGGTGAAGGAGAATTGAATTGTACAAAGTCTTC | SEQ ID NO: 2934 | Homo sapiens mRNA; cDNA DKFZp779F2127 (from clone DKFZp779F2127). [CR627148] |
| 583 | A_24_P915269 | SRGN | GGATGATATTCGGAAATATTCCTAGGTTTATCACGAGTTAGTGTGTTAGTGAGAC | SEQ ID NO: 2935 | Homo sapiens serglycin, mRNA (cDNA clone IMAGE:4888573), complete cds. [BC022313] |
| 584 | A_24_P91916 | NXT2 | AACCATGGTTCTGTAGTACTGCATTGAAAGTTAGACGTTTATTCTACTCATAGTGAGC | SEQ ID NO: 2936 | Homo sapiens nuclear transport factor 2-like export factor 2 (NXT2), mRNA [NM_018698] |
| 585 | A_24_P921366 | CALD1 | TCGTTGTTTACTGGTTGAGTATAAATTGTTGATGTATAACGAGGTAAAACTGAAGC | SEQ ID NO: 2937 | Homo sapiens caldesmon 1 (CALD1), transcript variant 1, mRNA [NM_033138] |
| 586 | A_24_P924697 | AK055915 | GGCCAGAATACCAAACAAATTATCAGACGACGTTAACTTATTGGTACTGGCTAAGGATA | SEQ ID NO: 2938 | Homo sapiens cDNA FLJ31353 fis, clone MESAN2000264. [AK055915] |
| 587 | A_24_P925505 | CD36 | CGTAGCGTCTTAGTACCACAGTTGGTCTGTTTTATCGTGTAAGTACCAAATATGAATGGC | SEQ ID NO: 2939 | CD36-collagen type I/thrombospondin receptor [gene exon] [human. Partial mRNA Partial, 369 nt]. [S67044] |
| 588 | A_24_P935986 | BCAT1 | ATGCTCGAAGCTTTGTAGAAGGACAGAATTAAACATCTAAAATGCTTTGTTACACCAGA | SEQ ID NO: 2940 | Homo sapiens branched chain aminotransferase 1, cytosolic (BCAT1), mRNA [NM_005504] |
| 589 | A_24_P936319 | BC030115 | GAAAGATACATGCATTCTATGGTAACAACTACTGCAATAACATCTGATGTTACATGCAC | SEQ ID NO: 2941 | Homo sapiens cDNA clone IMAGE:4801326. [BC030115] |
| 590 | A_24_P937095 | SLC30A1 | TTTGATGTAGGTCTACCGGATACTATGGTAATGCTATTTTGCTTTACTAACAAGGTCTG | SEQ ID NO: 2942 | Zinc transporter 1 (Zn-t) (Solute carrier family 30 member 1). [Source:Uniprot/SWISSPROT:Acc:Q9Y6M5] [ENST00000367000] |
| 591 | A_24_P940426 | QKI | AAGCTGTTGAATGAGTCTTAAAAATTATACTACTGTAAGTCGACCAAGTTTGGTGAAGC | SEQ ID NO: 2943 | Homo sapiens quaking homolog, KH domain RNA binding (mouse) (QKI), transcript variant 4, mRNA [NM_206855] |
| 592 | A_24_P940725 | C6orf111 | AATTATGATTAGTGAGTGGGTCTAACAGTTTAAGGAATTGATAAGTTACAAGTAGAGTGGG | SEQ ID NO: 2944 | Splicing factor, arginine/serine-rich 130 (Serine-arginine-rich splicing regulatory protein 130) (SRrp130) (SR-rich protein) (SR-related protein). [Source:Uniprot/SWISSPROT:Acc:Q8IF01] [ENST00000369239] |

Fig. 7-33

| No. | Probe ID No. | Symbols of genes | Sequence | SEQ ID NO: | Descriptions of genes (letters and numbers within [ ] indicates GenBank accession No.) |
|---|---|---|---|---|---|
| 593 | A_24_P941643 | PLCB1 | ATGATGTCAGTTTTGTGCCTTATGTATTTGCCTTGCTTGTTCTTTGT CGAATGTGTGAAATT | SEQ ID NO: 2945 | Homo sapiens phospholipase C, beta 1 (phosphoinositide-specific) (PLCB1), transcript variant 2, mRNA [NM_182734] |
| 594 | A_24_P942002 | CENTB2 | TGGATTCTCATGGTAGGATTGTGAGATGTTAATGTAAGGTCCAA AGTTGTCTACTTTTT | SEQ ID NO: 2946 | Homo sapiens centaurin, beta 2 (CENTB2), mRNA [NM_012287] |
| 595 | A_24_P942469 | SPAG9 | AAACAGATGTGTCATAATATTAACGTCCTAAAGAACAGTGTGT TGCAAATGGGATGGA | SEQ ID NO: 2947 | Homo sapiens cDNA FLJ26141 fis, clone TST03911. [AK129552] |
| 596 | A_24_P942773 | SLMAP | AAAGTACAATAGAATTTCTGGGAGTAGAGATTAAACTATTTGCACT AACACAGTGACGTC | SEQ ID NO: 2948 | Homo sapiens sarcolemma associated protein (SLMAP), mRNA [NM_007159] |
| 597 | A_24_P943957 | PIP5K3 | TTGGCTCTTATTAGGTATTGTAAATAGGGTTATATGCATATC AGCTTTGTGATGGC | SEQ ID NO: 2949 | Homo sapiens phosphatidylinositol-3-phosphate/phosphatidylinositol 5-kinase, type III (PIP5K3), transcript variant 2, mRNA [NM_015040] |
| 598 | A_24_P97526 | CMTM6 | GTGGATGCTTAGTGGTCAGTAATTGTTCTTTTCAGAAAGA TAGTATGTTCACTGG | SEQ ID NO: 2950 | Homo sapiens CKLF-like MARVEL transmembrane domain containing 6 (CMTM6), mRNA [NM_017801] |
| 599 | A_24_P98109 | SNX10 | AAAGTGGGCAGAGGGTACTACAAAAGCAAGCTTTTCATTTTCAC TAAGAGTTTAAAAGC | SEQ ID NO: 2951 | Homo sapiens sorting nexin 10 (SNX10), mRNA [NM_013322] |
| 600 | A_24_P99046 | STK38L | GCTAGTGTCTTTTGCTGATGTACAAATAAATGAATTGAGAATTT AGTGCATAGAGGTCC | SEQ ID NO: 2952 | Homo sapiens serine/threonine kinase 38 like (STK38L), mRNA [NM_015000] |
| 601 | A_32_P100109 | REPS2 | GTGTGGAGATAATTGGATCAACTGAGTGTGTTATTTTTGTTTAAGT CAGGTTGTGTGGAGAA | SEQ ID NO: 2953 | Homo sapiens RALBP1 associated Eps domain containing 2 (REPS2), transcript variant 1, mRNA [NM_004726] |
| 602 | A_32_P101313 | PTPLAD2 | AAAGTGTGAATAACTGATAGTCATTGCTGTATCATTGATGTATCA CTCAATTTTTGGTAA | SEQ ID NO: 2954 | Homo sapiens protein tyrosine phosphatase-like A domain containing 2 (PTPLAD2), mRNA [NM_001010915] |
| 603 | A_32_P108254 | FAM20A | TCGTTGGGTTGCCTTGCTCCGTTTTTCCAAAAAGCACTGGCTGA TCAAGGCCACCGACG | SEQ ID NO: 2955 | Homo sapiens family with sequence similarity 20, member A (FAM20A), mRNA [NM_017565] |
| 604 | A_32_P112452 | BI026064 | CGTTGGGAGGTGTTGATGAGTCTGTATGTTGGGTTCCAAGGTGCG ACATTTGAAGTGA | SEQ ID NO: 2956 | BI026064 CM0-MT0374-060201-774-h11 MT0374 Homo sapiens cDNA, mRNA sequence [BI026064] |
| 605 | A_32_P113564 | ZNF292 | GGGCCTTTTGGCTTTTATTGAATAGTCATTCATTGACCTGTTTAAGA CTTACTACCAATAAG | SEQ ID NO: 2957 | Zinc finger protein 292 [Source:Uniprot/SWISSPROT;Acc:Q6Q2B1] [ENST00000339907] |
| 606 | A_32_P11451 | NMD3 | CAGTTTAGGGGCAGTAGGTGCTTTTGTCATAAATATCTTCACCA CATCAAAAATGCTGC | SEQ ID NO: 2958 | Homo sapiens NMD3 homolog (S. cerevisiae) (NMD3), mRNA [NM_015939] |
| 607 | A_32_P115220 | C9orf66 | TTCTCAAAAAATGTTCGTCAGAACCTGGCGTGAATGCTCTTTC! GGGAGAAAGACTGA | SEQ ID NO: 2959 | Homo sapiens chromosome 9 open reading frame 66 (C9orf66), mRNA [NM_152569] |
| 608 | A_32_P115605 | ZNF294 | TGTGTCAGAGGATTATTAGTTGAGAGTGAAGTACTATGTGTGAGT TATAGTCTCTGAA | SEQ ID NO: 2960 | Homo sapiens zinc finger protein 294 (ZNF294), mRNA [NM_015565] |
| 609 | A_32_P117313 | DKFZP779L1068 | ATGACTGTAAGATGTTGAGAGTATGTTCTTACTCATTTCTGTAAT TGGCAGTAGTGTAGTC | SEQ ID NO: 2961 | Homo sapiens cDNA clone IMAGE:5555490 [BC110326] |
| 610 | A_32_P118325 | BU567832 | ATTAATTGACTAAATGGCATTAAGGAGGTCTGAGGAATTGC ATGTCAGATTCTGGA | SEQ ID NO: 2962 | AGENCOURT_10399047 NIH_MGC_82 Homo sapiens cDNA clone IMAGE:6614537 5', mRNA sequence [BU567832] |

Fig. 7-34

| No. | Probe ID No. | Symbols of genes | Sequence | SEQ ID NO: | Descriptions of genes (letters and numbers within [ ] indicates GenBank accession No.) |
|---|---|---|---|---|---|
| 611 | A_32_P123204 | AI381562 | AAGTGCTACAAATGGTCTCCTTTAAGCAGTGTGCTAATAATGTCATCAGTTTCAGTT | SEQ ID NO: 2963 | AI381562 te76g06.x1 Soares_NFL_T_GBC_S1 Homo sapiens cDNA clone IMAGE:2092666 3', mRNA sequence [AI381562] |
| 612 | A_32_P124580 | THC2610143 | ATTACGTGGGAGTAAAAGGAGCAGATGTTTTGTTTGTCAATTCTACCTAAATGTCTGTGTA | SEQ ID NO: 2964 | AA490192 aa43f10.r1 Soares_NhHMPu_S1 Homo sapiens cDNA clone IMAGE:823723 5', mRNA sequence [AA490192] |
| 613 | A_32_P125917 | THC2753798 | GCTATAAAGTGTAAGTGGAGGACGGTAAATTGTGAGTACAAAGTTTGTTTTTCACACAG | SEQ ID NO: 2965 | BF238843 601904455F1 NIH_MGC_54 Homo sapiens cDNA clone IMAGE:4132429 5', mRNA sequence [BF238843] |
| 614 | A_32_P126023 | THC2599380 | AGTGTTCTAGATTTCTGCTAGCAAACTGATATGAGGTAGAGTCCTGAAAGATCTTTCAGC | SEQ ID NO: 2966 | ALU5_HUMAN (P39192) Alu subfamily SC sequence contamination warning entry, partial (9%) [THC2599380] |
| 615 | A_32_P128980 | BC062780 | AGATGGGAGAACAGAGGAGTAGTGACAGGAGTAGAAGCAGTGTAGACCTTTGCATATGAT | SEQ ID NO: 2967 | Homo sapiens cDNA clone IMAGE:4700531, partial cds. [BC062780] |
| 616 | A_32_P129894 | MEGF9 | TTTAGACAACATTTGTAGAGACACCTCAAATTATATCACTGTTCTCTAGGGCAATATTCCC | SEQ ID NO: 2968 | Homo sapiens multiple EGF-like-domains 9 (MEGF9), mRNA [NM_001080497] |
| 617 | A_32_P131401 | AI276257 | TCAGAAAAAGAGAGTAAGGCACCACTCTGGGAAATTAAGGTAGCTTGCAGTAACAAGT | SEQ ID NO: 2969 | AI276257 qi65f01.x1 Soares_NhHMPu_S1 Homo sapiens cDNA clone IMAGE:1977209 3', mRNA sequence [AI276257] |
| 618 | A_32_P148824 | C1orf27 | GAAAAGCAGATGTTATGCTCAGCAGCACAAATTGAGTGAGAGACTACAAAGGATGATCTTC | SEQ ID NO: 2970 | Homo sapiens chromosome 1 open reading frame 27 (C1orf27), mRNA [NM_017847] |
| 619 | A_32_P149404 | LOC728371 | GTAAAGTGTGGAATTCTGTCGTTGATGATGGTGAGATGGTAGAGAATGCGGGATGA | SEQ ID NO: 2971 | PREDICTED: Homo sapiens similar to ankyrin repeat domain 20A (LOC728371), mRNA [XR_015273] |
| 620 | A_32_P153725 | KIAA1033 | TTTGTAAAAGATGGCAAGTTGTTAGCTGCAGTTTGAGTTGACTGGGGTTTCGTTCCCCAAT | SEQ ID NO: 2972 | Homo sapiens KIAA1033 (KIAA1033), mRNA [NM_015275] |
| 621 | A_32_P162183 | C2 | GGTTGACTTGACTCATGCTTGTTCACTTTCACTTTGAAAATTTAATAGTAGTATGGAAATTAAT | SEQ ID NO: 2973 | Homo sapiens complement component 2 (C2), mRNA [NM_000063] |
| 622 | A_32_P162250 | ARHGAP18 | AAGTCCTGAATAGGTCACTACTGGAAGAGATATTATCCTGGGTGAAAAGCTTTTGTTTGTG | SEQ ID NO: 2974 | Homo sapiens Rho GTPase activating protein 18 (ARHGAP18), mRNA [NM_033515] |
| 623 | A_32_P164203 | THC2683448 | TTGATGCTCATTGATGAGGTATTGTATGGATTACTGTGGAGTGCTGTTTACGCATGAT | SEQ ID NO: 2975 | Q7WZG3_PASPI (Q7WZG3) Ferric uptake regulator, partial (9%) [THC2683448] |
| 624 | A_32_P166272 | THC2650457 | ATACATTTAATTGGTCACGTTTTTTATATTGGAGAGTCGGTACAGAGTGTCGATTACTGC | SEQ ID NO: 2976 | ALU6_HUMAN (P39193) Alu subfamily SP sequence contamination warning entry, partial (12%) [THC2650457] |
| 625 | A_32_P167122 | RCOR3 | GTATGCTGAGGGATGTGGCTGTAATCTGATTTGACATGCATTAGAAGCACACAGTAGAAAAGT | SEQ ID NO: 2977 | Homo sapiens REST corepressor 3 (RCOR3), mRNA [NM_018254] |
| 626 | A_32_P170444 | SUB1 | TAAGGTATCTCTCCTGAAATTCTTCGCAGTTCATTTTTTATGGCAGTTAATCCAGTGAAAG | SEQ ID NO: 2978 | Activated RNA polymerase II transcriptional coactivator p15 (SUB1 homolog) (Positive cofactor 4) (PC4) (p14). [Source:Uniprot/SWISSPROT;Acc:P53999] [ENST00000265073] |
| 627 | A_32_P171313 | GNB4 | GATTTAACTGTTCTTAGATCTTTCTTACACAGTGATTCATTCCTGTATTGTACAGTGGC | SEQ ID NO: 2979 | Homo sapiens guanine nucleotide binding protein (G protein), beta polypeptide 4 (GNB4), mRNA [NM_021629] |

Fig. 7-35

| No. | Probe ID No. | Symbols of genes | Sequence | SEQ ID NO. | Descriptions of genes (letters and numbers within [ ] indicates GenBank accession No.) |
|---|---|---|---|---|---|
| 628 | A_32_P17163 | ENST00000368149 | TCGTTAGTGAGTTTTAAATGTCAGGGTAGATTTTATTTGTTTTT GTGTGTGTATGAG | SEQ ID NO: 2980 | Rho GTPase-activating protein 18 (MacGAP). [Source:Uniprot/SWISSPROT;Acc:Q8N392] [ENST00000368149] |
| 629 | A_32_P172578 | THC2661509 | ACTTAATCAATGTCAAAGATTCTAGGGATTGTCCATCTGATG CATTCCTTCTGTCG | SEQ ID NO: 2981 | |
| 630 | A_32_P17504 | THC2696682 | ATGTCTAAATTTGCTGTTGCACTATGCTGAAATATTCCCAGGGTTTTC CCGTGATGCGGAAA | SEQ ID NO: 2982 | |
| 631 | A_32_P177040 | WBSCR19 | AATGTTTGTATGTATTAATACAGGTGTTGCTGAAGGGAGGATGGT TTTTATCGTGATAG | SEQ ID NO: 2983 | Homo sapiens Williams Beuren syndrome chromosome region 19 (WBSCR19), mRNA [NM_175064] |
| 632 | A_32_P177685 | THC2632286 | TTTGACTGAGTATTGTAGATGCTTAATGAGTGAAATGAATTTGG AGGACGTGATGAAAG | SEQ ID NO: 2984 | AA665072 nu76b01.s1 NCI_CGAP_Alv1 Homo sapiens cDNA clone IMAGE:1216585, mRNA sequence [AA665072] |
| 633 | A_32_P178966 | ENST00000379426 | GTAATATACAGGGTGAACTGTCTTTACTGATACACAAGACAACTG TTAAAAGTGAATCC | SEQ ID NO: 2985 | Novel protein. [Source:Uniprot/SPTREMBL;Acc:Q5I4T1] [ENST00000379426] |
| 634 | A_32_P180435 | WBSCR19 | CCTTCAATCTTTGTATGTTATTACAGGTCGTGGTGAAGGGAGC ATGTTTTTATCTATG | SEQ ID NO: 2986 | Homo sapiens Williams Beuren syndrome chromosome region 19 (WBSCR19), mRNA [NM_175064] |
| 635 | A_32_P184417 | A_32_P184417 | AAGCTGTGTTGCGTGTGGTAGGGATTCAGTATTCCTAATAGTTTA TTTTAGGTACTATAC | SEQ ID NO: 2987 | |
| 636 | A_32_P184916 | GNB4 | CAATGTGACAGTGTTACATTTGGAGAGAAGTGTGAAATGTAACCA ATGGCTAGCACATAT | SEQ ID NO: 2988 | Homo sapiens guanine nucleotide binding protein (G protein), beta polypeptide 4 (GNB4), mRNA [NM_021629] |
| 637 | A_32_P193322 | RICTOR | ACGAGATAGGTTCTGTTTTATTAGTAATAGCTGACT ATTTGGAGGTTCGTCG | SEQ ID NO: 2989 | Homo sapiens rapamycin-insensitive companion of mTOR (RICTOR), mRNA [NM_152756] |
| 638 | A_32_P194032 | LONRF1 | GTTAGATGACGATGCAACATGGTTTATTCATGCTGCCCTA GAAACTTTTGTAATT | SEQ ID NO: 2990 | Homo sapiens LON peptidase N-terminal domain and ring finger 1 (LONRF1), mRNA [NM_152271] |
| 639 | A_32_P195387 | DKFZp779L1968 | ATATAACCTTGGAATTCTATTCTAATATGTGTTCTGGGTGGTT GTAGTATCAGTTCGG | SEQ ID NO: 2991 | Homo sapiens cDNA clone IMAGE:5555490 [BC010326] |
| 640 | A_32_P19752 | FAM76B | TGTGTCTTAGCGTGGTGTTCAATTAATTAAGCATTATTACCAGT AAGGGTCATTTGAC | SEQ ID NO: 2992 | Homo sapiens family with sequence similarity 76, member B (FAM76B), mRNA [NM_144664] |
| 641 | A_32_P20240 | SP3 | CTTAGGCTCTTAATTGTAGTTGAAATTCCAGTAGCTGGCTACTCAG ACCGAAAAGTTTTGT | SEQ ID NO: 2993 | Homo sapiens Rho-associated, coiled-coil containing protein kinase 1, mRNA (cDNA clone IMAGE:5269982), complete cds. [BC041849] |
| 642 | A_32_P203320 | ROCK1 | AACGGCACCATCAGTACATCAAGATCAGCTGATGGAAGGAGTAAAGAAA ATATCTCAAAATGAG | SEQ ID NO: 2994 | Homo sapiens DKFZp686N17231 (from clone DKFZp686N17231) [BX648357] |
| 643 | A_32_P203749 | AF086547 | CAGGTGTCATTCTGTAGACCTATGTCGTTAGATTTGTACATGC ATTTTTTTGCGGACTT | SEQ ID NO: 2995 | Homo sapiens full length insert cDNA clone ZE12B03. [AF086547] |
| 644 | A_32_P205553 | RPL26L1 | TTGGAATGTCGGAAGATTTCATTTCCTGTTTTGTTAGGTGTGGG CTCTGTAAATCTACT | SEQ ID NO: 2996 | Homo sapiens ribosomal protein L26-like 1 (RPL26L1), mRNA [NM_016093] |
| 645 | A_32_P210798 | BF513730 | AAACCACCTACCTAATGTGACTGCTAAATTTCTAGCTTCTTTGTT TTAAATATGCTCAGG | SEQ ID NO: 2997 | BF513730 UI-H-BW1-any-e-05-0-UI.s1 NCI_CGAP_Sub7 Homo sapiens cDNA clone IMAGE:3071696 3', mRNA sequence [BF513730] |

Fig. 7-36

| No. | Probe ID No. | Symbols of genes | Sequence | SEQ ID NO: | Descriptions of genes (letters and numbers within [ ] indicates GenBank accession No.) |
|---|---|---|---|---|---|
| 646 | A_32_P221552 | BE173582 | ATTTAACTGAGGTAGGACCACAGTGTTTCTAAATTCGGGGTTTCATAGAATGCCCTGAATCT | SEQ ID NO: 2998 | BE173582 RC2 HT0560-290200-014-F06 HT0560 Homo sapiens cDNA mRNA sequence [BE173582] |
| 647 | A_32_P224666 | CAPZA2 | AATGCTGTTTGAGATTTCTGAAATTAAATGAAAATAGTTATTCAGAAATGGATTTAATG | SEQ ID NO: 2999 | Homo sapiens capping protein (actin filament) muscle Z-line, alpha 2 (CAPZA2), mRNA [NM_006136] |
| 648 | A_32_P226678 | BX114764 | CTCTACATCCTTACCTAGGTAATTCAGGCATGCCAGTATTTGGAGGGTCCAAATA | SEQ ID NO: 3000 | BX114764 NCI_CGAP_GCB1 Homo sapiens cDNA clone IMAGp998M182012, mRNA sequence [BX114764] |
| 649 | A_32_P226786 | BC045174 | TTATTGGTGCATGTAAGGCATTATGCTGTGTTAATGAACGGATTAATGTGTTGATTGTT | SEQ ID NO: 3001 | Homo sapiens cDNA clone IMAGE:5273245. [BC045174] |
| 650 | A_32_P228438 | THC2637028 | CTGTCCTATTGCAGCCCTAGTGAATAGATAATGCCTTGAACTATTCCTATCACCACAGGT | SEQ ID NO: 3002 | Q8N4F7_HUMAN (Q8N4F7) Ring finger protein 175, partial (12%) [THC2637028] |
| 651 | A_32_P2333 | SUB1 | AGGAAGAAAAGGTATTTCTTTAAATCCAGAACAATGGAGCCAGCTGACAGAACAGATTTC | SEQ ID NO: 3003 | Homo sapiens SUB1 homolog (S. cerevisiae) (SUB1), mRNA [NM_006713] |
| 652 | A_32_P233314 | EXOC8 | AGGATTGGGAAATTTGGACATGACATGTAGTATAAAAGTCAGTCTATGGATAGTGCTT | SEQ ID NO: 3004 | Homo sapiens exocyst complex component 8 (EXOC8), mRNA [NM_175876] |
| 653 | A_32_P26895 | KIAA1600 | AATTGTTGGTCCCTCGGTGGAGAAAGTCTTCAGATGATGGTCATTGTGTACCTACACTCTCTT | SEQ ID NO: 3005 | KIAA1600 (KIAA1600), mRNA [Source:RefSeq_dna;Acc:NM_020940] |
| 654 | A_32_P31123 | THC2690780 | CATTAGGGAAAGTTTGGTGGGTGATTAGAGTTCAAGTTCGATTGTTGGCTCATTGTAGGAGTG | SEQ ID NO: 3006 | |
| 655 | A_32_P32315 | A_32_P32315 | AAAGTGGGAAGAACATTCAAGTCCTGAATTCCTGAATTCTCGTGTTTGGAAAAAGGTCAGTCCTCA | SEQ ID NO: 3007 | |
| 656 | A_32_P3742 | RFX3 | GCTCTCAAAATTGGCAGGAGCCTAAATAATAAGTGTTGTGTGGGGGATTGTATGTCTACTGTA | SEQ ID NO: 3008 | Transcription factor RFX3. [Source:Uniprot/SWISSPROT;Acc:P48380] [ENST00000362004] |
| 657 | A_32_P38745 | THC2656841 | AAAGTGTGTATTGAAAGATGTAGAAGTGAGTTGGAAAAAAGGATTCGTCTGTAATTGGT | SEQ ID NO: 3009 | |
| 658 | A_32_P43217 | PSMA6 | TTGTTGTTAGTTACCAGATCGGTGATGGGACTTAGGTGTGTGTTTGGTAACAACAAACA | SEQ ID NO: 3010 | Homo sapiens proteasome (prosome, macropain) subunit, alpha type, 6 (PSMA6), mRNA [NM_002791] |
| 659 | A_32_P44394 | AIM2 | GAAGGAGATAAGGTTCGACTTACATTCTTCACACTGTCAAAAATGGAGAAAACTACAG | SEQ ID NO: 3011 | Homo sapiens absent in melanoma 2 (AIM2), mRNA [NM_004833] |
| 660 | A_32_P49164 | AV714556 | AAATGAGACAGTTTGTTATTTGGCAAAGAAGAATTCATCATGTTCCTTCCTTTGTTTTTCGG | SEQ ID NO: 3012 | AV714556 AV714556 DCB Homo sapiens cDNA clone DCBADG06 5', mRNA sequence [AV714556] |
| 661 | A_32_P6107 | A_32_P6107 | ATGTAATGAATGTCAGAAAGCTAAGGTCTTTATAATTCAACATGTGATAGTACATCAGAGAAT | SEQ ID NO: 3013 | |
| 662 | A_32_P61145 | AK096154 | GATAGGATCTTAACAGTAAGGTAAGGTCTTTATAATTCAACATGTGATCTTTAGTCCTACCCG | SEQ ID NO: 3014 | Homo sapiens cDNA FLJ38835 fis, clone MESAN2002424. [AK096154] |
| 663 | A_32_P61857 | KIAA1468 | TCAGTGTTACAGTTCACTGAGATTTGAGAGTGTCTGTCACAGTCATGCAACTCGAAGTAG | SEQ ID NO: 3015 | Homo sapiens KIAA1468 (KIAA1468), mRNA [NM_020854] |
| 664 | A_32_P62342 | GLT8D3 | TGTGATGTAACGTAGTGATGTAACGATTGACGAATCTATGTGTGCCTTTATACATTTGATCTCTG | SEQ ID NO: 3016 | Homo sapiens glycosyltransferase 8 domain containing 3, mRNA (cDNA clone MGC:21651 IMAGE:4508300), complete cds. [BC039145] |

Fig. 7-37

| No. | Probe ID No. | Symbols of genes | Sequence | SEQ ID NO: | Descriptions of genes (letters and numbers within [ ] indicates GenBank accession No.) |
|---|---|---|---|---|---|
| 665 | A_32_P63113 | THC2706386 | AGAAAAAGAACAGAAGTCTGGGGTCCACAGATACTGTTTGCAGATGACTGTGTATTTT | SEQ ID NO: 3017 | Q9TGMO_GLOPA (Q9TGMO) NADH-ubiquinone oxidoreductase subunit 1, partial (6%) [THC2706386] |
| 666 | A_32_P66681 | TLR4 | TTACTGAGTGTTCAGAGTGTGTTTGGTTTGAGTCAGGTCTAGGGTGATTGAACATCCGTG | SEQ ID NO: 3018 | Homo sapiens toll-like receptor 4 (TLR4), mRNA [NM_138554] |
| 667 | A_32_P71118 | PSMC6 | AGGAGACGTGAGAAATGTTTGTACTGAAGGAGGTATGTCGAATTCGTGCTGATCATGA | SEQ ID NO: 3019 | Homo sapiens proteasome (prosome, macropain) 26S subunit, ATPase, 6 (PSMC6), mRNA [NM_002806] |
| 668 | A_32_P73222 | AA631847 | TTTCTTTGTTTGGAGAATCTGATAAGAACTTTAGGCTTACAAGCACGAAGCCCTCGAAG | SEQ ID NO: 3020 | np61b02.s1 NCI_CGAP_Br2 Homo sapiens cDNA clone IMAGE:1130763 3' similar to TR:G971838 G971838 60S RIBOSOMAL PROTEIN L34 :; mRNA sequence [AA631847] |
| 669 | A_32_P75115 | BF373107 | AGAAGTGAAAAACTGAAGAATGTGAAGTGTTTACGTGCCGTTACTCACACAGACGTGCT | SEQ ID NO: 3021 | BF373107 CM2-FT0123-280700-395-C12 FT0123 Homo sapiens cDNA, mRNA sequence [BF373107] |
| 670 | A_32_P79396 | PBEF1 | AGGGCCGATTATGTTTACATAGGACGCAGGCAGGAATTTTGTTACACTGGAAGAAGGAA | SEQ ID NO: 3022 | Homo sapiens pre-B-cell colony enhancing factor 1 (PBEF1), mRNA [NM_005746] |
| 671 | A_32_P81766 | TMEM167 | CCTCAGTACTGTCACTACAGACAATATTACATTCTGGAAATGTTATTGTGTTGATATCAGATACG | SEQ ID NO: 3023 | Homo sapiens transmembrane protein 167 (TMEM167), mRNA [NM_174909] |
| 672 | A_32_P83000 | FLJ31222 | ACCATCTGCTGGGACGGCGGACAGGCTCGTTCTGATCTCACTCCGAGAAAAGACTGAA | SEQ ID NO: 3024 | Homo sapiens cDNA FLJ31222 fis, clone KIDNE2004294. [AK055784] |
| 673 | A_32_P83256 | AK023663 | CAAATAGTGCTTCAAAGCATGCTCAGAATCAAGAATTGTCATGTAGATTGCACCGGAAGTT | SEQ ID NO: 3025 | Homo sapiens cDNA FLJ13601 fis, clone PLACE1010069. [AK023663] |
| 674 | A_32_P86400 | LYSMD3 | AAATGTTGCTCAGGTAATCAGTATTTCTTCCACGTATGCATATTGCACTGTTAGATC | SEQ ID NO: 3026 | Homo sapiens LysM, putative peptidoglycan-binding, domain containing 3 (LYSMD3), mRNA [NM_198273] |
| 675 | A_32_P877 | BM999343 | TAAAATGCTTGGACAACTCCACTGTCATTCTCAGAGATTCCATTGGGAAGCCATGCCTA | SEQ ID NO: 3027 | BM999343 UI-H-DPO-avf-i-24-0-Ui.s1 NCI_CGAP_Fs1 Homo sapiens cDNA clone IMAGE:5879751 3', mRNA sequence [BM999343] |
| 676 | A_32_P97046 | BU076193 | ATTTATATACACGATGGGCAGCCGAGCCTAATGCAGATCATAACATTAACTTTCCAAAGAAGT | SEQ ID NO: 3028 | im5fo6.x1 HR85 islet Homo sapiens cDNA clone IMAGE:6038939 3', mRNA sequence [BU076193] |
| 677 | A_32_P98435 | PCMTD1 | ACACTTTGCCATGGTCAAAGAATGAAGGACAATATGGAAAAGCCAATCTTGAAATATATC | SEQ ID NO: 3029 | Homo sapiens clone 122482 unknown mRNA. [AF293366] |

Fig. 8-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P341938 | NOG | GCCAGCGCTGCGGCTGGATTCCCATGAGTACCGATCATTCCGAGTGCAAGTGCTCGT | SEQ ID NO: 2373 | Homo sapiens noggin (NOG), mRNA [NM_005450] |
| 2 | A_24_P413126 | TMEPAI | AAGAAACTGCTTGTTGTATGCAGTAATCATTAGTGCAATGATGACATTCGAAAAGCT | SEQ ID NO: 2404 | Homo sapiens transmembrane, prostate androgen induced RNA (TMEPAI), transcript variant 1, mRNA [NM_020182] |
| 3 | A_32_P111394 | THC2643957 | GAATACAGTGTGTCCTTTTCATCGCATATTTGACTGAACGTAAGACACATCAATTATAAGG | SEQ ID NO: 2418 | |
| 4 | A_32_P125689 | THC2649341 | CGGTCTATCGCTTGCTTTAGGCTTTTGAATGAAAAGTGAGATGTCTCATCAGCTCAGATAG | SEQ ID NO: 2419 | |
| 5 | A_32_P164378 | THC2703271 | GAAAGAAGATGAAAAGGATTGGAATGAAGGAAAGGCAGCCTGGTTTTAGACTTTAATTTTG | SEQ ID NO: 2426 | |
| 6 | A_32_P179998 | DMRTC1 | ATATGCCAGAGTTTTATTCGTCTTGTGATTGGTGACATACGTGTGCACTGATGTGTATA | SEQ ID NO: 2430 | Homo sapiens DMRT-like family C1 (DMRTC1), mRNA [NM_033053] |
| 7 | A_23_P111321 | ARG1 | TGGAATCAGGAGACAAAGGTAGCACATGTGGAAAGGTAGTATGTGTCCATGTCATTCAAA | SEQ ID NO: 2459 | Homo sapiens arginase, liver (ARG1), mRNA [NM_000045] |
| 8 | A_23_P11201 | GPR34 | AGTAGGAGTGAAAGCACTTCAGAATTAAACCAGGATACTCCCTGCATGATACGTCTGTG | SEQ ID NO: 2461 | Homo sapiens G protein-coupled receptor 34 (GPR34), transcript variant 1, mRNA [NM_005300] |
| 9 | A_23_P119222 | RETN | CAATAAGCAGCCATTGGGCTTCGGAGTGCCAGAGCGTCACGTCCAGGGGGGACCTGGCTACTT | SEQ ID NO: 2469 | Homo sapiens resistin (RETN), mRNA [NM_020415] |
| 10 | A_23_P121716 | ANXA3 | TGGACATTCGAACAGAGTTCAAGAAGACATTATGGCTATTCCGTATATCAGGAATTAAAT | SEQ ID NO: 2475 | Homo sapiens annexin A3 (ANXA3), mRNA [NM_005139] |
| 11 | A_23_P14708 | SUHW4 | TCTTTGTACCTCCATAGAAGTGTTAGGCTGGCCAGGCGTGTAAGCTTACCTTAATTAAAGTT | SEQ ID NO: 2507 | Homo sapiens suppressor of hairy wing homolog 4 (Drosophila) (SUHW4), transcript variant 1, mRNA [NM_017661] |
| 12 | A_23_P151637 | RNASE2 | GTGGTAAGGCTACAAATGACCTGTCCTACTAACAAAACTGGCAAAAATTGTCAGCAGTG | SEQ ID NO: 2514 | Homo sapiens ribonuclease, RNase A family, 2 (liver, eosinophil-derived neurotoxin) (RNASE2), mRNA [NM_002934] |
| 13 | A_23_P152002 | BCL2A1 | TGTAACCATATTGCATTTGAAGGTATTCTCAATCAAGAAAGTTCTACGACAGCAATTGC | SEQ ID NO: 2515 | Homo sapiens BCL2-related protein A1 (BCL2A1), mRNA [NM_004049] |
| 14 | A_23_P159850 | COX7B | CAAATACGGGTAATGCTGTGTATTAGGTAGTGGAGGCCACTTTGTATTGTTACATGACATA | SEQ ID NO: 2525 | Homo sapiens cytochrome c oxidase subunit VIIb (COX7B), nuclear gene encoding mitochondrial protein, mRNA [NM_001866] |
| 15 | A_23_P170233 | CSTA | AACTGGTACTGAGTCATGAGTCATCCTTGCTGATAAGAATGAACGCGATCAATAAAGAAGCATTCT | SEQ ID NO: 2543 | Homo sapiens cystatin A (stefin A) (CSTA), mRNA [NM_005213] |
| 16 | A_23_P25235 | CLEC4D | CATTTACCCACCACGAGAGTATTCTGGCATAAGAATGAACGCGACAAGCTCAGGGAGAAA | SEQ ID NO: 2600 | Homo sapiens C-type lectin domain family 4, member D (CLEC4D), mRNA [NM_080387] |
| 17 | A_23_P253012 | GRAMD1C | GAATTCCAAGGAAGCATACGSTAGGGGTAACAGTGAACCTACCTGGGTTTGTTTTGTTTTG | SEQ ID NO: 2602 | Homo sapiens GRAM domain containing 1C (GRAMD1C), mRNA [NM_017577] |
| 18 | A_23_P302550 | RGS18 | GAGTGTAAGGCCCTAGGGAATTGGGACGTGCCAGATGTGTTCATATTCAGAAGTGTTA | SEQ ID NO: 2621 | Homo sapiens regulator of G-protein signalling 18 (RGS18), mRNA [NM_130782] |

Fig. 8-2

| No. | Probe ID No. | Symbols of genes | Sequence | SEQ ID NO: | Descriptions of genes (letters and numbers within [ ] indicates GenBank accession No.) |
|---|---|---|---|---|---|
| 19 | A_23_P307940 | CAPZA2 | CTACAAGATTGGGAAGAGATGCAAAGAGATGGATAAGAATGAACATT GCATGACCGGATGATT | SEQ ID NO: 2628 | Homo sapiens capping protein (actin filament) muscle Z-line, alpha 2 (CAPZA2), mRNA [NM_006136] |
| 20 | A_23_P314191 | ZDHHC17 | TGGATACTTTTAGCAAATAGGAAGTTAATTCTCAGGACTGAACA TGAATTAGTTCCTTGG | SEQ ID NO: 2634 | Homo sapiens zinc finger, DHHC-type containing 17 (ZDHHC17), mRNA [NM_015336] |
| 21 | A_23_P324633 | C9orf72 | TTTGTGGATTTAGTCGGTCGGGATTCAGTCGTGTAGAAATGTCTAA TAGTTCTCTATAGTCC | SEQ ID NO: 2640 | Homo sapiens chromosome 9 open reading frame 72 (C9orf72), transcript variant 1, mRNA [NM_018325] |
| 22 | A_23_P347198 | SP3 | GACCACTCAAATTTAAAGGGTAACCTTATGTAAAGTGTAGCTTAAAGTG TATTATAACAGTGTGG | SEQ ID NO: 2651 | Homo sapiens Sp3 transcription factor (SP3), transcript variant 1, mRNA [NM_003111] |
| 23 | A_23_P349083 | FCHO2 | GTGAAATGGTTAAACTTCTGCACTTTCTTAGTTACCACAGTCTT CATACCAAGTATTGGG | SEQ ID NO: 2652 | Homo sapiens FCH domain only 2 (FCHO2), mRNA [NM_138782] |
| 24 | A_23_P405873 | C9orf72 | GAGAATGGAAGATCAGGGTCAGAGTATTATTCCAATGCTTACTG GAGAAGTGATTCCTGT | SEQ ID NO: 2674 | Homo sapiens chromosome 9 open reading frame 72 (C9orf72), transcript variant 2, mRNA [NM_145005] |
| 25 | A_23_P41114 | CSTA | AAACAAATGAGACTTATGGAAAATTGGAAGCTGTGCAGTATAAA ACTCAAGTTGTTGCTG | SEQ ID NO: 2677 | Homo sapiens cystatin A (stefin A) (CSTA), mRNA [NM_005213] |
| 26 | A_23_P41664 | ENST00000334994 | TGGGTTGAGGAGGAGATCGAGTTCATAAACAAATTGTTCCTGAAA ATGAGGCAGAGGTCAT | SEQ ID NO: 2680 | Syneurin [CGLQ1891] [Source:Uniprot/SPTREMBL;Acc:Q7Z2Q7] [ENST00000334994] |
| 27 | A_23_P420431 | XKR3 | CAGAGGTCGGGCGCATAGAATCCTACAGTACAGCTTTCAGTTTT TAGAAAATGTGATAAT | SEQ ID NO: 2681 | Homo sapiens XK, Kell blood group complex subunit-related family, member 3 (XKR3), mRNA [NM_175878] |
| 28 | A_23_P434609 | S100A8 | AAAGCCATGAAGAAAATGAGGGTAGCCACAAAGATAGGTGAGTTAGTGGGCC CAGAGGCTGGGCCCT | SEQ ID NO: 2691 | Homo sapiens S100 calcium binding protein A8 (S100A8), mRNA [NM_002964] |
| 29 | A_23_P44257 | COMMD8 | AACATTTTACTTCTGCCGTTCTGTATGTTTCTAGGGAAACATTGGTCTG ATAAAAATAGGTGTG | SEQ ID NO: 2692 | Homo sapiens COMM domain containing 8 (COMMD8), mRNA [NM_017845] |
| 30 | A_23_P50907 | ITGAV | AAAGAGTGATTAAGTGAGGTTATTATTACCGGTAAATGGTAGATGGATTC TGCATTGTATTTCAGG | SEQ ID NO: 2700 | Homo sapiens integrin, alpha V (vitronectin receptor, alpha polypeptide, antigen CD51) (ITGAV), mRNA [NM_002210] |
| 31 | A_23_P59637 | DOCK4 | TTTTGGCAGTTGAGCAGTTGAATTTATCTTGAATTTATCATGTGTG TGTATTTCTGAAGCAG | SEQ ID NO: 2714 | Homo sapiens dedicator of cytokinesis 4 (DOCK4), mRNA [NM_014705] |
| 32 | A_23_P59921 | SUB1 | CAGAATTGGGAAAATGAGGTAGCGTAGGTAGTGTTCGGATTTTAAGG CAAAGTGCTAATTGAT | SEQ ID NO: 2715 | Homo sapiens SUB1 homolog (S. cerevisiae) (SUB1), mRNA [NM_006713] |
| 33 | A_23_P63343 | UTS2 | AGAATCTGAGAAAACCATACAAAGAAAAGTGAGACTCCGATTGCTT CTGGAAATACTGTGTC | SEQ ID NO: 2719 | Homo sapiens urotensin 2 (UTS2), transcript variant 1, mRNA [NM_021995] |
| 34 | A_23_P65768 | C15orf15 | TCCTGCATTGCCATCTACATACAATAAATATCAGATATTAGGATGTTAG ATTGCATCTCAGTGTT | SEQ ID NO: 2723 | Homo sapiens chromosome 15 open reading frame 15 (C15orf15), mRNA [NM_016304] |
| 35 | A_23_P66260 | ZNF267 | TGTGATGAATGTTGGTAAAGCCTTAGCTATAGGTCATAGGTGTCAC TACACATCGGAGAAGT | SEQ ID NO: 2724 | Homo sapiens zinc finger protein 267 (ZNF267), transcript variant 498723, mRNA [NM_003414] |
| 36 | A_23_P74001 | S100A12 | TGAAGGCTTTTACCCAGCAATGTCCTCAATGAGGGTCTTTCT TTCCCTGCCAAAACG | SEQ ID NO: 2738 | Homo sapiens S100 calcium binding protein A12 (S100A12), mRNA [NM_005621] |
| 37 | A_23_P7543 | ZFYVE16 | TCTGCCTCAGCAATTATCTAAATGATCTCGAATGCTGTCTGATAC GTGTGATCCATGGTGG | SEQ ID NO: 2740 | Homo sapiens zinc finger, FYVE domain containing 16 (ZFYVE16), mRNA [NM_014733] |
| 38 | A_23_P78092 | EVI2A | GCTGAATCAGACACTTGGAAAAGAAGAAGAAAACAGGTCACAGGACC CAACCTAGTGATGGAA | SEQ ID NO: 2746 | Homo sapiens ecotropic viral integration site 2A (EVI2A), transcript variant 1, mRNA [NM_001003927] |

Fig. 8-3

| No. | Probe ID No. | Symbols of genes | Sequence | SEQ ID NO: | Descriptions of genes (letters and numbers within [ ] indicates GenBank accession No.) |
|---|---|---|---|---|---|
| 39 | A_23_P82047 | BU507302 | TGTGTTTGGTTAATGTCAGGTGCCTGAACATTCAGCAGTTTATAAATTGCTTAATTTGTG | SEQ ID NO: 2746 | AGENCOURT_10309638 NIH_MGC_71 Homo sapiens cDNA clone IMAGE:6501220 5', mRNA sequence [BU507302] |
| 40 | A_23_P94230 | LY96 | TGAAGGTATTTCTGGGAGCCCAGAAGAAGAAATGCTCTCTTTGCTTGGAGTTGTCATGGTACA | SEQ ID NO: 2763 | Homo sapiens lymphocyte antigen 96 (LY96), mRNA [NM_015364] |
| 41 | A_23_P105648 | BX111927 | TTATGAGATGGTTCAGTTGAACTTCAAATAACAGTGCAGTAATTCACCTATATCTAAAGAGTGCC | SEQ ID NO: 2778 | BX111927 Soares_multiple_sclerosis_2NbHMSP Homo sapiens cDNA clone IMAGp998G05619, mRNA sequence [BX111927] |
| 42 | A_24_P11045 | THC2785765 | CCACCAGAAACGTAGACCTGATTTTCATGACAAATACGGTTAGCAACACAAGTCGGAATAG | SEQ ID NO: 2781 | COX7B_HUMAN (P24311) Cytochrome c oxidase polypeptide VIIb, mitochondrial precursor, partial (78%) [THC2785765] |
| 43 | A_24_P201702 | CLEC2B | ATTGGAATTCAAGTAAATACAACTGTTGCACTCAACATCAACATGGCGACCTAACTATAATTGACA | SEQ ID NO: 2815 | Homo sapiens C-type lectin domain family 2, member B (CLEC2B), mRNA [NM_005127] |
| 44 | A_24_P20996 | BC043173 | CTGAAAATGTTCATATATATATATATGAATGTCTCTTATGCTGAAGGGCTCTGATTGG | SEQ ID NO: 2818 | Homo sapiens cDNA clone IMAGE:5287121. [BC043173] |
| 45 | A_24_P235429 | ABCA1 | CCAAAGAGCCATGTGTCATGTAATACTGTAACCAGTTTGATATTGAGACATTAATTTGTAG | SEQ ID NO: 2823 | Homo sapiens ATP-binding cassette, sub-family A (ABC1), member 1 (ABCA1), mRNA [NM_005502] |
| 46 | A_24_P286054 | ZFYVE16 | GTGTATGTATTGTGCCATGTAAGTAATTGAAGAGTCTAAAATAACCAAATGGTAGAGGG | SEQ ID NO: 2842 | Zinc finger FYVE domain-containing protein 16 (Endofin) [Endosome-associated FYVE domain protein]. [Source:Uniprot/SWISSPROT;Acc:Q7Z3T8] [ENST00000380248] |
| 47 | A_24_P320326 | SUB1 | CAGAAAAACCGTGAAAGAAGAAGAAGAGAGGTGAGGACTCGAGAGGCCTGTCATGTTCTA | SEQ ID NO: 2857 | Homo sapiens SUB1 homolog (S. cerevisiae) (SUB1), mRNA [NM_006713] |
| 48 | A_24_P324581 | KIAA1466 | ATAATGCTCATAGAATGAATTGCTGTACCAACCAAGGCTAAAAAGAATTTAAGATAGCCC | SEQ ID NO: 2861 | Homo sapiens mRNA for KIAA1466 protein, partial cds. [AB040899] |
| 49 | A_24_P387869 | PKN2 | TTGTCCAGAGATCATTTATTTACCTTCCAAATTGTTTATTACCCAAGATCGTTTGGGAG | SEQ ID NO: 2885 | Homo sapiens protein kinase N2 (PKN2), mRNA [NM_006256] |
| 50 | A_24_P413669 | PFKFB2 | TGCAAATGGTTCTTTTATACTGTGGATGATACAGAGACTCTGTTACCTAAGATGTGATAAGC | SEQ ID NO: 2898 | Homo sapiens 6-phosphofructo-2-kinase/fructose-2,6-biphosphatase 2 (PFKFB2), transcript variant 2, mRNA [NM_001018053] |
| 51 | A_24_P450172 | AK095151 | TATGCCACTGAATAAAAGCTAGTTAAACGACGAGTAATTTTGGAT ATTAATCCTAGGCTAC | SEQ ID NO: 2902 | Homo sapiens cDNA FLJ37832 fis, clone BRSSN2009630. [AK095151] |
| 52 | A_24_P45620 | UTS2 | AGAAAGTTCAGGATTTCTGTGGACAAGATCCTAAGACATTTAGTGAGTCATCTTTTGGCC | SEQ ID NO: 2903 | Homo sapiens urotensin 2 (UTS2), transcript variant 1, mRNA [NM_021995] |
| 53 | A_24_P807201 | AK022997 | GTGAACATGTGATAAAATATTCAGTGACTTTCAGATTTATTTCTTGTTAGCCGGTGTGTC | SEQ ID NO: 2932 | Homo sapiens cDNA FLJ12935 fis, clone NT2RP2004982. [AK022997] |
| 54 | A_24_P890536 | CR627148 | AATTGCCTTGTGTACCCTAAGTATGGTGAAGGAGAATTGAATTCTAGAAAAGTCTTTC | SEQ ID NO: 2934 | Homo sapiens mRNA; cDNA DKFZp779F2127 (from clone DKFZp779F2127). [CR627148] |
| 55 | A_24_P153725 | KIAA1033 | TTTTGTAAAAGATGGCAAGTTTGTTACCTCACTTGAGTGGGGTTTCCTTTTCCCCAAT | SEQ ID NO: 2972 | Homo sapiens KIAA1033 (KIAA1033), mRNA [NM_015275] |
| 56 | A_32_P164203 | THC2663448 | TTGATGGTCATTGTACGGAGCTATTGTATGGATTAGTGTGGAGTGCTGTTTAGCCACATGAT | SEQ ID NO: 2975 | Q7WZG3_PASP1 (Q7WZG3) Ferric uptake regulator, partial (8%) [THC2663448] |

Fig. 8-4

| No. | Probe ID No. | Symbols of genes | Sequence | SEQ ID NO: | Descriptions of genes (letters and numbers within [ ] indicates GenBank accession No.) |
|---|---|---|---|---|---|
| 57 | A_32_P17504 | THC2698682 | ATGTCTATGCTGTTTCACTATGCTGCAAATATTCCAGCTTTTGCCCTTGATGCCGAAA | SEQ ID NO: 2982 | |
| 58 | A_32_P178966 | ENST00000379426 | GTAATATACAGGGTGAACTCTTTACTGATACACAGAAGACAACTGTTAAAAGTGAATCC | SEQ ID NO: 2985 | Novel protein. [Source:Uniprot/SPTREMBL;Acc:Q5T4T1] [ENST00000379426] |
| 59 | A_32_P224666 | CAPZA2 | AATGCTGTTTTGAGATTCTGAAATTAAATGAAAATACTTATTTCAGAAATGCATTAATG | SEQ ID NO: 2999 | Homo sapiens capping protein (actin filament) muscle Z-line, alpha 2 (CAPZA2), mRNA [NM_006136] |
| 60 | A_32_P226786 | BC045174 | TTATTGGTGCATGTAAGGCATTATCGTGTGTCTTAATGAAGGATTAATGCTGTTGATTGTT | SEQ ID NO: 3001 | Homo sapiens cDNA clone IMAGE:5273245. [BC045174] |
| 61 | A_32_P2333 | SUB1 | AGGAAGAAAAGGTATTCTTTAAATGCAGAACAATGGAGCCAGCTGACAGAACAGATTTC | SEQ ID NO: 3003 | Homo sapiens SUB1 homolog (S. cerevisiae) (SUB1), mRNA [NM_006713]. |

Fig. 21-1

| No | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P341938 | NOG | GCCAGGCGTGCGGCTGGAATTGCCATGGAGTAGCCCATGATTTCC GAGTGCAAGTGCTGGT | SEQ ID NO: 3030 | Homo sapiens noggin (NOG), mRNA [NM_005450] |
| 2 | A_23_P359174 | BC069659 | CCAAGGGTGCATACTAGGGTAAAGAAAAATTTTGTAATAGCAAC AGTGTTGGGATTTT | SEQ ID NO: 3031 | Homo sapiens cDNA clone IMAGE:7262526, with apparent retained intron [BC069659] |
| 3 | A_24_P15797 | NUDT22 | GCTGCCCTCAGATTCTCATTGGCGTTGGATGCCAAGACGACGTCG ACTGTCAGGAAAAAA | SEQ ID NO: 3032 | Homo sapiens cDNA FLJ34477 fis, clone HLUNG2003833. [AK091796] |
| 4 | A_24_P93039 | AK022351 | AAGTTGGTTTAATTTCGTTTTCATGAAAGGAAAAGATTAGGTTTC ATGAAAACAGTTGTC | SEQ ID NO: 3033 | Homo sapiens cDNA FLJ12289 fis, clone MAMMA1001788. [AK022351] |
| 5 | A_24_P931364 | AK022062 | TCCCGATCTGGAGTATGGTTTGGAAGTGTCATTGCTTTGTAGTAAG GCATTATTTCCTGGT | SEQ ID NO: 3034 | Homo sapiens cDNA FLJ12000 fis, clone HEMBB1001531. [AK022062] |
| 6 | A_32_P111394 | THC2643957 | GAATACAGTGTTCCTTTTCATCGGCGATATTTGACTGAACTAAGA CACATCAATTATAAGG | SEQ ID NO: 3035 | |
| 7 | A_32_P125569 | THC2649341 | GCTCTATCCTTGCCTTTGGCTTTTAGGCTTTAGGCTTTAGAATGAAAAGTGAGATGAGATGTC TGATACGCTCAGATAG | SEQ ID NO: 3036 | |
| 8 | A_32_P142802 | THC2699446 | CCGCCGCCACCACCATCCGAAGAAGAAAGGGGGTCAGGTATTCCTAGGCG TACGGGGACTGATAAA | SEQ ID NO: 3037 | |
| 9 | A_32_P19561 | THC2728305 | AAGAAGGGACAGTTACACAGTAATTGGGAAAAGTTCTGCAAGGA CAGATGTCATTGTC | SEQ ID NO: 3038 | |
| 10 | A_32_P209592 | THC2663167 | CAATGTAAAGCCAGAATATCAACGTCCTTTTGTCAAGATTTTCA AACCTATTTGGCTGAT | SEQ ID NO: 3039 | ALU1_HUMAN (P39188) Alu subfamily J sequence contamination warning entry, partial (5%) [THC2663167] |
| 11 | A_32_P228941 | THC2689491 | ACACCTAGTACAGGCTAGAAGTACTATAGTTGAGTAAGTTGGG ATGTGGAGTAGGCCCA | SEQ ID NO: 3040 | |
| 12 | A_32_P33304 | ANK3 | TGTTGGAATACGGCGGGTGATGTGTCTTTTATAAACTCACGTGA TTTAAAGGAAAGATGA | SEQ ID NO: 3041 | Homo sapiens cDNA FLJ44903 fis, clone BRAMY3005184, highly similar to Mus musculus ankyrin 3, epithelial (Ank3) mRNA [NM_016854] |
| 13 | A_32_P71171 | A_32_P71171 | TCTAGATAGTAATAGGAAGACAGAAATCCAGAGCGTCGATGGGT GGAGGGAGTGATTGA | SEQ ID NO: 3042 | |
| 14 | A_32_P98940 | THC2745859 | AAGAGTATTCCAAGATAGGCAAAGGTGTGTTGTTTTAGGAGGT GTATTCAGATTTGA | SEQ ID NO: 3043 | |
| 15 | A_23_P41864 | ENST00000334994 | TGGCTTGAGGCAGCATCGAGTTCATAAACAAATTGTGTGAAA ATGAGGCACAGGTGAT | SEQ ID NO: 3044 | Synleurin (CGL01891) [Source:Uniprot/SPTREMBL;Acc:Q7Z207] [ENST00000334994] |
| 16 | A_23_P65768 | C15orf15 | TCCTGCATTGCCATCTACATACTACATAATATCAGATATTACGGATGTTAG AATGCATCTCAGTGTT | SEQ ID NO: 3045 | Homo sapiens chromosome 15 open reading frame 15 (C15orf15), mRNA [NM_016304] |
| 17 | A_23_P70007 | HMMR | ACTATTCTTCAGAGTTTGTCATATACTGCTTCGTGTCATCTGCATG TCTACTCAGGATTTGA | SEQ ID NO: 3046 | Homo sapiens hyaluronan-mediated motility receptor (RHAMM) (HMMR), transcript variant 1, mRNA [NM_012484] |
| 18 | A_23_P70326 | CENPQ | GAATGGCTTACAGTTGTCTGGTCATGTGGAACTTGAAAAT GCTCAAATGCTTCAC | SEQ ID NO: 3047 | Homo sapiens centromere protein Q (CENPQ), mRNA [NM_018132] |

Fig. 21-2

| No. | Probe ID No. | Symbols of genes | Sequence | SEQ ID NO: | Descriptions of genes (letters and numbers within [ ] indicates GenBank accession No.) |
|---|---|---|---|---|---|
| 19 | A_23_P78092 | EVI2A | GCTGAATCAGACACTTGGAAAAGAACAAAACAGGTCACAGGACC CAACCTAGTGATGCAA | SEQ ID NO: 3048 | Homo sapiens ecotropic viral integration site 2A (EVI2A), transcript variant 1, mRNA [NM_001003927] |
| 20 | A_24_P11045 | THC2785765 | CCAGCAGAAACGTAGACCTGATTTCATGAGAAATACGGTAGCA ACAGAAGTCGGAATAG | SEQ ID NO: 3049 | COX7B_HUMAN (P24311) Cytochrome c oxidase polypeptide VIIb, mitochondrial precursor, partial (78%) [THC2785765] |
| 21 | A_24_P126741 | ENST00000309178 | AGGCTCCAAGCACAGTAAGCAAGATTGAAGATTAGTTGCAAGAGC TCAGAGGAGGGAGAAT | SEQ ID NO: 3050 | |
| 22 | A_24_P169378 | RPS7 | AAGTGAAATCTTCCAGAAAATCCAGAAAATCGGCTAGTAAGTGAA TTGGAGAAAAAGTTCA | SEQ ID NO: 3051 | Homo sapiens ribosomal protein S7 (RPS7), mRNA [NM_001011] |
| 23 | A_24_P201702 | CLEC2B | ATTGGAATTCAAGTAAATACAACTGTTCGACTCAAGATGCGGAC CTAACTATAATTGACA | SEQ ID NO: 3052 | Homo sapiens C-type lectin domain family 2, member B (CLEC2B), mRNA [NM_005127] |
| 24 | A_24_P276583 | TMCO1 | CCTTCATTTTCCTGCTATATTCTCTGTACTATGTCGATTCGACAG AAGATTCAGAAGATTC | SEQ ID NO: 3053 | Homo sapiens transmembrane and coiled-coil domains 1 (TMCO1), mRNA [NM_019026] |
| 25 | A_24_P333112 | A_24_P333112 | GGTGATCAGAATCAGAGGTATCAATGTGTGAGCGCAGAGGACCA AAAGGTATTGCAAGTT | SEQ ID NO: 3054 | |

Fig. 24-1

| No. | Probe ID No | Symbols of genes | Sequence | SEQ ID NO: | Descriptions of genes (letters and numbers within [ ] indicates GenBank accession No.) |
|---|---|---|---|---|---|
| 1 | A_23_P100263 | CMIP | GGCCGCGGAATTCTTTAGGTTCGTAATTGGAACCTTTGACCTGATCAAAGTGGACTT | SEQ ID NO: 3055 | Homo sapiens c-Maf-inducing protein (CMIP), transcript variant c-mip, mRNA [NM_198390] |
| 2 | A_23_P103561 | NAV1 | CCTCGCCAGAGATGGCTGGAGCCAGAAAAAGAAGGATGGTTTAAAAATGTTT | SEQ ID NO: 3056 | Homo sapiens neuron navigator 1 (NAV1), mRNA [NM_020443] |
| 3 | A_23_P109122 | RP5-860F19.3 | GGAGCCGGCGCGAGGTGGGTCACATTGCTCTGGTAAGTTGGAGAAACAGAACAA | SEQ ID NO: 3057 | Homo sapiens KIAA1442 protein, mRNA (cDNA clone IMAGE:5502800), complete cds. [BC054347] |
| 4 | A_23_P115161 | DARC | TCCGGTGAACTGAGAACTCAAGTCAGCTGGACTTCGAAGATGTATGGAATTCTTGTAT | SEQ ID NO: 3058 | Homo sapiens Duffy blood group, chemokine receptor (DARC), mRNA [NM_002036] |
| 5 | A_23_P117694 | CORO2B | ATTAGCTAGGATAGTAGTAGATGCATTATAGTCCATACGTGCTTTCCATGGCCGGCCCTA | SEQ ID NO: 3059 | Homo sapiens coronin, actin binding protein, 2B (CORO2B), mRNA [NM_006091] |
| 6 | A_23_P119143 | ICAM5 | GAGCCCCGGAGAGTCAGAGGGGGGTTATTTATTGGCTATTTACTTATTCATTT | SEQ ID NO: 3060 | Homo sapiens intercellular adhesion molecule 5, telencephalin (ICAM5), mRNA [NM_003259] |
| 7 | A_23_P142187 | HIF3A | ACCCCCCAGCTTCTTTCTACAGATGGTGGTACTCTTGGTCTCCCACAGGAAAAGGGGTG | SEQ ID NO: 3061 | Homo sapiens hypoxia inducible factor 3, alpha subunit (HIF3A), transcript variant 2, mRNA [NM_022462] |
| 8 | A_23_P144796 | PDLIM4 | TGCTCCACGCCTGCTTCTTAAGGTCCCGTCGGCCGTGTAAATATGTTTCACCTGT | SEQ ID NO: 3062 | Homo sapiens PDZ and LIM domain 4 (PDLIM4), mRNA [NM_003687] |
| 9 | A_23_P145681 | ACTL6B | CCCCAAAGTGGAAGAAGGAGAAGTACCCCAGGTCCAAGTCCTGGCATAACTA | SEQ ID NO: 3063 | Homo sapiens actin-like 6B (ACTL6B), mRNA [NM_016188] |
| 10 | A_23_P150407 | CREB3L1 | TTGCGGCTCCGTTGTTTATTTATGAAGTTAGTGCGGGGTTGGTGCTCGGTGGCC | SEQ ID NO: 3064 | Homo sapiens cAMP responsive element binding protein 3-like 1 (CREB3L1), mRNA [NM_052854] |
| 11 | A_23_P164258 | PIPOX | TGAATCCCCATAAACACCAGATTGAGTCTACCTTCTTTCTGGGCGGCTCCCTTT | SEQ ID NO: 3065 | Homo sapiens pipecolic acid oxidase (PIPOX), mRNA [NM_016518] |
| 12 | A_23_P164927 | SYNGR4 | CAAAGTCGCCGGGCTTGCTATGATGGCTGGAGAACTAAAATGCTTATCCAAATCAATAA | SEQ ID NO: 3066 | Homo sapiens synaptogyrin 4 (SYNGR4), mRNA [NM_012451] |
| 13 | A_23_P18119 | MPG2 | CGTGATGATAGGGATGAGTATATTGGCTCCGTGGTTGGACTTCTTGTCATCTTTTCTGGTAT | SEQ ID NO: 3067 | Homo sapiens interphotoreceptor matrix proteoglycan 2 (IMPG2), mRNA [NM_016247] |
| 14 | A_23_P204144 | KRT85 | CTCCCTGCGCGTTTCATGGTAGGGAGATGCATCCTAGTGTCGTCGTTGGCAGCTGTTT | SEQ ID NO: 3068 | Homo sapiens keratin 85 (KRT85), mRNA [NM_002283] |
| 15 | A_23_P204998 | FARP1 | TGCTCCTGAAGTGTGGTTGAAAGTGCGGCATTCTCTACTAGTATATATGTGCCCGTGT | SEQ ID NO: 3069 | Homo sapiens FERM, RhoGEF (ARHGEF) and pleckstrin domain protein 1 (chondrocyte-derived) (FARP1), transcript variant 1, mRNA [NM_005766] |
| 16 | A_23_P208482 | CLEC4M | GCACCCCAGATGTTCTTTGTCCATACAGTGTCCGATTTGGCGTTGTGAGTTGTA | SEQ ID NO: 3070 | Homo sapiens C-type lectin domain family 4, member M (CLEC4M), transcript variant 4, mRNA [NM_214677] |
| 17 | A_23_P209389 | CASP8 | GGCGGCCAGGACACCTGGCTAATTTTTAAAAATATTTTAGTAGAGACAGGGTTTCAGT | SEQ ID NO: 3071 | Homo sapiens caspase 8, apoptosis-related cysteine peptidase (CASP8), transcript variant C, mRNA [NM_033356] |
| 18 | A_23_P21495 | FCGBP | TCAGTCATCCACCAGGAACGGAACGAAGATTTCCTGAAGAAGAAGACAGGTCCCTCTGGAGGTTGCG | SEQ ID NO: 3072 | Homo sapiens Fc fragment of IgG binding protein (FCGBP), mRNA [NM_003890] |
| 19 | A_23_P258381 | SPSB4 | GCACCCGACTGCCCCACCTTAATGTGAATTTGACTGATGAATGAAGAGCGTTTGTAATA | SEQ ID NO: 3073 | Homo sapiens spIA/ryanodine receptor domain and SOCS box containing 4 (SPSB4), mRNA [NM_080862] |

Fig. 24-2

| No | Probe ID No. | Symbols of genes | Sequence | SEQ ID NO: | Descriptions of genes (letters and numbers within [ ] indicates GenBank accession No.) |
|---|---|---|---|---|---|
| 20 | A_23_P29079 | PFKL | CGACGCGGCTACGTCTTCGAGGACCGTTTGAACATCAGGACT TAAAGGTCAAGGTGGA | SEQ ID NO:3074 | Homo sapiens phosphofructokinase, liver (PFKL), transcript variant 1, mRNA [NM_001002021] |
| 21 | A_23_P329212 | ETS1 | GTCAACCCAGGCTGTATCGAGAATCCGGCTATACCTCGGATTACTT CATTAGGTATGGTATT | SEQ ID NO:3075 | Homo sapiens v-ets erythroblastosis virus E26 oncogene homolog 1 (avian) (ETS1), mRNA [NM_005238] |
| 22 | A_23_P341938 | NOG | GCCAGGGGTGCGGCTGGATTCGGCATCCAGTAGGGATCATTTGG GAGTGCAAGTGCTCGT | SEQ ID NO:3076 | Homo sapiens noggin (NOG), mRNA [NM_005450] |
| 23 | A_23_P344531 | SYNPO | TGGTCTGTGTGAAGATGAGAAGGTGCTTACTGAGTTAATG ATGAGTGACTATATTT | SEQ ID NO:3077 | Synaptopodin. [Source:Uniprot/SWISSPROT;Acc:Q8N3V7] [ENST00000307662] |
| 24 | A_23_P34554 | CACNA1E | CGGCCTCGATGATGTCTCTGTGACATGAGAAAAGGAAG ACAGAATTGGAAGCG | SEQ ID NO:3078 | Homo sapiens calcium channel, voltage-dependent, R type, alpha 1E subunit (CACNA1E), mRNA [NM_000721] |
| 25 | A_23_P358370 | FOXE1 | CCCCGCTACGACCACCACGGGCTACCAACCACGAGAGGCTTCACCG GGACCGGTCCGGCCAA | SEQ ID NO:3079 | H.sapiens HFKH4 mRNA for fork head like protein. [X94533] |
| 26 | A_23_P372144 | C19orf29 | CCCGGGCTCATGTCTGGAAATAGTTCGGTTTGTTTCTAAAAAGA GTTGTAGGTGGAAAA | SEQ ID NO:3080 | Homo sapiens chromosome 19 open reading frame 29 (C19orf29), transcript variant 2, mRNA [NM_021231] |
| 27 | A_23_P39265 | LYPD3 | TGCCTACTCCCCGCATCTTTGGGAATGGGTTCCCGATGTC TTCCTTAGTAGACTGT | SEQ ID NO:3081 | Homo sapiens LY6/PLAUR domain containing 3 (LYPD3), mRNA [NM_014400] |
| 28 | A_23_P398774 | PLD1 | ACTCTTGTGTGGAATCAATTTTTGATTCCGTGTATTGATCTG ATACACTCTCCCAA | SEQ ID NO:3082 | Homo sapiens cDNA FLJ34578 fis, clone KIDNE2008404, highly similar to PHOSPHOLIPASE D1 (EC 3.1.4.4). [AK091897] |
| 29 | A_23_P40334 | NPBWR2 | GGTGCGCCACGATGGGTGCCAAGCGTGTGTGAGGACAATGGGACTG GCGACAATGCCACGTT | SEQ ID NO:3083 | Homo sapiens neuropeptides B/W receptor 2 (NPBWR2), mRNA [NM_005286] |
| 30 | A_23_P407601 | C8orf6 | GTTCCTAGGTTAGTGTAGGGATTCTATTCTGAGATAAGAAC TTGGTGTCGGCTGAA | SEQ ID NO:3084 | Homo sapiens mRNA for hypothetical protein (C8orf6 gene). [AJ307469] |
| 31 | A_23_P49310 | ERN2 | GCCACCCTTCTTTTGGAGGAGGATTTCGAGGAGGAGGACCAAGCCAACTCCACTTCTTC CAGGAGGGTAGTCACT | SEQ ID NO:3085 | Homo sapiens endoplasmic reticulum to nucleus signalling 2 (ERN2), mRNA [NM_033266] |
| 32 | A_23_P50349 | TRIP10 | GGGAGGTTTGATGAGGGATTTCGGCCCCTCGAAAAGGCAGACAGGTTGGTTCCTTCCGGATA GGTCACTGTGTGCCA | SEQ ID NO:3086 | Homo sapiens thyroid hormone receptor interactor 10 (TRIP10), mRNA [NM_004240] |
| 33 | A_23_P74668 | C1orf158 | CCCACCCCTTCTTCCGGCCCTCGAAAGCGGCCAAGCCAACTCCACTTCTTC TCAAGAATTAAAGAT | SEQ ID NO:3087 | Homo sapiens chromosome 1 open reading frame 158 (C1orf158), mRNA [NM_152290] |
| 34 | A_23_P75867 | OR10A4 | AGTTCAACTGTACTTCTTCCGTCGAGAAGTCTGTCGTTCCTCCTGGAGAT AGGTTCAACTGGTC | SEQ ID NO:3088 | Homo sapiens olfactory receptor, family 10, subfamily A, member 4 (OR10A4), mRNA [NM_207186] |
| 35 | A_23_P84399 | CNTNAP2 | GTTGAGCACAATCGCTTAAAATATCAGGACGAAGTTGGGGAGGCAG GCAATGGAATAATG | SEQ ID NO:3089 | Homo sapiens contactin associated protein-like 2 (CNTNAP2), mRNA [NM_014141] |
| 36 | A_23_P87310 | LMO1 | CCCTCCTCGGGACGCCAGGCCGGCCGGACGCTGTACAGTCGTGTCTTGTAT ATACAGGGAACATTT | SEQ ID NO:3090 | Homo sapiens LIM domain only 1 (rhombotin 1) (LMO1), mRNA [NM_002315] |
| 37 | A_24_P102885 | WDTC1 | CTTCCAACGCCTCTCTTGTAGGTTGGTAATGAAGTATATTATTT GGTGAAGGAAACAGGT | SEQ ID NO:3091 | Homo sapiens WD and tetratricopeptide repeats 1 (WDTC1), mRNA [NM_015023] |
| 38 | A_24_P108517 | CRB3 | TGGCAACCTGCGGTCGGGAAGCCATCACTGCTATCATCGTGGTCT TCTCCCTGTTGGCTGC | SEQ ID NO:3092 | Homo sapiens crumbs homolog 3 (Drosophila) (CRB3), transcript variant 3, mRNA [NM_174881] |

Fig. 24-3

| No. | Probe ID No. | Symbols of genes | Sequence | SEQ ID NO: | Descriptions of genes (letters and numbers within [ ] indicates GenBank accession No.) |
|---|---|---|---|---|---|
| 39 | A_24_P117368 | AK055306 | GTGCCTGGGTCCCATTCAAACTCCAGCAGGGGGCGTTGGATCAG GCAAGCTTATTCCAAA | SEQ ID NO: 3093 | Homo sapiens cDNA FLJ30744 fis, clone FEBRA2000379. [AK055306] |
| 40 | A_24_P129107 | NKD2 | CCCCCACGCCACGCTACGGCCACAAGCGGTACGGCCAAAAGGG CAGGAGGGCCACTCG | SEQ ID NO: 3094 | Homo sapiens naked cuticle homolog 2 (Drosophila) (NKD2), mRNA [NM_033120] |
| 41 | A_24_P150426 | FAM124A | CCTGCCTGCGTCCTGCAGCTGAACCACAGTGGTTTCAAACACA GGTGCCCAGGGCACA | SEQ ID NO: 3095 | Homo sapiens family with sequence similarity 124A (FAM124A), mRNA [NM_145019] |
| 42 | A_24_P15182 | LOC646960 | CCCAGGAGGCCCCTGCCGGAACCGCCTGCGCCATCGCGGGCTGG GCCGCCCCTTCGAAG | SEQ ID NO: 3096 | PREDICTED: Homo sapiens similar to transmembrane protease, serine 9 (LOC646960), mRNA [XM_929928] |
| 43 | A_24_P15797 | NUDT22 | CCGGGGTGACATTCTCATTGCCGTGGATGCCAAGACCAGGTGG ACCTGTCAGGAAAAAA | SEQ ID NO: 3097 | Homo sapiens cDNA FLJ34477 fis, clone HLUNG2003833. [AK091796] |
| 44 | A_24_P161144 | MGC46336 | CCTTCCGTCGACACAGAGACGGGCTCAGGAGCGGCGTTTCTGTATGGC AGATCTTTCTCAGAGAG | SEQ ID NO: 3098 | Homo sapiens hypothetical protein MGC46336, mRNA (cDNA clone MGC:46336 IMAGE:5589928), complete cds. [BC036762] |
| 45 | A_24_P161531 | LOC729956 | TCTCGCATGTGCCCCGTCCTCTACGAGGCTGCCGTGAAATCCAG CTGAACGGCTACTGTT | SEQ ID NO: 3099 | PREDICTED: Homo sapiens hypothetical protein LOC729956 (LOC729956), mRNA [XM_001131873] |
| 46 | A_24_P166434 | PSORS1C2 | CCTACCGCGCCCAGTCGGTCGCTGAAGAGACCTGCCTGAAACTGG AGTCTGCCCCGTGAA | SEQ ID NO: 3100 | Homo sapiens psoriasis susceptibility 1 candidate 2 (PSORS1C2), mRNA [NM_014069] |
| 47 | A_24_P178877 | LOC339809 | TCGCCCCAGCCCCCAGGATGCTTGGCTTGGAAGGACTGAAAGGCATAGAG GGATTCTTTTGCTGGA | SEQ ID NO: 3101 | Homo sapiens mRNA for KIAA2012 protein. [AB095932] |
| 48 | A_24_P20795 | IRX4 | CCCTTCCCGACTGTGGGCGGCTGGACGGACCGAGGACTCCCCG GTAAGCAGTCTCAGAA | SEQ ID NO: 3102 | Homo sapiens iroquois homeobox protein 4 (IRX4), mRNA [NM_016358] |
| 49 | A_24_P209389 | MLXIPL | CCAGGCCCTTCCCATAGAGGCTTCTACGCTCGGCAGCCCGTATTCGGAG CGTGGGTTTGGGCCTT | SEQ ID NO: 3103 | Homo sapiens MLX interacting protein-like (MLXIPL), transcript variant 4, mRNA [NM_032954] |
| 50 | A_24_P218074 | ZNF467 | GGATGCCCCCGGCGGCCAAGCCCCTGGGCAAGAGGCGCCTGGCGGAC CGGGCTGCGGCCCAGG | SEQ ID NO: 3104 | Homo sapiens zinc finger protein 467 (ZNF467), mRNA [NM_207336] |
| 51 | A_24_P252223 | C6orf85 | ACACCCTCCGTTCGGCTAGGCTACGCTGTCAGCGTTTCAATAA AAGTTATGCAGAATG | SEQ ID NO: 3105 | Homo sapiens chromosome 6 open reading frame 85 (C6orf85), mRNA [NM_021945] |
| 52 | A_24_P254133 | APC2 | TGTGCCAGCCCCATGGTGGTCGGAGCCACCACCACGACTCTGGCGGG CCGAGAAAAGCCCTGGG | SEQ ID NO: 3106 | Homo sapiens adenomatosis polyposis coli 2 (APC2), mRNA [NM_005883] |
| 53 | A_24_P272845 | DOCK3 | GCGGGATTCATCATCCTCTGTCTGTGGTCACATGCCTCTAGTGAA GCAGAAAAGATGGTGA | SEQ ID NO: 3107 | Homo sapiens dedicator of cytokinesis 3 (DOCK3), mRNA [NM_004947] |
| 54 | A_24_P280497 | KIAA1545 | CATCCCCGGCCCACAGCAAGGCGGCCCCTGGAGACGTGAAGGTC AAGGAGGAGGCGCGGGG | SEQ ID NO: 3108 | Homo sapiens XTP9 (XTP9) mRNA, complete cds. [AF490258] |
| 55 | A_24_P306034 | ANKDD1A | CTCTCTCCCGGTTGTAGTCATCAATTCTGCGCAGTAAAAATTCTC GTCTATGAGCTGGAA | SEQ ID NO: 3109 | Homo sapiens cDNA FLJ25370 fis, clone CBR02141. [AK098736] |
| 56 | A_24_P315066 | ZMIZ2 | CACCGGACCTGGTTAGGAACACAATGAGGAGGTCGTTCTTCTG TTTGAAGAACTGAT | SEQ ID NO: 3110 | Homo sapiens zinc finger, MIZ-type containing 2 (ZMIZ2), transcript variant 1, mRNA [NM_031449] |
| 57 | A_24_P316454 | BC022826 | AGAACACAGAGGAGCCCGCCACCAATGAAGGTCATTGGTCTT CAAGATAAAGTGGGTA | SEQ ID NO: 3111 | Homo sapiens cDNA clone IMAGE:5441030, partial cds. [BC022826] |
| 58 | A_24_P331711 | THEM5 | TATCAGGTCCTCCACACGCAAAGATACAGAAGAGGAGGCTGAAG AGTGTCATCTGAGGG | SEQ ID NO: 3112 | Homo sapiens thioesterase superfamily member 5 (THEM5), mRNA [NM_182578] |
| 59 | A_24_P345837 | MSX1 | ACGGGGGCCTCCCAGGCAAAGAATACAGAGGAGGCTGAAG AAGCTGAAGATGGCCG | SEQ ID NO: 3113 | Homo sapiens msh homeobox 1 (MSX1), mRNA [NM_002448] |

Fig. 24-4

| No. | Probe ID No. | Symbols of genes | Sequence | SEQ ID NO: | Descriptors of genes (letters and numbers within [ ] indicate GenBank accession No.) |
|---|---|---|---|---|---|
| 60 | A_24_P346885 | CYB561D1 | CCTCCCTGCTCTGAAACTCTCCAGTGTGGTGTGAAACTGAGAAGA AACGGTTAGTCGGGCT | SEQ ID NO: 3114 | Homo sapiens cytochrome b-561 domain containing 1 (CYB561D1), mRNA [NM_182503] |
| 61 | A_24_P349274 | OR4X2 | GGAGGGTTCATGCATTCCTTTGGACAAATCGTTGTCATCTTCCA GGTGCTCTTCTGTGGC | SEQ ID NO: 3115 | Homo sapiens olfactory receptor, family 4, subfamily X, member 2 (OR4X2), mRNA [NM_001004727] |
| 62 | A_24_P366122 | ACBD4 | TACGGCGGGCTCCTATGAAGAGATGCTGGGATTCGGGATTCTACAGATTACTA CAAGCAGGCAGCATG | SEQ ID NO: 3116 | Homo sapiens acyl-Coenzyme A binding domain containing 4 (ACBD4), mRNA [NM_024722] |
| 63 | A_24_P385012 | BC030084 | TCGAGGTCATCTGTTGGGTGAAATACTGTTTATATGGTTAGTAC TAAAATTAAAAGTTAC | SEQ ID NO: 3117 | Homo sapiens cDNA clone IMAGE:4791887. [BC030084] |
| 64 | A_24_P39484 | AK025430 | CGCAGGTGCCCCACGGCTGCAGGGAGTCCAGGGGGGCCACCGACA CGCGCAAATCCGGC | SEQ ID NO: 3118 | Homo sapiens cDNA FLJ21777 fis, clone HEP00173. [AK025430] |
| 65 | A_24_P401270 | LOC649294 | TCCTCTCTGCTCCAAGCTCTCCCCATCATGAAATAATTCTGATAA CGAGAATGGACTTTG | SEQ ID NO: 3119 | Homo sapiens cDNA FLJ33940 fis, clone CTONG2018069. [AK091259] |
| 66 | A_24_P401294 | FLJ35934 | GCCACCGGCTTCTGCGCTCTGCAAGTGGCTTCAGCTAGAAGG GGTCCAGCGGGTGCGGC | SEQ ID NO: 3120 | Homo sapiens cDNA FLJ35934 fis, clone TEST12011315. [AK093253] |
| 67 | A_24_P405992 | SYNPO | GTCAGGGGGGCAAGCCCAAGTCGTTGGACCTGGTGGCCAACCTGC CCAAGGGGGCTCTCGC | SEQ ID NO: 3121 | Homo sapiens synaptopodin (SYNPO), mRNA [NM_007286] |
| 68 | A_24_P419028 | MOP-1 | ACGGGTCACTTTTCAGAGGTATAGTGTTCGTTTTTGATTCT CGAGTTAAAAGTAGAA | SEQ ID NO: 3122 | Homo sapiens mRNA for MOP-1, complete cds. [AB014771] |
| 69 | A_24_P478362 | NP511100 | ATCACCCCGGCCCGGAAGAGACCACTGCGAGCGCCTGCAACCGC AGGGGCGAATCCTAG | SEQ ID NO: 3123 | GB|AB065467.1|BAC05726.1 seven transmembrane helix receptor [Homo sapiens] [NP511100] |
| 70 | A_24_P542291 | LOC339352 | CACTTCCAGCCGTCTGGACTACTTCTGCAGAAGAGAGGAGCATTGACA GGAGGTTGCTCAAGCGC | SEQ ID NO: 3124 | PREDICTED: Homo sapiens similar to ATP binding domain 3 (LOC339352), mRNA [XR_017668] |
| 71 | A_24_P662177 | THC2566469 | GGGCAGGTAGGATTTCAATGGCATGTTACATAAGCCATGCCTCCTAA AGGGACAGAAATGTACA | SEQ ID NO: 3125 | |
| 72 | A_24_P689119 | A_24_P689119 | CGGGCGTGCCCACAACACAGCAGCAGCAGCAACCCAGGCTCGTCACTG CATCCCGCAGGGGGTC | SEQ ID NO: 3126 | |
| 73 | A_24_P752279 | A_24_P752279 | GCCAGCACCGTCTCCAGACGACCAAGAAGATCACCGCCAATGGGATTTGA CCTCAAGGGTCCTCCT | SEQ ID NO: 3127 | |
| 74 | A_24_P778928 | A_24_P778928 | TCCAGCCGGGCGCGACGACATGGGATCCGGATTGGCAAGAGCCGGGGT CAGAGAAAGACCCCGG | SEQ ID NO: 3128 | |
| 75 | A_24_P828125 | A_24_P828125 | CAGTCCCGCAGCCCCACACCAGCAGCAGAAGTCAGCCCCAGCATTGACA CCCAGCAGTGGGGGGC | SEQ ID NO: 3129 | |
| 76 | A_24_P848662 | CR594528 | CCTGGTGCCCCACGACGGGATCCTGCAAGAAATGAGGACTGA GGACTGCGGAGGGTCG | SEQ ID NO: 3130 | full-length cDNA clone CS0DM002YC17 of Fetal liver of Homo sapiens (human) [CR594528] |
| 77 | A_24_P916317 | FOXC1 | CAGAAGCCCGACAAGAAGATCACCCTCAATGGGATTTACCA GTTCATCATGGACGGC | SEQ ID NO: 3131 | Homo sapiens FOXC1 mRNA, partial cds. [AF343007] |
| 78 | A_24_P929524 | THC2534212 | TCCTGGACCTATTATGCCTCGTTCCTGGGAACGGTCCA GGTTGGCTGGCTCTCA | SEQ ID NO: 3132 | O60449_HUMAN (O60449) Neuronal thread protein AD7c-NTP, partial (15%) [THC2534212] |
| 79 | A_24_P930963 | LOC650392 | GCCCCATTTCAAGTATAACCAGGAGGGAAAATGGTGCTTGAAAT AAGCATGCCACAAAGG | SEQ ID NO: 3133 | Homo sapiens cDNA clone IMAGE:5264670. [BC036550] |
| 80 | A_32_P101073 | A_32_P101073 | GCGGGGCGGCGACGTGCGCGAGACCCTGTAGCGCGGGGACCTCAC CGAGCTGAGGAGGCGC | SEQ ID NO: 3134 | |

Fig. 24-5

| No. | Probe ID No. | Symbols of genes | Sequence | SEQ ID NO: | Descriptions of genes (letters and numbers within [ ] indicates GenBank accession No.) |
|---|---|---|---|---|---|
| 81 | A_32_P125589 | THC2649341 | GGGTCTATGCCTTGCTTAGCCTTTTGAATGAAAGTGAGATGTCTGATCAGCTGAGATAG | SEQ ID NO: 3135 | |
| 82 | A_32_P132356 | THC2635710 | GTGTTTTTCCCCGGCTGGAAATCTAAGAGCGATAGGGTTCTCCAAATAAACCGGCAAT | SEQ ID NO: 3136 | |
| 83 | A_32_P136622 | BC020341 | CCCAGCCGAAAGCTGCTCGAGCTTCAGATAGTGGGCAGCCCTCTGAGGCTGCAGCGG | SEQ ID NO: 3137 | Homo sapiens cDNA clone IMAGE:4177218. [BC020341] |
| 84 | A_32_P142802 | THC2899446 | CCGCGGCAACCACATCCGAAGGAAAGGGGTCAGGTATTCTAGGCGTACGGGGACTGATAAA | SEQ ID NO: 3138 | |
| 85 | A_32_P145764 | BC043547 | GGTCCCGTGCCTCTGTGTAACCAATAACCAATGCCATATAAATGGAAAAGTATAAAGAA | SEQ ID NO: 3139 | Homo sapiens, clone IMAGE:5171873, mRNA. [BC043547] |
| 86 | A_32_P156776 | THC2503530 | CCCCGCCTTTTTTCGTTAAGCATAATTGTCTTAGGTTTGCCTAGTTTCATTTAAGAA | SEQ ID NO: 3140 | AA360388 EST69518 T-cell lymphoma Homo sapiens cDNA 5' end similar to EST containing Alu repeat, mRNA sequence [AA360388] |
| 87 | A_32_P16662 | THC2567500 | TGGGTGGTGTGGGCTAAATGCTAAATGAAGTGAAAACAAGAAAAGCCAAGAAGGATCTGTGCTAATT | SEQ ID NO: 3141 | F10881 HSC3LC012 normalized infant brain cDNA Homo sapiens cDNA clone c-31c01 3', mRNA sequence [F10881] |
| 88 | A_32_P172002 | A_32_P172002 | AGTATGCATCCAAGGGG | SEQ ID NO: 3142 | |
| 89 | A_32_P199506 | BU191598 | GATCCTCTGAGGTTTCCAAGGAAGAAGACCCCGGCCTAATCCTCTGAAGTCGGAGGTCACAG | SEQ ID NO: 3143 | AGENCOURT_8099541 NIH_MGC_102 Homo sapiens cDNA clone IMAGE:6254414 5', mRNA sequence [BU191598] |
| 90 | A_32_P213509 | THC2663555 | GATTTGTTCCAGTGTGTTGGAGCCCCTTTTTAATGAAAATTGTCAACAGCTACAGTGGAAAAA | SEQ ID NO: 3144 | |
| 91 | A_32_P29130 | BG058000 | CCGGCGAACCTGCTTTGTAAGGAACTAAAACATTACATGCTGGTGAAGCAAAGATTTCA | SEQ ID NO: 3145 | BG058000 7f78d09.x1 Lupski_dorsal_root_ganglion Homo sapiens cDNA clone IMAGE:3303208 3', mRNA sequence [BG058000] |
| 92 | A_32_P334325 | RIMBP2 | ACCCGAGACGTGACCCCAATGCAAAGCCATTAGGAAGGTTCTGGAGTCGGGAAACCAAAG | SEQ ID NO: 3146 | Homo sapiens RIMS binding protein 2 (RIMBP2), mRNA [NM_015347] |
| 93 | A_32_P37943 | A_32_P37943 | CCGGGACGGAGGAGGGCGTGTCTGGGGGTCGGGAGCCGGTGGGGGTCGCTCTGGGGCGGCGTC | SEQ ID NO: 3147 | |
| 94 | A_32_P4466 | FL32214 | AACGGGCGGTGTGGCAAAACCTCTACAGTTGCATTAATAAGATCCAACATACGGCGAGAATG | SEQ ID NO: 3148 | Homo sapiens FLJ32214 protein, mRNA (cDNA clone IMAGE:4002459), complete cds. [BC104018] |
| 95 | A_32_P74615 | SP5 | GCCCCCCGATCCAGCTTGGGGGGCGTGACGGCCGGCAGAAGACGCACGTGCAGGCCTCTGG | SEQ ID NO: 3149 | Homo sapiens Sp5 transcription factor (SP5), mRNA [NM_001003845] |
| 96 | A_32_P78566 | THC2689192 | CTTCCCCGTGTCGGCGGCCCCTGTACTGTCTTCACACTCGGCCATCAGCTTGCACGCGTGC | SEQ ID NO: 3150 | Q7X069_ORYSA (Q7X069) Expressed protein, partial (6%) [TH2689192] |
| 97 | A_32_P79103 | BM932034 | GTGCTACAGAATGAAATAGGCATTTTAGGAAGGTGAGTCAGAAGTGGGAGTGGGGGATA | SEQ ID NO: 3151 | UI-E-EJ1-aji-k-24-o-UI.r1 UI-E-EJ1 Homo sapiens cDNA clone UI-E-EJ1-aji-k-24-o-UI 5', mRNA sequence [BM932034] |
| 98 | A_32_P82111 | LRFN2 | ATGCCGGACGTGAGCCCTGAGTGTTTGGAAAGGGGAGACTCCGGCTTTGTAATCACAAATG | SEQ ID NO: 3152 | Homo sapiens leucine rich repeat and fibronectin type III domain containing 2 (LRFN2), mRNA [NM_020737] |

Fig. 24-6

| No. | Probe ID No. | Symbols of genes | Sequence | SEQ ID NO: | Descriptions of genes (letters and numbers within [ ] indicates GenBank accession No.) |
|---|---|---|---|---|---|
| 99 | A_23_P102235 | SNRPG | ACAACAGAAGAATATTGGAATGGTGGTAATAGGAGGAATAGTATCATCATGTTAGAAGC | SEQ ID NO: 3153 | Homo sapiens small nuclear ribonucleoprotein polypeptide G (SNRPG), mRNA [NM_003096] |
| 100 | A_23_P108394 | THC2763023 | ATTCAGAAAGGTTGGTTGTGATAGATAGTAAGTGTGTTCATTTATTAGTGGTTGTCTG | SEQ ID NO: 3154 | Q81UM9_HUMAN (Q81UM9) ACSL3 protein, complete [THC2467888] |
| 101 | A_23_P110362 | MAP2K1IP1 | ACTGAGACAAGTGTGGAAGTTTCTTAATCTGACAGTGGTTCAGTGTGTAGGTTATCTT | SEQ ID NO: 3155 | Homo sapiens mitogen-activated protein kinase kinase 1 interacting protein 1 (MAP2K1IP1), mRNA [NM_021970] |
| 102 | A_23_P110611 | ZH2C2 | CTCTTGAAAAGGAGACTTCAGTGTGTTGGACTGTGTCAAACCAGGTTCTTGAATACTTAA | SEQ ID NO: 3156 | Homo sapiens zinc finger, H2C2 domain containing (ZH2C2), mRNA [NM_017676] |
| 103 | A_23_P111321 | ARG1 | TGGAATGAGGAGGACAAAGCTACCACATGTGAAAAGGTAGTATGTGTCCATGTCATTCAAA | SEQ ID NO: 3157 | Homo sapiens arginase, liver (ARG1), mRNA [NM_000045] |
| 104 | A_23_P11201 | GPR34 | AGTAGGAGTGAAAGGACTTCAGAGAATTTAAAGCAGGATAGTCCCTGCAATGATACATCTGTG | SEQ ID NO: 3158 | Homo sapiens G protein-coupled receptor 34 (GPR34), transcript variant 1, mRNA [NM_005300] |
| 105 | A_23_P112251 | LOC552891 | AGAATTCTTAAGTTCACAAGTGTTTTACTTCGACGATGTGGCTTTGATTTAATTTGGGAC | SEQ ID NO: 3159 | Homo sapiens hypothetical protein LOC552891 (LOC552891), mRNA [NM_004125] |
| 106 | A_23_P117852 | KIAA0101 | TACTGCTGCCATTTTTATTGGTTGTTGATTATGGAATGGTGCCATATTGTCACTCCTTC | SEQ ID NO: 3160 | Homo sapiens KIAA0101 (KIAA0101), transcript variant 1, mRNA [NM_014736] |
| 107 | A_23_P120048 | BAZ2B | TATTTCGTCTGAAGGTAATGATAGGCTATACAGAGTGTACAGTAATTATGGTGTAGCAAC | SEQ ID NO: 3161 | Homo sapiens bromodomain adjacent to zinc finger domain 2B (BAZ2B), mRNA [NM_013450] |
| 108 | A_23_P120316 | MTHFD2 | AGGATATTCGTTGCTATTAGTACTACTCATTTATGTATGTTACCCTTCAGTAAGTTCTCCC | SEQ ID NO: 3162 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 109 | A_23_P121622 | SULT1B1 | GAAATAGAGATTGTGTGTAGTTGATTGAAACGAGGGCAGTTATGAATTGATTTGGGCAAT | SEQ ID NO: 3163 | Homo sapiens mRNA for SULT1B2, complete cds. [D89479] |
| 110 | A_23_P121716 | ANXA3 | TGCACATTCGAACAGAGTTCAAGAAGCATTATGGCTATTCCCTAATTCAGGAATTAAAT | SEQ ID NO: 3164 | Homo sapiens annexin A3 (ANXA3), mRNA [NM_005139] |
| 111 | A_23_P128930 | PSMC6 | GAACAAGGAAGATTAGAACAGTTCAAGAAGCATTATGCAAAATCCATGCAGGTCCCATTACAAAGGATGGTGAA | SEQ ID NO: 3165 | Homo sapiens proteasome (prosome, macropain) 26S subunit, ATPase, 6 (PSMC6), mRNA [NM_002806] |
| 112 | A_23_P134714 | HRSP12 | TAAATTACACCTGTGTGCAGGTGATTACTCAATATAGGAAAGAGATACGGATTAGATAG | SEQ ID NO: 3166 | Homo sapiens heat-responsive protein 12 (HRSP12), mRNA [NM_005836] |
| 113 | A_23_P137366 | C1QB | CACCGACAGAAGACTGACTAGTGGGCATGCAGGGTGCCAACAGGATGTTTTGGGGTTCCT | SEQ ID NO: 3167 | Homo sapiens complement component 1, q subcomponent, B chain (C1QB), mRNA [NM_000491] |
| 114 | A_23_P141549 | RPS7 | GTCAAATGTAGATGGGAGCGGGCTCATAAAGGTTCATTTGGAGAAAGCAGAGGAAGAAT | SEQ ID NO: 3168 | Homo sapiens ribosomal protein S7 (RPS7), mRNA [NM_001011] |
| 115 | A_23_P143958 | RPL22L1 | ATTGGTCGAGTGGTTGCATCTGACAAGCAGAGACAAGTAGGAACTTCGTTACTTCCAGATTA | SEQ ID NO: 3169 | Homo sapiens ribosomal protein L22-like 1 (cDNA clone IMAGE:4865966), mRNA [BC049823] |
| 116 | A_23_P144497 | RPS3A | GCAAATGCGGAAGAAGATGATGGAAAATCATGATGCCGAGAGGTGCAGACAAATGACTTGAA | SEQ ID NO: 3170 | Homo sapiens ribosomal protein S3A (RPS3A), mRNA [NM_001006] |
| 117 | A_23_P14564 | GPR65 | AACAAGTTTAAATTGTTGCTGATCGAATTGCTAGTGTTTGTAACCGAAACAGGAAAG | SEQ ID NO: 3171 | Homo sapiens G protein-coupled receptor 65 (GPR65), mRNA [NM_003608] |

Fig. 24-7

| No. | Probe ID No. | Symbols of genes | Sequence | SEQ ID NO. | Descriptions of genes (letters and numbers within [ ] indicates GenBank accession No.) |
|---|---|---|---|---|---|
| 118 | A_23_P14708 | SUHW4 | TCTTGTAGCTGCATACAAGTGTTAGGCTGCCAGGCTGGTAAGGTTACCTTAATTAAAGTT | SEQ ID NO:3172 | Homo sapiens suppressor of hairy wing homolog 4 (Drosophila) (SUHW4), transcript variant 1, mRNA [NM_017661] |
| 119 | A_23_P14734 | RPS27L | TACAGATCACCACGGTTTTCAGCCATGCTCAGACAGTGGTTGCTTTGTAGGTTGTTGA | SEQ ID NO:3173 | Homo sapiens ribosomal protein S27-like (RPS27L), mRNA [NM_015920] |
| 120 | A_23_P151637 | RNASE2 | GTGGTAACCCAAATATGACCTGTCCTAGTAACAAAACTCGCAAAAATTGTGAGGAGAGTG | SEQ ID NO:3174 | Homo sapiens ribonuclease, RNase A family, 2 (liver, eosinophil-derived neurotoxin) (RNASE2), mRNA [NM_002934] |
| 121 | A_23_P152202 | BCL2A1 | TGTAACCATATTGCATTTGAAGGTATTCTCATCAAGAAACTTCACGACAGAAATTGC | SEQ ID NO:3175 | Homo sapiens BCL2-related protein A1 (BCL2A1), mRNA [NM_004049] |
| 122 | A_23_P153037 | ZNF624 | TGTGGTTAGATGCACATGGAGACACAGGTATGGAAGAATATACACCAGGGTGTTAATATTGA | SEQ ID NO:3176 | Homo sapiens zinc finger protein 624 (ZNF624), mRNA [NM_020787] |
| 123 | A_23_P155765 | HMGB2 | TAAAAATCGAGGTCGTAGCTTTTGATGGGTACTACACAGTTAGATTTTAGAGGTTG | SEQ ID NO:3177 | Homo sapiens high-mobility group box 2 (HMGB2), mRNA [NM_002129] |
| 124 | A_23_P155815 | NCAPG | AAGTTAGGAAGACGATGGAGGTGGAATCCTTAAGAATTATGTCGAGTCTATTTGCTTAA | SEQ ID NO:3178 | Homo sapiens non-SMC condensin I complex, subunit G (NCAPG), mRNA [NM_022346] |
| 125 | A_23_P156842 | EEF1E1 | AAGAAAAAGGAATGGTTCAGCAGTGGTTAGAATAACAGGGTCACTCAAGTGGAGTGGGCACT | SEQ ID NO:3179 | Homo sapiens eukaryotic translation elongation factor 1 epsilon 1 (EEF1E1), mRNA [NM_004280] |
| 126 | A_23_P157449 | POLR2K | GGTCTCTCTTGCTTCAAAATATCTTCTTGTACAGTACTCAGCATTTTAGATGTGGTTGAC | SEQ ID NO:3180 | Homo sapiens polymerase (RNA) II (DNA directed) polypeptide K, 7.0kDa (POLR2K), mRNA [NM_005034] |
| 127 | A_23_P159650 | COX7B | CAAATACGGTAATGCTGTATTAGCTAGCTGGACCCACTTCTGTATTGTTACATGGAGACATA | SEQ ID NO:3181 | Homo sapiens cytochrome c oxidase subunit VIIb (COX7B), nuclear gene encoding mitochondrial protein, mRNA [NM_001866] |
| 128 | A_23_P160466 | SLC19A2 | CTTGGTATGTCGCCATATTTATAGCAATGCTGAACTCAATGTGGAAGTGTATGTATCCA | SEQ ID NO:3182 | Homo sapiens solute carrier family 19 (thiamine transporter), member 2 (SLC19A2), mRNA [NM_006996] |
| 129 | A_23_P162596 | ACTR6 | TTAACGGGTTCAGTGGCAGCAGTTTTCCTTAGAAGGTAGTTTTGTGTGACTGTGAGCTAAACT | SEQ ID NO:3183 | Homo sapiens ARP6 actin-related protein 6 homolog (yeast) (ACTR6), mRNA [NM_022496] |
| 130 | A_23_P163025 | RNASE3 | AGGGACGACAGGTCAGAGAGTGGGAAACAATGGTTCCAAAACTGTTGACTTCCCAAATTTGTCT | SEQ ID NO:3184 | Homo sapiens ribonuclease, RNase A family, 3 (eosinophil cationic protein) (RNASE3), mRNA [NM_002935] |
| 131 | A_23_P167168 | IGJ | TTGGGTGATGTAAAACCAACTCCCTGCCACCAAAATAATTAAAATAGTCACATTGTTATC | SEQ ID NO:3185 | Homo sapiens immunoglobulin J polypeptide, linker protein for immunoglobulin alpha and mu polypeptides (IGJ), mRNA [NM_144646] |
| 132 | A_23_P170233 | CSTA | AACTGGCTACTGAGTCATGACTCCTGCTGATAAATATAACCATGAATAAAGAAGGATTCT | SEQ ID NO:3186 | Homo sapiens cystatin A (stefin A) (CSTA), mRNA [NM_005213] |
| 133 | A_23_P16325 | PDCD10 | CCAACCGACTAATTCATCAAAACCAACTTAATACTTCAGACGTTCAAAACTGTGGGCCTGAA | SEQ ID NO:3187 | Homo sapiens programmed cell death 10 (PDCD10), transcript variant 1, mRNA [NM_007217] |
| 134 | A_23_P18372 | B3GNT5 | AAATGTCAACAAAGGCAAAATAAAACTATCAGCTTGATGTGTCACTTGAATAGAAGCATGGT | SEQ ID NO:3188 | Homo sapiens UDP-GlcNAc:betaGal beta-1,3-N-acetylglucosaminyltransferase 5 (B3GNT5), mRNA [NM_032047] |
| 135 | A_23_P19291 | TUBB2A | ACTTCTCAGATCACAATCGTCATCCTTAGTGAACTTCTGTTGTCCTGAAGGATGGTGTTTG | SEQ ID NO:3189 | Homo sapiens tubulin, beta 2A (TUBB2A), mRNA [NM_001069] |

Fig. 24-8

| No. | Probe ID No. | Symbols of genes | Sequence | SEQ ID NO: | Descriptions of genes (letters and numbers within [ ] indicates GenBank accession No.) |
|---|---|---|---|---|---|
| 136 | A_23_P200030 | FPGT | TAAAAATTGGTAAACTAGAAGTAACTTGTCGACAACCCTAGTTATGATAGTTATGTGGG | SEQ ID NO: 3190 | Homo sapiens fucose-1-phosphate guanylyltransferase (FPGT), mRNA [NM_003838] |
| 137 | A_23_P200298 | AGL | TAGATTTTTAACAGGTGCATTGACTGAGTAAAGGTTTCGGTAGAATGCTTCATACTTGAGTG | SEQ ID NO: 3191 | Homo sapiens amylo-1, 6-glucosidase, 4-alpha-glucanotransferase (glycogen debranching enzyme, glycogen storage disease type III) (AGL), transcript variant 4, mRNA [NM_000028] |
| 138 | A_23_P200955 | A_23_P200955 | AGACCATGATGAACCTGAGATTGATGTCAAGAACTACCATGGTTATTTGTTTCATCTAC | SEQ ID NO: 3192 | |
| 139 | A_23_P20225 | RRM2B | TGCTGCTTTGTAAAAGTTAAAGATTGAAAGAGAATCTCATATTCCCAAGGCATTAGGA | SEQ ID NO: 3193 | Homo sapiens ribonucleotide reductase M2 B (TP53 inducible) (RRM2B), mRNA [NM_015713] |
| 140 | A_23_P204269 | USP15 | GACCAGGATAAATGAGGTATGTTGATCATGGCTTTGTTTATATCTTGATATTAAAGGTG | SEQ ID NO: 3194 | Homo sapiens ubiquitin specific peptidase 15 (USP15), mRNA [NM_006313] |
| 141 | A_23_P205336 | C14orf129 | CAATTCATTGCCAGACTTCATTGGAATGCTTGTTTGATGATGTATGTTCATTCTCAGCT | SEQ ID NO: 3195 | Homo sapiens chromosome 14 open reading frame 129 (C14orf129), mRNA [NM_016472] |
| 142 | A_23_P207299 | LOC51136 | CCAAAACAGGCAATTTGAAATTAGAAGTAGTGGTTTTAGAGAAGTCAGGTATTCTTCCTG | SEQ ID NO: 3196 | Homo sapiens PTD016 protein (LOC51136), mRNA [NM_016125] |
| 143 | A_23_P210274 | PREI3 | GGATCAGTATGCGTAGGATTACAGAATATTTTGTGTACTGTTATTTTGATCATCGGGAG | SEQ ID NO: 3197 | Homo sapiens preimplantation protein 3 (PREI3), transcript variant 1, mRNA [NM_015387] |
| 144 | A_23_P2129 | TMEM126B | CATATGCATCATTGGCTACAGTTCCATTTTGTGTACTGTTGTACTGACAAGTTTTG | SEQ ID NO: 3198 | Homo sapiens transmembrane protein 126B (TMEM126B), mRNA [NM_018480] |
| 145 | A_23_P213661 | HISPPD1 | GTATGTAAGTTTCTGTTCTGTGAAAATGTAGTAATGTAATGTAGTACGCAGTGTGGAGGTCATAAGG | SEQ ID NO: 3199 | Homo sapiens histidine acid phosphatase domain containing 1 (HISPPD1), mRNA [NM_015216] |
| 146 | A_23_P215751 | NDUFA5 | TAAAAGTGGAGTGCACTAAATAGTTGCAGTACGTTCTAATATAAGTGTAGGTGGGTATC | SEQ ID NO: 3200 | Homo sapiens NADH dehydrogenase (ubiquinone) 1 alpha subcomplex, 5, 13kDa (NDUFA5), nuclear gene encoding mitochondrial protein, mRNA [NM_005000] |
| 147 | A_23_P217319 | FGF13 | TTGCATGGAAGAAAGTTGGGTTCTTGGCATAGAGTTGCATGATATGTAAGATTTTGTGCA | SEQ ID NO: 3201 | Homo sapiens fibroblast growth factor 13 (FGF13), transcript variant 1A, mRNA [NM_004114] |
| 148 | A_23_P219928 | C4orf18 | CAGATGAGTTCATTTGCTTCTCTGTAGATGTGTTTCAGAGCCTAGGTACAGAGAATGTTTG | SEQ ID NO: 3202 | Homo sapiens chromosome 4 open reading frame 18 (C4orf18), transcript variant 2, mRNA [NM_016131] |
| 149 | A_23_P250002 | HACE1 | TAAGCAGTCATTGTCTTGTTGGCAGTAATGTTGAGAGACATGTAAGTTGAAAGTTTTGGTA | SEQ ID NO: 3203 | Homo sapiens HECT domain and ankyrin repeat containing, E3 ubiquitin protein ligase 1 (HACE1), mRNA [NM_020771] |
| 150 | A_23_P251937 | CPEB4 | GTATGTCAGTTAATTGTACTACTGGCGTGAATTCCATATAGTTTTAGTGTGTATGGGG | SEQ ID NO: 3204 | Homo sapiens cytoplasmic polyadenylation element binding protein 4 (CPEB4), mRNA [NM_030627] |
| 151 | A_23_P252201 | EAF2 | CAGGATTCGTGATATAGATGCCAGTCATGATACGTTGAAACAGAAAACAAGAAGGAACAGTCGGCCTTCTGAT | SEQ ID NO: 3205 | Homo sapiens ELL associated factor 2 (EAF2), mRNA [NM_018456] |
| 152 | A_23_P25235 | CLEC4D | CATTTAACCACGCAGAGATTCTGGGATAAGAATGAACCCGACAACTCTCAGGGAGAAA | SEQ ID NO: 3206 | Homo sapiens C-type lectin domain family 4, member D (CLEC4D), mRNA [NM_080387] |
| 153 | A_23_P252371 | RBBP8 | GGCAAGGAGCAGAAGAACATAGACGTTGAAACAGAAAACAAGAAGGATGAAGGACAGTTTTT | SEQ ID NO: 3207 | Homo sapiens retinoblastoma binding protein 8 (RBBP8), transcript variant 1, mRNA [NM_002894] |
| 154 | A_23_P26021 | COPS2 | TGTTTTTGATGAACTGCTTTGTTTGTTTTGCTGCATTTATGCCAAGAAAACAGGTT | SEQ ID NO: 3208 | Homo sapiens COP9 constitutive photomorphogenic homolog subunit 2 (Arabidopsis) (COPS2), mRNA [NM_004236] |

Fig. 24-9

| No. | Probe ID No. | Symbols of genes | Sequence | SEQ ID NO: | Descriptions of genes (letters and numbers within [ ] indicates GenBank accession No.) |
|---|---|---|---|---|---|
| 155 | A_23_P2705 | P2RY5 | TCTGTATTGTGTTTCCAAGTGTTGTTTGACCCTATAGTTTAGTAGTTTACATCGGAACA | SEQ ID NO: 3209 | Homo sapiens purinergic receptor P2Y, G-protein coupled, 5 (P2RY5), mRNA [NM_005767] |
| 156 | A_23_P302470 | SULT1B1 | TGTCTAAGTGCAGAAATGTGAAGAATAAGAGAATTGTGTGTAGTTGATCGAAACGAGGCCA | SEQ ID NO: 3210 | Homo sapiens sulfotransferase family, cytosolic, 1B, member 1 (SULT1B1), mRNA [NM_014465] |
| 157 | A_23_P302550 | RGS18 | GAGTCTAAGGCCGTAGGAGATTGGGCATGCTGGCACATTGGTTCATATTCAGAAAGTGTTA | SEQ ID NO: 3211 | Homo sapiens regulator of G-protein signaling 18 (RGS18), mRNA [NM_130782] |
| 158 | A_23_P30307 | CRSP9 | CAATTGTAGTGGACAGAATGAAGAATCAAACAGAAAATTGAAGGTCATAGGAGAGATCAGAAT | SEQ ID NO: 3212 | Homo sapiens cofactor required for Sp1 transcriptional activation, subunit 9, 33kDa (CRSP9), mRNA [NM_004270] |
| 159 | A_23_P305060 | PBEF1 | TGCCTGTGGCTCTAATATGCACCTCAAGATTTAAGGAGATAAATGTTTTAGAGAGAAT | SEQ ID NO: 3213 | Homo sapiens pre-B-cell colony enhancing factor 1 (PBEF1), mRNA [NM_005746] |
| 160 | A_23_P307940 | CAPZA2 | CTACAAGATTGGCAAAGAATGTCAAGTGAATGCAGAATGTGATAAGATGAACATTGCATGACCGGATCATT | SEQ ID NO: 3214 | Homo sapiens capping protein (actin filament) muscle Z-line, alpha 2 (CAPZA2), mRNA [NM_006136] |
| 161 | A_23_P308800 | GLS | CGGAAGAAGAGATAAGATACTGCGAATAGGCCCTCAAAGTTAAAAAAGAAAAAACTTTGC | SEQ ID NO: 3215 | Homo sapiens glutaminase C mRNA, complete cds. [AF158555] |
| 162 | A_23_P30956 | KIAA0776 | TTTTTGATTGTCAAATGTTCAAATGGTTGTTTTGTTGCCACAGTAAAGAAGAGTTTTTATTGTTT | SEQ ID NO: 3216 | Homo sapiens KIAA0776 (KIAA0776), mRNA [NM_015323] |
| 163 | A_23_P312246 | CCDC82 | GGGTTTATTAAGAAGATGACGTGTCAAGTGAATGAATGAGGTGTTGATATCCGTGCAGTTTAGTCA | SEQ ID NO: 3217 | Homo sapiens coiled-coil domain containing 82 (CCDC82), mRNA [NM_024725] |
| 164 | A_23_P314191 | ZDHHC17 | TGGATACTTTAGGAAATAGGAACTAATTGTCAGCACTGAACATGAATTAGTTCCTTGG | SEQ ID NO: 3218 | Homo sapiens zinc finger, DHHC-type containing 17 (ZDHHC17), mRNA [NM_015336] |
| 165 | A_23_P31671 | UQCRB | AAGCATAAGAAGAGTTGCTGAGAAGCCTTTATAATGACAGGATGTTCGGCATTAAGAGGG | SEQ ID NO: 3219 | Homo sapiens ubiquinol-cytochrome c reductase binding protein (UQCRB), mRNA [NM_006294] |
| 166 | A_23_P327022 | MDFIC | TTATGATTTCTTAATGTAATGTTTGTAAATGTTTTGTTGAAGTATATGGGTATCATGACTAAGTGCTA | SEQ ID NO: 3220 | Homo sapiens MyoD family inhibitor domain containing (MDFIC), mRNA [NM_199072] |
| 167 | A_23_P33045 | RPL26 | TACAAAGGTCAGACAAATTGGGAAGTAGTGTGTCAAGGTACAGAGGCGGTGAAATATGTATGCTAG | SEQ ID NO: 3221 | Homo sapiens ribosomal protein L26 (RPL26), mRNA [NM_000987] |
| 168 | A_23_P332439 | NUPL1 | ATTGAAATGTTGAATGTATTGAATGTGTCAAGGTACACAGCGGTGCCTTTGTAAATGTTC | SEQ ID NO: 3222 | Homo sapiens KIAA0410 mRNA, partial cds. [AB007870] |
| 169 | A_23_P339480 | HAT1 | AACATGAACAGCTGAAAGAGAGTTTCAGGAAGTAGTGCAAGATTACGCGGGTGTTATTG | SEQ ID NO: 3223 | Homo sapiens histone acetyltransferase 1 (HAT1), transcript variant 1, mRNA [NM_003642] |
| 170 | A_23_P347059 | MOBKL1A | CTAGAAGGAGGAAAAATCATCTAAGTATATGAAATCCAAGATAGGGGGTATATTACAAAGTG | SEQ ID NO: 3224 | Homo sapiens MOB1, Mps One Binder kinase activator-like 1A (yeast) (MOBKL1A), mRNA [NM_173468] |
| 171 | A_23_P348892 | MYSM1 | CATGTATCTTAAACCTATGAATTAAAAATAGTATTTAGATTGTAGGGTGAGTTAAATAGA | SEQ ID NO: 3225 | Homo sapiens mRNA for KIAA1915 protein, partial cds. [AB067502] |
| 172 | A_23_P349083 | FCHO2 | GTGAAATGGTTAAAGTTGTGGCACTTCTTAGTTAGTACCACAGTGTTCATACCAAGTATTGGG | SEQ ID NO: 3226 | Homo sapiens FCH domain only 2 (FCHO2), mRNA [NM_138782] |
| 173 | A_23_P353704 | RPS-1022P6.2 | TGTCTCCAGTAGTCTTTATTTGTATGATCATTGTTGTTGTGGGTTTGTT | SEQ ID NO: 3227 | Homo sapiens hypothetical protein KIAA1434 (KIAA1434), mRNA [NM_019593] |
| 174 | A_23_P355067 | TMCO1 | AAGTCAAGAAGTCTTTATTTGTATGATTCTTCTAGAGAGAGACAGATCAGACTGGGAA | SEQ ID NO: 3228 | Homo sapiens transmembrane and coiled-coil domains 1 (TMCO1), mRNA [NM_019026] |

Fig. 24-10

| No. | Probe ID No. | Symbols of genes | Sequence | SEQ ID NO: | Descriptions of genes (letters and numbers within [ ] indicates GenBank accession No.) |
|---|---|---|---|---|---|
| 175 | A_23_P37736 | TNFRSF17 | GATCTCTTAGGATGACTGTATTTTCAGTTGCCGATACAGCTTTTGTCTGCTAAGTGT | SEQ ID NO: 3229 | Homo sapiens tumor necrosis factor receptor superfamily, member 17 (TNFRSF17), mRNA [NM_001192] |
| 176 | A_23_P38275 | THC2504576 | TCTGGCGAAAATGAAGTTAAICCCTTGTGACTTGGACCGAAGCAACGAATGGAAAAG | SEQ ID NO: 3230 | RL26_BOVIN (P61257) 60S ribosomal protein L26, complete [THC2504576] |
| 177 | A_23_P390734 | FGFR1OP2 | CCAACAGATACAGAAATGCTTAACATCAGTTGAAACCTAAATTTGTTATGTGTGG | SEQ ID NO: 3231 | Homo sapiens FGFR1 oncogene partner 2 (FGFR1OP2), mRNA [NM_015633] |
| 178 | A_23_P405873 | C9orf72 | GAGAATGGAAGATCAGGGTGAGATATATTGGAATGCTTAGTGGAGAAGTGATTCCTGT | SEQ ID NO: 3232 | Homo sapiens chromosome 9 open reading frame 72 (C9orf72), transcript variant 2, mRNA [NM_145005] |
| 179 | A_23_P41114 | CSTA | AAACAAATGAGACTTATGGAAGAATTGGAAGCGTGTGCAGTATAAAACTCAAGTTGTTTGCTG | SEQ ID NO: 3233 | Homo sapiens cystatin A (stefin A) (CSTA), mRNA [NM_005213] |
| 180 | A_23_P41645 | ELL2 | TGTCTTTTGAAATGCTGCGAGTGAAAAAGGGAAGCATTATGTTACAAATCTGTTTGA | SEQ ID NO: 3234 | Homo sapiens elongation factor, RNA polymerase II 2 (ELL2), mRNA [NM_012081] |
| 181 | A_23_P41664 | ENST00000334994 | TGGGTTGGAGCAGATTGGACTTCATAAACAAATTGTGTGAAAATGAGGCACAGGTCAT | SEQ ID NO: 3235 | Synleurin (GGL01891). [Source:Uniprot/SPTREMBL;Acc:Q7ZQ7] [ENST00000334994] |
| 182 | A_23_P421563 | LSM3 | CATAAGAGAAACCTGCAGATTCATTTTAACATTTTTTGAATATTAAGAAATAATTCCGGGGATTCTTCGACTC | SEQ ID NO: 3236 | Homo sapiens LSM3 homolog, U6 small nuclear RNA associated (S. cerevisiae) (LSM3), mRNA [NM_014463] |
| 183 | A_23_P42975 | PRKAR2B | GCCACATTTTTAGAACACGTGTTAACATTGTTTGGAAACCTTCTCAGAGGCTGGGCCCT | SEQ ID NO: 3237 | Homo sapiens protein kinase, cAMP-dependent, regulatory, type II, beta (PRKAR2B), mRNA [NM_002736] |
| 184 | A_23_P434809 | S100A8 | AAAGCCATGAAGAAAGCCACAGAAAAGAGCTAGGTACTGAGTTACTGGGGG | SEQ ID NO: 3238 | Homo sapiens S100 calcium binding protein A8 (S100A8), mRNA [NM_002964] |
| 185 | A_23_P44257 | COMMD8 | AACATTTTACTTCTGGGCTTCTATGTTTGGGAAACATTGCTCTGATAAAATAGGTGTC | SEQ ID NO: 3239 | Homo sapiens COMM domain containing 8 (COMMD8), mRNA [NM_017845] |
| 186 | A_23_P48166 | TWF1 | TGGAGGAGGACCATAGGCTGAAGCTGTTATTTCAGTCAGGAAGACTACTTGTCATGAAGGT | SEQ ID NO: 3240 | Homo sapiens twinfilin, actin-binding protein, homolog 1 (Drosophila) (TWF1), mRNA [NM_002822] |
| 187 | A_23_P48897 | CCPG1 | AAGTCAGAAGAGGCTCATATATATAATTCTAATGTGCCACCTATGTCCATTCCATGTAGCA | SEQ ID NO: 3241 | Homo sapiens cell cycle progression restoration protein (CPR3), mRNA, complete cds [AF011794] |
| 188 | A_23_P500956 | B3GNT2 | TCCTGGTGGTATCATAGTGTAATTTAGTATTGAGGTGATGTTAGACTAACATTCTGATTCCTTAATGGGG | SEQ ID NO: 3242 | Homo sapiens UDP-GlcNAc:betaGal beta-1,3-N-acetylglucosaminyltransferase 2 (B3GNT2), mRNA [NM_006577] |
| 189 | A_23_P501080 | ZNF92 | GAATATTAAGGGTACTTGAGGTACATGTGAGACTAAGACATTCTTTGCAGTATAGTGAG | SEQ ID NO: 3243 | Homo sapiens zinc finger protein 92 (ZNF92), transcript variant 1, mRNA [NM_007139] |
| 190 | A_23_P502425 | MRPL47 | GTTTCCACATGTTGCTGAAAGGGCAAAAGTCAAGTCTTGTCTAAGATGTGAACTATTAA | SEQ ID NO: 3244 | Homo sapiens mitochondrial ribosomal protein L47 (MRPL47), nuclear gene encoding mitochondrial protein, transcript variant 1, mRNA [NM_020409] |
| 191 | A_23_P50907 | ITGAV | AAAGAGTGATTAAGTGAGGTTATTACCCGTAAATGGTCCATGTGCATTGTATTCAGG | SEQ ID NO: 3245 | Homo sapiens integrin, alpha V (vitronectin receptor, alpha polypeptide, antigen CD51) (ITGAV), mRNA [NM_002210] |
| 192 | A_23_P51317 | CCDC76 | CCCTTGTTATAAGTTTATGTCAAGTAAGGTAGTTGTTAAGTTAGTTACCCATGTCCC | SEQ ID NO: 3246 | Homo sapiens coiled-coil domain containing 76 (CCDC76), mRNA [NM_019083] |

Fig. 24-11

| No. | Probe ID No. | Symbols of genes | Sequence | SEQ ID NO: | Descriptions of genes (letters and numbers within [ ] indicates GenBank accession No.) |
|---|---|---|---|---|---|
| 193 | A_23_P52846 | THC2694735 | TTTATGCGTTTTCACTACGAATAACAAGTAGAACAGTAGAACAGA TGATTAGTACAGGAG | SEQ ID NO: 3247 | AB003177 proteasome subunit p27 [Homo sapiens] (expn=-1, wgp=0, cg=0), partial (9%) [THC2694735] |
| 194 | A_23_P53668 | NFYB | TGGGTCATATTGTGCATACGATTTGTAACCTGCTGTTTTTCAG TTAACAATATATTGGG | SEQ ID NO: 3248 | Homo sapiens nuclear transcription factor Y, beta (NFYB), mRNA [NM_006166] |
| 195 | A_23_P56759 | KRCC1 | GATATCCGTGTTCATACCACTTTCTTATGTGAATAGGTTCTTT AACTGTAACAAAGGC | SEQ ID NO: 3249 | Homo sapiens lysine-rich coiled-coil 1 (KRCC1), mRNA [NM_016618] |
| 196 | A_23_P58266 | S100P | CGAAAAGTGTTTGTTGGCAATTATTGGGGTAGGCTGAGGGTGCT CATGTACCTCTGATTA | SEQ ID NO: 3250 | Homo sapiens S100 calcium binding protein P (S100P), mRNA [NM_005980] |
| 197 | A_23_P59637 | DOCK4 | TTTGGCAGTGAGCAGTTGAATTGAATTTATCTTGAATTATCATGTGTG TGTATTTCTGAAGAG | SEQ ID NO: 3251 | Homo sapiens dedicator of cytokinesis 4 (DOCK4), mRNA [NM_014705] |
| 198 | A_23_P59921 | SUB1 | CAGATTGGGAAAATGAGGTAGGTAGGTTAGTGTCGGGATTTAAAGG CAAAGTGCTAATTGAT | SEQ ID NO: 3252 | Homo sapiens SUB1 homolog (S. cerevisiae) (SUB1), mRNA [NM_006713] |
| 199 | A_23_P60565 | ZNF354A | AAACCAAAGGTCATCGAAGAATACATCGTTGAGAGAGATGTAAT AAATGTAAGTGATGTG | SEQ ID NO: 3253 | Homo sapiens zinc finger protein 354A (ZNF354A), mRNA [NM_005649] |
| 200 | A_23_P61674 | CLK4 | GAAAGGCATGAGTTTGTCCATTGTGAGAGTTTGTTTAATAAAA CCAGATACAGAGTTTA | SEQ ID NO: 3254 | Homo sapiens CDC-like kinase 4 (CLK4), mRNA [NM_020666] |
| 201 | A_23_P63896 | FAS | ATGTCTATCCACAGGCTAACCCACTCATGAATACGAGATGTTAG AGCTATGACGTTTCAG | SEQ ID NO: 3255 | Homo sapiens Fas (TNF receptor superfamily, member 6) (FAS), transcript variant 1, mRNA [NM_000043] |
| 202 | A_23_P65768 | C15orf15 | TCCTGCATTGCCATCACATAATATCAGATATACGGATGTTAG ATTGCATCCAGTGTT | SEQ ID NO: 3256 | Homo sapiens chromosome 15 open reading frame 15 (C15orf15), mRNA [NM_016304] |
| 203 | A_23_P66260 | ZNF267 | TGTTGATGAATGTGTCAGTTGGTAAAGGCTTCAGGCATAGGTCATACCTCAC TACAGATCGGAGAAGT | SEQ ID NO: 3257 | Homo sapiens zinc finger protein 267 (ZNF267), transcript variant 498723, mRNA [NM_003414] |
| 204 | A_23_P70007 | HMMR | AGTATTCTTCAGAGATTTCTCATATAGTGCTTGTCATGTGGATG TCTACTCAGCATTGA | SEQ ID NO: 3258 | Homo sapiens hyaluronan-mediated motility receptor (RHAMM) (HMMR), transcript variant 2, mRNA [NM_012484] |
| 205 | A_23_P70328 | CENPQ | CAATGGCTTACAGTTTCTTCTGTCTGGTCATCTGGAAGTTGAAAAAT CCTCAAATGGCTTCAC | SEQ ID NO: 3259 | Homo sapiens centromere protein Q (CENPQ), mRNA [NM_018132] |
| 206 | A_23_P71727 | CKS2 | GATAAAAGTTCTTGGAGTTCAGTTTTGTCTTAAGTGCGTGTTTG AGTTACTAGTGAAAACAGT | SEQ ID NO: 3260 | Homo sapiens CDC28 protein kinase regulatory subunit 2 (CKS2), mRNA [NM_001827] |
| 207 | A_23_P7221 | RPL34 | CCGAGGAGCAGAGAAAATCGGTTGTGAAAGTGTTGAAGGCAGAAGCAC AGAGTCAGAAAGGTAA | SEQ ID NO: 3261 | Homo sapiens ribosomal protein L34 (RPL34), transcript variant 2, mRNA [NM_033625] |
| 208 | A_23_P7229 | RPL34 | CGAACCCGTGTTGATAGAATGTTACCTTTATACCAAGAAGGT TGGGAAAGCACCAAAA | SEQ ID NO: 3262 | Homo sapiens ribosomal protein L34 (RPL34), transcript variant 2, mRNA [NM_033625] |
| 209 | A_23_P72503 | KLHL2 | TTTTGATATTTAACAATAGCTTAACAGTTTAAATGCCACTCTG AGGAATGGAACCTGGTG | SEQ ID NO: 3263 | Homo sapiens kelch-like 2, Mayven (Drosophila) (KLHL2), mRNA [NM_007246] |
| 210 | A_23_P73114 | PROS1 | CCGAGACAAATTTAACAAAAGGACAGAGAGAGACAGGGGATATAGT GAATATGGTATCATTG | SEQ ID NO: 3264 | Homo sapiens protein S (alpha) (PROS1), mRNA [NM_000313] |
| 211 | A_23_P74001 | S100A12 | TGAAGGCTTTTACCCAGAATGCCTGCAATGTGCTGAATGAGGTGTTTTCT TTGCCTCACGAAAATC | SEQ ID NO: 3265 | Homo sapiens S100 calcium binding protein A12 (S100A12), mRNA [NM_005621] |
| 212 | A_23_P75769 | MS4A4A | CACCAAAAGATCAACAGAACACAAATGCTCCAGAAATCTATGCTGAC TGTGTGAGAGAGCCT | SEQ ID NO: 3266 | Homo sapiens membrane-spanning 4-domains, subfamily A, member 4 (MS4A4A), transcript variant 1, mRNA [NM_024021] |

Fig. 24-12

| No. | Probe ID No. | Symbols of genes | Sequence | SEQ ID NO: | Descriptions of genes (letters and numbers within [ ] indicate GenBank accession No.) |
|---|---|---|---|---|---|
| 213 | A_23_P76480 | BF213738 | AAATCGAACACAGGACAATGGGTAGATGGAGCTACATTTACCAAAT CGTTTGGCATGCAGAGG | SEQ ID NO: 3267 | BF213738 601847628F1 NIH_MGC_55 Homo sapiens cDNA clone IMAGE:4078519 5' mRNA sequence [BF213738] |
| 214 | A_23_P78392 | EVI2A | GGTGAATCAGACAGTTGGAAAAGAAGAAAAACAGTGTCAGACGGAGC CAACCTAGTGATGCAA | SEQ ID NO: 3268 | Homo sapiens ecotropic viral integration site 2A (EVI2A), transcript variant 1, mRNA [NM_001003927] |
| 215 | A_23_P82047 | BU507302 | TGTGTTTGTTAATGTCAGCTGGCTGAACATTCAGGCAGTTTATA AATGCTTAATTGTG | SEQ ID NO: 3269 | AGENCOURT_10309688 NIH_MGC_71 Homo sapiens cDNA clone IMAGE:6501220 5' mRNA sequence [BU507302] |
| 216 | A_23_P83278 | CHMP5 | CATTGGTCTTTTATTTTCCATTAAGAGACTCATTGTTGGGA AATGCTTCTTCGTAC | SEQ ID NO: 3270 | Homo sapiens chromatin modifying protein 5 (CHMP5), mRNA [NM_016410] |
| 217 | A_23_P87769 | C12orf46 | GTAAGAAATATCGTCAGTCGTCGTAATGCATATGCATATGCAGTGTTT GGATATACTCTGTTT | SEQ ID NO: 3271 | Homo sapiens chromosome 12 open reading frame 48 (C12orf48), mRNA [NM_017915] |
| 218 | A_23_P87879 | CD69 | TGTGCAATATGTGATGTGGCAAATCCTATGCATATAGCATATAGTATTGAAG TAAAGTCTCAGACCTAG | SEQ ID NO: 3272 | Homo sapiens CD69 molecule (CD69), mRNA [NM_001781] |
| 219 | A_23_P94095 | ANKRD46 | GGTTGTTGTCTATTTCGTGGGAGGGCAGAAGCTAAACATTCCCTTGATGGTCTCAAG CTTGCTCTTTCATGTG | SEQ ID NO: 3273 | Homo sapiens ankyrin repeat domain 46 (ANKRD46), mRNA [NM_198401] |
| 220 | A_23_P94230 | LY96 | TGAAGGTATTTCTGGAGGGCAGAAGCTAAACATTCCCATGATGGTCTCAAG AGTTTGTCATCCTACA | SEQ ID NO: 3274 | Homo sapiens lymphocyte antigen 96 (LY96), mRNA [NM_015364] |
| 221 | A_23_P94501 | ANXA1 | TCCTTGCAGAAAGCTTGCCCAACATGGTGATAGATTTTT CTATGATGAGAAGACT | SEQ ID NO: 3275 | Homo sapiens annexin A1 (ANXA1), mRNA [NM_000700] |
| 222 | A_23_P95594 | NAT1 | GGATTCTTTGGATTTGCATTTGTTATGTAATTTCAGGAGGAAT ACTGAACATGTGAGTG | SEQ ID NO: 3276 | Homo sapiens N-acetyltransferase 1 (arylamine N-acetyltransferase) (NAT1), mRNA [NM_000662] |
| 223 | A_23_P99980 | HMGB1 | TAAAGGCTGTGTTTTGGTTGTTGGAATCAATGGTTATTGAC TGTTCTGATTGTGCTG | SEQ ID NO: 3277 | Homo sapiens high-mobility group box 1 (HMGB1), mRNA [NM_002128] |
| 224 | A_24_P100387 | GK | TGTTCAAAGAATTAGGTATATTGTTCACCGAAATGAAGTGACT TATTAGCCATTCAGGG | SEQ ID NO: 3278 | Homo sapiens glycerol kinase (GK), transcript variant 1, mRNA [NM_203391] |
| 225 | A_24_P100830 | AMN1 | TTATGAGAACAATGGTTCAGTTCAGTTCAAATAACAGTGCAGTAATTCACCTA TATCTAAAAGACTCCC | SEQ ID NO: 3279 | Homo sapiens antagonist of mitotic exit network homolog (S. cerevisiae) (AMN1), mRNA [NM_207371] |
| 226 | A_24_P105648 | BX111927 | TCCAAGAGTAGTCCAGGTGTAGAGAAAGAAATATGTCATCTACA TCGAGCCAGGTGCACGG | SEQ ID NO: 3280 | BX111927 Soares_multiple_sclerosis_2NbHMSP Homo sapiens cDNA clone IMAGp998G05619, mRNA sequence [BX111927] |
| 227 | A_24_P106306 | RPL26L1 | CCACCAGAAACGTACAGCGTGATTTTCATGACAAATACGGTAGCA ACAGAAGTCGGAATAG | SEQ ID NO: 3281 | Homo sapiens ribosomal protein L26-like 1 (RPL26L1), mRNA [NM_016093] |
| 228 | A_24_P11045 | THC2785765 | ATTTCAAATGCAGAGATAGTTGACTCATTTAAAGCTAAATTTTGT TACTGATTCAATTATA | SEQ ID NO: 3282 | COX7B_HUMAN (P24311) Cytochrome c oxidase polypeptide VIIb, mitochondrial precursor , partial (78%) [THC2785765] |
| 229 | A_24_P114249 | GALNT3 | CATACCATGCTGTGTGTGGTTGGTTGTCCAGAAAGGAGATTCAATGGAGCTTCCCACA TACTGATTCAATTATA | SEQ ID NO: 3283 | Homo sapiens UDP-N-acetyl-alpha-D-galactosamine:polypeptide N-acetylgalactosaminyltransferase 3 (GalNAc-T3) (GALNT3), mRNA [NM_004482] |
| 230 | A_24_P118362 | A_24_P118382 | CATACCATGCTGTGTGTGGTTGGTTGTCCAGAAAGGAGATTCAATGGAGCTTCCCACA TTCACCAAATAAGCTC | SEQ ID NO: 3284 | |
| 231 | A_24_P127621 | A_24_P127621 | TCGAAGCAAGTAGCACAGAAAGGCATTTCAATGCAGCTTCCCACA TTGTCAGAAATATTAG | SEQ ID NO: 3285 | |

Fig. 24-13

| No. | Probe ID No | Symbols of genes | Sequence | SEQ ID NO. | Descriptions of genes (letters and numbers within [ ] indicates GeneBank accession No.) |
|---|---|---|---|---|---|
| 232 | A_24_P133391 | ANKRD12 | TTTGGAATGGAGTATGCCTGAAAAGGTTTTGGATTCAGAAAG AAAAGGATGGTTAGT | SEQ ID NO: 3286 | Homo sapiens ankyrin repeat domain 12 (ANKRD12), mRNA [NM_015208] |
| 233 | A_24_P134392 | STCH | TGAGTAACTTATTTTGTATCAGGAATGTTTTGGTACTGTGTTT CACTCAAACCACTGAC | SEQ ID NO: 3287 | Homo sapiens stress 70 protein chaperone, microsome-associated, 60kDa (STCH), mRNA [NM_006948] |
| 234 | A_24_P135242 | A_24_P135242 | GATGGCAAGAAAAGCTGGCAACTAGTTGTACCTGCAGAACCCA AACTGGCATTTGTCAT | SEQ ID NO: 3288 | |
| 235 | A_24_P135551 | LOC130865 | TAACAGCATAGCTGTCGCCTGTGGGCATTCACCCAAAAGGTGGTTA TCAGTAGAGTAAAACT | SEQ ID NO: 3289 | PREDICTED: Homo sapiens similar to 60S ribosomal protein L26 (Silica-induced gene 20 protein) (SIG-20), (LOC130865), mRNA [XR_019454] |
| 236 | A_24_P144566 | LOC401975 | TGTCGATGTGAAGACTAGTAATGATGGGTAGTTGTTAATCTGTCT GTGTTGGTTTTACTGA | SEQ ID NO: 3290 | PREDICTED: Homo sapiens similar to ribosomal protein S3a, (LOC401975), mRNA [XR_017247] |
| 237 | A_24_P152753 | LOC285260 | TGTCTCATACGGAATCCGTGTGCGATTATCCAGAAAGGATGAAG ATTCACCCAAATAAGCT | SEQ ID NO: 3291 | PREDICTED: Homo sapiens similar to ribosomal protein L31 (LOC285260), mRNA [XR_019376] |
| 238 | A_24_P153324 | LOC390413 | GAAGGTTAACAGGTTTCAATTAACGATGCTGGGGATTGTCAGAAC CATATATTGGAGGGTA | SEQ ID NO: 3292 | PREDICTED: Homo sapiens similar to 60S ribosomal protein L7 (LOC390413), mRNA [XR_018341] |
| 239 | A_24_P165964 | P2RY14 | TTTTTCTGGAAAACGACGGATTTTACTTCTGTGGAGACATGGCAT AGGGTTACTGACTTAT | SEQ ID NO: 3293 | Homo sapiens purinergic receptor P2Y, G-protein coupled, 14 (P2RY14), transcript variant 2, mRNA [NM_014879] |
| 240 | A_24_P175176 | PHTF2 | AGATTGAGGTTAACTTACGTAGAGTTGGGAGTTGATTTAATTAAGATAGA GTATAGCCTCGAACAG | SEQ ID NO: 3294 | Homo sapiens putative homeodomain transcription factor 2 (PHTF2), mRNA [NM_020432] |
| 241 | A_24_P188678 | RPL34 | CCTTTGTTACCTTTATAACCAAGAAGAGTTGGCAAAGGAGGCACAAAATCTG CATGTGTGTGCCC | SEQ ID NO: 3295 | Homo sapiens ribosomal protein L34 (RPL34), transcript variant 2, mRNA [NM_033625] |
| 242 | A_24_P201702 | CLEC2B | ATTGGAATTCAAGTAACGTAAATAGAAGCTGTTCCACTCAACATGGGGAC CTAACTATAATTGACA | SEQ ID NO: 3296 | Homo sapiens C-type lectin domain family 2, member B (CLEC2B), mRNA [NM_005127] |
| 243 | A_24_P203909 | RPL34 | GAGGGGTTCGTGGTGTAAGAGTTAAAGTTCTTATGAAATGTCC AAACAAACAAACATG | SEQ ID NO: 3297 | Homo sapiens ribosomal protein L34 (RPL34), transcript variant 2, mRNA [NM_033625] |
| 244 | A_24_P20996 | BC043173 | CTGGAAAATGTTCATATATGTATATATGTAGGAGAATGATTCTTATGCT GAAGGGCTCTGATTGG | SEQ ID NO: 3298 | Homo sapiens cDNA clone IMAGE:5287121, [BC043173] |
| 245 | A_24_P213375 | A_24_P213375 | AAATGTGTTGGATGATCAAAAAATGGGACGAGAATGATTCTTCAT CTGTTCTGTGTGGTT | SEQ ID NO: 3299 | |
| 246 | A_24_P213783 | RPL31 | CTTTGTTGGTTACCATGTACCTGTTACCCACTTTCAAAATCTACAG ACAGTCAATGTGGATG | SEQ ID NO: 3300 | Homo sapiens ribosomal protein L31 (RPL31), mRNA [NM_000993] |
| 247 | A_24_P221375 | A_24_P221375 | TACTTTGGTTACCCATGTACCGACCACTTTCAAAATCTACAGA GAGTCAATGTGGAGGA | SEQ ID NO: 3301 | |
| 248 | A_24_P225308 | ARID4B | GTTGAAAAATGGTTCAAGTTATTGAAATTTGTACAGGACTGTAA AGATTGTTGACAGCA | SEQ ID NO: 3302 | Homo sapiens AT rich interactive domain 4B (RBP1-like) (ARID4B), transcript variant 1, mRNA [NM_016374] |
| 249 | A_24_P225719 | PREI3 | GACTATTTTCTTAGTGAATATTTATACTAAGGTAGTGAGTGAGA TTGGTGATCTGGCTG | SEQ ID NO: 3303 | Homo sapiens preimplantation protein 3 (PREI3), mRNA [NM_015387] |
| 250 | A_24_P235429 | ABCA1 | GGAAAGAGCCATGTGTCATGTAATACTCAACCACTTTGATATTG AGACATTAATTTGTAC | SEQ ID NO: 3304 | Homo sapiens ATP-binding cassette, sub-family A (ABC1), member 1 (ABCA1), mRNA [NM_005502] |

Fig. 24-14

| No. | Probe ID No. | Symbols of genes | Sequence | SEQ ID NO. | Descriptions of genes (letters and numbers within [ ] indicates GenBank accession No.) |
|---|---|---|---|---|---|
| 251 | A_24_P236008 | SCYL2 | ATAGACTATGCTAGTCTGCTGGTTTTTGTTGTTTTATTTGGAATGCTTATAAGCCTCC | SEQ ID NO: 3305 | Homo sapiens mRNA for KIAA1360 protein, partial cds. [AB037781] |
| 252 | A_24_P243749 | PDK4 | ATTTGACATTGTGTGTAATTCATGGTGGCTAGTGTTGTGGTGCTTCTGGTAATGGTA | SEQ ID NO: 3306 | Homo sapiens pyruvate dehydrogenase kinase, isozyme 4 (PDK4), mRNA [NM_002612] |
| 253 | A_24_P24890 | A_24_P24890 | ATGAAGGCAGATTTGGTGTTGTATGTTGTTAGGTTCCTCTCTAGTTTGTACGTGGGCTGTGTACT | SEQ ID NO: 3307 | |
| 254 | A_24_P264549 | A_24_P264549 | ATTCATAGTAGGATACAGAAACATGATCAAAGGTGTTACACATGGACTTGGATTACAATATG | SEQ ID NO: 3308 | |
| 255 | A_24_P268917 | RAB33B | CCCAGAATCTAATGTAGTTCGGTCATTAATAACAATGGATTATTGAAAGTATATTGCAAAT | SEQ ID NO: 3309 | Homo sapiens RAB33B, member RAS oncogene family (RAB33B), mRNA [NM_031296] |
| 256 | A_24_P276553 | TMCO1 | CCTTCATTTCCTGTATATTCTCTGTACTATGTGCATTCGACAGAACATTCAGAAAGATTC | SEQ ID NO: 3310 | Homo sapiens transmembrane and coiled-coil domains 1 (TMCO1), mRNA [NM_019026] |
| 257 | A_24_P278460 | MLSTD2 | AGGGATGGAACGAACATATGGTTAGGATTACAGAAGCAGTGGTTAGTTACACGTTCTTGTCTG | SEQ ID NO: 3311 | Homo sapiens male sterility domain containing 2 (MLSTD2), mRNA [NM_032228] |
| 258 | A_24_P286054 | ZFYVE16 | GTGTATGTATTCTGGAATGTAAGTAATTGAACAGTCTTAAAATAACCAAAGTTAGAAGGG | SEQ ID NO: 3312 | Zinc finger FYVE domain-containing protein 16 (Endofin) (Endosome-associated FYVE domain protein). [Source:Uniprot/SWISSPROT;Acc:Q7Z3T8] [ENST00000380248] |
| 259 | A_24_P298238 | A_24_P298238 | ATGTTGAAGGAAATGAGAATTGAGGTTGTTTCGAATTCAGGAAGGCACACAAGTTAAAAAC | SEQ ID NO: 3313 | |
| 260 | A_24_P298604 | LOC731599 | GATGGAAATCATGACGAGAGGTCCGGCAAATGACTTGAAAGAATTGGTCAATAAAATGAT | SEQ ID NO: 3314 | PREDICTED: Homo sapiens hypothetical protein LOC731599 (LOC731599), mRNA [XR_015536] |
| 261 | A_24_P303118 | RPL34 | CAGAGGAGCAGAAAATCGTTGTGAAAGTGTTGAAGGAGACAAGCACAGAGCAGAAAGCTAA | SEQ ID NO: 3315 | Homo sapiens ribosomal protein L34 (RPL34), transcript variant 2, mRNA [NM_033625] |
| 262 | A_24_P306527 | ENST00000348989 | ACCGCATCGTGCGTGGTATCCAGAGAAATGTAATGAGGATGAAGATTCACCAAATAAGT | SEQ ID NO: 3316 | PREDICTED: Homo sapiens similar to ribosomal protein L31 (LOC729005), mRNA [XM_001133428] |
| 263 | A_24_P315326 | LOC341412 | AAGTCGTATACGTTTGGTTACCAATGTAGGCGGTTACCCGGCTTTGAAAAATCTACAGGGAATG | SEQ ID NO: 3317 | AGENCOURT_10640955 NIH_MGC_126 Homo sapiens cDNA clone IMAGE:6723568 5', mRNA sequence [CA455253] |
| 264 | A_24_P316074 | LOC730902 | TATCAATGGTGTGACGCGGTACCCAAATCTGAAGTGTTGCAGGTTCTTCCCTTGGTCAAATCTT | SEQ ID NO: 3318 | PREDICTED: Homo sapiens similar to 60S ribosomal protein L7 (LOC730902), mRNA [XR_015600] |
| 265 | A_24_P320328 | SUB1 | CAGAAAAGCTGTAAAGAAGAAAGACAGGTGAGAGTTCGATAAGGGATGTGCGTCATCTCTA | SEQ ID NO: 3319 | Homo sapiens SUB1 homolog (S. cerevisiae) (SUB1), mRNA [NM_006713] |
| 266 | A_24_P324224 | A_24_P324224 | AAAGCTGTCTGGGCCAAAGAAATAAGGAATTCGTAAGGGATGTGCCGTTGTCAGAAAA | SEQ ID NO: 3320 | |
| 267 | A_24_P324561 | KIAA1466 | ATAATAGCTATAGAATGGTACCGTAGGAACCAAGGGTAAAGAATTTAAGTAGGCC | SEQ ID NO: 3321 | Homo sapiens mRNA for KIAA1466 protein, partial cds [AB040899] |
| 268 | A_24_P33213 | A_24_P33213 | GACCATATATTAGATGGGGTACCCAAATCTGAAGTCAGTATAAAGAACTTTATCTACAAGG | SEQ ID NO: 3322 | |
| 269 | A_24_P333052 | A_24_P333052 | TAGACATCAAGAAAATGGATAGTGTTCAAAAATGCGGGACAAAGTTAACCATGGCAAAA | SEQ ID NO: 3323 | |
| 270 | A_24_P333112 | A_24_P333112 | GGTCATCAGAATCAGAGGTATCAAGTGTGAGCCCACAGGAGGACAAAAGGTATTGGAACTT | SEQ ID NO: 3324 | |

Fig. 24-15

| No | Probe ID No | Symbols of genes | Sequence | SEQ ID NO: | Descriptions of genes (letters and numbers within [ ] indicates GenBank accession No.) |
|---|---|---|---|---|---|
| 271 | A_24_P33607 | LOC652558 | TAAGAAATAATTGCTTTGACAGAGACAGGCTTTGATTGCTCCATGCTGGTAAATATGG | SEQ ID NO: 3325 | PREDICTED: Homo sapiens similar to 60S ribosomal protein L7 (LOC652558), mRNA [XR_019396] |
| 272 | A_24_P344537 | ZNF625 | TCGAGCGTTAAAATCCATCAAAGGACTCACACTGGAGAAAAAACCTGTAGTCCAACACT | SEQ ID NO: 3326 | Homo sapiens zinc finger protein 625 (ZNF625), mRNA [NM_145233] |
| 273 | A_24_P349636 | LOC388401 | AGTTGCTTCGAGATAAGAGTTGATTGCTGTGATCTCTTGGTAAATATGGATCAAGTG | SEQ ID NO: 3327 | PREDICTED: Homo sapiens similar to 60S ribosomal protein L7 (LOC388401), mRNA [XR_016679] |
| 274 | A_24_P364025 | UBE2D1 | ATGTGATGGGTGTAGTCATTAGGAAAGCATTTAAATCACTGAGTATTTTGTGATGGTTC | SEQ ID NO: 3328 | Homo sapiens ubiquitin-conjugating enzyme E2D 1 (UBC4/5 homolog, yeast) (UBE2D1), mRNA [NM_003338] |
| 275 | A_24_P364307 | AYTL1 | TGTAACTGTTGTTCTAGGTAATGCTTCTCTCTGAAGAAAGTTCAAGCGTCTGTGTAA | SEQ ID NO: 3329 | Homo sapiens mRNA; cDNA DKFZp686H22112 (from clone DKFZp686H22112), [BX641069] |
| 276 | A_24_P366165 | LOC391126 | AGTTCCAAGCAAATCAAAATACGAAAAATGGCATTCAATGCACCTTCCCACATTGACAGG | SEQ ID NO: 3330 | PREDICTED: Homo sapiens similar to 60S ribosomal protein L26 (Silica-induced gene 20 protein (SIG-20) (LOC391126), mRNA [XR_019504] |
| 277 | A_24_P366546 | RPL31P10 | CGGCTGTCAAGAAAAACGTAATGAAGATGAAGATTCAAATAAGCTCTATACTTTGGTTACC | SEQ ID NO: 3331 | PREDICTED: Homo sapiens similar to 60S ribosomal protein L31 (LOC390283), mRNA [XR_018695] |
| 278 | A_24_P367191 | LOC652890 | AGTTAACATGCTGAGGAGCTGTAGAGCCATATATTGCTGTGGGTACCGAAATCGTGAAGTC | SEQ ID NO: 3332 | PREDICTED: Homo sapiens similar to 60S ribosomal protein L7 (LOC652890), mRNA [XR_019544] |
| 279 | A_24_P367199 | A_24_P367199 | TGTTATGCTCAGCACCAAGAGTGTGCCAAATCAGAAGAAGGTGTAATGACCTGAGA | SEQ ID NO: 3333 | |
| 280 | A_24_P367369 | A_24_P367369 | ATTTAAAGGTTCGATGTGTAGATTCTCTGGTCGAGAAGTTAAGGGTTAAGAACAAAGACATCTAA | SEQ ID NO: 3334 | |
| 281 | A_24_P375932 | A_24_P375932 | ATGTAAAATGGAGAGAGCAATGGGTCGATTCTAAGAAGCTGGAGTCTGTAGATTCTCGGTC | SEQ ID NO: 3335 | |
| 282 | A_24_P381625 | PSMC6 | ATGAAAGCAGTGAGAAAGTGGAGAAAACGGCAAATCAGATACAGAAGACCTCTTTAAATTGGACTACAA | SEQ ID NO: 3336 | Homo sapiens proteasome (prosome, macropain) 26S subunit, ATPase, 6 (PSMC6), mRNA [NM_002806] |
| 283 | A_24_P383999 | RPS3A | TGGTTTTACTAAAAAACGGCAAACAATCAGATACAGAAGACCTCTTATGCCCAGGACGGAACG | SEQ ID NO: 3337 | Homo sapiens ribosomal protein S3A (RPS3A), mRNA [NM_001006] |
| 284 | A_24_P384411 | A_24_P384411 | ATGGAAGCAAATCAATAAGAGTGAAGCTTGAACAGATAATGCTTTGACAGGCTCGGATCTCTTG | SEQ ID NO: 3338 | |
| 285 | A_24_P384539 | LOC730452 | CAAGAAAAGGTGGGAAGCTTGTATGTAGGGAGCAGACAAACCAAATTGGCATTTGTCATCAGGA | SEQ ID NO: 3339 | PREDICTED: Homo sapiens similar to 60S ribosomal protein L7 (LOC730452), mRNA_011258951 |
| 286 | A_24_P392622 | A_24_P392622 | CATGAGAATTGTTCCTTGGCCACAGTGATCTATCAGTTCATCAATAAGACATATTGTAGACACGAA | SEQ ID NO: 3340 | |
| 287 | A_24_P9378 | CCPG1 | TACTTTTTGTGGCTGGAACGAACTTGATCAGTTCATCAATAAGTTTTTCTAAACGGGTGT | SEQ ID NO: 3341 | Homo sapiens cell cycle progression 1 (CCPG1), transcript variant 1, mRNA [NM_004748] |
| 288 | A_24_P403303 | PHF20L1 | AAAGGCCAGTTAAAAGGTTATAAAGCTCTTAATTAGATCTCAATTGGTATCAGGAATAGACGTAAAGG | SEQ ID NO: 3342 | Homo sapiens PHD finger protein 20-like 1 (PHF20L1), transcript variant 3, mRNA [NM_198513] |
| 289 | A_24_P414556 | TTC33 | TACTCAACATTTGGTATATATTGTTTGAGTAATGGCATTGCTGTTTGTTTTGTGTAATTGTGA | SEQ ID NO: 3343 | Homo sapiens tetratricopeptide repeat domain 33 (TTC33), mRNA [NM_012332] |
| 290 | A_24_P41551 | LOC641790 | AAGGAGATGGGAAGCTCCTGATGTGGGCATTGATATGAGGCACAACAAAGTAGTCTGGAAA | SEQ ID NO: 3344 | PREDICTED: Homo sapiens similar to ribosomal protein L31 (LOC641790), mRNA [XR_018025] |

Fig. 24-16

| No. | Probe ID No. | Symbols of genes | Sequence | SEQ ID NO: | Descriptions of genes (letters and numbers within [ ] indicates GenBank accession No.) |
|---|---|---|---|---|---|
| 291 | A_24_P418712 | A_24_P418712 | AGGCTGAACAAAGGCTGTGTGGGCCAAAGAAATAAGGAATATCGATACCATATCTGTGTTA | SEQ ID NO: 3345 | |
| 292 | A_24_P4877 | ZCRB1 | GAAAAATTAATACTATCATGTTAATACTATTGTTCATCCCAAGAAAAAGATATTTTA | SEQ ID NO: 3346 | Homo sapiens zinc finger CCHC-type and RNA binding motif 1 (ZCRB1), mRNA [NM_033114] |
| 293 | A_24_P50437 | BC065737 | TGCGAATGATGAAGTTGCATTTAGAAAATTCCTGATTACTGAAGATGTTCAGGGCAAA | SEQ ID NO: 3347 | Homo sapiens cDNA clone IMAGE:30404477, partial cds. [BC065737] |
| 294 | A_24_P538403 | ROCK1 | TTAAGAGGTTTGTTGGAGTTTGCATAAATTGAGTACAATGTTTGCATCAAACTACGTGCTAC | SEQ ID NO: 3348 | Homo sapiens Rho-associated, coiled-coil containing protein kinase 1 (ROCK1), mRNA [NM_005406] |
| 295 | A_24_P54178 | TMED5 | GCTGTATATGCATTGGATGATTAATGTTATGCTGTTCTTCATGTGAATGTCAAGACA | SEQ ID NO: 3349 | Homo sapiens transmembrane emp24 protein transport domain containing 5 (TMED5), mRNA [NM_016040] |
| 296 | A_24_P557232 | CB111670 | GTTTCTCTTGGTCAAAAACACACTCAAGTCGTCTCGAAGTTCGAAGGATTCAGCAAAGA | SEQ ID NO: 3350 | K-EST0153390 L5HLK1 Homo sapiens cDNA clone L5HLK1-3-D02 5', mRNA sequence [CB111670] |
| 297 | A_24_P56252 | AF086032 | GTATCTAAAACTGAACAGCTACTGTGCTATATTGATTTATTGGTAGTATTGAGACAGACC | SEQ ID NO: 3351 | Homo sapiens full length insert cDNA clone YW75G09 [AF086032] |
| 298 | A_24_P57837 | THC2567891 | AAGAATCGGGAAGAGCTCTTATGGTGAGTAGGAGCCAAATGCGGAAGAAGATCATGGAAA | SEQ ID NO: 3352 | Q6NXR8_HUMAN (Q6NXR8) Ribosomal protein S3a, partial (91%) [THC2567891] |
| 299 | A_24_P587938 | A_24_P587938 | CTTCAAGAGCAAAAAGGTGAGATGCTGGGAACAGCGAGGACCAGATAAGAGTCTTAT | SEQ ID NO: 3353 | |
| 300 | A_24_P606663 | LOC392030 | TGTGCGGTTGCCCAGGAAAAAGCGTAATGCGGGGTGAAGATTCACCAAATAAGCTGGATAGTTT | SEQ ID NO: 3354 | PREDICTED: Homo sapiens hypothetical LOC392030 (LOC392030), mRNA [XR_018063] |
| 301 | A_24_P62860 | STAM2 | GTCTATATGGTACTTGATCTACATTTAAGTGGAGCATATTAGGCAGTATTTGAAAGCTCAGT | SEQ ID NO: 3355 | Homo sapiens signal transducing adaptor molecule (SH3 domain and ITAM motif) 2 (STAM2), mRNA [NM_005843] |
| 302 | A_24_P630039 | AL049321 | AAGATGAGACAATACAAAGTTAGATTTTTGGAGGATATTAAAACTGCAAGAAGAGAGGGG | SEQ ID NO: 3356 | Homo sapiens mRNA; cDNA DKFZp564D156 (from clone DKFZp564D156). [AL049321] |
| 303 | A_24_P63347 | PF4V1 | CTACATATTTACCTTGAATGTTACAATTAGCTTGCCAATAAATATTAGTAGCTCTTAAGC | SEQ ID NO: 3357 | Homo sapiens platelet factor 4 variant 1 (PF4V1), mRNA [NM_002620] |
| 304 | A_24_P652786 | THC2533996 | TGCTTGTTCGTATCTCAGCCCGGAAGATGATTATCCTGAGGAATGACATTGAGCTTGTTT | SEQ ID NO: 3358 | Homo sapiens mRNA; cDNA DKFZp564D156 (from clone DKFZp564D156) partial (42%) [THC2533996] |
| 305 | A_24_P685729 | A_24_P685729 | TTGAAGACCTCTTATGATGTGAAGAAGACTATAGTGATTATTGTTTGTCTGTTTTGTGTGG | SEQ ID NO: 3359 | |
| 306 | A_24_P6975 | LOC342994 | GGAAGACTTCGAGGGGTTCGTGCTTCGTGCTGTAAGACCTAAAGTTGTTATGAAATTGTCAAAAAGA | SEQ ID NO: 3360 | PREDICTED: Homo sapiens similar to ribosomal protein L34 (LOC342994), mRNA [XM_938484] |
| 307 | A_24_P75158 | PTAR1 | GGATTAGATTGTTCTTATGTGACCATGTACGAAGGCGAGGTATAAAGTATTGTATTTCTG | SEQ ID NO: 3361 | Homo sapiens mRNA; cDNA DKFZp313P0917 (from clone DKFZp313P0917). [AL326283] |
| 308 | A_24_P755505 | A_24_P755505 | ATACAGAAGACCTCTTATGGTCAGCACCAACAAGAGAAAGTAAAAATGCTGAAGAAGCCCAA | SEQ ID NO: 3362 | |
| 309 | A_24_P78358 | LOC643981 | TTACTGAAGATGTTCAGGGCAAAAAACTGGCTAACTTCCAGGCATGGATGTTATTCGTAAGA | SEQ ID NO: 3363 | PREDICTED: Homo sapiens similar to 40S ribosomal protein S3a (V-fos transformation effector protein) (LOC643981), mRNA [XR_018444] |

Fig. 24-17

| No. | Probe ID No. | Symbols of genes | Sequence | SEQ ID NO: | Descriptions of genes [letters and numbers within [ ] indicates GenBank accession No.] |
|---|---|---|---|---|---|
| 310 | A_24_P792734 | PSMC6 | AGAAGGTTAAGGGAGTTAGTGAATGAAATGGAATTGATAC TCTGCATAGAGTTAAA | SEQ ID NO: 3364 | Homo sapiens proteasome (prosome, macropain) 26S subunit, ATPase, 6 (PSMC6), mRNA [NM_002806] |
| 311 | A_24_P82630 | SMCHD1 | TGTTTAATATGTAACACGTAAGAACAACAATTGAAATTTGTTCTAA GATTTAATACTAGTCT | SEQ ID NO: 3365 | Homo sapiens mRNA for KIAA0650 protein, partial cds. [AB014550] |
| 312 | A_24_P83966 | LOC730887 | ACAAAAGGCAGAGAACAACAAGTGGAACACAGAGAAAGTTTTCT GGTGTGTCTAAGAAGG | SEQ ID NO: 3366 | PREDICTED: Homo sapiens similar to 40S ribosomal protein S7 (S8) (LOC730887), mRNA [XR_015607] |
| 313 | A_24_P84806 | LOC729449 | GAATTGCTTTGACAGATAACGCTTTGCGATCTCTTGGAAAATAT GGGATCATGTGTATGG | SEQ ID NO: 3367 | PREDICTED: Homo sapiens similar to 60S ribosomal protein L7 (LOC729449), mRNA [XR_015548] |
| 314 | A_24_P850167 | A_24_P850167 | TAAATGAACTAATCTACAAGCGTGCTTAGTGACTTTCAGATTTATTC AGTTGAGTTTGGTAG | SEQ ID NO: 3368 | |
| 315 | A_24_P867201 | AK022997 | CTGACATGTGATAAGTATATTCAGTGACTTTTCAGATTTATTCT TGTTAGGCGGCTGTGTC | SEQ ID NO: 3369 | Homo sapiens cDNA FLJ12935 fis, clone NT2RP2004982. [AK022997] |
| 316 | A_24_P91852 | DYNLT3 | ATACATATAGAGAGCGGAACCATAACTCATTGAATTTGGAGAG GAATAAGCTTAGCGTT | SEQ ID NO: 3370 | Homo sapiens dynein, light chain, Tctex-type 3 (DYNLT3), mRNA [NM_006520] |
| 317 | A_24_P93596 | BCAT1 | ATGCTCTGAAGGTTTTGTAGAAGCACAATTAAACATCTAAAATG GGTTGTTACACCAGA | SEQ ID NO: 3371 | Homo sapiens branched chain aminotransferase 1, cytosolic (BCAT1), mRNA [NM_005504] |
| 318 | A_24_P940426 | QKI | AAGGTTGAATGAGTCTAAAAATTATACTACGTGTTAAGTGGA CCAAGTTTGGTGAAGC | SEQ ID NO: 3372 | Homo sapiens quaking homolog, KH domain RNA binding (mouse) (QKI), transcript variant 4, mRNA [NM_206855] |
| 319 | A_24_P99046 | STK38L | GCTATCGTCTTTTGCTGATCACACAAATAAATGAATTCAGAATT TAGTGCATAGAGGTGG | SEQ ID NO: 3373 | Homo sapiens serine/threonine kinase 38 like (STK38L), mRNA [NM_015000] |
| 320 | A_32_P10100 | A_32_P10100 | TATGAGGAAATAGTATCATCATGTTAGAGCCTTGGAATGAGTA TAAATAATGGCTGGTC | SEQ ID NO: 3374 | |
| 321 | A_32_P105397 | THC2642694 | TAAAATGCTACTACAGTATTCTACCACATGCAGGCTGAATGTATAT TAGAGTAATTGTCTGG | SEQ ID NO: 3375 | Q6IDT1_HUMAN (Q6IDT1) Protein transactivated by hepatitis B virus E antigen, partial (11%) [THC2642694] |
| 322 | A_32_P107035 | DB527271 | GTTTTATGTGAAATAGAGTTTCAGATTTATGTAAGACGAGAGAGT TTTTAATACGTCAGAG | SEQ ID NO: 3376 | DB527271 RIKEN full-length enriched human cDNA library, testis Homo sapiens cDNA clone H013095P12 3', mRNA sequence [DB527271] |
| 323 | A_32_P109036 | ZNF493 | AAAGACGTGAATACTGTGGTGAGATGTTAGTAAACAGGAGAGT TCATGCTTAATAAAAG | SEQ ID NO: 3377 | Homo sapiens zinc finger protein 493 (ZNF493), transcript variant 1, mRNA [NM_175910] |
| 324 | A_32_P113154 | LOC730861 | AGGAGGCAGTGCAAGAATGTGTTAAAGTTCAGAGTTAAAACAGT ACCAAAATAAAAGTCC | SEQ ID NO: 3378 | PREDICTED: Homo sapiens similar to 40S ribosomal protein S3a (V-fos transformation effector protein) (LOC730861), mRNA [XR_015591] |
| 325 | A_32_P114215 | COMMD6 | AATTGGTACATCTCAAAGTCATGGAGCTTCAGTTCGGCAACAA AACTAAATAAGGATGG | SEQ ID NO: 3379 | Homo sapiens COMM domain containing 6 (COMMD6), transcript variant 2, mRNA [NM_203495] |
| 326 | A_32_P11451 | NMD3 | CAGTTTAGGGCAGTAGGCTGCTTTGTCATAAATATGTTACC ACATCAAAATGTCTC | SEQ ID NO: 3380 | Homo sapiens NMD3 homolog (S. cerevisiae) (NMD3), mRNA [NM_015938] |
| 327 | A_32_P11931 | LOC441073 | GTGTGATGCATGGCATCGGAAAGGATGATGAAGTTCAGGTTGT ACGTGGACAGTATAAA | SEQ ID NO: 3381 | PREDICTED: Homo sapiens similar to 60S ribosomal protein L26 (Silica-induced gene 20 protein) (SIG-20) (LOC441073), mRNA [XR_016376] |
| 328 | A_32_P125549 | RPL31P4 | TCTACAGACAGTCAATGTGGATGAGAACTAATCCCTGATCCTCA GATACAGTCAAATAAAG | SEQ ID NO: 3382 | PREDICTED: Homo sapiens ribosomal protein L31 pseudogene 4 (RPL31P4), mRNA [XR_018222] |

Fig. 24-18

| No. | Probe ID No. | Symbols of genes | Sequence | SEQ ID NO: | Descriptors of genes (letters and numbers within [ ] indicates GenBank accession No.) |
|---|---|---|---|---|---|
| 329 | A_32_P125317 | THC2753798 | GGTTATAAAGTGTAAGTGGAGAGACGGCTAAATTGTGAGTACAAAGTTTCTTTTCACAACAG | SEQ ID NO: 3383 | BF238843 601904455F1 NIH_MGC_54 Homo sapiens cDNA clone IMAGE:4132429 5', mRNA sequence [BF238843] |
| 330 | A_32_P127454 | A_32_P127454 | GGAAGAGGTTGGATTGTATTGGGAGTTGTGTTGGCTACATATGTCCATGTAACAATACAGAA | SEQ ID NO: 3384 | |
| 331 | A_32_P128781 | A_32_P128781 | CATATATTGCATGGGGGGTAGGCGCAATGTGAAGTCAGTAAATGAACTAATCTACAAGAGTG | SEQ ID NO: 3385 | |
| 332 | A_32_P135818 | RPS3A | GTTCGTTCATGTGTCTGTGTTCTGGTTTAATAAAAACGGAACAATCAGATATGGAAGAC | SEQ ID NO: 3386 | Homo sapiens ribosomal protein S3A (RPS3A), mRNA [NM_001006] |
| 333 | A_32_P137266 | KIAA1799 | AAGTGGGACACCCAAATGTAGAAGTGGTTGTCAACATGTAATGGCTTTGAATGAACGACAAG | SEQ ID NO: 3387 | Homo sapiens KIAA1799 protein (KIAA1799), mRNA [NM_032437] |
| 334 | A_32_P145153 | RPL31 | ATCGGTGTGGCAGGTGTCGCAGAAAAACGTAATGAAGGATGAAGATTCACCAAATAAGCCATAT | SEQ ID NO: 3388 | Homo sapiens ribosomal protein L31 (RPL31), mRNA [NM_000993] |
| 335 | A_32_P153725 | KIAA1033 | TTTTGTAAAAGATGGGAAGTTGTTACCTGACTCACTTGAGTGGGGTTTCGTTTCCCCCAAT | SEQ ID NO: 3389 | Homo sapiens KIAA1033 (KIAA1033), mRNA [NM_015275] |
| 336 | A_32_P155364 | RPL7 | TCAACAGGCTTATTAGAAAAATGAACCAAGGTGTCTACCATGATTATTTTCTATCAGGTGG | SEQ ID NO: 3390 | Homo sapiens ribosomal protein L7 (RPL7), mRNA [NM_000971] |
| 337 | A_32_P158746 | RPL17 | TTTTGCTCCACATGCTAAAAATGGCTAAAAAATGAGAGAGTAATGGTGAAGTTAAGGGTTTAGATGTAG | SEQ ID NO: 3391 | Homo sapiens ribosomal protein L17 (RPL17), transcript variant 1, mRNA [NM_000985] |
| 338 | A_32_P164203 | THC2663448 | TTGATGGTCATTGTAGGAGCTATTGTATGGATTACTGTGGAGTGCTGTTTACCACATGAT | SEQ ID NO: 3392 | Q7WZG3_PASP1 (Q7WZG3) Ferric uptake regulator, partial (8%). [THC2663448] |
| 339 | A_32_P165340 | SRP9 | ACATGAAATATGTTTGTATAAATTGTCATGTTGAACAACATTTAGCATGGTAAGTT | SEQ ID NO: 3393 | Homo sapiens signal recognition particle 9kDa (SRP9), mRNA [NM_003133] |
| 340 | A_32_P170444 | SUB1 | TAGGATCTCTCCTGAAATTCTTGGAGTCATTTTTATGGCAGTTAATCGAGTGAAAC | SEQ ID NO: 3394 | Activated RNA polymerase II transcriptional coactivator p15 (SUB1 homolog) (Positive cofactor 4) (PC4) (p14). [Source:Uniprot/SWISSPROT;Acc:P53999] [ENST00000265073] |
| 341 | A_32_P1712 | RNASE2 | TCCAGGTGCCTTTAATGTACTGTAACGTGACGACAACTCCAAGTCCACAGCAATATTTCAAACT | SEQ ID NO: 3395 | Homo sapiens ribonuclease, RNase A family, 2 (liver, eosinophil-derived neurotoxin) (RNASE2), mRNA [NM_002934] |
| 342 | A_32_P176819 | CMAH | GATTATATATGCTAGGTGATTCTGAAGATAGAAGAATTCAATGGTGGAATTTGTCTCC | SEQ ID NO: 3396 | Homo sapiens cytidine monophosphate-N-acetylneuraminic acid hydroxylase (CMP-N-acetylneuraminate monooxygenase) (CMAH) on chromosome 6 [NR_002174] |
| 343 | A_32_P178966 | ENST00000379426 | GTAATATACAGGGTGAACTCTTACTGATACAGACAAGACAACTGTTAAAAAGTGAATCG | SEQ ID NO: 3397 | Novel protein. [Source:Uniprot/SPTREMBL;Acc:Q5T4T1] [ENST00000379426] |
| 344 | A_32_P184394 | TFEC | AGTTGCTTATGGCATACAAGGGTAAAATTAATTCAGGTATTTAATCTTAAATAATTATTAT | SEQ ID NO: 3398 | Homo sapiens transcription factor EC (TFEC), transcript variant 1, mRNA [NM_012252] |
| 345 | A_32_P190488 | hCG_26523 | CCCAGGCAAGGTGCGTTATCGCACGTAGCGTAAAACGTGGACAAAAGAGACGGCAAAAAGATCCTTGAA | SEQ ID NO: 3399 | PREDICTED: Homo sapiens similar to 60S ribosomal protein L26 (LOC646161), mRNA [XR_018048] |
| 346 | A_32_P193322 | RICTOR | ACCACATGAGTTTCTTCTTTTTATTTAGTAATACGGTGCTACATATTGGGAGGTCTCGG | SEQ ID NO: 3400 | Homo sapiens rapamycin-insensitive companion of mTOR (RICTOR), mRNA [NM_152756] |

Fig. 24-19

| No. | Probe ID No. | Symbols of genes | Sequence | SEQ ID NO: | Descriptions of genes (letters and numbers within [ ] indicates GenBank accession No.) |
|---|---|---|---|---|---|
| 347 | A_32_P196483 | RPS3A | GGGGCGAAGAAGAAAGTGGTTGATCCATTTCTAAGAAAGATTG GTATGATGTGAAGCA | SEQ ID NO:3401 | Homo sapiens ribosomal protein S3A (RPS3A), mRNA [NM_001006] |
| 348 | A_32_P19752 | FAM76B | TTGTGCTTTAGCCTGTTTTTCCACTATTAATTAGGATTTGAC TAAGGTCATTTTGAG | SEQ ID NO:3402 | Homo sapiens family with sequence similarity 76, member B (FAM76B), mRNA [NM_144664] |
| 349 | A_32_P208178 | RPS3A | GGAAAAGAGGTAGAAAGGCTTGCCAATCTATTTATCGTCTCCA TGATGTCTTCGTTAGA | SEQ ID NO:3403 | Homo sapiens ribosomal protein S3A (RPS3A), mRNA [NM_001006] |
| 350 | A_32_P224666 | CAPZA2 | AATGGTGTTTTGGAATTGTGAAATTAAATGAAAATAGTTATTTC AGAAATGCATTTAATG | SEQ ID NO:3404 | Homo sapiens capping protein (actin filament) muscle Z-line, alpha 2 (CAPZA2), mRNA [NM_006136] |
| 351 | A_32_P22539 | hCG_26523 | ACTACGAAGGTCAGCAAATTGGCAAAGTGGTCCAGGTTTACAGG AAGAAATATGTTATGT | SEQ ID NO:3405 | PREDICTED: Homo sapiens similar to 60S ribosomal protein L26 (Silica-induced gene 20 protein) (SIG-20) (LOC400055), mRNA [XM_374987] |
| 352 | A_32_P226786 | BC045174 | TTATTGGTGCATGTAAGCCATTATCTGTCTTAATGAACCGATT AATGTGTTGATTGTT | SEQ ID NO:3406 | Homo sapiens cDNA clone IMAGE:5273245, [BC045174] |
| 353 | A_32_P2333 | SUB1 | AGGAAGAAAAGGTATTTCTTTAAATCCAGAACAATGGAGCCAGG TGACAGAACAGATTTC | SEQ ID NO:3407 | Homo sapiens SUB1 homolog (S. cerevisiae) (SUB1), mRNA [NM_006713] |
| 354 | A_32_P4532 | LOC643932 | GATTCCAGACAGCAGCATTGGAAAAGACATAGAAAAGGCTTGCCAAT CTATGGTCTCCATGAT | SEQ ID NO:3408 | PREDICTED: Homo sapiens similar to 40S ribosomal protein S3a (v-fos transformation effector protein) (LOC643932), mRNA [XR_017289] |
| 355 | A_32_P49164 | AV714556 | AAATGGAGACTTGTTATTTGCCAAAGAAGATTCATCATGTTCC TTCCTTCTTTTTCCC | SEQ ID NO:3409 | AV714556 AV714556 DCB Homo sapiens cDNA clone DCBADG06 5', mRNA sequence [AV714556] |
| 356 | A_32_P49392 | A_32_P49392 | AATTCTGCCAAATCTGGAAGAAGATGATGGAAATCATGACCGA GAGGTGCAGACAAATG | SEQ ID NO:3410 | |
| 357 | A_32_P58074 | RPS3A | GTTGGTTTTACTAAAAAAGGCAAAAATCAGATGGCAAATGGCAGTATACGGAAGACCTG TTATGCTCAGGACACA | SEQ ID NO:3411 | Homo sapiens ribosomal protein S3A (RPS3A), mRNA [NM_001006] |
| 358 | A_32_P66934 | BX641014 | AATGGGAGTTGCCAGCATTCTGTCTAAAATGGCAGTTGTGTAGG TTTATTCTTAGAAA | SEQ ID NO:3412 | Homo sapiens mRNA; cDNA DKFZp686l19109 (from clone DKFZp686l19109). [BX641014] |
| 359 | A_32_P68586 | ARL1 | TTGGGTTACCTGCGTTGAAGGACCGAAAATGGCAGATATTCAAA ACGTCAGGAACCAAAG | SEQ ID NO:3413 | Homo sapiens ADP-ribosylation factor-like 1 (ARL1), mRNA [NM_001177] |
| 360 | A_32_P7118 | PSMC6 | AGCAGACCTGAGAAATGTTTGTACTGAAGCAGGTATGTTCGGAA TTGGTGCGTGATCATGA | SEQ ID NO:3414 | Homo sapiens proteasome (prosome, macropain) 26S subunit, ATPase, 6 (PSMC6), mRNA [NM_002806] |
| 361 | A_32_P73222 | AA631847 | TTTCTTTGTTTTGGACAATCTCATAAGAAGCTTTAGGTCTTACAAG GAGGAAGCCCTGGAAG | SEQ ID NO:3415 | np61b02.s1 NCI_CGAP_Br2 Homo sapiens cDNA clone IMAGE:1130763 3' similar to TR:G971838 G971838 60S RIBOSOMAL PROTEIN L34 ;, mRNA sequence [AA631847] |
| 362 | A_32_P63782 | RPL26 | AGGTTGTACATGGACACTATAAAGGTCAGCAAATTGGCAAAGTA GTCCAGGTTTACAGGA | SEQ ID NO:3416 | Homo sapiens ribosomal protein L26 (RPL26), mRNA [NM_000987] |
| 363 | A_32_P9382 | RP11-11C5.2 | AACAAAGCAGGAAAAATATTGAGAAGGGATCGTGTTTACAGAGAG GACTTCTTTAAAGTGT | SEQ ID NO:3417 | Homo sapiens similar to RIKEN cDNA 2410129H14, mRNA [NM_001071775] |

DETECTION OF DIGESTIVE ORGAN CANCER, GASTRIC CANCER, COLORECTAL CANCER, PANCREATIC CANCER, AND BILIARY TRACT CANCER BY GENE EXPRESSION PROFILING

CROSS-REFERENCE TO RELATED APPLICATIONS

This application is a divisional of U.S. patent application Ser. No. 13/391,858, filed Feb. 23, 2012, which in turn is a 371 of PCT/JP2010/063122, filed Aug. 3, 2010, which claims the benefit of Japanese Patent Application No. 2009-193702, filed Aug. 24, 2009, the contents of each of which are incorporated herein by reference.

FIELD OF THE INVENTION

The present invention relates to detection and diagnosis of digestive organ cancer, gastric cancer, colorectal cancer, pancreatic cancer, and biliary tract cancer via gene expression analysis using peripheral blood as a material.

BACKGROUND OF THE INVENTION

Digestive organ cancer is the most common form of malignant tumor among the Japanese. According to a survey by the Ministry of Health, Labour and Welfare, 177,000 patients die annually. Early detection and treatment can result in complete healing. The earlier the stage of the lesions, the fewer clinical symptoms are presented. Hence, some digestive organ cancer cases are detected in an advanced state, resulting in a poor prognostic outcome.

Gastric cancer is the most common form of digestive system malignant tumor among the Japanese. According to a survey by the Ministry of Health, Labour and Welfare, 50,000 patients die annually. Also, colorectal cancer is the form of digestive system malignant tumor that ranks $3^{rd}$ highest number in terms of deaths due to site-specific cancer (including both males and females) among the Japanese. According to a survey by the Ministry of Health, Labour and Welfare, 41,000 patients die annually. Both gastric cancer and colorectal cancer can be cured by early detection and treatment. The earlier the stage of the lesions, the fewer clinical symptoms are presented. Hence, some cases are detected in an advanced state, resulting in a poor prognostic outcome. Opportunities for early detection include many incidental detections by endoscopic examination and/or imaging studies upon examination and many detections during investigation of symptoms that are not directly associated with cancer. Currently, no hemodiagnosis marker useful for early detection of digestive organ cancer exists. It is extremely important to establish a system capable of diagnosing the presence of digestive organ cancer at as early a stage as possible.

In particular, pancreatic cancer is a form of digestive system malignant tumor that ranks the $5^{th}$ highest in terms of the number of deaths due to site-specific cancer (including both males and females) among the Japanese. According to a survey by the Ministry of Health, Labour and Welfare, 23,000 patients die annually. Cancer detection is very difficult and early cancer detection is rare. 75% of cases diagnosed with pancreatic cancer are already inoperable cases. Pancreatic cancer is a digestive organ cancer resulting in extremely poor prognosis such that the patients die within 1 to 2 years after detection (According a survey by the Center for Cancer Control and Information Services, National Cancer Center, http, colon, forward slash, forward slash, ganjoho, dot, jp, forward slash, public, forward slash, cancer, forward slash, data, forward slash, pancreas, dot, html). Although an advanced diagnostic technique for pancreatic cancer has long been desired, no useful early diagnosis method has been established.

Furthermore, biliary tract cancer is a form of malignant tumor that ranks $6^{th}$ highest in terms of the number of deaths due to site-specific cancer (including both males and females) among the Japanese. According to a survey by the Ministry of Health, Labour and Welfare, 15,000 patients die annually. In most cases, early detection is difficult because of the lack of subjective symptoms.

Recent development in DNA microarray techniques and human genome sequencing have enabled extensive gene expression analysis of all genes. Accordingly, new types of cancer diagnosis, prognostic prediction, prediction of recurrence rate after treatment, and the like have become possible. The present inventors have analyzed the pathological conditions of various diseases and developed for the purpose of developing a diagnostic tool through application of gene expression analysis such as analysis of gene expression profiles in chronic hepatitis patients (see non-patent documents 1 to 3) and gene expression analysis of liver tissue in diabetes mellitus patients. However, these forms of analysis are problematic in terms of their excessive invasiveness, and hospitalization and tissue (organ tissue such as liver tissue) sampling are required. Thereafter, a method requiring less invasiveness has been reported, wherein a gene group capable of distinguishing type C cirrhosis from type C liver cancer and peripheral blood mononuclear cells are used (see patent document 1 and non-patent document 4). This method is advantageous for patients because blood is used in this method and thus it offers a low degree of invasiveness for patients. However, the method is problematic in that collection of peripheral blood mononuclear cells requires several separation processes, the method is complicated as an actual test method, and the method requires much time for the test results to be obtained.

PRIOR ART DOCUMENTS

Patent Document

Patent document 1 JP Patent Publication (Kokai) No. 2008-126 A

Non-Patent Documents

Non-patent document 1 MASAO HONDA et al., GASTROENTEROLOGY 2001; 120:955-966
Non-patent document 2 MASAO HONDA et al., Am J Gastroenterol 2005; 100: 2019-2030
Non-patent document 3 YUKIHIRO SHIROTA et al., HEPATOLOGY Vol. 33, No. 4, 2001, 832-840
Non-patent document 4 YOSHIO SAKAI et al., Cancer Research; 68 (24) 2008. 10267-10279

SUMMARY OF THE INVENTION

Problem to be Solved by the Invention

An object of the present invention is to provide:
a method for detecting digestive organ cancer, gastric cancer, colorectal cancer, pancreatic cancer, and biliary tract cancer by analyzing genes with expression levels that vary in association with digestive organ cancer, gastric cancer, colorectal cancer, pancreatic cancer, and biliary tract cancer, whereby invasiveness to patients is low and genes can be easily extracted from patients; and an in vitro diagnostic.

Means for Solving the Problem

The present inventors have initiated clinical trials to verify if digestive organ cancer, gastric cancer, colorectal cancer, pancreatic cancer, and biliary tract cancer can be diagnosed by gene expression analysis using peripheral blood, and thus found that such diagnosis is possible.

Peripheral blood can be collected in a manner that requires a relatively low degree of invasiveness, and thus its practicality and usefulness in clinical examination are extremely high. Peripheral blood is composed of cell components including, in addition to erythrocytes and blood platelets, leukocytes containing lymphocytes, monocytes, and granulocytes. These cell components are thought to vary their phenotypes and functions depending on lesions in an in vivo environment.

The present inventors have conducted gene expression analysis of peripheral blood from 24 digestive organ cancer patients and 8 normal healthy subjects. Specifically, they have found that digestive organ cancer cases can be distinguished from normal healthy subjects by clustering analysis conducted using data from analysis with about 23,000 probes on DNA microarrays. Through comparison of the gene expression of a group of digestive organ cancer cases with that of a group of normal healthy subjects, 868 probes corresponding to genes with expression levels that differ significantly between the groups were found. With the use of the probe set, hierarchical clustering was performed for the above digestive organ cancer case group and the above normal healthy subject group, so that 2 clusters were formed. Thus the present inventors have found that the digestive organ cancer cases can be distinguished from the normal healthy subjects. Also, a prediction model was applied to 40 cancer cases and 13 normal healthy subject cases (differing from the cancer cases and the normal healthy subjects used for extraction of 868 probes), so that cancer cases and normal healthy subjects were determined. As a result, 39 out of 40 previously diagnosed cancer cases were determined to be actually cancer cases, and the probability that such cases had been properly diagnosed was 97.5%. Moreover, 9 out of 13 previously diagnosed normal healthy subject cases were determined to be normal healthy subject cases, and the probability that such cases had been properly diagnosed was 69.2%. The percentage of cases correctly determined was 90.6% (48/53).

Furthermore, the present inventors have conducted gene expression analysis of peripheral blood from 39 digestive organ cancer patients and peripheral blood from 15 normal healthy subjects. Specifically, they have found that digestive organ cancer cases can be distinguished from normal healthy subjects by clustering analysis conducted using data from analysis with about 23,000 probes on DNA microarrays. Through comparison of the gene expression of a group of digestive organ cancer cases with that of a group of normal healthy subjects, 25 probes corresponding to genes with expression levels that differ significantly between the groups were found. With the use of the probe set, hierarchical clustering was performed for the above digestive organ cancer case group and the above normal healthy subject group, so that 2 clusters were formed. Thus the present inventors have found that the digestive organ cancer cases can be distinguished from the normal healthy subjects.

As a result of the use of the above probes, the percentage of cases correctly determined was 92.3%.

Also, the present inventors have conducted gene expression analysis of peripheral blood from 8 gastric cancer patients and 8 normal healthy subjects. Specifically, they have found that gastric cancer cases can be distinguished from normal healthy subjects by clustering analysis conducted using data from analysis with about 22,000 probes on DNA microarrays. Through comparison of the gene expression of a group of gastric cancer cases with that of a group of normal healthy subjects, 713 probes corresponding to genes with expression levels that differ significantly between the groups were found. With the use of the probe set, hierarchical clustering was performed for the above gastric cancer case group and the above normal healthy subject group, so that 2 clusters were formed. Thus the present inventors have found that the gastric cancer cases can be distinguished from the normal healthy subjects. Also, a prediction model was applied to 10 cancer cases and 13 normal healthy subject cases (differing from the cancer cases and the normal healthy subjects used for extraction of 713 probes), so that cancer cases and normal healthy subjects were determined. As a result, 7 out of 10 previously diagnosed cancer cases were determined to be actually cancer cases, and the probability that such cases had been properly diagnosed was 70%. Moreover, 13 out of 13 previously diagnosed normal healthy subject cases were determined to be normal healthy subject cases, and the probability that such cases had been properly diagnosed was 100%. The percentage of cases correctly determined was 87.0% (20/23).

The present inventors have conducted gene expression analysis of peripheral blood from 8 colorectal cancer patients and 8 normal healthy subjects. Specifically, they have found that colorectal cancer cases can be distinguished from normal healthy subjects by clustering analysis conducted using data from analysis with about 22,000 probes on DNA microarrays. Through comparison of the gene expression of a group of colorectal cancer cases with that of a group of normal healthy subjects, 771 probes corresponding to genes with expression levels that differ significantly between the groups were found. With the use of the probe set, hierarchical clustering was performed for the above colorectal cancer case group and the above normal healthy subject group, so that 2 clusters were formed. Thus, colorectal cancer cases were distinguished from the normal healthy subjects. Also, a prediction model was applied to 10 cancer cases and 13 normal healthy subject cases (differing from the cancer cases and the normal healthy subjects used for extraction of 771 probes), so that cancer cases and normal healthy subjects are determined. As a result, 9 out of 10 previously diagnosed cancer cases were determined to be actually cancer cases, and the probability that such cases had been properly diagnosed was 90%. Moreover, 13 out of 13 previously diagnosed normal healthy subject cases were determined to be normal healthy subject cases, and the probability that such cases had been properly diagnosed was 100%. The percentage of cases correctly determined was 95.7% (22/23).

The present inventors have conducted gene expression analysis of peripheral blood from 8 pancreatic cancer patients and 8 normal healthy subjects. Specifically, they have found that pancreatic cancer cases can be distinguished from normal healthy subjects by clustering analysis conducted using data from analysis with about 22,000 probes on DNA microarrays. Through comparison of the gene expression of a group of pancreatic cancer cases with that of a group of normal healthy subjects, 677 probes corresponding to genes with expression levels that differ significantly between the groups were found. With the use of the probe set, hierarchical clustering was performed for the above pancreatic cancer case group and the above normal healthy subject group, so that 2 clusters were formed. Thus the present inventors have found that pancreatic cancer cases can be distinguished from the normal healthy subjects. Also, a prediction model was applied to 20 cancer cases and 13 normal healthy subject cases (differing from the cancer cases and the normal healthy subjects used for extraction of 677 probes), so that cancer cases and normal healthy subjects were determined. As a result, 15 out of 20 previously diagnosed cancer cases were determined to be actually cancer cases, and the probability that such cases had been properly diagnosed was 75%. Moreover, 13 out of 13 previously diagnosed normal healthy subject cases were determined to be normal healthy subject cases, and the probability that such cases had been properly diagnosed was 100%. The percentage of cases correctly determined was 84.8% (28/33).

The present inventors have conducted gene expression analysis of peripheral blood from 8 biliary tract cancer patients and 8 normal healthy subjects. Specifically, they have found that biliary tract cancer cases can be distinguished from normal healthy subjects by clustering analysis conducted (to form 3 clusters) using data from analysis with about 22,000 probes on DNA microarrays. Through comparison of the gene expression of a group of biliary tract cancer cases with that of a group of normal healthy subjects, 363 probes corresponding to genes with expression levels that differ significantly between the groups were found. With the use of the probe set, hierarchical clustering was performed for the above biliary tract cancer case group and the above normal healthy subject group, so that 2 clusters were formed. Thus the present inventors have found that the biliary tract cancer cases can be distinguished from the normal healthy subjects. Also, a prediction model was applied to 8 cancer cases and 13 normal healthy subject cases (differing from the cancer cases and the normal healthy subjects used for extraction of 363 probes), so that cancer cases and normal healthy subjects were determined. As a result, 8 out of 8 previously diagnosed cancer cases were determined to be actually cancer cases, and the probability that such cases had been properly diagnosed was 100%. Moreover, 13 out of 13 previously diagnosed normal healthy subject cases were determined to be normal healthy subject cases, and the probability that such cases had been properly diagnosed was 100%. The percentage of cases correctly determined was 100% (21/21).

Based on these results, it was found that examination of changes in expression of the gene set in peripheral blood enables diagnosis of digestive organ cancer, gastric cancer, colorectal cancer, pancreatic cancer, and biliary tract cancer. Thus, the present invention was completed. The method of the present invention enables preparation of a new practical diagnostic kit for diagnosis of digestive organ cancer by applying a DNA microarray developmental technique, a real-time PCR method, and an ELISA method.

Currently, general tumor markers covered by health insurance are not always useful for all digestive organ cancer patients. However, the detection sensitivity of the gene expression analysis of the present invention is 90.6%, allowing digestive organ cancer to be specified with very high detection sensitivity through convenient blood collection.

Specifically, the present invention is as follows.

[1] A reagent for detecting digestive organ cancer by measuring the expression of genes corresponding to probes consisting of nucleotide sequences shown in SEQ ID NO: 220, 506, 508, 523, 538, 554, 570, 589, 597, 602, 618, 654, 689, 701, 726, 744, 762, 763, 781, 795, and 849 in peripheral blood, wherein the reagent contains all probes consisting of the nucleotide sequences shown in SEQ ID NOs: 220, 506, 508, 523, 538, 554, 570, 589, 597, 602, 618, 654, 689, 701, 726, 744, 762, 763, 781, 795, and 849; or a reagent for detecting digestive organ cancer by measuring the expression of genes corresponding to probes consisting of the nucleotide sequences shown in SEQ ID NOs: 3030 to 3054 in peripheral blood, wherein the reagent contains all probes consisting of the nucleotide sequences shown in SEQ ID NOs: 3030 to 3054.

[2] The reagent for detecting digestive organ cancer according to [1], containing a DNA microarray in which the probes of [1] bind to a substrate.

[3] A method for detecting digestive organ cancer, comprising obtaining the gene expression profiles of all genes corresponding to probes consisting of the nucleotide sequences shown in SEQ ID NOs: 220, 506, 508, 523, 538, 554, 570, 589, 597, 602, 618, 654, 689, 701, 726, 744, 762, 763, 781, 795, and 849 in peripheral blood from a subject, or all genes corresponding to probes consisting of the nucleotide sequences shown in SEQ ID NOs: 3030 to 3054 in peripheral blood from a subject and then detecting digestive organ cancer based on the expression profiles.

[4] A reagent for detecting gastric cancer by measuring the expression of genes corresponding to probes consisting of the nucleotide sequences shown in SEQ ID NOs: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578 in peripheral blood, wherein the reagent contains all probes consisting of the nucleotide sequences shown in SEQ ID NO: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578.

[5] The reagent for detecting gastric cancer according to [4], containing a DNA microarray in which the probes of [4] bind to a substrate.

[6] A method for detecting gastric cancer, comprising obtaining the gene expression profiles of all genes corresponding to probes consisting of the nucleotide sequences shown in SEQ ID NOs: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578 in peripheral blood from a subject and then detecting gastric cancer based on the expression profiles.

[7] A reagent for detecting colorectal cancer by measuring the expression of genes corresponding to probes consisting of the nucleotide sequences shown in SEQ ID NOs: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340, wherein the reagent contains all probes consisting of the nucleotide sequences shown in SEQ ID NOs: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340.

[8] The reagent for detecting colorectal cancer according to [7], containing a DNA microarray in which the probes of [7] bind to a substrate.

[9] A method for detecting colorectal cancer, comprising obtaining the gene expression profiles of all genes corresponding to probes consisting of the nucleotide sequences shown in SEQ ID NOs: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340 in peripheral blood from a subject and then detecting colorectal cancer based on the gene expression profiles.

[10] A reagent for detecting pancreatic cancer by measuring the expression of genes corresponding to probes consisting of the nucleotide sequences shown in SEQ ID NOs: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003, wherein the reagent contains all probes consisting of the nucleotide sequences shown in SEQ ID NO: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003.

[11] The reagent for detecting pancreatic cancer according to [10], containing a DNA microarray in which the probes of [10] bind to a substrate.

[12] A method for detecting pancreatic cancer, comprising obtaining the gene expression profiles of all genes corresponding to probes consisting of the nucleotide sequences shown in SEQ ID NOs: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003 in peripheral blood from a subject and detecting pancreatic cancer based on the expression profiles.

[13] A reagent for detecting biliary tract cancer by measuring the expression of genes corresponding to probes consisting of the nucleotide sequences shown in SEQ ID NOs: 3055 to 3417, which contains all probes consisting of the nucleotide sequences shown in SEQ ID NOs: 3055 to 3417.

[14] The reagent for detecting biliary tract cancer according to [13], containing a DNA microarray in which the probes of [13] bind to a substrate.

[15] A method for detecting biliary tract cancer, comprising obtaining the gene expression profiles of all genes corresponding to probes consisting of the nucleotide sequences shown in SEQ ID NOs: 3055 to 3417 in peripheral blood from a subject, and then detecting biliary tract cancer based on the expression profiles.

This description includes the disclosure of the description and drawings of Japanese Patent Application No. 2009-193702, from which the present application claims priority.

Effects of the Invention

The expression levels of the genes corresponding to the probes of the present invention vary among digestive organ cancer, gastric cancer, colorectal cancer, pancreatic cancer, and biliary tract cancer. Through analysis of the expression profiles of these genes, digestive organ cancer, gastric cancer, colorectal cancer, pancreatic cancer, or biliary tract cancer can be detected. Furthermore, a risk of developing digestive organ cancer, gastric cancer, colorectal cancer, pancreatic cancer, or biliary tract cancer can be predicted, for example.

BRIEF DESCRIPTION OF THE DRAWINGS

FIG. 1-1 shows 868 probes of a 1$^{st}$ probe group that can be used for detection of digestive organ cancer.

FIG. 1-2 shows 868 probes that can be used for detection of digestive organ cancer (continuation).

FIG. 1-3 shows 868 probes that can be used for detection of digestive organ cancer (continuation).

FIG. 1-4 shows 868 probes that can be used for detection of digestive organ cancer (continuation).

FIG. 1-5 shows 868 probes that can be used for detection of digestive organ cancer (continuation).

FIG. 1-6 shows 868 probes that can be used for detection of digestive organ cancer (continuation).

FIG. 1-7 shows 868 probes that can be used for detection of digestive organ cancer (continuation).

FIG. 1-8 shows 868 probes that can be used for detection of digestive organ cancer (continuation).

FIG. 1-9 shows 868 probes that can be used for detection of digestive organ cancer (continuation).

FIG. 1-10 shows 868 probes that can be used for detection of digestive organ cancer (continuation).

FIG. 1-11 shows 868 probes that can be used for detection of digestive organ cancer (continuation).

FIG. 1-12 shows 868 probes that can be used for detection of digestive organ cancer (continuation).

FIG. 1-13 shows 868 probes that can be used for detection of digestive organ cancer (continuation).

FIG. 1-14 shows 868 probes that can be used for detection of digestive organ cancer (continuation).

FIG. 1-15 shows 868 probes that can be used for detection of digestive organ cancer (continuation).

FIG. 1-16 shows 868 probes that can be used for detection of digestive organ cancer (continuation).

FIG. 1-17 shows 868 probes that can be used for detection of digestive organ cancer (continuation).

FIG. 1-18 shows 868 probes that can be used for detection of digestive organ cancer (continuation).

FIG. 1-19 shows 868 probes that can be used for detection of digestive organ cancer (continuation).

FIG. 1-20 shows 868 probes that can be used for detection of digestive organ cancer (continuation).

FIG. 1-21 shows 868 probes that can be used for detection of digestive organ cancer (continuation).

FIG. 1-22 shows 868 probes that can be used for detection of digestive organ cancer (continuation).

FIG. 1-23 shows 868 probes that can be used for detection of digestive organ cancer (continuation).

FIG. 1-24 shows 868 probes that can be used for detection of digestive organ cancer (continuation).

FIG. 1-25 shows 868 probes that can be used for detection of digestive organ cancer (continuation).

FIG. 1-26 shows 868 probes that can be used for detection of digestive organ cancer (continuation).

FIG. 1-27 shows 868 probes that can be used for detection of digestive organ cancer (continuation).

FIG. 1-28 shows 868 probes that can be used for detection of digestive organ cancer (continuation).

FIG. 1-29 shows 868 probes that can be used for detection of digestive organ cancer (continuation).

FIG. 1-30 shows 868 probes that can be used for detection of digestive organ cancer (continuation).

FIG. 1-31 shows 868 probes that can be used for detection of digestive organ cancer (continuation).

FIG. 1-32 shows 868 probes that can be used for detection of digestive organ cancer (continuation).

FIG. 1-33 shows 868 probes that can be used for detection of digestive organ cancer (continuation).

FIG. 1-34 shows 868 probes that can be used for detection of digestive organ cancer (continuation).

FIG. 1-35 shows 868 probes that can be used for detection of digestive organ cancer (continuation).

FIG. 1-36 shows 868 probes that can be used for detection of digestive organ cancer (continuation).

FIG. 1-37 shows 868 probes that can be used for detection of digestive organ cancer (continuation).

FIG. 1-38 shows 868 probes that can be used for detection of digestive organ cancer (continuation).

FIG. 1-39 shows 868 probes that can be used for detection of digestive organ cancer (continuation).

FIG. 1-40 shows 868 probes that can be used for detection of digestive organ cancer (continuation).

FIG. 1-41 shows 868 probes that can be used for detection of digestive organ cancer (continuation).

FIG. 1-42 shows 868 probes that can be used for detection of digestive organ cancer (continuation).

FIG. 1-43 shows 868 probes that can be used for detection of digestive organ cancer (continuation).

FIG. 1-44 shows 868 probes that can be used for detection of digestive organ cancer (continuation).

FIG. 1-45 shows 868 probes that can be used for detection of digestive organ cancer (continuation).

FIG. 1-46 shows 868 probes that can be used for detection of digestive organ cancer (continuation).

FIG. 1-47 shows 868 probes that can be used for detection of digestive organ cancer (continuation).

FIG. 1-48 shows 868 probes that can be used for detection of digestive organ cancer (continuation).

FIG. 2 shows 21 probes with expression levels that differed significantly particularly between digestive organ cancer patients and normal healthy subjects, from among the 868 probes shown in FIG. 1.

FIG. 3-1 shows 713 probes that can be used for detection of gastric cancer.

FIG. 3-2 shows 713 probes that can be used for detection of gastric cancer (continuation).

FIG. 3-3 shows 713 probes that can be used for detection of gastric cancer (continuation).

FIG. 3-4 shows 713 probes that can be used for detection of gastric cancer (continuation).

FIG. 3-5 shows 713 probes that can be used for detection of gastric cancer (continuation).

FIG. 3-6 shows 713 probes that can be used for detection of gastric cancer (continuation).

FIG. 3-7 shows 713 probes that can be used for detection of gastric cancer (continuation).

FIG. 3-8 shows 713 probes that can be used for detection of gastric cancer (continuation).

FIG. 3-9 shows 713 probes that can be used for detection of gastric cancer (continuation).

FIG. 3-10 shows 713 probes that can be used for detection of gastric cancer (continuation).

FIG. 3-11 shows 713 probes that can be used for detection of gastric cancer (continuation).

FIG. 3-12 shows 713 probes that can be used for detection of gastric cancer (continuation).

FIG. 3-13 shows 713 probes that can be used for detection of gastric cancer (continuation).

FIG. 3-14 shows 713 probes that can be used for detection of gastric cancer (continuation).

FIG. 3-15 shows 713 probes that can be used for detection of gastric cancer (continuation).

FIG. 3-16 shows 713 probes that can be used for detection of gastric cancer (continuation).

FIG. 3-17 shows 713 probes that can be used for detection of gastric cancer (continuation).

FIG. 3-18 shows 713 probes that can be used for detection of gastric cancer (continuation).
FIG. 3-19 shows 713 probes that can be used for detection of gastric cancer (continuation).
FIG. 3-20 shows 713 probes that can be used for detection of gastric cancer (continuation).
FIG. 3-21 shows 713 probes that can be used for detection of gastric cancer (continuation).
FIG. 3-22 shows 713 probes that can be used for detection of gastric cancer (continuation).
FIG. 3-23 shows 713 probes that can be used for detection of gastric cancer (continuation).
FIG. 3-24 shows 713 probes that can be used for detection of gastric cancer (continuation).
FIG. 3-25 shows 713 probes that can be used for detection of gastric cancer (continuation).
FIG. 3-26 shows 713 probes that can be used for detection of gastric cancer (continuation).
FIG. 3-27 shows 713 probes that can be used for detection of gastric cancer (continuation).
FIG. 3-28 shows 713 probes that can be used for detection of gastric cancer (continuation).
FIG. 3-29 shows 713 probes that can be used for detection of gastric cancer (continuation).
FIG. 3-30 shows 713 probes that can be used for detection of gastric cancer (continuation).
FIG. 3-31 shows 713 probes that can be used for detection of gastric cancer (continuation).
FIG. 3-32 shows 713 probes that can be used for detection of gastric cancer (continuation).
FIG. 3-33 shows 713 probes that can be used for detection of gastric cancer (continuation).
FIG. 3-34 shows 713 probes that can be used for detection of gastric cancer (continuation).
FIG. 3-35 shows 713 probes that can be used for detection of gastric cancer (continuation).
FIG. 3-36 shows 713 probes that can be used for detection of gastric cancer (continuation).
FIG. 3-37 shows 713 probes that can be used for detection of gastric cancer (continuation).
FIG. 3-38 shows 713 probes that can be used for detection of gastric cancer (continuation).
FIG. 3-39 shows 713 probes that can be used for detection of gastric cancer (continuation).
FIG. 4-1 shows 107 probes with expression levels that differed significantly particularly between gastric cancer patients and normal healthy subjects, from among 713 probes shown in FIG. 3.
FIG. 4-2 shows 107 probes with expression levels that differed significantly particularly between gastric cancer patients and normal healthy subjects, from among the 713 probes shown in FIG. 3 (continuation).
FIG. 4-3 shows 107 probes with expression levels that differed significantly particularly between gastric cancer patients and normal healthy subjects, from among the 713 probes shown in FIG. 3 (continuation).
FIG. 4-4 shows 107 probes with expression levels that differed significantly particularly between gastric cancer patients and normal healthy subjects, from among the 713 probes shown in FIG. 3 (continuation).
FIG. 4-5 shows 107 probes with expression levels that differed significantly particularly between gastric cancer patients and normal healthy subjects, from among the 713 probes shown in FIG. 3 (continuation).
FIG. 4-6 shows 107 probes with expression levels that differed significantly particularly between gastric cancer patients and normal healthy subjects, from among the 713 probes shown in FIG. 3 (continuation).
FIG. 5-1 shows 771 probes that can be used for detection of colorectal cancer.
FIG. 5-2 shows 771 probes that can be used for detection of colorectal cancer (continuation).
FIG. 5-3 shows 771 probes that can be used for detection of colorectal cancer (continuation).
FIG. 5-4 shows 771 probes that can be used for detection of colorectal cancer (continuation).
FIG. 5-5 shows 771 probes that can be used for detection of colorectal cancer (continuation).
FIG. 5-6 shows 771 probes that can be used for detection of colorectal cancer (continuation).
FIG. 5-7 shows 771 probes that can be used for detection of colorectal cancer (continuation).
FIG. 5-8 shows 771 probes that can be used for detection of colorectal cancer (continuation).
FIG. 5-9 shows 771 probes that can be used for detection of colorectal cancer (continuation).
FIG. 5-10 shows 771 probes that can be used for detection of colorectal cancer (continuation).
FIG. 5-11 shows 771 probes that can be used for detection of colorectal cancer (continuation).
FIG. 5-12 shows 771 probes that can be used for detection of colorectal cancer (continuation).
FIG. 5-13 shows 771 probes that can be used for detection of colorectal cancer (continuation).
FIG. 5-14 shows 771 probes that can be used for detection of colorectal cancer (continuation).
FIG. 5-15 shows 771 probes that can be used for detection of colorectal cancer (continuation).
FIG. 5-16 shows 771 probes that can be used for detection of colorectal cancer (continuation).
FIG. 5-17 shows 771 probes that can be used for detection of colorectal cancer (continuation).
FIG. 5-18 shows 771 probes that can be used for detection of colorectal cancer (continuation).
FIG. 5-19 shows 771 probes that can be used for detection of colorectal cancer (continuation).
FIG. 5-20 shows 771 probes that can be used for detection of colorectal cancer (continuation).
FIG. 5-21 shows 771 probes that can be used for detection of colorectal cancer (continuation).
FIG. 5-22 shows 771 probes that can be used for detection of colorectal cancer (continuation).
FIG. 5-23 shows 771 probes that can be used for detection of colorectal cancer (continuation).
FIG. 5-24 shows 771 probes that can be used for detection of colorectal cancer (continuation).
FIG. 5-25 shows 771 probes that can be used for detection of colorectal cancer (continuation).
FIG. 5-26 shows 771 probes that can be used for detection of colorectal cancer (continuation).
FIG. 5-27 shows 771 probes that can be used for detection of colorectal cancer (continuation).
FIG. 5-28 shows 771 probes that can be used for detection of colorectal cancer (continuation).
FIG. 5-29 shows 771 probes that can be used for detection of colorectal cancer (continuation).
FIG. 5-30 shows 771 probes that can be used for detection of colorectal cancer (continuation).
FIG. 5-31 shows 771 probes that can be used for detection of colorectal cancer (continuation).
FIG. 5-32 shows 771 probes that can be used for detection of colorectal cancer (continuation).

FIG. 5-33 shows 771 probes that can be used for detection of colorectal cancer (continuation).

FIG. 5-34 shows 771 probes that can be used for detection of colorectal cancer (continuation).

FIG. 5-35 shows 771 probes that can be used for detection of colorectal cancer (continuation).

FIG. 5-36 shows 771 probes that can be used for detection of colorectal cancer (continuation).

FIG. 5-37 shows 771 probes that can be used for detection of colorectal cancer (continuation).

FIG. 5-38 shows 771 probes that can be used for detection of colorectal cancer (continuation).

FIG. 5-39 shows 771 probes that can be used for detection of colorectal cancer (continuation).

FIG. 5-40 shows 771 probes that can be used for detection of colorectal cancer (continuation).

FIG. 5-41 shows 771 probes that can be used for detection of colorectal cancer (continuation).

FIG. 6-1 shows 116 probes with expression levels that differed significantly particularly between colorectal cancer patients and normal healthy subjects, from among the 771 probes shown in FIG. 5.

FIG. 6-2 shows 116 probes with expression levels that differed significantly particularly between colorectal cancer patients and normal healthy subjects, from among the 771 probes shown in FIG. 5 (continuation).

FIG. 6-3 shows 116 probes with expression levels that differed significantly particularly between colorectal cancer patients and normal healthy subjects, from among the 771 probes shown in FIG. 5 (continuation).

FIG. 6-4 shows 116 probes with expression levels differed significantly particularly between colorectal cancer patients and normal healthy subjects, from among the 771 probes shown in FIG. 5 (continuation).

FIG. 6-5 shows 116 probes with expression levels differed significantly particularly between colorectal cancer patients and normal healthy subjects, from among the 771 probes shown in FIG. 5 (continuation).

FIG. 6-6 shows 116 probes with expression levels differed significantly particularly between colorectal cancer patients and normal healthy subjects, from among the 771 probes shown in FIG. 5 (continuation).

FIG. 6-7 shows 116 probes with expression levels differed significantly particularly between colorectal cancer patients and normal healthy subjects, from among the 771 probes shown in FIG. 5 (continuation).

FIG. 7-1 shows 677 probes that can be used for detection of pancreatic cancer.

FIG. 7-2 shows 677 probes that can be used for detection of pancreatic cancer (continuation).

FIG. 7-3 shows 677 probes that can be used for detection of pancreatic cancer (continuation).

FIG. 7-4 shows 677 probes that can be used for detection of pancreatic cancer (continuation).

FIG. 7-5 shows 677 probes that can be used for detection of pancreatic cancer (continuation).

FIG. 7-6 shows 677 probes that can be used for detection of pancreatic cancer (continuation).

FIG. 7-7 shows 677 probes that can be used for detection of pancreatic cancer (continuation).

FIG. 7-8 shows 677 probes that can be used for detection of pancreatic cancer (continuation).

FIG. 7-9 shows 677 probes that can be used for detection of pancreatic cancer (continuation).

FIG. 7-10 shows 677 probes that can be used for detection of pancreatic cancer (continuation).

FIG. 7-11 shows 677 probes that can be used for detection of pancreatic cancer (continuation).

FIG. 7-12 shows 677 probes that can be used for detection of pancreatic cancer (continuation).

FIG. 7-13 shows 677 probes that can be used for detection of pancreatic cancer (continuation).

FIG. 7-14 shows 677 probes that can be used for detection of pancreatic cancer (continuation).

FIG. 7-15 shows 677 probes that can be used for detection of pancreatic cancer (continuation).

FIG. 7-16 shows 677 probes that can be used for detection of pancreatic cancer (continuation).

FIG. 7-17 shows 677 probes that can be used for detection of pancreatic cancer (continuation).

FIG. 7-18 shows 677 probes that can be used for detection of pancreatic cancer (continuation).

FIG. 7-19 shows 677 probes that can be used for detection of pancreatic cancer (continuation).

FIG. 7-20 shows 677 probes that can be used for detection of pancreatic cancer (continuation).

FIG. 7-21 shows 677 probes that can be used for detection of pancreatic cancer (continuation).

FIG. 7-22 shows 677 probes that can be used for detection of pancreatic cancer (continuation).

FIG. 7-23 shows 677 probes that can be used for detection of pancreatic cancer (continuation).

FIG. 7-24 shows 677 probes that can be used for detection of pancreatic cancer (continuation).

FIG. 7-25 shows 677 probes that can be used for detection of pancreatic cancer (continuation).

FIG. 7-26 shows 677 probes that can be used for detection of pancreatic cancer (continuation).

FIG. 7-27 shows 677 probes that can be used for detection of pancreatic cancer (continuation).

FIG. 7-28 shows 677 probes that can be used for detection of pancreatic cancer (continuation).

FIG. 7-29 shows 677 probes that can be used for detection of pancreatic cancer (continuation).

FIG. 7-30 shows 677 probes that can be used for detection of pancreatic cancer (continuation).

FIG. 7-31 shows 677 probes that can be used for detection of pancreatic cancer (continuation).

FIG. 7-32 shows 677 probes that can be used for detection of pancreatic cancer (continuation).

FIG. 7-33 shows 677 probes that can be used for detection of pancreatic cancer (continuation).

FIG. 7-34 shows 677 probes that can be used for detection of pancreatic cancer (continuation).

FIG. 7-35 shows 677 probes that can be used for detection of pancreatic cancer (continuation).

FIG. 7-36 shows 677 probes that can be used for detection of pancreatic cancer (continuation).

FIG. 7-37 shows 677 probes that can be used for detection of pancreatic cancer (continuation).

FIG. 8-1 shows 61 probes with expression levels that differed significantly particularly between pancreatic cancer patients and normal healthy subjects, from among the 677 probes shown in FIG. 7.

FIG. 8-2 shows 61 probes with expression levels that differed significantly particularly between pancreatic cancer patients and normal healthy subjects, from among the 677 probes shown in FIG. 7 (continuation).

FIG. 8-3 shows 61 probes with expression levels that differed significantly particularly between pancreatic cancer patients and normal healthy subjects, from among the 677 probes shown in FIG. 7 (continuation).

FIG. 8-4 shows 61 probes with expression levels that differed significantly particularly between pancreatic cancer patients and normal healthy subjects, from among the 677 probes shown in FIG. 7 (continuation).

FIG. 9 shows the results of hierarchical clustering using 23352 probes for digestive organ cancer cases and normal healthy subjects.

FIG. 10 shows the results of hierarchical clustering using 868 probes corresponding to genes with expression levels that were observed to be attenuated or enhanced in digestive organ cancer cases compared with normal healthy subjects.

Figure 11:
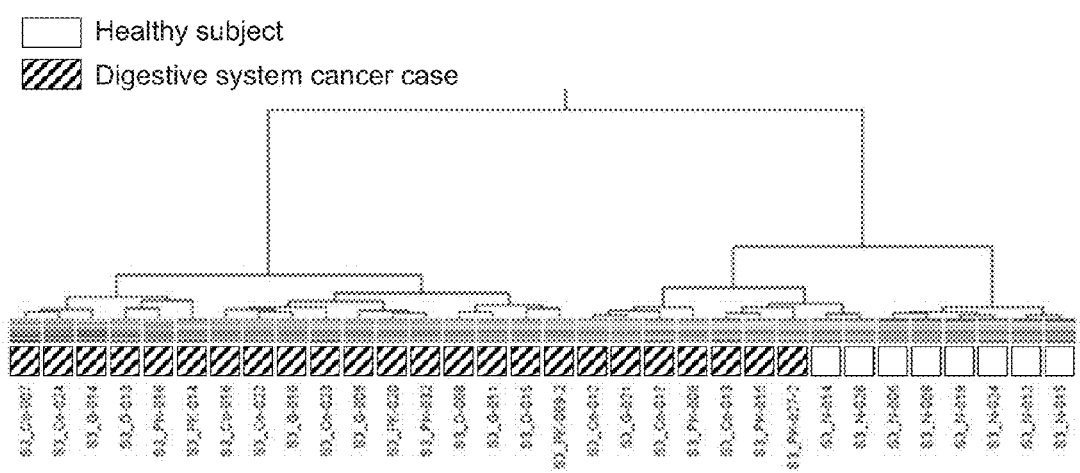

FIG. 11 shows the results of hierarchical clustering using 21 probes corresponding to genes with expression levels that were observed to be attenuated in digestive organ cancer cases at levels 0.4 times or less or enhanced in the same at levels 2.5 times or more than normal healthy subjects.

Figure 12:
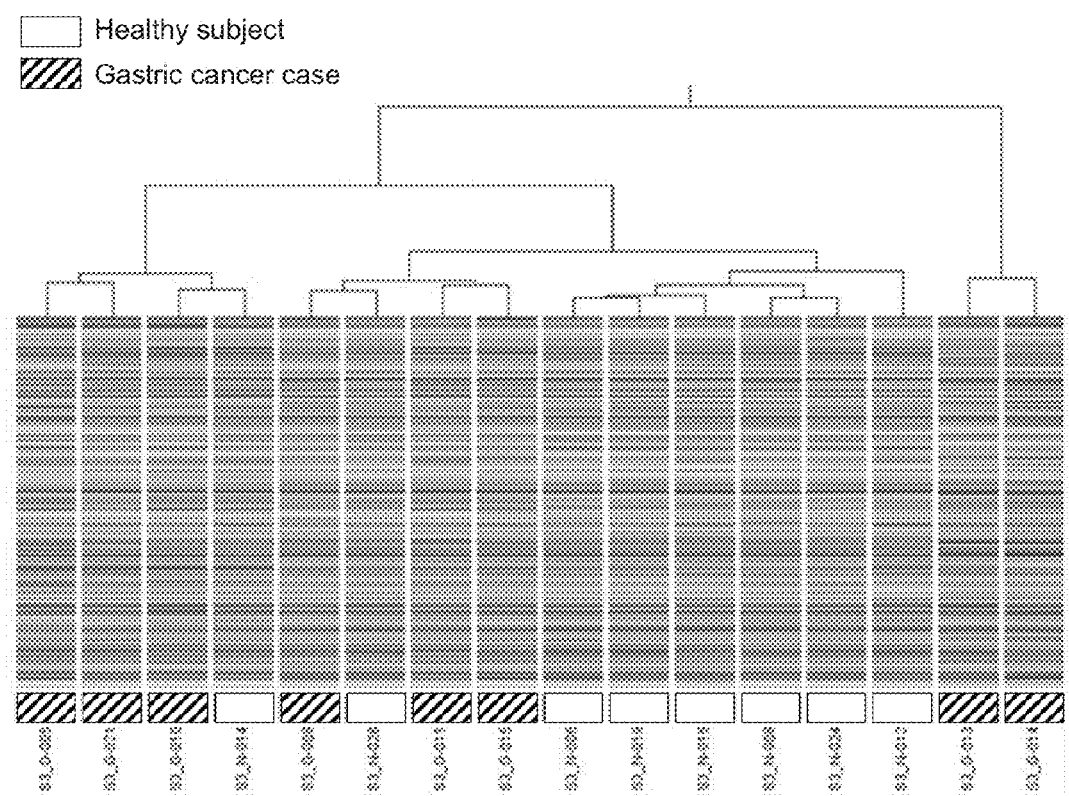

FIG. 12 shows the results of hierarchical clustering using 22155 probes for gastric cancer cases and normal healthy subjects.

Figure 13:
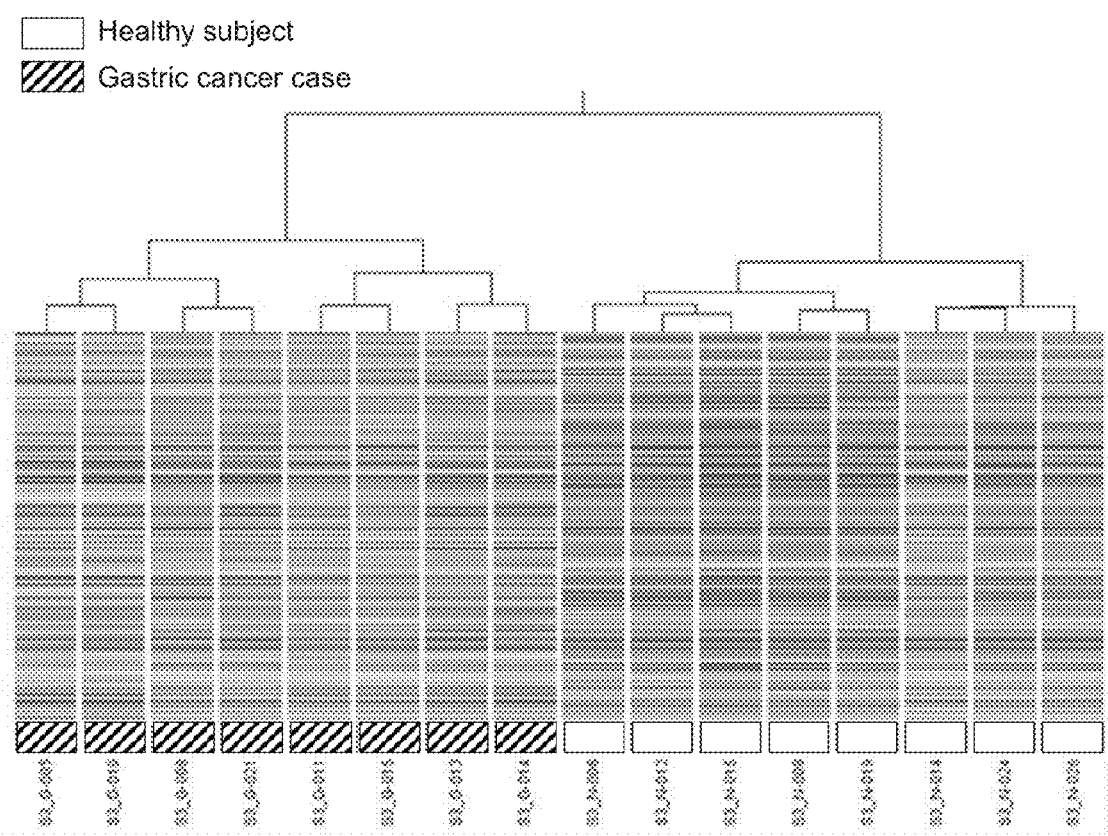

FIG. 13 shows the results of hierarchical clustering using 713 probes corresponding to genes with expression levels that were observed to be attenuated in gastric cancer cases at levels 0.5 times or less or enhanced in the same at levels 2.0 times or more than normal healthy subjects.

Figure 14:
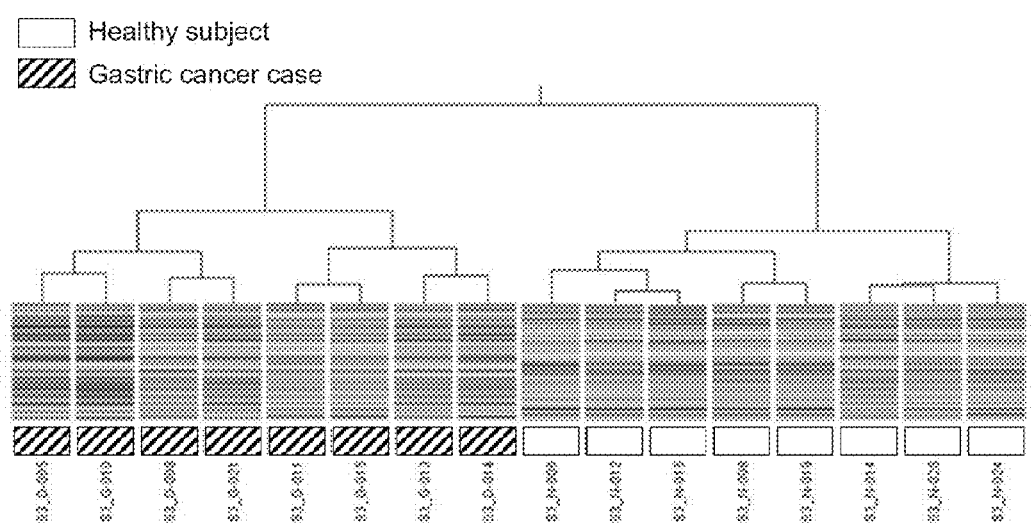

FIG. 14 shows the results of hierarchical clustering using 107 probes corresponding to genes with expression levels that were observed to be attenuated in gastric cancer cases at levels 0.33 times or less or enhanced in the same at levels 3 times or more than normal healthy subjects.

Figure 15:
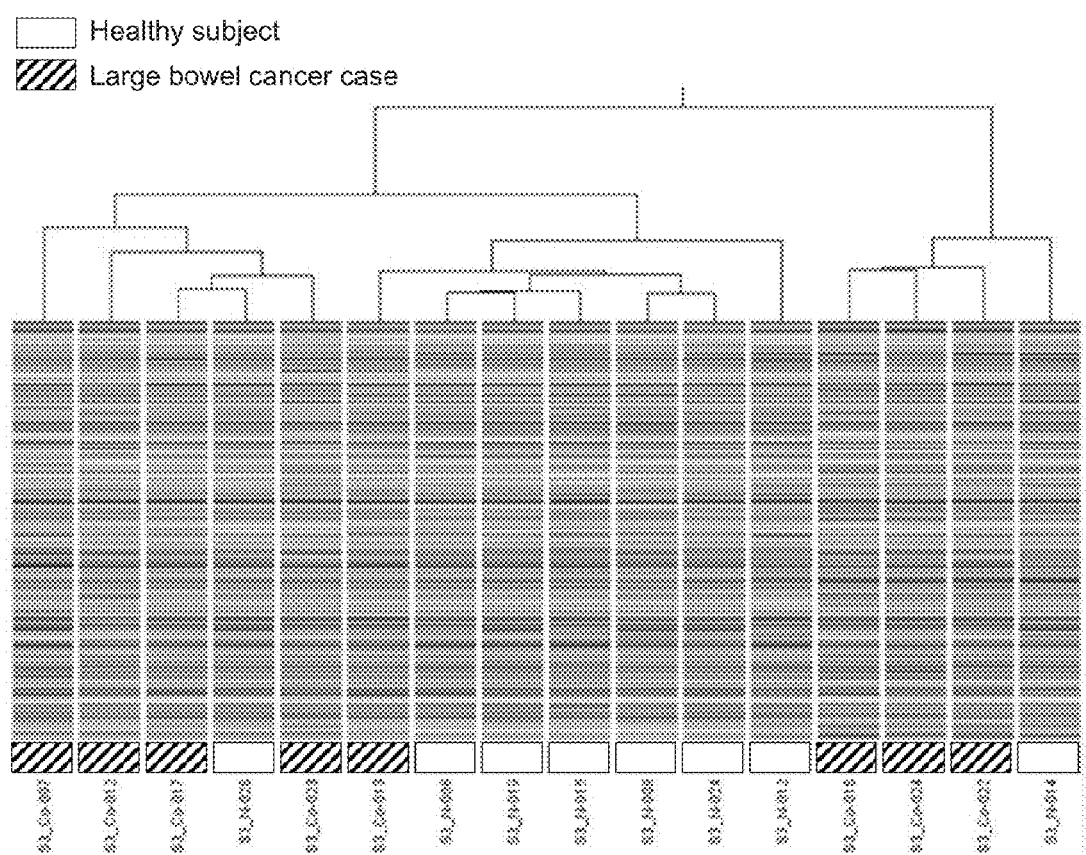

FIG. 15 shows the results of hierarchical clustering using 22181 probes for gastric cancer cases and normal healthy subjects.

Figure 16:
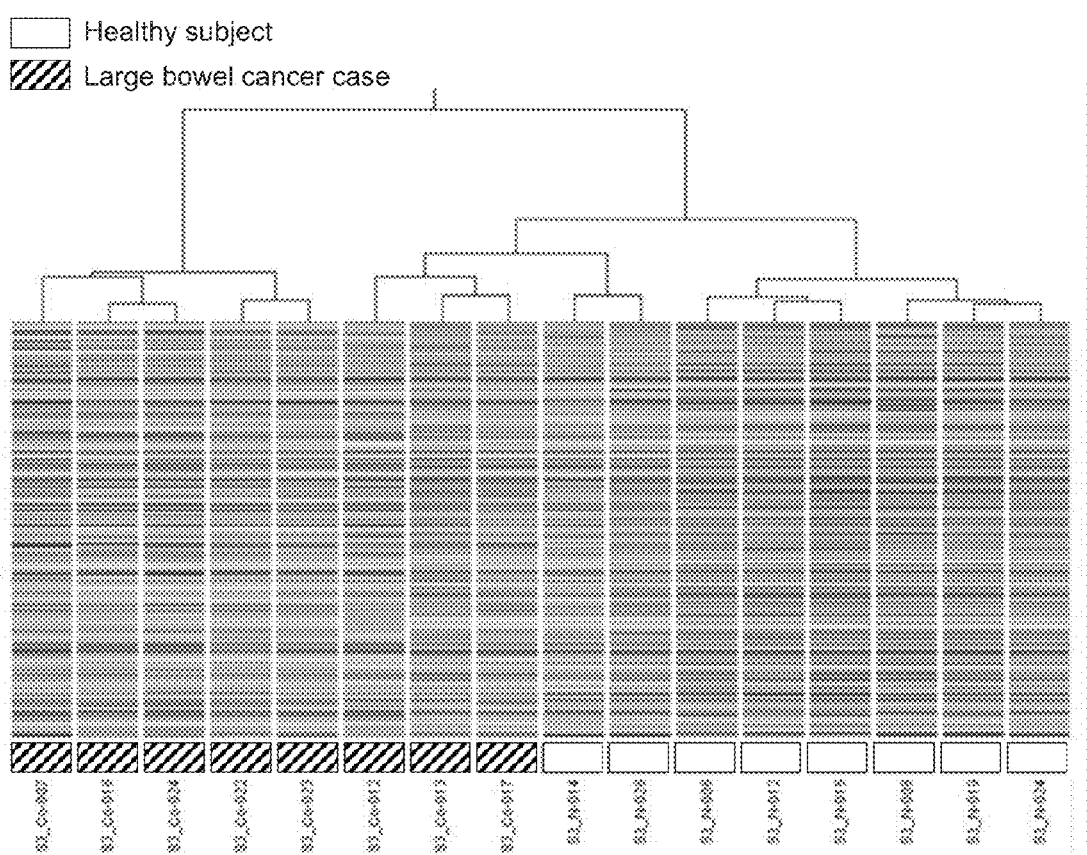

FIG. 16 shows the results of hierarchical clustering using 771 probes corresponding to genes with expression levels that were observed to be attenuated in colorectal cancer cases at levels 0.5 times or less or enhanced in the same at levels 2 times or more than normal healthy subjects.

Figure 17:
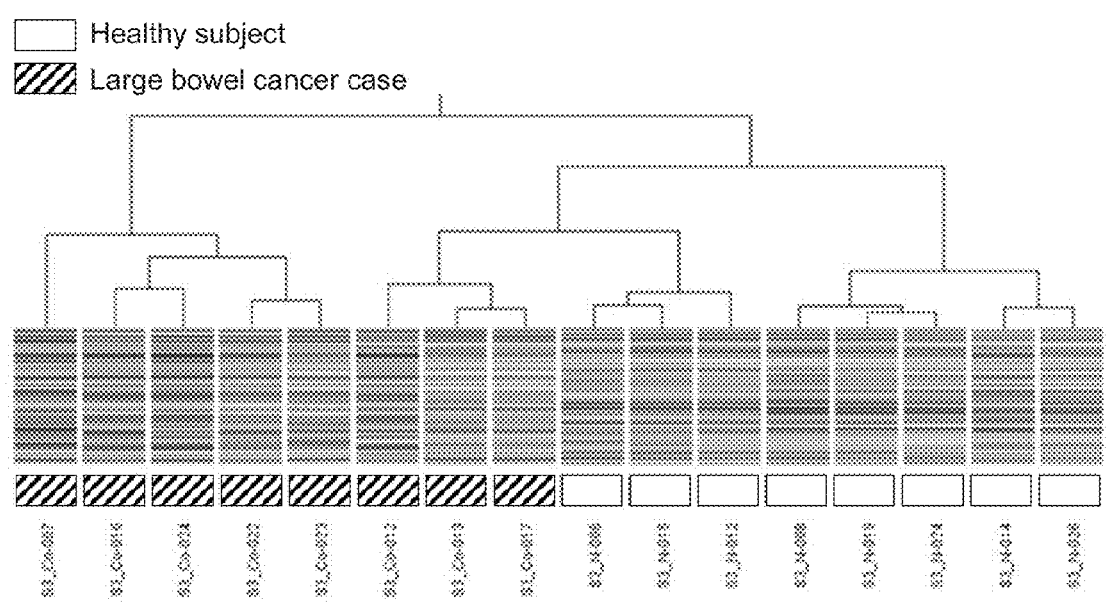

FIG. 17 shows the results of hierarchical clustering using 116 probes corresponding to genes with expression levels that were observed to be attenuated in colorectal cancer cases at levels 0.33 times or less or enhanced in the same at levels 3 times or more than normal healthy subjects.

Figure 18:
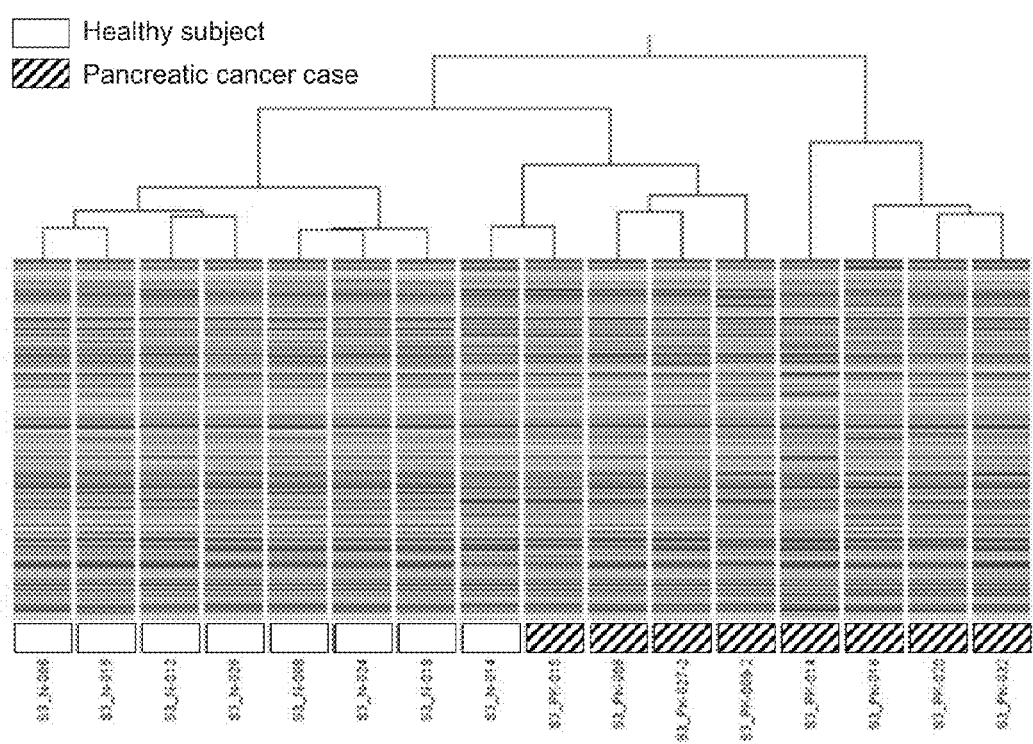

FIG. 18 shows the results of hierarchical clustering using 22149 probes for pancreatic cancer cases and normal healthy subjects.

Figure 19:
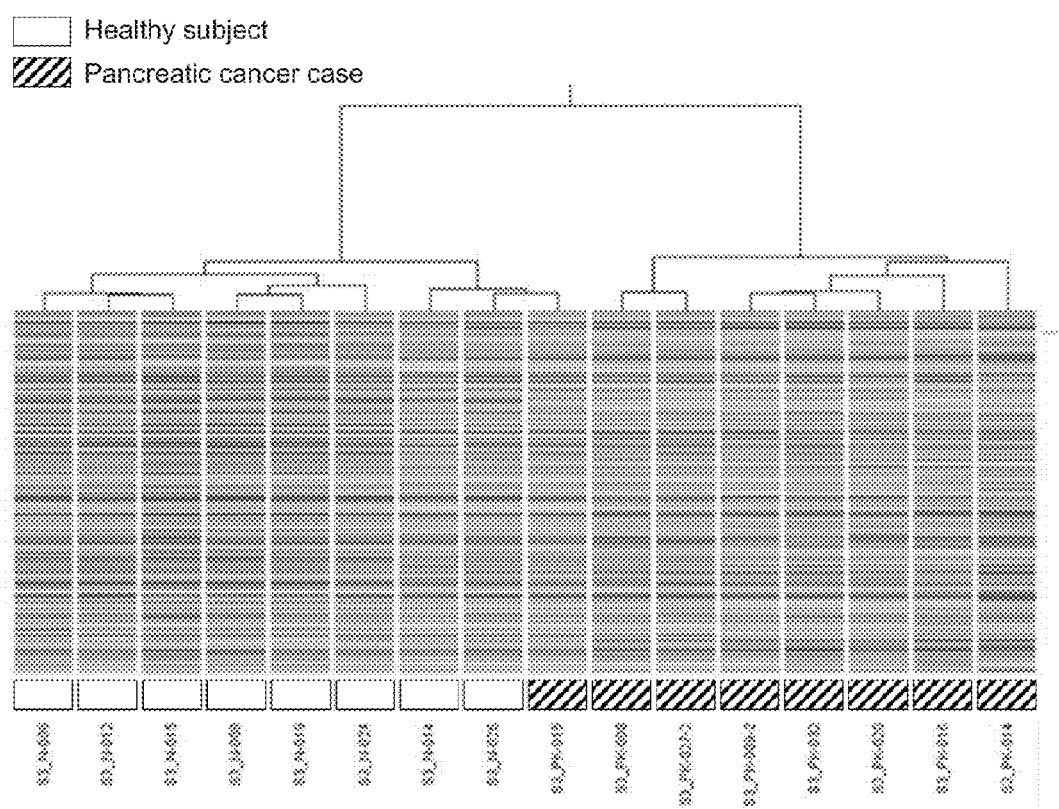

FIG. 19 shows the results of hierarchical clustering using 677 probes corresponding to genes with expression levels that were observed to be attenuated in pancreatic cancer cases at levels 0.5 times or less or enhanced in the same at levels 2 times or more than normal healthy subjects.

Figure 20:
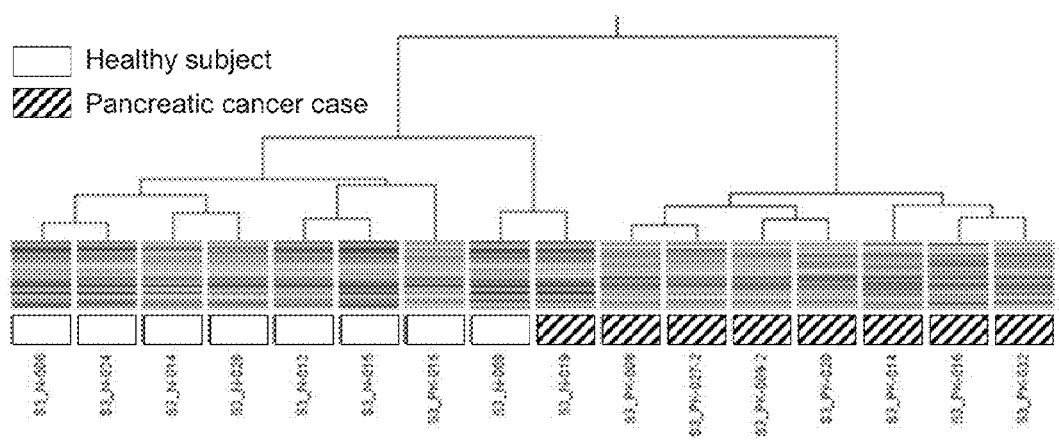

FIG. 20 shows the results of hierarchical clustering using 61 probes corresponding to genes with expression levels that were observed to be attenuated in pancreatic cancer cases at levels 0.33 times or less or enhanced in the same at levels 3 times or more than normal healthy subjects.

FIG. 21-1 shows 25 probes of a $2^{nd}$ probe group that can be used for detection of digestive organ cancer.

FIG. 21-2 shows 25 probes of a $2^{nd}$ probe group that can be used for detection of digestive organ cancer (continuation).

Figure 22:
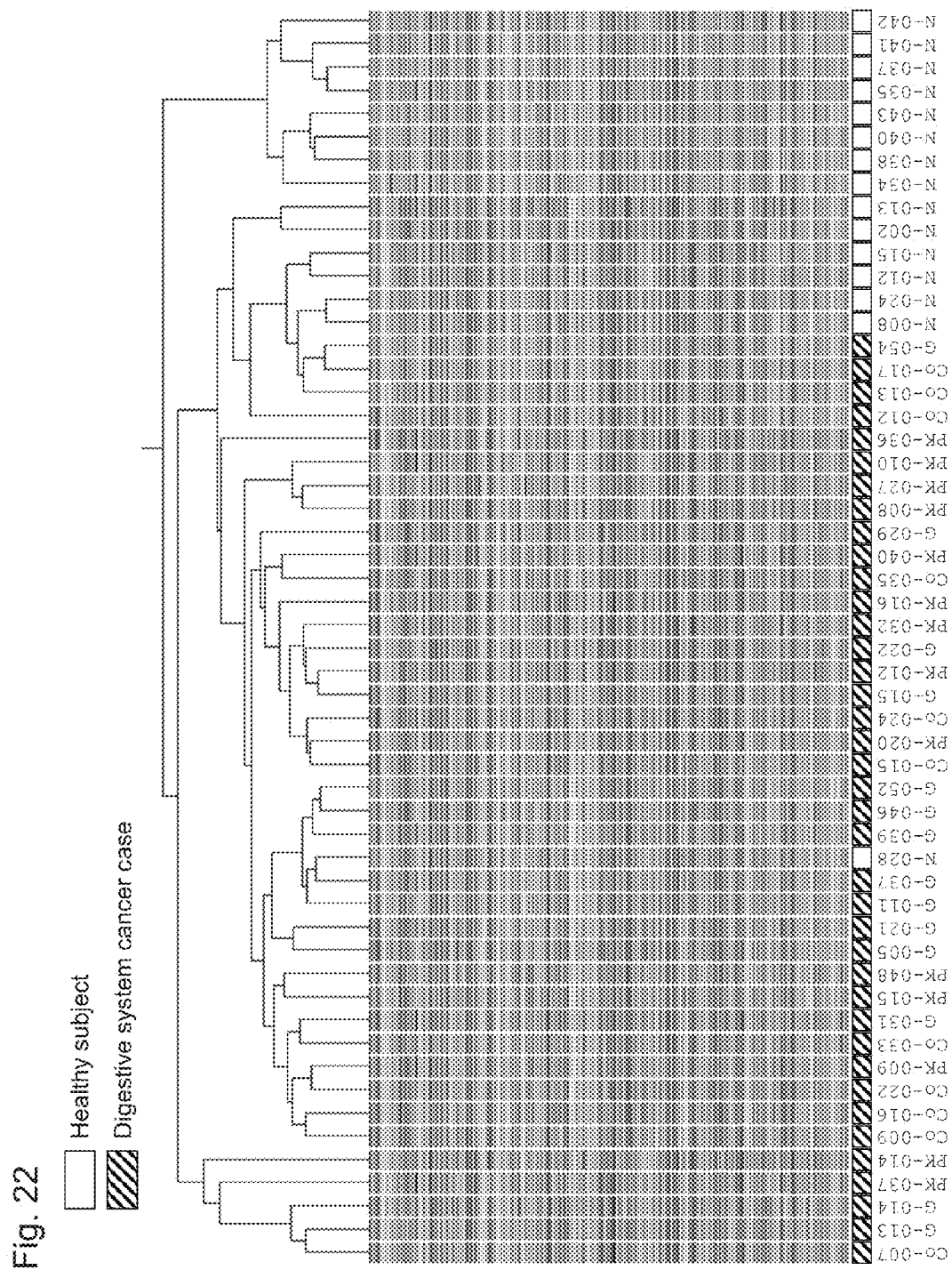

FIG. 22 shows the results of hierarchical clustering using 23278 probes for digestive organ cancer cases and normal healthy subjects.

Figure 23:
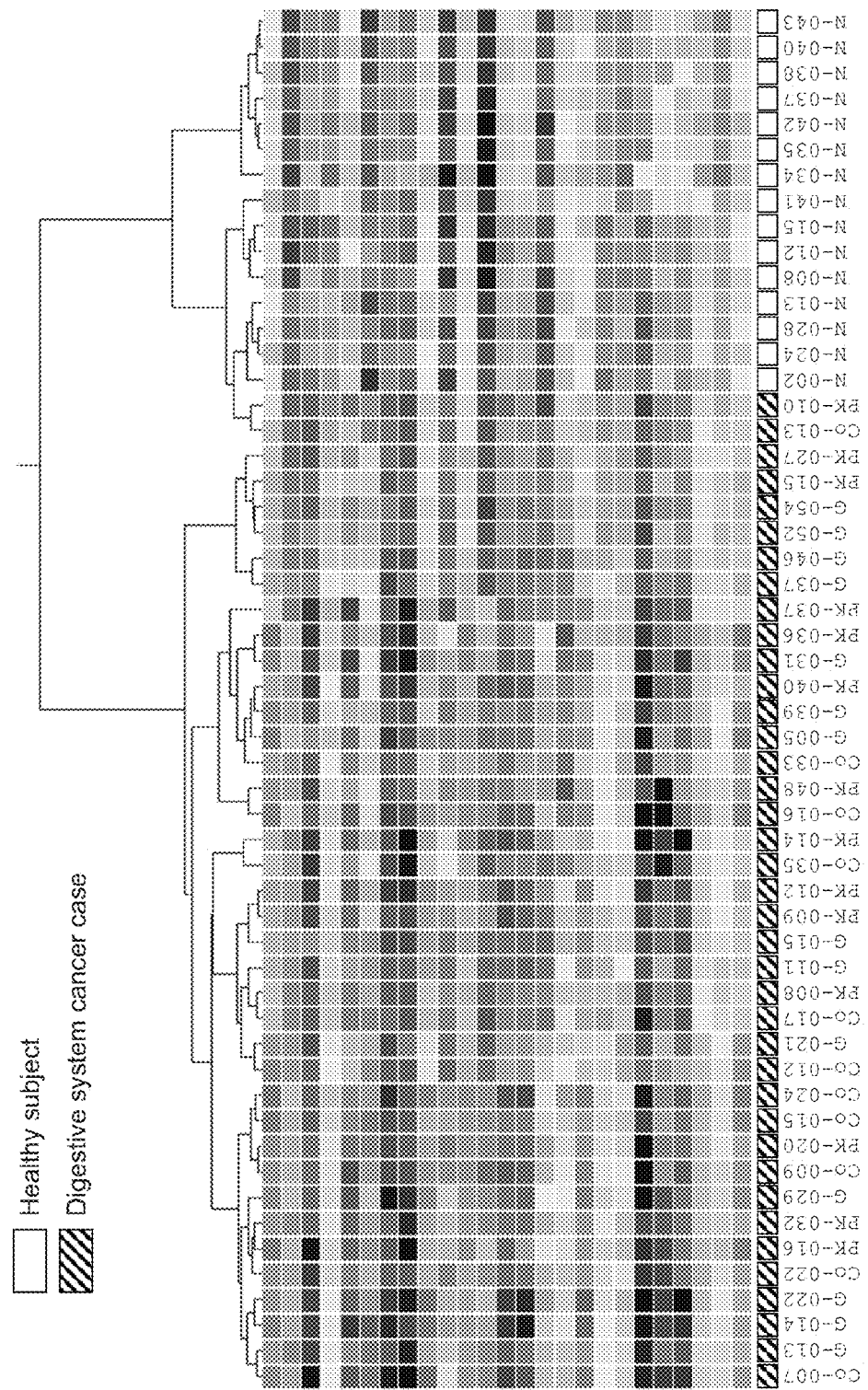

FIG. 23 shows the results of hierarchical clustering using 25 probes corresponding to genes with expression levels that were observed to be attenuated or enhanced in digestive organ cancer cases compared with normal healthy subjects.

FIG. 24-1 shows 363 probes that can be used for detection of biliary tract cancer.

FIG. 24-2 shows 363 probes that can be used for detection of biliary tract cancer (continuation).

FIG. 24-3 shows 363 probes that can be used for detection of biliary tract cancer (continuation).

FIG. 24-4 shows 363 probes that can be used for detection of biliary tract cancer (continuation).

FIG. 24-5 shows 363 probes that can be used for detection of biliary tract cancer (continuation).

FIG. 24-6 shows 363 probes that can be used for detection of biliary tract cancer (continuation).

FIG. 24-7 shows 363 probes that can be used for detection of biliary tract cancer (continuation).

FIG. 24-8 shows 363 probes that can be used for detection of biliary tract cancer (continuation).

Figure 9:
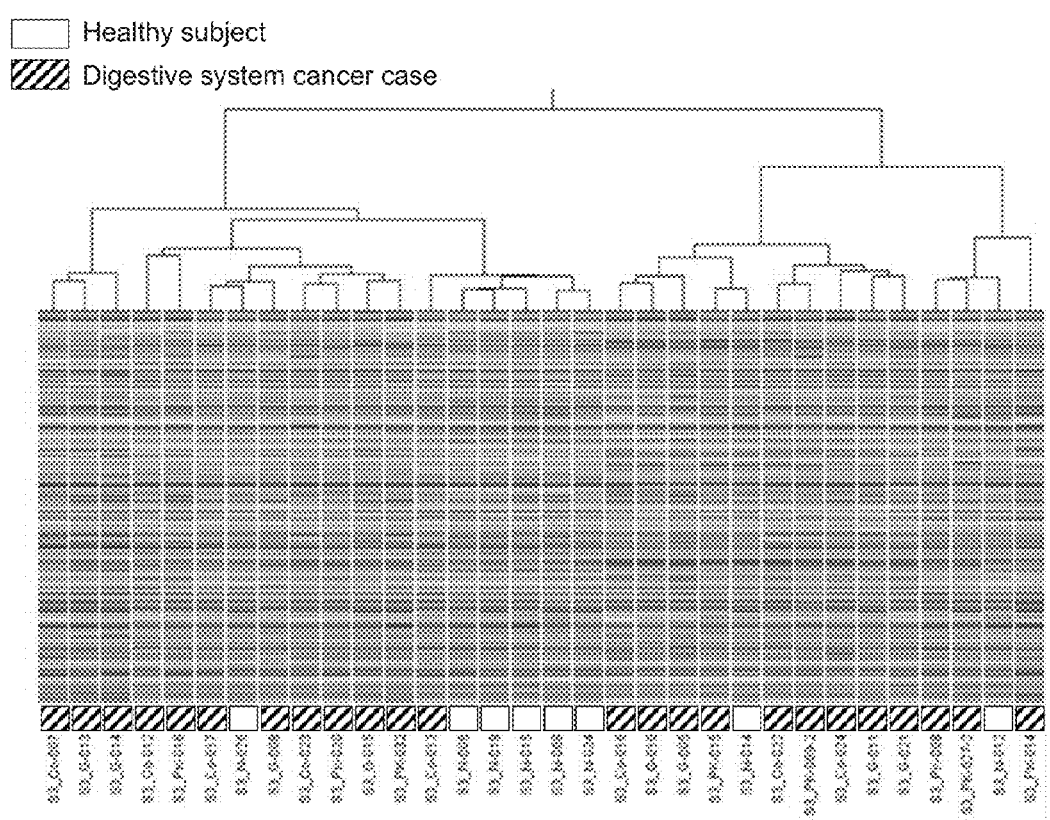

FIG. 24-9 shows 363 probes that can be used for detection of biliary tract cancer (continuation).

Figure 10:
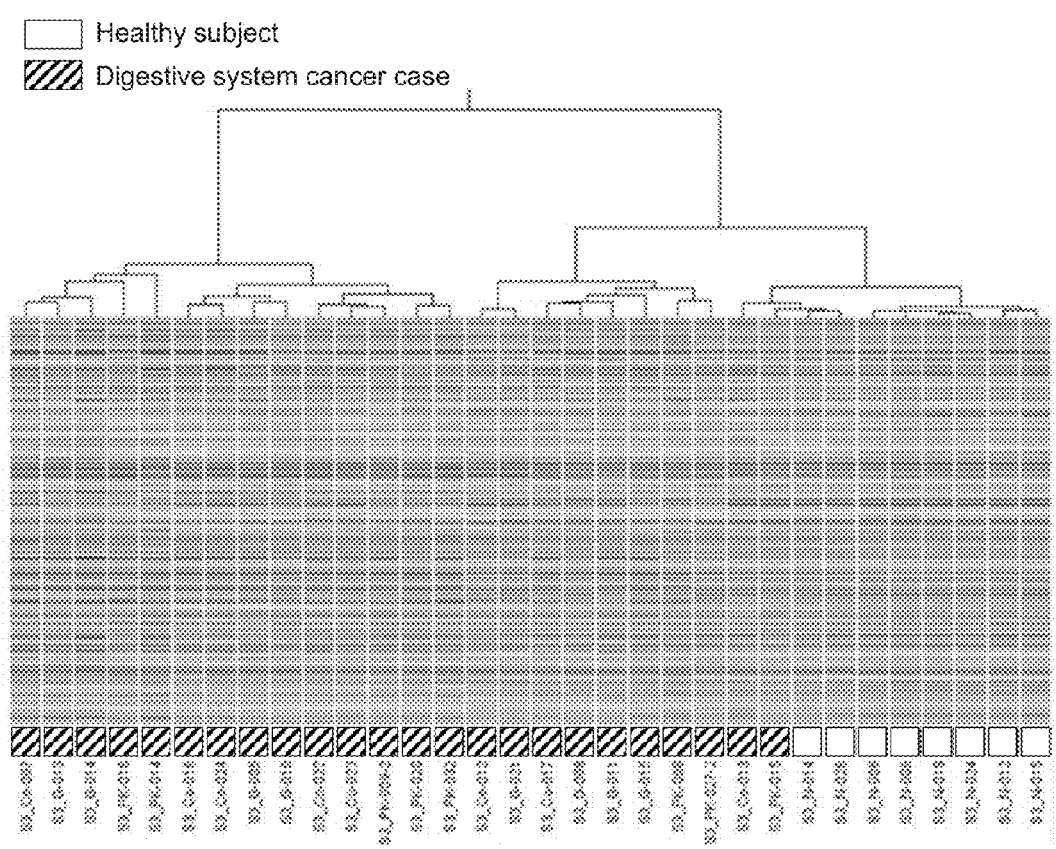

FIG. 24-10 shows 363 probes that can be used for detection of biliary tract cancer (continuation).

FIG. 24-11 shows 363 probes that can be used for detection of biliary tract cancer (continuation).

FIG. 24-12 shows 363 probes that can be used for detection of biliary tract cancer (continuation).

FIG. 24-13 shows 363 probes that can be used for detection of biliary tract cancer (continuation).

FIG. 24-14 shows 363 probes that can be used for detection of biliary tract cancer (continuation).

FIG. 24-15 shows 363 probes that can be used for detection of biliary tract cancer (continuation).

FIG. 24-16 shows 363 probes that can be used for detection of biliary tract cancer (continuation).

FIG. 24-17 shows 363 probes that can be used for detection of biliary tract cancer (continuation).

FIG. 24-18 shows 363 probes that can be used for detection of biliary tract cancer (continuation).

FIG. 24-19 shows 363 probes that can be used for detection of biliary tract cancer (continuation).

Figure 25:
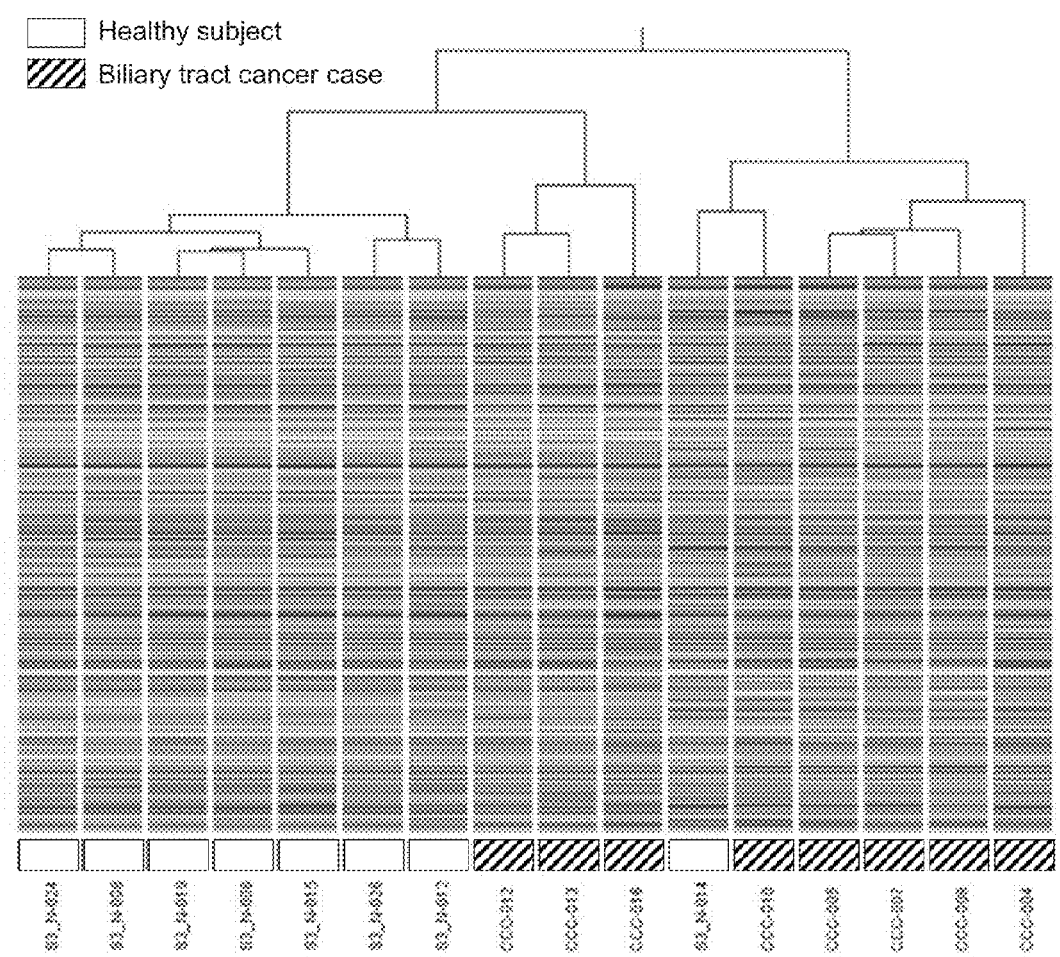

FIG. 25 shows the results of hierarchical clustering using 22066 probes for biliary tract cancer cases and normal healthy subjects.

Figure 26:
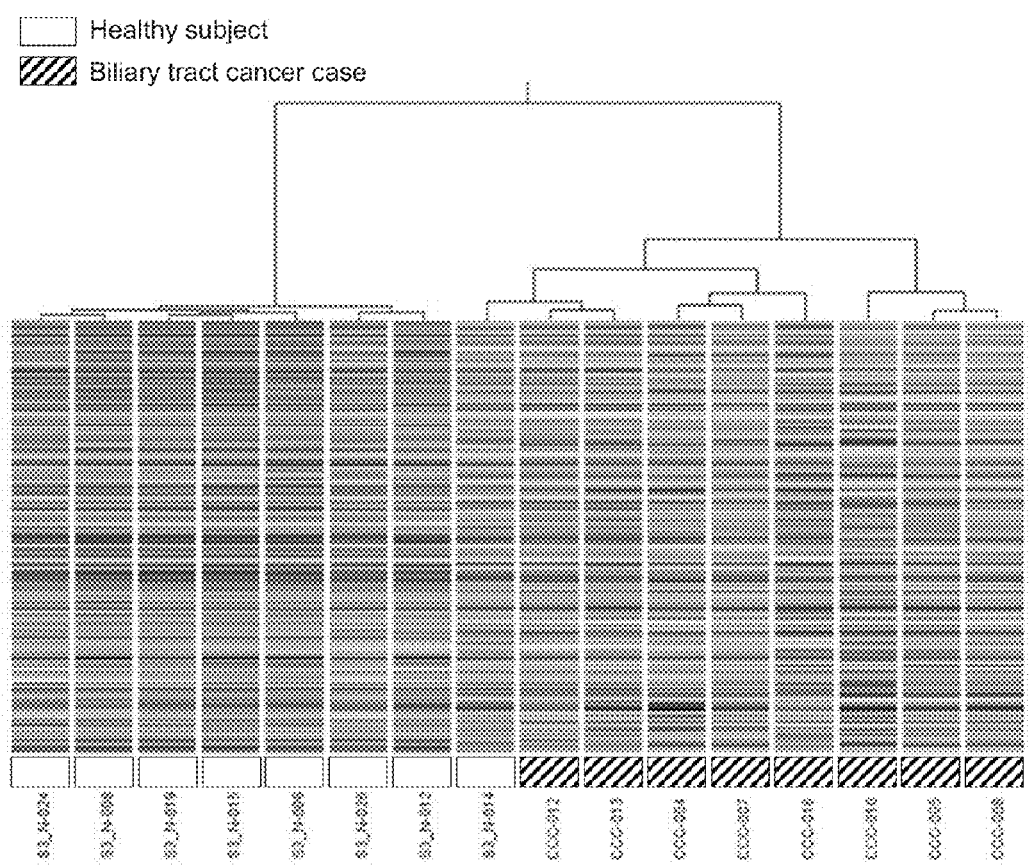

FIG. 26 shows the results of hierarchical clustering using 363 probes corresponding to genes with expression levels that were observed to be attenuated in biliary tract cancer cases at levels 0.33 times or less or enhanced in the same at levels 3 times or more than normal healthy subjects.

DETAILED DESCRIPTION OF THE INVENTION

In the present invention, examples of digestive organ cancer include gastric cancer, colorectal cancer, pancreatic cancer, and biliary tract cancer. All of these types of digestive organ cancer can be detected by the method for detecting digestive organ cancer of the present invention. Moreover, gastric cancer, colorectal cancer, pancreatic cancer, or biliary tract cancer can be specifically detected by the method for detecting gastric cancer, colorectal cancer, pancreatic cancer, or biliary tract cancer of the present invention.

The method of the present invention comprises measuring the expression in peripheral blood of:

a gene group with an expression level that varies in digestive organ cancer patients compared with normal healthy subjects;

a gene group with an expression level that varies in gastric cancer patients compared with normal healthy subjects;

a gene group with an expression level that varies in colorectal cancer patients compared with normal healthy subjects;

a gene group with an expression level that varies in pancreatic cancer patients compared with normal healthy subjects; or a gene group with an expression level that varies in biliary tract cancer patients compared with normal healthy subjects, so as to obtain the expression profile of each gene group, and then detecting digestive organ cancer, gastric cancer, colorectal cancer, pancreatic cancer, or biliary tract cancer. Here, examples of such variation in expression include attenuated expression and enhanced expression.

Gene expression in peripheral blood is measured by extracting and isolating mRNA from peripheral blood and then measuring mRNA. mRNA can be extracted and isolated from peripheral blood by a known method. Examples of mRNA that can be extracted and isolated from peripheral blood include mRNAs derived from, in addition to erythrocytes and blood platelets, leukocytes including lymphocytes, monocytes, and granulocytes in peripheral blood, for example.

In the method of the present invention, the expression levels of the above genes are measured.

In the present invention, the term "gene expression level" refers to a gene expression amount, expression intensity, or expression frequency. Such a gene expression level can be generally analyzed based on the production amount of a transcript corresponding to a gene, or the production amount of the translation product therefrom, activity, and the like. Also, the term "expression profiles" refers to information concerning the expression level of each gene. A gene expression level may be expressed with an absolute value or a relative value. In addition, expression profiles may also be referred to as expression patterns.

Expression levels may be measured by measuring gene transcripts (that is, mRNA) or measuring gene translation products (that is, proteins). Preferably, gene expression levels are measured by measuring gene transcripts. An example of a gene transcript is cDNA obtained from mRNA via reverse transcription.

A gene transcript can be measured by measuring the degree of gene expression using nucleotides containing full-length nucleotide sequences or partial nucleotide sequences of the above genes, or sequences complementary thereto, specifically, nucleotides consisting of the nucleotide sequences consisting of the nucleotide sequences of the genes or partial sequences of the genes, or sequences complementary thereto, as probes or primers. These nucleotides are nucleotides capable of hybridizing to the genes, nucleotides capable of binding to the genes, or nucleotides for detection, which can be used for detection of the genes. The degree of gene expression can be measured by a method using a microarray (microchip), a Northern blot method, or a quantitative PCR method using a gene to be quantitatively determined or a fragment thereof as a target, for example. Examples of a quantitative PCR method include an agarose gel electrophoresis method, a fluorescent probe method, an RT-PCR method, a real-time PCR method, an ATAC-PCR method (Kato, K. et al., Nucl. Acids Res., 25, 4694-4696, 1997), a Taqman PCR method (SYBR (trademark) Green method) (Schmittgen T D, Methods 25, 383-385, 2001), Body Map method (Gene, 174, 151-158 (1996)), a serial analysis of gene expression (SAGE) method (U.S. Pat. Nos. 527,154 and 544,861, EP Publication No. 0761822), and a MAGE method (Micro-analysis of Gene Expression) (JP Patent Publication (Kokai) No. 2000-232888 A). All methods listed herein can be performed by known techniques. The amount of messenger RNA (mRNA) transcribed from the full-length sequence or a partial sequence of the above gene may be measured using these methods. Specifically, the amount of mRNA can be measured using nucleotide probes or primers hybridizing to the mRNA. The base length of a probe or a primer to be used for measurement ranges from 10 bp to 100 bp, preferably ranges from 20 bp to 80 bp, and further preferably ranges from 50 bp to 70 bp.

A DNA microarray (DNA chip) can be prepared by immobilizing nucleotides consisting of the nucleotide sequences of the above genes or partial sequences thereof, or nucleotides containing complementary sequences thereof on an appropriate substrate.

Examples of a substrate for immobilization include glass plates, quartz plates, silicon wafers. Examples of the size of such a substrate include 3.5 mm×5.5 mm, 18 mm×18 mm, and 22 mm×75 mm. The size thereof can be set variously depending on the number of spots for probes or the size of the spots on a substrate. Polynucleotides or fragments thereof can be immobilized by the following methods. Polynucleotides or fragments thereof can be electrostatically bound to a solid-phase support surface-treated with a polycation such as polylysine, polyethylene imine, or polyalkylamine with the use of the electric charge of nucleotides. Alternatively, nucleotides, into which a functional group such as an amino group, an aldehyde group, an SH group, or biotin has been introduced, are covalently bound to the surface of a solid phase to which a functional group such as an amino group, an aldehyde group, or an epoxy group has been introduced. Immobilization may be performed using an array system. A DNA microarray is prepared by immobilizing at least one of genes corresponding to the above 868 probes or a fragment thereof to a substrate, the DNA microarray is brought into contact with subject-derived mRNA or cDNA labeled with a fluorescent substance for hybridization, and then fluorescence intensity on the DNA microarray is measured, so that the type and the amount of the mRNA can be determined. As a result, a gene(s) with expression levels that vary in a subject, can be detected, so that the gene expression profile can be obtained. A fluorescent substance for labeling subject-derived mRNA is not limited and any commercially available fluorescent substance can be used. For example, Cy3 and Cy5 may be used. mRNA can be labeled by a known method.

In the present invention, the term "probe" refers to the sequence of a nucleotide arranged on a DNA microarray. One nucleotide sequence is designated for one probe ID No. There is a single gene that corresponds to a plurality of probes comprising different nucleotide sequences. The expression "a probe(s) correspond(ing) to a gene(s)" means that the sequence of the probe is complementary to a partial nucleotide sequence of the gene or a sequence complementary thereto, so that the gene can hybridize to the probe. The nucleotide sequence of a gene corresponding to a probe contains the nucleotide sequence of the probe or a nucleotide sequence complementary thereto as a partial sequence.

Examples of nucleotides to be used as probes or primers in the present invention include nucleotides containing the sequences of the above genes, nucleotides consisting of the sequences of fragments thereof, and nucleotides consisting of sequences complementary to these sequences. Further examples of nucleotides to be used in the present invention include nucleotides hybridizing under stringent conditions to nucleotides having the above nucleotide sequences and nucleotides consisting of the sequences of the fragments thereof. Specific examples of such a nucleotide include a nucleotide and the like containing the nucleotide sequence having the degree of homology with the above nucleotide sequences, about 80% or more, preferably about 90% or more, and more preferably about 95% or more on an overall average. Hybridization can be performed according to a method known in the art or a method according thereto, such as the methods described in Current Protocols in Molecular Biology (Current protocols in molecular biology (edited by Frederick M. Ausubel et al., 1987)). Also, when a commercially available library is used, hybridization can be performed according to the methods described in the attached instructions. Here, the term "stringent conditions" refers to conditions of about "1×SSC, 0.1% SDS, 37° C.," more stringent conditions refer to conditions of about "0.5×SSC, 0.1% SDS, and 42° C.," and even more stringent conditions refer to conditions of about "0.2×SSC, 0.1% SDS, 65° C." As such, higher stringency of hybridization conditions enables isolation of a nucleotide having high homology with the probe sequence. Here, the above combinations of SSC, SDS, and temperature are merely examples. Persons skilled in the art can realize stringency similar to the above by appropriately combining the above or other factors (e.g., probe concentration, probe length, and reaction time for hybridization) for determination of stringency for hybridization. Moreover, these genes may have variants. Hence, examples of genes to be used in the present invention include variants of the above genes. The nucleotide sequences of variants can be obtained by accessing a gene database. Examples of the nucleotides of the present invention include nucleotides containing the nucleotide sequences of the variants or nucleotides consisting of the sequences of the fragments thereof.

Also, as a nucleotide to be used in the present invention, either a nucleotide consisting of a sense strand of the above gene or a nucleotide consisting of the antisense strand of the same can be used.

FIG. 1 (FIG. 1-1 to FIG. 1-48) shows 868 probes of the 1$^{st}$ probe group that can be used for detection of digestive organ cancer. FIG. 1 shows probe ID numbers, symbols of genes corresponding to the probes, the nucleotide sequences (SEQ ID NOs: 1-868) of the probes, and descriptions of genes corresponding to the probes (gene names and GenBank accession numbers). The full-length sequences of these genes are known. Arbitrary partial sequences can be used as nucleotides for detection of the genes. FIG. 2 shows the nucleotide sequences (SEQ ID NOs: 220, 506, 508, 523, 538, 554, 570, 589, 597, 602, 618, 654, 689, 701, 726, 744, 762, 763, 781, 795, and 849) of 21 probes with expression levels that differ significantly particularly between digestive organ cancer patients and normal healthy subjects, from among the 868 probes shown in FIG. 1. In FIG. 1, genes corresponding to 555 probes (No. 1 to No. 555) (SEQ ID NOs: 1-555) exhibit attenuated expression in digestive organ cancer patients compared with normal healthy subjects. Genes corresponding to 313 probes (No. 556 to No. 868) (SEQ ID NOs: 556-868) exhibit enhanced expression in digestive organ cancer patients compared with normal healthy subjects. Also, in FIG. 2, genes corresponding to probes No. 1 to No. 6 (SEQ ID NOs: 220, 506, 508, 523, 538, and 554) exhibit attenuated expression in digestive organ cancer patients compared with normal healthy subjects. Genes corresponding to probes No. 7 to No. 21 (SEQ ID NOs: 570, 589, 597, 602, 618, 654, 689, 701, 726, 744, 762, 763, 781, 795, and 849) exhibit enhanced expression in digestive organ cancer patients compared with normal healthy subjects.

Furthermore, FIG. 21 (FIG. 21-1 and FIG. 21-2) shows 25 probes of the 2$^{nd}$ probe group that can be used for detection of digestive organ cancer. FIG. 21 shows probe ID numbers, symbols of genes corresponding to the probes, the nucleotide sequences (SEQ ID NOs: 3030-3054) of the probes, and descriptions of genes corresponding to the probes (gene names and GenBank accession numbers). The full-length sequences of these genes are known. Arbitrary partial sequences can be used as nucleotides for detection of the genes.

FIG. 3 (FIG. 3-1 to FIG. 3-39) shows 713 probes that can be used for detection of gastric cancer. FIG. 3 shows probe ID numbers, symbols of genes corresponding to the probes, the nucleotide sequences (SEQ ID NOs: 869-1581) of the probes, and descriptions of genes corresponding to the probes (gene names and GenBank accession numbers). The full-length sequences of these genes are known. Arbitrary partial sequences can be used as nucleotides for detection of the genes. FIG. 4 (FIG. 4-1 to FIG. 4-6) shows the nucleotide sequences (SEQ ID NO: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578) of 107 probes with expression levels that differ significantly particularly between gastric cancer patients and normal healthy subjects, from among the 713 probes shown in FIG. 3. In FIG. 3, genes corresponding to 84 probes (No. 1 to No. 84) (SEQ ID NOs: 869-952) exhibit attenuated expression in gastric cancer patients compared with normal healthy subjects. Genes corresponding to 629 probes (No. 85 to No. 713) (SEQ ID NOs: 953-1581) exhibit enhanced expression in gastric cancer patients compared with normal healthy subjects. Also, in FIG. 4, genes corresponding to probes No. 1 to No. 6 (SEQ ID NOs: 923, 927, 929, 932, 946, and 952) exhibit attenuated expression in gastric cancer patients compared with normal healthy subjects. Genes corresponding to probes No. 7 to No. 107 (SEQ ID NOs: 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578) exhibit enhanced expression in gastric cancer patients compared with normal healthy subjects.

FIG. 5 (FIG. 5-1 to FIG. 5-41) shows 771 probes that can be used for detection of colorectal cancer. FIG. 5 shows probe ID numbers, symbols of genes corresponding to the probes, the nucleotide sequences (SEQ ID NOs: 1582-2352) of the probes, and descriptions of genes corresponding to the probes (gene names and GenBank accession numbers). The full-length sequences of these genes are known. Arbitrary partial sequences can be used as nucleotides for detection of the genes. FIG. 6 (FIG. 6-1 to FIG. 6-6) shows 116 probes (SEQ ID NO: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340) with expression levels that differ significantly particularly between colorectal cancer patients and normal healthy subjects, from among 771 probes shown in FIG. 5. In FIG. 5, genes corresponding to 125 probes (No. 1 to No. 125) (SEQ ID NOs: 1582-1706) exhibit attenuated expression in colorectal cancer patients compared with normal healthy subjects. Genes corresponding to 646 probes (No. 126 to No. 771) (SEQ ID NOs: 1707-2352) exhibit enhanced expression in colorectal cancer patients compared with normal healthy subjects. Also, in FIG. 6, genes corresponding to probes No. 1 to No. 9 (SEQ ID NOs: 1583, 1601, 1611, 1614, 1644, 1651, 1678, 1680, and 1684) exhibit attenuated expression in colorectal cancer patients compared with normal healthy subjects. Genes corresponding to probes No. 10 to No. 116 (SEQ ID NOs: 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340) exhibit enhanced expression in colorectal cancer patients compared with normal healthy subjects. FIG. 7 (FIG. 7-1 to FIG. 7-37) shows 677 probes that can be used for detection of pancreatic cancer.

FIG. 7 shows probe ID numbers, symbols of genes corresponding to the probes, the nucleotide sequences (SEQ ID NOs: 2353-3029) of the probes, and descriptions of genes corresponding to the probes (gene names and GenBank accession numbers). The full-length sequences of these genes are known. Arbitrary partial sequences can be used as nucleotides for detection of the genes. FIG. 8 (FIG. 8-1 to FIG. 8-3) shows 61 probes (SEQ ID NOs: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003) with expression levels that differ significantly particularly between pancreatic cancer patients and normal healthy subjects, from among 677 probes. In FIG. 7, genes corresponding to 96 probes (No. 1 to No. 96) (SEQ ID NOs: 2353-2448) exhibit attenuated expression in pancreatic cancer patients compared with normal healthy subjects. Genes corresponding to 581 probes (No. 97 to No. 677) (SEQ ID NO: 2449 to 3029) exhibit enhanced expression in pancreatic cancer patients compared with normal healthy subjects. Also, in FIG. 8, genes corresponding to probes No. 1 to No. 6 (SEQ ID NOs: 2373, 2404, 2418, 2419, 2426, and 2430) exhibit attenuated expression in pancreatic cancer patients compared with normal healthy subjects. Genes corresponding to probes No. 7 to No. 61 (SEQ ID NOs: 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003) exhibit enhanced expression in pancreatic cancer patients compared with normal healthy subjects.

FIG. 24 (FIG. 24-1 to FIG. 24-19) shows 363 probes that can be used for detection of biliary tract cancer. FIG. 24 shows probe ID numbers, symbols of genes corresponding to the probes, the nucleotide sequences (SEQ ID NOs: 3055-3417) of the probes, and descriptions of genes corresponding to the probes (gene names and GenBank accession numbers). The full-length sequences of these genes are known. Arbitrary partial sequences can be used as nucleotides for detection of the genes. In FIG. 24, genes corresponding to 98 probes (No. 1 to No. 98) (SEQ ID NOs: 3055-3152) exhibit attenuated expression in biliary tract cancer patients compared with normal healthy subjects. Genes corresponding to 265 probes (No. 99 to No. 363) (SEQ ID NOs: 3153-3417) exhibit enhanced expression in biliary tract cancer patients compared with normal healthy subjects.

The method for detecting digestive organ cancer of the present invention comprises measuring the expression levels of genes (described in the rightmost column in FIG. 1) in peripheral blood of a subject using at least one of 868 probes shown in FIG. 1, wherein the genes correspond to the 868 probes. At this time, with the use of at least 1 to 867 probes from among the 868 probes shown in FIG. 1, specifically at least 1, 2, 3, 4, 5, 6, 7, 8, 9, 10, 50, 100, 150, 200, 250, 300, 350, 400, 450, 500, 550, 600, 650, 700, 750, 800, 850, 867, or 868 probes, the expression levels of the genes corresponding thereto are measured. Also, with the use of at least one of probes corresponding to genes that exhibit attenuated expression in a group of digestive organ cancer patients, the expression level of the gene corresponding thereto may be measured. Also, with the use of at least one of probes corresponding to genes that exhibit enhanced expression in a group of digestive organ cancer patients, the expression level of the gene corresponding to the probe may be measured. Furthermore, with the use of a combination of at least one of probes corresponding to genes that exhibit attenuated expression in a group of digestive organ cancer patients and at least one of probes corresponding to genes that exhibit enhanced expression in the group of digestive organ cancer patients, the expression levels of the genes corresponding to the probes may be measured. Specifically, with the use of at least one of 555 probes (No. 1 to No. 555) (SEQ ID NOs: 1-555) shown in FIG. 1, the expression level of at least one of the genes corresponding to the probes may be measured. At this time, with the use of at least 1 to 554 probes from among the 555 probes, specifically at least 1, 2, 3, 4, 5, 6, 7, 8, 9, 10, 50, 100, 150, 200, 250, 300, 350, 400, 450, 500, 550, 554, or 555 probes, the expression levels of the genes corresponding thereto may be measured. Also, with the use of at least one of 313 probes (No. 556 to No. 868) (SEQ ID NOs: 556-868) shown in FIG. 1, the expression level of the gene corresponding thereto may be measured. At this time, with the use of at least 1 to 312 probes from among the 313 probes, specifically at least 1, 2, 3, 4, 5, 6, 7, 8, 9, 10, 50, 100, 150, 200, 250, 300, 312, or 313 probes, the expression levels of the genes corresponding thereto may be measured. Furthermore, with the use of a combination of at least one of the 555 probes (No. 1 to No. 555) (SEQ ID NOs: 1-555) shown in FIG. 1 and at least one of the 313 probes (No. 556 to No. 868) (SEQ ID NOs: 556-868) shown in FIG. 1, the expression levels of the genes corresponding thereto may be measured.

Furthermore, with the use of at least one of 21 probes shown in FIG. 2 corresponding particularly to genes with expression levels that vary significantly from among genes corresponding to the above 868 probes, the expression levels of the genes (described in the rightmost column in FIG. 2) corresponding to the probes may be measured. At this time, with the use of the 21 probes, specifically 1, 2, 3, 4, 5, 6, 7, 8, 9, 10, 11, 12, 13, 14, 15, 16, 17, 18, 19, 20, or 21 probes, the expression levels of the genes corresponding to the probes may be measured. Also, with the use of at least one of probes No. 1 to No. 6 (from among the 21 probes shown in FIG. 2) corresponding to genes that exhibit attenuated expression in digestive organ cancer patients compared with normal healthy subjects, the expression levels of the genes may be measured. With the use of, from among the 21 probes shown in FIG. 2, at least one of probes No. 7 to No. 21 corresponding to genes that exhibit enhanced expression in digestive organ cancer patients compared with normal healthy subjects, the expression levels of the genes may be measured. Furthermore, with the use of a combination of at least one of the probes No. 1 to No. 6 and at least one of the probes No. 7 to No. 21, the expression levels of the genes may be measured. At this time, 1, 2, 3, 4, 5, or 6 probes of the probes No. 1 to No. 6 may be used and 1, 2, 3, 4, 5, 6, 7, 8, 9, 10, 11, 12, 13, 14, or 15 probes of the probes No. 7 to No. 21 may be used.

The method for detecting digestive organ cancer of the present invention comprises measuring the expression levels of genes (described in the rightmost column in FIG. 1A) in peripheral blood of a subject using at least one of 25 probes shown in FIG. 21, wherein the genes correspond to the 25 probes. At this time, with the use 1, 2, 3, 4, 5, 6, 7, 8, 9, 10, 11, 12, 13, 14, 15, 16, 17, 18, 19, 20, 21, 22, 23, 24, or probes shown in FIG. 1A, the expression levels of the genes corresponding thereto may be measured. Also, with the use of at least one of probes corresponding to genes that exhibit attenuated expression in a group of digestive organ cancer patients, the expression level of the gene corresponding thereto may be measured. Also, with the use of at least one of probes corresponding to genes that exhibit enhanced expression in a group of digestive organ cancer patients, the expression level of the gene corresponding thereto may be measured. Furthermore, with the use of a combination of at least one of probes corresponding to genes that exhibit attenuated expression in a group of digestive organ cancer patients and at least one of probes corresponding to genes that exhibit enhanced expression in the group of digestive organ cancer patients, the expression levels of the genes corresponding to the probes may be measured. Specifically, with the use of at least one of 14 probes (No. 1 to No. 14) (SEQ ID NOs: 3030-3043) shown in FIG. 21, the expression level of at least one of the genes corresponding to the probes may be measured. At this time, with the use of 14 probes, specifically, 1, 2, 3, 4, 5, 6, 7, 8, 9, 10, 11, 12, 13, or 14 probes, the expression levels of the genes corresponding thereto may be measured. Also, with the use of at least one of 11 probes (No. 15 to No. 25) (SEQ ID NOs: 3044-3054) shown in FIG. 21, the expression level of the gene corresponding to the probe may be measured. At this time, with the use of 11 probes, specifically, 1, 2, 3, 4, 5, 6, 7, 8, 9, 10, or 11 probes, the expression levels of the genes corresponding thereto may be measured. Furthermore, with the use of a combination of at least one of 14 probes (No. 1 to No. 14) (SEQ ID NOs: 3030-3043) shown in FIG. 21 and at least one of 11 probes (No. 15 to No. 25) (SEQ ID NOs: 3044-3054) shown in FIG. 21, the expression levels of the genes corresponding thereto may be measured.

The method for detecting gastric cancer of the present invention comprises measuring the expression levels of genes in peripheral blood of a subject (described in the rightmost column in FIG. 3) using at least one of 713 probes shown in FIG. 3, wherein the genes correspond to the 713 probes. At this time, with the use of at least 1 to 712 probes from among the 713 probes shown in FIG. 3, specifically at least 1, 2, 3, 4, 5, 6, 7, 8, 9, 10, 50, 100, 150, 200, 250, 300, 350, 400, 450, 500, 550, 600, 650, 700, 712, or 713 probes, the expression levels of the genes corresponding thereto may be measured. Also, with the use of at least one of probes corresponding to genes that exhibit attenuated expression in a group of gastric cancer patients, the expression level of the gene corresponding thereto may be measured. Also, with the use of at least one of probes corresponding to genes that exhibit enhanced expression in a group of gastric cancer patients, the expression level of the gene corresponding to the probe may be measured. Furthermore, with the use of a combination of at least one of probes corresponding to genes that exhibit attenuated expression in a group of gastric cancer patients and at least one of probes corresponding to genes that exhibit enhanced expression in the group of gastric cancer patients, the expression levels of the genes corresponding to the probes may be measured. Specifically, with the use of at least one of 84 probes (No. 1 to No. 84) (SEQ ID NOs: 869-952) shown in FIG. 1, the expression level of at least one of the genes corresponding to the probes may be measured. At this time, with the use of at least 1 to 83 probes from among the 84 probes, specifically at least 1, 2, 3, 4, 5, 6, 7, 8, 9, 10, 20, 30, 40, 50, 60, 70, 80, 83, or 84 probes, the expression levels of the genes corresponding thereto may be measured. Also, with the use of at least one of 629 probes (No. 85 to No. 713) (SEQ ID NOs: 953-1581) shown in FIG. 3, the expression levels of the genes corresponding to the probes may be measured. At this time, with the use of at least 1 to 628 probes from among the 629 probes, specifically at least 1, 2, 3, 4, 5, 6, 7, 8, 9, 10, 50, 100, 150, 200, 250, 300, 350, 400, 450, 500, 550, 600, 628, or 629 probes, the expression levels of the genes corresponding thereto may be measured. Furthermore, with the use of a combination of at least one of the 84 probes (No. 1 to No. 84) (SEQ ID NOs: 869-952) shown in FIG. 3 and at least one of the 629 probes (No. 85 to No. 713) (SEQ ID NOs: 953-1581) shown in FIG. 3, the expression levels of the genes corresponding to the probes may be measured.

Furthermore, with the use of at least one of 107 probes shown in FIG. 4 corresponding particularly to genes with expression levels that vary significantly from among the genes corresponding to the above 713 probes, the expression levels of the genes (described in the rightmost column in FIG. 4) corresponding to the probes may be measured. At this time, with the use of the 107 probes, specifically at least 1, 2, 3, 4, 5, 6, 7, 8, 9, 10, 20, 30, 40, 50, 60, 70, 80, 90, 100, 106, or 107 probes, the expression levels of the genes corresponding to the probes may be measured. Also, with the use of at least one of probes No. 1 to No. 6 (from among the 107 probes shown in FIG. 4) corresponding to genes that exhibit attenuated expression in gastric cancer patients compared with normal healthy subjects, the expression levels of the genes may be measured. With the use of, from among the 107 probes shown in FIG. 4, at least one of probes No. 7 to No. 107 corresponding to genes that exhibit enhanced expression in gastric cancer patients compared with normal healthy subjects, the expression levels of the genes may be measured. Furthermore, with the use of a combination of at least one of the probes No. 1 to No. 6 and at least one of the probes No. 7 to No. 107, the expression levels of the genes may be measured. At this time, 1, 2, 3, 4, 5, or 6 probes of the probes No. 1 to No. 6 may be used and at least 1, 2, 3, 4, 5, 6, 7, 8, 9, 10, 20, 30, 40, 50, 60, 70, 80, 90, or 100, or 101 probes of the probes No. 7 to No. 107 may be used.

The method for detecting colorectal cancer of the present invention comprises measuring the expression levels of genes in peripheral blood of a subject (described in the rightmost column in FIG. 5) using at least one of 771 probes shown in FIG. 5, wherein the genes correspond to the 771 probes. At this time, with the use of at least 1 to 770 probes from among the 771 probes shown in FIG. 5, specifically at least 1, 2, 3, 4, 5, 6, 7, 8, 9, 10, 50, 100, 150, 200, 250, 300, 350, 400, 450, 500, 550, 600, 650, 700, 750, 770, or 771 probes, the expression levels of the genes corresponding thereto may be measured. Also, with the use of at least one of probes corresponding to genes that exhibit attenuated expression in a group of colorectal cancer patients, the expression level of the gene corresponding thereto may be measured. Also, with the use of at least one of probes corresponding to genes that exhibit enhanced expression in a group of colorectal cancer patients, the expression level of the gene corresponding to the probe may be measured. Furthermore, with the use of a combination of at least one of probes corresponding to genes that exhibit attenuated expression in a group of colorectal cancer patients and at least one of probes corresponding to genes that exhibit enhanced expression in the group of colorectal cancer patients, the expression levels of the genes corresponding to the probes may be measured. Specifically, with the use of at least one of 125 probes (No. 1 to No. 125) (SEQ ID NOs: 1582-1706) shown in FIG. 5, the expression level of at least one of the genes corresponding to the probes may be measured. At this time, with the use of at least 1 to 124 probes from among the 125 probes, specifically at least 1, 2, 3, 4, 5, 6, 7, 8, 9, 10, 20, 30, 40, 50, 60, 70, 80, 90, 100, 110, 120, 124, or 125 probes, the expression levels of the genes corresponding thereto may be measured. Also, with the use of at least one of 646 probes (No. 126 to No. 771) (SEQ ID NOs: 1707-2352) shown in FIG. 5, the expression levels of the genes corresponding thereto may be measured. At this time, with the use of at least 1 to 645 probes from among the 646 probes, specifically at least 1, 2, 3, 4, 5, 6, 7, 8, 9, 10, 50, 100, 150, 200, 250, 300, 350, 400, 450, 500, 550, 600, 645, or 646 probes, the expression levels of the genes corresponding thereto may be measured. Furthermore, with the use of a combination of at least one of the 125 probes (No. 1 to No. 125) (SEQ ID NOs: 1582-1706) shown in FIG. 5 and at least one of the 646 probes (No. 126 to No. 771) (SEQ ID NOs: 1707-2352) shown in FIG. 5, the expression levels of the genes corresponding thereto may be measured.

Furthermore, with the use of at least one of 116 probes shown in FIG. 6 corresponding particularly to genes with expression levels that vary significantly from among the genes corresponding to the above 771 probes, the expression levels of the genes (described in the rightmost column in FIG. 6) corresponding to the probes may be measured. At this time, with the use of the 116 probes, specifically 1, 2, 3, 4, 5, 6, 7, 8, 9, 10, 20, 30, 40, 50, 60, 70, 80, 90, 100, 110, or 115, or 116 probes, the expression levels of the genes corresponding to the probes may be measured. Also, with the use of at least one of probes No. 1 to No. 9 (from among the 116 probes shown in FIG. 6) corresponding to genes that exhibit attenuated expression in colorectal cancer patients compared with normal healthy subjects, the expression levels of the genes may be measured. With the use of, from among the 116 probes shown in FIG. 6, at least one of probes No. 10 to No. 116 corresponding to genes that exhibit enhanced expression in colorectal cancer patients compared with normal healthy subjects, the expression levels of the genes may be measured. Furthermore, with the use of a combination of at least one of the probes No. 1 to No. 9 and at least one of the probes No. 10 to No. 116, the expression levels of the genes may be measured. At this time, 1, 2, 3, 4, 5, 6, 7, 8, or 9 probes of the probes No. 1 to No. 9 may be used and at least 1, 2, 3, 4, 5, 6, 7, 8, 9, 10, 20, 30, 40, 50, 60, 70, 80, 90, 100, or 109, or 110 probes of the probes No. 10 to No. 116 may be used.

The method for detecting pancreatic cancer of the present invention comprises measuring the expression levels of genes in peripheral blood of a subject (described in the rightmost column in FIG. 7) using at least one of 677 probes shown in FIG. 7, wherein the genes correspond to the 677 probes. At this time, with the use of at least 1 to 676 probes from among the 677 probes shown in FIG. 7, specifically at least 1, 2, 3, 4, 5, 6, 7, 8, 9, 10, 50, 100, 150, 200, 250, 300, 350, 400, 450, 500, 550, 600, 650, 676, or 677 probes, the expression levels of the genes corresponding thereto may be measured. Also, with the use of at least one of probes corresponding to genes that exhibit attenuated expression in a group of pancreatic cancer patients, the expression level of the gene corresponding thereto may be measured. Also, with the use of at least one of probes corresponding to genes that exhibit enhanced expression in a group of pancreatic cancer patients, the expression level of the gene corresponding to the probe may be measured. Furthermore, with the use of a combination of at least one of probes corresponding to genes that exhibit attenuated expression in a group of pancreatic cancer patients and at least one of probes corresponding to genes that exhibit enhanced expression in the group of pancreatic cancer patients, the expression levels of the genes corresponding to the probes may be measured. Specifically, with the use of at least one of 96 probes (No. 1 to No. 96) (SEQ ID NOs: 2353-2448) shown in FIG. 7, the expression level of at least one of the genes corresponding to the probes may be measured. At this time, with the use of at least 1 to 95 probes from among the 96 probes, specifically at least 1, 2, 3, 4, 5, 6, 7, 8, 9, 10, 20, 30, 40, 50, 60, 70, 80, 90, or 95, or 96 probes, the expression levels of the genes corresponding thereto may be measured. Also, with the use of at least one of 581 probes (No. 97 to No. 677) (SEQ ID NOs: 2449-3029) shown in FIG. 7, the expression levels of the genes corresponding thereto may be measured. At this time, with the use of at least 1 to 580 probes from among the 581 probes, specifically at least 1, 2, 3, 4, 5, 6, 7, 8, 9, 10, 50, 100, 150, 200, 250, 300, 350, 400, 450, 500, 550, or 580, or 581 probes, the expression levels of the genes corresponding thereto may be measured. Furthermore, with the use of a combination of at least one of the 96 probes (No. 1 to No. 96) (SEQ ID NOs: 2353-2448) shown in FIG. 7 and at least one of the 581 probes (No. 97 to No. 677) (SEQ ID NOs: 2449-3029) shown in FIG. 7, the expression levels of the genes corresponding thereto may be measured.

Furthermore, with the use of at least one of 61 probes shown in FIG. 8 corresponding particularly to genes with expression levels that vary significantly (from among the genes corresponding to the above 677 probes), the expression levels of the genes (described in the rightmost column in FIG. 8) corresponding to the probes may be measured. At this time, with the use of the 61 probes, specifically at least 1, 2, 3, 4, 5, 6, 7, 8, 9, 10, 20, 30, 40, 50, or 60, or 61 probes, the expression levels of the genes corresponding to the probes may be measured. Also, with the use of at least one of probes No. 1 to No. 6 (from among the 61 probes shown in FIG. 8) corresponding to genes that exhibit attenuated expression in pancreatic cancer patients compared with normal healthy subjects, the expression levels of the genes may be measured. With the use of, from among the 61 probes shown in FIG. 8, at least one of probes No. 7 to No. 61 corresponding to genes that exhibit enhanced expression in pancreatic cancer patients compared with normal healthy subjects, the expression levels of the genes may be measured. Furthermore, with the use of a combination of at least one of the probes No. 1 to No. 6 and at least one of the probes No. 7 to No. 61, the expression levels of the genes may be measured. At this time, 1, 2, 3, 4, 5, or 6 probes of the probes No. 1 to No. 6 may be used and 1, 2, 3, 4, 5, 6, 7, 8, 9, 10, 20, 30, 40, 50, or 54, or 55 probes of the probes No. 7 to No. 61 may be used.

The method for detecting biliary tract cancer of the present invention comprises measuring the expression levels of genes in peripheral blood of a subject (described in the rightmost column in FIG. 24) using at least one of 363 probes shown in FIG. 24 (FIG. 24-1 to FIG. 24-19), wherein the genes correspond to the 363 probes. At this time, with the use of at least 1 to 362 probes from among the 363 probes shown in FIG. 24, specifically at least 1, 2, 3, 4, 5, 6, 7, 8, 9, 10, 50, 100, 150, 200, 250, 300, 350, or 362, or 363 probes, the expression levels of the genes corresponding thereto may be measured. Also, with the use of at least one of probes corresponding to genes that exhibit attenuated expression in a group of biliary tract cancer patients, the expression level of the gene corresponding thereto may be measured. Also, with the use of at least one of probes corresponding to genes that exhibit enhanced expression in a group of biliary tract cancer patients, the expression level of the gene corresponding to the probe may be measured. Furthermore, with the use of a combination of at least one of probes corresponding to genes that exhibit attenuated expression in a group of biliary tract cancer patients and at least one of probes corresponding to genes that exhibit enhanced expression in the group of biliary tract cancer patients, the expression levels of the genes corresponding to the probes may be measured. Specifically, with the use of at least one of 98 probes (No. 1 to No. 98) (SEQ ID NOs: 3055-3152) shown in FIG. 24, the expression level of at least one of the genes corresponding to the probes may be measured. At this time, with the use of at least 1 to 97 probes from among the 98 probes, specifically at least 1, 2, 3, 4, 5, 6, 7, 8, 9, 10, 20, 30, 40, 50, 60, 70, 80, 90, or 97, or 98 probes, the expression levels of the genes corresponding thereto may be measured. Also, with the use of at least one of 265 probes (No. 99 to No. 363) (SEQ ID NOs: 3153-3417) shown in FIG. 24, the expression levels of the genes corresponding thereto may be measured. At this time, with the use of at least 1 to 264 probes from among the 265 probes, specifically at least 1, 2, 3, 4, 5, 6, 7, 8, 9, 10, 50, 100, 150, 200, 250, 264, or 265 probes, the expression levels of the genes corresponding thereto may be measured. Furthermore, with the use of a combination of at least one of the 98 probes (No. 1 to No. 98) (SEQ ID NOs: 3055-3152) shown in FIG. 24 and at least one of the 265 probes (No. 99 to No. 363) (SEQ ID NOs: 3153-3417) shown in FIG. 24, the expression levels of the genes corresponding thereto may be measured.

The method of the present invention enables identification of a patient with digestive organ cancer, gastric cancer, colorectal cancer, pancreatic cancer, or biliary tract cancer. Specifically, the presence of digestive organ cancer, gastric cancer, colorectal cancer, pancreatic cancer, or biliary tract cancer can be detected.

Subjects may exhibit unknown pathological conditions. When such a subject with unknown pathological conditions is used, whether the subject is normal or affected with digestive organ cancer, gastric cancer, colorectal cancer, pancreatic cancer, or biliary tract cancer can be determined and diagnosed.

In the present invention, the above determination of the pathological conditions of digestive organ cancer, gastric cancer, colorectal cancer, pancreatic cancer, or biliary tract cancer, prognostic prediction, and the like are broadly referred to as detection of digestive organ cancer, gastric cancer, colorectal cancer, pancreatic cancer, or biliary tract cancer.

Furthermore, the pathological conditions of a subject can be determined by obtaining the expression profiles of one or more genes corresponding to the above probes (specifically, 868 probes or 25 probes for digestive organ cancer, 713 probes for gastric cancer, 771 probes for colorectal cancer, 677 probes for pancreatic cancer, and 363 probes for biliary tract cancer) and then analyzing the expression profiles. If expression profiles obtained from a subject are analogous to expression profiles obtained from a digestive organ cancer, gastric cancer, colorectal cancer, pancreatic cancer, or biliary tract cancer patient, the subject can be determined as having digestive organ cancer, gastric cancer, colorectal cancer, pancreatic cancer, or biliary tract cancer. Also, expression profiles obtained from a subject are compared with expression profiles obtained from a normal subject and then evaluation and determination can be made based on a difference in expression profiles between the subject and the normal subject.

Gene expression profiling comprises recording the patterns of expression signals such as fluorescence intensities in the form of digital numerical values or color images. Gene expression profiles can be compared using pattern comparison software. Cox hazard analysis, discriminant analysis, and the like can be used herein. A discriminant analysis model is constructed in advance for evaluation and determination of pathological conditions, prediction of pathological conditions, or prognostic prediction, data concerning gene expression profiles obtained from a subject are input into the discriminant analysis model, and thus determination of pathological conditions, prediction of pathological conditions, or prognostic prediction can also be performed. For example, pathological conditions, prediction of pathological conditions, or prognostic prediction can be evaluated and determined by obtaining a discriminant via discriminant analysis, relating fluorescence intensities to pathological conditions, predicting pathological conditions, or conducting prognostic prediction, and then substituting the numerical value representing the expression signal of the subject into the discriminant.

The present invention encompasses an in vitro diagnostic or a kit for detecting digestive organ cancer, gastric cancer, colorectal cancer, pancreatic cancer, or biliary tract cancer, which contains: nucleotides consisting of the nucleotide sequences of genes with expression levels that vary in digestive organ cancer patients compared with normal healthy subjects, genes with expression levels that vary in gastric cancer patients compared with normal healthy subjects, genes with expression levels that vary in colorectal cancer patients compared with normal healthy subjects, genes with expression levels that vary in pancreatic cancer patients compared with normal healthy subjects, or genes with expression levels that vary in biliary tract cancer patients compared with normal healthy subjects for measurement of the expression levels of these genes, or nucleotides containing partial sequences thereof.

The reagent contains nucleotides consisting of the nucleotide sequences of the above genes or nucleotides containing partial sequences thereof as probes or primers. The reagent is also a substrate such as a microarray on which nucleotides consisting of the nucleotide sequences of the above genes or nucleotides containing partial sequences thereof have been immobilized.

For example, a reagent or a kit for detecting digestive organ cancer contains at least one of the above 868 or 25 probes that can be used for detection of digestive organ cancer and is capable of measuring the expression level of at least one of genes corresponding to the probes. Also, a reagent or a kit for detecting gastric cancer contains at least one of the above 713 probes that can be used for detection of gastric cancer and is capable of measuring the expression level of at least one of genes corresponding to the probes. Also, a reagent or a kit for detecting colorectal cancer contains at least one of the above 771 probes that can be used for detection of colorectal cancer and is capable of measuring the expression level of at least one of genes corresponding to the probes. Moreover, a reagent or a kit for detecting pancreatic cancer contains at least one of 677 probes that can be used for detection of pancreatic cancer, and is capable of measuring the expression level of at least one of genes corresponding to the probes. Furthermore, a reagent or a kit for detecting biliary tract cancer contains at least one of 363 probes that can be used for detection of biliary tract cancer and is capable of measuring the expression level of at least one of genes corresponding to the probes.

The present invention encompasses a system for detecting digestive organ cancer, gastric cancer, colorectal cancer, pancreatic cancer, or biliary tract cancer of a subject by the method for detecting digestive organ cancer, gastric cancer, colorectal cancer, pancreatic cancer, or biliary tract cancer of the present invention.

The system for detecting digestive organ cancer, gastric cancer, colorectal cancer, pancreatic cancer, or biliary tract cancer of the present invention comprises:

(a) a data input means for inputting data concerning the gene expression profiles of a subject (here, the "data concerning gene expression profiles to be input" refers to data representing the expression level of each gene, such as a numerical value for signals in each gene;

(b) a memory means for storing the thus constructed discriminant model;

(c) a data processing means for applying data input using the input means (a) to the discriminant model stored in the memory means (b), and then determining the pathological conditions of digestive organ cancer, gastric cancer, colorectal cancer, pancreatic cancer, or biliary tract cancer; and (d) a data output means for outputting data concerning the determination of predicted pathological conditions of digestive organ cancer, gastric cancer, colorectal cancer, pancreatic cancer, or biliary tract cancer, prediction of the pathological conditions, and prognostic prediction.

The data input means (a) contains a key board or an external memory device storing data, for example. The memory means (b) contains a hard disk, for example. The data processing means receives a discriminant model from the memory means and processing the input data, sends the processing result to the data output means, and then displaying the processing result with the data output means. The data processing means contains a central processing unit (CPU) and the like for processing data. Also, the output means contains a monitor, a printer, and the like for displaying the results.

The system of the present invention can be constructed using a commercially available personal computer and the like.

Examples

The present invention will be specifically described using the following examples, but the present invention is not limited to these examples.

Materials and experimental methods employed in the examples are as follows.

Object

Blood samples collected from patients diagnosed by a doctor as having digestive organ cancer, gastric cancer, colorectal cancer, pancreatic cancer, or biliary tract cancer were designated as a digestive organ cancer case, a gastric cancer case, a colorectal cancer case, a pancreatic cancer case, and a biliary tract cancer case, respectively. Regarding a control group, blood samples provided with the consent of patients who had received health checkups for residents held by local governments and consented to provide their blood were used herein. Blood samples were examined through a search for the following test items, and patients who exhibited normal values were designated as normal healthy subjects.

Test items: systolic blood pressure, diastolic blood pressure, number of erythrocytes, number of leukocytes, hemoglobin value, hematocrit value, liver functions (GOT, GPT, γ-GTP), renal functions (creatinine value), lipid metabolism (LDL cholesterol value, HDL cholesterol value, total cholesterol value), protein in urine, urinary blood Collection of Peripheral Blood:

Peripheral blood was collected from patients using PAXgene™ RNA blood collecting tube (Becton, Dickinson and Company, Japan, Medical Device Marketing Authorization No. (Iryo-kiki Seizo Hanbai Ninsho No.): 218AFBZX00014000).

RNA Extraction and Hybridization

RNA was extracted via a PAXgene™ RNA blood collecting tube according to protocols using a PAXgene Blood RNA Kit (QIAGEN GmbH, Hilden, Germany). RNA was amplified based on the thus extracted RNA using a Quick-Amp Labeling Kit, 1 color (Agilent Technologies, Santa Clara, Calif.), and at the same time labeled with a Cy3 dye. The thus labeled RNA was mixed using a Gene Expression Hybridization Kit (Agilent Technologies, Santa Clara, Calif.), followed by hybridization to Whole Human Genome oligo DNA microarrays (Agilent Technologies, Santa Clara, Calif.). In addition, the process from RNA amplification to hybridization was performed according to experimental protocols disclosed by Agilent Technologies.

Image Analysis and Data Analysis of DNA Microarrays:

The fluorescence intensity of each spot on the oligo DNA microarrays was acquired using a DNA microarray scanner (Agilent Technologies, Santa Clara, Calif.). The thus acquired images were processed with Feature Extraction software (Agilent Technologies, Santa Clara, Calif.), so that the fluorescence intensity of each spot was quantitated. The fluorescence intensity of a probe at each spot was calculated by quantitation.

The numerical values of the fluorescence intensities of all probes on the microarrays were normalized using GeneSpring GX (Agilent Technologies, Santa Clara, Calif.). A quality check was performed for the fluorescence intensity of each probe based on the thus normalized numerical value representing the enhanced or attenuated expression of each probe. Only probes that had passed the quality check were subjected as analytical objects to hierarchical clustering. Also, similarly, with the use of GeneSpring GX, genes with expression levels that were observed to differ between the digestive organ cancer patient group and the normal healthy subject group, were examined using Welch t-test as a statistic analysis tool. Candidate probes were extracted using the Benjamini and Hochberg False Discovery Rate as a multiple test and p<0.05 as significant value. Furthermore, similarly, with the use of GeneSpring GX, predictive determination was performed to determine if a subject belonged to a cancer case group or a normal healthy subject group (differing from the cancer case group or the normal healthy subject group used for extraction of candidate probes) using a class prediction tool and support vector machines for calculation.

The following results were obtained from the examples
1. Detection of Digestive Organ Cancer (1)
Hierarchical Clustering:

Hierarchical clustering was performed using a GeneSpring GX hierarchical clustering tool and 23352 probes that had passed a quality check. As shown in FIG. 9, 5 clusters were formed. In the $1^{st}$ cluster, 3 out of 3 cases (100%) were digestive organ cancer cases. In the $2^{nd}$ cluster, 8 out of 9 cases (88.9%) were digestive organ cancer cases. In the $3^{rd}$ cluster, 5 out of 6 cases (83.3%) and in the $4^{th}$ cluster, 9 out of 10 cases (90.0%) were digestive organ cancer cases. In the $5^{th}$ cluster, 3 out of 4 cases (75.0%) were digestive organ cancer cases. Hence, digestive organ cancer cases and normal healthy subjects were separately clustered.

Genes with expression levels that were observed to differ between a digestive organ cancer case group and a normal healthy subject group:

Similarly, with the use of a GeneSpring GX Statistic Analysis tool, probes capable of discriminating between a digestive organ cancer case group and a normal healthy subject group were examined using the Benjamini and Hochberg false discovery rate for a multiple test and p<0.0005. As a result, the expression of 868 probes was observed to differ between the two groups.

Also, normalized numerical values for fluorescence intensities of the 868 probes were compared using a Fold Change tool between the digestive organ cancer case group and the normal healthy subject group. The expression of 555 probes was observed to be attenuated regardless of multiplying factor, and the expression of 313 probes was observed to be enhanced regardless of multiplying factor, in the digestive organ cancer case group, compared with normal healthy subjects. Also, the expression of 6 probes was observed to be attenuated at levels 0.4 times or less that of the normal healthy subject group and the expression of 15 probes was observed to be enhanced at levels 2.5 times or more that of the normal healthy subject group.

Hierarchical clustering with 868 probes corresponding to genes with expression levels that were observed to be attenuated or enhanced in digestive organ cancer cases compared with normal healthy subjects:

Hierarchical clustering was performed for subject cancer cases and normal healthy subjects using a total of 868 probes including the above 555 probes and 313 probes. As shown in FIG. 10, 3 clusters were formed. In the $1^{st}$ cluster, 14 out of 14 cases (100%) were digestive organ cancer cases. In the $2^{nd}$ cluster, 8 out of 8 cases (100%) were digestive organ cancer cases. In the $3^{rd}$ cluster, 8 out of 10 cases (80%) were normal healthy subject cases. Thus, digestive organ cancer cases and normal healthy subjects were separately clustered.

Predictive determination using 868 probes corresponding to genes with expression levels that were observed to be attenuated or enhanced in digestive organ cancer cases compared with normal healthy subjects:

Similarly with the use of a GeneSpring GX Class Prediction tool, a prediction model was prepared based on 868 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 39 out of 40 separately analyzed cancer cases were determined with the prediction model to be cancer cases and the probability that such cases had been properly diagnosed was 97.5%. Also, 9 out of 13 normal healthy subject cases were determined with prediction model to be normal healthy subjects, and the probability that such cases had been properly diagnosed was 69.2%. Altogether, 48 out of 53 such cases were correct answers. Thus, the percentage of cases determined correctly was 90.6% (48/53).

Hierarchical clustering with 21 probes corresponding to genes with expression levels that were observed to be attenuated at levels 0.4 times or less the normal healthy subject group or enhanced at levels 2.5 times or more the normal healthy subject group:

Hierarchical clustering was performed using a total of 21 probes including the above 6 probes and 15 probes for subject cancer cases and normal healthy subjects. As shown in FIG. 11, 3 clusters were formed. In the $1^{st}$ cluster, 17 out of 17 cases (100%) were digestive organ cancer cases. In the $2^{nd}$ cluster, 7 out of 9 cases (77.8%) were digestive organ cancer cases. In the $3^{rd}$ cluster, 6 out of 6 cases (100%) were normal healthy subject cases. Thus, digestive organ cancer cases and normal healthy subjects were separately clustered.

Predictive determination using 21 probes corresponding to genes with expression levels that were observed to be attenuated at levels 0.4 times or less the normal healthy subject group or enhanced at levels 2.5 times or more the normal healthy subject group:

Similarly, with the use of a GeneSpring GX Class Prediction tool, a prediction model was prepared based on 21 probes observed to exhibit differences in expression, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 37 out of 40 separately analyzed cancer cases were determined with the prediction model to be cancer cases and the probability that such cases had been properly diagnosed was 92.5%. Also, 12 out of 13 normal healthy subjects were determined with the prediction model to be normal healthy subjects, and the probability that such cases had been properly diagnosed was 92.3%. Altogether, 49 out of 53 such cases were correct answers. Thus, the percentage of cases determined correctly was 92.5% (49/53).

1-2. Detection of Digestive Organ Cancer (2)

In a manner similar to that in the above detection of digestive organ cancer (1), 39 cancer cases and 15 normal healthy subject cases were examined using a GeneSpring GX hierarchical clustering tool and 23278 probes that had passed a quality check. As shown in FIG. 22, 5 clusters were formed. In the $1^{st}$ cluster, 5 out of 5 cases (100%) were digestive organ cancer cases. In the $2^{nd}$ cluster, 29 out of 30 cases (96.7%) were digestive organ cancer cases. In the $3^{rd}$ cluster, 1 out of 1 case (100%) and in the $4^{th}$ cluster, 6 out of 10 cases (60%) were digestive organ cancer cases. In the $5^{th}$ cluster, 8 out of 8 cases (100%) were normal healthy subject cases. Thus, the digestive organ cancer cases and the normal healthy subjects were separately clustered.

Furthermore, in a manner similar to that in the above detection of digestive organ cancer (1), probes capable of discriminating between a group of 39 digestive organ cancer cases and a group of 15 normal healthy subject cases were examined using a GeneSpring GX Statistic Analysis tool. Probes were extracted using Benjamini and Hochberg False Discovery Rate as a multiple test and p<0.000005. The normalized numerical values of fluorescence intensities of the thus extracted probes were compared between the group of digestive organ cancer cases and the group of normal healthy subjects using a Fold Change tool. Thus, the expression of 14 probes was observed to be attenuated at levels 0.33 times or less that of the normal healthy subject group and the expression of 11 probes was observed to be enhanced at levels 3 times or more that of the normal healthy subject group (FIG. 21, SEQ ID NOs: 3030-3054).

Hierarchical clustering with 25 probes corresponding to genes with expression levels that were observed to be attenuated or enhanced in digestive organ cancer cases compared with normal healthy subjects:

Hierarchical clustering was performed using a total of 25 probes including the above 14 probes and 11 probes for subject cancer cases and normal healthy subjects. As shown in FIG. 23, 3 clusters were formed. In the $1^{st}$ cluster, 31 out of 31 cases (100%) were digestive organ cancer cases. In the $2^{nd}$ cluster, 6 out of 6 cases (100%) were digestive organ cancer cases. In the $3^{rd}$ cluster, 15 out of cases (88.2%) were normal healthy subject cases. Thus, the digestive organ cancer cases and the normal healthy subjects were separately clustered.

Predictive determination using 25 probes corresponding to genes with expression levels that were observed to be attenuated or enhanced in digestive organ cancer cases compared with normal healthy subjects:

Similarly, with the use of a GeneSpring GX Class Prediction tool, a prediction model was prepared based on 25 probes observed to exhibit differences in expression, using Support Vector Machines. The prediction model was applied to cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 37 out of 37 separately analyzed cancer cases were determined with the prediction model to be cancer cases and the probability that such cases had been properly diagnosed was 100%. Also, 11 out of 15 normal healthy subjects were determined with the prediction model to be normal healthy subjects, and the probability that such cases had been properly diagnosed was 73.3%. Altogether, 48 out of 52 such cases were correct answers. Thus, the percentage of cases determined correctly was 92.3% (48/52).

2. Detection of Gastric Cancer

Hierarchical Clustering:

Hierarchical clustering was performed using a GeneSpring GX hierarchical clustering tool and 22155 probes that had passed a quality check. As shown in FIG. 12, 4 clusters were formed. In the $1^{st}$ cluster, 6 out of 6 cases (100%) were gastric cancer cases. In the $2^{nd}$ cluster, 3 out of 4 cases (75%) were normal healthy subject cases. In the $3^{rd}$ cluster, 3 out of 4 cases (75%) and in the $4^{th}$ cluster, 2 out of 2 cases (100%) were normal healthy subject cases. Hence, gastric cancer cases and normal healthy subjects were separately clustered.

Genes with expression levels that were observed to differ between a gastric cancer case group and a normal healthy subject group:

Similarly, with the use of a GeneSpring GX Statistic Analysis tool, probes capable of discriminating between a gastric cancer case group and a normal healthy subject group were examined using the Benjamini and Hochberg false discovery rate for a multiple test and p<0.05. As a result, the expression of 3453 probes was observed to differ between the two groups.

Also, normalized numerical values for fluorescence intensities of the 3453 probes were compared using a Fold Change tool between the gastric cancer case group and the normal healthy subject group. The expression of 84 probes was observed to be attenuated in the gastric cancer case group at levels 0.5 times or less that of the normal healthy subject group and the expression of 629 probes was observed to be enhanced in the gastric cancer case group at levels 2 times or more that of the normal healthy subject group. Also, the expression of 6 probes was observed to be attenuated in the gastric cancer case group at levels 0.33 times or less that of the normal healthy subject group and the expression of 101 probes was observed to be enhanced in the gastric cancer case group at levels 3 times or more that of the normal healthy subject group.

Hierarchical clustering with 713 probes corresponding to genes with expression levels that were observed to be attenuated at levels 0.5 times or less or enhanced at levels 2 times or more that of the normal healthy subject group:

Hierarchical clustering was performed for subject cancer cases and normal healthy subjects using a total of 713 probes including the above 84 probes and 629 probes. As shown in FIG. 13, 2 clusters were formed, in which a cluster of cancer cases accounting for 100% and a cluster of normal healthy subject cases accounting for 100%.

Predictive determination using 713 probes corresponding to genes with expression levels that were observed to be attenuated at levels 0.5 times or less or enhanced at levels 2 times or more that of the normal healthy subject group:

Similarly with the use of a GeneSpring GX Class Prediction tool, a prediction model was prepared based on 713 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 7 out of 10 separately analyzed cancer cases were determined with the prediction model to be cancer cases and the probability that such cases had been properly diagnosed was 70%. Also, 13 out of 13 normal healthy subject cases were determined with prediction model to be normal healthy subject cases, and the probability that such cases had been properly diagnosed was 100%. Altogether, 20 out of 23 such cases were correct answers. Thus, the percentage of cases determined correctly was 87.0% (20/23).

Hierarchical clustering with 107 probes corresponding to genes with expression levels that were observed to be attenuated at levels 0.33 times or less or enhanced at levels 3 times or more that of the normal healthy subject group:

Hierarchical clustering was performed for subject cancer cases and normal healthy subjects using a total of 107 probes including the above 6 probes and 101 probes. As shown in FIG. 14, 2 clusters were formed, in which a cluster of cancer cases accounting for 100% and a cluster of normal healthy subject cases accounting for 100%.

Predictive determination using 107 probes corresponding to genes with expression levels that were observed to be attenuated at levels 0.33 times or less or enhanced at levels 3 times or more that of the normal healthy subject group:

Similarly with the use of a GeneSpring GX Class Prediction tool, a prediction model was prepared based on 107 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 8 out of 10 separately analyzed cancer cases were determined with the prediction model to be cancer cases and the probability that such cases had been properly diagnosed was 80%. Also, 13 out of 13 normal healthy subject cases were determined with prediction model to be normal healthy subject cases, and the probability that such cases had been properly diagnosed was 100%. Altogether, 21 out of 23 such cases were correct answers. Thus, the percentage of cases determined correctly was 91.3% (21/23).

3. Detection of Colorectal Cancer

Hierarchical Clustering:

Hierarchical clustering was performed using a GeneSpring GX hierarchical clustering tool and 22181 probes that had passed a quality check. As shown in FIG. 15, 3 clusters were formed. In the $1^{st}$ cluster, 4 out of 5 cases (80%) were colorectal cancer cases. In the $2^{nd}$ cluster, 6 out of 7 cases (85.7%) were normal healthy subject cases. In the $3^{rd}$ cluster, 3 out of 4 cases (75%) were colorectal cancer cases. Hence, colorectal cancer cases and normal healthy subjects were separately clustered.

Also, normalized numerical values for fluorescence intensities of the 5267 probes were compared using a Fold Change tool between the colorectal cancer case group and the normal healthy subject group. The expression of 125 probes was observed to be attenuated in the large bowel case group at levels 0.5 times or less that of the normal healthy subject group and the expression of 646 probes was observed to be enhanced in the colorectal cancer case group at levels 2 times or more that of the normal healthy subject group. Also, the expression of 9 probes was observed to be attenuated in the colorectal cancer case group at levels 0.33 times or less that of the normal healthy subject group and the expression of 107 probes was observed to be enhanced in the colorectal cancer case group at levels 3 times or more that of the normal healthy subject group.

Hierarchical clustering with 771 probes corresponding to genes with expression levels that were observed to be attenuated at levels 0.5 times or less or enhanced at levels 2 times or more that of the normal healthy subject group:

Hierarchical clustering was performed for subject cancer cases and normal healthy subjects using a total of 771 probes including the above 125 probes and 646 probes. As shown in FIG. 16, 3 clusters were formed. In the $1^{st}$ cluster, 5 out of 5 cases (100%) were colorectal cancer cases. In the $2^{nd}$ cluster, 3 out of 5 cases (60.0%) were colorectal cancer cases. In the $3^{rd}$ cluster, 7 out of 7 cases (100%) were normal healthy subject cases.

Predictive determination using 771 probes corresponding to genes with expression levels that were observed to be attenuated at levels 0.5 times or less or enhanced at levels 2 times or more that of the normal healthy subject group:

Similarly with the use of a GeneSpring GX Class Prediction tool, a prediction model was prepared based on 771 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 9 out of 10 separately analyzed cancer cases were determined with the prediction model to be cancer cases and the probability that such cases had been properly diagnosed was 90%. Also, 13 out of 13 normal healthy subject cases were determined with prediction model to be normal healthy subject cases, and the probability that such cases had been properly diagnosed was 100%. Altogether, 22 out of 23 such cases were correct answers. Thus, the percentage of cases determined correctly was 95.7% (22/23).

Hierarchical clustering with 116 probes corresponding to genes with expression levels that were observed to be attenuated at levels 0.33 times or less or enhanced at levels 3 times or more that of the normal healthy subject group:

Hierarchical clustering was performed using a total of 116 probes including the above 9 probes and 107 probes for subject cancer cases and normal healthy subjects. As shown in FIG. 17, 3 clusters were formed. In the $1^{st}$ cluster, 5 out of 5 cases (100%) were colorectal cancer cases. In the $2^{nd}$ cluster, 3 out of 6 cases (50.0%) were colorectal cancer cases. In the $3^{rd}$ cluster, 5 out of 5 cases (100%) were normal healthy subject cases.

Predictive determination using 116 probes corresponding to genes with expression levels that were observed to be attenuated at levels 0.33 times or less or enhanced at levels 3 times or more that of the normal healthy subject group:

Similarly with the use of a GeneSpring GX Class Prediction tool, a prediction model was prepared based on 116 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 9 out of 10 separately analyzed cancer cases were determined with the prediction model to be cancer cases and the probability that such cases had been properly diagnosed was 90%. Also, 13 out of 13 normal healthy subject cases were determined with prediction model to be normal healthy subject cases, and the probability that such cases had been properly diagnosed was 100%. Altogether, 22 out of 23 such cases were correct answers. Thus, the percentage of cases determined correctly was 95.7% (22/23).

4. Detection of Pancreatic Cancer

Hierarchical Clustering:

Hierarchical clustering was performed using a GeneSpring GX hierarchical clustering tool and 22149 probes that had passed a quality check. As shown in FIG. 18, 3 clusters were formed. In the $1^{st}$ cluster, 7 out of 7 cases (100%) were normal healthy subject cases. In the $2^{nd}$ cluster, 4 out of 5 cases (80%) were pancreatic cancer cases. In the $3^{rd}$ cluster, 4 out of 4 cases (100%) were pancreatic cancer cases. Hence, pancreatic cancer cases and normal healthy subjects were separately clustered.

Genes with expression levels that were observed to differ between a pancreatic cancer case group and a normal healthy subject group:

Similarly, with the use of a GeneSpring GX Statistic Analysis tool, probes capable of discriminating between a pancreatic cancer case group and a normal healthy subject group were examined using the Benjamini and Hochberg false discovery rate for a multiple test and $p<0.05$. As a result, the expression of 3301 probes was observed to differ between the two groups.

Also, normalized numerical values for fluorescence intensities of the 3301 probes were compared using a Fold Change tool between the pancreatic cancer case group and the normal healthy subject group. The expression of 96 probes was observed to be attenuated in the pancreatic cancer case group at levels 0.5 times or less that of the normal healthy subject group and the expression of 581 probes was observed to be enhanced in the pancreatic cancer case group at levels 2 times or more that of the normal healthy subject group. Also, the expression of 6 probes was observed to be attenuated in the pancreatic cancer case group at levels 0.33 times or less that of the normal healthy subject group and the expression of 55 probes was observed to be enhanced in the pancreatic cancer case group at levels 3 times or more that of the normal healthy subject group.

Hierarchical clustering with 677 probes corresponding to genes with expression levels that were observed to be attenuated at levels 0.5 times or less or enhanced at levels 2 times or more that of the normal healthy subject group:

Hierarchical clustering was performed for subject cancer cases and normal healthy subjects using a total of 677 probes including the above 96 probes and 581 probes. As shown in FIG. 19, 2 clusters were formed. In the $1^{st}$ cluster, 8 out of 9 cases (88.9%) were normal healthy subject cases. In the $2^{nd}$ cluster, 7 out of 7 cases (100%) were pancreatic cancer cases.

Predictive determination using 677 probes corresponding to genes with expression levels that were observed to be attenuated at levels 0.5 times or less or enhanced at levels 2 times or more that of the normal healthy subjects:

Similarly with the use of a GeneSpring GX Class Prediction tool, a prediction model was prepared based on 677 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 15 out of 20 separately analyzed cancer cases were determined with the prediction model to be pancreatic cancer cases and the probability that such cases had been properly diagnosed was 75%. Also, 13 out of 13 normal healthy subject cases were determined with prediction model to be normal healthy subject cases, and the probability that such cases had been properly diagnosed was 100%. Altogether, 28 out of 33 such cases were correct answers. Thus, the percentage of cases determined correctly was 84.8% (28/33).

Hierarchical clustering with 61 probes corresponding to genes with expression levels that were observed to be attenuated at levels 0.33 times or less or enhanced at levels 3 times or more that of the normal healthy subject group:

Hierarchical clustering was performed for subject cancer cases and normal healthy subjects using a total of 61 probes including the above 6 probes and 55 probes. As shown in FIG. 20, 2 clusters were formed. In the $1^{st}$ cluster, 8 out of 9 cases (88.9%) were normal healthy subject cases. In the $2^{nd}$ cluster, 7 out of 7 cases (100%) were pancreatic cancer cases.

Predictive determination using 61 probes corresponding to genes with expression levels that were observed to be attenuated at levels 0.33 times or less or enhanced at levels 3 times or more that of the normal healthy subjects:

Similarly with the use of a GeneSpring GX Class Prediction tool, a prediction model was prepared based on 61 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 15 out of 20 separately analyzed cancer cases were determined with the prediction model to be pancreatic cancer cases and the probability that such cases had been properly diagnosed was 75%. Also, 9 out of 13 normal healthy subject cases were determined with prediction model to be normal healthy subject cases, and the probability that such cases had been properly diagnosed was 69.2%. Altogether, 24 out of 33 such cases were correct answers. Thus, the percentage of cases determined correctly was 72.7% (24/33).

5. Detection of Biliary Tract Cancer
Hierarchical Clustering

Hierarchical clustering was performed using a GeneSpring GX hierarchical clustering tool and 22066 probes that had passed a quality check. As shown in FIG. 25, 3 clusters were formed. In the 1$^{st}$ cluster, 7 out of 7 cases (100%) were normal healthy subject cases. In the 2$^{nd}$ cluster, 3 out of 3 cases (100%) were biliary tract cancer cases. In the 3$^{rd}$ cluster, 5 out of 6 cases (83.3%) were biliary tract cancer cases. Hence, biliary tract cancer cases and normal healthy subjects were separately clustered.

Genes with expression levels that were observed to differ between a biliary tract cancer case group and a normal healthy subject group:

Similarly, with the use of a GeneSpring GX Statistic Analysis tool, probes capable of discriminating between a biliary tract cancer case group and a normal healthy subject group were examined using the Benjamini and Hochberg false discovery rate for a multiple test and p<0.05. As a result, the expression of 8090 probes was observed to differ between the two groups.

Also, normalized numerical values for fluorescence intensities of the 8090 probes were compared using a Fold Change tool between the biliary tract cancer case group and the normal healthy subject group. The expression of 98 probes was observed to be attenuated in the biliary tract cancer case group at levels 0.33 times or less that of the normal healthy subject group and the expression of 265 probes was observed to be enhanced in the biliary tract cancer case group at levels 3 times or more that of the normal healthy subject group.

Hierarchical clustering with 363 probes corresponding to genes with expression levels that were observed to be attenuated at levels 0.33 times or less or enhanced at levels 3 times or more that of the normal healthy subject group:

Hierarchical clustering was performed for subject cancer cases and normal healthy subjects using a total of 363 probes including the above 98 probes and 265 probes. As shown in FIG. 26, 2 clusters were formed. In the 1$^{st}$ cluster, 7 out of 7 cases (100%) were normal healthy subject cases. In the 2$^{nd}$ cluster, 8 out of 9 cases (88.9%) were biliary tract cancer cases.

Predictive determination using 363 probes corresponding to genes with expression levels that were observed to be attenuated at levels 0.33 times or less or enhanced at levels 3 times or more that of the normal healthy subjects:

Similarly with the use of a GeneSpring GX Class Prediction tool, a prediction model was prepared based on 363 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 8 out of 8 separately analyzed cancer cases were determined with the prediction model to be cancer cases and the probability that such cases had been properly diagnosed was 100%. Also, 13 out of 13 normal healthy subject cases were determined with prediction model to be normal healthy subject cases, and the probability that such cases had been properly diagnosed was 100%. Altogether, 21 out of 21 such cases were correct answers. Thus, the percentage of cases determined correctly was 100% (21/21).

All publications, patents, and patent applications cited in this description are herein incorporated by reference in their entirety

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09441276B2). An electronic copy of the "Sequence Listing" will also be available from the USPTO upon request and payment of the fee set forth in 37 CFR 1.19(b)(3).

The invention claimed is:

1. A reagent consisting of:
a set of probes bound to a solid support
wherein the set of probes consists of the nucleotide sequences of SEQ ID NOs: 1583, 1601, 1611, 1614, 1644, 1651, 1678, 1680, 1684, 1737, 1746, 1750, 1751, 1757,
1760, 1765, 1766, 1773, 1778, 1779, 1780, 1782, 1787, 1794, 1795, 1798, 1802, 1831, 1836,
1837, 1853, 1854, 1869, 1871, 1873, 1876, 1880, 1890, 1892, 1896, 1925, 1942, 1950, 1953,
1962, 1970, 1977, 1978, 1985, 1990, 1991, 2000, 2004, 2007, 2011, 2018, 2019, 2023, 2032,
2046, 2050, 2054, 2077, 2085, 2088, 2095, 2105, 2126, 2128, 2132, 2138, 2140, 2143, 2144,
2145, 2147, 2158, 2160, 2161, 2173, 2175, 2176, 2180, 2191, 2193, 2198, 2207, 2209, 2213,
2217, 2218, 2223, 2227, 2233, 2247, 2255, 2257, 2258, 2261, 2266, 2268, 2269, 2273, 2280,
2286, 2296, 2306, 2317, 2320, 2322, 2325, 2332, 2334, 2336, 2339, and 2340.

2. The reagent according to claim 1, wherein the reagent is a DNA microarray.

3. A method for detecting colorectal cancer in a subject, comprising
(i) measuring the expression of genes of the subject using the reagent of claim 1, to obtain an expression profile;
(ii) determining a difference in expression profiles between the subject and a normal subject;
(iii) detecting colorectal cancer based on the difference in expression profiles between a subject and a normal subject; and
(iv) identifying that the subject has colorectal cancer.

4. The method of claim 3, wherein the measuring step is conducted by contacting nucleic acid molecules extracted from a blood or tissue sample obtained from the subject, with the reagent, under conditions suitable for hybridizing the nucleic acid molecules of the subject, under stringent conditions, to the probes of the reagent.

5. The method of claim 3, wherein the genes of the subject are mRNA molecules extracted from peripheral blood obtained from the subject.

* * * * *